United States Patent
Busch et al.

(10) Patent No.: US 8,569,352 B2
(45) Date of Patent: Oct. 29, 2013

(54) IMIDAZOLE BASED LXR MODULATORS

(75) Inventors: Brett B. Busch, San Diego, CA (US);
Brenton T. Flatt, Poway, CA (US);
Xiao-Hui Gu, San Diego, CA (US);
Shao-Po Lu, San Diego, CA (US);
Richard Martin, San Diego, CA (US);
Raju Mohan, Encinitas, CA (US);
Michael Charles Nyman, San Diego, CA (US); Edwin Schweiger, San Diego, CA (US); William C. Stevens, Jr., San Diego, CA (US); Tie-Lin Wang, San Diego, CA (US); Yinong Xie, San Diego, CA (US)

(73) Assignee: Exelixis Patent Company LLC, South San Francisco, CA (US)

( * ) Notice: Subject to any disclaimer, the term of this patent is extended or adjusted under 35 U.S.C. 154(b) by 787 days.

(21) Appl. No.: 11/993,529

(22) PCT Filed: Jun. 26, 2006

(86) PCT No.: PCT/US2006/024757
§ 371 (c)(1),
(2), (4) Date: Dec. 4, 2009

(87) PCT Pub. No.: WO2007/002563
PCT Pub. Date: Jan. 4, 2007

(65) Prior Publication Data
US 2010/0075964 A1 Mar. 25, 2010

Related U.S. Application Data

(60) Provisional application No. 60/694,372, filed on Jun. 27, 2005, provisional application No. 60/736,120, filed on Nov. 10, 2005.

(51) Int. Cl.
*A61K 31/4174* (2006.01)
*C07D 233/64* (2006.01)

(52) U.S. Cl.
USPC .......................... 514/399; 548/343.5

(58) Field of Classification Search
USPC .............. 548/399, 343.5; 514/343.5, 399
See application file for complete search history.

(56) References Cited

U.S. PATENT DOCUMENTS

| | | |
|---|---|---|
| 4,559,394 A | 12/1985 | McDaniel |
| 4,895,867 A | 1/1990 | Huang et al. |
| 5,466,823 A | 11/1995 | Talley et al. |
| 5,504,215 A | 4/1996 | Talley et al. |
| 5,760,068 A | 6/1998 | Talley et al. |
| 6,071,955 A | 6/2000 | Elias et al. |
| 6,184,215 B1 | 2/2001 | Elias et al. |
| 6,294,558 B1 | 9/2001 | Ando et al. |
| 6,358,634 B1 | 3/2002 | Igarashi et al. |
| RE37,936 E | 12/2002 | Huang et al. |

(Continued)

FOREIGN PATENT DOCUMENTS

| | | |
|---|---|---|
| CN | 1599724 A | 3/2005 |
| DE | 103 15 569 A1 | 10/2004 |

(Continued)

OTHER PUBLICATIONS

Bennett, et al., "Liver X receptor agonist as a treatment for atherosclerosis", Expert Opinion on Therapeutic Patents, 2004, 14(7), 967-982.

(Continued)

*Primary Examiner* — Kamal Saeed
*Assistant Examiner* — Janet L Coppins
(74) *Attorney, Agent, or Firm* — Fox Rothschild LLP; Gerard P. Norton; Robert N. Henrie, II

(57) ABSTRACT

Compounds of the invention, such as compounds of Formulae IIa, IIb, IIc or IId, and pharmaceutically acceptable salts, isomers, and prodrugs thereof, are useful as modulators of the activity of liver X receptors, where $R^1$, $R^2$, $R^{21}$, $R^3$ and G are defined herein. Pharmaceutical compositions containing the compounds and methods of using the compounds are also disclosed.

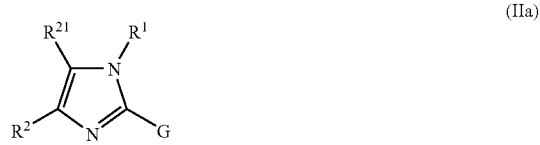

(IIa)

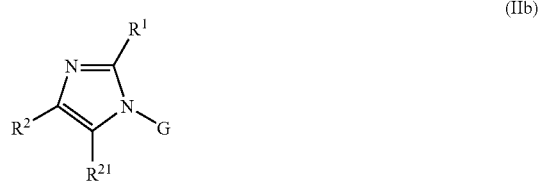

(IIb)

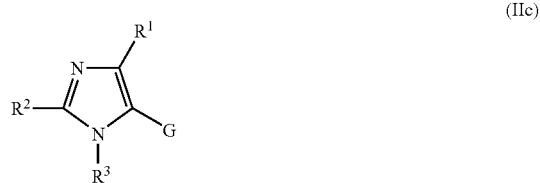

(IIc)

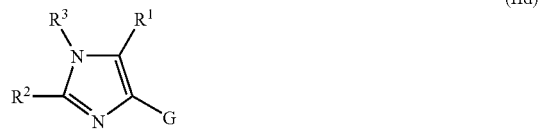

(IId)

31 Claims, No Drawings

(56) References Cited

U.S. PATENT DOCUMENTS

| | | |
|---|---|---|
| 6,492,411 B1 | 12/2002 | Talley et al. |
| 6,555,563 B1 | 4/2003 | Le et al. |
| 6,635,655 B1 | 10/2003 | Jayyosi et al. |
| 7,566,709 B2 | 7/2009 | Schiemann et al. |
| 7,998,995 B2 * | 8/2011 | Boren et al. ............ 514/397 |
| 2002/0035156 A1 | 3/2002 | Roniker et al. |
| 2004/0063691 A1 | 4/2004 | Smith et al. |
| 2004/0152739 A1 | 8/2004 | Hanau et al. |
| 2004/0157883 A1 | 8/2004 | Chen et al. |
| 2004/0248956 A1 | 12/2004 | Hagmann et al. |
| 2005/0004115 A1 | 1/2005 | Sharma et al. |
| 2006/0241157 A1 | 10/2006 | Conner et al. |
| 2006/0276650 A1 | 12/2006 | Schadt et al. |
| 2007/0010531 A1 | 1/2007 | Schadt et al. |
| 2008/0090834 A1 | 4/2008 | Hoover et al. |

FOREIGN PATENT DOCUMENTS

| | | |
|---|---|---|
| DE | 103 15 571 A1 | 10/2004 |
| DE | 103 15 573 A1 | 10/2004 |
| EP | 0 839 810 A1 | 5/1996 |
| EP | 0 839 810 A1 | 5/1998 |
| EP | 1 285 908 A1 | 2/2003 |
| EP | 1 398 029 A | 3/2004 |
| EP | 1 884 513 A | 2/2008 |
| JP | 57026653 A | 2/1982 |
| JP | 63-054370 A | 3/1988 |
| JP | 2004-137270 A | 5/2004 |
| JP | 2004-146368 A | 5/2004 |
| JP | 2006-104191 A | 4/2006 |
| JP | 2008-526887 A | 7/2008 |
| WO | 01/42241 A1 | 6/2001 |
| WO | 0170703 A3 | 5/2002 |
| WO | 02090335 A1 | 11/2002 |
| WO | 03/086287 A2 | 10/2003 |
| WO | 03086390 A1 | 10/2003 |
| WO | 03063781 A3 | 12/2003 |
| WO | 03075921 A3 | 12/2003 |
| WO | 2004/011446 A | 2/2004 |
| WO | 2004/013135 A1 | 2/2004 |
| WO | 2004/033432 A | 4/2004 |
| WO | 2004/056740 A1 | 7/2004 |
| WO | 2004/069158 A | 8/2004 |
| WO | 2004/071447 A2 | 8/2004 |
| WO | 2004/080972 A | 9/2004 |
| WO | 2004/089303 A2 | 10/2004 |
| WO | 2004/089888 A1 | 10/2004 |
| WO | 2004/089932 A1 | 10/2004 |
| WO | 2004/106307 A2 | 12/2004 |
| WO | 2005000295 A1 | 1/2005 |
| WO | 2005/009435 A | 2/2005 |
| WO | 2005/012263 A | 2/2005 |
| WO | 2005/037199 A2 | 4/2005 |
| WO | 2005/037271 A1 | 4/2005 |
| WO | 2005/037763 A1 | 4/2005 |
| WO | 2005/044130 A1 | 5/2005 |
| WO | 2005/047266 A | 5/2005 |
| WO | WO 2005/047266 A * | 5/2005 |
| WO | WO-2005/047266 A1 * | 5/2005 |
| WO | 2005/049578 A | 6/2005 |
| WO | 2005/054176 A1 | 6/2005 |
| WO | 2005/066137 A | 7/2005 |
| WO | 2005102389 A9 | 11/2005 |
| WO | 2006/028029 A1 | 3/2006 |
| WO | 2006/044528 A | 4/2006 |
| WO | 2006/074445 A2 | 7/2006 |
| WO | 2006/076202 A | 7/2006 |
| WO | 2007/002559 A | 1/2007 |
| WO | 2008/073825 A1 | 6/2008 |

OTHER PUBLICATIONS

Tischenko et al., "Some derivatives of 1,2,5-triphenylimidazole", Deposited Doc. (1980) SPSTL 358Khp-D80, Caplus Accession No. 1982:423694, 8pp.

Tischenko et al., "Synthesis and luminescence of 1,2,5-triphenylimidazoles", Sisintill Org Lyuminofory, 1972, 93-9.

Lettau et al., "Imidazol-N-oxide 1); Eline einfache Synthese substituierter Imidazole", Zeischrift fuer Chemie, 1971, 11(1), 10-11.

Schubert et al., "Diimidazoles. II. Synthesis of aliphatically and aromatically bridged N,N'-diimidazoles", Journal fuer Praktische Chemie (Leipzig), 1963, 22(3-4), 130-9.

Yanborisov et al., "Synthesis and pharmaceutical activity of heteroylpyruvic acids and their derivatives", Khimiko-Farmatsevticheskii Zhurnal [Pharmaceutical Chemistry Journal], 1998, 32(9), 480-2.

Kalaany et al., "LXRs regulate the balance between fat storage and oxidation", Cell Metabolism, 2005, vol. 1, 231-244 and Supplemental Data (4 sheets).

Giorelli et al., "Immunomodulatory properties of increased levels of liver X receptor β in peripheral blood mononuclear cells from multiple sclerosis patients", Experimental Neurology, 2007, vol. 294, 759-766.

Zanlungo et al., "The Molecular and Metabolic Basis of Biliary Cholesterol Secretion and Gallstone Disease". Frontiers in Bioscience, 2003, vol. 8, 1166-1174.

Zelcer et al., "Liver X receptors as integrators of metabolic and inflammatory signaling", The Journal of Clinical Investigation, 2006, 116(3), 607-614.

Joseph et al., "Synthetic LXR ligand inhibits the development of atherosclerosis in mice", PNAS, 2002, 99(11), 7604-7609.

Tontonoz et al., "Liver X Receptor Signaling Pathways in Cardiovascular Disease", Molecular Endocrinology, 2003, 17(6), 985-993.

Goralski et al., "Chipping away at gallstones", Nature Medicine, 2004, 10(12), 1301-1302.

Finn, J. et al., "Discovery of a Potent and Selective Series of Pyrazole Bacterial Methionyl-Tma Sythetase Inhibitors", Bioorganic & Medicinal Chemistry Letters, 2003, 13(13), 2231-2234.

Bennett et al., "Liver X Receptor Agonist as a Treatment for Atherosclerosis", Expert Opinion on Therapeutic Patents, 2004, 14(7), 967-982.

Patent summary of JP4590825 corresponding to JP application 2004-253298 published Sep. 9, 2004.

* cited by examiner

IMIDAZOLE BASED LXR MODULATORS

CROSS-REFERENCE TO RELATED APPLICATIONS

This application is a US national phase of international application PCT/US2006/024757 filed on Jun. 26, 2006, which claims priority to U.S. Provisional Application No. 60/694,372, filed Jun. 27, 2005, and U.S. Provisional Application No. 60/736,120, filed Nov. 10, 2005. All of the above applications are incorporated by reference herein in their entireties.

FIELD OF THE INVENTION

This invention relates to compounds that modulate the activity of liver X receptors (LXRs). The invention also provides pharmaceutical compositions comprising the compounds of the invention and methods of utilizing those compositions for modulating the activity of liver X receptor. In particular, imidazole isomers and derivatives are provided for modulating the activity of LXRs.

BACKGROUND OF THE INVENTION

Nuclear Receptors

Nuclear receptors are a superfamily of regulatory proteins that are structurally and functionally related and are receptors for, e.g., steroids, retinoids, vitamin D and thyroid hormones (see, e.g., Evans (1988) *Science* 240:889-895). These proteins bind to cis-acting elements in the promoters of their target genes and modulate gene expression in response to ligands for the receptors.

Nuclear receptors can be classified based on their DNA binding properties (see, e.g., Evans, supra and Glass (1994) *Endocr. Rev.* 15:391-407): For example, one class of nuclear receptors includes the glucocorticoid, estrogen, androgen, progestin and mineralocorticoid receptors which bind as homodimers to hormone response elements (HREs) organized as inverted repeats (see, e.g., Glass, supra). A second class of receptors, including those activated by retinoic acid, thyroid hormone, vitamin $D_3$, fatty acids/peroxisome proliferators (i.e., peroxisome proliferator activated receptors or PPARs) and ecdysone, bind to HREs as heterodimers with a common partner, the retinoid X receptors (i.e., RXRs, also known as the 9-cis retinoic acid receptors; see, e.g., Levin et al. (1992) *Nature* 355:359-361 and Heyman et al. (1992) *Cell* 68:397-406).

RXRs are unique among the nuclear receptors in that they bind DNA as a homodimer and are required as a heterodimeric partner for a number of additional nuclear receptors to bind DNA (see, e.g., Mangelsdorf et al. (1995) *Cell* 83:841-850). The latter receptors, termed the class II nuclear receptor subfamily, include many which are established or implicated as important regulators of gene expression.

There are three RXR genes (see, e.g., Mangelsdorf et al. (1992) *Genes Dev.* 6:329-344), coding for RXRα, β, and γ, all of which are able to heterodimerize with any of the class II receptors, although there appear to be preferences for distinct RXR subtypes by partner receptors in vivo (see, e.g., Chiba et al. (1997) *Mol. Cell. Biol.* 17:3013-3020). In the adult liver, RXRα is the most abundant of the three RXRs (see, e.g., Mangelsdorf et al. (1992) *Genes Dev.* 6:329-344), suggesting that it might have a prominent role in hepatic functions that involve regulation by class II nuclear receptors. See also, Wan et al. (2000) *Mol. Cell. Biol.* 20:4436-4444.

Orphan Nuclear Receptors

Included in the nuclear receptor superfamily of regulatory proteins are nuclear receptors for whom the ligand is known and those which lack known ligands. Nuclear receptors falling in the latter category are referred to as orphan nuclear receptors. The search for activators for orphan receptors has led to the discovery of previously unknown signaling pathways (see, e.g., Levin et al., (1992), supra and Heyman et al., (1992), supra). For example, it has been reported that bile acids, which are involved in physiological processes such as cholesterol catabolism, are ligands for the framesoid X receptor (FXR).

Because it is known that products of intermediary metabolism act as transcriptional regulators in bacteria and yeast, such molecules may serve similar functions in higher organisms (see, e.g., Tomkins (1975) *Science* 189:760-763 and O'Malley (1989) *Endocrinology* 125:1119-1120). For example, one biosynthetic pathway in higher eukaryotes is the mevalonate pathway, which leads to the synthesis of cholesterol, bile acids, porphyrin, dolichol, ubiquinone, carotenoids, retinoids, vitamin D, steroid hormones and farnesylated proteins.

LXRα and LXRβ

LXRα is found predominantly in the liver, with lower levels found in kidney, intestine, spleen and adrenal tissue (see, e.g., Willy, et al. (1995) Gene Dev. 9(9):1033-1045) LXRβ is ubiquitous in mammals and was found in nearly all tissues examined. LXRs are activated by certain naturally occurring, oxidized derivatives of cholesterol (see, e.g., Lehmann, et al. (1997) J. Biol. Chem. 272(6):3137-3140). LXRα is activated by oxycholesterol and promotes cholesterol metabolism (Peet et al. (1998) Cell 93:693-704). Thus, LXRs appear to play a role in, e.g., cholesterol metabolism (see, e.g., Janowski, et al. (1996) Nature 383:728-731).

Nuclear Receptors and Disease

Nuclear receptor activity has been implicated in a variety of diseases and disorders, including, but not limited to, hypercholesterolemia (see, e.g., International Patent Application Publication No. WO 00/57915), osteoporosis and vitamin deficiency (see, e.g., U.S. Pat. No. 6,316,5103), hyperlipoproteinemia (see, e.g., International Patent Application Publication No. WO 01/60818), hypertriglyceridemia, lipodystrophy, hyperglycemia and diabetes mellitus (see, e.g., International Patent Application Publication No. WO 01/82917), atherosclerosis and gallstones (see, e.g., International Patent Application Publication No. WO 00/37077), disorders of the skin and mucous membranes (see, e.g., U.S. Pat. Nos. 6,184,215 and 6,187,814, and International Patent Application Publication No. WO 98/32444), acne (see, e.g., International Patent Application Publication No. WO 00/49992), and cancer, Parkinson's disease and Alzheimer's disease (see e.g., International Patent Application Publication No. WO 00/17334). Activity of nuclear receptors, including LXRs, FXRs and PPARs, and orphan nuclear receptors, has been implicated in physiological processes including, but not limited to, bile acid biosynthesis, cholesterol metabolism or catabolism, and modulation of cholesterol 7α-hydroxylase gene (CYP7A1) transcription (see, e.g., Chiang et al. (2000) J. Biol. Chem. 275:10918-10924), HDL metabolism (see, e.g., Urizar et al. (2000) J. Biol. Chem. 275:39313-39317 and International Patent Application Publication No. WO 01/03705), and increased cholesterol efflux and increased expression of ATP binding cassette transporter protein (ABC1) (see, e.g., International Patent Application Publication No. WO 00/78972).

Thus, there is a need for compounds, compositions and methods of modulating the activity of nuclear receptors, including LXRs, FXRs, PPARs and orphan nuclear receptors.

3

Such compounds are useful in the treatment, prevention, inhibition or amelioration of one or more symptoms of diseases or disorders in which nuclear receptor activity is implicated.

SUMMARY OF THE INVENTION

In one aspect, the present invention provides a compound according the following formulas IIa-d,

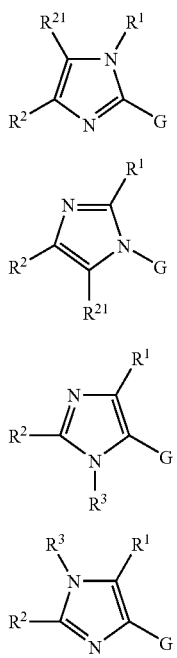

or a pharmaceutically acceptable salt, isomer, or prodrug thereof, which are useful as modulators of the activity of liver X receptors (LXR), where $R^1$, $R^2$, $R^{21}$, $R^3$, K and G are defined herein.

Compounds for use in compositions and methods for modulating the activity of nuclear receptors are provided. In particular, compounds of the invention which are useful for modulating liver X receptors, LXRα and LXRβ, FXR, PPAR and/or orphan nuclear receptors are provided.

In one embodiment, the compounds provided herein are agonists of LXR. In another embodiment, the compounds provided herein are antagonists of LXR. Agonists that exhibit low efficacy are, in certain embodiments, antagonists.

Another aspect of this invention is directed to methods of treating, preventing, inhibiting, or ameliorating the symptoms of a disease or disorder that is modulated or otherwise affected by nuclear receptor activity or in which nuclear receptor activity is implicated, comprising administering to a subject in need thereof a therapeutically effective amount of a compound of formulae IIa, IIb, IIc, or IId, or a pharmaceutically acceptable derivative thereof.

Another aspect of this invention is directed to methods of reducing cholesterol levels in a subject in need thereof, comprising administering an effective cholesterol level-reducing amount of a compound of formulae IIa, IIb, IIc or IId, or a pharmaceutically acceptable derivative thereof.

Another aspect of this invention is directed to methods of treating, preventing, inhibiting, or ameliorating one or more symptoms of a disease or disorder which is affected by cholesterol, triglyceride, or bile acid levels, comprising administering to a subject in need thereof a therapeutically effective amount of a compound of formulae IIa, IIb, IIc or IId, or a pharmaceutically acceptable derivative thereof.

Another aspect of this invention is directed to methods of modulating nuclear receptor activity, comprising contacting the nuclear receptor with a compound of formulae IIa, IIb, IIc or IId, or a pharmaceutically acceptable derivative thereof.

Another aspect of this invention is directed to methods of modulating cholesterol metabolism, comprising administering an effective cholesterol metabolism-modulating amount of a compound of formulae IIa, IIb, IIc or IId, or a pharmaceutically acceptable derivative thereof.

Another aspect of this invention is directed to methods of treating, preventing, inhibiting or ameliorating one or more symptoms of hypocholesterolemic in a subject in need thereof, comprising administering a therapeutically effective amount of a compound of formulae IIa, IIb, IIc or IId, or a pharmaceutically acceptable derivative thereof.

Another aspect of this invention is directed to methods of increasing cholesterol efflux from cells of a subject, comprising administering an effective cholesterol efflux-increasing amount of a compound of formulae IIa, IIb, IIc or IId, or a pharmaceutically acceptable derivative thereof.

Another aspect of this invention is directed to methods of increasing the expression of ATP-Binding Cassette (ABC1) in the cells of a subject, comprising administering an effective ABC1 expression-increasing mount of a compound of formulae IIa, IIb, IIc or IId, or a pharmaceutically acceptable derivative thereof.

Another aspect of this invention is directed to in vitro methods for altering nuclear receptor activity, comprising contacting the nuclear receptor with a compound of formulae IIa, IIb, IIc or IId, or a pharmaceutically acceptable derivative thereof.

Another aspect of this invention is directed to methods of reducing cholesterol levels in a subject in need thereof, comprising administering an effective cholesterol level-reducing amount of a compound of formulae IIa, IIb, IIc or IId, or a pharmaceutically acceptable derivative thereof.

Another aspect of this invention is directed to pharmaceutical compositions comprising a pharmaceutically acceptable carrier, excipient and/or diluent and a compound of formulae IIa, IIb, IIc or IId.

Another aspect of this invention is directed to regulation of cholesterol transport and inflammatory signaling pathways that are implicated in human disease pathology including atherosclerosis and associated diseases such as myocardial infarction and ischemic stroke in a subject in need thereof, comprising administering an effective cholesterol transport and inflammatory signaling pathways regulating amount of a compound of formulae IIa, IIb, IIc or IId, or a pharmaceutically acceptable derivative thereof.

Another aspect of this invention is directed to treatment of the metabolic syndrome which comprises a constellation of disorders of the body's metabolism including obesity, hypertension and insulin resistance and diabetes including treatment of diseases resulting from compromised metabolism and immunity including atherosclerosis and diabetes as well as autoimmune disorders and diseases in a subject in need thereof, comprising administering a therapeutically effective amount of a compound of formulae IIa, IIb, IIc or IId, or a pharmaceutically acceptable derivative thereof.

DETAILED DESCRIPTION OF THE INVENTION

In a first embodiment, the present invention provides a compound according to one of the following formulas,

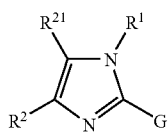

IIa

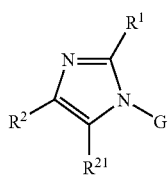

IIb

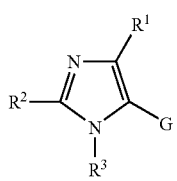

IIc

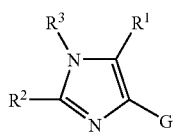

IId or a pharmaceutically acceptable salt, isomer, or prodrug thereof, wherein, (A) $R^1$ is -$L^1$-$R^5$, wherein
  $L^1$ is a bond, $L^5$, $L^6$, $L^5$-$L^6$-$L^5$-, or $L^6$-$L^5$-$L^6$-, wherein
    each $L^5$ is independently —[C($R^{15}$)$_2$]$_m$—, wherein
      each $R^{15}$ is independently hydrogen, halogen, ($C_1$-$C_6$)alkyl, ($C_3$-$C_6$)cycloalkyl, or ($C_1$-$C_6$)haloalkyl; and
    each $L^6$ is independently —CS—, —CO—, —SO$_2$—, —O—, —CON($R^{11}$)—, —CONR$^{11}$N($R^{11}$)—, —C(=N$R^{11}$)—, —C(=NO$R^{11}$)—, or —C(=NN($R^{11}$)$_2$)—, -aryl-, —$C_3$-$C_8$cycloalkyl-, -heteroaryl-, or -heterocyclyl-,
      wherein the aryl, cycloalkyl, heteroaryl, or heterocyclyl is optionally substituted with one or more $R^{14}$;
    or each $L^6$ is independently $C_2$-$C_6$ alidiyl,
      wherein the alidiyl chain is optionally interrupted by —C($R^{11}$)$_2$—, —C($R^{11}$)$_2$C($R^{11}$)$_2$—, —C($R^{11}$)=C($R^{11}$)—, —C($R^{11}$)$_2$O—, —C($R^{11}$)$_2$NR$^{11}$—, —C≡C—, —O—, —S—, —N($R^{10}$)CO—, —NR$^{10}$)CO$_2$—, —CON($R^{10}$)—, —CO—, —OC(=O)—, —OC(=O)N($R^{10}$), —SO$_2$—, —N($R^{10}$)SO$_2$—, or —SO$_2$N($R^{10}$); and
  $R^5$ is aryl, heterocyclyl, heteroaryl, —($C_3$-$C_6$)cycloalkyl, —C, or —B—C, wherein
    B is —[C($R^{15}$)$_2$]$_m$— or —$C_3$-$C_8$ cycloalkyl-; and
    C is halogen, —$C_1$-$C_6$alkyl, —$C_1$-$C_6$haloalkyl, —SO$_2$R$^{11}$, —SR$^{11}$, —SO$_2$N($R^{11}$)$_2$, —SO$_2$NR$^{11}$COR$^{11}$,
    —C≡N, —C(O)OR$^{11}$, —CON($R^{11}$)$_2$, or —N($R^{11}$)$_2$,
  wherein $R^5$ is optionally substituted with one or more $R^{5a}$, wherein
    each $R^{5a}$ is independently halogen, nitro, heteroaryl, heterocyclyl, $C_2$-$C_6$ alkenyl, $C_2$-$C_6$ alkynyl, $C_3$-$C_g$ cycloalkyl, ($C_3$-$C_8$ cycloalkyl)-$C_1$-$C_6$ alkyl-, ($C_3$-$C_8$ cycloalkenyl)-$C_1$-$C_6$ alkyl-, ($C_3$-$C_8$ cycloalkyl)-$C_2$-$C_6$ alkenyl-, aryl, arylalkyl, aryloxy, aryloxyaryl, aryl$C_{1-6}$ alkoxy, $C_1$-$C_6$ alkyl, $C_1$-$C_6$ haloalkyl, SO$_2$R$^{11}$, OR$^{11}$, SR$^{11}$, N$_3$, SO$_2$R$^{11}$, COR$^{11}$, SO$_2$N($R^{11}$)$_2$, SO$_2$NR$^{11}$COR$^{11}$, C≡N, C(O)OR$^{11}$, CON($R^{11}$)$_2$, CON($R^{11}$)OR$^{11}$, OCON($R^{11}$)$_2$, NR$^{11}$COR$^{11}$, NR$^{11}$CON($R^{11}$)$_2$, NR$^{11}$COOR$^{11}$, or N($R^{11}$)$_2$, wherein
      each $R^{5a}$ is optionally substituted with one or more groups which independently are -halogen, —$C_1$-$C_6$ alkyl, aryloxy $C_{0-6}$ alkylSO$_2$R$^{11}$, $C_{0-6}$ alkylCOOR$^{11}$, $C_{0-6}$ alkoxyaryl, $C_1$-$C_6$ haloalkyl, —SO$_2$R$^{11}$, —OR$^{11}$, —SR$^{11}$, —N$_3$, —SO$_2$R$^{11}$, —COR$^{11}$, —SO$_2$N($R^{11}$)$_2$, —SO$_2$NR$^{11}$COR$^{11}$, —C≡N, —C(O)OR$^{11}$, —CON($R^{11}$)$_2$, —CON($R^{11}$)OR$^{11}$, —OCON($R^{11}$)$_2$, —NR$^{11}$COR$^{11}$, —NR$^{11}$CON($R^{11}$)$_2$, —NR$^{11}$COOR$^{11}$, or —N($R^{11}$)$_2$;

$R^2$ and $R^{21}$ are -$L^3$-$R^7$, wherein
  each $L^3$ is independently a bond or —(CH$_2$)$_m$—V$^1$—(CH$_2$)$_n$—, wherein
    n is 0-6; and
    V$^1$ is —C($R^{11}$)$_2$—, —C($R^{11}$)$_2$C($R^{11}$)$_2$—, —C($R^{11}$)=C($R^{11}$)—, —C($R^{11}$)$_2$O—, —C($R^{11}$)$_2$NR$^{11}$—, —C≡C—, —O—, —S—, —NR$^{11}$—, —N($R^{10}$)CO—, —N($R^{10}$)CO$_2$—, —OCO—, —CO—, —CS—, —CONR$^{10}$—, —C(=N—R$^{11}$)—, —C(=N—OR$^{11}$)—, —C[=N—N($R^{11}$)$_2$], —CO$_2$—, —OC(=O)—, —OC(=O)N($R^{10}$)—, —SO$_2$—, —N($R^{10}$)SO$_2$—, —SO$_2$N($R^{10}$)—, —NR$^{10}$CONR$^{10}$—, —NR$^{10}$CSNR$^{10}$—, $C_3$-$C_6$cycloalkyl, or $C_3$-$C_6$ cyclohaloalkyl;
  or each $L^3$ is independently $C_2$-$C_6$ alidiyl,
    wherein the alidiyl chain is optionally interrupted by —C($R^{11}$)$_2$—, —C($R^{11}$)$_2$C($R^{11}$)$_2$—, —C($R^{11}$)=C($R^{11}$)—, —C($R^{11}$)$_2$O—, —C($R^{11}$)$_2$NR$^{11}$—, —C≡C—, —O—, —S—, —N($R^{10}$)CO—, —N($R^{10}$)CO$_2$—, —NR$^{11}$—, —CON($R^{10}$)—, —CO—, —CO$_2$—, —OC(=O)—, —OC(=O)N($R^{10}$)—, —SO$_2$—, —N($R^{10}$)SO$_2$—, or —SO$_2$N($R^{10}$)—; and
  each $R^7$ is independently hydrogen, halogen, nitro, aryl, heteroaryl, heterocyclyl, -Z, —Y—Z, or —X—Y—Z, wherein
    X is —O—;
    Y is —[C($R^{15}$)$_2$]$_m$—, $C_2$-$C_6$alkenyl, or —$C_3$-$C_8$cycloalkyl; and
    Z is —H, halogen, —OR$^{11}$, —C(=O)R$^{11}$, —C(=O)OR$^{11}$, —C(=O)N($R^{11}$)$_2$, —N($R^{11}$)$_2$, —C(=N—OH)R$^{11}$, —C(=S)N($R^{11}$)$_2$, —CN, —S(=O)$_2$N($R^{11}$)$_2$, —C(=O)N($R^{11}$)N($R^{11}$)$_2$, —C(=O)N($R^{11}$)(OR$^{11}$), —OC(=O)—R$^{11}$, or —OC(=O)—N($R^{11}$)$_2$,
  wherein $R^7$ is optionally substituted with one or more $R^{7a}$, wherein
    $R^{7a}$ is halogen, haloaryl, aryloxy, aralkyloxy, aryloxyalkyl, aryl$C_0$-$C_6$ alkylcarboxy, C($R^{11}$)=C($R^{11}$)—COOH, aryl, heteroaryl, heterocyclyl, heterocyclyloxy, heteroaryloxy, —Z', —Y'—Z', or —X'—Y'—Z', wherein
    X' is —O—;
    Y' is —[C($R^{15}$)$_2$]$_m$— or —$C_3$-$C_8$cycloalkyl; and
    Z' is —H, halogen, —OR$^{11}$, —SR$^{11}$, —S(=O)$_2$R$^{11}$, —C(=O)R$^{11}$, —C(=O)OR$^{11}$, —C(=O)N($R^{11}$)$_2$, —N($R^{11}$)$_2$, N($R^{11}$)C(=O)R$^{11}$, S(=O)$_2$N($R^{11}$)C(=O)R$^{11}$, —CN, —S(=O)$_2$N($R^{11}$)$_2$, —C(=O)N($R^{11}$)N($R^{11}$)$_2$, —C(=O)N($R^{11}$)

(OR$^{11}$), —OC(=O)—R$^{11}$, —OC(=O)—OR$^{11}$, —N(R$^{11}$)C(O)—R$^{11}$, or —N(R$^{11}$)S(O=)$_2$R$^{11}$, wherein each R$^{7a}$ is optionally substituted with one or more R$^8$, wherein each R$^8$ is independently halogen, $C_1$-$C_6$ alkyl, $C_1$-$C_6$ alkoxy, $C_1$-$C_6$ haloalkyl, $C_1$-$C_6$ haloalkyl (OR$^{11}$), $C_0$-$C_6$ alkylOR$^{11}$, $C_0$-$C_6$ alkylCON(R$^{11}$)$_2$, $C_0$-$C_6$ alkylCOR$^{11}$, $C_0$-$C_6$ alkylCOOR$^{11}$, or $C_0$-$C_6$ alkylSO$_2$R$^{11}$, provided that R$^2$ and R$^{21}$ are not simultaneously hydrogen, R$^3$ is -L-R$^6$, wherein L is a bond, —X$^3$—(CH$_2$)$_n$—X$^3$—, —(CH$_2$)$_m$—X$^3$—(CH$_2$)$_n$— or —(CH$_2$)$_{1+w}$—Y$^3$—(CH$_2$)$_w$—, wherein n is 0-6; each w is independently 0-5; and each X$^3$ is independently a bond, —C(R$^{11}$)$_2$—, —C(R$^{11}$)$_2$C(R$^{11}$)$_2$—, —C(R$^{11}$)=C(R$^{11}$)—, —C≡C—, —CO—, —CS—, —CONR$^{10}$—, —C(=N)(R$^{11}$)—, —C(=N—OR$^{11}$)—, —C[=N—N(R$^{11}$)$_2$], —CO$_2$—, —SO$_2$—, or —SO$_2$N(R$^{10}$)—; and Y$^3$ is —O—, —S—, N(R$^{10}$)CO—, —N(R$^{10}$)CO$_2$—, —OCO—, —OC(=O)N(R$^{10}$)—, —NR$^{10}$CONR$^{10}$—, —N(R$^{10}$)SO$_2$—, or —NR$^{10}$CSNR$^{10}$—;

or L is $C_{2-6}$ alidiyl chain wherein the alidiyl chain is optionally interrupted by —C(R$^{11}$)$_2$—, —C(R$^{11}$)$_2$C(R$^{11}$)$_2$—, —C(R$^{11}$)=C(R$^{11}$)—, —C(R$^{11}$)$_2$O—, C(R$^{11}$)$_2$NR$^{11}$—, —C≡C—, —O—, —S—, —N(R$^{10}$)CO—, —N(R$^{10}$)CO$_2$—, —CON(R$^{10}$)—, —CO—, —CO$_2$—, —OC(=O)—, —OC(=O)N(R$^{10}$)—, —SO$_2$—, —N(R$^{10}$)SO$_2$—, or —SO$_2$N(R$^{10}$); and R$^6$ is $C_1$-$C_6$ alkyl, $C_1$-$C_6$ haloalkyl, aryl, $C_3$-$C_8$ cycloalkyl, heteroaryl, heterocyclyl, —CN, —C(=O)R$^{11}$, —C(=O)OR$^{11}$, —C(=O)N(R$^{11}$)$_2$, —N(R$^{11}$)$_2$, —SO$_2$R$^{11}$, —S(=O)$_2$N(R$^{11}$)$_2$, —C(=O)N(R$^{11}$)N(R$^{11}$)$_2$, —C(=O)N(R$^{11}$)(OR$^{11}$), wherein the aryl, heteroaryl, cycloalkyl, or heterocyclyl is optionally substituted with one or more R$^{6a}$, wherein each R$^{6a}$ is independently —Z", —Y"—Z", or —X"—Y"—Z", wherein X" is —O—;

Y" is —[C(R$^{15}$)$_2$]$_m$—, —$C_2$-$C_6$ alkenyl, $C_3$-$C_8$ cycloalkyl, heterocyclyl, aryl, or heteroaryl, wherein the aryl, heteroaryl, cycloalkyl, or heterocyclyl is optionally substituted with at least one group which is each independently Z";

Z" is —H, —CN, halogen, —OR$^{11}$, —C(=O)R$^{11}$, —C(=O)OR$^{11}$, —C(=O)N(R$^{11}$)$_2$, —N(R$^{11}$)$_2$, —N$_3$, —SO$_2$R$^{11}$, —S(=O)$_2$N(R$^{11}$)$_2$, —C(=O)N(R$^{11}$)N(R$^{11}$)$_2$, —N(R$^{11}$)C(=O) N(R$^{11}$)$_2$, —OC(=O)—OR$^{11}$, —C(=O)N(R$^{11}$)(OR$^{11}$), —OC(=O)—R$^{11}$, —OC(=O)—N(R$^{11}$)$_2$, or —N(R$^{11}$)COOR$^{11}$; and G is a group of the formula,

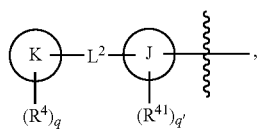

wherein

J is aryl, heteroaryl, or absent;
K is aryl, heteroaryl, or absent;
provided that (i) if K is absent, then q is 1 and R$^4$ is bonded directly to L$^2$; and each R$^4$ and R$^{41}$ is independently halogen, oxo, nitro, CR$^{11}$=CR$^{11}$COOR$^{11}$, aryloxy, aralkyloxy, aryloxyalkyl, aryl$C_0$-$C_6$ alkylcarboxy, aryl, heteroaryl, heterocyclyl, heteroaryloxy, heterocyclyloxy, -E-G$^1$, or -D-E-G$^1$, wherein D is —O—;
E is —[C(R$^{15}$)$_2$]$_m$— or —$C_3$-$C_8$cycloalkyl; and
G$^1$ is —$C_1$-$C_6$alkyl, —$C_1$-$C_6$haloalkyl, —COR$^{11}$, —COOR$^{11}$, —CON(R$^{11}$)$_2$, —C≡N, —OR$^{11}$, —OCON(R$^{11}$)$_2$, —OCOOR$^{11}$, —N$_3$, NR$^{11}$COR$^{11}$, —NR$^{11}$SO$_2$R$^{11}$, —N(R$^{11}$)$_2$, —NR$^{11}$COOR$^{11}$, —SO$_2$R$^{11}$, —SO$_2$NR$^{11}$COR$^{11}$, —SO$_2$N(R$^{11}$)$_2$, —SOR$^{11}$, or —SR$^{11}$, wherein each R$^4$ is optionally substituted with one or more R$^{4a}$, wherein each R$^{4a}$ is independently halogen, aryloxy, aralkyloxy, aryloxyalkyl, $C_1$-$C_6$ alkoxyaryl, arylC$_0$-$C_6$ alkylcarboxy, -G', -E'-G', or -D'-E'-G', wherein D' is —O—;
E' is —[C(R$^{15}$)$_2$]$_m$— or —$C_3$-$C_8$cycloalkyl-; and
G' is —H, -halogen, —COR$^{11}$, —COOR$^{11}$, —OR$^{11}$, —NR$^{11}$SO$_2$R$^{11}$, —SO$_2$R$^{11}$, —SO$_2$N(R$^{11}$)$_2$, or —SR$^{11}$, L$^2$ is a bond or —[C(R$^{15}$)$_2$]$_n$—V$^2$—[C(R$^{15}$)$_2$]$_m$—, wherein V$^2$ is independently —C(R$^{11}$)$_2$—, —C(R$^{11}$)$_2$C(R$^{11}$)$_2$—, —C(R$^{11}$)=C(R$^{11}$)—, —C(R$^{11}$)$_2$O—, —C(R$^{11}$)$_2$NR$^{11}$—, —C≡C—, —O—, —S—, —SO$_2$—, —N(R$^{10}$)CO—, —N(R$^{10}$)CO$_2$—, —CONR$^{10}$)—, —CON(R$^{11}$)—, —CON(R$^{11}$)O—, —CO—, —CS—, —CO$_2$—, —OC(=O)—, —OC(=O)N(R$^{11}$)—, —N(R$^{10}$)SO$_2$—, —SO$_2$N(R$^{10}$)—, —NR$^{10}$CONR$^{10}$—, —NR$^{10}$CSNR$^{10}$—, $C_3$-$C_6$cycloalkyl-, or $C_3$-$C_6$cyclohaloalkyl, or V$^2$ is $C_{2-6}$ alidiyl, wherein alidiyl chain is optionally interrupted by —C(R$^{11}$)$_2$—, —C(R$^{11}$)$_2$C(R$^{11}$)$_2$, —C(R$^{11}$)=C(R$^{11}$)—, —C(R$^{11}$)$_2$O—, —C(R$^{11}$)$_2$NR$^1$—, —C(R$^{11}$)$_2$ NR$^{11}$, —C≡C—, —O—, —S—, —N(R$^{10}$)CO—, —N(R$^{10}$)CO$_2$—, —CON(R$^{10}$)—, —CON(R$^{11}$)—, —CON(R$^{11}$)O—, —CO—, —CO$_2$—, —OC(=O)—, —OC(=O)N(R$^{10}$)—, —SO$_2$—, N(R$^{10}$)SO$_2$— or —SO$_2$N(R$^{10}$)—;

or V$^2$ is aryl, heteroaryl, or heterocyclyl, each of which is optionally substituted with one or more R$^9$, wherein each R$^9$ is independently halogen, $C_1$-$C_6$ haloalkyl, $C_1$-$C_6$ alkyl, $C_1$-$C_6$ alkyloxy, $C_0$-$C_6$ alkyl or $C_1$-$C_6$ alkylCOOR$^{11}$;

each m is 0, 1, 2, 3, 4, 5, or 6;
q is 0, 1, 2, 3, 4, or 5,
provided that q is 0 if and only if K is not phenyl; and
q' is 0, 1, 2, 3, or 4, each R$^{10}$ is independently -R$^{11}$, —C(=O)R$^{11}$, —CO$_2$R$^{11}$, or —SO$_2$R$^{11}$;

each R$^{11}$ is independently -hydrogen, —$C_1$-$C_6$ alkyl, $C_2$-$C_6$ alkenyl, $C_2$-$C_6$ alkynyl, $C_3$-$C_8$ cycloalkyl, ($C_3$-$C_8$ cycloalkyl)-$C_1$-$C_6$ alkyl-, ($C_3$-$C_8$ cycloalkenyl)-$C_1$-$C_6$ alkyl-, ($C_3$-$C_8$ cycloalkyl)-$C_2$-$C_6$ alkenyl-, —$C_1$-$C_6$ haloalkyl, —N(R$^{12}$)$_2$, aryl, —($C_1$-$C_6$)alkyl-aryl, heteroaryl, —($C_1$-$C_6$)alkyl-heteroaryl, heterocyclyl, or —($C_1$-$C_6$)alkyl-heterocyclyl, wherein any of R$^{11}$ is optionally substituted with one or more radicals of R$^{12}$;

each R$^{12}$ is independently halogen, $C_1$-$C_6$haloalkyl, $C_1$-$C_6$ alkyl, $C_1$-$C_6$ alkoxy, ($C_0$-$C_6$ alkyl)C=O (OR$^{13}$); C$_0$-C$_6$ alkylOR$^{13}$, C$_0$-C$_6$ alkylCOR$^{13}$, C$_0$-C$_6$ alkylSO$_2$R$^{13}$, C$_0$-C$_6$ alkylCON(R$^{13}$)$_2$, C$_0$-C$_6$ alkylCONR$^{13}$OR$^{13}$, C$_0$-C$_6$ alkylSO$_2$N(R$^{13}$)$_2$, C$_0$-C$_6$ alkylSR$^{13}$, C$_0$-C$_6$ haloalkylOR$^{13}$, aryloxy, aralkyloxy, aryloxyalkyl, C$_{0-6}$alkoxyaryl, arylC$_{0-6}$alkylcarboxy, —C$_0$-C$_6$ alkylN(R$^{13}$)$_2$, —NR$^{13}$SO$_2$R$^{13}$, or —OC$_{0-6}$alkylCOOR$^{13}$;

each R$^{13}$ is independently hydrogen, C$_1$-C$_6$ alkyl, C$_2$-C$_6$ alkenyl, C$_2$-C$_6$ alkynyl, C$_3$-C$_8$ cycloalkyl, (C$_3$-C$_8$ cycloalkyl)-C$_1$-C$_6$ alkyl-, (C$_3$-C$_8$ cycloalkenyl)-C$_1$-C$_6$ alkyl-, or (C$_3$-C$_8$ cycloalkyl)-C$_2$-C$_6$ alkenyl-;

each R$^{14}$ is independently C$_1$-C$_6$ alkyl, C$_1$-C$_6$ alkoxy, halogen, C$_1$-C$_6$ haloalkyl, C$_0$-C$_6$ alkylCON(R$^{11}$)$_2$, C$_0$-C$_6$ alkylCONR$^{11}$OR$^{11}$, C$_0$-C$_6$alkylOR$^{11}$, or C$_0$-C$_6$ alkylCOOR$^{11}$; and (B) provided that
  (i) when L$^2$ is a bond, both J and K are not absent;
  (ii) if the compound If defined by formula IIa, then
    a. if J is phenyl and K is thienyl, furyl, or thiazoyl and q is 0, then R$^1$ is not 4-(NH$_2$SO$_2$)phenyl, 4-(NH$_2$SO$_2$)-3-fluorophenyl, p-(CH$_3$SO$_2$)phenyl-, or 4p-(CH$_3$SO$_2$)-3-fluorophenyl-; and
    b. if R$^5$ is pyridyl or phenyl optionally substituted with one or more R$^{5a}$ and L$^1$ is a bond, then G is not p-(NH$_2$SO$_2$)phenyl or p-(CH$_3$SO$_2$)phenyl-;
  (iii) if the compound is defined by formula IIc or IId, then G is not p-(NH$_2$SO$_2$)phenyl or p-(CH$_3$SO$_2$)phenyl-;
  (iv) the compound is not 1-(biphenyl-4-yl)-2,5-diphenyl-1H-imidazole.

In one embodiment, the invention provides the compound according to formula IIa, IIc, or IId, wherein:

R$^1$ is L$^1$-R$^5$, wherein
  L$^1$ is a bond, L$^5$, L$^6$, -L$^5$-L$^6$-L$^5$-, or -L$^6$-L$^5$-L$^6$-, wherein
    each L$^5$ is independently —[C(R$^{15}$)$_2$]$_m$—, wherein
      m is 0, 1, 2, 3, or 4; and
      each R$^{15}$ is independently hydrogen, halogen, (C$_1$-C$_6$)alkyl, or (C$_1$-C$_6$)haloalkyl; and
    L$^6$ is —CO—, —SO$_2$—, —O—, —CON(R$^{11}$)—, —C$_3$-C$_6$cycloalkyl-, or -heterocyclyl-,
      wherein the cycloalkyl, or heterocyclyl is optionally substituted with one or more R$^{14}$; and R$^5$ is aryl, heterocyclyl, heteroaryl, —C, or —B—C, wherein
    B is —[C(R$^{15}$)$_2$]$_m$— or —C$_3$-C$_6$cycloalkyl-; and
    C is halogen, —C$_1$-C$_6$alkyl, or —C$_1$-C$_6$haloalkyl;
    wherein R$^5$ is optionally substituted with one or more R$^{5a}$, wherein
      each R$^{5a}$ is independently halogen, nitro, heteroaryl, heterocyclyl, C$_2$-C$_6$ alkenyl, C$_2$-C$_6$ alkynyl, (C$_3$-C$_8$ cycloalkyl)-C$_1$-C$_6$ alkyl-, (C$_3$-C$_8$ cycloalkenyl)-C$_1$-C$_6$ alkyl-, (C$_3$-C$_8$ cycloalkyl)-C$_2$-C$_6$ alkenyl-; aryl, arylalkyl, aryloxy, aryloxyaryl, arylC$_{1-6}$ alkoxy, C$_1$-C$_6$ alkyl, C$_1$-C$_6$ haloalkyl, C$_3$-C$_6$cycloalkyl, SO$_2$R$^{11}$, OR$^{11}$, SR$^{11}$, N$_3$, SO$_2$R$^{11}$, COR$^{11}$, SO$_2$N(R$^{11}$)$_2$, SO$_2$NR$^{11}$COR$^{11}$, C≡N, C(O)OR$^{11}$, CON(R$^{11}$)$_2$, CON(R$^{11}$)OR$^{11}$, OCON(R$^{11}$)$_2$, NR$^{11}$COR$^{11}$, NR$^{11}$CON(R$^{11}$)$_2$, NR$^{11}$COOR$^{11}$, or N(R$^{11}$)$_2$, wherein
        each R$^{5a}$ is optionally substituted with one or more groups which independently are -halogen, —C$_1$-C$_6$ alkyl, aryloxy CO—6 alkylSO$_2$R$^{11}$, C$_{0-6}$ alkylCOOR$^{11}$, C$_{0-6}$ alkoxyaryl, —C$_1$-C$_6$ haloalkyl, —SO$_2$R$^{11}$, —OR$^{11}$, —SR$^{11}$, —N$_3$, —SO$_2$R$^{11}$, —COR$^{11}$, ⁻SO$_2$N(R$^{11}$)$_2$, —SO$_2$NR$^{11}$COR$^{11}$, —C(O)R$^{11}$, —C≡N, —C(O)R$^{11}$, —CON(R$^{11}$)$_2$, —CON(R$^{11}$)

OR$^{11}$, —OCON(R$^{11}$)$_2$, —NR$^{11}$COR$^{11}$, —NR$^{11}$CON(R$^{11}$)$_2$, —NR$^{11}$COOR$^{11}$, or —N(R$^{11}$)$_2$;

R$^2$ is -L$^3$-R$^7$, wherein L$^3$ is a bond; and
  R$^7$ is halogen, aryl, heteroaryl, heterocyclyl, -Z, or —Y—Z, wherein
    Y is —[C(R$^{15}$)$_2$]$_m$— or —C$_3$-C$_6$cycloalkyl; and
    Z is —H, halogen, —OR$^{11}$, —C(=O)R$^{11}$, C(=O)OR$^{11}$, —C(=O)N(R$^{11}$)$_2$, —N(R$^{11}$)$_2$, —C(=N—OH)R$^{11}$, —C(=S)N(R$^{11}$)$_2$, —CN, —S(=O)$_2$N(R$^{11}$)$_2$, —C(=O)N(R$^{11}$)N(R$^{11}$)$_2$, or —C(=O)N(R$^{11}$)(OR$^{11}$);
  wherein R$^7$ is optionally substituted with one or more R$^{7a}$, wherein
    R$^{7a}$ is halogen —Z', —Y'—Z', or —X'—Y'—Z', wherein
      X' is —O—;
      Y' is —[C(R$^{15}$)$_2$]$_m$— or —C$_3$-C$_6$cycloalkyl; and
      Z' is —H, halogen, —OR$^{11}$, —SR$^{11}$, —S(=O)$_2$R$^{11}$, —C(=O)R$^{11}$, —C(=O)OR$^{11}$, —C(=O)N(R$^{11}$)$_2$, —N(R$^{11}$)$_2$, N(R$^{11}$)C(=O)R$^{11}$, —CN, —S(=O)$_2$ N(R$^{11}$)$_2$, —C(=O)N(R$^{11}$)(OR$^{11}$), or —N(R$^{11}$)S(O=)$_2$R$^{11}$, R$^{21}$ and R$^3$ are each independently hydrogen, halogen, C$_1$-C$_6$alkyl, or C$_1$-C$_6$haloalkyl; and
G is a group of the formula,

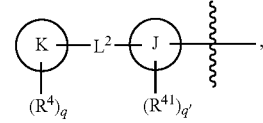

wherein
  J is aryl or heteroaryl;
  K is aryl or heteroaryl;
  each R$^4$ and R$^{41}$ is independently halogen, aryloxy, aralkyloxy, aryloxyalkyl, arylC$_0$-C$_6$ alkylcarboxy, aryl, heteroaryl, heterocyclyl, heteroaryloxy, heterocyclyloxy, -E-G$^1$, or -D-E-G', wherein
    D is —O—;
    E is —[C(R$^{15}$)$_2$]$_m$— or —C$_3$-C$_6$cycloalkyl; and
    G$^1$ is —C$_1$-C$_6$alkyl, —C$_1$-C$_6$haloalkyl, —COR$^{11}$, —COOR$^{11}$, —CON(R$^{11}$)$_2$, —C≡N, —OR$^{11}$, —OCON(R$^{11}$)$_2$, NR$^{11}$COR$^{11}$, —NR$^{11}$SO$_2$R$^{11}$, —N(R$^{11}$)$_2$, —NR$^{11}$COOR$^{11}$, —SOR$^{11}$, —SO$_2$R$^{11}$, —SO$_2$NR$^{11}$COR$^{11}$, —SO$_2$N(R$^{11}$)$_2$, or —SR$^{11}$,
  L$^2$ is a bond;
  q is 1, 2, or 3; and
  q' is 0, 1, 2, or 3;

each R$^{10}$ is independently —R$^{11}$, —C(=O)R$^{11}$, —CO$_2$R$^{11}$, or —SO$_2$R$^{11}$;

each R$^{11}$ is independently -hydrogen, —C$_1$-C$_6$ alkyl, C$_2$-C$_6$ alkenyl, C$_2$-C$_6$ alkynyl, (C$_3$-C$_8$ cycloalkyl)-C$_1$-C$_6$ alkyl-, (C$_3$-C$_8$ cycloalkenyl)-C$_1$-C$_6$ alkyl-, or (C$_3$-C$_8$ cycloalkyl)-C$_2$-C$_6$ alkenyl-; C$_1$-C$_6$ alkyl, C$_2$-C$_6$ alkenyl, C$_2$-C$_6$ alkynyl, (C$_3$-C$_8$ cycloalkyl)-C$_1$-C$_6$ alkyl-, (C$_3$-C$_8$ cycloalkenyl)-C$_1$-C$_6$ alkyl-, (C$_3$-C$_8$ cycloalkyl)-C$_2$-C$_6$ alkenyl-, —C$_3$-C$_8$ cycloalkyl, —C$_1$-C$_6$ haloalkyl, —N(R$^{12}$)$_2$, aryl, —(C$_1$-C$_6$) alkyl-aryl, —(C$_1$-C$_6$)alkyl-heteroaryl, heterocyclyl, or —(C$_1$-C$_6$)alkyl-heterocyclyl,
  wherein any of R$^{11}$ is optionally substituted with one or more radicals of R$^{12}$;
  each R$^{12}$ is independently halogen, C$_0$-C$_6$alkylN(R$^{13}$)$_2$, C$_1$-C$_6$haloalkyl, C$_1$-C$_6$ alkyl, C$_1$-C$_6$ alkoxy, (C$_0$-C$_6$ alkyl)C═O(OR$^{13}$); C$_0$-C$_6$ alkylOR$^{13}$, C$_0$-C$_6$ alkyl-
COR$^{13}$, C$_0$-C$_6$ alkylSO$_2$R$^{13}$, C$_0$-C$_6$ alkylCON(R$^{13}$)$_2$,
C$_0$-C$_6$ alkylCONR$^{13}$R$^{13}$, C$_0$-C$_6$ alkylSO$_2$N(R$^{13}$)$_2$,
C$_0$-C$_6$ alkylSR$^{13}$, C$_0$-C$_6$ haloalkylOR$^{13}$, aryloxy,
aralkyloxy, aryloxyalkyl, C$_{0-6}$alkoxyaryl, arylC$_{0-6}$
alkylcarboxy, C$_0$-C$_6$ alkyl, —NR$^{13}$SO$_2$R$^{13}$, or
—OC$_{0-6}$alkylCOOR$^{13}$;

each R$^{13}$ is independently hydrogen, C$_1$-C$_6$ alkyl, C$_2$-C$_6$ alkenyl, C$_2$-C$_6$ alkynyl, (C$_3$-C$_8$ cycloalkyl)-C$_1$-C$_6$ alkyl-, (C$_3$-C$_8$ cycloalkenyl)-C$_1$-C$_6$ alkyl-, or (C$_3$-C$_8$ cycloalkyl)-C$_2$-C$_6$ alkenyl-; and each R$^{14}$ is independently C$_1$-C$_6$ alkyl, C$_1$-C$_6$ alkoxy, halogen, C$_1$-C$_6$ haloalkyl, C$_0$-C$_6$ alkylCON(R$^{11}$)$_2$, C$_0$-C$_6$alkylCONR$^{11}$OR$^{11}$, C$_0$-C$_6$ alkylOR$^{11}$, or C$_0$-C$_6$ alkylCOOR$^{11}$.

In one embodiment, the invention provides the compound according to formula IIa, IIb, IIc, or IId, wherein:

R$^1$ is -L$^1$-R$^5$, wherein
  L$^1$ is a bond, —C$_3$-C$_8$ cycloalkyl- or L$^5$, wherein
    each L$^5$ is independently —[C(R$^{15}$)$_2$]$_m$—, wherein
      m is 0, 1, 2, or 3; and
    each R$^{15}$ is independently hydrogen, halogen, (C$_1$-C$_6$) alkyl, or (C$_1$-C$_6$)haloalkyl; and
  R$^5$ is aryl, heterocyclyl, heteroaryl, —C, or —B—C, wherein
    B is —[C(R$^{15}$)$_2$]$_m$ or —C$_3$-C$_6$cycloalkyl-; and
    C is —C$_1$-C$_6$alkyl or —C$_1$-C$_6$haloalkyl;
  wherein R$^5$ is optionally substituted with one or more R$^{5a}$, wherein
    each R$^{5a}$ is independently halogen, nitro, heteroaryl, heterocyclyl, C$_2$-C$_6$ alkenyl, C$_2$-C$_6$ alkynyl, (C$_3$-C$_8$ cycloalkyl)-C$_1$-C$_6$ alkyl-, (C$_3$-C$_8$ cycloalkenyl)-C$_1$-C$_6$ alkyl-, (C$_3$-C$_8$ cycloalkyl)-C$_2$-C$_6$ alkenyl-, aryl, arylalkyl, aryloxy, aryloxyaryl, arylC$_{1-6}$alkoxy, C$_1$-C$_6$ alkyl, C$_1$-C$_6$ haloalkyl, C$_3$-C$_6$cycloalkyl, SO$_2$R$^{11}$, OR$^{11}$, SR$^{11}$, N$_3$, SO$_2$R$^{11}$, COR$^{11}$, SO$_2$N(R$^{11}$)$_2$, SO$_2$NR$^{11}$COR$^{11}$, C≡N, C(O)OR$^{11}$, CON(R$^{11}$)$_2$, CON(R$^{11}$)OR$^{11}$, OCON(R$^{11}$)$_2$, NR$^{11}$COR$^{11}$, NR$^{11}$CON(R$^{11}$)$_2$, NR$^{11}$COOR$^{11}$, or N(R$^{11}$)$_2$, wherein
      each R$^{5a}$ is optionally substituted with one or more groups which independently are -halogen, —C$_1$-C$_6$ alkyl, aryloxy, C$_{0-6}$ alkylSO$_2$R$^{11}$, C$_{0-6}$ alkylCOOR$^{11}$, C$_{0-6}$ alkoxyaryl, —C$_1$-C$_6$ haloalkyl, —SO$_2$R$^{11}$, —OR$^{11}$, —SR$^{11}$, —N$_3$, —SO$_2$R$^{11}$, —COR$^{11}$, ⁻SO$_2$N(R$^{11}$)$_2$, —SO$_2$NR$^{11}$COR$^{11}$, —C≡N, —C(O)OR$^{11}$, —CON(R$^{11}$)$_2$, —CON(R$^{11}$)OR$^{11}$, —OCON(R$^{11}$)$_2$, —NR$^{11}$COR$^{11}$, —NR$^{11}$CON(R$^{11}$)$_2$, —NR$^{11}$COOR$^{11}$, or —N(R$^{11}$)$_2$;

R$^2$ is -L$^3$-R$^7$, wherein L$^3$ is a bond; and
  R$^7$ is —Z or —Y—Z, wherein
    Y is —[C(R$^{15}$)$_2$]$_m$— or —C$_3$-C$_6$cycloalkyl; and
    Z is —H, halogen, —OR$^{11}$, —C(═O)R$^{11}$, —C(═O)OR$^{11}$, —C(═O)N(R$^{11}$)$_2$, —N(R$^{11}$)$_2$, —C(═N—OH)R$^{11}$, —C(═S)N(R$^{11}$)$_2$, —CN, —S(═O)N(R$^{11}$)$_2$, —OC(═O)R$^{11}$, or —OC(═O)—N(R$^{11}$)$_2$;

R$^{21}$ and R$^3$ are each independently hydrogen, halogen, C$_1$-C$_6$ alkyl, or C$_1$-C$_6$ haloalkyl; and G is a group of the formula,

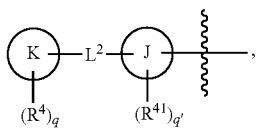

wherein
  J is aryl or heteroaryl;
  K is aryl or heteroaryl;
  each R$^4$ and R$^{41}$ is independently halogen, heteroaryl, heterocyclyl, -G$^1$, -E-G$^{13}$, or -D-E-G$^1$,
  wherein
    D is —O—;
    E is —[C(R$^{15}$)$_2$]$_m$ or —C$_3$-C$_6$cycloalkyl; and
    G$^1$ is —C$_1$-C$_6$alkyl, —C$_1$-C$_6$haloalkyl, —COR$^{11}$, —COOR$^{11}$, —CON(R$^{11}$)$_2$, —C≡N, —OR$^{11}$, —SOR$^{11}$, —SO$_2$R$^{11}$, —SO$_2$N(R$^{11}$)$_2$, or —SR$^{11}$;
  L$^2$ is a bond;
  q is 1, 2, or 3; and
  q' is 0, 1, 2 or 3;

each R$^{10}$ is independently -R$^{11}$, —C(═O)R$^{11}$, —CO$_2$R$^{11}$, or —SO$_2$R$^{11}$;

each R$^{11}$ is independently -hydrogen, —C$_1$-C$_6$ alkyl, C$_2$-C$_6$ alkenyl, C$_2$-C$_6$ alkynyl, (C$_3$-C$_8$ cycloalkyl)-C$_1$-C$_6$ alkyl-, (C$_3$-C$_8$ cycloalkenyl)-C$_1$-C$_6$ alkyl-, (C$_3$-C$_8$ cycloalkyl)-C$_2$-C$_6$ alkenyl-, —C$_3$-C$_8$ cycloalkyl, —(C$_1$-C$_6$)alkyl-(C$_3$-C$_8$)cycloalkyl, —C$_1$-C$_6$ haloalkyl, —N(R$^{12}$)$_2$, aryl, —(C$_1$-C$_6$)alkyl-aryl, heteroaryl, —(C$_1$-C$_6$)alkyl-heteroaryl, heterocyclyl, or —(C$_1$-C$_6$)alkyl-heterocyclyl,
  wherein any of R$^{11}$ is optionally substituted with one or more radicals of R$^{12}$;
  each R$^{12}$ is independently halogen, OR$^{13}$, N(R$^{13}$)$_2$, C$_1$-C$_6$haloalkyl, C$_1$-C$_6$ alkyl, C$_1$-C$_6$ alkoxy, (C$_0$-C$_6$ alkyl)C═O(OR$^{13}$); C$_0$-C$_6$ alkylOR$^{13}$, C$_0$-C$_6$ alkyl-COR$^{13}$, C$_0$-C$_6$ alkylSO$_2$R$^{13}$, C$_0$-C$_6$ alkylCON(R$^{13}$)$_2$, C$_0$-C$_6$ alkyl CONR$^{13}$OR$^{13}$, C$_0$-C$_6$ alkylSO$_2$N(R$^{13}$)$_2$, C$_0$-C$_6$ alkylSR$^{13}$, C$_0$-C$_6$ haloalkylOR$^{13}$, aryloxy, aralkyloxy, aryloxyalkyl, C$_{0-6}$alkoxyaryl, arylC$_{0-6}$ alkylcarboxy, C$_0$-C$_6$ alkyl, —NR$^{13}$SO$_2$R$^{13}$, or —OC$_{0-6}$ alkylCOOR$^{13}$;

each R$^{13}$ is independently hydrogen C$_1$-C$_6$ alkyl, C$_2$-C$_6$ alkenyl, C$_2$-C$_6$ alkynyl, (C$_3$-C$_8$ cycloalkyl)-C$_1$-C$_6$ alkyl-, (C$_3$-C$_8$ cycloalkenyl)-C$_1$-C$_6$ alkyl-, or (C$_3$-C$_8$ cycloalkyl)-C$_2$-C$_6$ alkenyl-;

each R$^{14}$ is independently C$_1$-C$_6$ alkyl, C$_1$-C$_6$ alkoxy, halogen, C$_1$-C$_6$ haloalkyl, C$_0$-C$_6$ alkylCON(R$^{11}$)$_2$, C$_0$-C$_6$ alkylCONR$^{11}$OR$^{11}$, C$_0$-C$_6$ alkylOR$^{11}$, or C$_0$-C$_6$ alkyl-COOR$^{11}$.

In one embodiment, the invention provides the compound according to formula IIa or IIb, wherein:

R$^1$ is -L$^1$-R$^5$, wherein
  L$^1$ is a bond, L$^5$, L$^6$, -L$^5$-L$^6$-L$^5$-, or -L$^6$-L$^5$-L$^6$-, wherein
    each L$^5$ is independently —[C(R$^{15}$)$_2$]$_m$, wherein
      m is 0, 1, 2, 3, or 4; and
    each R$^{15}$ is independently hydrogen, halogen, (C$_1$-C$_6$) alkyl, or (C$_1$-C$_6$)haloalkyl; and
    L$^6$ is —CO—, —SO$_2$—, —O—, —CON(R$^{11}$)—, —C$_3$-C$_6$cycloalkyl-, or -heterocyclyl-,
      wherein the cycloalkyl, or heterocyclyl is optionally substituted with one or more R$^{14}$; and
  R$^5$ is aryl, heterocyclyl, heteroaryl, —C, or —B—C, wherein
    B is —[C(R$^{15}$)$_2$]$_m$— or —C$_3$-C$_6$cycloalkyl-; and
    C is halogen, —C$_1$-C$_6$alkyl, or —C$_1$-C$_6$haloalkyl;
  wherein R$^5$ is optionally substituted with one or more R$^{5a}$, wherein
    each R$^{5a}$ is independently halogen, nitro, heteroaryl, heterocyclyl, C$_2$-C$_6$ alkenyl, C$_2$-C$_6$ alkynyl, (C$_3$-C$_8$ cycloalkyl)-C$_1$-C$_6$ alkyl-, (C$_3$-C$_8$ cycloalkenyl)-C$_1$-C$_6$ alkyl-, (C$_3$-C$_8$ cycloalkyl)-C$_2$-C$_6$ alkenyl-, aryl, arylalkyl, aryloxy, aryloxyaryl, arylC$_1$-C$_6$ alkoxy, C$_1$-C$_6$ alkyl, C$_1$-C$_6$ haloalkyl, C$_3$-C$_6$cycloalkyl, SO$_2$R$^{11}$, OR$^{11}$, SR$^{11}$, N$_3$, SO$_2$R$^{11}$, COR$^{11}$, SO$_2$NR$^{11}$)$_2$, $SO_2NR^{11}COR^{11}$, $C\equiv N$, $C(O)OR^{11}$, $CON(R^{11})_2$, $CON(R^{11})OR^{11}$, $OCON(R^{11})_2$, $NR^{11}COR^{11}$, $NR^{11}CON(R^{11})_2$, $NR^{11}COOR^{11}$, or $N(R^{11})_2$, wherein each $R^{5a}$ is optionally substituted with one or more groups which independently are -halogen, $-C_1-C_6$ alkyl, aryloxy CO—6 alkyl$SO_2R^{11}$, $C_{0-6}$ alkyl-$COOR^{11}$, Cab alkoxyaryl, $-C_1-C_6$ haloalkyl, $-SO_2R^{11}$, $-OR^{11}$, $-SR^{11}$, $-N_3$, $-SO_2R^{11}$, $-COR^{11}$, $^-SO_2N(R^{11})_2$, $-SO_2NR^{11}COR^{11}$, $-C\equiv N$, $-C(O)OR^{11}$, $-CON(R^{11})_2$, $-CON(R^{11})OR^{11}$, $-OCON(R^{11})_2$, $-NR^{11}COR^{11}$, $-NR^{11}CON(R^{11})_2$, $-NR^{11}COOR^{11}$, or $-N(R^{11})_2$;

$R^2$ is $-L^3-R^7$, wherein $L^3$ is a bond; and $R^7$ is halogen, aryl, heteroaryl, heterocyclyl, -Z, or —Y—Z, wherein Y is $-[C(R^{15})_2]_m-$ or $-C_3-C_6$cycloalkyl; and Z is —H, halogen, $-OR^{11}$, $-C(=O)R^{11}$, $-C(=O)OR^{11}$, $-C(=O)N(R^{11})_2$, $-N(R^{11})_2$, $-C(=N-OH)R^{11}$, $-C(=S)N(R^{11})_2$, $-CN$, $-S(=O)_2N(R^{11})_2$, $-C(=O)N(R^{11})N(R^{11})_2$, or $-C(=O)N(R^{11})(OR^{11})$;

wherein $R^7$ is optionally substituted with one or more $R^{7a}$, wherein $R^{7a}$ is halogen, —Z', or —X'—Y'—Z', wherein X' is —O—;

Y' is $-[C(R^{15})_2]_m-$ or $-C_3-C_6$cycloalkyl; and

Z' is —H, halogen, $-OR^{11}$, $-S(=O)_2R^{11}$, $-C(=O)R^{11}$, $-C(=O)OR^{11}$, $-C(=O)N(R^{11})_2$, $-N(R^{11})_2$, $-N(R^{11})C(=O)R^{11}$, $-CN$, $-S(=O)_2N(R^{11})_2$, $-C(=O)N(R^{11})(OR^{11})$, or $-N(R^{11})S(O=)_2R^{11}$;

$R^{21}$ is hydrogen, halogen, $C_1-C_6$alkyl, or $C_1-C_6$haloalkyl; and

G is a group of the formula,

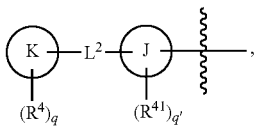

wherein

J is aryl or heteroaryl;

K is aryl or heteroaryl;

each $R^4$ and $R^{41}$ is independently halogen, aryloxy, aralkyloxy, aryloxyalkyl, aryl$C_0-C_6$ alkylcarboxy, aryl, heteroaryl, heterocyclyl, heteroaryloxy, heterocyclyloxy, $-G^1$, $-E-G^1$, or $-D-E-G^1$, wherein D is —O—;

E is $-[C(R^{15})_2]_m-$ or $-C_3-C_6$cycloalkyl; and $G^1$ is $-C_1-C_6$alkyl, $-C_1-C_6$haloalkyl, $-COR^{11}$, $-COOR^{11}$, $-CON(R^{11})_2$, $-C\equiv N$, $-OR^{11}$, $-OCON(R^{11})_2$, $-NR^{11}COR^{11}$, $-NR^{11}SO_2R^{11}$, $-N(R^{11})_2$, $-NR^{11}COOR^{11}$, $-SOR^{11}$, $-SO_2R^{11}$, $-SO_2NR^{11}COR^{11}$, $-SO_2N(R^{11})_2$, or $-SR^{11}$, $L^2$ is a bond;

q is 1, 2, or 3; and q' is 0, 1, 2, or 3;

each $R^{10}$ is independently $-R^{11}$, $-C(=O)R^{11}$, $-CO_2R^{11}$, or $-SO_2R^{11}$;

each $R^{11}$ is independently -hydrogen, $-C_1-C_6$ alkyl, $C_2-C_6$ alkenyl, $C_2-C_6$ alkynyl, $(C_3-C_8$ cycloalkyl$)-C_1-C_6$ alkyl-, $(C_3-C_8$ cycloalkenyl$)-C_1-C_6$alkyl-, $(C_3-C_8$ cycloalkyl$)-C_2-C_6$ alkenyl-, $-C_3-C_8$ cycloalkyl, $-C_1-C_6$ haloalkyl, $-N(R^{12})_2$, aryl, $-(C_1-C_6)$alkyl-aryl, heteroaryl, $-(C_1-C_6)$alkyl-heteroaryl, heterocyclyl, or $-(C_1-C_6)$alkyl-heterocyclyl, wherein any of $R^{11}$ is optionally substituted with one or more radicals of $R^{12}$;

each $R^{12}$ is independently halogen, $C_0-C_6$alkyl $N(R^{13})_2$, $C_1-C_6$haloalkyl, $C_1-C_6$ alkyl, $C_1-C_6$ alkoxy, $(C_0-C_6$ alkyl$)C=O(OR^{13})$; $C_0-C_6$ alkyl$OR^{13}$, $C_0-C_6$ alkyl-$COR^{13}$, $C_0-C_6$ alkyl$SO_2R^{13}$, $C_0-C_6$ alkyl$CON(R^{13})_2$, $C_0-C_6$alkyl $CONR^{13}OR^{13}$, $C_0-C_6$ alkyl $SO_2N(R^{13})_2$, $C_0-C_6$ alkyl$SR^{13}$, $C_0-C_6$ haloalkyl$OR^{13}$, aryloxy, aralkyloxy, aryloxyalkyl, $C_{0-6}$alkoxyaryl, aryl $C_{0-6}$ alkylcarboxy, $C_0-C_6$ alkyl, $-NR^{13}SO_2R^{13}$, or $-OC_{0-6}$alkyl$COOR^{13}$;

each $R^{13}$ is independently hydrogen $C_1-C_6$ alkyl, $C_2-C_6$ alkenyl, $C_2-C_6$alkynyl, $(C_3-C_8$ cycloalkyl$)-C_1-C_6$ alkyl-, $(C_3-C_8$ cycloalkenyl$)-C_1-C_6$ alkyl-, or $(C_3-C_8$ cycloalkyl$)-C_2-C_6$ alkenyl-; and each $R^{14}$ is independently $C_1-C_6$ alkyl, $C_1-C_6$ alkoxy, halogen, $C_1-C_6$ haloalkyl, $C_0-C_6$ alkyl$CON(R^{11})_2$, $C_0-C_6$alkyl$CONR^{11}OR^{11}$, $C_0-C_6$ alkyl$OR^{11}$, or $C_0-C_6$alkyl$COOR^{11}$.

In one embodiment, the invention provides the compound according to formula IIa or IIb, wherein:

$R^1$ is $-L^1-R^5$, wherein $L^1$ is a bond, $-C_3-C_8$ cycloalkyl-, or $L^5$, wherein each $L^5$ is independently $-[C(R^{15})_2]_m-$, wherein m is 0, 1, 2, or 3; and each $R^{15}$ is independently hydrogen, halogen, $(C_1-C_6)$ alkyl, or $(C_1-C_6)$haloalkyl; and $R^5$ is aryl, heterocyclyl, heteroaryl, —C, or —B—C, wherein B is $-[C(R^{15})_2]_m-$ or $-C_3-C_6$cycloalkyl-; and C is $-C_1-C_6$alkyl or $-C_1-C_6$haloalkyl;

wherein $R^5$ is optionally substituted with one or more $R^{5a}$, wherein each $R^{5a}$ is independently halogen, nitro, heteroaryl, heterocyclyl, $C_2-C_6$ alkenyl, $C_2-C_6$ alkynyl, $(C_3-C_8$ cycloalkyl$)-C_1-C_6$ alkyl-, $(C_3-C_8$ cycloalkenyl$)-C_1-C_6$ alkyl-, $(C_3-C_8$ cycloalkyl$)-C_2-C_6$ alkenyl, aryl, aralkyl, aryloxy, aryloxyaryl, aryl $C_{1-6}$alkoxy, $C_1-C_6$ alkyl, $C_1-C_6$ haloalkyl, $C_3-C_6$cycloalkyl, $SO_2R^{11}$, $OR^{11}$, $SR^{11}$, $N_3$, $SO_2R^{11}$, $COR^{11}$, $SO_2N(R^{11})_2$, $SO_2NR^{11}COR^{11}$, $C\equiv N$, $C(O)OR^{11}$, $CON(R^{11})_2$, $CON(R^{11})OR^{11}$, $OCON(R^{11})_2$, $NR^{11}COR^{11}$, $NR^{11}CON(R^{11})_2$, $NR^{11}COOR^{11}$, or $N(R^{11})_2$, wherein each $R^{5a}$ is optionally substituted with one or more groups which independently are -halogen, $-C_1-C_6$ alkyl, aryloxy, $C_{0-6}$ alkyl$SO_2R^{11}$, $C_{0-6}$ alkyl$COOR^{11}$, $C_{0-6}$ alkoxyaryl, $-C_1-C_6$ haloalkyl, $-SO_2R^{11}$, $-OR^{11}$, $-SR^{11}$, $-N_3$, $-SO_2R^{11}$, $-COR^{11}$, $^-SO_2N(R^{11})_2$, $-SO_2NR^{11}COR^{11}$, $-C\equiv N$, $-C(O)OR^{11}$, $-CON(R^{11})_2$, $-CON(R^{11})OR^{11}$, $-OCON(R^{11})_2$, $-NR^{11}COR^{11}NR^{11}CON(R^{11})_2$, $-NR^{11}COOR^{11}$, or $N(R^{11})_2$;

$R^2$ is $-L^3-R^7$, wherein $L^3$ is a bond; and $R^7$ is —Z or —Y—Z, wherein

Y is $-[C(R^{15})_2]_m-$ or $-C_3-C_6$cycloalkyl; and

Z is —H, halogen, $-OR^{11}$, $-C(=O)R^{11}$, $-C(=O)OR^{11}$, $-C(=O)N(R^{11})_2$, $-N(R^{11})_2$, $-C(=N-OH)R^{11}$, $-C(=S)N(R^{11})_2$, $-CN$, $-S(=O)_2N(R^{11})_2$, $-OC(=O)-R^{11}$, or $-OC(=O)-N(R^{11})_2$;

$R^{21}$ is hydrogen, halogen, $C_1$-$C_6$ alkyl, or $C_1$-$C_6$ haloalkyl; and

G is a group of the formula,

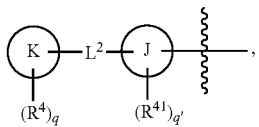

wherein
J is aryl or heteroaryl;
K is aryl or heteroaryl;
each $R^4$ and $R^{41}$ is independently halogen, heteroaryl, heterocyclyl, -$G^1$, -E-$G^1$, or -D-E-$G^1$, wherein
D is —O—;
E is —[C($R^{15}$)$_2$]$_m$— or —$C_3$-$C_6$cycloalkyl; and
$G^1$ is —$C_1$-$C_6$alkyl, —$C_1$-$C_6$haloalkyl, —COR$^{11}$, COOR$^{11}$, —CON(R$^{11}$)$_2$, —C≡N, —OR$^{11}$, —SOR$^{11}$, —SO$_2$R$^{11}$, —SO$_2$N(R$^{11}$)$_2$, or —SR$^{11}$;
$L^2$ is a bond;
q is 1, 2, or 3; and
q' is 0, 1, 2 or 3;
each $R^{10}$ is independently $R^{11}$, —C(=O)R$^{11}$, —CO$_2$R$^{11}$, or —SO$_2$R$^{11}$;
each $R^{11}$ is independently -hydrogen, —$C_1$-$C_6$ alkyl, $C_2$-$C_6$ alkenyl, $C_2$-$C_6$ alkynyl, ($C_3$-$C_8$ cycloalkyl)-$C_1$-$C_6$ alkyl-, ($C_3$-$C_8$ cycloalkenyl)-$C_1$-$C_6$ alkyl-, ($C_3$-$C_8$ cycloalkyl)-$C_2$-$C_6$ alkenyl-$C_3$-$C_8$ cycloalkyl, —$C_1$-$C_6$ haloalkyl, —N(R$^{12}$)$_2$, aryl, —(C$_1$-C$_6$)alkyl-aryl, heteroaryl, —(C$_1$-C$_6$)alkyl-heteroaryl, heterocyclyl, or —(C$_1$-C$_6$)alkyl-heterocyclyl,
wherein any of $R^{11}$ is optionally substituted with one or more radicals of $R^{12}$;
each $R^{12}$ is independently halogen, OR$^{13}$, N(R$^{13}$)$_2$, $C_1$-$C_6$haloalkyl, $C_1$-$C_6$ alkyl, $C_1$-$C_6$ alkoxy, (C$_0$-C$_6$ alkyl)C=O(OR$^{13}$); C$_0$-C$_6$ alkylOR$^{13}$, C$_0$-C$_6$ alkyl-COR$^{13}$, C$_0$-C$_6$ alkylSO$_2$R$^{13}$, C$_0$-C$_6$ alkylCON(R$^{13}$)$_2$, C$_0$-C$_6$ alkylCONR$^{13}$OR$^{13}$, C$_0$-C$_6$ alkylSO$_2$N(R$^{13}$)$_2$, C$_0$-C$_6$ alkylSR$^{13}$, C$_0$-C$_6$ haloalkylOR$^{13}$, aryloxy, aralkyloxy, aryloxyalkyl, C$_{0-6}$alkoxyaryl, arylC$_{0-6}$alkylcarboxy, C$_0$-C$_6$ alkyl, —NR$^{13}$SO$_2$R$^{13}$, or —OC$_{0-6}$alkylCOOR$^{13}$;
each $R^{13}$ is independently hydrogen, $C_1$-$C_6$ alkyl, $C_2$-$C_6$ alkenyl, $C_2$-$C_6$ alkynyl, ($C_3$-$C_8$ cycloalkyl)-$C_1$-$C_6$ alkyl-, ($C_3$-$C_8$ cycloalkenyl)-$C_1$-$C_6$ alkyl-, or ($C_3$-$C_8$ cycloalkyl)-$C_2$-$C_6$ alkenyl-;
each $R^{14}$ is independently $C_1$-$C_6$ alkyl, $C_1$-$C_6$ alkoxy, halogen, $C_1$-$C_6$ haloalkyl, C$_0$-C$_6$ alkylCON(R$^{11}$)$_2$, C$_0$-C$_6$ alkylCONR$^{11}$OR$^{11}$, C$_0$-C$_6$ alkylOR$^{11}$, or C$_0$-C$_6$ alkyl-COOR$^{11}$.

In one embodiment, the invention provides the compound according to formula IIa, IIb, IIc, and IId, wherein $R^1$ is $L^1$-$R^5$, wherein $L^1$ is a bond, and $R^2$, $R^{21}$, $R^3$, $R^5$, K and G are as defined for formulas IIa-d; such compounds are hereafter designated formulas IIa-d.

In another embodiment, the invention provides the compound according to formulas IIa-d,
wherein $R^1$ is $L^1$-$R^5$,
wherein $L^1$ is a bond; and $R^5$ is aryl optionally substituted with one or more $R^{5a}$, and $R^2$, $R^{21}$, $R^3$, and G are as defined for formulas IIa-d; such compounds are hereafter designated formulas IVa-d.

In another embodiment, the invention provides the compound of formula N,

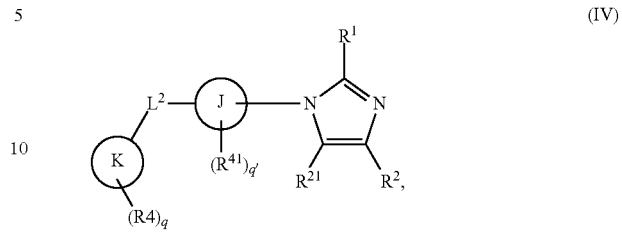

or a pharmaceutically acceptable salt, isomer, or prodrug thereof, wherein $R^1$ is as defined for formula IVa-d, and $R^2$, $R^{21}$, $R^4$, $R^{41}$, J, K, $L^2$, q, and q' a are as defined for formula IIa-d.

In another embodiment, the invention provides the compound according of the formula N, wherein $L^2$ is a bond.

In another embodiment, the invention provides the compound according of the formula N, wherein K is phenyl.

In another embodiment, the invention provides the compound according of the formula N, wherein $L^2$ is a bond and K is phenyl.

In another embodiment, the invention provides the compound according of the formula N, wherein $L^2$ is a bond and J is phenyl.

In another embodiment, the invention provides the compound according of the formula N, wherein J is phenyl.

In another embodiment, the invention provides the compound according of the formula N, wherein J is phenyl, and K is phenyl.

In another embodiment, the invention provides the compound according of the formula N, wherein J is phenyl, K is phenyl, and $L^2$ is a bond.

In another embodiment, the invention provides the compound of formula V,

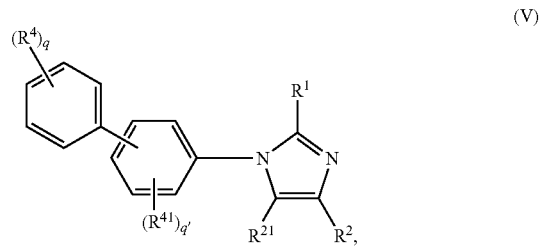

or a pharmaceutically acceptable salt, isomer, or prodrug thereof, wherein $R^1$ is as defined for formula IVa-d, and $R^2$, $R^{21}$, $R^4$, $R^{41}$, q, and q' are as defined for formula IIa-d.

In another embodiment, the invention provides the compound of formula VII,

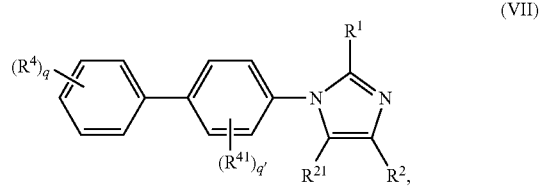

or a pharmaceutically acceptable salt, isomer, or prodrug thereof, wherein $R^{21}$ is H, -halogen, —$C_1$-$C_6$alkyl, or $C_1$-$C_6$haloalkyl; $R^1$ is as defined for formula IVa-d; and $R^2$, $R^4$, $R^{41}$, q, and q' are as defined for formula IIa-d.

In another embodiment, the invention provides the compound according of the formula VII, wherein each $R^{41}$ is independently halogen, -$G^{1\prime}$-E-$G^{1\prime}$ or D-E-$G^1$, wherein
D is —O—;
E is —[C($R^{15}$)$_2$]$_m$—;
$G^1$ is —$C_1$-$C_6$alkyl, —$C_1$-$C_6$haloalkyl, halogen, —COR$^{11}$, —COOR$^{11}$, —CON($R^{11}$)$_2$, —C≡N, —OR$^{11}$, —NR$^{11}$COR$^{11}$, —NR$^{11}$SO$_2$R$^{11}$, —SO$_2$R$^{11}$, or —SO$_2$N($R^{11}$)$_2$.

In another embodiment, the invention provides the compound according of the formula VII, wherein each $R^{41}$ is independently halogen, -$G^{1\prime}$ or -E-$G^1$, wherein
E is —[C($R^{15}$)$_2$]$_m$,
wherein each $R^{15}$ is independently hydrogen or halogen; and
$G^1$ is —$C_1$-$C_6$alkyl, —$C_1$-$C_6$haloalkyl, or halogen,
such compounds are hereafter designated formula VIIa.

In another embodiment, the invention provides the compound according of the formula VII, wherein each $R^4$ is independently halogen, aryl, heteroaryl, heterocyclyl, -$G^1$, or -E-$G^1$, wherein
E is —[C($R^{15}$)$_2$]$_m$—; and
$G^1$ is —$C_1$-$C_6$alkyl, —$C_1$-$C_6$haloalkyl, halogen, —COR$^{11}$, —COOR$^{11}$, —CON($R^{11}$)$_2$, —C≡N, —OR$^{11}$, —N($R^{11}$)$_2$, —SO$_2$R$^{11}$, —SO$_2$N($R^{11}$)$_2$, or —SR$^{11}$.

In another embodiment, the invention provides the compound according of the formula VII, wherein each $R^4$ is independently halogen, aryl, heteroaryl, heterocyclyl, G" or -E-$G^1$, wherein
E is —[C($R^{15}$)$_2$]$_m$—, wherein
each $R^{15}$ is independently hydrogen or halogen; and
$G^1$ is —$C_1$-$C_6$alkyl, —$C_1$-$C_6$haloalkyl, halogen, —OR$^{11}$, or —SO$_2$R$^{11}$,
such compounds are hereafter designated formula VIM.

In another embodiment, the invention provides the compound according of the formula VII, wherein $R^2$ is -$L^3$-$R^7$, wherein $L^3$ is a bond; and
$R^7$ is hydrogen, halogen, nitro, aryl, heteroaryl, heterocyclyl, -Z, or —Y—Z, wherein
Y is —[C($R^{15}$)$_2$]$_m$—, —($C_3$-$C_6$)cycloalkyl-, or $C_2$-$C_6$alkenyl;
Z is —H, halogen, —OR$^{11}$, —C(=O)R$^{11}$, —C(=O)OR$^{11}$, —C(=O)N($R^{11}$)$_2$, —N($R^{11}$)$_2$, —C(=N—OH)R$^{11}$, —C(=S)N($R^{11}$)$_2$, —CN, —S(=O)$_2$N($R^{11}$)$_2$, —C(=O)N($R^{11}$)N($R^{11}$)$_2$, —C(=O)N($R^{11}$)(OR$^{11}$), —OC(=O)—R$^{11}$, or —OC(=O)—N($R^{11}$)$_2$.

In another embodiment, the invention provides the compound according of the formula VII, wherein $R^2$ is -$L^3$-$R^7$, wherein $L^3$ is a bond; and
$R^7$ is hydrogen, halogen, -Z, or —Y—Z, wherein
Y is —[C($R^{15}$)$_2$]$_m$—, —($C_3$-$C_6$)cycloalkyl-, or $C_2$-$C_6$alkenyl,
wherein each $R^{15}$ is independently H, halogen, or ($C_1$-$C_6$)alkyl; and
Z is —H, halogen, —OR$^{11}$, —C(=O)R$^{11}$, —C(=O)OR$^{11}$, —C(=O)N($R^{11}$)$_2$, —C(=N—OH)R$^{11}$, or —C(=S)N($R^{11}$)$_2$,
such compounds are hereafter designated formula IIc.

In another embodiment, the invention provides the compound according of the formula VIIIa, wherein each $R^4$ is independently halogen, aryl, heteroaryl, heterocyclyl, -$G^{1\prime}$ or -E-$G^1$, wherein E is —[C($R^{15}$)$_2$]$_m$—, wherein
each $R^{15}$ is independently hydrogen or halogen; and
$G^1$ is —$C_1$-$C_6$alkyl, —$C_1$-$C_6$haloalkyl, halogen, —OR$^{11}$, or —SO$_2$R$^{11}$,
such compounds are hereafter designated formula VIId.

In another embodiment, the invention provides the compound according of the formula VIM, wherein $R^2$ is -$L^3$-$R^7$, wherein $L^3$ is a bond; and
$R^7$ is hydrogen, halogen, -Z, or —Y—Z, wherein
Y is —[C($R^{15}$)$_2$]$_m$—, —($C_3$-$C_6$)cycloalkyl-, or $C_2$-$C_6$alkenyl,
wherein each $R^{15}$ is independently H, halogen, or ($C_1$-$C_6$)alkyl; and
Z is —H, halogen, —OR$^{11}$, —C(=O)R$^{11}$, —C(=O)OR$^{11}$, —C(=O)N($R^{11}$)$_2$, —C(=N—OH)R$^{11}$, or —C(=S)N($R^{11}$)$_2$,
such compounds are hereafter designated formula VIIe.

In another embodiment, the invention provides the compound according of the formula VIIc, wherein each $R^{41}$ is independently halogen, -$G^{1\prime}$ or -E-$G^1$, wherein
E is —[C($R^{15}$)$_2$]$_m$—,
wherein each $R^{15}$ is independently hydrogen or halogen; and
$G^1$ is —$C_1$-$C_6$alkyl, —$C_1$-$C_6$haloalkyl, or halogen,
such compounds are hereafter designated formula VIIf.

In another embodiment, the invention provides the compound according of the formula VIId, wherein $R^2$ is -$L^3$-$R^7$, wherein $L^3$ is a bond; and
$R^7$ is hydrogen, halogen, -Z, or —Y—Z, wherein
Y is —[C($R^{15}$)$_2$]$_m$—, —($C_3$-$C_6$)cycloalkyl-, or $C_2$-$C_6$alkenyl,
wherein each $R^{15}$ is independently H, halogen, or ($C_1$-$C_6$)alkyl; and
Z is —H, halogen, —OR$^{11}$, —C(=O)OR$^{11}$, —C(=O)OR$^{11}$, —C(=O)N($R^{11}$)$_2$, —C(=N—OH)R$^{11}$, or —C(=S)N($R^{11}$)$_2$,
such compounds are hereafter designated formula VIIg.

In another embodiment, the invention provides the compound according of the formula VIIe, wherein each $R^{5a}$ is independently halogen, $C_1$-$C_6$ alkyl, $C_1$-$C_6$ haloalkyl, $C_3$-$C_8$cycloalkyl, —OR$^{11}$, —SO$_2$R$^{11}$, —COR$^{11}$, —SO$_2$N($R^{11}$)$_2$, —C≡N, —C(O)OR$^{11}$, —CON($R^{11}$)$_2$, NR$^{11}$COR$^{11}$, or —N($R^{11}$)$_2$.

In another embodiment, the invention provides the compound according of the formula VIIe, wherein each $R^{5a}$ is independently halogen, $C_1$-$C_6$ alkyl, $C_1$-$C_6$ haloalkyl, $C_3$-$C_8$cycloalkyl, —OR$^{11}$, —SO$_2$R$^{11}$, —COR$^{11}$, —SO$_2$N($R^{11}$)$_2$, —C≡N, —C(O)OR$^{11}$, —CON($R^{11}$)$_2$, —NR$^{11}$COR$^{11}$, or —N($R^{11}$)$_2$; and $R^{21}$ is —H.

In another embodiment, the invention provides the compound according of the formula VIII; wherein each $R^{5a}$ is independently halogen, $C_1$-$C_6$ alkyl, or $C_1$-$C_6$ haloalkyl.

In another embodiment, the invention provides the compound according of the formula Miff, wherein each $R^{5a}$ is independently halogen, $C_1$-$C_6$ alkyl, or $C_1$-$C_6$ haloalkyl; and $R^{21}$ is H.

In another embodiment, the invention provides the compound according of the formula VII, wherein each $R^{5a}$ is independently halogen, $C_1$-$C_6$ alkyl, $C_1$-$C_6$ haloalkyl, $C_3$-$C_8$cycloalkyl, —OR$^{11}$, —SO$_2$R$^{11}$, —COR$^{11}$, —SO$_2$N($R^{11}$)$_2$, —C≡N, —C(O)OR$^{11}$, —CON($R^{11}$)$_2$, —NR$^{11}$COR$^{11}$, or N($R^{11}$)$_2$.

In another embodiment, the invention provides the compound according of the formula VII, wherein each $R^{5a}$ is independently halogen, $C_1$-$C_6$ alkyl, or $C_1$-$C_6$ haloalkyl.

In another embodiment, the invention provides the compound according of the formula VII, wherein each $R^{5a}$ is independently halogen, $C_1$-$C_6$ alkyl, or $C_1$-$C_6$ haloalkyl; and $R^{21}$ is —H.

In another embodiment, the invention provides the compound according of the formula VIIg, wherein each $R^{5a}$ is independently halogen, $C_1$-$C_6$ alkyl, or $C_1$-$C_6$ haloalkyl.

In another embodiment, the invention provides the compound according of the formula VIIg, wherein each $R^{5a}$ is independently halogen, $C_1$-$C_6$ alkyl, or $C_1$-$C_6$ haloalkyl; and $R^{21}$ is —H.

In another embodiment, the invention provides the compound according to formula VII, wherein $R^{21}$ is hydrogen, halogen, nitro, cyano, aryl, heteroaryl, heterocyclyl, —$C_1$-$C_6$ alkyl-heterocyclyl, —$C_1$-$C_6$ alkyl-heteroaryl, —$C_1$-$C_6$ alkyl-aryl, -Z, —Y—Z, or —X—Y—Z, wherein X is —O—;

Y is —[C($R^{15}$)$_2$]$_m$, —$C_2$-$C_6$ alkenyl, or $C_3$-$C_8$ cycloalkyl; and Z is —H, —CN, halogen, —OR$^{11}$, —C(=O)R$^{11}$, —C(=O)OR$^{11}$, —C(=O)N(R$^{11}$)$_2$, —N(R$^{11}$)$_2$, —CN, —N$_3$, —SO$_2$R$^{11}$, —S(=O)$_2$N(R$^{11}$)$_2$, —C(=O)N(R$^{11}$)N(R$^{11}$)$_2$, —C(=O)N(R$^{11}$)(OR$^{11}$), —OC(=O)—R$^{11}$, —OC(=O)—N(R$^{11}$)$_2$, or —N(R$^{11}$)COOR$^{11}$.

In another embodiment, the invention provides the compound according to formula VII, wherein $R^{21}$ is hydrogen, halogen, nitro, cyano, $C_1$-$C_6$alkyl, or $C_1$-$C_6$haloalkyl.

In another embodiment, the invention provides the compound according to any of formulas VIIa-VIIg, wherein $R^{21}$ is hydrogen, halogen, nitro, cyano, $C_1$-$C_6$alkyl, or $C_1$-$C_6$haloalkyl.

In another embodiment, the invention provides the compound of formula VIII,

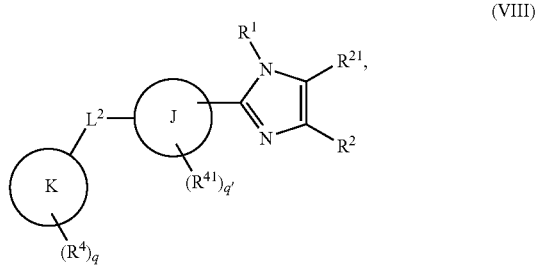

(VIII)

or a pharmaceutically acceptable salt, isomer, or prodrug thereof, wherein $R^1$ is as defined for formula IVa-d, and $R^2$, $R^{21}$, $R^4$, $R^{41}$, J, K, $L^2$, q, and q' a are as defined for formula IIa-d.

In another embodiment, the invention provides the compound according to formula VIII wherein K is phenyl or pyridyl.

In another embodiment, the invention provides the compound according to formula VIII wherein K is phenyl.

In another embodiment, the invention provides the compound according to formula VDT wherein K is pyridyl.

In another embodiment, the invention provides the compound according to formula VIII wherein J is phenyl.

In another embodiment, the invention provides the compound according to formula VIII wherein J is phenyl and K is phenyl.

In another embodiment, the invention provides the compound of formula IX,

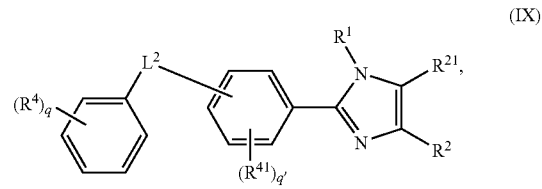

(IX)

or a pharmaceutically acceptable salt, isomer, or prodrug thereof, wherein $R^1$ is as defined for formula IVa-d, and $R^2$, $R^{21}$, $R^4$, $R^{41}$, $L^2$, q, and q' are as defined for formula IIa-d.

In another embodiment, the invention provides the compound of formula X,

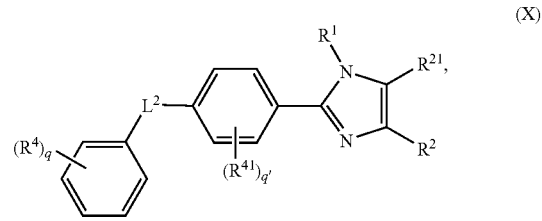

(X)

or a pharmaceutically acceptable salt, isomer, or prodrug thereof, wherein $R^1$ is as defined for formula IVa-d, and $R^2$, $R^{21}$, $R^4$, $R^{41}$, $L^2$, q, and q' are as defined for formula IIa-d.

In another embodiment, the invention provides the compound according to formula X, wherein $L^2$ is a bond; such compounds are designated hereafter as formula XI.

In another embodiment, the invention provides the compound according to formula XI, wherein each $R^{5a}$ is independently halogen, $C_1$-$C_6$ alkyl, $C_1$-$C_6$ haloalkyl, $C_3$-$C_8$cycloalkyl, —OR$^{11}$, —SO$_2$R$^{11}$, —COR$^{11}$, —SO$_2$N(R$^{11}$)$_2$, —C≡N, —C(O)OR$^{11}$, —CON(R$^{11}$)$_2$, —NR$^{11}$COR$^{11}$, or —N(R$^{11}$)$_2$.

In another embodiment, the invention provides the compound according to formula XI, wherein each $R^{5a}$ is independently halogen, $C_1$-$C_6$ alkyl, or $C_1$-$C_6$ haloalkyl, such compounds are designated hereafter as formula XIa.

In another embodiment, the invention provides the compound according to formula XI, wherein $R^2$ is -$L^3$-$R^7$, wherein $L^3$ is a bond; and $R^7$ is hydrogen, halogen, nitro, aryl, heteroaryl, heterocyclyl, -Z, or —Y—Z, wherein Y is —[C($R^{15}$)$_2$]$_m$—, —($C_3$-$C_6$)cycloalkyl-, or $C_2$-$C_6$ alkenyl;

Z is —H, halogen, —OR$^{11}$, —C(=O)R$^{11}$, —C(=O)OR$^{11}$, —C(=O)N(R$^{11}$)$_2$, —N(R$^{11}$)$_2$, —C(=N—OH)R$^{11}$, —C(=S)N(R$^{11}$)$_2$, —CN, —S(=O)$_2$N(R$^{11}$)$_2$, —C(=O)N(R$^{11}$)N(R$^{11}$)$_2$, —C(=O)N(R$^{11}$)(OR$^{11}$), —OC(=O)—R$^{11}$, or —OC(O)—N(R$^{11}$)$_2$.

In another embodiment, the invention provides the compound according to formula XI, wherein $R^2$ is -$L^3$-$R^7$, wherein $L^3$ is a bond; and $R^7$ is hydrogen, halogen, -Z, or —Y—Z, wherein Y is —[C($R^{15}$)$_2$]$_m$—, —($C_3$-$C_6$)cycloalkyl-, or $C_2$-$C_6$ alkenyl;

wherein each $R^5$ is independently H, halogen, or ($C_1$-$C_6$)alkyl; and

Z is —H, halogen, —OR$^{11}$, —C(═O)R$^{11}$, —C(═O)OR$^{11}$, —C(═O)N(R$^{11}$)$_2$, —C(═N—OH)R$^{11}$, or —C(═S)N(R$^{11}$)$_2$, such compounds are designated hereafter as formula XIb.

In another embodiment, the invention provides the compound according to formula XI, wherein each R$^4$ is independently halogen, aryl, heteroaryl, heterocyclyl, -G$^1$ or -E-G$^1$, wherein E is —[C(R$^{15}$)$_2$]$_m$—; and G$^1$ is —C$_1$-C$_6$ alkyl, —C$_2$-C$_6$ haloalkyl, halogen, —COR$^{11}$, —COOR$^{11}$, —CON(R$^{11}$)$_2$, —C≡N, —OR$^{11}$, —N(R$^{11}$)$_2$, —SO$_2$R$^{12}$, —SO$_2$N(R$^{11}$)$_2$, or —SR$^{11}$.

In another embodiment, the invention provides the compound according to formula XI, wherein each R$^4$ is independently halogen, aryl, heteroaryl, heterocyclyl, -G$^{2'}$ or -E-G$^1$, wherein E is —[C(R$^{15}$)$_2$]$_m$—, wherein each R$^{15}$ is independently hydrogen or halogen; and G$^1$ is —C$_1$-C$_6$ alkyl, —C$_1$-C$_6$ haloalkyl, halogen, —OR$^{11}$, or —SO$_2$R$^{11}$.

In another embodiment, the invention provides the compound according to formula XIa, wherein R$^2$ is -L$^3$-R$^7$, wherein L$^3$ is a bond; and R$^7$ is hydrogen, halogen, -Z, or —Y—Z, wherein Y is —[C(R$^{15}$)$_2$]$_m$—, —(C$_3$-C$_6$)cycloalkyl-, or C$_2$-C$_6$ alkenyl;

wherein each R$^{15}$ is independently H, halogen, or (C$_1$-C$_6$)alkyl; and

Z is —H, halogen, —OR$^{11}$, —C(═O)R$^{11}$, —C(═O)OR$^{11}$, —C(═O)N(R$^{11}$)$_2$, —C(═N—OH)R$^{11}$, or —C(═S)N(R$^{11}$)$_2$, such compounds are designated hereafter as formula XId.

In another embodiment, the invention provides the compound according to formula XIb, wherein each R$^4$ is independently halogen, aryl, heteroaryl, heterocyclyl, -G$^1$ or -E-G$^1$, wherein E is —[C(R$^{15}$)$_2$]$_m$—, wherein each R$^{15}$ is independently hydrogen or halogen; and G$^1$ is —C$_1$-C$_6$ alkyl, —C$_1$-C$_6$ haloalkyl, halogen, —OR$^{11}$, or —SO$_2$R$^{11}$.

In another embodiment, the invention provides the compound according to formula XId, wherein each R$^4$ is independently halogen, aryl, heteroaryl, heterocyclyl, -G$^{1'}$ or -E-G$^1$, wherein E is —[C(R$^{15}$)$_2$]$_m$—, wherein each R$^{15}$ is independently hydrogen or halogen; and G$^1$ is —C$_1$-C$_6$ alkyl, —C$_1$-C$_6$ haloalkyl, halogen, —OR$^{11}$, or —SO$_2$R$^{11}$.

In another embodiment, the invention provides the compound according to formula XI, wherein R$^{21}$ is hydrogen, halogen, nitro, cyano, aryl, heteroaryl, heterocyclyl, —C$_1$-C$_6$ alkyl-heterocyclyl, —C$_1$-C$_6$ alkyl-heteroaryl, —C$_1$-C$_6$ alkyl-aryl, -Z, —Y—Z, or —X—Y—Z, wherein X is —O—;

Y is —[C(R$^{15}$)$_2$]$_m$—, —(C$_3$-C$_6$)cycloalkyl-, —C$_2$-C$_6$ alkenyl, or C$_3$-C$_8$ cycloalkyl; and Z is —H, —CN, halogen, —OR$^{11}$, —C(═O)R$^{11}$, —C(═O)OR$^{11}$, —C(═O)N(R$^{11}$)$_2$, —N(R$^{11}$)$_2$, —CN, —N$_3$, —SO$_2$R$^{11}$, —S(═O)$_2$N(R$^{11}$)$_2$, —C(═O)N(R$^{11}$)N(R$^{11}$)$_2$, —C(═O)N(R$^{11}$)(OR$^{11}$), —OC(═O)—R$^{11}$, —OC(═O)—N(R$^{11}$)$_2$, or —N(R$^{11}$)COOR$^{11}$.

In another embodiment, the invention provides the compound according to formula XI, wherein R$^{21}$ is hydrogen, halogen, nitro, cyano, C$_1$-C$_6$ alkyl, or C$_1$-C$_6$ haloalkyl.

In another embodiment, the invention provides the compound according to any of formulas XIa-XId, wherein R$^{21}$ is hydrogen, halogen, nitro, cyano, C$_1$-C$_6$ alkyl, or C$_1$-C$_6$ haloalkyl.

In another embodiment, the invention provides the compound according to formula VIII, wherein J is thienyl.

In another embodiment, the invention provides the compound according to formula VIII, wherein J is thienyl and K is phenyl.

In another embodiment, the invention provides the compound of formula XII,

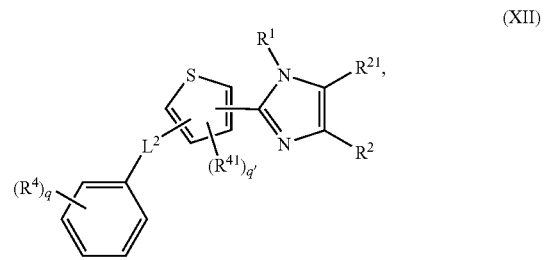

(XII)

or a pharmaceutically acceptable salt, isomer, or prodrug thereof, where R$^1$ is as defined for formula IVa-d, and R$^2$, R$^{21}$, R$^4$, R$^{41}$, L$^2$, q, and q' are as defined for formula IIa-d.

In another embodiment, the invention provides the compound of formula XIII,

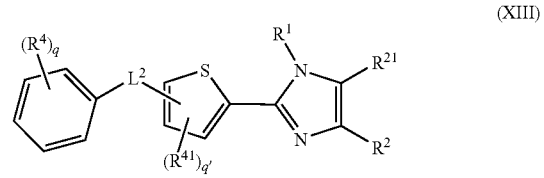

(XIII)

or a pharmaceutically acceptable salt, isomer, or prodrug thereof, where R$^1$ is as defined for formula IVa-d, and R$^2$, R$^{21}$, R$^4$, R$^{41}$, L$^2$, q, and q' are as defined for formula IIa-d.

In another embodiment, the invention provides the compound of formula XIV,

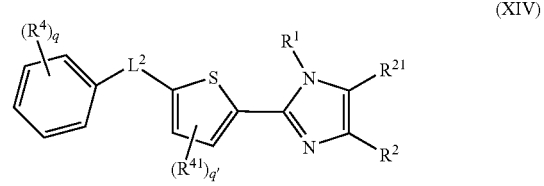

(XIV)

or a pharmaceutically acceptable salt, isomer, or prodrug thereof, where R$^1$ is as defined for formula IVa-d, and R$^2$, R$^{21}$, R$^4$, R$^{41}$, L$^2$, q, and q' are as defined for formula IIa-d.

In another embodiment, the invention provides the compound according to formula XIV, wherein L$^2$ is a bond, such compounds are designated hereafter as formula XV.

In another embodiment, the invention provides the compound according to formula XV, wherein each R$^{5a}$ is independently halogen, C$_1$-C$_6$ alkyl, C$_1$-C$_6$ haloalkyl, C$_3$-C$_8$ cycloalkyl, —OR$^{11}$, —SO$_2$R$^{11}$, —COR$^{11}$, —SO$_2$N(R$^{11}$)$_2$, —C≡N, —C(O)OR$^{11}$, —CON(R$^{11}$)$_2$, NR$^{11}$COR$^{11}$, or —N(R$^{11}$)$_2$.

In another embodiment, the invention provides the compound according to formula XV, wherein each $R^{5a}$ is independently halogen, $C_1$-$C_6$ alkyl, or $C_1$-$C_6$ haloalkyl, such compounds are designated hereafter as formula XVa.

In another embodiment, the invention provides the compound according to formula XV, wherein $R^2$ is -$L^3$-$R^7$, wherein $L^3$ is a bond; and
$R^7$ is hydrogen, halogen, nitro, aryl, heteroaryl, heterocyclyl, -Z, or —Y—Z, wherein
Y is —[C($R^{15}$)$_2$]$_m$—, —($C_3$-$C_6$)cycloalkyl-, or $C_2$-$C_6$ alkenyl;
Z is —H, halogen, —$OR^{11}$, —C(=O)$R^{11}$, —C(=O)$OR^{11}$, —C(=O)N($R^{11}$)$_2$, —N($R^{11}$)$_2$, —C(=N—OH)$R^{11}$, —C(=S)N($R^{11}$)$_2$, —CN, —S(=O)$_2$N($R^{11}$)$_2$, —C(=O)N($R^{11}$)N($R^{11}$)$_2$, —C(=O)N($R^{11}$)(O$R^{11}$), —OC(=O)—$R^{11}$, or —OC(=O)—N($R^{11}$)$_2$.

In another embodiment, the invention provides the compound according to formula XV, wherein $R^2$ is -$L^3$-$R^7$, wherein $L^3$ is a bond; and
$R^7$ is hydrogen, halogen, -Z, or —Y—Z, wherein
Y is —[C($R^{15}$)$_2$]$_m$—, —($C_3$-$C_6$)cycloalkyl-, or $C_2$-$C_6$ alkenyl,
wherein each $R^{5a}$ is independently H, halogen, or ($C_1$-$C_6$)alkyl; and
Z is —H, halogen, —$OR^{11}$, —C(=O)$R^{11}$, —C(=O)$OR^{11}$, —C(=O)N($R^{11}$)$_2$, —C(=N—OH)$R^{11}$, or —C(=S)N($R^{11}$)$_2$,
such compounds are designated hereafter as formula XVb.

In another embodiment, the invention provides the compound according to formula XV, wherein each $R^4$ is independently halogen, aryl, heteroaryl, heterocyclyl, -$G^{1'}$ or -E-$G^1$, wherein
E is —[C($R^5$)$_2$]$_m$—; and
$G^1$ is —$C_1$-$C_6$ alkyl, —$C_1$-$C_6$ haloalkyl, halogen, —$COR^{11}$, —$COOR^{11}$, —CON($R^{11}$)$_2$, —C≡N, —$OR^{11}$, —N($R^{11}$)$_2$, —$SO_2R^{11}$, —$SO_2$N($R^{11}$)$_2$, or —$SR^{11}$.

In another embodiment, the invention provides the compound according to formula XV, wherein each $R^4$ is independently halogen, aryl, heteroaryl, heterocyclyl, -$G^{1'}$ or -E-$G^1$, wherein
E is —[C($R^5$)$_2$]$_m$—, wherein
each $R^{15}$ is independently hydrogen or halogen; and
$G^1$ is —$C_1$-$C_6$ alkyl, —$C_1$-$C_6$ haloalkyl, halogen, —$OR^{11}$, or —$SO_2R^{11}$.

In another embodiment, the invention provides the compound according to formula XVa,
$R^2$ is -$L^3$-$R^7$, wherein $L^3$ is a bond; and
$R^7$ is hydrogen, halogen, -Z, or —Y—Z, wherein
Y is —[C($R^{15}$)$_2$]$_m$—, —($C_3$-$C_6$)cycloalkyl-, or $C_2$-$C_6$ alkenyl,
wherein each $R^{15}$ is independently H, halogen, or ($C_1$-$C_6$)alkyl; and
Z is —H, halogen, —$OR^{11}$, —C(=O)$R^{11}$, —C(=O)$OR^{11}$, —C(=O)N($R^{11}$)$_2$, —C(=N—OH)$R^{11}$, or —C(=S)N($R^{11}$)$_2$,
such compounds are designated hereafter as formula XVd.

In another embodiment, the invention provides the compound according to formula XVb, wherein each $R^4$ is independently halogen, aryl, heteroaryl, heterocyclyl, -$G^{1'}$ or -E-$G^1$, wherein
E is —[C($R^{15}$)$_2$]$_m$—, wherein
each $R^{15}$ is independently hydrogen or halogen; and
$G^1$ is —$C_1$-$C_6$ alkyl, —$C_1$-$C_6$ haloalkyl, halogen, —$OR^{11}$, or —$SO_2R^{11}$.

In another embodiment, the invention provides the compound according to formula XVd, wherein each $R^4$ is independently halogen, aryl, heteroaryl, heterocyclyl, -$G^{1'}$ or -E-$G^1$, wherein
E is —[C($R^{15}$)$_2$]$_m$—, wherein
each $R^{15}$ is independently hydrogen or halogen; and
$G^1$ is —$C_1$-$C_6$ alkyl, —$C_1$-$C_6$ haloalkyl, halogen, —$OR^{11}$, or —$SO_2R^{11}$.

In another embodiment, the invention provides the compound according to formula XV, wherein $R^{21}$ is hydrogen, halogen, nitro, cyano, aryl, heteroaryl, heterocyclyl, —$C_1$-$C_6$ alkyl-heterocyclyl, —$C_1$-$C_6$ alkyl-heteroaryl, —$C_1$-$C_6$ allyl-aryl, -Z, —Y—Z, or —X—Y—Z, wherein
X is —O—;
Y is —[C($R^{15}$)$_2$]$_m$—, —$C_2$-$C_6$ alkenyl, or $C_3$-$C_8$ cycloalkyl; and
Z is —H, —CN, halogen, —$OR^{11}$, —C(=O)$R^{11}$, —C(=O)$OR^{11}$, —C(=O)N($R^{11}$)$_2$, —N($R^{11}$)$_2$, —CN, —$N_3$, —$SO_2R^{11}$, —S(=O)$_2$N($R^{11}$)$_2$, —C(=O)N($R^{11}$)N($R^H$)$_2$, —C(=O)N($R^{11}$)(O$R^{11}$), —OC(=O)—$R^{11}$, —OC(=O)—N($R^{11}$)$_2$, or —N($R^{11}$)$COOR^{11}$.

In another embodiment, the invention provides the compound according to formula XV, wherein $R^{21}$ is hydrogen, halogen, nitro, cyano, $C_1$-$C_6$ alkyl, or $C_1$-$C_6$ haloalkyl.

In another embodiment, the invention provides the compound according to any of formulas XVa-XVd, wherein $R^{21}$ is hydrogen, halogen, nitro, cyano, $C_1$-$C_6$ alkyl, or $C_1$-$C_6$ haloalkyl.

In another embodiment, the invention provides the compound according to formula VIII, wherein K is pyridinyl.

In another embodiment, the invention provides the compound according to formula XVI,

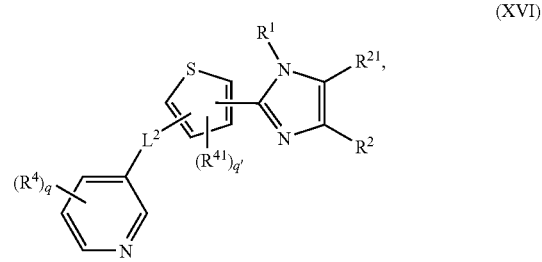

(XVI)

or a pharmaceutically acceptable salt, isomer, or prodrug thereof, where $R^1$ is as defined for formula IVa-d, and $R^2$, $R^{21}$, $R^4$, $R^{41}$, $L^2$, q, and q' are as defined for formula IIa-d.

In another embodiment, the invention provides the compound according to formula XVII,

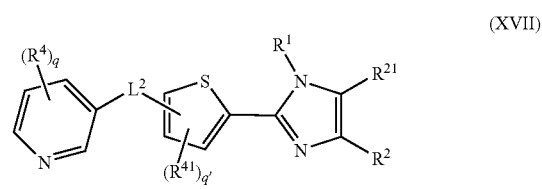

(XVII)

or a pharmaceutically acceptable salt, isomer, or prodrug thereof, where $R^1$ is as defined for formula IVa-d, and $R^2$, $R^{21}$, $R^4$, $R^{41}$, $L^2$, q, and q' are as defined for formula IIa-d.

In another embodiment, the invention provides the compound according to formula XVIII,

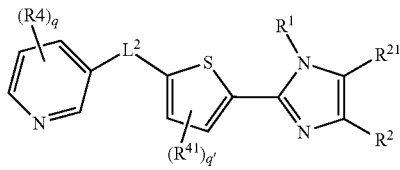

(XVIII)

or a pharmaceutically acceptable salt, isomer, or prodrug thereof, where $R^1$ is as defined for formula IVa-d, and $R^2$, $R^{21}$, $R^4$, $R^{41}$, $L^2$, q, and q' are as defined for formula IIa-d.

In another embodiment, the invention provides the compound according to formula XVIII, wherein $L^2$ is a bond, such compounds are designated hereafter as formula XIX.

In another embodiment, the invention provides the compound according to formula XIX, wherein each $R^{5a}$ is independently halogen, $C_1$-$C_6$ alkyl, $C_1$-$C_6$ haloalkyl, $C_3$-$C_8$ cycloalkyl, —$OR^{11}$, —$SO_2R^{11}$, —$COR^{11}$, —$SO_2N(R^{11})_2$, —C≡N, —C(O)$OR^{11}$, —CON($R^{11}$)$_2$, —$NR^{11}COR^{11}$, or —N($R^{11}$)$_2$.

In another embodiment, the invention provides the compound according to formula XIX, wherein each $R^{5a}$ is independently halogen, $C_1$-$C_6$ alkyl, or $C_1$-$C_6$ haloalkyl, such compounds are designated hereafter as formula XIXa.

In another embodiment, the invention provides the compound according to formula XIX, wherein $R^2$ is -$L^3$-$R^7$, wherein $L^3$ is a bond; and
$R^7$ is hydrogen, halogen, nitro, aryl, heteroaryl, heterocyclyl, -Z, or —Y—Z, wherein
Y is —[C($R^{15}$)$_2$]$_m$—, —($C_3$-$C_6$)cycloalkyl-, or $C_2$-$C_6$ alkenyl; and
Z is —H, halogen, —$OR^{11}$, —C(=O)$R^{11}$, —C(=O)$OR^{11}$, —C(=O)N($R^{11}$)$_2$, —N($R^{11}$)$_2$, —C(=N—OH)$R^{11}$, —C(=S)N($R^{11}$)$_2$, —CN, —S(=O)$_2$N($R^{11}$)$_2$, —C(=O)N($R^{11}$)N($R^{11}$)$_2$, —C(=O)N($R^{11}$)(O$R^{11}$), —OC(=O)—$R^{11}$, or —OC(=O)—N($R^{11}$)$_2$.

In another embodiment, the invention provides the compound according to formula XIX, wherein $R^2$ is -$L^3$-$R^7$, wherein $L^3$ is a bond; and
$R^7$ is hydrogen, halogen, -Z, or —Y—Z, wherein
Y is —[C($R^{15}$)$_2$]$_m$—, —($C_3$-$C_6$)cycloalkyl-, or $C_2$-$C_6$ alkenyl; and
wherein each $R^{15}$ is independently H, halogen, or ($C_1$-$C_6$)alkyl; and
Z is —H, halogen, —$OR^{11}$, —C(=O)$R^{11}$, —C(=O)$OR^{11}$, —C(=O)N($R^{11}$)$_2$, —C(=N—OH)$R^{11}$, or —C(=S)N($R^{11}$)$_2$,
such compounds are designated hereafter as formula XIXb.

In another embodiment, the invention provides the compound according to formula XIX, wherein each $R^4$ is independently halogen, aryl, heteroaryl, heterocyclyl, -$G^{1'}$ or -E-$G^1$, wherein
E is —[C($R^{15}$)$_2$]$_m$—; and
$G^1$ is —$C_1$-$C_6$ alkyl, —$C_1$-$C_6$haloalkyl, halogen, —$COR^{11}$, —$COOR^{11}$, —CON($R^{11}$)$_2$, —C≡N, —$OR^{11}$, —N($R^{11}$)$_2$, —$SO_2R^{11}$, —$SO_2N(R^{11})_2$, or —$SR^{11}$.

In another embodiment, the invention provides the compound according to formula XIX, wherein each $R^4$ is independently halogen, aryl, heteroaryl, heterocyclyl, -$G^{1'}$ or -E-$G^1$, wherein E is —[C($R^{15}$)$_2$]$_m$—, wherein
each $R^{15}$ is independently hydrogen or halogen; and
$G^1$ is —$C_1$-$C_6$ alkyl, —$C_1$-$C_6$ haloalkyl, halogen, —$OR^{11}$, or —$SO_2R^{11}$.

In another embodiment, the invention provides the compound according to formula XIXa, wherein $R^2$ is -$L^3$-$R^7$, wherein $L^3$ is a bond; and
$R^7$ is hydrogen, halogen, -Z, or —Y—Z, wherein
Y is —[C($R^{15}$)$_2$]$_m$—, —($C_3$-$C_6$)cycloalkyl-, or $C_2$-$C_6$ alkenyl,
wherein each $R^{15}$ is independently H, halogen, or ($C_1$-$C_6$)alkyl; and
Z is —H, halogen, —$OR^{11}$, —C(=O)$R^{11}$, —C(=O)$OR^{11}$, —C(=O)N($R^{11}$)$_2$, —C(=N—OH)$R^{11}$, or —C(=S)N($R^{11}$)$_2$
such compounds are designated hereafter as formula XIXd.

In another embodiment, the invention provides the compound according to formula XIXb, wherein each $R^4$ is independently halogen, aryl, heteroaryl, heterocyclyl, -$G^{1'}$ or -E-$G^1$, wherein E is —[C($R^{15}$)$_2$]$_m$—, wherein
each $R^{15}$ is independently hydrogen or halogen; and
$G^1$ is —$C_1$-$C_6$ alkyl, —$C_1$-$C_6$ haloalkyl, halogen, —$OR^{11}$, or —$SO_2R^1$.

In another embodiment, the invention provides the compound according to formula XIXd, wherein each $R^4$ is independently halogen, aryl, heteroaryl, heterocyclyl, -$G^{1'}$ or -E-$G^1$, wherein E is —[C($R^{11}$)$_2$]$_m$—, wherein
each $R^{15}$ is independently hydrogen or halogen; and
$G^1$ is —$C_1$-$C_6$ alkyl, —$C_1$-$C_6$ haloalkyl, halogen, —$OR^{11}$, or —$SO_2R^{11}$.

In another embodiment, the invention provides the compound according to formula XIX, wherein $R^{21}$ is hydrogen, halogen, nitro, cyano, aryl, heteroaryl, heterocyclyl, —$C_1$-$C_6$ alkyl-heterocyclyl, —$C_1$-$C_6$ alkyl-heteroaryl, —$C_1$-$C_6$ alkyl-aryl, -Z, —Y—Z, or —X—Y—Z, wherein
X is —O—;
Y is —[C($R^{15}$)$_2$]$_m$—, —$C_2$-$C_6$ alkenyl, or $C_3$-$C_8$ cycloalkyl; and
Z is —H, —CN, halogen, —$OR^{11}$, —C(=O)$R^{11}$, —C(=O)$OR^{11}$, —C(=O)N($R^{11}$)$_2$, —N($R^{11}$)$_2$, —CN, —$N_3$, —$SO_2R^{11}$, —S(=O)$_2$N($R^{11}$)$_2$, —C(=O)N($R^{11}$)N($R^{11}$)$_2$, —C(=O)N($R^{11}$)(O$R^{11}$), —OC(=O)—$R^{11}$, —OC(=O)—N($R^{11}$)$_2$, or —N($R^{11}$)COO$R^{11}$.

In another embodiment, the invention provides the compound according to formula XIX, wherein $R^{21}$ is hydrogen, halogen, nitro, cyano, $C_1$-$C_6$ alkyl, or $C_1$-$C_6$ haloalkyl.

In another embodiment, the invention provides the compound according to any of formulas XIXa-XIXd, wherein $R^{21}$ is hydrogen, halogen, nitro, cyano, $C_1$-$C_6$ alkyl, or $C_1$-$C_6$ haloalkyl.

In another embodiment, the invention provides the compound according to formula IIIa-d, wherein $R^1$ is heteroaryl optionally substituted with one or more $R^{5a}$.

In another embodiment, the invention provides the compound according to formulas IIIa-d, wherein $R^1$ is thienyl, furyl, pyrrolyl, pyridinyl, pyrimidinyl, pyrazidinyl, pyrazolyl, quinolinyl, or isoquinolinyl, all of which are optionally substituted with one or more $R^{5a}$.

In another embodiment, the invention provides the compound according to formulas Ia-d, wherein $R_1$ is thienyl, furyl, pyrrolyl, pyridinyl, pyrimidinyl, pyrazidinyl, pyrazolyl, quinolinyl, or isoquinolinyl, all of which are optionally substituted with one or more $R^{5a}$; and J is phenyl.

In another embodiment, the invention provides the compound according to formula IIa-d, wherein $R^1$ is thienyl, furyl, pyrrolyl, pyridinyl, pyrimidinyl, pyrazidinyl, pyrazolyl, quinolinyl, or isoquinolinyl, all of which are optionally substituted with one or more $R^{5a}$; and K is phenyl.

In another embodiment, the invention provides the compound according to formula IIIa-d, wherein $R^1$ is thienyl, furyl, pyrrolyl, pyridinyl, pyrimidinyl, pyrazidinyl, pyrazolyl, quinolinyl, or isoquinolinyl, all of which are optionally substituted with one or more $R^{5a}$; J is phenyl; and K is phenyl.

In another embodiment, the invention provides the compound according to formula IIa-d, wherein $R^1$ is thienyl, furyl, pyrrolyl, pyridinyl, pyrimidinyl, pyrazidinyl, pyrazolyl, quinolinyl, or isoquinolinyl, all of which are optionally substituted with one or more $R^{5a}$; J is phenyl; K is phenyl; and $L^2$ is a bond.

In another embodiment, the invention provides the compound according to formula Ia-d, wherein $R^1$ is thienyl, furyl, pyrrolyl, pyridinyl, pyrimidinyl, pyrazidinyl, pyrazolyl, quinolinyl, or isoquinolinyl, all of which are optionally substituted with at least one or more $R^{5a}$;
J is phenyl; K is phenyl; $L^2$ is a bond;
and $R^2$ is -$L^3$-$R^7$, wherein $L^3$ is a bond; and
$R^7$ is hydrogen, halogen, -Z, or —Y—Z, wherein
Y is —[C($R^{11}$)$_2$]$_m$—, —($C_3$-$C_6$)cycloalkyl-, or $C_2$-$C_6$ alkenyl,
wherein each $R^{15}$ is independently H, halogen, or ($C_1$-$C_6$)alkyl; and
Z is —H, halogen, —O$R^{11}$, —C(=O)$R^{11}$, —C(=O)O$R^{11}$, —C(=O)N($R^{11}$)$_2$, —C(=N—OH)$R^{11}$, or —C(=S)N($R^{11}$)$_2$.

In another embodiment, the invention provides the compound according to formula IIa-d, wherein $R^1$ is thienyl, furyl, pyrrolyl, pyridinyl, pyrimidinyl, pyrazidinyl, pyrazolyl, quinolinyl, or isoquinolinyl, all of which are optionally substituted with one or more $R^{5a}$;
J is phenyl; K is phenyl; $L^2$ is a bond;
and each $R^4$ is independently halogen, aryl, heteroaryl, heterocyclyl, -$G^{1'}$ or -E-$G^1$, wherein E is —[C($R^{11}$)$_2$]$_m$—, wherein
each $R^{15}$ is independently hydrogen or halogen; and
$G^1$ is —$C_1$-$C_6$ alkyl, —$C_1$-$C_6$haloalkyl, halogen, —O$R^{11}$, or —SO$_2R^{11}$.

In another embodiment, the invention provides the compound according to formula IIIa-d, wherein $R^1$ is thienyl, furyl, pyrrolyl, pyridinyl, pyrimidinyl, pyrazidinyl, pyrazolyl, quinolinyl, or isoquinolinyl, all of which are optionally substituted with one or more $R^{5a}$;
J is phenyl; K is phenyl; $L^2$ is a bond;
and each $R^{41}$ is independently halogen, -$G^{1'}$ or -E-G, wherein
E is —[C($R^{15}$)$_2$]$_m$—,
wherein each $R^{15}$ is independently hydrogen or halogen; and
$G^1$ is —$C_1$-$C_6$ alkyl, —$C_1$-$C_6$ haloalkyl, or halogen.

In another embodiment, the invention provides the compound according to formula IIIa-d, wherein $R^1$ is thienyl, furyl, pyrrolyl, pyridinyl, pyrimidinyl, pyrazidinyl, pyrazolyl, quinolinyl, or isoquinolinyl, all of which are optionally substituted with one or more $R^{5a}$;
J is phenyl; K is phenyl; $L^2$ is a bond;
and $R^{21}$ is hydrogen, halogen, nitro, cyano, $C_1$-$C_6$ alkyl, or $C_1$-$C_6$ haloalkyl.

In another embodiment, the invention provides the compound according to formula IIa-d, wherein $L^1$ is —[C($R^{15}$)$_2$]$_{m'}$- or —$C_3$-$C_8$ cycloalkyl, wherein
m' is any of 1 to 4; and
each $R^{15}$ is independently hydrogen, halogen, ($C_1$-$C_6$) alkyl, or ($C_1$-$C_6$)haloalkyl, and $R^2$, $R^{21}$, $R^3$, $R^5$, and G are as defined for formulas IIa-d.

In another embodiment, the invention provides the compound of formula XX,

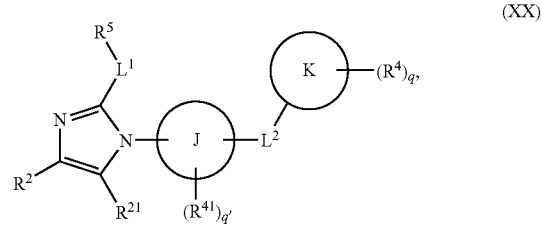

(XX)

or a pharmaceutically acceptable salt, isomer, or prodrug thereof, wherein
$L^1$ is —[C($R^{15}$)$_2$]$_{m'}$— or —$C_3$-$C_8$ cycloalkyl, wherein
m' is any of 1 to 3; and
each $R^{15}$ is independently hydrogen, halogen, ($C_1$-$C_6$) alkyl, or ($C_1$-$C_6$)haloalkyl,
and $R^2$, $R^{21}$, $R^4$, $R^{41}$, $R^5$, $L^2$, J, K, q, and q' are as defined for formula IIa-d.

In another embodiment, the invention provides the compound according to formula XX, wherein J is phenyl.

In another embodiment, the invention provides the compound according to formula XX, wherein K is phenyl.

In another embodiment, the invention provides the compound according to formula XX, wherein J is phenyl and K is phenyl.

In another embodiment, the invention provides the compound according to formula XX, wherein J is phenyl; K is phenyl; and $L^2$ is a bond.

In another embodiment, the invention provides the compound of formula XXI,

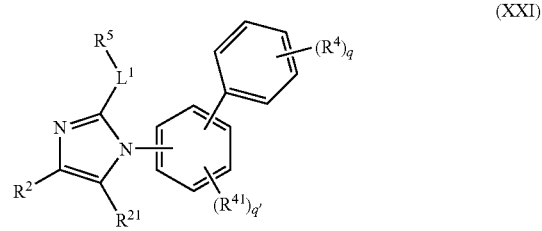

(XXI)

or a pharmaceutically acceptable salt, isomer, or prodrug thereof, where $L^1$ is as defined in formula XX, and $R^2$, $R^{21}$, $R^4$, $R^{41}$, $R^5$, q, and q' are as defined for formula IIa-d.

In another embodiment, the invention provides the compound according to formula XXII,

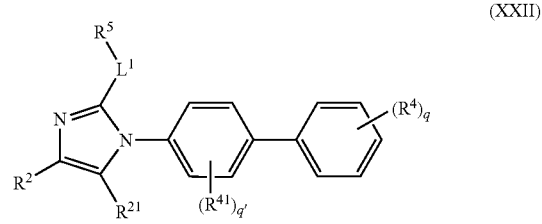

(XXII)

or a pharmaceutically acceptable salt, isomer, or prodrug thereof, where $L^1$ is as defined in formula XX, and $R^2$, $R^{21}$, $R^4$, $R^{41}$, $R^5$, q, and q' are as defined for formula IIa-d.

In another embodiment, the invention provides the compound according to formula XXII, wherein each $R^{15}$ is independently —H or —($C_1$-$C_2$)alkyl; m' is 1 or 2; and $R^{15}$ is phenyl optionally substituted with one or more $R^{5a}$, such compounds are designated hereafter as formula XXIII.

In another embodiment, the invention provides the compound according to formula XXIII, wherein $R^2$ is -$L^3$-$R^7$, wherein $L^3$ is a bond; and
$R^7$ is hydrogen, halogen, -Z, or —Y—Z, wherein
Y is —[C($R^{15}$)$_2$]$_m$—, —($C_3$-$C_6$)cycloalkyl-, or $C_2$-$C_6$alkenyl,
wherein each $R^{15}$ is independently H, halogen, —($C_3$-$C_6$)cycloalkyl-, or ($C_1$-$C_6$)alkyl; and
Z is —H, halogen, —$OR^{11}$, —C(=O)$R^{11}$, —C(=O)$OR^{11}$, —C(=O)N($R^{11}$)$_2$, —C(=N—OH)$R^{11}$, or —C(=S)N($R^{11}$)$_2$.

In another embodiment, the invention provides the compound according to formula XXIII, wherein each $R^4$ is independently halogen, aryl, heteroaryl, heterocyclyl, -$G^{1'}$ or -E-$G^1$, wherein E is —[C($R^{15}$)$_2$]$_m$—, wherein
each $R^{5a}$ is independently hydrogen or halogen; and
$G^1$ is —$C_1$-$C_6$ alkyl, —$C_1$-$C_6$ haloalkyl, halogen, —$OR^{11}$, or —$SO_2R^{11}$.

In another embodiment, the invention provides the compound according to formula XXIII, wherein each $R^{41}$ is independently halogen, -$G^{1'}$ or -E-$G^1$, wherein
E is —[C($R^{15}$)$_2$]$_m$—,
wherein each $R^{15}$ is independently hydrogen or halogen; and
$G^1$ is —$C_1$-$C_6$ alkyl, —$C_1$-$C_6$ haloalkyl, or halogen.

In another embodiment, the invention provides the compound according to formula XXIII, wherein $R^{21}$ is hydrogen, halogen, nitro, cyano, $C_1$-$C_6$ alkyl, or $C_1$-$C_6$ haloalkyl.

In another embodiment, the invention provides the compound according to formula XXII, wherein $R^{15}$ is —H; m is 1, 2, or 3; and $R^{15}$ is heterocyclyl optionally substituted with one or more $R^{5a}$,
such compounds are designated hereafter as formula XXIV.

In another embodiment, the invention provides the compound according to formula XXIV, wherein $R^2$ is -$L^3$-$R^7$, wherein $L^3$ is a bond; and
$R^7$ is hydrogen, halogen, -Z, or —Y—Z, wherein
Y is —[C($R^{15}$)$_2$]$_m$—, —($C_3$-$C_6$)cycloalkyl-, or $C_2$-$C_6$ alkenyl,
wherein each $R^{15}$ is independently H, halogen, —($C_3$-$C_6$)cycloalkyl-, or ($C_1$-$C_6$)alkyl; and
Z is —H, halogen, —$OR^{11}$, —C(=O)$R^{11}$, —C(=O)$OR^{11}$, —C(=O)N($R^{11}$)$_2$, —C(=N—OH)$R^{11}$, or —C(=S)N($R^{11}$)$_2$.

In another embodiment, the invention provides the compound according to formula XXIV, wherein each $R^4$ is independently halogen, aryl, heteroaryl, heterocyclyl, -$G^{1'}$ or -E-$G^1$, wherein E is —[C($R^{15}$)$_2$]$_m$—, wherein
each $R^{15}$ is independently hydrogen or halogen; and
$G^1$ is —$C_1$-$C_6$ alkyl, —$C_1$-$C_6$ haloalkyl, halogen, —$OR^{11}$, or —$SO_2R^{11}$.

In another embodiment, the invention provides the compound according to formula XXIV, wherein each $R^{41}$ is independently halogen, -$G^{1'}$ or -E-$G^1$, wherein
E is —[C($R^{15}$)$_2$]$_m$—,
wherein each $R^{15}$ is independently hydrogen or halogen; and
$G^1$ is —$C_1$-$C_6$ alkyl, —$C_1$-$C_6$ haloalkyl, or halogen.

In another embodiment, the invention provides the compound according to formula XXIV, wherein $R^{21}$ is hydrogen, halogen, nitro, cyano, $C_1$-$C_6$ alkyl, or $C_1$-$C_6$ haloalkyl.

In another embodiment, the invention provides the compound according to formula XXII, wherein each $R^{15}$ is independently —H or —($C_1$-$C_2$)alkyl; m is 1, 2, 3, or 4; and $R^{15}$ is heterocyclyl optionally substituted with one or more $R^{5a}$, such compounds are designated hereafter as formula XXIVa.

In another embodiment, the invention provides the compound according to formula XXIVa, wherein $R^2$ is -$L^3$-$R^7$, wherein $L^3$ is a bond; and
$R^7$ is hydrogen, halogen, -Z, or —Y—Z, wherein
Y is —[C($R^{15}$)$_2$]$_m$—, —($C_3$-$C_6$)cycloalkyl-, or $C_2$-$C_6$ alkenyl,
wherein each $R^{15}$ is independently H, halogen, or ($C_1$-$C_6$)alkyl; and
Z is —H, halogen, —$OR^{11}$, —C(=O)$R^{11}$, —C(=O)$OR^{11}$, —C(=O)N($R^{11}$)$_2$, —C(=N—OH)$R^{11}$, or —C(=S)N($R^{11}$)$_2$.

In another embodiment, the invention provides the compound according to formula XXIVa, wherein each $R^4$ is independently halogen, aryl, heteroaryl, heterocyclyl, -$G^{1'}$ or -E-$G^1$, wherein E is —[C($R^{15}$)$_2$]$_m$—, wherein
each $R^{15}$ is independently hydrogen or halogen; and
$G^1$ is —$C_1$-$C_6$ alkyl, —$C_1$-$C_6$ haloalkyl, halogen, —$OR^{11}$, or —$SO_2R^{11}$.

In another embodiment, the invention provides the compound according to formula XXIVa, wherein each $R^{41}$ is independently halogen, -$G^{1'}$ or -E-$G^1$, wherein
E is —[C($R^{15}$)$_2$]$_m$—,
wherein each $R^{15}$ is independently hydrogen or halogen; and
$G^1$ is —$C_1$-$C_6$ alkyl, —$C_1$-$C_6$ haloalkyl or halogen.

In another embodiment, the invention provides the compound according to formula XXIVa, wherein $R^{21}$ is hydrogen, halogen, nitro, cyano, $C_1$-$C_6$ alkyl, or $C_1$-$C_6$ haloalkyl.

In another embodiment, the invention provides the compound of formula XXVI,

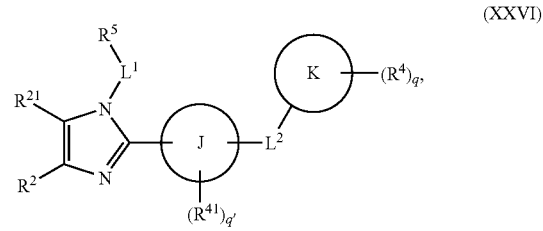

(XXVI)

or a pharmaceutically acceptable salt, isomer, or prodrug thereof, wherein
$L^1$ is —[C($R^{15}$)$_2$]$_m$— or —$C_3$-$C_8$ cycloalkyl, wherein
m' is any of 1 to 3; and
each $R^{15}$ is independently hydrogen, halogen, ($C_1$-$C_6$) alkyl, ($C_3$-$C_6$)cycloalkyl, or ($C_1$-$C_6$)haloalkyl,
and $R^2$, $R^{21}$, $R^4$, $R^{41}$, $R^5$, $L^2$, J, K, q, and q' are as defined for formula IIa-d.

In another embodiment, the invention provides the compound according to formula XXVI, wherein J is aryl.

In another embodiment, the invention provides the compound according to formula XXVI, wherein J is phenyl.

In another embodiment, the invention provides the compound according to formula XXVI, wherein J is heteroaryl, such compounds are referred to hereafter as compounds of formula XXVIa.

In another embodiment, the invention provides the compound according to formula XXVIa wherein K is aryl.

In another embodiment, the invention provides the compound according to formula XXVIa wherein K is phenyl.

In another embodiment, the invention provides the compound according to formula XXVI, wherein K is aryl.

In another embodiment, the invention provides the compound according to formula XXVI, wherein K is heteroaryl, such compounds are referred to hereafter as compounds of formula XXVIb. In another embodiment, the invention provides the compound according to formula XXVIb wherein J is aryl.

In another embodiment, the invention provides the compound according to formula XXVIb wherein J is phenyl.

In another embodiment, the invention provides the compound according to formula XXVI, wherein K is phenyl.

In another embodiment, the invention provides the compound according to formula XXVI, wherein J is phenyl and K is phenyl.

In another embodiment, the invention provides the compound according to formula XXVI, wherein J is phenyl; K is phenyl; and $L^2$ is a bond.

In another embodiment, the invention provides the compound of formula XXVII,

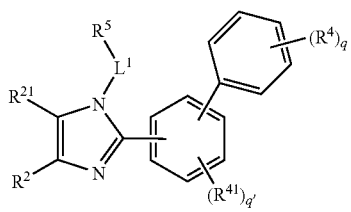

(XXVII)

or a pharmaceutically acceptable salt, isomer, or prodrug thereof, where $L^1$ is as defined in formula XXVI, and $R^2$, $R^{21}$, $R^4$, $R^{41}$, $R^5$, q, and q' are as defined for formula IIa-d.

In another embodiment, the invention provides the compound according to formula XXVIII,

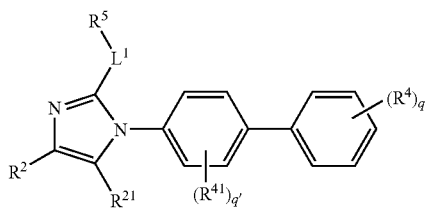

(XXVIII)

or a pharmaceutically acceptable salt, isomer, or prodrug thereof, where $L^1$ is as defined in formula XXVI, and $R^2$, $R^{21}$, $R^4$, $R^{41}$, $R^5$, q, and q' are as defined for formula IIa-d.

In another embodiment, the invention provides the compound according to formula XXVIII, wherein $R^2$ is -$L^3$-$R^7$, wherein $L^3$ is a bond; and
$R^7$ is hydrogen, halogen, -Z, or —Y—Z, wherein
Y is —[C($R^{15}$)$_2$]$_m$—, —($C_3$-$C_6$)cycloalkyl-, or $C_2$-$C_6$ alkenyl,
wherein each $R^{5a}$ is independently H, halogen, —($C_3$-$C_6$)cycloalkyl-, or —($C_1$-$C_6$)alkyl; and
Z is —H, halogen, —O$R^{11}$, —C(═O)$R^{11}$, —C(═O)O$R^{11}$, —C(═O)N($R^{11}$)$_2$, —C(═N—OH)$R^{11}$, or —C(═S)N($R^{11}$)$_2$.

In another embodiment, the invention provides the compound according to formula XXVIII, wherein each $R^4$ is independently halogen, aryl, heteroaryl, heterocyclyl, -$G^{1'}$ or -E-$G^1$, wherein E is —[C($R^{15}$)$_2$]$_m$—, wherein
each $R^{15}$ is independently hydrogen or halogen; and
$G^1$ is —$C_1$-$C_6$ alkyl, —$C_1$-$C_6$ haloalkyl, halogen, —O$R^{11}$, or —SO$_2R^1$.

In another embodiment, the invention provides the compound according to formula XXVIII, wherein each $R^{41}$ is independently halogen, -$G^{1'}$ or -E-$G^1$, wherein
E is —[C($R^{15}$)$_2$]$_m$—,
wherein each $R^{15}$ is independently hydrogen or halogen; and
$G^1$ is —$C_1$-$C_6$ alkyl, —$C_1$-$C_6$ haloalkyl, or halogen.

In another embodiment, the invention provides the compound according to formula XXVII, wherein each $R^{15}$ is independently —H, —($C_1$-$C_6$)alkyl, or —($C_3$-$C_6$)cycloalkyl; m' is 1 or 2; and $R^{15}$ is phenyl optionally substituted with one or more $R^{5a}$, such compounds are designated hereafter as formula XXIX.

In another embodiment, the invention provides the compound according to formula XXIX, wherein $R^2$ is -$L^3$-$R^7$, wherein $L^3$ is a bond; and
$R^7$ is hydrogen, halogen, -Z, or —Y—Z, wherein
Y is —[C($R^{15}$)$_2$]$_m$—, —($C_3$-$C_6$)cycloalkyl-, or $C_2$-$C_6$ alkenyl,
wherein each $R^{15}$ is independently H, halogen, —($C_3$-$C_6$)cycloalkyl-, or —($C_1$-$C_6$)alkyl; and
Z is —H, halogen, —O$R^{11}$, —C(═O)$R^{11}$, —C(═O)O$R^{11}$, —C(═O)N($R^{11}$)$_2$, —C(═N—OH)$R^{11}$, or —C(═S)N($R^{11}$)$_2$.

In another embodiment, the invention provides the compound according to formula XXIX, wherein each $R^4$ is independently halogen, aryl, heteroaryl, heterocyclyl, -$G^{1'}$ or -E-$G^1$, wherein E is —[C($R^{15}$)$_2$]$_m$—, wherein
each $R^{15}$ is independently hydrogen or halogen; and
$G^1$ is —$C_1$-$C_6$ alkyl, —$C_1$-$C_6$ haloalkyl, halogen, —O$R^{11}$, or —SO$_2R^{11}$.

In another embodiment, the invention provides the compound according to formula XXIX, wherein each $R^{41}$ is independently halogen, -$G^{1'}$ or -E-$G^1$, wherein
E is —[C($R^{15}$)$_2$]$_m$—,
wherein each $R^{15}$ is independently hydrogen or halogen; and
$G^1$ is —$C_1$-$C_6$ alkyl, —$C_1$-$C_6$ haloalkyl, or halogen.

In another embodiment, the invention provides the compound according to formula XXIX, wherein $R^{21}$ is hydrogen, halogen, nitro, cyano, $C_1$-$C_6$ alkyl, or $C_1$-$C_6$ haloalkyl.

In another embodiment, the invention provides the compound according to formula XXVIII, wherein $R^{15}$ is —H; m is 1, 2, or 3; and $R^5$ is heterocyclyl optionally substituted with one or more $R^{5a}$, such compounds are designated hereafter as formula XXX.

In another embodiment, the invention provides the compound according to formula XXX, wherein $R^2$ is -$L^3$-$R^7$, wherein $L^3$ is a bond; and
$R^7$ is hydrogen, halogen, -Z, or —Y—Z, wherein
Y is —[C($R^{15}$)$_2$]$_m$—, —($C_3$-$C_6$)cycloalkyl-, or $C_2$-$C_6$ alkenyl,
wherein each $R^{15}$ is independently H, halogen, —($C_3$-$C_6$)cycloalkyl-, or —($C_1$-$C_6$)alkyl; and
Z is —H, halogen, —O$R^{11}$, —C(═O)$R^{11}$, —C(═O)O$R^{11}$, —C(═O)N($R^{11}$)$_2$, —C(═N—OH)$R^{11}$, or —C(═S)N($R^{11}$)$_2$.

In another embodiment, the invention provides the compound according to formula XXX, wherein each $R^4$ is independently halogen, aryl, heteroaryl, heterocyclyl, -$G^{1'}$ or -E-$G^1$, wherein E is —[C($R^{15}$)$_2$]$_m$—, wherein
each $R^{5a}$ is independently hydrogen or halogen; and
$G^1$ is —$C_1$-$C_6$ alkyl, —$C_1$-$C_6$ haloalkyl, halogen, —O$R^{11}$, or —SO$_2R^1$.

In another embodiment, the invention provides the compound according to formula XXX, wherein each $R^{41}$ is independently halogen, -$G^{1\prime}$ or -E-$G^1$, wherein
E is —[C($R^{15}$)$_2$]$_m$—,
wherein each $R^{15}$ is independently hydrogen or halogen; and
$G^1$ is —$C_1$-$C_6$ alkyl, —$C_1$-$C_6$haloalkyl, or halogen.

In another embodiment, the invention provides the compound according to formula XXX, wherein $R^{21}$ is hydrogen, halogen, nitro, cyano, $C_1$-$C_6$ alkyl, or $C_1$-$C_6$ haloalkyl.

In another embodiment, the invention provides the compound according to formula XXVIII, wherein each $R^{15}$ is independently —H or —($C_1$-$C_2$)alkyl; m is 1, 2, 3, or 4; and $R^{15}$ is heterocyclyl optionally substituted with one or more $R^{5a}$, such compounds are designated hereafter as formula XXXI.

In another embodiment, the invention provides the compound according to formula XXXI, wherein $R^2$ is -$L^3$-$R^7$, wherein $L^3$ is a bond; and
$R^7$ is hydrogen, halogen, -Z, or —Y—Z, wherein
Y is —[C($R^{15}$)$_2$]$_m$—, —($C_3$-$C_6$)cycloalkyl-, or $C_2$-$C_6$ alkenyl,
wherein each $R^{15}$ is independently H, halogen, —($C_3$-$C_6$)cycloalkyl-, or ($C_1$-$C_6$)alkyl; and
Z is —H, halogen, —$OR^{11}$, —C(=O)$R^{11}$, —C(=O)$OR^{11}$, —C(=O)N($R^{11}$)$_2$, —C(=N—OH)$R^{11}$, or —C(=S)N($R^{11}$)$_2$.

In another embodiment, the invention provides the compound according to formula XXXI, wherein each $R^4$ is independently halogen, aryl, heteroaryl, heterocyclyl, -$G^{1\prime}$ or -E-$G^1$, wherein E is —[C($R^{15}$)$_2$]$_m$—, wherein
each $R^{15}$ is independently hydrogen or halogen; and
$G^1$ is —$C_1$-$C_6$ alkyl, —$C_1$-$C_6$haloalkyl, halogen, —$OR^{11}$, or —$SO_2R^{11}$.

In another embodiment, the invention provides the compound according to formula XXXI, wherein each $R^{41}$ is independently halogen, -$G^{1\prime}$ or -E-$G^1$, wherein
E is —[C($R^{15}$)$_2$]$_m$—,
wherein each $R^{15}$ is independently hydrogen or halogen; and
$G^1$ is —$C_1$-$C_6$ alkyl, —$C_1$-$C_6$haloalkyl or halogen.

In another embodiment, the invention provides the compound according to formula XXXI, wherein $R^{21}$ is hydrogen, halogen, nitro, cyano, $C_1$-$C_6$ alkyl, or $C_1$-$C_6$haloalkyl.

In another embodiment, the invention provides the compound according to formula XXII, wherein each $R^{15}$ is independently —H or —($C_1$-$C_2$)alkyl; m' is 1 or 2; and $R^{15}$ is heteroaryl optionally substituted with one or more $R^{5a}$.

In another embodiment, the invention provides the compound according to formula XXII, wherein each $R^{15}$ is independently —H or —($C_1$-$C_2$)alkyl; m' is 1 or 2; $R^{15}$ is heteroaryl optionally substituted with one or more $R^{5a}$; and $R^2$ is -$L^3$-$R^7$, wherein
$L^3$ is a bond; and
$R^7$ is hydrogen, halogen, -Z, or —Y—Z, wherein
Y is —[C($R^{15}$)$_2$]$_m$— or $C_2$-$C_6$ alkenyl,
wherein each $R^{15}$ is independently H, halogen, or ($C_1$-$C_6$)alkyl; and
Z is —H, halogen, —$OR^{11}$, —C(=O)$R^{11}$, —C(=O)$OR^{11}$, —C(=O)N($R^{11}$)$_2$, —C(=N—OH)$R^{11}$, or —C(=S)N($R^{11}$)$_2$.

In another embodiment, the invention provides the compound according to formula XXII, wherein each $R^{15}$ is independently —H or —($C_1$-$C_2$)alkyl; m' is 1 or 2;
$R^5$ is heteroaryl optionally substituted with one or more $R^{5a}$; and each $R^4$ is independently halogen, aryl, heteroaryl, heterocyclyl, -$G^1$, or -E-$G^1$, wherein
E is —[C($R^{15}$)$_2$]$_m$—, wherein
each $R^{15}$ is independently hydrogen or halogen; and
$G^1$ is —$C_1$-$C_6$ alkyl, —$C_1$-$C_6$ haloalkyl, halogen, —$OR^{11}$, or —$SO_2R^{11}$.

In another embodiment, the invention provides the compound according to formula XXII, wherein each $R^{15}$ is independently —H or —($C_1$-$C_2$)alkyl; m' is 1 or 2; $R^{15}$ is heteroaryl optionally substituted with one or more $R^{5a}$; and each $R^{41}$ is independently halogen, -$G^1$, or -E-$G^1$, wherein
E is —[C($R^{15}$)$_2$]$_m$—,
wherein each $R^{15}$ is independently hydrogen or halogen; and
$G^1$ is —$C_1$-$C_6$ alkyl, —$C_1$-$C_6$ haloalkyl, or halogen.

In another embodiment, the invention provides the compound according to formula XXVII, wherein each $R^{15}$ is independently —H or —($C_1$-$C_2$)alkyl; m' is 1 or 2; and $R^5$ is heteroaryl optionally substituted with one or more $R^{5a}$.

In another embodiment, the invention provides the compound according to formula XXVII, wherein each $R^{5a}$ is independently —H or —($C_1$-$C_2$)alkyl; m' is 1 or 2; $R^{15}$ is heteroaryl optionally substituted with one or more $R^{5a}$; and
$R^2$ is -$L^3$-$R^7$, wherein
$L^3$ is a bond; and
$R^7$ is hydrogen, halogen, -Z, or —Y—Z, wherein
Y is —[C($R^{15}$)$_2$]$_m$— or $C_2$-$C_6$ alkenyl,
wherein each $R^{15}$ is independently H, halogen, or ($C_1$-$C_6$)alkyl; and
Z is —H, halogen, —$OR^{11}$, —C(=O)$R^{11}$, —C(=O)$OR^{11}$, —C(=O)N($R^{11}$)$_2$, —C(=N—OH)$R^{11}$, or —C(=S)N($R^{11}$)$_2$.

In another embodiment, the invention provides the compound according to formula XXVII, wherein each $R^{15}$ is independently —H or —($C_1$-$C_2$)alkyl; m' is 1 or 2; $R^{15}$ is heteroaryl optionally substituted with one or more $R^{5a}$; and each $R^4$ is independently halogen, aryl, heteroaryl, heterocyclyl, -$G^1$, or -E-$G^1$, wherein
E is —[C($R^{15}$)$_2$]$_m$—, wherein
each $R^{15}$ is independently hydrogen or halogen; and
$G^1$ is —$C_1$-$C_6$ alkyl, —$C_1$-$C_6$haloalkyl, halogen, —$OR^{11}$, or —$SO_2R^{11}$.

In another embodiment, the invention provides the compound according to formula XXVII, wherein each $R^{15}$ is independently —H or —($C_1$-$C_2$)alkyl; m' is 1 or 2; $R^{15}$ is heteroaryl optionally substituted with one or more $R^{5a}$; and each $R^{41}$ is independently halogen, -$G^1$, or -E-$G^1$, wherein
E is —[C($R^{15}$)$_2$]$_m$—,
wherein each $R^{15}$ is independently hydrogen or halogen; and
$G^1$ is —$C_1$-$C_6$ alkyl, —$C_1$-$C_6$ haloalkyl, or halogen.

In another embodiment, the invention provides the compound according to formulas XXXII and XXXIII,

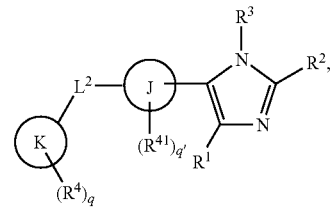

(XXXII)

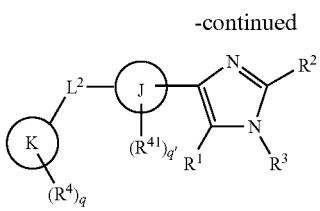

(XXXIII)

or a pharmaceutically acceptable salt, isomer, or prodrug thereof, wherein $R^3$ is hydrogen, $C_1$-$C_6$ alkyl, or $C_1$-$C_6$ haloalkyl, and $R^1$, $R^2$, $R^4$, $R^{41}$, $L^2$, q, and q' are as defined for formulas IIa-d.

In another embodiment, the invention provides the compound according to formulas XXXII and XXXIII, wherein J is aryl; K is aryl; and $L^2$ is a bond.

In another embodiment, the invention provides the compound according to formulas XXXII and XXXIII, wherein J is phenyl; K is phenyl; and $L^2$ is a bond.

In another embodiment, the invention provides the compound according to formulas XXXII and XXXIII, wherein J is phenyl; K is phenyl; $L^2$ is a bond; and $R^1$ is phenyl optionally substituted with one or more $R^{5a}$.

In another embodiment, the invention provides the compound according to formulas XXXII and XXXIII, wherein J is phenyl; K is phenyl; $L^2$ is a bond; $R^1$ is phenyl optionally substituted with one or more $R^{5a}$; and each $R^4$ is independently halogen, aryl, heteroaryl, heterocyclyl, -$G^{1'}$ or -E-$G^1$, wherein
E is —$[C(R^{15})_2]_m$—; and
$G^1$ is —$C_1$-$C_6$ alkyl, —$C_1$-$C_6$ haloalkyl, halogen, —$COR^{11}$, —$COOR^{11}$, —$CON(R^{11})_2$, —C≡N, —$OR^{11}$, —$NR^{11})_2$, —$SO_2R^{11}$, —$SO_2N(R^{11})_2$, or —$SR^{11}$.

In another embodiment, the invention provides the compound according to formulas XXXII and XXXIII, wherein J is phenyl; K is phenyl; $L^2$ is a bond; $R^1$ is phenyl optionally substituted with one or more $R^{5a}$; and each $R^{41}$ is independently halogen, -$G^1$ or -E-$G^1$, wherein
E is —$[C(R^{15})_2]_m$—,
wherein each $R^{15}$ is independently hydrogen or halogen; and
$G^1$ is —$C_1$-$C_6$ alkyl, —$C_1$-$C_6$ haloalkyl, or halogen.

In another embodiment, the invention provides the compound according to formulas XXXII and XXXIII, wherein J is phenyl; K is phenyl; $L^2$ is a bond; $R^1$ is phenyl optionally substituted with one or more $R^{5a}$; and $R^2$ is -$L^3$-$R^7$, wherein
$L^3$ is a bond; and
$R^7$ is hydrogen, halogen, -Z, or —Y—Z, wherein
Y is —$[C(R^{15})_2]_m$—, —$(C_3$-$C_6)$cycloalkyl-, or $C_2$-$C_6$alkenyl,
wherein each $R^{15}$ is independently H, halogen, or $(C_1$-$C_6)$alkyl; and
Z is —H, halogen, —$OR^{11}$, —C(=O)$R^{11}$, —C(=O)$OR^{11}$, —C(=O)N($R^{11})_2$, —C(=N—OH)$R^{11}$, or —C(=S)N($R^{11})_2$.

In another embodiment, the invention provides the compound according to formulas XXXII and XXXIII, wherein J is phenyl; K is phenyl; $L^2$ is a bond; $R^1$ is phenyl optionally substituted with one or more $R^{5a}$; and each $R^{2a}$ is independently halogen, $C_1$-$C_6$ alkyl, $C_1$-$C_6$ alkoxy, or $C_1$-$C_6$ haloalkyl.

In another embodiment, the invention provides the compound according to formulas XXXII and XXXIII, wherein J is heteroaryl; K is aryl; and $L^2$ is a bond.

In another embodiment, the invention provides the compound according to formulas XXXII and XXXIII, wherein J is thienyl, pyrrolyl, furanyl, pyridyl, pyrimidyl, or pyrazinyl; K is phenyl; and $L^2$ is a bond.

In another embodiment, the invention provides the compound according to formulas XXXII and XXXIII, wherein J is thienyl, pyrrolyl, furanyl, pyridyl, pyrimidyl, or pyrazinyl; K is phenyl; $L^2$ is a bond; and $R^1$ is phenyl optionally substituted with one or more $R^{5a}$.

In another embodiment, the invention provides the compound according to formulas XXXII and XXXIII, wherein J is thienyl, pyrrolyl, furanyl, pyridyl, pyrimidyl, or pyrazinyl; K is phenyl; $L^2$ is a bond; $R^1$ is phenyl optionally substituted with one or more $R^{5a}$; and each $R^4$ is independently halogen, aryl, heteroaryl, heterocyclyl, -$G^{1'}$ or -E-$G^1$, wherein
E is —$[C(R^{15})_2]_m$—; and
$G^1$ is —$C_1$-$C_6$ alkyl, —$C_1$-$C_6$ haloalkyl, halogen, —$COR^{11}$, —$COOR^{11}$, —$CON(R^{11})_2$, —C≡N, —$OR^{11}$, —$N(R^{11})_2$, —$SO_2R^{11}$, —$SO_2N(R^{11})_2$, or —$SR^{11}$.

In another embodiment, the invention provides the compound according to formulas XXXII and XXXIII, wherein J is thienyl, pyrrolyl, furanyl, pyridyl, pyrimidyl, or pyrazinyl; K is phenyl; $L^2$ is a bond; $R^1$ is phenyl optionally substituted with one or more $R^{5a}$; and each $R^{41}$ is independently halogen, -$G^{1'}$ or -E-$G^1$, wherein
E is —$[C(R^{15})_2]_m$—,
wherein each $R^{15}$ is is independently hydrogen or halogen; and
$G^1$ is —$C_1$-$C_6$ alkyl, —$C_1$-$C_6$ haloalkyl, or halogen.

In another embodiment, the invention provides the compound according to formulas XXXII and XXXIII, wherein J is thienyl, pyrrolyl, furanyl, pyridyl, pyrimidyl, or pyrazinyl; K is phenyl; $L^2$ is a bond; $R^1$ is phenyl optionally substituted with one or more $R^{5a}$; and $R^2$ is -$L^3$-$R^7$, wherein
$L^3$ is a bond; and
$R^7$ is hydrogen, halogen, -Z, or —Y—Z, wherein
Y is —$[C(R^{15})_2]_m$—, —$(C_3$-$C_6)$cycloalkyl-, or $C_2$-$C_6$ alkenyl,
wherein each $R^{15}$ is independently H, halogen, or $(C_1$-$C_6)$alkyl; and
Z is —H, halogen, —$OR^{11}$, —C(=O)$R^{11}$, —C(=O)$OR^{11}$, —C(=O)N($R^{11})_2$, —C(=N—OH)$R^{11}$, or —C(=S)N($R^{11})_2$ In another embodiment, the invention provides the compound according to formulas XXXII and XXXIII, wherein J is thienyl, pyrrolyl, furanyl, pyridyl, pyrimidyl, or pyrazinyl; K is phenyl; $L^2$ is a bond; $R^1$ is phenyl optionally substituted with one or more $R^a$; and each $R^{5a}$ is independently halogen, $C_1$-$C_6$ alkyl, $C_1$-$C_6$ alkoxy, or $C_1$-$C_6$ haloalkyl.

In another embodiment, the invention provides the compound according to formulas XXXII and XXXIII, wherein J is heteroaryl; K is heteroaryl; and $L^2$ is a bond.

In another embodiment, the invention provides the compound according to formulas XXXII and XXXIII, wherein J is thienyl, pyrrolyl, furanyl, pyridyl, pyrimidyl, or pyrazinyl; K is pyridyl, pyrimidyl, or pyrazinyl; and $L^2$ is a bond.

In another embodiment, the invention provides the compound according to formulas XXXII and XXXIII, wherein J is thienyl, pyrrolyl, furanyl, pyridyl, pyrimidyl, or pyrazinyl; K is pyridyl, pyrimidyl, or pyrazinyl; $L^2$ is a bond; and $R^1$ is phenyl optionally substituted with one or more $R^{5a}$.

In another embodiment, the invention provides the compound according to formulas XXXII and XXXIII, wherein J is thienyl, pyrrolyl, furanyl, pyridyl, pyrimidyl, or pyrazinyl; K is pyridyl, pyrimidyl, or pyrazinyl; $L^2$ is a bond; $R^1$ is phenyl optionally substituted with one or more $R^{5a}$; and each $R^4$ is independently halogen, aryl, heteroaryl, heterocyclyl, -$G^1$' or -E-$G^1$, wherein E is —[C($R^{11}$)$_2$]$_m$—; and
$G^1$ is —$C_1$-$C_6$ alkyl, —$C_1$-$C_6$ haloalkyl, halogen, —COR$^{11}$, —COOR$^{11}$, —CON(R$^{11}$)$_2$, —C≡N, —OR$^{11}$, —N(R$^{11}$)$_2$, —SO$_2$R$^{11}$, —SO$_2$N(R$^{11}$)$_2$, or —SR$^{11}$.

In another embodiment, the invention provides the compound according to formulas XXXII and XXXIII, wherein J is thienyl, pyrrolyl, furanyl, pyridyl, pyrimidyl, or pyrazinyl; K is pyridyl, pyrimidyl, or pyrazinyl; $L^2$ is a bond; $R^1$ is phenyl optionally substituted with one or more $R^{5a}$; and each $R^{41}$ is independently halogen, -$G^1$' or -E-$G^1$, wherein E is —[C($R^{15}$)$_2$]$_m$—,
wherein each $R^{15}$ is independently hydrogen or halogen; and
$G^1$ is —$C_1$-$C_6$ alkyl, —$C_6$-$C_6$ haloalkyl, or halogen.

In another embodiment, the invention provides the compound according to formulas XXXII and XXXIII, wherein J is thienyl, pyrrolyl, furanyl, pyridyl, pyrimidyl, or pyrazinyl; K is pyridyl, pyrimidyl, or pyrazinyl; $L^2$ is a bond; $R^1$ is phenyl optionally substituted with one or more $R^{5a}$; and $R^2$ is -$L^3$-$R^7$, wherein $L^3$ is a bond; and
$R^7$ is hydrogen, halogen, -Z, or —Y—Z, wherein
Y is —[C($R^{15}$)$_2$]$_m$—, —($C_3$-$C_6$)cycloalkyl-, or $C_2$-$C_6$ alkenyl,
wherein each $R^{15}$ is independently H, halogen, or ($C_1$-$C_6$)alkyl; and
Z is —H, halogen, —OR$^{11}$, —C(=O)R$^{11}$, —C(=O)OR$^{11}$, —C(=O)N(R$^{11}$)$_2$, —C(=N—OH)R$^{11}$, or —C(=S)N(R$^{11}$)$_2$.

In another embodiment, the invention provides the compound according to formulas XXXII and XXXIII, wherein J is thienyl, pyrrolyl, furanyl, pyridyl, pyrimidyl, or pyrazinyl; K is pyridyl, pyrimidyl, or pyrazinyl; $L^2$ is a bond; $R^1$ is phenyl optionally substituted with one or more $R^{5a}$; and each $R^{5a}$ is independently halogen, $C_1$-$C_6$ alkyl, $C_1$-$C_6$ alkoxy, or $C_1$-$C_6$ haloalkyl.

In another embodiment, the invention provides the compound according to formulas XXXIV and XXXV,

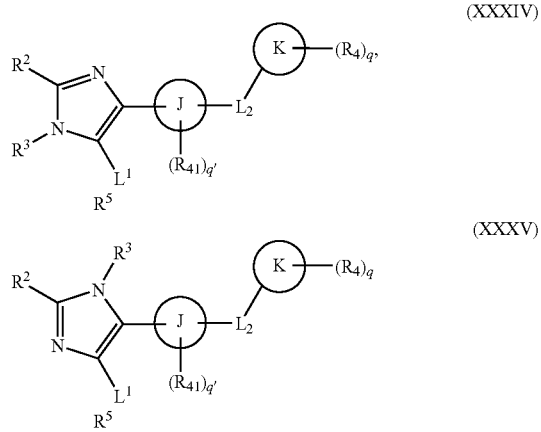

(XXXIV)

(XXXV)

or a pharmaceutically acceptable salt, isomer, or prodrug thereof, wherein $R^3$ is hydrogen, $C_1$-$C_6$ alkyl, or $C_1$-$C_6$ haloalkyl, and $R^{11}$, $R^2$, $R^4$, $R^{41}$, $L^2$, q, and q' are as defined for formulas IIa-d.

In another embodiment, the invention provides the compound according to formulas XXXIV and XXXV, wherein J is aryl; K is aryl; and $L^2$ is a bond.

In another embodiment, the invention provides the compound according to formulas XXXIV and XXXV, wherein J is phenyl; K is phenyl; and $L^2$ is a bond.

In another embodiment, the invention provides the compound according to formulas XXXIV and XXXV, wherein J is phenyl; K is phenyl; and $L^2$ is a bond; each $R^{15}$ is independently —H or —($C_1$-$C_2$)alkyl; m' is 1 or 2; and $R^{15}$ is heteroaryl optionally substituted with one or more $R^{5a}$.

In another embodiment, the invention provides the compound according to formulas XXXIV and XXXV, wherein J is phenyl; K is phenyl; and $L^2$ is a bond; each $R^{15}$ is independently —H or —($C_1$-$C_2$)alkyl; m' is 1 or 2; $R^{15}$ is heteroaryl optionally substituted with one or more $R^{5a}$; and $R^2$ is -$L^3$-$R^7$, wherein $L^3$ is a bond; and
$R^7$ is hydrogen, halogen, -Z, or —Y—Z, wherein
Y is —[C($R^{15}$)$_2$]$_m$— or $C_2$-$C_6$ alkenyl,
wherein each $R^{15}$ is independently H, halogen, or ($C_1$-$C_6$)alkyl; and
Z is —H, halogen, —OR$^{11}$, —C(=O)R$^{11}$, —C(=O)OR$^{11}$, —C(=O)N(R$^{11}$)$_2$, —C(=N—OH)R$^{11}$, or —C(=S)N(R$^{11}$)$_2$.

In another embodiment, the invention provides the compound according to formulas XXXIV and XXXV, wherein J is phenyl; K is phenyl; and $L^2$ is a bond; each $R^{15}$ is independently —H or —($C_1$-$C_2$)alkyl; m' is 1 or 2; $R^{15}$ is heteroaryl optionally substituted with one or more $R^{5a}$; and each $R^4$ is independently halogen, aryl, heteroaryl, heterocyclyl, -$G^1$, or -E-$G^1$, wherein E is —[C($R^{15}$)$_2$]$_m$—, wherein
each $R^{15}$ is independently hydrogen or halogen; and
$G^1$ is —$C_1$-$C_6$ alkyl, —$C_1$-$C_6$ haloalkyl, halogen, —OR$^{11}$, or —SO$_2$R$^{11}$.

In another embodiment, the invention provides the compound according to formulas XXXIV and XXXV, wherein J is phenyl; K is phenyl; and $L^2$ is a bond; each $R^{15}$ is independently —H or —($C_1$-$C_2$)alkyl; m' is 1 or 2; $R^{15}$ is heteroaryl optionally substituted with one or more $R^{5a}$; and each $R^{41}$ is independently halogen, -$G^1$, or -E-$G^1$, wherein E is —[C($R^{15}$)$_2$]$_m$—,
wherein each $R^{15}$ is independently hydrogen or halogen; and
$G^1$ is —$C_1$-$C_6$ alkyl, —$C_1$-$C_6$ haloalkyl, or halogen.

In another embodiment, the invention provides the compound according to formulas XXXIV and XXXV, wherein J is phenyl; K is phenyl; $L^2$ is a bond; and each $R^{15}$ is independently —H or —($C_1$-$C_2$)alkyl; m' is 1 or 2; and $R^{15}$ is phenyl optionally substituted with one or more $R^{5a}$.

In another embodiment, the invention provides the compound according to formulas XXXIV and XXXV, wherein J is phenyl; K is phenyl; $L^2$ is a bond; each $R^{15}$ is independently —H or —($C_1$-$C_2$)alkyl; m' is 1 or 2; and $R^{15}$ is phenyl optionally substituted with one or more $R^{5a}$; and each $R^4$ is independently halogen, aryl, heteroaryl, heterocyclyl, -$G^1$ or -E-$G^1$, wherein E is —[C($R^{15}$)$_2$]$_m$—; and
$G^1$ is —$C_1$-$C_6$ alkyl, —$C_1$-$C_6$haloalkyl, halogen, —COR$^{11}$, —COOR$^{11}$, —CON(R$^{11}$)$_2$, —CN, —OR$^{11}$, —N(R$^{11}$)$_2$, —SO$_2$R$^{11}$, —SO$_2$N(R$^{11}$)$_2$, or —SR$^{11}$.

In another embodiment, the invention provides the compound according to formulas XXXIV and XXXV, wherein J is phenyl; K is phenyl; $L^2$ is a bond; each $R^{15}$ is independently —H or —($C_1$-$C_2$)alkyl; m' is 1 or 2; and $R^{15}$ is phenyl optionally substituted with one or more $R^{5a}$; and each $R^{41}$ is independently halogen, -$G^1$ or -E-$G^1$, wherein E is —[C($R^{15}$)$_2$]$_m$—,
wherein each $R^{15}$ is independently hydrogen or halogen; and
$G^1$ is —$C_1$-$C_6$ alkyl, —$C_1$-$C_6$ haloalkyl, or halogen.

In another embodiment, the invention provides the compound according to formulas XXXIV and XXXV, wherein J is phenyl; K is phenyl; $L^2$ is a bond; each $R^{15}$ is independently —H or —($C_1$-$C_2$)alkyl; m' is 1 or 2; and $R^5$ is phenyl optionally substituted with one or more $R^{5a}$; and $R^2$ is -$L^3$-$R^7$, wherein $L^3$ is a bond; and $R^7$ is hydrogen, halogen, -Z, or —Y—Z, wherein
Y is —[C($R^{15}$)$_2$]$_m$—, —($C_3$-$C_6$)cycloalkyl-, or $C_2$-$C_6$ alkenyl,
wherein each $R^{15}$ is independently H, halogen, or ($C_1$-$C_6$)alkyl; and
Z is —H, halogen, —$OR^{11}$, —C(=O)$R^{11}$, —C(=O)$OR^{11}$, —C(=O)N($R^{11}$)$_2$, —C(=N—OH)$R^{11}$, or —C(=S)N($R^{11}$)$_2$.

In another embodiment, the invention provides the compound according to formulas XXXIV and XXXV, wherein J is phenyl; K is phenyl; $L^2$ is a bond; each $R^{15}$ is independently —H or —($C_1$-$C_2$)alkyl; m' is 1 or 2; and $R^{15}$ is phenyl optionally substituted with one or more $R^{5a}$; and each $R^{5a}$ is independently halogen, $C_1$-$C_6$ alkyl, $C_1$-$C_6$ alkoxy, or $C_1$-$C_6$ haloalkyl.

In another embodiment, the invention provides the compound according to formulas XXXIV and XXXV, wherein J is phenyl; K is phenyl; $L^2$ is a bond; $R^{15}$ is —H; m is 1, 2, or 3; and $R^{15}$ is heterocyclyl optionally substituted with one or more $R^{5a}$.

In another embodiment, the invention provides the compound according to formulas XXXIV and XXXV, wherein J is phenyl; K is phenyl; $L^2$ is a bond; $R^{15}$ is —H; m is 1, 2, or 3;
$R^{15}$ is heterocyclyl optionally substituted with one or more Rsa; and each $R^4$ is independently halogen, aryl, heteroaryl, heterocyclyl, -$G^{1'}$ or -E-$G^1$, wherein
E is —[C($R^{15}$)$_2$]$_m$—; and
$G^1$ is —$C_1$-$C_6$ alkyl, —$C_1$-$C_6$ haloalkyl, halogen, —$COR^{11}$, —$COOR^{11}$, —CON($R^{11}$)$_2$, —C≡N, —$OR^{11}$, —N($R^{11}$)$_2$, —$SO_2R^{11}$, —$SO_2N(R^{11})_2$, or —$SR^{11}$.

In another embodiment, the invention provides the compound according to formulas XXXIV and XXXV, wherein J is phenyl; K is phenyl; $L^2$ is a bond; $R^{15}$ is —H; m is 1, 2, or 3; $R^{15}$ is heterocyclyl optionally substituted with one or more $R^{5a}$; and each $R^{41}$ is independently halogen, -$G^{1'}$ or -E-$G^1$, wherein
E is —[C($R^{15}$)$_2$]$_m$—,
wherein each $R^{15}$ is independently hydrogen or halogen; and
$G^1$ is —$C_1$-$C_6$ alkyl, —$C_1$-$C_6$ haloalkyl, or halogen.

In another embodiment, the invention provides the compound according to formulas XXXIV and XXXV, wherein J is phenyl; K is phenyl; $L^2$ is a bond; $R^{15}$ is —H; m is 1, 2, or 3;
$R^{15}$ is heterocyclyl optionally substituted with one or more $R^{5a}$; and $R^2$ is -$L^3$-$R^7$, wherein
$L^3$ is a bond; and
$R^7$ is hydrogen, halogen, -Z, or —Y—Z, wherein
Y is —[C($R^{15}$)$_2$]$_m$—, —($C_3$-$C_6$)cycloalkyl-, or $C_2$-$C_6$alkenyl,
wherein each $R^{15}$ is independently H, halogen, or ($C_1$-$C_6$)alkyl; and
Z is —H, halogen, —$OR^{11}$, —C(=O)$R^{11}$, —C(=O)$OR^{11}$, —C(=O)N($R^{11}$)$_2$, —C(=N—OH)$R^{11}$, or —C(=S)N($R^{11}$)$_2$.

In another embodiment, the invention provides the compound according to formulas XXXIV and XXXV, wherein J is phenyl; K is phenyl; $L^2$ is a bond; $R^{15}$ is —H; m is 1, 2, or 3; $R^{15}$ is heterocyclyl optionally substituted with one or more $R^{5a}$; and each $R^{5a}$ is independently halogen, $C_1$-$C_6$ alkyl, $C_1$-$C_6$ alkoxy, or $C_1$-$C_6$ haloalkyl.

In another embodiment, the invention provides the compound according to formula IIa-d, wherein J is aryl or heteroaryl.

In another embodiment, the invention provides the compound according to formula IIa-d, wherein J is phenyl, pyridyl, thienyl, pyrrolyl, furanyl, pyrimidinyl, pyrazinyl, imidazoyl, pyrazoyl, oxazoyl, thiazoyl, isoxazoyl, isothiazoyl, triazoyl, triazinyl, tetrazoyl, or tetrazinyl.

In another embodiment, the invention provides the compound according to formula IIa-d, wherein J is phenyl, pyridyl, thienyl, pyrrolyl, or furanyl.

In another embodiment, the invention provides the compound according to formula IIa-d, wherein J is phenyl, pyridyl, or thienyl.

In another embodiment, the invention provides the compound according to formula IIa-d, wherein J is phenyl.

In another embodiment, the invention provides the compound according to formula IIa-d, wherein J is pyridyl.

In another embodiment, the invention provides the compound according to formula IIa-d, wherein J is thienyl.

In another embodiment, the invention provides the compound according to formula IIa-d, wherein K is aryl or heteroaryl.

In another embodiment, the invention provides the compound according to formula IIa-d, wherein K is phenyl, pyridyl, thienyl, pyrrolyl, furanyl, pyrimidinyl, pyrazinyl, imidazoyl, pyrazoyl, oxazoyl, thiazoyl, isoxazoyl, isothiazoyl, triazoyl, triazinyl, tetrazoyl, or tetrazinyl.

In another embodiment, the invention provides the compound according to formula IIa-d, wherein K is phenyl, pyridyl, thienyl, pyrrolyl, or furanyl.

In another embodiment, the invention provides the compound according to formula IIa-d, wherein K is phenyl or pyridyl.

In another embodiment, the invention provides the compound according to formula IIa-d, wherein K is pyridyl.

In another embodiment, the invention provides the compound according to formula IIa-d, wherein K is phenyl.

In another embodiment, the invention provides the compound according to formula IIa-d, wherein $L^2$ is a bond.

In another embodiment, the invention provides the compound according to formula IIa-d, wherein J is aryl or heteroaryl; and K is aryl or heteroaryl.

In another embodiment, the invention provides the compound according to formula IIa-d, wherein J is aryl or heteroaryl; K is aryl or heteroaryl; and $L^2$ is a bond.

In another embodiment, the invention provides the compound according to formula IIa-d, wherein
J is phenyl, pyridyl, thienyl, pyrrolyl, furanyl, pyrimidinyl, pyrazinyl, imidazoyl, pyrazoyl, oxazoyl, thiazoyl, isoxazoyl, isothiazoyl, triazol, triazinyl, tetrazoyl, or tetrazinyl;
K is phenyl, pyridyl, thienyl, pyrrolyl, furanyl, pyrimidinyl, pyrazinyl, imidazoyl, pyrazoyl, oxazoyl, thiazoyl, isoxazoyl, isothiazoyl, triazolyl, triazinyl, tetrazoyl, or tetrazinyl; and
$L^2$ is a bond.

In another embodiment, the invention provides the compound according to formula IIa-d, wherein J is phenyl, pyridyl, thienyl, pyrrolyl, or furanyl; K is phenyl, pyridyl, thienyl, pyrrolyl, or furanyl; and $L^2$ is a bond.

In another embodiment, the invention provides the compound according to formula IIa-d, wherein J is phenyl, pyridyl, or thienyl; K is phenyl or pyridyl; and $L^2$ is a bond.

In another embodiment, the invention provides the compound according to formula IIIa-d, wherein J is phenyl; K is phenyl; and $L^2$ is a bond.

In another embodiment, the invention provides the compound according to formula IIa-d, wherein J is pyridyl; K is phenyl; and $L^2$ is a bond.

In another embodiment, the invention provides the compound according to formula IIa-d, wherein J is thienyl; K is phenyl; and $L^2$ is a bond.

In another embodiment, the invention provides the compound according to formula IIa-d, wherein J is phenyl; K is pyridyl; and $L^2$ is a bond.

In another embodiment, the invention provides the compound according to formula IIa-d, wherein J is pyridyl; K is pyridyl; and $L^2$ is a bond.

In another embodiment, the invention provides the compound according to formula IIa-d, wherein J is thienyl; K is pyridyl; and $L^2$ is a bond.

In another embodiment, the invention provides the compound according to formula IIa-d, wherein $R^{15}$ is aryl, heterocyclyl, or heteroaryl, wherein $R^{15}$ is optionally substituted with one or more $R^{5a}$.

In another embodiment, the invention provides the compound according to formula IIa-d, wherein $R^{15}$ is aryl or heteroaryl, wherein $R^5$ is optionally substituted with one or more $R^{5a}$.

In another embodiment, the invention provides the compound according to formula IIa-d, wherein $R^{15}$ is phenyl, pyridyl, thienyl, pyrrolyl, furanyl, pyrimidinyl, pyrazinyl, imidazoyl, pyrazoyl, oxazoyl, thiazoyl, isoxazoyl, isothiazoyl, triazoyl, triazinyl, tetrazoyl, or tetrazinyl wherein $R^5$ is optionally substituted with one or more $R^{5a}$.

In another embodiment, the invention provides the compound according to formula IIa-d, wherein $L^1$ is a bond; and $R^{15}$ is phenyl, pyridyl, thienyl, pyrrolyl, furanyl, pyrimidinyl, pyrazinyl, imidazoyl, pyrazoyl, oxazoyl, thiazoyl, isoxazoyl, isothiazoyl, triazoyl, triazinyl, tetrazoyl, or tetrazinyl, wherein $R^{15}$ is optionally substituted with one or more $R^{5a}$.

In another embodiment, the invention provides the compound according to formula IIa-d, wherein $L^1$ is a bond; and $R^{15}$ is phenyl, pyridyl, thienyl, pyrrolyl, or furanyl, wherein $R^5$ is optionally substituted with one or more $R^{5a}$.

In another embodiment, the invention provides the compound according to formula IIa-d, wherein $L^1$ is a bond; and $R^{15}$ is phenyl optionally substituted with one or more $R^{5a}$.

In another embodiment, the invention provides the compound according to formula IIa-d, wherein $L^1$ is a bond; and $R^5$ is pyridyl optionally substituted with one or more $R^{5a}$.

In another embodiment, the invention provides the compound according to formula IIa-d, wherein $L^1$ is a bond; and $R^{15}$ is thienyl optionally substituted with one or more $R^{5a}$.

In another embodiment, the invention provides the compound according to formula IIa-d wherein $R^{21}$ is hydrogen, halogen, nitro, cyano, aryl, heteroaryl, heterocyclyl, —$C_1$-$C_6$ alkyl-heterocyclyl, —$C_1$-$C_6$ alkyl-heteroaryl, —$C_1$-$C_6$ alkyl-aryl, -Z, —Y—Z, or —X—Y—Z, wherein
X is —O—;
Y is —[C(R$^{15}$)$_2$]$_m$—, —$C_2$-$C_6$ alkenyl, or $C_3$-$C_8$ cycloalkyl; and Z is —H, —CN, halogen, —OR$^{11}$, —C(=O)R$^{11}$, —C(=O)OR$^{11}$, —C(=O)N(R$^{11}$)$_2$, —N(R$^{11}$)$_2$, —CN, —N$_3$, —SO$_2$R$^1$, —S(=O)$_2$N(R$^{11}$)$_2$, —C(=O)N(R$^{11}$)N(R$^{11}$)$_2$, —C(=O)N(R$^{11}$)(OR$^{11}$), —OC(=O)—R$^1$, —OC(=O)—N(R$^{11}$)$_2$, or —N(R$^{11}$)COOR$^{11}$.

In another embodiment, the invention provides the compound according to formula IIa-d wherein $R^{21}$ is hydrogen, halogen, nitro, cyano, $C_1$-$C_6$ alkyl, or $C_1$-$C_6$ haloalkyl.

In another embodiment, the invention provides the compound according to formula IIa-d wherein $R^3$ is hydrogen, aryl, heteroaryl, heterocyclyl, —$C_1$-$C_6$ alkyl-heterocyclyl, —$C_1$-$C_6$ alkyl-heteroaryl, —$C_1$-$C_6$ alkyl-aryl, -Z, or —Y—Z wherein
Y is —[C(R$^{15}$)$_2$]$_m$—, —$C_2$-$C_6$ alkenyl, or $C_3$-$C_8$ cycloalkyl; and
Z is —H, —CN, halogen, —OR$^{11}$, —C(=O)R$^{11}$, —C(=O)OR$^{11}$, —C(=O)N(R$^{11}$)$_2$, —N(R$^{11}$)$_2$, —CN, —N$_3$, —SO$_2$R$^{11}$, —S(=O)$_2$N(R$^{11}$)$_2$, —C(=O)N(R$^{11}$)N(R$^{11}$)$_2$, —C(=O)N(R$^{11}$)(OR$^{11}$), —OC(=O)—R$^{11}$, —OC(=O)—N(R$^{11}$)$_2$, or —N(R$^{11}$)COOR$^{11}$.

In another embodiment, the invention provides the compound according to formula IIa-d wherein $R^3$ is hydrogen, $C_1$-$C_6$ alkyl, or $C_1$-$C_6$ haloalkyl.

In another embodiment, the invention provides the compound according to any of the formulas IIa-d, IIIa-d, IVa-d, IV-XXIV, and XXVI-XXXV wherein $R^2$ is -$L^3$-$R^7$, wherein $L^3$ is a bond; and
$R^7$ is hydrogen, halogen, -Z, or —Y—Z, wherein
Y is —[C(R$^{15}$)$_2$]$_m$—, —($C_3$-$C_6$)cycloalkyl-, or $C_2$-$C_6$ alkenyl,
wherein each $R^{15}$ is independently H, halogen, or ($C_1$-$C_6$)alkyl; and
Z is —H, halogen, —OR$^{11}$, —C(=O)R$^{11}$, —C(=O)OR$^{11}$, —C(=O)N(R$^{11}$)$_2$, —C(=N—OH)R$^{11}$, or —C(=S)N(R$^{11}$)$_2$.

In another embodiment, the invention provides the compound according to any of the formulas IIa-d, IIIa-d, IVa-d, IV-XXV, and XXVI-XXXV, wherein $R^2$ is -$L^3$-$R^7$, wherein $L^3$ is a bond; and
$R^7$ is hydrogen, halogen, or —[C(R$^{15}$)$_2$]—Z, wherein each $R^{15}$ is is independently H, halogen, or ($C_1$-$C_2$) alkyl; and
Z is —H, halogen, —OR$^{11'''}$, —C(=O)R$^{11'''}$, —C(=O)OR$^{11'''}$, —C(=O)N(R$^{11'''}$)$_2$, —C(=N—OH)R$^{11'''}$, or —C(=S)N(R$^{11'''}$)$_2$,
wherein $R^{11'''}$ is —H or —($C_1$-$C_6$ alkyl).

In another embodiment, the invention provides the compound according to any of the formulas IIa-d, IIIa-d, IVa-d, IV-XXIV, and XXVI-XXXV, wherein $R^2$ is -halogen, —CF$_3$, —CH$_2$OH, —CH$_2$SO$_2$ Me, —C(CH$_3$)$_2$OH, or —C(CH$_3$)$_2$SO$_2$ Me.

In another embodiment, the invention provides the compound according to any of the formulas IIa-d, IIIa-d, IVa-d, IV-XXIV, and XXVI-XXXV, wherein $R^2$ is -halogen, —CF$_3$, —CH$_2$OH, or —C(CH$_3$)$_2$OH.

In another embodiment, the invention provides the compound according to any of the formulas IIa-d, IIa-d, IVa-d, IV-XXIV, and XXVI-XXXV, wherein $R^2$ is —CF$_3$ or —C(CH$_3$)$_2$OH.

In another embodiment, the invention provides the compound according to any of the formulas IIa-d, IIIa-d, IVa-d, IV-XXIV, and XXVI-XXXV, wherein
each $R^4$ is independently halogen, aryl, heteroaryl, heterocyclyl, -G$^1$ or -E-G, wherein
E is —[C(R$^{15}$)$_2$]$_m$—, wherein
each $R^{15}$ is is independently hydrogen or halogen; and $G^1$ is —$C_1$-$C_6$ alkyl, —$C_1$-$C_6$ haloalkyl, halogen, —$OR^{11}$, or —$SO_2R^{11}$.

In another embodiment, the invention provides the compound according to any of the formulas IIa-d, IIa-d, IVa-d, IV-XXIV, and XXVI-XXXV, wherein
each $R^4$ is independently halogen, —$CH_2$— $G^1$, —C(H)(F)— $G^1$, —$CF_2$— $G^1$, wherein
$G^1$ is —$C_1$-$C_6$ alkyl, —$C_1$-$C_6$ haloalkyl, —F, —$OR^{11'}$, or —$SO_2R^{11'}$
wherein $R^{11'}$ is —H or —$C_1$-$C_6$ alkyl.

In another embodiment, the invention provides the compound according to any of the formulas IIa-d, IIIa-d, IVa-d, IV-XXIV, and XXVI-XXXV, wherein each $R^4$ is independently —$CH_3$, —$CF_3$, —$CF_2H$, —$CH_2F$, —OH, —OMe, —$CH_2OH$, or —$SO_2$ ($C_1$-$C_3$ alkyl).

In one embodiment, the invention provides the compound according to any of the formulas IIa-d, IIa-d, IVa-d, IV-XXIV, and XXVI-XXXV, wherein
each $R^{41}$ is independently halogen, -$G^1$ or -E-$G^1$, wherein
E is —[C($R^{15}$)$_2$]$_m$—,
wherein each $R^{15}$ is independently hydrogen or halogen; and
$G^1$ is —$C_1$-$C_6$ alkyl, —$C_1$-$C_6$ haloalkyl, or halogen.

In another embodiment, the invention provides the compound according to formulas IIa-d, IIIa-d, Iva-d, IV-XXIV, and XXVI-XXXV, wherein each $R^{41}$ is independently halogen, methyl or trifluoromethyl.

In another embodiment, the invention provides the compound according to formulas to formulas IIa-d, IIa-d, IVa-d, IV-XXIV, and XXVI-XXXV, wherein $R^{21}$ is hydrogen, halogen, nitro, cyano, aryl, heteroaryl, heterocyclyl, —$C_1$-$C_6$ alkyl-heterocyclyl, —$C_1$-$C_6$ alkyl-heteroaryl, —$C_1$-$C_6$ alkyl-aryl, -Z, —Y—Z, or —X—Y—Z, wherein
X is —O—;
Y is —[C($R^{15}$)$_2$]$_m$—, —$C_2$-$C_6$ alkenyl, or $C_3$-$C_8$ cycloalkyl;
Z is —H, —CN, halogen, —$OR^{11}$, —C(=O)$R^{11}$, —C(=O)$OR^{11}$, —C(=O)N($R^{11}$)$_2$, —N($R^{11}$)$_2$, —CN, —$N_3$, —$SO_2R^{11}$, —S(=O)$_2$N($R^{11}$)$_2$, C(=O)N($R^{11}$)N($R^{11}$)$_2$, —C(=O)N($R^{11}$)(O$R^{11}$), —OC(=O)—$R^{11}$, —OC(=O)—N($R^{11}$)$_2$, or —N($R^{11}$)COO$R^{11}$;

In another embodiment, the invention provides the compound according to formulas IIa-d, IIIa-d, IVa-d, IV-XXIV, and XXVI-XXXV, wherein $R^{21}$ is hydrogen, halogen, nitro, cyano, $C_1$-$C_6$alkyl, or $C_1$-$C_6$ haloalkyl.

In another embodiment, the invention provides the compound according to formula IIa-d, wherein $R^1$ is -$L^1$-$R^5$, wherein $L^1$ is a bond, —[C($R^{15}$)$_2$]$_m$—, or —$C_3$-$C_8$ cycloalkyl-; and
$R^5$ is phenyl or pyridyl, each optionally substituted with one or two $R^{5a}$, wherein each $R^{5a}$ is independently -halogen, —$C_1$-$C_6$ alkoxy, —$C_1$-$C_6$ alkyl, or —$C_t$-$C_6$ haloalkyl;
$R^2$, $R^{21}$, and $R^3$ are each independently —H, —[C($R^{15}$)$_2$]$_m$—OH, —$C_1$-$C_6$ alkyl, —$C_1$-$C_6$ haloalkyl, halogen, —C(O)N($R^{11}$)$_2$, or —COO$R^{11}$;
$L^2$ is a bond;
J is phenyl, pyridyl, or thienyl;
K is phenyl, or pyridyl;
each $R^{41}$ is -halogen, —$C_1$-$C_6$ alkyl, or $C_1$-$C_6$-haloalkyl; and
each $R^4$ is -halogen, —[C($R^{15}$)$_2$]$_m$—OH, —$SO_2R^{11}$, —$SO_2N(R^{11})_2$, —C(O)N($R^{11}$)$_2$, —COO$R^{11}$, —$C_1$-$C_6$ alkyl, or —$C_1$-$C_6$ haloalkyl.

In another embodiment, the invention provides the compound according to formula IVa-d, wherein
$R^1$ is -$L^1$-$R^5$, wherein
$L^1$ is a bond, —[C($R^{15}$)$_2$]$_m$—, or —$C_3$-$C_8$ cycloalkyl-; and
$R^5$ is phenyl or pyridyl, each optionally substituted with one or two $R^{5a}$, wherein
each $R^{5a}$ is independently -halogen, —$C_1$-$C_6$ alkoxy, —$C_1$-$C_6$ alkyl, or —$C_1$-$C_6$ haloalkyl;
$R^2$, $R^{21}$, and $R^3$ are each independently —H, —[C($R^{15}$)$_2$]$_m$—OH, —$C_1$-$C_6$ alkyl, —$C_1$-$C_6$ haloalkyl, halogen, —C(O)N($R^{11}$)$_2$, or —COO$R^{11}$;
$L^2$ is a bond;
J is phenyl, pyridyl, or thienyl;
K is phenyl; or pyridyl;
each $R^{41}$ is -halogen, —$C_1$-$C_6$ alkyl, or $C_1$-$C_6$-haloalkyl; and
each $R^4$ is -halogen, —[C($R^{15}$)$_2$]$_m$—OH, —$SO_2R^{11}$, —$SO_2N(R^{11})_2$, —C(O)N($R^{11}$)$_2$, —COO$R^{11}$, —$C_1$-$C_6$ alkyl, or —$C_1$-$C_6$ haloalkyl.

In a second aspect, the invention provides intermediate compounds according to one of the formulas XXVa-d,

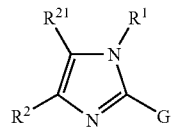

XXVa

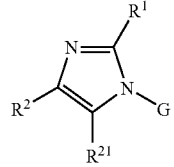

XXVb

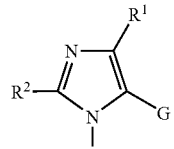

XXVc

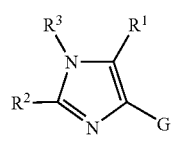

XXVd or a pharmaceutically acceptable salt, isomer, or prodrug thereof, wherein,
$R^1$ is -$L^1$-$R^5$, wherein
$L^1$ is a bond, $L^5$, $L^6$, -$L^5$-$L^6$-$L^5$-, or -$L^6$-$L^5$-$L^6$-, wherein
each $L^5$ is independently —[C($R^{15}$)$_2$]$_m$—, wherein
each $R^{15}$ is independently hydrogen, halogen, ($C_1$-$C_6$)alkyl, or ($C_1$-$C_6$)haloalkyl; and
each $L^6$ is independently —CS—, —CO—, —$SO_2$—, —O—, —CON($R^{11}$)—, —CON$R^{11}$N($R^{11}$)—, —C(=N$R^1$)—, —C(=NO$R^{11}$)—, or —C(=NN($R^{11}$)$_2$)—, -aryl, —$C_3$-$C_8$ cycloalkyl-, -heteroaryl-, or -heterocyclyl-;
wherein the aryl, cycloalkyl, heteroaryl, or heterocyclyl is optionally substituted with one or more $R^{14}$;
or each $L^6$ is independently $C_2$-$C_6$ alidiyl, wherein the alidiyl chain is optionally interrupted by  
—C($R^{11}$)$_2$—, —C($R^{11}$)$_2$C($R^{11}$)$_2$—, —C($R^{11}$)=C($R^{11}$)—, —C($R^{11}$)$_2$O—, —C($R^{11}$)$_2$N$R^{11}$—, —C≡C—, —O—, —S—, —N($R^{10}$)CO—, —N($R^{10}$)CO$_2$—, —CON($R^{10}$)—, —CO—, —CO$_2$—, —OC(=O)—, —OC(=O)N($R^{10}$)—, —SO$_2$—, —N($R^{10}$)SO$_2$—, or —SO$_2$N($R^{10}$); and  
$R^5$ is aryl, heterocyclyl, heteroaryl, —C, or —B—C, wherein  
B is —[C($R^{15}$)$_2$]$_m$— or —C$_3$-C$_8$ cycloalkyl-; and  
C is halogen, —C$_1$-C$_6$ alkyl, —C$_1$-C$_6$ haloalkyl, —SO$_2$$R^{11}$, —S$R^{11}$, —SO$_2$N($R^{11}$)$_2$, —SO$_2$N$R^{11}$CO$R^{11}$, —C≡N, —C(O)O$R^{11}$, —CON($R^{11}$)$_2$, or —N($R^{11}$)$_2$,  
wherein $R^{15}$ is optionally substituted with one or more $R^{5a}$, wherein  
each $R^{5a}$ is independently halogen, nitro, heteroaryl, heterocyclyl, C$_2$-C$_6$ alkenyl, C$_2$-C$_6$ alkynyl, C$_3$-C$_8$ cycloalkyl, (C$_3$-C$_8$cycloalkyl)-C$_1$-C$_6$ alkyl-, (C$_3$-C$_8$ cycloalkenyl)-C$_1$-C$_6$ alkyl-, (C$_3$-C$_8$ cycloalkyl)-C$_2$-C$_6$ alkenyl-, aryl, arylalkyl, aryloxy, aryloxyaryl, arylC$_{1-6}$lkoxy, C$_1$-C$_6$ alkyl, C$_1$-C$_6$ haloalkyl, SO$_{02}$$R^{11}$, O$R^{11}$, S$R^{11}$, N$_3$, SO$_2$$R^{11}$, CO$R^{11}$, SO$_2$N($R^{11}$)$_2$, SO$_2$N$R^{11}$CO$R^{11}$, C≡N, C(O)O$R^{11}$, CON($R^{11}$)$_2$, CON($R^{11}$)O$R^{11}$OCON($R^{11}$)$_2$, N$R^{11}$CO$R^{11}$, N$R^{11}$CON($R^{11}$)$_2$, N$R^{11}$COO$R^{11}$, or N($R^{11}$)$_2$, wherein  
each $R^{5a}$ is optionally substituted with one or more groups which independently are -halogen, —C$_1$-C$_6$ alkyl, aryloxy C$_0$-C$_6$ alkylSO$_2$$R^{11}$, C$_{1-6}$ alkyl-COO$R^{11}$, C$_{0-6}$ alkoxyaryl, C$_1$-C$_6$ haloalkyl, —SO$_2$$R^{11}$, —O$R^{11}$, —S$R^{11}$, —N$_3$, —SO$_2$$R^{11}$, —CO$R^{11}$, SO$_2$N($R^{11}$)$_2$, —SO$_2$N$R^{11}$CO$R^{11}$, —C≡N, —C(O)O$R^{11}$, —CON($R^{11}$)$_2$, —CON($R^{11}$)O$R^{11}$, —OCON($R^{11}$)$_2$—N$R^{11}$CO$R^{11}$, —N$R^{11}$CON($R^{11}$)$_2$, —N$R^{11}$COO$R^{11}$, or —N($R^{11}$)$_2$;

$R^2$ and $R^{21}$ are -L$^3$-$R^7$, wherein  
each L$^3$ is independently a bond or —(CH$_2$)$_m$-V$^1$—(CH$_2$)$_n$— wherein  
n is 0-6; and  
V$^1$ is —C($R^{11}$)$_2$—, —C($R^{11}$)$_2$C($R^{11}$)$_2$, —C($R^{11}$)=C($R^{11}$)—, —C($R^{11}$)$_2$—, —C($R^{11}$)$_2$N$R^{11}$—, —C≡C—, —O—, —S—, —N$R^{10}$—, —N($R^{10}$)CO—, —N($R^{10}$)CO$_2$—, —OCO—, —CO—, —CS—, —CON$R^{10}$—, —C(=N—$R^{11}$)—, —C(=N—O$R^{11}$)—, —C[=N—N($R^{11}$)$_2$], —CO$_2$—, —OC(=O)—, —OC(=O)N($R^{10}$)—, —SO$_2$—, —N($R^{10}$)SO$_2$—, —SO$_2$N($R^{10}$)—, —N$R^{10}$CON$R^{10}$—, —N$R^{10}$CSN$R^{10}$—, C$_3$-C$_6$ cycloalkyl, or C$_3$-C$_6$ cyclohaloalkyl;  
or each L$^3$ is independently C$_2$-C$_6$ alidiyl,  
wherein the alidiyl chain is optionally interrupted by —C($R^{11}$)$_2$—, —C($R^{11}$)$_2$C($R^{11}$)$_2$—, —C($R^{11}$)=C($R^{11}$)—, —C($R^{11}$)$_2$O—, —C($R^{11}$)$_2$N$R^{11}$—, —C≡C—, —O—, —S—, —N($R^{10}$)CO—, —N($R^{10}$)CO$_2$—, —N$R^{11}$—, —CON($R^{10}$)—, —CO—, —CO$_2$—, —OC(=O)—, —OC(=O)N($R^{10}$)—, —SO$_2$—, —N($R^{10}$)SO$_2$—, or —SO$_2$N($R^{10}$)—; and  
each $R^7$ is independently hydrogen, halogen, nitro, aryl, heteroaryl, heterocyclyl, -Z, —Y—Z, or —X—Y—Z, wherein  
X is —O—;  
Y is —[C($R^{15}$)$_2$]$_m$— or C$_2$-C$_6$ alkenyl, —C$_3$-C$_8$cycloalkyl; and  
Z is —H, halogen, —O$R^{11}$, —C(=O)$R^{11}$, —C(=O)O$R^{11}$, —C(=O)N($R^{11}$)$_2$, —N($R^{11}$)$_2$, —C(=N—OH)$R^{11}$, —C(=S)N($R^{11}$)$_2$, —CN, —S(=O)$_2$N($R^{11}$)$_2$, —C(=O)N($R^{11}$)N($R^{11}$)$_2$, —C(=O)N($R^{11}$)(O$R^{11}$), —OC(=O)—$R^{11}$, or —OC(=O)—N($R^{)}$)$_2$,  
wherein $R^7$ is optionally substituted with one or more $R^{7a}$, wherein  
$R^{7a}$ is halogen, haloaryl, aryloxy, aralkyloxy, aryloxyalkyl, arylC$_0$-C$_6$ alkylcarboxy, C($R^{11}$)=C($R^{11}$)—COOH, aryl, heteroaryl, heterocyclyl, heterocyclyloxy, heteroaryloxy, —Z', —Y'—Z', or —X'—Y'—Z', wherein  
X' is —O—;  
Y' is —[C($R^{15}$)$_2$]$_m$— or —C$_3$-C$_8$cycloalkyl; and  
Z' is —H, halogen, —O$R^{11}$, —S$R^{11}$, —S(=O)$_2$$R^{11}$, —C(=O)$R^{11}$, —C(=O)O$R^{11}$, —C(=O)N($R^{11}$)$_2$, —N($R^{11}$)$_2$, —N($R^{11}$)C(=O)$R^{11}$, —S(=O)$_2$N($R^{11}$)C(=O)$R^{11}$, —CN, —S(=O)$_2$N($R^{11}$)$_2$, —C(=O)N($R^{11}$)N($R^{11}$)$_2$, —C(=O)N($R^{11}$)(O$R^{11}$), —OC(=O)—$R^{11}$, —OC(=O)—O$R^{11}$, —N($R^{11}$)C(=O)—$R^{11}$, or —N($R^{11}$)S(O=)$_2$$R^{11}$,  
wherein each $R^{7a}$ is optionally substituted with one or more $R^8$,  
wherein each $R^8$ is independently halogen, C$_1$-C$_6$ alkyl, C$_1$-C$_6$ alkoxy, C$_1$-C$_6$ haloalkyl, C$_1$-C$_6$ haloalkyl(O$R^{11}$), C$_0$-C$_6$ alkylO$R^{11}$, C$_0$-C$_6$ alkylCON($R^{11}$)$_2$, C$_0$-C$_6$ alkylCO$R^{11}$, C$_0$-C$_6$ alkylCOO$R^{11}$, or C$_0$-C$_6$ alkylSO$_2$$R^{11}$,  
provided that $R^2$ and $R^{21}$ are not simultaneously hydrogen  
$R^3$ is -L-$R^6$, wherein  
L is a bond, —X$^3$—(CH$_2$)$_n$—X$^3$—, —(CH$_2$)$_m$—X$^3$—(CH$_2$)$_n$— or —(CH$_2$)$_{1+w}$—Y$^3$—(CH$_2$)$_w$— wherein  
n is 0-6; each w is independently 0-5; and  
each X$^3$ is independently a bond, —C($R^{11}$)$_2$—, —C($R^{11}$)$_2$C($R^{11}$)$_2$—, —C($R^{11}$)($R^{11}$)—, —C≡C—, —CO—, —CS—, —CON$R^{10}$—, —C(=N)($R^{11}$)—, —C(=N—O$R^{11}$)—, —C[=N—N($R^{11}$)$_2$], —CO$_2$—, —SO$_2$—, or —SO$_2$N($R^{10}$)—; and  
Y$^3$ is —O—, —S—, —N$R^7$—, —N($R^{10}$)CO—, —N($R^{10}$)CO$_2$—, —OCO—, —OC(=O)N($R^{10}$)—, —N$R^{10}$CON$R^{10}$—, —N($R^{10}$)SO$_2$—, or —N$R^{10}$CSN$R^{10}$—;  
or L is C$_{2-6}$ alidiyl chain wherein the alidiyl chain is optionally interrupted by —C($R^{11}$)$_2$—, —C($R^{11}$)$_2$C($R^{11}$)$_2$—, —C($R^{11}$)=C($R^{11}$)—, —C($R^{11}$)$_2$O—, —C($R^{11}$)$_2$N$R^{11}$—, —C≡C—, —O—, —S—, —N($R^{10}$)CO—, —N($R^{10}$)CO$_2$—, —CON($R^{10}$)—, —CO—, —CO$_2$—, —OC(=O)—, —OC(=O)N($R^{10}$)—, —SO$_2$—, —N($R^{11}$)SO$_2$—, or —SO$_2$N($R^{10}$); and  
$R^6$ is C$_1$-C$_6$ alkyl, C$_1$-C$_6$ haloalkyl, aryl, C$_3$-C$_8$ cycloalkyl, heteroaryl, heterocyclyl, —CN, —C(=O)$R^{11}$, —C(=O)O$R^{11}$, —C(=O)N($R^{11}$)$_2$, —N($R^{11}$)$_2$, —SO$_2$$R^{11}$, —S(=O)$_2$N($R^{11}$)$_2$, —C(=O)N($R^{11}$)N($R^{11}$)$_2$, or —C(=O)N($R^{11}$)(O$R^{11}$), wherein  
the aryl, heteroaryl, cycloalkyl, or heterocyclyl is optionally substituted with one or more $R^{6a}$, wherein  
each $R^{6a}$ is independently —Z", —Y"—Z", or —X"—Y"—Z", wherein  
X" is —O—;  
Y" is —[C($R^{15}$)$_2$]$_m$—, —C$_2$-C$_6$ alkenyl, C$_3$-C$_8$ cycloalkyl, heterocyclyl, aryl, or heteroaryl, wherein the aryl, heteroaryl, cycloalkyl, or heterocyclyl is optionally substituted with at least one group which is each independently Z";  
Z" is —H, —CN, halogen, —O$R^{11}$, —C(=O)$R^{11}$, —C(=O)O$R^{11}$, —C(=O)N($R^{11}$)$_2$, —N($R^{11}$)$_2$, —N$_3$, —SO$_2$$R^{11}$, —S(=O)$_2$N($R^{11}$)$_2$, —C(=O)N($R^{11}$)N($R^{11}$)$_2$, —N($R^{11}$)C(=O)N($R^{11}$)$_2$, —OC (=O)—OR$^{11}$, —C(=O)N(R$^{11}$)(OR$^{11}$), —OC(=O)—R$^{11}$, —OC(=O)—N(R$^{11}$)$_2$, or —N(R$^{11}$)COOR$^{11}$; and G is a group of the formula,

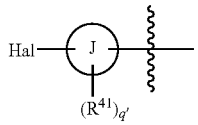

wherein
Hal is halogen;
J is aryl or heteroaryl;
each R$^{41}$ is independently -halogen, nitro, CR$^{11}$=CR$^{11}$COOR$^{11}$, aryloxy, aralkyloxy, aryloxyalkyl, arylC$_0$-C$_6$ alkylcarboxy, aryl, heteroaryl, heterocyclyl, heteroaryloxy, heterocyclyloxy, -G$^{1'}$-E-G$^{1''}$ or -D-E-G$^1$, wherein
D is —O—;
E is —[C(R$^{15}$)$_2$]$_m$— or —C$_3$-C$_8$cycloalkyl; and
G$^1$ is —C$_1$-C$_6$ alkyl, —C$_1$-C$_6$ haloalkyl, —COR$^{11}$, —COOR$^{11}$, —CON(R$^{11}$)$_2$, —C≡N, —OR$^{11}$, —OCON(R$^{11}$)$_2$, —OCOOR$^{11}$, —N$_3$, —NR$^{11}$COR$^{11}$, —NR$^{11}$SO$_2$R$^{11}$, —N(R$^{11}$)$_2$, —NR$^{11}$COOR$^{11}$, —SOR$^{11}$, —SO$_2$R$^{11}$, —SO$_2$NR$^{11}$COR$^{11}$, —SO$_2$N(R$^{11}$)$_2$, or —SR$^{11}$;
wherein each R$^4$ is optionally substituted with one or more R$^{4a}$,
wherein each R$^{4a}$ is independently halogen, aryloxy, aralkyloxy, aryloxyalkyl, C$_1$-C$_6$ alkoxyaryl, arylC$_0$-C$_6$ alkylcarboxy, -G', -E'-G', or -D'-E'-G', wherein
D' is —O—;
E' is —[C(R$^{15}$)$_2$]$_m$— or —C$_3$-C$_8$cycloalkyl-; and
G' is —H, -halogen, —COR$^{11}$, —COOR$^{11}$, C≡N, —OR$^{11}$, —NR$^{11}$SO$_2$R$^{11}$, —SO$_2$R$^{11}$, —SO$_2$N(R$^{11}$)$_2$, or —SR$^{11}$;
each m is 0, 1, 2, 3, 4, 5, or 6; and
q' is 0, 1, 2, 3, or 4,
each R$^{10}$ is independently —R$^{11}$, —C(=O)R$^{11}$, —CO$_2$R$^{11}$, or —SO$_2$R$^{11}$;
each R$^{11}$ is independently -hydrogen, —C$_1$-C$_6$ alkyl, C$_2$-C$_6$ alkenyl, C$_2$-C$_6$ alkynyl, C$_3$-C$_8$ cycloalkyl, (C$_3$-C$_8$ cycloalkyl)-C$_1$-C$_6$ alkyl-, (C$_3$-C$_8$ cycloalkenyl)-C$_1$-C$_6$ alkyl-, (C$_3$-C$_8$ cycloalkyl)-C$_2$-C$_6$ alkenyl-, —C$_1$-C$_6$ haloalkyl, —N(R$^{12}$)$_2$, aryl, —(C$_6$-C$_6$)alkyl-aryl, heteroaryl, —(C$_1$-C$_6$)alkyl-heteroaryl, heterocyclyl, or —(C$_1$-C$_6$)alkyl-heterocyclyl,
wherein any of R$^{11}$ is optionally substituted with one or more radicals of R$^{12}$;
each R$^{12}$ is independently halogen, C$_1$-C$_6$ haloalkyl, C$_1$-C$_6$ alkyl, C$_1$-C$_6$ alkoxy, (C$_0$-C$_6$ alkyl)C=O(OR$^{13}$); C$_0$-C$_6$ alkylOR$^{13}$, C$_0$-C$_6$ alkylCOR$^{13}$, C$_0$-C$_6$ alkylSO$_2$R$^{13}$, C$_0$-C$_6$ alkylCON(R$^{13}$)$_2$, C$_0$-C$_6$ alkylCONR$^{13}$OR$^{13}$, C$_0$-C$_6$ alkylSO$_2$N(R$^{13}$)$_2$, C$_0$-C$_6$ alkylSR$^{13}$, C$_0$-C$_6$ haloalkylOR$^{13}$, aryloxy, aralkyloxy, aryloxyalkyl, C$_{0-6}$alkoxyaryl, arylC$_{0-6}$ alkylcarboxy, -C$_0$-C$_6$ alkylN(R$^{13}$)$_2$, —NR$^{13}$SO$_2$R$^{13}$, or —OC$_{0-6}$alkylCOOR$^{13}$;
each R$^{13}$ is independently hydrogen, C$_1$-C$_6$ alkyl, C$_2$-C$_6$ alkenyl, C$_2$-C$_6$ alkynyl, C$_3$-C$_8$ cycloalkyl, (C$_3$-C$_8$ cycloalkyl)-C$_1$-C$_6$ alkyl-, (C$_3$-C$_8$ cycloalkenyl)-C$_1$-C$_6$ alkyl-, or (C$_3$-C$_8$ cycloalkyl)C$_2$-C$_6$ alkenyl-;

each R$^{14}$ is independently C$_1$-C$_6$ alkyl, C$_1$-C$_6$ alkoxy, halogen, C$_1$-C$_6$ haloalkyl, C$_0$-C$_6$ alkylCON(R$^{11}$)$_2$, C$_0$-C$_6$ alkylCONR$^{11}$OR$^{11}$, C$_0$-C$_6$ alkylOR$^{11}$, or C$_0$-C$_6$ alkylCOOR$^{11}$.

In another embodiment, the invention provides the compound according to formula XXVa-d, wherein Hal is —Cl, —Br, or —I.

In another embodiment, the invention provides the compound according to formula XXVa-d, wherein Hal is —Cl.

In another embodiment, the invention provides the compound according to formula XXVa-d, wherein Hal is —Br.

In another embodiment, the invention provides the compound according to formula XXVa-d, wherein Hal is —I.

In another embodiment, the invention provides the compound according to formula XXVa-d, wherein J is aryl or heteroaryl.

In another embodiment, the invention provides the compound according to formula XXVa-d, wherein J is phenyl, pyridyl, thienyl, pyrrolyl, furanyl, pyrimidinyl, pyrazinyl, imidazoyl, pyrazoyl, oxazoyl, thiazoyl, isoxazoyl, isothiazoyl, triazoyl, triazinyl, tetrazoyl, or tetrazinyl.

In another embodiment, the invention provides the compound according to formula XXVa-d, wherein J is phenyl, pyridyl, thienyl, pyrrolyl, or furanyl.

In another embodiment, the invention provides the compound according to formula XXVa-d, wherein J is phenyl, pyridyl, or thienyl.

In another embodiment, the invention provides the compound according to formula XXVa-d, wherein J is phenyl.

In another embodiment, the invention provides the compound according to formula XXVa-d, wherein J is pyridyl.

In another embodiment, the invention provides the compound according to formula XXVa-d, wherein J is thienyl.

In another embodiment, the invention provides the compound according to formula XXVa-d, wherein R$^5$ is aryl, heterocyclyl, or heteroaryl, wherein R$^{15}$ is optionally substituted with one or more R$^{5a}$.

In another embodiment, the invention provides the compound according to formula XXVa-d, wherein R$^5$ is aryl or heteroaryl, wherein R$^{15}$ is optionally substituted with one or more R$^{5a}$.

In another embodiment, the invention provides the compound according to formula XXVa-d, wherein R$^5$ is phenyl, pyridyl, thienyl, pyrrolyl, furanyl, pyrimidinyl, pyrazinyl, imidazoyl, pyrazoyl, oxazoyl, thiazoyl, isoxazoyl, isothiazoyl, triazoyl, triazinyl, tetrazoyl, or tetrazinyl wherein R$^5$ is optionally substituted with one or more R$^{5a}$.

In another embodiment, the invention provides the compound according to formula XXVa-d, wherein L$^1$ is a bond.

In another embodiment, the invention provides the compound according to formula XXVa-d, wherein L$^1$ is a bond; and R$^5$ is phenyl, pyridyl, thienyl, pyrrolyl, furanyl, pyrimidinyl, pyrazinyl, imidazoyl, pyrazoyl, oxazoyl, thiazoyl, isoxazoyl, isothiazoyl, triazoyl, triazinyl, tetrazoyl, or tetrazinyl, wherein R$^5$ is optionally substituted with one or more R$^a$.

In another embodiment, the invention provides the compound according to formula XXVa-d, wherein L$^1$ is a bond; and R$^5$ is phenyl, pyridyl, thienyl, pyrrolyl, or furanyl, wherein R$^5$ is optionally substituted with one or more R$^{5a}$.

In another embodiment, the invention provides the compound according to formula XXVa-d, wherein L$^1$ is a bond; and R$^5$ is phenyl optionally substituted with one or more R$^{5a}$.

In another embodiment, the invention provides the compound according to formula XXVa-d, wherein L$^1$ is a bond; and R$^5$ is pyridyl optionally substituted with one or more R$^a$.

In another embodiment, the invention provides the compound according to formula XXVa-d, wherein $L^1$ is a bond; and $R^5$ is thienyl optionally substituted with one or more $R^{5a}$.

In another embodiment, the invention provides the compound according to formulas XXVa-d, wherein $R^2$ is -$L^3$-$R^7$, wherein $L^3$ is a bond; and
  $R^7$ is hydrogen, halogen, -Z, or —Y—Z, wherein
    Y is —[C($R^{15}$)$_2$]$_m$—, —($C_3$-$C_6$)cycloalkyl-, or $C_2$-$C_6$ alkenyl,
      wherein each $R^{15}$ is independently H, halogen, or ($C_1$-$C_6$)alkyl; and
    Z is —H, halogen, —O$R^{11}$, —C(=O)$R^{11}$, —C(=O)O$R^{11}$, —C(=O)N($R^{11}$)$_2$, —C(=N—OH)$R^{11}$, or —C(=S)N($R^{11}$)$_2$.

In another embodiment, the invention provides the compound according to formulas XXVa-d, wherein $R^2$ is -$L^3$-$R^7$, wherein $L^3$ is a bond; and
  $R^7$ is hydrogen, halogen, or —[C($R^{15}$)$_2$]—Z, wherein
    each $R^{15}$ is is independently H, halogen, or ($C_1$-$C_2$) alkyl; and
    Z is —H, halogen, —O$R^{11''}$, —C(=O)$R^{11''}$, —C(=O)O$R^{11''}$, —C(=O)N($R^{11''}$)$_2$, —C(=N—OH)$R^{11''}$, or —C(=S)N($R^{11}$)$_2$,
      wherein $R^{11''}$ is —H or —($C_1$-$C_6$ alkyl).

In another embodiment, the invention provides the compound according to formulas XXVa-d, wherein $R^2$ is -halogen, —$CF_3$, —$CH_2OH$, —$CH_2SO_2$Me, —C($CH_3$)$_2$OH, or —C($CH_3$)$_2SO_2$Me.

In another embodiment, the invention provides the compound according to formulas XXVa-d, wherein $R^2$ is -halogen, —$CF_3$, —$CH_2OH$, or —C($CH_3$)$_2$OH.

In another embodiment, the invention provides the compound according to formulas XXVa-d, wherein $R^2$ is —$CF_3$ or —C($CH_3$)$_2$OH.

In one embodiment, the invention provides the compound according to formulas XXVa-d, wherein each $R^{41}$ is independently halogen, -$G^1$ or -E-$G^1$, wherein
  E is —[C($R^{15}$)$_2$]$_m$—,
    wherein each $R^{15}$ is independently hydrogen or halogen; and
  $G^1$ is —$C_1$-$C_6$ alkyl, —$C_1$-$C_6$ haloalkyl, or halogen.

In another embodiment, the invention provides the compound according to formula XXVa-d, wherein $R^1$ is L-$R^5$, wherein $L^1$ is a bond; and
  $R^5$ is phenyl or pyridyl, each optionally substituted with one or two $R^{5a}$, wherein each $R^{5a}$ is independently -halogen, —$CH_3$, or —$CF_3$;
  $R^2$ is —H, —C($R^2$)$_2$OH, —$CH_3$, —$CF_3$, or halogen, wherein
    each $R^{20}$ is independently —H, —F, —$CH_3$, or —$CF_3$;
  J is phenyl, pyridyl, or thienyl; and
  each $R^{41}$ is -halogen, —$CH_3$, —$CH_2CH_3$, —$CF_3$, —$CF_2CF_3$, or —$CH_2CF_3$.

In another embodiment, the invention provides the compound according to formula XXVa-d, wherein q' is 0 or 1; $R^1$ is $L^1$-$R^5$, wherein $L^1$ is a bond; and
  $R^5$ is phenyl optionally substituted with one or two $R^{5a}$, wherein each $R^{5a}$ is independently -halogen, —$CH_3$, or —$CF_3$;
  each $R^2$ is —H, —C($R^2$)$_2$OH, —$CH_3$, —$CF_3$, or halogen, wherein
  each $R^{20}$ is independently —H, —F, —$CH_3$, or —$CF_3$; and
  $R^{41}$ is -halogen, —$CH_3$, —$CH_2CH_3$, —$CF_3$, —$CF_2CF_3$, or —$CH_2CF_3$.

In another embodiment, the invention provides the compound according to formulas XXVa-d, wherein each $R^{41}$ is independently halogen, methyl or trifluoromethyl. In another embodiment, the invention provides the compound according any of the previous embodiments wherein $R^{21}$ is hydrogen.

In a third aspect, the invention provides a pharmaceutical composition comprising a compound of any of formulas IIa-d, IIIa-d, IVa-d, XXVa-d, or IV-XXXV, or a pharmaceutically acceptable derivative thereof, in a pharmaceutically acceptable carrier.

In another embodiment, the invention provides a pharmaceutical composition comprising a compound of formula IV, or a pharmaceutically acceptable derivative thereof, in a pharmaceutically acceptable carrier.

In another embodiment, the invention provides a pharmaceutical composition comprising a compound of formula V, or a pharmaceutically acceptable derivative thereof, in a pharmaceutically acceptable carrier.

In another embodiment, the invention provides a pharmaceutical composition comprising a compound of formula VI, or a pharmaceutically acceptable derivative thereof, in a pharmaceutically acceptable carrier In another embodiment, the invention provides a pharmaceutical composition comprising a compound of formula VII, or a pharmaceutically acceptable derivative thereof, in a pharmaceutically acceptable carrier.

In another embodiment, the invention provides a pharmaceutical composition comprising a compound of formula IIa-d, or a pharmaceutically acceptable derivative thereof, in a pharmaceutically acceptable carrier.

In a fourth aspect, the invention provides a kit, comprising a packaging material and a compound of any of formula IIa-d, IIIa-d, IVa-d, XXVa-d, or IV-XXXV, or a pharmaceutically acceptable derivative thereof, which is effective for modulating the activity of a nuclear receptor or for treatment, prevention, inhibition, or amelioration of one or more symptoms of nuclear receptor mediated diseases or disorders.

In another embodiment, the invention provides a kit, comprising a packaging material, and a compound of formula IIa-d, or a pharmaceutically acceptable derivative thereof, which is effective for modulating the activity of a nuclear receptor or for treatment, prevention, inhibition, or amelioration of one or more symptoms of nuclear receptor mediated diseases or disorders.

In another embodiment, the invention provides a kit, comprising a packaging material, a compound of formula IIa-d, or a pharmaceutically acceptable derivative thereof, which is effective for modulating the activity of a nuclear receptor or for treatment, prevention, inhibition, or amelioration of one or more symptoms of nuclear receptor mediated diseases or disorders, further comprising a label that indicates that the compound of formula IIa-d, or pharmaceutically acceptable derivative thereof, is used for modulating the activity of a nuclear receptor or for treatment, prevention or amelioration of one or more symptoms of nuclear receptor mediated diseases or disorders, or diseases or disorders in which nuclear receptor activity is implicated.

In a sixth aspect, the invention provides a method of treating, preventing, inhibiting, or ameliorating the symptoms of a disease or disorder that is modulated or otherwise affected by nuclear receptor activity or in which nuclear receptor activity is implicated, comprising administering to a subject in need thereof a therapeutically effective amount of a compound of any of formula IIa-d, IIIa-d, IVa-d, XXVa-d, or IV-XXXV.

In a preferred embodiment of the sixth aspect, the invention provides a method of treating, preventing, inhibiting, or ameliorating the symptoms of a disease or disorder that is modulated or otherwise affected by nuclear receptor activity or in which nuclear receptor activity is implicated, comprising administering to a subject in need thereof a therapeutically effective amount of a compound according to part (A) of formulas IIa-d.

When part (A) of formulas IIa-d is referenced herein with respect to methods of using compounds of the invention, such as for treatment, prevention, inhibition, or amelioration of disease, or for use in preparation of a medicament for the treatment, prevention, or amelioration of disease, it is meant that all compounds defined by part (A) are included and the provisos of part (B) of the same formulas are not to be considered when determining the scope of the compounds defined for the uses therein.

In a preferred embodiment of the sixth aspect, the invention provides the method wherein the disease or disorder is hypercholesterolemia, hyperlipoproteinemia, hypertriglyceridemia, lipodystrophy, hyperglycemia, diabetes mellitus, dyslipidemia, atherosclerosis, gallstone disease, acne vulgaris, acneiform skin conditions, diabetes, Parkinson's disease, cancer, Alzheimer's disease, inflammation, immunological disorders, lipid disorders, obesity, conditions characterized by a perturbed epidermal barrier function, conditions of disturbed differentiation or excess proliferation of the epidermis or mucous membrane, or cardiovascular disorders.

In a seventh aspect, the invention provides a method of reducing cholesterol levels in a subject in need thereof, comprising administering an effective cholesterol level-reducing amount of a compound of any of formula IIa-d, IIIa-d, IVa-d, XXVa-d, or IV-XXXV.

In a preferred embodiment of the seventh aspect, the invention provides a method of reducing cholesterol levels in a subject in need thereof, comprising administering an effective cholesterol level-reducing amount of a compound according to part (A) of formulas IIa-d.

In an eighth aspect, the invention provides a method of treating, preventing, or ameliorating one or more symptoms of a disease or disorder which is affected by cholesterol, triglyceride, or bile acid levels, comprising administering to a subject in need thereof a therapeutically effective amount of a compound of any of formula IIa-d, IIIa-d, IVa-d, XXVa-d, or IV-XXXV.

In a preferred embodiment of the eighth aspect, the invention provides a method of treating, preventing, or ameliorating one or more symptoms of a disease or disorder which is affected by cholesterol, triglyceride, or bile acid levels, comprising administering to a subject in need thereof a therapeutically effective amount of a compound according to part (A) of formulas IIa-d.

In a ninth aspect, the invention provides a method of modulating nuclear receptor activity, comprising contacting the nuclear receptor with a compound of any of formula IIa-d, IIa-d, IVa-d, XXVa-d, or TV-XXXV.

In a preferred embodiment of the ninth aspect, the invention provides a method of modulating nuclear receptor activity, comprising contacting the nuclear receptor with a compound according to part (A) of formulas IIa-d.

In an embodiment of the ninth aspect, the invention provides the method wherein the nuclear receptor is an orphan nuclear receptor.

In an embodiment of the ninth aspect, the invention provides the method wherein the nuclear receptor is a liver X receptor.

In a preferred embodiment of the ninth aspect, the invention provides the method wherein the nuclear receptor is a liver X receptor, wherein the liver X receptor is LXRα or LXRβ.

In an eleventh aspect, the invention provides a method of modulating cholesterol metabolism, comprising administering an effective cholesterol metabolism-modulating amount of a compound of any of formula IIa-d, IIIa-d, IVa-d, XXVa-d, or IV-XXXV.

In a preferred embodiment of the eleventh aspect, the invention provides a method of modulating cholesterol metabolism, comprising administering an effective cholesterol metabolism-modulating amount of a compound according to part (A) of formulas IIa-d.

In a twelfth aspect, the invention provides a method of treating, preventing or ameliorating one or more symptoms of hypocholesterolemia in a subject in need thereof, comprising administering a therapeutically effective amount of a compound of any of formula IIa-d, IIIa-d, IVa-d, XXVa-d, or IV-XXXV.

In a preferred embodiment of the twelfth aspect, the invention provides a method of treating, preventing or ameliorating one or more symptoms of hypocholesterolemia in a subject in need thereof, comprising administering a therapeutically effective amount of a compound according to part (A) of formulas IIa-d.

In a thirteenth aspect, the invention provides a method of increasing cholesterol efflux from cells of a subject, comprising administering an effective cholesterol efflux-increasing amount of a compound of any of formula IIa-d, IIIa-d, IVa-d, XXVa-d, or IV-XXXV.

In a preferred embodiment of the thirteenth aspect, the invention provides a method of increasing cholesterol efflux from cells of a subject, comprising administering an effective cholesterol efflux-increasing amount of a compound according to part (A) of formulas IIa-d.

In a fourteenth aspect, the invention provides a method of increasing the expression of ATP-Binding Cassette (ABC1) in the cells of a subject, comprising administering an effective ABC1 expression-increasing amount of a compound of any of formula IIa-d, IIIa-d, IVa-d, XXVa-d, or IV-XXXV.

In the following embodiments of the first aspect, it is understood that the following provisos apply:

(i) when $L^2$ is a bond, both J and K are not absent;

(ii) if the compound If defined by formula IIaa, then a. if J is phenyl and K is thienyl, furyl, or thiazoyl and q is 0, then $R^1$ is not 4-$(NH_2SO_2)$phenyl, 4-$(NH_2SO_2)$-3-fluorophenyl, p-$(CH_3SO_2)$phenyl-, or 4p-$(CH_3SO_2)$-3-fluorophenyl-; and b. if $R^5$ is pyridyl or phenyl optionally substituted with one or more $R^{5a}$ and $L^1$ is a bond, then G is not p-$(NH_2SO_2)$phenyl or p-$(CH_3SO_2)$phenyl-;

(iii) if the compound If defined by formula IIcc or IIdd, then G is not p-$(NH_2SO_2)$phenyl or p-$(CH_3SO_2)$phenyl- (iv) the compound is not 1-(biphenyl-4-yl)-2,5-diphenyl-1H-imidazole.

One embodiment of the invention relates to compounds represented by formulae IIaa, IIbb, IIcc or IIdd:

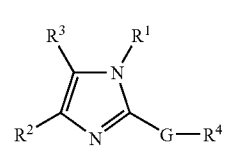

IIaa

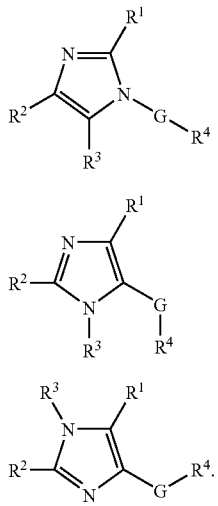

as an isomer, a mixture of stereoisomers, a racemic mixture thereof of stereoisomers, or as a tautomer; or as a pharmaceutically acceptable salt, prodrug, solvate or polymorph thereof.

Each $R^1$ substitutent is independently selected from the group consisting of $R^5$ and -$L_1$-$R^5$.

Another embodiment is that $R^1$ substitutent is $R^5$; Preferred $R^5$ is selected from the group consisting of 5-12 membered aromatic or non-aromatic ring, 5-12 membered heterocyclyl or heteroaryl having one or more heteroatoms N, O or S; $R^5$ is optionally substituted at a substitutable position with one or more radicals of $R^{5a}$. $R^5$ is preferably thienyl, furanyl, piperidinyl, pyrrolidinyl, piperazinyl, morpholinyl, thiazolyl, indolyl, oxazolyl, isoxazolyl, pyridinyl, pyrimidinyl, imidazolyl and phenyl.

Examples of $R^{5a}$ groups include halogen, $C_{1-6}$ haloalkyl, hydroxy, nitro, $C_{1-6}$ aliphatic group, $C_{1-6}$ alkoxy, $C_{0-6}$ alkylOR$^{11}$, OCOR$^{11}$, OCON(R$^{11}$)$_2$, NR$^{11}$COR$^{11}$, NR$^{11}$CON(R$^{11}$)$_2$, $C_{0-6}$ alkylSO$_2$R$^{11}$, $C_{1-6}$alkyl SR$^{11}$, $C_0$alkyl SO$_2$N(R$^{11}$)$_2$; arylalkyl, aryloxyaryl, aryl $C_{1-6}$ alkoxy, OC$_{1-6}$ alkylCOR$^{11}$, OC$_{1-6}$ alkylN(R$^{11}$)$_2$, $C_{0-6}$ alkylN(R$^{11}$)$_2$; $C_{0-6}$ alkylOR$^{11}$, $C_{0-6}$ alkylN(R$^{11}$)$_2$, $C_{0-6}$ alkylCOOR$^{11}$, $C_{0-6}$ alkyl COON(R$^{11}$)$_2$, $C_{0-6}$ alkylCON(R$^{11}$)$_2$; $C_{0-6}$ alkylC=N, OC$_{0-6}$ alkylCOOR$^{11}$, $C_{0-6}$ alkylOCON(R$^{11}$)$_2$, or $C_{1-6}$ alkylOC$_{1-6}$ alkyl. $R^{5a}$ is optionally substituted at substitutable position with SO$_2$R$^{11}$, $C_{0-6}$ alkoxyaryl, 5-12 membered aromatic or non-aromatic ring, or 5-12 membered heterocyclyl or heteroaryl having one or more heteroatoms N, O or S. Preferably, $R^{5a}$ is Cl, Br, F, $C_{1-6}$ alkyl, $C_{1-6}$ haloalkyl, $C_{1-6}$ alkoxy, OC$_{0-6}$ alkylCOOR$^{11}$, NR$^{11}$COR$^{11}$, $C_{0-6}$ alkylCON(R$^{11}$)$_2$, NO$_2$, and OC$_{1-6}$ alkylCON(R$^{11}$)$_2$. Examples of $R^{5a}$ include OCH$_2$C(CH$_3$)$_3$, Cl, F, Br, OCH$_2$CH(CH$_3$)$_2$, OCH$_2$CH$_3$, CF$_3$, COOH, OCH$_3$, OH, NO$_2$, OCOCH(CH$_3$)$_2$, OCOC(CH$_3$)$_3$, NHCOCH$_3$, OCON(CH$_3$)$_2$, OCONHCH$_3$, OCON(CH$_2$)$_2$H$_3$, OCONHCH(CH$_3$)$_2$, O(CH$_2$)$_2$, CONH$_2$, O(CH)(CH$_3$)$_2$, $C_{1-6}$ alkyl, OCH$_2$COOH, OCH$_2$COOC(CH$_3$)$_3$, O(CH$_2$)$_2$N(CH$_2$CH$_3$)$_2$, OC(CH$_3$)$_2$COOC(CH$_3$)$_3$, or OCH$_2$CH$_2$OH. More preferably, $R^{5a}$ is Cl, F, or CF$_3$, Another embodiment is that $R^1$ substitutent is -$L_1$-$R^5$. Preferred $R^5$ is selected from the group consisting of 5-12 membered aromatic or non-aromatic ring, 5-12 membered heterocyclyl or heteroaryl having one or more heteroatoms N, O or S; $R^5$ is optionally substituted at a substitutable position with one or more radicals of $R^{5a}$. Examples of preferred $R^5$ include phenyl, pyridinyl, oxazolyl, thienyl, thiazolyl, morpholinyl, furanyl, imidazolyl, piperazinyl, pyrimidinyl, isoxazolyl or piperidinyl, more preferably, oxazolyl, pyridinyl, phenyl, furanyl, thienyl or thiazolyl.

Embodiments for $L_1$ include a direct bond, $C_{1-6}$alkoxy, carbonyl, SO$_2$, CS, CON(R$^{11}$)$_2$, CONR$^{11}$OR$^{11}$, CONR$^{11}$N(R$^{11}$)$_2$, —C(=NR$^{11}$)—, —C(=NOR$^{11}$)—, —C(=NN(R$^{11}$)$_2$)—, 5-12 membered aromatic or non-aromatic ring, 5-12 membered heteroaryl or heterocyclyl having one or more heteroatoms N, O, or S which is optionally substituted at a substitutable position with one or more radicals of $R^{14}$. Another embodiment for $L_1$ is —(CH$_2$)$_m$—V—(CH$_2$)$_n$—; or V—(CH$_2$)$_n$—V; m is 0-6; n is 0-6; V is independently —C(R$^{11}$)$_2$—, —C(R$^{11}$)$_2$C(R$^{11}$)$_2$—, —C(R$^{11}$)=C(R$^{11}$)—, —C(R$^{11}$)$_2$O—, —C(R$^{11}$)$_2$NR$^{11}$—, —C≡C—, —O—, —S—, —N(R$^{11}$)CO—, —N(R$^{10}$)CO$_2$—, —CON(R$^{10}$)—, —CO—, —CO$_2$—, —OC(=O)—, —OC(=O)N(R$^{11}$)—, —CONR$^{11}$OR$^{11}$—, —CONR$^{11}$NR$^{11}$—, —CONR$^{11}$—, —SO$_2$—, —N(R$^{10}$)SO$_2$—, —SO$_2$N(R$^{10}$)—, cycloC$_{3-6}$ alkyl, —NR$^{10}$CSNR$^{10}$—, cycloC$_{3-6}$haloalkyl or —NR$^{10}$CONR$^{10}$. A preferred $L_1$ is selected from the group consisting of CONH, $C_{1-6}$ alidiyl, CO, SO$_2$, CH$_2$, CH$_2$O, CH$_2$CH$_2$, C=O, CONH, CONHC(CH$_3$)$_2$, CONH(CH$_2$)$_3$CH$_2$, OCH$_2$CH$_2$, OCH$_2$CO, OCH$_2$CH$_2$N(CH$_3$)$_2$, and CONHCH$_2$CH$_2$N(CH$_3$)$_2$. More preferred $L_1$ is selected from the group consisting of CH$_2$, CH$_2$O, CH$_2$CH$_2$, C=O, SO$_2$, CONH, CONHC(CH$_3$)$_2$, CONH(CH$_2$)$_3$OCH$_2$, CONHCH$_2$CH$_2$N(CH$_3$)$_2$; OCH$_2$ and OCH$_2$CH$_2$. Preferred $R^5$ is selected from the group consisting of phenyl, pyridinyl, oxazolyl, thienyl, thiazolyl, furanyl, morpholinyl, imidazolyl, piperazinyl, pyrimidinyl, isoxazolyl and piperidinyl. Other preferred $R^{5a}$ includes halogen, haloalkyl, OCH$_2$CON(CH$_3$)$_2$, OCH$_2$COOC(CH$_3$)$_3$, OCH$_2$CH$_2$N(CH$_2$CH$_3$)$_2$, OCH$_2$COOH, OC(CH$_3$)$_2$COOC(CH$_3$)$_2$, OCON(CH$_3$)$_2$, OCONHCH$_3$, OCH$_2$CH$_2$OH, OCONHCH$_2$CHCH$_3$, or NHCOCH$_3$.

Another embodiment is that $R^2$ is independently selected from the group consisting of $R^7$ and $L_3$-$R^7$; Each $R^7$ is independently selected from hydrogen, $C_{1-6}$ alkyl, halogen, $C_{1-6}$ haloalkyl, $C_{1-6}$alkoxy, $C_{1-6}$ haloalkylOR$^{11}$, $C_{0-6}$ alkylCOOR$^{11}$, $C_{1-6}$ alkylCON(R$^{11}$)$_2$, $C_{0-6}$ alkylN(R$^{11}$)$_2$, $C_{0-6}$ alkylOR$^{11}$, $C_{0-6}$ alkylC=N, cycloC$_{3-6}$ alkylC=N, $C_{0-6}$ alkyl CONR$^{11}$N(R$^{11}$)$_2$, $C_{0-6}$ alkylCONR$^{11}$OR$^{11}$, $C_{0-6}$ alkylO-COR$^{11}$, $C_{0-6}$ alkylSO$_2$N(R$^{11}$)$_2$, cycloC$_{3-6}$alkyl, cycloC$_{3-6}$ alkylOR$^{11}$, $C_{0-6}$alkylCOR$^{11}$; 5-12 membered aromatic or non-aromatic ring; or 5-12 membered heteroaryl and heterocyclyl having one or more heteroatoms N, O or S; $R^7$ is optionally substituted at a substitutable position with one or more radicals of $R^{7a}$;

Another embodiment is that $R^2$ is $R^7$, selected from the group consisting of 5-12 membered aromatic or non-aromatic ring; 5-12 membered heteroaryl and heterocyclyl having one or more heteroatoms N, O or S. $R^7$ is optionally substituted at a substitutable position with one or more radicals of $R^{7a}$;

Preferred $R^7$ is phenyl, pyridinyl, thienyl, furanyl, piperidinyl, pyrrolidinyl, piperazinyl, morpholinyl, thiazolyl, indolyl, oxazolyl, pyridinyl, isoxazolyl, pyrimidinyl, naphthyl, hydrogen, CF$_3$, $C_{1-6}$ alkylC=N, CH$_2$OH, COOCH$_3$, COON(R$^{11}$)$_2$ or COOR$^{11}$. Other examples of $R^7$ include trifluoromethyl, CH$_2$C=N, C(CH$_3$)$_2$C=N, COOCH$_3$, CH$_2$OH, CONHCH$_2$CH$_3$, CONHOCH$_2$CH(OH)CH$_2$OH, CONHCH$_2$CH$_2$N(CH$_3$)$_2$, CONHCH$_2$CH$_2$OCH$_3$, CONHCH$_2$CH$_2$OCH$_3$, CH$_2$COOCH$_3$, CON(CH$_3$)$_2$, COOCH(CH$_3$)$_2$, CONHCH$_2$CH$_2$OCH$_3$, OCOCH(CH$_3$)$_2$, OCH$_2$CON(CH$_3$)$_2$, CH$_2$CONHCH$_2$(CH$_3$), C(CH$_3$)$_2$OH, COOH, nitro, cycloC$_{3-6}$ alkyl, cycloC$_{3-4}$ alkylOR$^{11}$, cycloC$_{3-6}$ alkylC=N, or COOCH(CH$_3$)$_2$. More preferably, $R^7$ is CF$_3$, COOCH$_3$, COOH, or CONHCH$_2$CH$_3$. When $R^7$ is phenyl or pyridinyl, preferred $R^{7a}$ is selected from the group consisting of halogen, $C_{1-6}$ alkyl, $C_{1-6}$ alkoxy, and $C_{1-6}$ haloalkyl. Examples of $R^{7a}$ include halogen, trifluoromethyl, $C_{1-6}$ alkyl, $C_1$ alkoxy, CH=CHCOOH, $CH_2COOH$, $OCH_2COOH$, OCONHCH($CH_3$)$_2$, NHCOCH$_3$, OH, OCH$_3$, COOH, COOCH$_3$, OCH$_2$C(CH$_3$)$_3$, OCH$_2$CH(CH$_3$)$_2$, OCH(CH$_3$)$_2$0COCH(CH$_3$)$_2$, OCONHCH$_3$, OCH$_2$CH$_3$, and OCH(CH$_3$)$_2$.

Another embodiment is that $R^2$ is $L_3$-$R^7$. A preferred $L_3$ is independently selected from a direct bond, —CS—, —CO—, —CONH—, —CONR$^{11}$, —C(=NR$^{11}$)—, —C(=NOR$^{11}$)—, —C(=NN(R$^{11}$)$_2$)—; (CH$_2$)$_m$—V$_1$—(CH$_2$)$_n$— or —V—(CH$_2$)$_n$—V—; m is 0-6; n is 0-6; V$_1$ is independently —C(R$^{11}$)$_2$—, —C(R$^{11}$)$_2$C(R$^{11}$)$_2$—, —C(R$^{11}$)=C(R$^{11}$)—, —C(R$^{11}$)$_2$O—, —C(R$^{11}$)$_2$NR$^{11}$—, —C—, —O—, —S—, —NR$^{11}$—, —CR$^{11}$NR$^{11}$—, —N(R$^{10}$)CO—, —N(R$^{10}$)CO$_2$, —CON(R$^{10}$)—, —OCO—, —CO—, —CO$_2$—, —OC(=O)—, —OC(=O)N(R$^{10}$)—, —SO$_2$—, —N(R$^{10}$)SO$_2$—, —NR$^{10}$CONR$^{10}$—, cycloC$_{3-6}$ alkyl, —NR$^{10}$CSNR$^{10}$—, cycloC$_{3-6}$haloalkyl or —SO$_2$N(R$^{10}$). More preferably, $L_3$ is CH$_2$, CO, OCH$_2$, CH$_2$OCH$_2$, CONH, CH$_2$OCOH$_2$, CH$_2$NHCH$_2$, CH$_2$NC(CH$_3$)$_2$, CH$_2$N(CH$_3$)CH$_2$, CH$_2$COCH$_3$, CH$_2$N(CH$_3$)$_2$CH$_2$, cyclohexamine or cyclopropanamine.

Each $R^{7a}$ is independently a halogen, $C_{1-6}$ alkyl, CR$^{11}$=CR$^{11}$COOR$^{11}$, $C_{1-6}$ alkoxy, $C_{0-6}$ alkylOR$^{11}$, $C_{0-6}$ alkylOCOOR$^{11}$, $C_{0-6}$alkylNR$^{11}$COR$^{11}$, CO$_{0-6}$ alkyl SO$_2$NCOR$^{11}$, $C_{0-6}$ alkylSO$_2$N(R$^{11}$)$_2$; $C_{0-6}$ alkylSR$^{11}$, (C$_{0-6}$ alkyl)C=O(OR$^{11}$), OVOR$^{11}$, $C_{1-6}$ haloalkyl, OC$_{1-6}$ haloalkyl, haloaryl, aryloxy, aralkyloxy, aryloxyalkyl, $C_{1-6}$ alkoxyaryl, arylC$_{0-6}$ alkylcarboxy, NR$^{11}$SO$_2$R$^{11}$, OC$_{1-6}$ alkyl, OC$_{0-6}$ alkylCOOR$^{11}$, $C_{0-6}$ alkoxyheteroaryl, $C_{0-6}$ alkoxyheterocyclyl, cycloC$_{3-6}$alkylCOOR$^{11}$, cycloC$_{3-6}$ alkylamine; 5-12 membered aromatic or non-aromatic ring, or 5-12 membered heteroaryl or heterocyclyl having one or more heteroatoms N, O or S; Examples of $R^{7a}$ is selected from the group consisting of halogen, trifluoromethyl, $C_{1-6}$ alkyl, $C_1$ alkoxy, CH=CHCOOH, CH$_2$COOH, OCH$_2$COOH, OCONHCH(CH$_3$)$_2$, NHCOCH$_3$, OH, OCH$_3$, COOH, COOCH$_3$, OCH$_2$C(CH$_3$)$_3$, OCH$_2$CH(CH$_3$)$_2$, OCH(CH$_3$)$_2$0 OCH(CH$_3$)$_2$, OCONHCH$_3$, OCH$_2$CH$_3$, and OCH(CH$_3$)$_2$.

Each $R^{7a}$ may be substituted at a substitutable position with one or more radicals of $R^8$; Each $R^8$ is independently $C_{1-6}$ alkyl, $C_{1-6}$ alkoxy, $C_{1-6}$ haloalkyl, $C_{1-6}$ haloalkylOR$^{11}$, CO$_0$ alkylOR$^{11}$, $C_{0-6}$ alkylCON(R$^{11}$)$_2$, $C_{0-6}$ alkylCOR$^{11}$, $C_{0-6}$ alkylCOOR$^{11}$, NR$^{11}$COOR$^{11}$, or $C_{0-6}$ alkylSO$_2$R$^{11}$.

Examples of $R^{7a}$ are selected from the group consisting of halogen, trifluoromethyl, $C_{1-6}$ alkyl, $C_{1-6}$alkoxy, CH=CHCOOH, CH$_2$COOH, OCH$_2$COOH, OCONHCH(CH$_3$)$_2$, NHCOCH$_3$, OH, OCH$_3$, COOH, COOCH$_3$, OCH$_2$C(CH$_3$)$_3$, OCH$_2$CH(CH$_3$)$_2$, OCH(CH$_3$)$_2$0COCH(CH$_3$)$_2$, OCONHCH$_3$, OCH$_2$CH$_3$, and OCH(CH$_3$)$_2$.

Each $R^3$ is independently selected from the group consisting of $R^6$ and -L-$R^6$. One embodiment is that $R^3$ is $R^6$ and is independently hydrogen, $C_{1-6}$ alkyl, $C_{1-6}$ alkoxy, $C_{1-6}$ haloalkyl, $C_{0-6}$haloalkylOR$^{11}$, $C_{0-6}$alkylOR$^{11}$, CO$_{0-6}$ alkylCON(R$^{11}$)$_2$, OCON(R$^{11}$)$_2$, $C_{0-6}$alkylCOR$^{11}$, CONR$^{11}$R$^{11}$, $C_{0-6}$ alkylCOOR$^{11}$; 5-12 membered aromatic or non-aromatic ring; 5-12 membered heteroaryl or heterocyclyl having one or more heteroatoms N, O or S; Each $R^6$ may be substituted at a substitutable position with one or more radicals of $R^{6a}$; Preferred $R^6$ is hydrogen or optionally substituted phenyl.

Each $R^{6a}$ is independently halogen, $C_{1-6}$ alkyl, $C_{1-6}$ alkoxy, $C_{1-6}$ haloalkyl, $C_{0-6}$ haloalkylOR$^{11}$, CON(R$^{11}$)$_2$, CONR$^{11}$R$^{11}$, $C_{0-6}$ alkylCOOR$^{11}$, CR$^{11}$=CR$^{11}$COOR$^{11}$, $C_{0-6}$ alkylOR$^{11}$, $C_{0-6}$ alkylCOR$^{11}$, $C_{0-6}$alkylSO$_2$R$^{11}$, $C_{0-6}$alkylOCOOR$^{11}$, $C_{0-6}$ alkylNR$^{11}$OR$^{11}$, $C_{0-6}$ alkyl SO$_2$NR$^{11}$COR$^{11}$, $C_{0-6}$alkyl SO$_2$N(R$^{11}$)$_2$; $C_{0-6}$ alkylSR$^{11}$, (C$_{0-6}$ alkyl)C=O(OR$^{11}$), OVOR$^{11}$, OC$_{0-6}$ haloalkyl, aryloxy, aralkyloxy, aryloxyalkyl, $C_{1-6}$ alkoxyaryl, arylC$_{0-6}$ alkylcarboxy, NR$^{11}$SO$_2$R$^{11}$, OC$_{0-6}$ alkyl, OC$_{0-6}$alkylCOOR$^{11}$, $C_{0-6}$ alkoxyheteroaryl, $C_{0-6}$ alkoxyheterocyclyl, cycloalkylCOOR$^{11}$.

Another embodiment is that $R^3$ is L-$R^6$, L is independently selected from direct bond, —CO—, —CONH—, —CONR$^{11}$—, —C(=NR$^{11}$)—, —C(=NOR$^{11}$)—, —CS—, —C(=NN(R$^{11}$)$_2$)—; $C_{2-6}$ alidiyl chain wherein the alidiyl chain is optionally interrupted by —C(R$^{11}$)$_2$—, —C(R$^{11}$)$_2$C(R$^{11}$)$_2$—, —C(R$^{11}$)=C(R$^{11}$)—, —C≡C—, —O—, —S—, —N(R$^{10}$)CO—, —N(R$^{10}$)CO$_2$, —NR$^{11}$—, —OR$^{11}$—, —CON(R$^{10}$)—, —CO—, —CO$_2$—, —OC(=O)—, —OC(=O)N(R$^{10}$)—, —SO$_2$—, —N(R$^{10}$)SO$_2$—, or —SO$_2$N(R$^{10}$)—; —(CH$_2$)$_m$—V$_0$—(CH$_2$)$_n$— or —V$_0$(CH$_2$)$_n$—V$_0$—; m is 0-6; n is 0-6; V$_0$ is independently —C(R$^{11}$)$_2$—, —C(R$^{11}$)$_2$—, C(R$^{11}$)$_2$—, —C(R$^{11}$)=C(R$^{11}$)—C(R$^{11}$)$_2$—, —C(R$^{11}$)$_2$NR$^{11}$—, —C≡C—, —O—, —S—, —NR$^{11}$—, —CR$^{11}$NR$^{11}$—, —N(R$^{10}$)CO—, —N(R$^{10}$)CO$_2$—, —CON(R$^{10}$)—, —OCO—, —COR$^{11}$—, —COOR$^{11}$—, —CO—, —CO$_2$, —OC(=O), —OC(=O)N(R$^{10}$)—, —SO$_2$—, —N(R$^{10}$)SO$_2$—, —NR$^{10}$COR$^{10}$—, —NR$^{10}$CSNR$^{10}$—, cycloC$_{3-6}$haloalkyl or —SO$_2$N(R$^{10}$)—. Examples of L include O, CH$_2$, CH$_2$O, CH$_2$CH$_2$, C=O, SO$_2$, CONH, CONHC(CH$_3$)$_2$, CONH(CH$_2$)$_3$OCH$_2$, CONHCH$_2$CH$_2$N(CH$_3$)$_2$ or OCH$_2$CH$_2$.

Each $R^4$ is independently selected from $C_{1-6}$ alkyl, CR$^{11}$=CR$^{11}$COOH, $C_{1-6}$ alkoxy, $C_{0-6}$alkylOR$^{11}$, $C_{0-6}$ alkylCOR$^{11}$, $C_{0-6}$ alkylSO$_2$R$^{11}$, $C_{0-6}$ alkylOCOOR$^{11}$, CO$_0$ alkylNR$^{11}$COR$^{11}$, $C_{0-6}$ alkylSO$_2$NR$^{11}$COR$^{11}$, $C_{0-6}$ alkylSO$_2$N(R$^{11}$)$_2$, $C_{0-6}$alkylSR$^{11}$, (C$_{0-4}$ alkyl)C=O(OR$^{11}$), OVOR$^{11}$, halogen, $C_{1-4}$ haloalkyl, $C_0$alkylC≡N, OC$_{0-6}$ haloalkyl, aryloxy, aralkyloxy, aryloxyalkyl, $C_{1-4}$ alkoxyaryl, arylC$_{0-6}$alkylCOOR$^{11}$, NR$^{11}$SO$_2$R$^{11}$, OC$_{1-6}$ alkyl, OC$_{0-6}$ alkylCOOR$^{11}$, $C_{0-6}$ alkoxyheteroaryl, $C_{0-6}$ alkoxyheterocyclyl, cycloalkylCOOR$^{11}$, a 5-12 membered aromatic ring or non-aromatic ring, or 5-12 membered heteroaryl or heterocyclyl having one or more heteroatoms N, O or S. Preferred $R^4$ is selected from the group consisting of OH, CN, C(CH$_3$)$_2$H, SO$_2$CH$_3$, SO$_2$C(CH$_3$)$_3$, SO$_2$CH$_2$CH$_3$, SCH$_2$CH$_3$, SCH$_3$, OCH$_3$, $C_{1-6}$ alkyl, CH$_2$COOH, C(CH$_3$)$_2$COOH, NHSO$_2$CH$_3$, F, Cl, Br, cyclobutane-COOH, OC(CH$_3$)$_2$ OOH, CF$_3$, C(CH$_3$)$_2$COOH, CH$_2$COOCH$_3$, CH$_2$CH$_2$COOH, OCH$_2$COOCH$_3$, and COCH$_3$. More preferably, $R^4$ is SO$_2$CH$_3$, SO$_2$CH$_2$CH$_3$, SCH$_2$CH$_3$, or SCH$_3$.

Each $R^4$ is optionally substituted at a substitutable position with one or more radicals of $R^{4a}$. Each $R^{4a}$ is independently selected from $C_{1-6}$ alkyl, (C$_{1-6}$ alkyl)C=O(OR$^{11}$); $C_{1-6}$ alkoxy, $C_{0-6}$ alkylOR$^{11}$, $C_{0-6}$ alkylCOR$^{11}$, $C_{0-6}$alkylSO$_2$R$^{11}$, $C_{0-6}$alkyl SO$_2$N(R$^{11}$)$_2$; $C_{0-4}$ alkylSR$^{11}$, (C$_{0-4}$ alkyl)C=O(OR$^{11}$), halogen, $C_{1-6}$ haloalkyl, aryloxy, aralkyloxy, aryloxyalkyl, $C_{1-6}$ alkoxyaryl, arylC$_{0-6}$alkylCOOR$^{11}$, CO$_{0-6}$ alkylC≡N, NR$^{11}$SO$_2$R$^{11}$, OC$_{1-6}$ alkyl, or OC$_{0-6}$alkylCOOR$^{11}$.

Each $R^{11}$ is independently selected from R$^{11}$, C(=O)R$^{11}$, CO$_2$R$^{11}$, SO$_2$R$^{11}$.

Each $R^{11}$ is independently selected from hydrogen or substituted or unsubstituted $C_{1-8}$ aliphatic group; $C_{1-4}$ haloalkyl; N(R$^{12}$)$_2$; 5-12 membered aromatic or non-aromatic ring, or 5-12 membered heteroaryl or heterocyclyl having one or more heteroatoms, N, S or O; which is optionally substituted at a substitutable position with one or more radicals of $R^{12}$.

Each $R^{12}$ is independently halogen, $C_{1-6}$haloalkyl, $C_{1-6}$ alkyl, $C_{1-6}$ alkoxy, (C$_{1-6}$ alkyl)C=O(OR$^{13}$); $C_{0-6}$ alkylCOR$^{13}$, $C_{0-6}$ alkylSO$_2$R$^{13}$, $C_{0-6}$ alkylCON(R$^{13}$)$_2$, $C_{0-6}$ alkylCONR$^{13}$OR$^{13}$, C$_{0-6}$ alkylOR$^{13}$, C$_{1-6}$ alkyl SO$_2$N(R$^{13}$)$_2$, C$_{0-6}$ alkylSR$^{13}$, (C$_{0-4}$ alkyl)C=O(OR$^{13}$), C$_{0-6}$haloalkylOR$^{13}$, aryloxy, aralkyloxy, aryloxyalkyl, C$_{0-6}$ alkoxyaryl, arylCO$_6$ alkylcarboxy, C$_{0-6}$ alkylNR$^{13}$SO$_2$R$^{13}$, OC$_{1-6}$ alkyl, or OC$_{1-6}$ alkylCOOH.

Each R$^{13}$ is independently hydrogen or substituted or unsubstituted C$_{1-8}$ aliphatic group.

Each R$^{14}$ is independently C$_{1-4}$ alkyl, C$_{1-4}$ alkoxy, halogen, C$_{1-4}$ haloalkyl, C$_{0-6}$ alkylCON(R$^{11}$)$_2$, C$_{0-6}$alkyl CONR$^{11}$OR$^{11}$, C$_{0-6}$ alkylOR$^{11}$, or C$_{0-6}$alkylCOOR$^{11}$.

Another embodiment of the invention is that G is independently G1, G2 or G3;

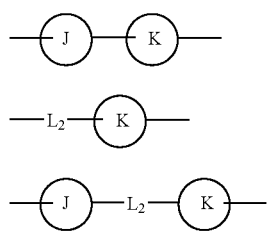

G1

G2

G3

Each Ring J or Ring K may be independently absent, same or different and is independently selected from a 5-12 membered aromatic or non-aromatic ring, or 5-12 membered heterocyclyl or heteroaryl having one or more hetero atoms, N, S or O.

Each Ring J or Ring K independently is optionally substituted at a substitutable position with one or more radicals of R$^4$. Ring J is preferably a phenyl ring or a 5-6 membered heteroaryl ring. Examples of Ring J include phenyl, pyridinyl, thienyl, furanyl, morpholinyl, thiazolyl, indolyl, oxazolyl, biphenyl, naphthyl, piperidinyl, piperazinyl, or imidazolyl. A preferred Ring J is thienyl or phenyl. Ring J is optionally substituted at a substitutable position with one or more radicals of R$^4$. Suitable Ring J substituents designated as R$^4$ include methylsulfonyl, or C$_{1-6}$ aliphatic group or substituents selected from the group consisting of CR$^{11}$=CR$^{11}$COOR$^{11}$, C$_{1-6}$ alkyl, C$_{1-6}$ alkoxy, C$_{0-6}$alkylOR$^{11}$, C$_{1-6}$alkylCOR$^{11}$, C$_0$— alkylSO$_2$R$^{11}$, C$_{0-6}$alkylO-COOR$^{11}$, C$_{0-6}$ alkylCON(R$^{11}$)$_2$, OC$_{1-6}$ alkylCON(R$^{11}$)$_2$, C$_{0-6}$ alkylC=N, C$_{1-6}$ alkylNR$^{11}$COR$^{11}$, C$_0$—alkylSO$_2$NR$^{11}$COR$^{11}$, C$_0$ alkyl SO$_2$N(R$^{11}$)$_2$, C$_{0-6}$ alkylSR$^{11}$, (CO$_{0-6}$ alkyl) C=O(OR$^{11}$), OVOR$^{11}$, halogen, C$_{1-6}$haloalkyl, OC$_{1-6}$haloalkyl, aryloxy, aralkyloxy, aryloxyalkyl, C$_{1-6}$ alkoxyaryl, arylC$_{0-6}$ alkylCOOR$^{11}$, NR$^{11}$SO$_2$R$^{11}$, OC$_{1-6}$ alkyl, OC$_{0-6}$alkylCOOR$^{11}$, C$_{0-6}$-alkoxyheteroaryl, C$_{0-6}$ alkoxyheterocyclyl, cycloalkylCOOR$^{11}$, a 5-12 membered aromatic ring or non-aromatic ring, and 5-12 membered heteroaryl or heterocyclyl having one or more heteroatoms N, O or S. Examples of preferred R$^4$ include OH, CN, C(CH$_3$)$_2$OH, SO$_2$CH$_3$, SO$_2$NH$_2$, SO$_2$CH$_2$CH$_3$, SO$_2$C(CH$_3$)$_3$, SCH$_2$CH$_3$, SCH$_3$, OCH$_3$, C$_{1-6}$ alkyl, CH$_2$COOH, C(CH$_3$)$_2$COOH, NHSO$_2$CH$_3$, F, Cl, Br, C(CH$_2$CH$_3$)$_2$COOH, CH$_2$COOCH$_3$, C(CH$_3$)$_2$COOCH$_3$, CH$_2$CH$_2$COOH, CH=CHCOOH, OCH$_2$COOCH$_3$, COCH$_3$, OCH$_3$, COOC(CH$_3$)$_3$, cyclobutane-COOH, OC(CH$_3$)$_2$COOH, CH$_2$CH$_3$, CH$_3$, CH(CH$_3$)$_2$, CH$_2$COOCH$_3$, OCON(CH$_2$CH$_3$)$_2$, NHCOCH$_3$, or CF$_3$.

Examples of Ring K include phenyl, pyridinyl, thienyl, furanyl, morpholinyl, thiazolyl, indolyl, oxazolyl, biphenyl, naphthyl, piperidinyl, piperazinyl, isoxazolyl, pyrimidinyl, or imidazolyl. Ring K is optionally substituted at a substitutable position with one or more radicals of R$^4$. Suitable Ring K substituents designated as R$^4$ include methylsulfonyl, or C$_{1-6}$ aliphatic group or substituents selected from the group consisting of CR$^{11}$=CR$^{11}$COOR$^{11}$, C$_{1-4}$ alkyl, C$_{1-4}$ alkoxy, C$_{0-6}$ alkylOR$^{11}$, C$_{1-6}$ alkylCOR$^{11}$, C$_{0-6}$ alkylSO$_2$R$^{11}$, C$_{0-6}$ alkylO-COOR$^{11}$, CO$_{0-6}$ alkylNR$^{11}$COR$^{11}$, C$_{0-6}$ alkylSO$_2$NR$^{11}$COR$^{11}$, C$_{0-6}$alkylSO$_2$N(R$^{11}$)$_2$, C$_{0-6}$ alkylSR$^{11}$, (C$_{0-6}$alkyl)C=O(OR$^{11}$), OVOR$^{11}$, halogen, C$_{1-6}$haloalkyl, OC$_{1-6}$ haloalkyl, C$_{1-6}$ alkylC=N, aryloxy, aralkyloxy, aryloxyalkyl, C$_{1-6}$ alkoxyaryl, arylC$_{0-6}$alkylcarboxy, NR$^{11}$SO$_2$R$^{11}$, OC$_{1-6}$ alkyl, OC$_{0-6}$ alkylCOOR$^{11}$, C$_{0-6}$ alkoxyheteroaryl, C$_{0-6}$alkoxyheterocyclyl, cycloalkyl COOR$^{11}$, a 5-12 membered aromatic ring or non-aromatic ring, and 5-12 membered heteroaryl or heterocyclyl having one or more heteroatoms N, O or S. Preferably, Ring K is phenyl, pyridinyl, thienyl, furanyl, morpholinyl, thiazolyl, indolyl, oxazolyl, biphenyl, naphthyl, piperidinyl, piperazinyl, isoxazolyl, pyrimidinyl, or imidazolyl. When Ring K is a phenyl or pyridinyl, it is preferably substituted by methylsulfonyl.

Examples of preferred R$^4$ groups include OH, CN, C(CH$_3$)$_2$ H, SO$_2$CH$_3$, SO$_2$NH$_2$, SO$_2$CH$_2$CH$_3$, SO$_2$C(CH$_3$)$_3$, SCH$_2$CH$_3$, SCH$_3$, OCH$_3$, C$_{1-4}$ alkyl, CH$_2$COOH, C(CH$_3$)$_2$ OOH, NHSO$_2$CH$_3$, F, Cl, Br, C(CH$_2$CH$_3$)$_2$COOH, CH$_2$COOCH$_3$, C(CH$_3$)$_2$COOCH$_3$, CH$_2$CH$_2$COOH, CH=CHCOOH, OCH$_2$COOCH$_3$, COCH$_3$, OCH$_3$, COOC (CH$_3$)$_3$, cyclobutane-COOH, OC(CH$_3$)$_2$COOH, CH$_2$CH$_3$, CH$_3$, CH(CH$_3$)$_2$, CH$_2$COOCH$_3$, OCON(CH$_2$CH$_3$)$_2$, NHCOCH$_3$, or CF$_3$, -L$_2$ is —(CH$_2$)$_m$—V$_2$—(CH$_2$)$_n$— or —V$_2$—(CH$_2$)$_m$—V$_2$—; m is 0-6; n is 0-6; V$_2$ is independently —C(R$^{11}$)$_2$—, —C(R$^{11}$)$_2$C(R$^{11}$)$_2$—, —CR$^{11}$=C (R$^{11}$—C(R$^{11}$)$_2$O—, —C(R$^{11}$)$_2$NR$^{11}$—, —C≡C—, —O—, —S—, —N(R$^{10}$)CO—, —N(R$^{10}$)CO$_2$—, —CON(R$^{10}$)—, —CON(R$^{10}$)—, —CON(R$^{11}$)O—, —CO—, —CO$_2$—, —OR$^{11}$N—, —OR$^{11}$COO—, —OC(=O)—, —OC(=O)N (R$^{10}$)—, —SO$_2$—, —N(R$^{11}$)SO$_2$—, —NR$^{10}$CONR$^{10}$—, cycloC$_{3-6}$ alkyl, —NR$^{11}$CSNR$^{10}$—, cycloC$_{3-6}$haloalkyl or —SO$_2$N(R$^{10}$)—; C$_{0-6}$ alidiyl chain wherein alidiyl chain is optionally interrupted by —C(R$^{11}$)$_2$—, —C(R$^{11}$)$_2$ C(R$^{11}$)$_2$—, —C(R$^{11}$)=C(R$^{11}$)—, —C(R$^{11}$)$_2$O—, —C≡C—, —O—, —S—, —N(R$^{10}$)CO—, —N(R$^{10}$) CO$_2$—, —CON(R$^{10}$)—, —CON(R$^{11}$)—, —CON(R$^{11}$)O—, —CO—, —CO$_2$—, —OC(=O)—, —OC(=O)N(R$^{10}$)—, —SO$_2$—, —N(R$^{10}$)SO$_2$—, cycloC$_{3-6}$alkyl or —SO$_2$N (R$^{10}$)—; 5-12 membered aromatic or non-aromatic ring, 5-12 membered heteroaryl or heterocyclyl having one or more heteroatoms, N, S or O which is optionally substituted at a substitutable position with one or more radicals of R$^9$. Alternatively, L$_2$ is a direct bond, —CS—, —C$_{1-6}$ alkyl-, —C$_{1-6}$ alkoxy-, —C$_{0-6}$ alkylCOO—, —CH=CHCOO—, —C$_{0-6}$alkylCONR$^{11}$—, —OC$_{0-6}$alkylCOO—, —C$_{0-6}$alkylSO$_2$—, —C$_{0-6}$alkyN(R$^{11}$)—, —C$_{0-6}$ alkylN(R$^{11}$)—, —C$_{0-6}$ alkylCO—, -cycloalkylamine-, —C(=NR)—, —C(=NOR$^{11}$)—, —C(=NN(R$^{11}$)$_2$)—; 5-12 membered aromatic or non-aromatic ring, or 5-12 membered heteroaryl or heterocyclyl having one or more heteroatoms, N, S or O which is optionally substituted at a substitutable position with one or more radicals of R$^9$. A preferred L$_2$ is selected from the group consisting of —CONH—, —CONHCH$_2$—, —CH$_2$O—, —OCH$_2$COOCH$_2$—, —CONHCH$_2$—, and —C≡C—.

Another embodiment is that G is G$^1$, R$^1$ is R$^5$ and R$^2$ is R$^7$. When G of formulae IIaa, IIbb, IIcc, or IIdd is G1, a more preferred embodiment of this invention relates to a compound having one or more features selected from the group consisting of:
a) R$^1$ is phenyl, pyridinyl, thienyl, furanyl, morpholinyl, thiazolyl, indolyl, oxazolyl, isoxazolyl, pyrimidinyl, or imidazolyl; R$^5$ is optionally substituted at a substitutable position with one or more radicals of R$^{5a}$;

b) $R^{5a}$ is halogen, trifluoromethyl, $OCONHCH(CH_3)_2$, $NHCOCH_3$, OH, $OCH_3$, COOH, $COOCH_3$, $OCH_2C(CH_3)_3$, $OCH_2CH(CH_3)_2$, $OCH_2CH_2N(CH_3)_2$, $OCH(CH_3)_2{}_0COCH(CH_3)_2$, $OCONHCH_3$, $OCH_2CH_3$, or $OCH(CH_3)_2$;

c) $R^2$ is trifluoromethyl, $COOCH_3$, $CH_2OH$, $CONHCH_2CH_3$, $CONHOCH_2CH(OH)CH_2OH$, $CONHCH_2CH_2N(CH_3)_2$, $CONHCH_2CH_2OCH_3$, $CONHCH_2CH_2OCH_3$, $CH_2COOCH_3$, $CON(CH_3)_2$, $COOCH(CH_3)_2$, $CONHCH_2CH_2CH_2O$ $CH_3$, $OCOCH(CH_3)_2$, $OCH_2CON(CH_3)_2$, $CH_2CONHCH_2$ $(CH_3)$, $C(CH_3)_2OH$, COOH, nitro or $COOCH(CH_3)_2$;

d) $R^3$ is hydrogen or optionally substituted phenyl;

e) Ring J is thienyl, thiazolyl, furanyl, pyridinyl or phenyl;

a) Ring K is optionally substituted phenyl or pyridinyl; and b) $R^4$ is OH, CN, $C(CH_3)_2OH$, $SO_2CH_3$, $SO_2C(CH_3)_3$, $CH_3$, $SO_2NH_2$, $SO_2CH_2CH_3$, $SCH_2CH_3$, $SCH_3$, $OCH_3$, $CF_3$, $OCF_3$, $CH_2CF_3$, $C_{1-6}$alkyl, halogen or $CH_2COOH$.

Another embodiment is that G is $G^1$, $R^1$ is $R^5$ and $R^2$ is $R^7$. When G of formulae IIaa, IIbb, IIcc, or IIdd is G1, a more preferred embodiment of this invention relates to a compound having one or more features selected from the group consisting of:

a) $R^1$ is thienyl, furanyl, morpholinyl, thiazolyl, indolyl, oxazolyl, pyridinyl, imidazolyl, isoxazolyl, pyrimidinyl or phenyl; $R^5$ is optionally substituted at a substitutable position with one or more radicals of $R^{5a}$;

b) $R^{5a}$ is halogen, trifluoromethyl, $OCONH(CH_2)_2CH_3$, $OCONH(CH_2CH_3)_2$, $NHCOCH_3$, OH, $OCH_3$, COOH, $COOCH_3$, $OCH_2C(CH_3)_3$, $OCH_2CH(CH_3)_2$, $OCH(CH_3)_2{}_0COCH(CH_3)_2$, $OCONHCH_3$, $OCH_2CH_3$, or $OCH(CH_3)_2$;

c) $R^2$ is $R^7$ independently selected from $CH_2C\equiv N$, $C(CH_3)_2C\equiv N$, cyclo$C_{3-6}$ alkyl$C\equiv N$, thienyl, furanyl, morpholinyl, thiazolyl, indolyl, oxazolyl, pyridinyl, imidazolyl, isoxazolyl, pyrimidinyl or phenyl; $R^7$ is optionally substituted at a substitutable position with one or more radicals of $R^{7a}$;

d) $R^{7a}$ is selected from the group consisting of halogen, trifluoromethyl, $C_{1-6}$alkyl, $C_{1-6}$alkoxy, CH=CHCOOH, $CH_2COOH$, $OCH_2COOH$, $OCONHCH(CH_3)_2$, $NHCOCH_3$, OH, $OCH_3$, COOH, $COOCH_3$, $OCH_2C(CH_3)_3$, $OCH_2CH(CH_3)_2$, $OCH(CH_3)_2{}_0COCH(CH_3)_2$, $OCONHCH_3$, $OCH_2CH_3$, and $OCH(CH_3)_2$;

e) $R^3$ is hydrogen or optionally substituted phenyl;

f) Ring J is thienyl, thiazolyl, furanyl, pyridinyl, or phenyl;

g) Ring K is optionally substituted phenyl or pyridinyl; and h) $R^4$ is OH, CN, $C(CH_3)_2OH$, CH=CHCOOH, $SO_2CH_3$, $SO_2NH_2$, $SO_2CH_2CH_3$, $SCH_2CH_3$, $SO_2C(CH_3)_3$, $SCH_3$, $OCH_3$, $C_{1-6}$ alkyl, $CF_3$, F, Cl, or Br.

Another embodiment is that G is $G^1$, $R^1$ is $L_1$-$R^5$ and $R^2$ is $R^7$. When G of formulae IIaa, IIbb, IIcc, or IIdd is G1, a more preferred embodiment of this invention relates to a compound having one or more features selected from the group consisting of:

a) $R^1$ is $L_1$-$R^5$; $R^5$ is phenyl, pyridinyl, morpholinyl, oxazolyl, furanyl, thiazolyl or thienyl; $R^5$ is optionally substituted with $R^{5a}$;

b) $R^{5a}$ is halogen or trifluoromethyl;

c) $L_1$ is CS, $CH_2$, $CH_2O$, $CH_2CH_2$, C—O, $SO_2$, CONH, $CONHC(CH_3)_2$, $CONH(CH_2)_3OCH_2$, $OCH_2$, $OCH_2CO$, or $OCH_2CH_2$;

d) $R^2$ is trifluoromethyl, $CONHCH_2CH_2N(CH_3)_2$, $CONHCH_2CH_2N(CH_3)_2$, or $CONHCH_2CH_2OCH_3$.

e) $R^3$ is hydrogen or phenyl optionally substituted with $R^{6a}$;

f) Ring J is thienyl, pyridinyl, furanyl, thiazolyl or phenyl; Ring K is substituted phenyl or pyridinyl; and g) $R^4$ is $SO_2CH_3$, $SO_2NH_2$, $SO_2CH_2CH_3$, $SCH_2CH_3$, $SCH_3$, $OCH_3$, $C_{1-6}$ alkyl, halogen or $CH_2COOH$.

Another embodiment is that G is G1, $R^1$ is $R^5$ and $R^2$ is $L_3R^7$. When G of formulae IIaa, IIbb, IIcc, or IIdd is G1, a more preferred embodiment of this invention relates to a compound having one or more features selected from the group consisting of:

a) $R^1$ is $R^5$ selected from the group consisting of thienyl, furanyl, morpholinyl, thiazolyl, indolyl, oxazolyl, pyridinyl, imidazolyl, isoxazolyl, pyrimidinyl and phenyl; $R^5$ is optionally substituted at a substitutable position with one or more radicals of $R^{5a}$;

b) $R^{5a}$ is $OCH_2C(CH_3)_3$, Cl, F, Br, $OCH_2CH(CH_3)_2$, $OCH_2CH_3$, $CF_3$, COOH, $OCH_3$, OH, $NO_2$, $OCOCH(CH_3)_2$, $NHCOCH_3$, $OCONHCH(CH_3)_2$, $O(CH_2)_2$, $CONH_2$, $O(CH)(CH_3)_2$, $C_{1-6}$alkyl, $OCH_2COOH$, $OCH_2COOC(CH_3)_3$, $O(CH_2)_2N(CH_2CH_3)_2$, $OCOC(CH_3)_3$, $OC(CH_2)_2COOH$, $OCONH(CH_3)_2$, $OCONCH_3$, $OCONHCH_2CH_2CH_3$, $OC(CH_3)_2COOC(CH_3)_3$, and $O(CH_2)_2OH$.

c) $R^2$ is $L_3$-$R^7$; $R^7$ is phenyl, pyridinyl, thienyl, furanyl, morpholinyl, thiazolyl, oxazolyl, piperidinyl, imidazolyl, piperazinyl, or pyridinyl;

d) $L_3$ is —CO—, —$C_{1-6}$ alidiyl-, —CONH—, —$CONR^{11}$—, —$CONR^{11}R^{11}$—, —$CH_2OCH_2$—, —$CH_2OCH_2CH_2$—, —$OCH_2$—, —$CH_2N(CH_3)_2$—, —$CH_2NHCH_2$—, —$CONR^{11}O$—, —$CH_2OCOCH_2$—, —$CH_3N(CH_3)(CH_2)$—, —$CH_2N(cyclopropane)CH_2$—, —$CH_2NC(CH_3)_2CH_2$—, —$CH_2N(cyclohexane)CH_2$—, —$CH_2NCH(CH_3)_2CH_2$—, —$CH_2N(CF_3)(CH_2)_2$—, $CH_2N(CH_3)(CH_2)CH_2OCOCH_2CH_2$—, —$CONHCH_2CH_2N(CH_3)_2$—, or —$CH_2N(CH_2C\equiv N)CH_2$—, —CS—;

e) $R^{7a}$ is selected from the group consisting of halogen, $C_{1-6}$alkyl, $C_{1-6}$ alkoxy, $CF_3$, $OCH_2CH_2COOH$, $CH_2COOH$, $COOCH_3$, $CH_2OH$ and $OCH_3$.

f) $R^3$ is hydrogen or phenyl optionally substituted with $R^{6a}$;

g) Ring J is thienyl, pyridinyl, thiazolyl or phenyl;

h) Ring K is substituted phenyl or pyridinyl; and i) $R^4$ is $SO_2CH_3$, $SO_2CH_2CH_3$, $SCH_2CH_3$, $SCH_3$, $SO_2NH_2$, $OCH_3$, $C_{1-6}$alkyl, $CH_2COOH$, $C(CH_3)_2$ OOH, $NHSO_2CH_3$, F, Cl, Br, $CF_3$ or $COCH_3$;

Another embodiment is that G is $G^1$, $R^1$ is $L_1$-$R^5$ and $R^2$ is $L_3$-$R^7$. When G of formulae IIaa, IIbb, IIcc, or IIdd is G1, a more preferred embodiment of this invention relates to a compound having one or more features selected from the group consisting of:

a) $R^5$ is $L_1$-$R^5$; $R^5$ is selected from the group consisting of thienyl, furanyl, morpholinyl, thiazolyl, indolyl, imidazolyl, piperazinyl, piperidinyl, oxazolyl, pyridinyl, isoxazolyl, pyrimidinyl, imidazolyl and phenyl; $R^5$ is optionally substituted at a substitutable position with one or more radicals of $R^{5a}$;

b) $R^{5a}$ is $C_{1-6}$ alkyl, $C_{1-6}$ alkoxy, COOH, halogen or trifluoromethyl;

c) $L_1$ is CS, $CH_2$, $CH_2O$, $CH_2CH_2$, $OCH_2CH_2$, $OCH_2CO$, C=O, $SO_2$, CONH, $CONHC(CH_3)_2$, $CONH(CH_2)_3CH_2$, or $CONHCH_2CHN(CH_3)_2$;

d) $R^2$ is $L_3$-$R^7$; $R^7$ is selected from the group consisting of phenyl, pyridinyl, thienyl, furanyl, morpholinyl, thiazolyl, oxazolyl, pyridinyl, isoxazolyl, pyrimidinyl, imidazolyl, $CF_3$, cyclo$C_{3-6}$ alkyl$C\equiv N$, $CO_0$ alkyl$C\equiv N$ and $COOCH_3$; $R^7$ is optionally substituted at a substitutable position with one or more radicals of $R^{7a}$;

e) $L_3$ is $CH_2$, CS, $CH_2OCH_2$, $NC(CH_3)_2$, $CH_2NH(CH_2)_2$, CONH, CO, $CONR^{11}$, $OCH_2$, $CH_2N(CH_3)_2CH_2$, $CH_2OCOCH_2$, $CH_2CONHCH_2$, $CH_2CONHCH_2CH_2$, cycloalkylamine, $CH_2N(CH_3)CH_2$, or $CH_2NCH(CH_3)_2$ $H_2$;
f) $R^{7a}$ is selected from the group consisting of halogen, trifluoromethyl, $C_{1-6}$alkyl, $C_{1-6}$alkoxy, $CH=CHCOOH$, $CH_2COOH$, $OCH_2COOH$, $OCONH-CH(CH_3)_2$, $NHCOCH_3$, OH, $OCH_3$, COOH, $COOCH_3$, $OCH_2C(CH_3)_3$, $OCH_2CH(CH_3)_2$, $OCH(CH_3)_2OCOCH(CH_3)_2$, $OCONHCH_3$, $OCH_2CH_3$, $CH_2N(CH_2)CH_2CF_3$, and $OCH(CH_3)_2$;
g) $R^3$ is hydrogen or phenyl optionally substituted with $R^{6a}$;
h) Ring J is thienyl, thiazolyl, pyridinyl, furanyl or phenyl; Ring K is optionally substituted phenyl or pyridinyl; and
i) $R^4$ is $SO_2CH_3$, $SO_2CH_2CH_3$, $SCH_2CH_3$, $SCH_3$, $OCH_3$, $C_{1-5}$ alkyl, $CH_2COOH$, $C(CH_3)_2COOH$, $NHSO_2CH_3$, F, Cl, or Br.

Another embodiment is that G is G2 and $R^1$ is $R^5$ and $R^2$ is $R^7$. When G of formulae IIaa, IIbb, IIcc, or IIdd is G2, a more preferred embodiment of this invention relates to a compound having one or more features selected from the group consisting of:
a) $R^1$ is $R^5$ selected from the group consisting of thienyl, furanyl, morpholinyl, thiazolyl, indolyl, oxazolyl, pyridinyl, isoxazolyl, pyrimidinyl, imidazolyl and phenyl; $R^5$ is optionally substituted at a substitutable position with one or more radicals of $R^a$;
b) $R^2$ is $R^7$ selected from the group consisting of phenyl, pyridinyl, thienyl, furanyl, morpholinyl, thiazolyl, oxazolyl, pyridinyl, isoxazolyl, pyrimidinyl, imidazolyl, $CF_3$, cyclo$C_{3-6}$ alkylC≡N, $C_{0-6}$ alkylC≡N, and $COOCH_3$; $R^7$ is optionally substituted at a substitutable position with one or more radicals of $R^{7a}$;
c) $R^3$ is hydrogen or optionally substituted phenyl;
d) $L_2$ is selected from the group consisting of —CONH—, —CONHCH$_2$—, —CH$_2$O—, —OCH$_2$COOCH$_2$—, —O—, C≡C—, —OCH$_2$CH$_2$—, and —CONHOCH$_2$CH(OH)CH$_2$O—, —CS—;
e) Ring J or K is substituted phenyl, biphenyl, pyridinyl, piperidinyl, piperazinyl, morpholinyl, furanyl, thienyl, or naphthyl; and
f) $R^4$ is selected from the group consisting of OH, CN, $C(CH_3)_2OH$, $SO_2CH_3$, $SO_2CH_2CH_3$, $SO_2CH_2CH_2CH_3$, $SCH_2CH_3$, $SCH_3$, $OCH_3$, $C_{1-6}$ alkyl, $CH_2COOH$, $C(CH_3)_2COOH$, $NHSO_2CH_3$, F, Cl, Br, $C(CH_3)_2COOH$, $CH_2COOCH_3$, $C(CH_3)_2COOCH_3$, $CH_2CH_2COOH$, $OCH_2CON(R^{11})_2$, $OCH_2CH_2N(CH_3)_2$, $OCH_2COOH$, $OCH_2COOCH_3$, $CH_2OH$, $COCH_3$, $COOC(CH_3)_3$, cyclobutane-COOH, $OC(CH_3)_2COOH$ and $CF_3$.

Another embodiment is that G is G2, $R^1$ is $L_1$-$R^5$ and $R^2$ is $R^7$. When G of formulae IIaa, IIbb, IIcc, or IIdd is G2, a more preferred embodiment of this invention relates to a compound having one or more features selected from the group consisting of:
a) $R^1$ is $L^1$-$R^5$; $R^5$ is substituted phenyl or pyridinyl;
b) $R^{5a}$ is halogen, trifluoromethyl, $C_{1-6}$ alkyl, $C_{1-6}$ haloalkyl, nitro, $C_{1-6}$ alkoxy, or $OCON(C_{1-6}$-alkyl$)_2$;
c) $L_1$ is $CH_2$, $CH_2O$, $CH_2CH_2$, C=O, $SO_2$, CONH, $CONHC(CH_3)_2$, $CONH(CH_2)_3OCH_2$, $CONHCH_2CH_2N(CH_3)_2$ or $OCH_2CH_2$, —CS—;
d) $R^2$ is $R^7$ is selected from the group consisting of phenyl, pyridinyl, thienyl, furanyl, morpholinyl, thiazolyl, oxazolyl, pyridinyl, $CF_3$, cyclo$C_3$— alkylC≡N, $C_{0-6}$ alkylC≡N or $COOCH_3$;

e) $R^3$ is hydrogen or phenyl optionally substituted with $R^6$;
f) Ring J or K is substituted phenyl, thienyl, furanyl, piperazinyl, piperidinyl or pyridinyl;
g) $L_2$ is CONH, $CONHCH_2$, $CH_2O$, $OCH_2COOCH_2$, O, C≡$C_1$-$C_8$—, $OCH_2CH_2$ or $CONHOCH_2CH(OH)CH_2O$; and
h) $R^4$ is selected from the group consisting of halogen, $C_{1-6}$ haloalkyl, $C_{1-6}$ alkylCOOR$^{11}$, and methyl sulfonyl.

Another embodiment is that G is G2, $R^1$ is $R^5$ and $R^2$ is $L_3R^7$. When G of formulae IIaa, IIbb, IIcc, or IIdd is G2, a more preferred embodiment of this invention relates to a compound having one or more features selected from the group consisting of:
a) $R^1$ is $R^5$ selected from the group consisting of thienyl, furanyl, morpholinyl, thiazolyl, indolyl, oxazolyl, pyridinyl, imidazolyl, isoxazolyl, pyrimidinyl and phenyl; $R^5$ is optionally substituted at a substitutable position with one or more radicals of $R^{5a}$;
b) $R^{5a}$ is halogen or trifluoromethyl;
c) $R^2$ is $L_3$-$R^7$; $R^7$ is selected from the group consisting of phenyl, pyridinyl, thienyl, furanyl, morpholinyl, thiazolyl, oxazolyl, pyridinyl, phenyl, imidazolyl, isoxazole, pyrimidinyl, $CF_3$, cyclo$C_{3-6}$ alkylC≡N, $C_{0-6}$ alkylC≡N and $COOCH_3$; $R^7$ is optionally substituted at a substitutable position with one or more radicals of $R^{7a}$;
d) $L_3$ is —CS—, $CH_2$, $CH_2OCH_2$, $NCH_2$ $(CH_2)_2$, $CH_2N(CH_2)_2$, $CH_2CN$, CONH, CO, or $CONHCH_2$;
e) $R^3$ is hydrogen or optionally substituted phenyl;
f) Ring J or K is substituted phenyl, furanyl, thienyl, pyridinyl, biphenyl or naphthyl;
g) $L_2$ is CONH, CS, $CONHCH_2$, $CH_2O$, $OCH_2COOCH_2$, $OCH_2CH_2$, or or $OCH_2$; and
h) $R^4$ is $SO_2CH_3$, $SO_2CH_2CH_3$, $SCH_2CH_3$, $CH_2COOH$, $C(CH_3)_2COOH$, $NHSO_2CH_3$, F, Cl, Br, $SCH_3$, $OCH_3$, $C_{1-6}$ alkyl, $COOCH_2CO$, $OCH_3$, $CH_2COOH$, $CH_2COOCH_3$, $CH(CH_3)_2COOH$, $OC(CH_3)_2COOH$, $COOC(CH_3)_3$, cyclobutane-COOH, $C(CH_3)_2COOH$, $OCH_2COOCH_3$, and $CF_3$.

Another embodiment is that G is G3, $R^1$ is $R^5$ and $R^2$ is $R^7$. When G of formulae IIaa, IIbb, IIcc, or IIdd is G3, a more preferred embodiment of this invention relates to a compound having one or more features selected from the group consisting of:
a) $R^1$ is $R^5$ selected from the group consisting of thienyl, furanyl, morpholinyl, thiazolyl, indolyl, oxazolyl, pyridinyl, imidazolyl, isoxazole, pyrimidinyl and phenyl; $R^5$ is optionally substituted at a substitutable position with one or more radicals of $R^{5a}$;
b) $R^2$ is $R^7$ selected from the group consisting of phenyl, pyridinyl, thienyl, furanyl, morpholinyl, thiazolyl, oxazolyl, pyridinyl, imidazolyl, isoxazole, pyrimidinyl, $CF_3$, halogen, cyclo$C_3$ \$ alkylC≡N, $C_0$— alkylC≡N and $COOCH_3$; $R^7$ is optionally substituted at a substitutable position with one or more radicals of $R^{5a}$;
c) $R^3$ is hydrogen or optionally substituted phenyl;
d) $L_2$ is selected from the group consisting of —CONH—, —CONHCH$_2$—, —CS—, —CH$_2$O—, —OCH$_2$COOCH$_2$—, —COOCH$_2$—, —CO—, —OCH$_2$—, —OCO—, —NHCON—, —O—, —OCH$_2$CH$_2$—, —OCON—, and —SO$_2$—;
e) Ring J or K is substituted phenyl, biphenyl, pyridinyl, piperidinyl, piperazinyl, morpholinyl, thienyl, pyrimidinyl or naphthyl;
f) $R^4$ is methylsulfonyl, halogen, haloalkyl, $CH_2COOH$, $OCH_2$-phenyl, $CH_2COO$-phenyl, $OCH_2COOH$, or $OCH_2CHN(CH_3)_2$; and g) $R^{5a}$ is $OCH_2C(CH_3)_3$, Cl, F, Br, $OCH_2CH(CH_3)_2$, $OCH_2CH_3$, $CF_3$, COOH, $OCH_3$, OH, $NO_2$, $OCOCH(CH_3)_2$, $NHCOCH_3$, $OCONHCH(CH_3)_2$, $O(CH_2)_2$, $CONH_2$, $O(CH)(CH_3)_2$, $C_{1-6}$ alkyl, $OCH_2COOH$, $OCH_2COOC(CH_3)_3$, $O(CH_2)_2N(CH_2CH_3)_2$, $OCOC(CH_3)_3$, $OC(CH_2)_2COOH$, $OCONH(CH_3)_2$, $OCONCH_3$, $OCONHCH_2CH_2CH_3$, $OC(CH_3)_2COOC(CH_3)_3$, and $O(CH_2)_2OH$.

Another embodiment is that G is G3, $R^1$ is $L_1$-$R^5$ and $R^2$ is $R^7$. When G of formulae IIaa, IIbb, IIcc, or IIdd is G3, a more preferred embodiment of this invention relates to a compound having one or more features selected from the group consisting of:

a) $R^1$ is $L_1$-$R^5$; $R^5$ is substituted phenyl or pyridinyl;
b) $R^{5a}$ is halogen or trifluoromethyl;
c) $L_1$ is $CH_2$, $CH_2O$, $CH_2CH_2$, C=O, $SO_2$, CONH, CONHC(CH_3)_2, CS, $CONH(CH_2)_3OCH_2$, $CONHCH_2CH_2N(CH_3)_2$ or $OCH_2CH_2$;
d) $R^2$ is halogen, $C_{1-6}$ alkyl, $C_{1-6}$ alkoxy, $C_{1-6}$ carboxyalkyl, or $CF_3$;
e) $R^3$ is hydrogen or phenyl optionally substituted with $R^{6a}$;
f) Ring J or K is phenyl, pyridinyl, thienyl, furanyl, piperidinyl, pyrrolidinyl, piperazinyl, morpholinyl, thiazolyl, indolyl, oxazolyl, isoxazolyl, pyrimidinyl, imidazolyl, or biphenyl; and
g) $L_2$ is CS, CONH, $CONHCH_2$, $CH_2O$, $OCH_2COOCH_2$, $OCH_2$ or $OCH_2CH_2$;
h) $R^4$ is selected from the group consisting of halogen, $C_{1-6}$— haloalkyl, $C_{1-6}$alkylCOOR$^{11}$, and methyl sulfonyl.

Another embodiment is that G is G3, $R^1$ is $R^5$ and $R^2$ is $L_3R^7$. When G of formulae IIaa, IIbb, IIcc, or IIdd is G3, a more preferred embodiment of this invention relates to a compound having one or more features selected from the group consisting of:

a) $R^1$ is selected from the group consisting of thienyl, furanyl, morpholinyl, thiazolyl, indolyl, oxazolyl, pyridinyl, isoxazolyl, imidazolyl, pyrimidinyl and phenyl; $R^5$ is optionally substituted at a substitutable position with one or more radicals of $R^{5a}$;
b) $R^2$ is $L_3$-$R^7$; $R^7$ is phenyl, pyridinyl, thienyl, furanyl, morpholinyl, thiazolyl, oxazolyl, piperidinyl, imidazolyl, piperazinyl, pyridinyl, isoxazolyl, imidazolyl, pyrimidinyl, $CF_3$, cyclo$C_{3-6}$ alkylCN, $C_{0-6}$alkylC≡N and $COOCH_3$; $R^7$ is optionally substituted at a substitutable position with one or more radicals of $R^{7a}$;
c) $L_3$ is —CO—, —CS—, —$C_{1-6}$ alidiyl-, —CONH—, —CONR$^{11}$—, —CONR$^{11}$R$^{11}$—, —$CH_2OCH_2$—, —$CH_2OCH_2CH_2$—, —$OCH_2$—, —$CH_2N(CH_3)_2$—, —$CH_2NHCH_2$—, —CONR$^{11}$O—, —$CH_2OCOCH_2$—, —$CH_3N(CH_3)(CH_2)$—, —$CH_2N(cyclopropane)CH_2$—, —$CH_2NC(CH_3)_2CH_2$—, —$CH_2N(cyclohexane)CH_2$—, —$CH_2NCH(CH_3)_2CH_2$—, —$CH_2N(CF_3)(CH_2)_2$—, —$CH_2N(CH_3)(CH_2)CH_2OCOCH_2CH_2$—, —$CONHCH_2CH_2N(CH_3)_2$—, or —$CH_2N(CH_2C≡N)CH_2$—;
d) $R^3$ is hydrogen or optionally substituted phenyl;
e) Ring J or K is substituted phenyl, furanyl, thienyl, pyridinyl, biphenyl or naphthyl; and
f) $L_2$ is CONH, $CONHCH_2$, $CH_2O$, $OCH_2COOCH_2$, CS or $CONHCH_2$;
g) $R^4$ is $SO_2CH_3$, $SO_2CH_2CH_3$, $SCH_2CH_3$, $SCH_3$, $SO_2NH_2$, $OCH_3$, $C_{1-6}$ alkyl, $CH_2COOH$, $C(CH_3)_2COOH$, $NHSO_2CH_3$, F, Cl, Br, $CF_3$ or $COCH_3$.

Another embodiment of this invention relates to a composition comprising a compound of the present invention or a tautomer or a pharmaceutically acceptable salt thereof, and a pharmaceutically acceptable carrier. It will be appreciated that the compounds of this invention may be derivatized at functional groups to provide prodrug derivatives which are capable of conversion back to the parent compounds in vivo. Examples of such prodrugs include the physiologically acceptable and metabolically labile ester derivatives, such as methoxymethyl esters, methylthiomethyl esters, or pivaloyloxymethyl esters derived from a hydroxyl group of the compound or a carbamoyl moiety derived from an amino group of the compound. Additionally, any physiologically acceptable equivalents of the compounds of the present invention, similar to metabolically labile esters or carbamates, which are capable of producing the parent compounds of the present invention in vivo, are within the scope of this invention.

Another embodiment of this invention relates to compounds represented by formulae IIaa-1, IIaa-2, IIaa-3 or IIaa-4 (Embodiment IIaa):

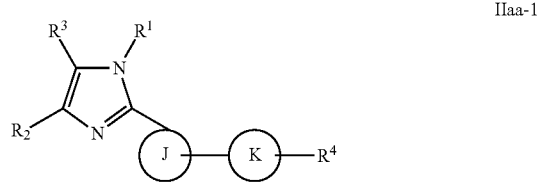

IIaa-1

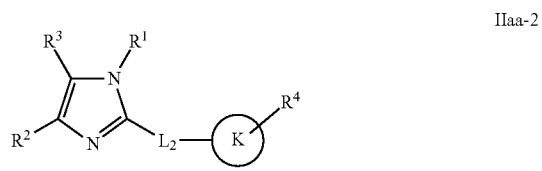

IIaa-2

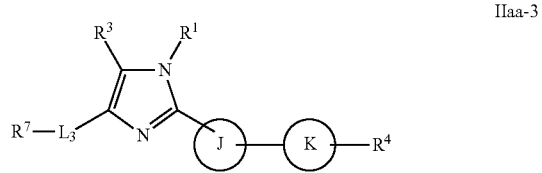

IIaa-3

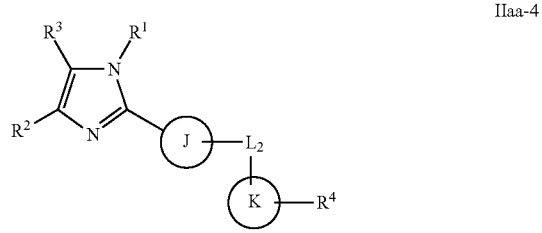

IIaa-4

Another embodiment of this invention relates to compounds represented by formulae IIbb-1, IIbb-2, IIbb-3, or Ibb-4 (Embodiment IIb):

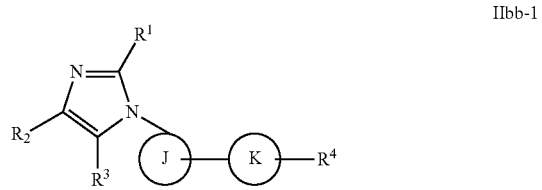

IIbb-1

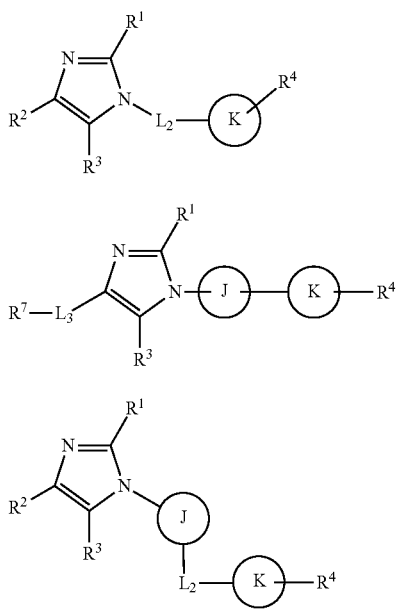

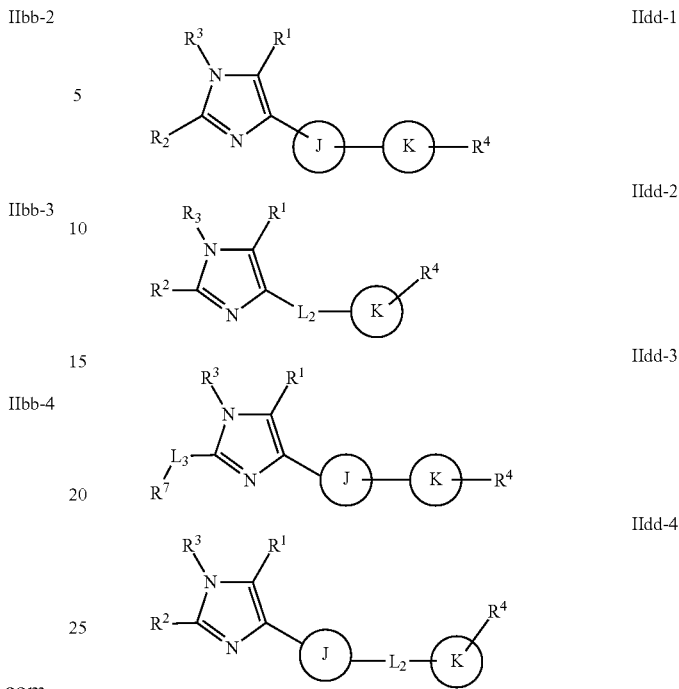

Another embodiment of this invention relates to compounds represented by formulae IIc-1, IIcc-2, IIcc-3, or IIcc-4 (Embodiment IIcc):

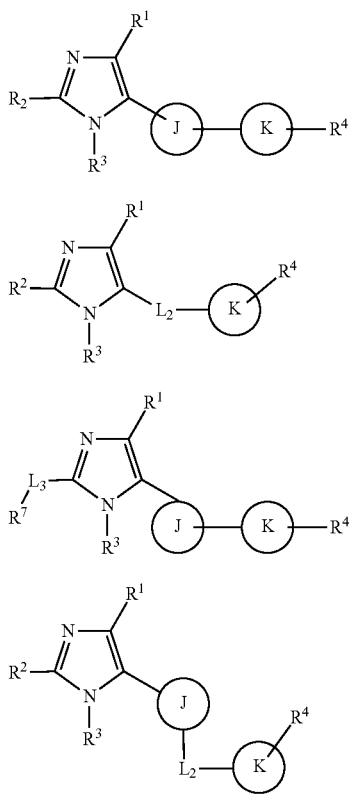

Another embodiment of this invention relates to compounds represented by formulae IIdd-1, IIdd-2, IIdd-3, or IIdd-4 (Embodiment IIdd):

Of the above embodiments IIaa-IIdd, $R^1$ is $R^5$ selected from the group consisting of thienyl, furanyl, morpholinyl, thiazolyl, indolyl, oxazolyl, pyridinyl, isoxazolyl, pyrimidinyl, imidazolyl, and phenyl; $R^5$ is optionally substituted at a substitutable position with one or more radicals of $R^{5a}$. Preferred $R^5$ is phenyl or pyridinyl optionally substituted with $R^{5a}$.

$R^2$ is $R^7$ selected from the group consisting of trifluoromethyl, $COOCH_3$, $CH_2OH$, $CONHCH_2CH_3$, $CONHOCH_2CH(OH)CH_2OH$, $CONHCH_2CH_2N(CH_3)_2$, $CONHCH_2CH_2OCH_3$, $CONHCH_2CH_2OCH_3$, $CH_2COOCH_3$, $CON(CH_3)_2$, $COOCH(CH_3)_2$, $CONHCH_2CH_2CH_2OCH_3$, $OCOCH(CH_3)_2$, $OCH_2CON(CH_3)_2$, $CH_2CONHCH_2(CH_3)$, $C(CH_3)_2OH$, $COOH$, nitro or $COOCH(CH_3)_2$, $CH_2C\equiv N$, $C(CH_3)_2C\equiv N$, cyclo$C_{3-6}$alkylC$\equiv$N, thienyl, furanyl, morpholinyl, thiazolyl, indolyl, oxazolyl, pyridinyl, imidazolyl, isoxazolyl, pyrimidinyl and phenyl; $R^7$ is optionally substituted at a substitutable position with one or more radicals of $R^{7a}$.

$L_1$ is independently selected from direct bond, —CO—, —CONH—, —CONR$^{11}$—, —C(=NR$^{11}$)—, —C(=NOR$^{11}$)—, —C(=NN(R$^{11}$)$_2$)—; $C_{2-6}$ alidiyl chain wherein the alidiyl chain is optionally interrupted by —C(R$^{11}$)$_2$—, —C(R$^{11}$)$_2$C(R$^{11}$)$_2$—, —C(R$^{11}$)=C(R$^{11}$)—, —C$\equiv$C—, —O—, —S—, —N(R$^{10}$)CO—, —N(R$^{10}$)CO$_2$—, —NR$^{11}$—, —OR$^{10}$—, —CON(R$^{10}$)—, —CO—, —CO$_2$—, —OC(O)—, —OC(=O)N(R$^{10}$)—, —SO$_2$—, —N(R$^{10}$)SO$_2$—, or —SO$_2$N(R$^{10}$)—; —(CH$_2$)$_m$—V$_0$—(CH$_2$)$_n$— or —V$_0$—(CH$_2$)—V$_0$—; m is 0-6; n is 0-6; V$_0$ is independently —C(R$^{11}$)$_2$—, —C(R$^{11}$)$_2$C(R$^{11}$)$_2$—, —C(R$^{11}$)=C(R$^{11}$)—, —C(R$^{11}$)$_2$O—, —C(R$^{11}$)$_2$NR$^{11}$—, —C$\equiv$C—, —O—, —S—, —NR$^{11}$—, —CR$^{11}$NR$^{11}$—, —N(R$^{10}$)CO—, —N(R$^{10}$)CO$_2$—, —CON(R$^{10}$)—, —OCO—, —COR$^{11}$—, —COOR$^{11}$—, —CO—, —CO$_2$—, —OC(=O), —OC(=O)N(R$^{10}$)—, —SO$_2$—, —N(R$^{10}$)SO$_2$—, —NR$^{11}$COR$^{11}$—, —NR$^{10}$CSNR$^{10}$—, cycloC$_{3-6}$haloalkyl or —SO$_2$N(R$^{10}$)—; More specifically, L$_1$ is selected from the group consisting of —CONH—, —C$_{1-6}$ alkyl-, —Cl$_6$ alkoxy-, —CO—, —SO₂—, —CH₂—, —CH₂O—, —CH₂CH₂—, —C=O—, —CONH—, —CONHC(CH₃)₂—, —CONH(CH₂)₃CH₂—, —OCH₂CH₂—, —OCH₂CH₂N(CH₃)₂—, and —CONHCH₂CH₂N(CH₃)₂—.

$L_3$ is independently selected from direct bond, —CO—, —CONH—, —CONR¹¹—, —C(=NR¹¹)—, —C(=NOR¹¹)—, —C(=NN(R¹¹)₂)—; $C_{2-6}$ alidiyl chain wherein the alidiyl chain is optionally interrupted by —C(R¹¹)₂—, —C(R¹¹)₂C(R¹¹)₂—, —CR¹¹=C(R¹¹)—, —C≡C—, —O—, —S—, —N(R¹⁰)CO—, —N(R¹⁰)₂, —NR¹¹—, —OR¹¹—, —CON(R¹⁰)—, —CO—, —CO₂—, —OC(=O)—, —OC(=O)N(R¹⁰)—, —SO₂—, —N(R¹⁰)SO₂—, or —SO₂N(R¹⁰)—; —(CH₂)ₘ—V₀—(CH₂)ₙ— or —V₀—(CH₂)ₙ—V₀—; m is 0-6; n is 0-6; V₀ is independently —C(R¹¹)₂—, —C(R¹¹)₂C(R¹¹)₂—, —C(R¹¹)=C(R¹¹)—, —C(R¹¹)₂O—, —C(R¹¹)₂NR¹¹—, —C≡C—, —O—, —S—, —NR¹¹—, —CR¹¹NR¹¹—, —N(R¹⁰)CO—, —N(R¹⁰)CO₂—, —CON(R¹⁰)—, —OCO—, —COR¹¹—, —COOR¹¹—, —CO—, —CO₂, —OC(=O), —OC(O)N(R¹⁰)—, —SO₂—, —N(R¹⁰)SO₂—, —NR¹⁰COR¹¹—, —NR¹⁰CSNR¹⁰—, cycloC₃₋₄ haloalkyl or —SO₂N(R¹⁰)—. More specifically, $L_3$ is —CO—, —C₁₋₆ alidiyl-, —CONH—, —CONR¹¹—, —CONR¹¹NR¹¹—, —CH₂OCH₂—, —CH₂O CH₂CH₂—, —OCH₂—, —CH₂N(CH₃)₂—, —CH₂NHCH₂—, —CONR¹¹O—, —CH₂OCOCH₂—, —CH₃N(CH₃)(CH₂)—, —CH₂N(cyclopropane)CH₂—, —CH₂NC(CH₃)₂CH₂—, —CH₂N(cyclohexane)CH₂—, —CH₂NCH(CH₃)₂CH₂—, —CH₂N(CF₃)(CH₂)₂—, —CH₂N(CH₃)(CH₂)CH₂OCOCH₂CH₂—, —CONHCH₂CH₂N(CH₃)₂—, or —CH₂N(CH₂C≡N)CH₂—.

$R^{7a}$ is selected from the group consisting of halogen, trifluoromethyl, C₁₋₆ alkyl, C₁₋₆alkoxy, CH=CHCOOH, CH₂COOH, OCH₂COOH, OCONHCH(CH₃)₂, NHCOCH₃, OH, OCH₃, COOH, COOCH₃, OCH₂C(CH₃)₃, OCH₂CH(CH₃)₂, OCH(CH₃)₂COCH(CH₃)₂, OCONHCH₃, OCH₂CH₃, or OCH(CH₃)₂.

$L_2$ is independently selected from direct bond, —CO—, —CONH—, —CONR¹¹—, —C(=NR¹¹)—, —C(=NOR¹¹)—, —C(=NN(R¹¹)₂)—; $C_{2-6}$ alidiyl chain wherein the alidiyl chain is optionally interrupted by —C(R¹¹)₂—, —C(R¹¹)₂C(R¹¹)₂—, —C(R¹¹)=C(R¹¹)—, —C≡C—, —O—, —S—, —N(R¹⁰)CO—, —N(R¹⁰)CO₂, —NR¹¹—, —OR¹¹—, CON(R¹⁰)—, —CO—, —CO₂—, —OC(=O)—, —OC(=O)N(R¹⁰)—, —SO₂—, —N(R¹¹)SO₂—, or —SO₂N(R¹¹)—; —(CH₂)ₘ—V₀—(CH₂), or —V₀—(CH₂)ₙ—V₀—; m is 0-6; n is 0-6; V₀ is independently —C(R¹¹)₂—, —C(R¹¹)₂C(R¹¹)₂—, —C(R¹¹)=C(R¹¹)—, —C(R¹¹)₂O—, —C(R¹¹)₂NR¹¹—, —C≡C—, —O—, —S—, —NR¹¹—, —CR¹¹NR¹¹—, —N(R¹⁰)CO—, —N(R¹⁰)CO₂—, —CON(R¹⁰)—, —OCO—, —COR¹¹—, —COOR¹¹—, —CO—, —CO₂, —OC(=O), —OC(=O)N(R¹⁰)—, —SO₂—, —N(R¹⁰)SO₂—, —NR¹⁰COR¹⁰—, —NR¹¹CSNR¹⁰—, cycloC₃₋₆haloalkyl or —SO₂N(R¹⁰)—. More specifically, $L_2$ is selected from the group consisting of —CONH—, —CONHCH₂—, —CH₂O—, —OCH₂COOCH₂—, —O—, C≡C—, —OCH₂CH₂, and —CONHOCH₂CH(OH)CH₂O —.

$R^{5a}$ is independently selected from the group consisting of OCH₂C(CH₃)₃, Cl, F, Br, OCH₂CH(CH₃)₂, OCH₂CH₃, CF₃, COOH, OCH₃, OH, NO₂, OCOCH(CH₃)₂, OCOC(CH₃)₃, NHCOCH₃, OCON(CH₃)₂, OCONHCH₃, OCON(CH₂)₂CH₃, OCONHCH(CH₃)₂, O(CH₂)₂, CONH₂, O(CH)(CH₃)₂, C₁₋₆ alkyl, OCH₂COOH, OCH₂COOC(CH₃)₃, O(CH₂)₂N(CH₂CH₃)₂, OC(CH₃)₂COOC(CH₃)₃, and OCH₂CH₂OH. $R^4$ is selected from the group consisting of SO₂CH₃, SO₂C(CH₃)₃, SO₂NH₂, SO₂CH₂CH₃, SCH₂CH₃, SCH₃, OCH₃, C₁₋₆ alkyl, CH₂COOH, C(CH₃)₂COOH, NHSO₂CH₃, F, Cl, Br, C(CH₃)₂COOH, CH₂COOCH₃, C(CH₃)₂COOCH₃, CH₂CH₂COOH, OCH₂COOCH₃, COCH₃, COOC(CH₃)₃, cyclobutane-COOH, OC(CH₃)₂COOH, COOCH₂CH₃, OCF₃, and CF₃.

Another embodiment of this invention relates to compounds as described above wherein G is selected from the group consisting of:

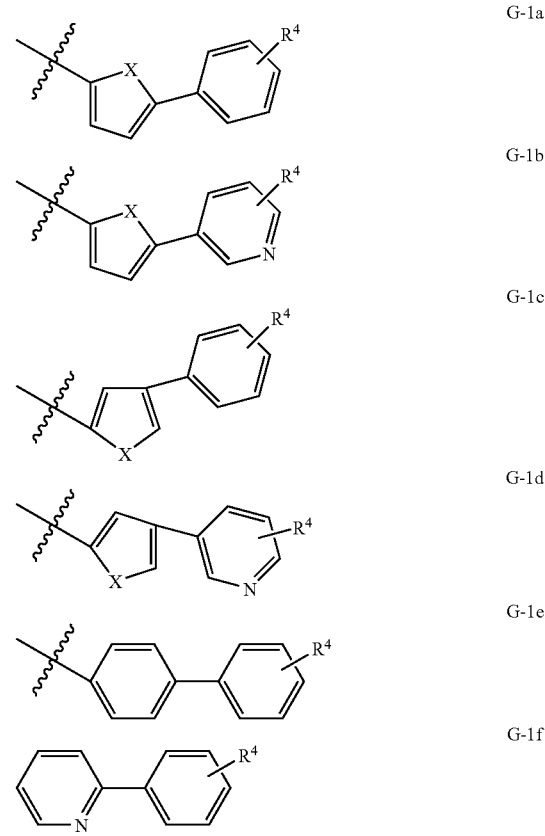

G-1a

G-1b

G-1c

G-1d

G-1e

G-1f

Of the above compounds, R is selected from the group consisting of C₀₋₆ alidiyl chain wherein the alidiyl chain is optionally interrupted by —C(R¹¹)₂—, —C(R¹¹)₂C(R¹¹)₂—, —C(R¹¹)=C(R¹¹)—, —C(R¹¹)₂O—, —C(R¹¹)₂NR¹¹—, —C≡C—, —O—, —S—, —N(R¹⁰)CO—, —N(R¹⁰)CO₂—, —CON(R¹⁰)—, —CO—, —CO₂—, —OC(=O)—, —OC(=O)N(R¹⁰)—, —SO₂—, —N(R¹⁰)SO₂—, or —SO₂N(R¹⁰)—.

Each $R^4$ is independently selected from, C₁₋₆ alkyl, CR¹¹=CR¹¹COOR¹¹, C₁₋₆ alkoxy, C₀₋₆ alkylOR¹¹, C₀₋₆alkylCOR¹¹, C₀₋₆ alkylSO₂R¹¹, C₀₋₆ alkylOCOOR¹¹, C₀₋₆ alkylNR¹¹COR¹¹, C₀₋₆ alkylSO₂NR¹¹COR¹¹, C₀₋₆ alkyl SO₂N(R¹¹)₂, C₀₋₆ alkylSR¹¹, (C₀₋₆ alkyl)C=O(OR¹¹), OVOR¹¹, halogen, C₁₋₆haloalkyl, C₁₋₆haloalkylOR¹¹, OC₁₋₆haloalkyl, aryloxy, aralkyloxy, aryloxyalkyl, C₁₋₆alkoxyaryl, arylC₁₋₆ alkylcarboxy, NR¹¹SO₂R¹¹, OC₀₋₆ alkyl, OC₀₋₆ alkylCOOR¹¹, C₀₋₆alkylC≡N, C₀₋₆ alkoxyheteroaryl, C₀₋₆alkoxyheterocyclyl, cycloalkylCOOR¹¹, a 5-12 membered aromatic ring or non-aromatic ring, or 5-12 membered heteroaryl or heterocyclyl having one or more heteroatoms N, O or S. Preferred $R^4$ is selected from the group consisting of SO₂CH₃, SO₂C(CH₃)₃, SO₂CH₂CH₃, SCH₂CH₃, SCH₃, OCH₃, C₁₋₆ alkyl, CH₂COOH, C(CH₃)₂COOH, NHSO₂CH₃, F, Cl, Br, cyclobutane-COOH, OC(CH$_3$)$_2$COOH, CF$_3$, C(CH$_3$)$_2$COOH, CH$_2$COOCH$_3$, CH$_2$CH$_2$COOH, OCH$_2$COOCH$_3$, and COCH$_3$. More preferably, R$^4$ is SO$_2$CH$_3$, SO$_2$CH$_2$CH$_3$, SCH$_2$CH$_3$, or SCH$_3$.

X is selected from the group consisting of S, NR$^{11}$ and O.

Each R$^4$ is optionally substituted at a substitutable position with one or more radicals of R$^{4a}$; Each R$^{4a}$ is independently selected from, C$_{1-6}$, alkyl, (C$_{1-6}$ alkyl)C=O(OR$^{11}$); C$_{1-6}$ alkoxy, C$_{0-6}$ alkylOR$^{11}$, C$_{0-6}$ alkylCOR$^{11}$, C$_{0-6}$ alkylSO$_2$R$^{11}$, CO$_{0-6}$ alkylSO$_2$N(R$^{11}$)$_2$; C$_{0-6}$ alkylSR$^{11}$, (C$_{0-6}$ alkyl)OC=O(OR$^{11}$), halogen, C$_{1-6}$ haloalkyl, aryloxy, aralkyloxy, aryloxyalkyl, C$_{1-6}$ alkoxyaryl, arylC$_{0-6}$ alkylcarboxy, NR$^{11}$SO$_2$R$^{11}$, OC$_{1-6}$ alkyl, C$_{0-6}$ alkylC≡N, or OC$_{0-6}$ alkyl-COOR$^{11}$.

Definitions

The following definitions apply to the terms used herein, unless expressly stated to the contrary. So, for example, "alkyl" is defined hereinbelow as containing from 1 to 12 carbon atoms, but a substituent defined as C$_{1-6}$ alkyl is limited to an alkyl moiety of from 1 to 6 carbons. All selections of any variables in connection with any of the general structures or formulas herein are understood to be proper only when said selection yields a stable chemical structure as recognized by one skilled in the art.

When particular embodiments are referred to by structure only, all otherwise unnamed chemical groups making up that structure are as defined in each individual embodiment of that structure. So, for example, when it is stated, "In another embodiment, the invention provides the compound according to any one of formulas Ia-d, wherein K is phenyl or pyridyl," it is meant that another embodiment of the invention comprises each embodiment of any one of formulas Ia-d described in the specification in which K is phenyl or pyridyl and all other moieties are as defined in the particular embodiments.

For simplicity, chemical moieties are defined and referred to throughout primarily as univalent chemical moieties (e.g., alkyl, aryl, etc.). Nevertheless, such terms are also used to convey corresponding multivalent moieties under the appropriate structural circumstances clear to those skilled in the art. For example, while an "alkyl" moiety generally refers to a monovalent radical (e.g. CH$_3$—CH$_2$—), in certain circumstances a bivalent linking moiety can be "alkyl," in which case those skilled in the art will understand the alkyl to be a divalent radical (e.g., —CH$_2$—CH$_2$—), which is equivalent to the term "alkylene." (Similarly, in circumstances in which a divalent moiety is required and is stated as being "aryl," those skilled in the art will understand that the term "aryl" refers to the corresponding divalent moiety, arylene.) All atoms are understood to have their normal number of valences for bond formation (i.e., 4 for carbon, 3 for N, 2 for 0, and 2, 4, or 6 for S, depending on the oxidation state of the S). On occasion a moiety may be defined, for example, as (A)$_a$-B—, wherein a is 0 or 1. In such instances, when a is 0 the moiety is B— and when a is 1 the moiety is A—B—. Similarly, C$_{0-6}$ alkylOR$^{11}$ includes both —OR$^{11}$ and C$_1$-C$_6$—OR$^{11}$, and —[C(R$^{15}$)$_2$]$_m$— is a bond when m is 0. In the instances when a moiety is a divalent radical, there is no implied limitation on the location of the two bonds connecting the linking radical to its two supporting chemical units. For example, for a divalent cyclohexyl radical, the cyclohexyl can be connected either through two separate chemical bonds to two distinct carbons atoms within the ring; or the two bonds can be connected to the same carbon atom in the ring. In an illustrative example, if a divalent cyclopropyl radical connects two phenyl rings together, this definition encompasses both 1,2-diphenylcyclopropyl and 1,1-diphenylcyclopropyl units.

As used herein the singular forms "a", "an", and "the" include plural referents unless the context clearly dictates otherwise. For example, "a compound" refers to one or more of such compounds, while "the enzyme" includes a particular enzyme as well as other family members and equivalents thereof as known to those skilled in the art. As used in the specification and appended claims, unless specified to the contrary, the following terms have the meaning indicated.

The term "absent" as used herein means the group is replaced by a single bond. If replacing the group with a bond results in two connected moieties both defined as bonds, then -bond-bond-groups are understood to reduce to a single bond.

The term "interrupted by" as used herein means the group specified is inserted at any point within the specified chain, but not at the termini. For example, if a C$_3$ alkyl chain, as defined herein, is interrupted by —O—, then the following groups would be encompassed: —CH$_2$—O—CH$_2$CH$_2$—, —CH$_2$CH$_2$—O—CH$_2$, —CH(CH$_3$)—O—CH$_2$—, and —CH$_2$—O—CH(CH$_3$)—.

The terms "aliphatic" and "aliphatic group" as used herein means straight-chain, branched or cyclic C$_1$-C$_{12}$ (unless stated otherwise) hydrocarbon radicals which are completely saturated or which contain one or more units of unsaturation but which are not aromatic. For example, suitable aliphatic groups include substituted or unsubstituted linear, branched or cyclic alkyl, alkenyl, alkynyl groups and hybrids thereof such as (cycloalkyl)alkyl, (cycloalkenyl)alkyl or (cycloalkyl)alkenyl.

The terms "alkyl", "alkoxy", "hydroxyalkyl", "alkoxyalkyl", and "alkoxycarbonyl", used alone or as part of a larger moiety include both straight and branched chains containing one to twelve carbon atoms.

The terms "alkenyl" and "alkynyl" used alone or as part of a larger moiety include both straight and branched chains containing two to twelve carbon atoms.

The term "alkoxy" refers to an —O-alkyl radical, where alkyl is defined herein.

"Alkyl" refers to a straight or branched hydrocarbon chain radical consisting solely of carbon and hydrogen atoms, containing no unsaturation, having from one to twelve carbon atoms, preferably one to eight, and which is attached to the rest of the molecule by a single bond, e.g., methyl, ethyl, n-propyl, 1-methylethyl (iso-propyl), n-butyl, n-pentyl, 1,1-dimethylethyl (t-butyl), and the like. Unless stated otherwise specifically in the specification, the alkyl radical is optionally substituted by one or more substituents selected from the group consisting of halo, cyano, nitro, —OR$^{11}$, —N(R$^{11}$)$_2$, —COR$^{11}$, —COOR$^{11}$, —CON(R$^{11}$)$_2$, —N(R$^{11}$)COOR$^0$, —N(R$^{11}$)COR$^{11}$, —NSO$_2$R$^{11}$, —N(R$^{11}$)SO$_2$R$^{11}$, —SO$_2$OR$^{11}$, —SO$_2$R$^{11}$, and —SO$_2$N(R$^{11}$)$_2$ where each R$^{10}$ and R$^{11}$ are as defined above in the First aspect of the invention. Unless stated otherwise specifically in the specification, it is understood that for radicals, as defined below, that contain a substituted alkyl group that the substitution can occur on any carbon of the alkyl group.

"Alkenyl" refers to a straight or branched hydrocarbon chain radical consisting solely of carbon and hydrogen atoms, containing at least one double bond, having from two to eight carbon atoms, and which is attached to the rest of the molecule by a single bond or a double bond, e.g., ethenyl, prop-1-enyl, but-1-enyl, pent-1-enyl, penta-1,4-dienyl, and the like. Unless stated otherwise specifically in the specification, the alkenyl radical is optionally substituted by one or more substituents selected from the group consisting of halo, cyano, nitro, —OR$^{11}$, —N(R$^{11}$)$_2$, —COR$^{11}$, —COOR$^{11}$, —CON(R$^{11}$)$_2$, —N(R$^{11}$)COOR$^{10}$, —N(R$^{11}$)COR$^{11}$, —NSO$_2$R$^{11}$, —N(R$^{11}$)SO$_2$R$^{11}$, —SO$_2$OR$^{11}$, —SO$_2$R$^{11}$, and —$SO_2N(R^{11})_2$ where each $R^{10}$ and $R^{11}$ are as defined above in the First aspect of the invention. Unless stated otherwise specifically in the specification, it is understood that for radicals, as defined below, that contain a substituted alkenyl group that the substitution can occur on any carbon of the alkenyl group.

"Aryl" refers to aromatic monocyclic or multicyclic ring system containing from 6 to 19 carbon atoms, where the ring system is optionally partially or fully saturated. Aryl groups include, but are not limited to groups such as fluorenyl, phenyl and naphthyl. Unless stated otherwise specifically in the specification, the term "aryl" is meant to include aryl radicals optionally substituted by one or more substituents selected from the group consisting of alkyl, alkenyl, halogen, haloalkyl, haloalkenyl, cyano, nitro, aryl, aralkyl, cycloalkyl, cycloalkylalkyl, heteroaryl, heteroarylalkyl, heterocyclyl, heterocyclylalkyl, $R^o$—$OR^{11}$, $R^o$—$N(R^{11})_2$—, $R^o$—$COR^{11}$, $R^o$—$COOR^{11}$, $R^o$—$CON(R^{11})_2$, $R^o$—$N(R^{11})COOR^{10}$, $R^o$—$N(R^{11})COR^{11}$, $R^o$—$NSO_2R^{11}$, $R^{11}$—$N(R^{11})SO_2R^{11}$, $R^{11}$—$SO_2OR^{11}$, $R^o$—$SO_2R^{11}$, and $R^o$—$SO_2N(R^{11})_2$ where each $R^o$ is independently selected from a substituted or an unsubstituted aliphatic group, an unsubstituted heteroaryl or heterocyclic ring, phenyl (Ph), substituted Ph, —OPh, substituted —OPh, or substituted —$CH_2Ph$. Examples of substitutents on the aliphatic group or phenyl ring of $R^o$ include amino, alkylamino, dialkylamino, aminocarbonyl, halogen, alkyl, alkylaminocarbonyl, dialkylaminocarbonyl, alkylaminocarbonyloxy, dialkylaminocarbonyloxy, alkoxy, nitro, cyano, carboxy, alkoxycarbonyl, alkylcarbonyl, hydroxy, haloalkoxy or haloalkyl.

An aliphatic group or non-aromatic heterocyclic ring may contain one or more substituents. Examples of suitable substituents on the saturated carbon of an aliphatic group or of non-aromatic heterocyclic ring include those listed above for unsaturated carbon of an aryl or heteroaryl group and including the following: =O, =S, =$NNHR^o$, =$NN(R^o)_2$, =N—, =$NNHC(O)R^o$, =$NNHCO_2$ (alkyl), =$NNHSO_2$ (alkyl), or =$NR^o$, where $R^o$ is independently selected from hydrogen, unsubstituted or substituted aliphatic group, an unsubstituted heteroaryl or heterocyclic ring, phenyl (Ph), substituted Ph, —OPh, substituted —OPh, —$CH_2$ Ph or substituted —$CH_2$ Ph. Examples of substituents on the aliphatic group include amino, alkylamino, dialkylamino, aminocarbonyl, halogen, alkyl, alkylaminocarbonyl, dialkylaminocarbonyl, alkylaminocarbonyloxy, dialkylaminocarbonyloxy, alkoxy, nitro, cyano, carboxy, alkoxycarbonyl, alkylcarbonyl, hydroxy, haloalkoxy or haloalkyl.

Suitable substituents on the nitrogen of a non-aromatic heterocyclic ring include —$R^o$, —$N(R^o)_2$, —$C(O)R^o$, $CO_2R^o$, —$C(O)C(O)R^o$, —$SO_2R^o$, —$SO_2N(R^o)_2$, —$C(=S)N(R^o)_2$, —$C(=NH)$—$N(R^o)_2$, and $NR^oRSO_2R^o$ wherein each $R^o$ is independently selected from hydrogen, unsubstituted or substituted aliphatic group, an unsubstituted heteroaryl or heterocyclic ring, phenyl (Ph), substituted Ph, —OPh, substituted —OPh, or substituted —$CH_2$ Ph. Examples of substitutents on the aliphatic group or the phenyl ring include amino, alkylamino, dialkylamino, aminocarbonyl, halogen, alkyl, alkylaminocarbonyl, dialkylaminocarbonyl, alkylaminocarbonyloxy, dialkylaminocarbonyloxy, alkoxy, nitro, cyano, carboxy, alkoxycarbonyl, alkylcarbonyl, hydroxy, haloalkoxy or haloalkyl.

The term "alkoxyaryl" as used herein means an aryl group, as defined herein, substituted with one or more alkoxy groups, as defined herein. Examples of alkoxyaryl groups include, but are not limited to, methoxyphenyl, butyloxyphenyl, and dimethoxynaphthyl.

"Aralkyl" or "arylalkyl" refers to a radical of the formula -RaRb where Ra is an alkyl radical as defined above and Rb is one or more aryl radicals as defined above, e.g., benzyl, diphenylmethyl and the like. The aryl radical(s) and the alkyl radical is optionally substituted as described above.

The term "aralkyloxy" or "arylalkoxy" as used herein, means an aralkyl group, as defined herein, appended to the parent molecule through a oxygen atom. Examples of aralkyloxy include, but are not limited to, benzyloxy, 2-phenylethoxy, 4-phenylbutoxy, 9-fluorenylmethoxy, and the like.

The term "arylalkylcarboxy" as used herein, means an arylakyl group, as defined herein, appended to the parent molecule through a carboxy group, as defined herein. The carboxy group can be bonded in either sense; either with the carbonyl carbon bonded to the arylalkyl group and the oxygen bonded to the parent molecule; or the carbonyl bonded to the parent molecule and the oxygen bonded to the arylalkyl group. Examples of arylalkylcarboxy groups include, but are not limited to, benzylacetoxy, (benzyloxy)carbonyl, (2-phenylethoxy)carbonyl, phenyl-acetyloxy, and 1-oxo-5-phenyl-pentyloxy.

The term "aryloxy" as used herein, means an aryl group, as defined herein, appended to a parent molecule through an oxygen atom. Examples of "aryloxy" groups include, but are not limited to phenoxy, 1-naphthyloxy, and 2-naphthyloxy.

"Alkylene" and "alkylene chain" refer to a straight or branched divalent hydrocarbon chain, linking the rest of the molecule to a radical group, consisting solely of carbon and hydrogen, containing no unsaturation and having from one to twelve carbon atoms, preferably having from one to eight carbons, e.g., methylene, ethylene, propylene, n-butylene, and the like. The alkylene chain may be attached to the rest of the molecule and to the radical group through one carbon within the chain or through any two carbons within the chain. The alkylene chain is optionally substituted by one or more substituents selected from the group consisting of halo, cyano, nitro, —$OR^{11}$, —$N(R^{11})_2$, —$COR^{11}$, —$COOR^{11}$, —$CON(R^{11})_2$, —$N(R^{11})COOR^{10}$, —$N(R^{11})COR^{11}$, —$NSO_2R^{11}$, —$N(R^{11})SO_2R^{11}$, —$SO_2OR^{11}$, —$SO_2R^{11}$, and —$SO_2N(R^{11})_2$ where each $R^{10}$ and $R^{11}$ are as defined above in the First aspect of the invention. The alkylene chain may be attached to the rest of the molecule through any two carbons within the chain.

"Alkenylene" and "alkenylene chain" refer to a straight or branched divalent hydrocarbon chain linking the rest of the molecule to a radical group, consisting solely of carbon and hydrogen, containing at least one double bond and having from two to twelve carbon atoms, e.g., ethenylene, propenylene, n-butenylene, and the like. The alkenylene chain is attached to the rest of the molecule through a single bond and to the radical group through a double bond or a single bond. The points of attachment of the alkenylene chain to the rest of the molecule and to the radical group can be through one carbon or any two carbons within the chain. The alkenylene chain is optionally substituted by one or more substituents selected from the group consisting of halo, cyano, nitro, —$OR^{11}$, —$N(R^{11})_2$, —$COR^{11}$, —$COOR^{11}$, —$CON(R^{11})_2$, —$N(R^{11})COOR^{10}$, —$N(R^{11})COR^{11}$, —$NSO_2R^{11}$, —$N(R^{11})SO_2R^{11}$, —$SO_2{}_{OR}{}^{11}$, —$SO_2R^{11}$, and —$SO_2N(R^{11})_2$ where each $R^{10}$ and $R^{11}$ are as defined above in the First aspect of the invention.

The term "aryloxyalkyl" as used herein, means an alkyl group appended to the parent molecule, wherein the alkyl group is substituted with one aryloxy group, as defined herein. Examples of aryloxyalkyl groups include, but are not limited to phenoxymethyl, naphthyloxybutyl, and phenoxyhexyl.

The term "aryloxyaryl" as used herein, means an aryl group appended to the parent molecule, wherein the aryl group is substituted with one aryloxy group, as defined herein. Examples of aryloxyaryl groups include, but are not limited to phenoxyphenyl, naphthyloxyphenyl, and phenoxynaphthyl.

The term "carbonyl" as used herein, means a —C(=O)— group.

The term "carboxy" as used herein, means a —C(=O)O— group.

"Cycloalkyl" refers to a stable monovalent monocyclic or bicyclic hydrocarbon radical consisting solely of carbon and hydrogen atoms, having from three to ten carbon atoms (unless stated otherwise), and which is saturated or includes one more unsaturated units (but is not aromatic) and is attached to the rest of the molecule by a single bond, e.g., cyclopropyl, cyclobutyl, cyclopentyl, cylcopent-1-enyl, cyclohexyl, cyclohex-2,4-dienyl, decalinyl and the like. Unless otherwise stated specifically in the specification, the term "cycloalkyl" is meant to include cycloalkyl radicals which are optionally substituted by one or more substituents independently selected from the group consisting of alkyl, alkenyl, halo, haloalkyl, haloalkenyl, cyano, nitro, aryl, aralkyl, cycloalkyl, cycloalkylalkyl, heterocyclyl, heterocyclylalkyl, heteroaryl, heteroarylalkyl, —OR$^{11}$, —N(R$^{11}$)$_2$, —COR$^{11}$, —COOR$^{11}$, —CON(R$^{11}$)$_2$, —N(R$^{11}$)COOR$^{10}$, —N(R$^{11}$)COR$^{11}$, —NSO$_2$R$^{11}$, —N(R$^{11}$)SO$_2$R$^{11}$, —SO$_2$OR$^{11}$, —SO$_2$R$^{11}$, and —SO$_2$N(R$^{11}$)$_2$ where each R$^{10}$ and R$^{11}$ are as defined above in the first aspect of the invention.

"Cycloalkylalkyl" refers to a radical of the formula RaRd where Ra is an alkyl radical as defined above and Rd is a cycloalkyl radical as defined above. The alkyl radical and the cycloalkyl radical may be optionally substituted as defined above.

The term "cyclohaloalkyl" as used herein means a cycloalkyl group, as defined herein which is substituted by one or more halo groups, as defined herein. Examples of "cyclohaloalkyl" groups include, but are not limited to, bromocyclohexyl, trifluorocyclopentyl, dichlorocyclohexyl and the like.

"Halo" or "Halogen" refers to bromo, chloro, fluoro or iodo.

"Haloalkyl" refers to an alkyl radical, as defined above, that is substituted by one or more halo radicals, as defined above, e.g., trifluoromethyl, difluoromethyl, trichloromethyl, 2,2,2-trifluoroethyl, 1-fluoromethyl-2-fluoroethyl, 3-bromo-2-fluoropropyl, 1-bromomethyl-2-bromoethyl, and the like.

"Haloalkenyl" refers to an alkenyl radical, as defined above, that is substituted by one or more halo radicals, as defined above, e.g., 2-bromoethenyl, 3-bromoprop-1-enyl, and the like.

The term "haloaryl" as used herein, means an aryl group, as defined herein, substituted with one or more halo groups. Examples of haloaryl groups include, but are not limited to, bromophenyl, fluorophenyl, pentafluorophenyl, chloronaphthyl, chloro-iodophenyl, and the like.

"Heterocyclyl" refers to a stable 3- to 18-membered non-aromatic ring radical which consists of carbon atoms and from one to five heteroatoms selected from the group consisting of nitrogen, oxygen and sulfur. For purposes of this invention, the heterocyclyl radical may be a monocyclic, bicyclic, tricyclic or tetracyclic ring system, which may include fused or bridged ring systems; and the nitrogen, carbon or sulfur atoms in the heterocyclyl radical is optionally oxidized; the nitrogen atom is optionally quaternized; and the heterocyclyl radical may be partially or fully saturated. Examples of such heterocyclyl radicals include, but are not limited to, dioxolanyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, thiazolidinyl, tetrahydrofuranyl, trithianyl, tetrahydropyranyl, thiomorpholinyl, thiamorpholinyl, 1-oxo-thiomorpholinyl, and 1,1-dioxo-thiomorpholinyl. Unless stated otherwise specifically in the specification, the term "heterocyclyl" is meant to include heterocyclyl radicals as defined above which are optionally substituted by one or more substituents selected from the group consisting of alkyl, alkenyl, halo, haloalkyl, haloalkenyl, nitro, aryl, aralkyl, cycloalkyl, cycloalkylalkyl, heterocyclyl, heterocyclylalkyl, heteroaryl, heteroarylalkyl, —OR$^{11}$, —N(R$^{11}$)$_2$—, —COR$^{11}$, COOR$^{11}$, —CON(R$^{11}$)$_2$, —N(R$^{11}$)COOR$^{10}$, —N(R$^{11}$)COR$^{11}$, —NSO$_2$R$^{11}$, —N(R$^{11}$)SO$_2$R$^{11}$, —SO$_2$OR$^{11}$, —SO$_2$R$^{11}$, and —SO$_2$N(R$^{11}$)$_2$ where each R$^{10}$ and R$^{11}$ are as defined above in the First aspect of the invention.

"Heterocyclylalkyl" refers to a radical of the formula —RaRe where Ra is an alkyl radical as defined above and Re is a heterocyclyl radical as defined above, and if the heterocyclyl is a nitrogen-containing heterocyclyl, the heterocyclyl may be attached to the alkyl radical at the nitrogen atom. The heterocyclyl radical and the alkyl radical are optionally substituted as defined above.

The term "heterocyclyloxy" as used herein, means a heterocyclyl group, as defined herein, appended to a parent molecule through an oxygen atom. Examples of "heterocyclyloxy" groups include, but are not limited to piperidinyloxy, tetrahydrofuranyloxy, tetrahydrotheinyloxy tetrahydropyranyloxy, dihydropyranyloxy, pyrrolidinyloxy, oxetanyloxy, and oxiranyloxy.

"Heteroaryl" refers to a 3- to 18-membered aromatic ring radical which consists of carbon atoms and from one to five heteroatoms selected from the group consisting of nitrogen, oxygen and sulfur. For purposes of this invention, the heteroaryl radical may be a monocyclic, bicyclic, tricyclic or tetracyclic ring system, which may include fused or bridged ring systems; and the nitrogen, carbon or sulfur atoms in the heteroaryl radical is optionally oxidized; the nitrogen atom is optionally quaternized. Examples include, but are not limited to, azepinyl, acridinyl, benzimidazolyl, benzthiazolyl, benzindolyl, benzothiadiazolyl, benzonaphthofuranyl, benzoxazolyl, benzodioxolyl, benzodioxinyl, benzopyranyl, benzopyranonyl, benzofuranyl, benzofuranonyl, benzothienyl (benzothiophenyl), benzotriazolyl, benzo[4,6]imidazo[1,2-a]pyridinyl, carbazolyl, cinnolinyl, dibenzofuranyl, furanyl, furanonyl, isothiazolyl, imidazolyl, indolyl, indazolyl, isoindolyl, indolinyl, isoindolinyl, indolizinyl, isoxazolyl, naphthyridinyl, oxadiazolyl, 2-oxoazepinyl, oxazolyl, oxiranyl, phenazinyl, phenothiazinyl, phenoxazinyl, phthalazinyl, phthalimidyl pteridinyl, purinyl, pyrrolyl, pyrazolyl, pyridinyl, pyrazinyl, pyrimidinyl, pyridazinyl, quinazolinyl, quinoxalinyl, quinolinyl, quinuclidinyl, isoquinolinyl, thiazolyl, thiadiazolyl, triazolyl, tetrazolyl, triazinyl, and thiophenyl. Unless stated otherwise specifically in the specification, the term "heteroaryl" is meant to include heteroaryl radicals as defined above which are optionally substituted by one or more substituents selected from the group consisting of alkyl, alkenyl, halo, haloalkyl, haloalkenyl, nitro, aryl, aralkyl, cycloalkyl, cycloalkylalkyl, heterocyclyl, heterocyclylalkyl, heteroaryl, heteroarylalkyl, —OR$^{11}$, —N(R$^{11}$)$_2$—, —COR$^{11}$, —COOR$^{11}$, —CON(R$^{11}$)$_2$, —N(R$^{11}$)COOR$^{10}$, —N(R$^{11}$)COR$^{11}$, —NSO$_2$R$^{11}$, —N(R$^{11}$)SO$_2$R$^{11}$, —SO$_2$OR$^{11}$, —SO$_2$R$^{11}$, and —SO$_2$N(R$^{11}$)$_2$ where each R$^{10}$ and R$^{11}$ are as defined above in the First aspect of the invention. For purposes of this invention, the term "N-heteroaryl" refers to heteroaryl radicals as defined above containing at least one nitrogen atom in ring.

The term "heteroaryloxy" as used herein, means a heteroaryl group, as defined herein, appended to a parent molecule through an oxygen atom. Examples of "heteroaryloxy" groups include, but are not limited to pyridyloxy, indolyloxy, and quinolyloxy.

"Heteroarylalkyl" refers to a radical of the formula -$R_aR_f$ where $R_a$ is an alkyl radical as defined above and $R^f$ is a heteroaryl radical as defined above, and if the heteroaryl is a nitrogen-containing heteroaryl, the heteroaryl may be attached to the alkyl radical at the nitrogen atom. The heteroaryl radical and the alkyl radical are optionally substituted as defined above.

The term "linker group" or "linker" means an organic moiety that connects two parts of a compound. Linkers are typically comprised of an atom such as oxygen or sulfur, a unit such as —NH—, —CH$_2$—, —CO—, —CONH—, or a chain of atoms, such as an alidiyl chain. The molecular mass of a linker is typically in the range of about 14 to 200, preferably in the range of 14 to 96 with a length of up to about six atoms. Examples of linkers include a saturated or unsaturated $C_{1-6}$ alidiyl chain which is optionally substituted, and wherein one or two saturated carbons of the chain are optionally replaced by —CO—, —COCO—, —CONH—, —CONHNH—, —CO$_2$—, —NHCO$_2$—, —O—, —NHCONH—, —OCONH—, —NHNH—, —NHCO—, —S—, —SO—, —SO$_2$—, —NH—, —SO$_2$NH—, or —NHSO$_2$—.

The term "alidyl" or "alidiyl chain" refers to an optionally substituted, straight or branched carbon chain that may be fully saturated or have one or more units of unsaturation. The optional substituents are as described above for an aliphatic group. Alidiyl chain used herein may include alidiyl chains containing 0-4 fluorine substituents. An "agonist for a nuclear receptor" is an agent that, when bound to the nuclear receptor, activates nuclear receptor activity to activate or repress gene function. In some cases, nuclear receptors can act through second messenger signaling pathways, and the invention would apply to these actions as well. The activation can be similar in degree to that provided by a natural hormone for the receptor, or can be stronger (optionally referred to as a "strong agonist"), or can be weaker (optionally referred to as a "weak agonist" or "partial agonist"). An example of a hormone for a nuclear receptor is thyroid hormone, which is a natural hormone for the thyroid receptor. A "putative agonist" is an agent to be tested for agonist activity.

Partial agonists or partial antagonists bind to receptors and yield a response less than that of a full agonist at saturating ligand concentrations. A partial agonist will block binding of a full agonist and suppress receptor activity to the level induced by the partial agonist alone. For example, partial agonists bind to receptors and induce only part of the changes in the receptors that are induced by agonists. The differences can be qualitative or quantitative. Thus, a partial agonist can induce some of the conformation changes induced by agonists, but not others, or it may only induce certain changes to a limited extent. Some of these compounds are naturally produced. For example, many plant estrogens (phytoestrogens), such as genistein, can behave as partial estrogen receptor agonists.

An "antagonist for a nuclear receptor" is an agent that reduces or blocks activity mediated by the receptor in response to an agonist of the receptor. The activity of the antagonist can be mediated, e.g., by blocking binding of the agonist to the receptor, or by altering receptor configuration and/or activity of the receptor. A "putative antagonist" is an agent to be tested for antagonist activity.

A "nuclear receptor" is a receptor that activates or represses transcription of one or more genes in the nucleus (but can also have second messenger signaling actions), typically in conjunction with other transcription factors. The nuclear receptor is activated by the natural cognate ligand for the receptor. Nuclear receptors are ordinarily found in the cytoplasm or nucleus, rather than being membrane-bound. Nuclear receptor is a member of a superfamily of regulatory proteins that are receptors for, e.g., steroids, retinoids, vitamin D and thyroid hormones. These proteins bind to cis-acting elements in the promoters of their target genes and modulate gene expression in response to a ligand therefor. Nuclear receptors may be classified based on their DNA binding properties. For example, the glucocorticoid, estrogen, androgen, progestin and mineralocorticoid receptors bind as homodimers to hormone response elements (HREs) organized as inverted repeats. Another example are receptors, including those activated by retinoic acid, thyroid hormone, vitamin $D_3$, fatty acids/peroxisome proliferators and ecdysone, that bind to HREs as heterodimers with a common partner, the retinoid X receptor (RXR). Among the latter receptors is LXR.

As used herein, an orphan nuclear receptor is a nuclear receptor for which the natural ligand is unknown.

As used herein, liver X receptor or LXR refers to a nuclear receptor implicated in cholesterol biosynthesis. As used herein, the term LXR refers to both LXRα and LXRβ, two forms of the protein found in mammals. Liver X receptor-α or LXRα refers to the receptor described in U.S. Pat. Nos. 5,571, 696, 5,696,233 and 5,710,004, and Willy et al. (1995) Gene Dev. 9(9):1033-1045. Liver X receptor-β or LXRβ refers to the receptor described in Peet et al. (1998) Curr. Opin. Genet. Dev. 8(5):571-575; Song et al. (1995) Ann. N.Y. Acad. Sci. 761:38-49; Alberti et al. (2000) Gene 243(1-2):93-103; and references cited therein; and in U.S. Pat. Nos. 5,571,696, 5,696,233 and 5,710,004.

As used herein, compounds which are "commercially available" may be obtained from standard commercial sources including Acros Organics (Pittsburgh Pa.), Aldrich Chemical (Milwaukee Wis., including Sigma Chemical and Fluka), Apin Chemicals Ltd. (Milton Park UK), Avocado Research (Lancashire U.K.), BDH Inc. (Toronto, Canada), Bionet (Cornwall, U.K.), Chemservice Inc. (West Chester Pa.), Crescent Chemical Co. (Hauppauge N.Y.), Eastman Organic Chemicals, Eastman Kodak Company (Rochester N.Y.), Fisher Scientific Co. (Pittsburgh Pa.), Fisons Chemicals (Leicestershire UK), Frontier Scientific (Logan Utah), ICN Biomedicals, Inc. (Costa Mesa Calif.), Key Organics (Cornwall U.K.), Lancaster Synthesis (Windham N.H.), Maybridge Chemical Co. Ltd. (Cornwall U.K.), Parish Chemical Co. (Orem Utah), Pfaltz & Bauer, Inc. (Waterbury Conn.), Polyorganix (Houston Tex.), Pierce Chemical Co. (Rockford Ill.), Riedel de Haen A G (Hannover, Germany), Spectrum Quality Product, Inc. (New Brunswick, N.J.), TCI America (Portland Oreg.), Trans World Chemicals, Inc. (Rockville Md.), and Wako Chemicals USA, Inc. (Richmond Va.).

As used herein, "suitable conditions" for carrying out a synthetic step are explicitly provided herein or may be discerned by reference to publications directed to methods used in synthetic organic chemistry. The reference books and treatise set forth above that detail the synthesis of reactants useful in the preparation of compounds of the present invention, will also provide suitable conditions for carrying out a synthetic step according to the present invention.

As used herein, "methods known to one of ordinary skill in the art" may be identified though various reference books and databases. Suitable reference books and treatise that detail the synthesis of reactants useful in the preparation of compounds of the present invention, or provide references to articles that describe the preparation, include for example, "Synthetic Organic Chemistry", John Wiley & Sons, Inc., New York; S. R. Sandler et al., "Organic Functional Group Preparations," 2nd Ed., Academic Press, New York, 1983; H. O. House, "Modern Synthetic Reactions", 2nd Ed., W. A. Benjamin, Inc. Menlo Park, Calif. 1972; T. L. Gilchrist, "Heterocyclic Chemistry", 2nd Ed., John Wiley & Sons, New York, 1992; J. March, "Advanced Organic Chemistry: Reactions, Mechanisms and Structure", 4th Ed., Wiley-Interscience, New York, 1992. Specific and analogous reactants may also be identified through the indices of known chemicals prepared by the Chemical Abstract Service of the American Chemical Society, which are available in most public and university libraries, as well as through on-line databases (the American Chemical Society, Washington, D.C. may be contacted for more details). Chemicals that are known but not commercially available in catalogs may be prepared by custom chemical synthesis houses, where many of the standard chemical supply houses (e.g., those listed above) provide custom synthesis services.

"Prodrugs" is meant to indicate a compound that may be converted under physiological conditions or by solvolysis to a biologically active compound of the invention. Thus, the term "prodrug" refers to a metabolic precursor of a compound of the invention that is pharmaceutically acceptable. A prodrug may be inactive when administered to a subject in need thereof, but is converted in vivo to an active compound of the invention. Prodrugs are typically rapidly transformed in vivo to yield the parent compound of the invention, for example, by hydrolysis in blood. The prodrug compound often offers advantages of solubility, tissue compatibility or delayed release in a mammalian organism (see, Bundgard, H., *Design of Prodrugs* (1985), pp. 7-9, 21-24 (Elsevier, Amsterdam). A discussion of prodrugs is provided in Higuchi, T., et al., "Pro-drugs as Novel Delivery Systems," A.C.S. Symposium Series, Vol. 14, and in Bioreversible Carriers in Drug Design, ed. Edward B. Roche, American Pharmaceutical Association and Pergamon Press, 1987, both of which are incorporated in full by reference herein. The term "prodrug" is also meant to include any covalently bonded carriers which release the active compound of the invention in vivo when such prodrug is administered to a mammalian subject. Prodrugs of a compound of the invention may be prepared by modifying functional groups present in the compound of the invention in such a way that the modifications are cleaved, either in routine manipulation or in vivo, to the parent compound of the invention. By virtue of knowledge of pharmacodynamic processes and drug metabolism in vivo, those of skill in this art, once a pharmaceutically active compound is known, can design prodrugs of the compound (see, e.g., Nogrady (1985) *Medicinal Chemisiy A Biochemical Approach*, Oxford University Press, New York, pages 388-392). Prodrugs include compounds of the invention wherein a hydroxy, amino or mercapto group is bonded to any group that, when the prodrug of the compound of the invention is administered to a mammalian subject, cleaves to form a free hydroxy, free amino or free mercapto group, respectively.

Examples of prodrugs include, but are not limited to, acetate, formate and benzoate derivatives of alcohol and amine functional groups in the compounds of the invention and the like.

"Polymorph" refers to the different crystal forms of a compound, resulting from the possibility of at least two different arrangements of the molecules of the compound in the solid state. Polymorphs of a given compound will be different in crystal structure but identical in liquid or vapor states. Different polymorphic forms of a given substance may differ from each other with respect to one or more physical properties, such as solubility and dissociation, true density, crystal shape, compaction behavior, flow properties, and/or solid state stability.

"Stable compound" and "stable structure" are meant to indicate a compound that is sufficiently robust to survive isolation to a useful degree of purity from a reaction mixture, and formulation into an efficacious therapeutic agent.

"Mammal" includes humans and domestic animals, such as cats, dogs, swine, cattle, sheep, goats, horses, rabbits, and the like.

"Optional" or "optionally" means that the subsequently described event of circumstances may or may not occur, and that the description includes instances where said event or circumstance occurs and instances in which it does not. For example, "optionally substituted aryl" means that the aryl radical may or may not be substituted and that the description includes both substituted aryl radicals as defined herein and aryl radicals having no substitution.

"Pharmaceutically acceptable carrier, diluent or excipient" includes without limitation any adjuvant, carrier, excipient, glidant, sweetening agent, diluent, preservative, dye/colorant, flavor enhancer, surfactant, wetting agent, dispersing agent, suspending agent, stabilizer, isotonic agent, solvent, or emulsifier which has been approved by the United States Food and Drug Administration as being acceptable for use in humans or domestic animals.

"Pharmaceutically acceptable salt" includes both acid and base addition salts.

"Pharmaceutically acceptable acid addition salt" refers to those salts which retain the biological effectiveness and properties of the free bases, which are not biologically or otherwise undesirable, and which are formed with inorganic acids such as hydrochloric acid, hydrobromic acid, sulfuric acid, nitric acid, phosphoric acid and the like, and organic acids such as acetic acid, trifluoroacetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, and the like.

"Pharmaceutically acceptable base addition salt" refers to those salts which retain the biological effectiveness and properties of the free acids, which are not biologically or otherwise undesirable. These salts are prepared from addition of an inorganic base or an organic base to the free acid. Salts derived from inorganic bases include, but are not limited to, the sodium, potassium, lithium, ammonium, calcium, magnesium, iron, zinc, copper, manganese, aluminum salts and the like. Preferred inorganic salts are the ammonium, sodium, potassium, calcium, and magnesium salts. Salts derived from organic bases include, but are not limited to, salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, 2-dimethylaminoethanol, 2-diethylaminoethanol, dicyclohexylamine, lysine, arginine, histidine, caffeine, procaine, hydrabamine, choline, betaine, ethylenediamine, glucosamine, methylglucamine, theobromine, purines, piperazine, piperidine, N-ethylpiperidine, polyamine resins and the like. Particularly preferred organic bases are isopropylamine, diethylamine, ethanolamine, trimethylamine, dicyclohexylamine, choline and caffeine.

"Pharmaceutically acceptable derivative" refers to pharmaceutically acceptable salts as defined herein and also includes esters, prodrugs, solvates and polymorphs of the compounds of the invention.

"Therapeutically effective amount" refers to that amount of a compound of the invention which, when administered to a mammal, preferably a human, is sufficient to effect treatment, as defined below, for a disease-state associated with nuclear receptor activity. The amount of a compound of the invention which constitutes a "therapeutically effective amount" will vary depending on the compound, the condition and its severity, and the age of the mammal to be treated, but can be determined routinely by one of ordinary skill in the art having regard to his own knowledge and to this disclosure.

"Modulating" or "modulate" refers to the treating, prevention, suppression, enhancement or induction of a function or condition. For example, the compounds of the present invention can modulate hyperlipidemia by lowering cholesterol in a human, thereby suppressing hyperlipidemia.

"Treating" or "treatment" as used herein covers the treatment of a disease or condition associated with the nuclear receptor activity as disclosed herein, in a mammal, preferably a human, and includes:
  i. Preventing a disease or condition associated with the nuclear receptor activity from occurring in a mammal, in particular, when such mammal is predisposed to the disease or condition but has not yet been diagnosed as having it;
  ii. inhibiting a disease or condition associated with the nuclear receptor activity, i.e., arresting its development; or
  iii. relieving a disease or condition associated with the nuclear receptor activity, i.e., causing regression of the condition.

The compounds of formulae IIaa, IIbb, IIcc, or IIdd or their pharmaceutically acceptable salts may contain one or more asymmetric centers and may thus give rise to enantiomers, diastereomers, and other stereoisomeric forms that may be defined, in terms of absolute stereochemistry, as (R)- or (S)- or, as (D)- or (L)- for amino acids. The present invention is meant to include all such possible isomers, as well as, their racemic and optically pure forms. Optically active (+) and (−), (R)- and (S)-, or (D)- and (L)-isomers may be prepared using chiral synthons or chiral reagents, or resolved using conventional techniques, such as reverse phase HPLC. When the compounds described herein contain olefinic double bonds or other centers of geometric asymmetry, and unless specified otherwise, it is intended that the compounds include both E and Z geometric isomers. It will be apparent to one skilled in the art that certain compounds of this invention may exist in tautomeric forms, all such tautomeric forms of the compounds being within the scope of the invention. Unless otherwise stated, structures depicted herein are also meant to include all stereochemical forms of the structure; i.e., the R and S configurations for each asymmetric center. Therefore, single stereochemical isomers as well as enantiomeric and diastereomeric mixtures of the present compounds are within the scope of the invention. Unless otherwise stated, structures depicted herein are also meant to include compounds which differ only in the presence of one or more isotopically enriched atoms. For example, compounds having the present structure except for the replacement of a hydrogen atom by a deuterium or tritium, or the replacement of a carbon atom by a $^{13}C$- or $^{14}C$-enriched carbon are within the scope of this invention.

The chemical naming protocol and structure diagrams used herein employ and rely on the chemical naming features as utilized by the ChemDraw program (available from Cambridgesoft Corp., Cambridge, Mass.). In particular, the compound names were derived from the structures using the Autonom program as utilized by Chemdraw Ultra or ISIS base (MDL Corp.).

The term "atherosclerosis" refers to process whereby atherosclerotic plaques form within the inner lining of the artery wall leading to atherosclerotic cardiovascular diseases. Atherosclerotic cardiovascular diseases can be recognized and understood by physicians practicing in the relevant fields of medicine, and include without limitation, restenosis, coronary heart disease (also known as coronary artery heart disease or ischemic heart disease), cerebrovascular disease including ischemic stroke, multi-infarct dementia, and peripheral vessel disease, including intermittent claudication, and erectile dysfunction.

The term "dyslipidemia" refers to abnormal levels of lipoproteins in blood plasma including both depressed and/or elevated levels of lipoproteins (e.g., elevated levels of Low Density Lipoprotein, (LDL), Very Low Density Lipoprotein (VLDL) and depressed levels of High Density Lipoprotein (HDL) (less than 40 mg/dL)).

As used herein, "$EC_{50}$" refers to a dosage, concentration or amount of a particular test compound that elicits a dose-dependent response at 50% of maximal expression of a particular response that is induced, provoked or potentiated by the particular test compound.

The term "cholesterol" refers to a steroid alcohol that is an essential component of cell membranes and myelin sheaths and, as used herein, incorporates its common usage. Cholesterol also serves as a precursor for steroid hormones and bile acids.

The term "triglyceride(s)" ("TGs"), as used herein, incorporates its, common usage. TGs consist of three fatty acid molecules esterified to a glycerol molecule and serve to store fatty acids which are used by muscle cells for energy production or are taken up and stored in adipose tissue.

The term "hyperlipidemia" refers to the presence of an abnormally elevated level of lipids in the blood. Hyperlipidemia can appear in at least three for MS (ES): (1) hypercholesterolemia, i.e., an elevated LDL cholesterol level (120 mg/dL and above); (2) hypertriglyceridemia, i.e., an elevated triglyceride level; (150 mg/dL and above) and (3) combined hyperlipidemia, i.e., a combination of hypercholesterolemia and hypertriglyceridemia.

Exemplary Primary Hyperlipidemia include, but are not limited to, the following:
  (1) Familial Hyperchylomicronemia, a rare genetic disorder which causes a deficiency in an enzyme, LP lipase, that breaks down fat molecules. The LP lipase deficiency can cause the accumulation of large quantities of fat or lipoproteins in the blood;
  (2) Familial Hypercholesterolemia, a relatively common genetic disorder caused where the underlying defect is a series of mutations in the LDL receptor gene that result in malfunctioning LDL receptors and/or absence of the LDL receptors. This brings about ineffective clearance of LDL by the LDL receptors resulting in elevated LDL and total cholesterol levels in the plasma;
  (3) Familial Combined Hyperlipidemia, also known as multiple lipoprotein-type hyperlipidemia; an inherited disorder where patients and their affected first-degree relatives can at various times manifest high cholesterol and high triglycerides. Levels of HDL cholesterol are often moderately decreased;

(4) Familial Defective Apolipoprotein B-100 is a relatively common autosomal dominant genetic abnormality. The defect is caused by a single nucleotide mutation that produces a substitution of glutamine for arginine which can cause reduced affinity of LDL particles for the LDL receptor. Consequently, this can cause high plasma LDL and total cholesterol levels; Familial Dysbetalipoproteinemia, also referred to as Type 1 Hyperlipoproteinemia, is an uncommon inherited disorder resulting in moderate to severe elevations of serum triglyceride (TG) and cholesterol levels with abnormal apolipoprotein E function. HDL levels are usually normal; and Familial Hypertriglyceridemia, is a common inherited disorder in which the concentration of plasma VLDL is elevated. This can cause mild to moderately elevated triglyceride levels (and usually not cholesterol levels) and can often be associated with low plasma HDL levels.

Risk factors in exemplary Secondary Hyperlipidemia include, but are not limited to, the following: (1) disease risk factors, such as a history of type 1 diabetes, type 2 diabetes, Cushing's syndrome, hypothyroidism and certain types of renal failure; (2) drug risk factors, which include, birth control pills; hormones, such as estrogen, and corticosteroids; certain diuretics; and various beta. blockers; (3) dietary risk factors include dietary fat intake per total calories greater than 40%; saturated fat intake per total calories greater than 10%; cholesterol intake greater than 300 mg per day; habitual and excessive alcohol use; and obesity; and (4) non-genetic dyslipidemias.

The methods of the present invention can be used effectively in combination with one or more additional active diabetes agents depending on the desired target therapy (see, e.g., Turner, N. et al. Prog. Drug Res. (1998) 51:33-94; Haffner, S. Diabetes Care (1998) 21: 160178; and DeFronzo, R. et al. (eds.), Diabetes Reviews (1997) Vol. 5 No. 4). A number of studies have investigated the benefits of combination therapies with oral agents (see, e.g., Mahler, R., J. Clin. Endocrinol. Metab. (1999)84:1165-71; United Kingdom Prospective Diabetes Study Group: UKPDS 28, Diabetes Care $(1998)_{21:87}$-92; Bardin, C. W. (ed.), CURRENT THERAPY IN ENDOCRINOLOGY AND METABOLISM, 6th Edition (Mosby—Year Book, Inc., St. Louis, Mo. 1997); Chiasson, J. et al., Ann. Intern. Med. (1994) 121: 928-935; Coniff, R. et al., Clin. Ther. (1997) 19: 16-26; Coniff, R. et al., Am. J. Med. (1995) 98: 443-451; and Iwamoto, Y. et al, Diabet. Med. (1996)13: 365-370; Kwiterovich, P. Am. J. Cardiol (1998) 82(12A):3U-17U). These studies indicate that diabetes and hyperlipidemia modulation can be further improved by the addition of a second agent to the therapeutic regimen. As used herein, "$IC_{50}$" refers to an amount, concentration or dosage of a particular test compound that achieves a 50% inhibition of a maximal response, such as modulation of nuclear receptor, including the LXRα or LXRβ activity, in an assay that measures such response.

As used herein, "LXRα" (LXR alpha) refers to all mammalian forms of such receptor including, for example, alternative splice isoforms and naturally occurring isoforms. Representative LXRα species include, without limitation the rat (Genbank Accession NM_031627), mouse (Genbank Accession BC012646), and human (GenBank Accession No. U22662) forms of the receptor.

As used herein, "LXRβ" (LXR beta) refers to all mammalian forms of such receptor including, for example, alternative splice isoforms and naturally occurring isoforms. Representative LXRβ species include, without limitation the rat (GenBank Accession NM_031626), mouse (Genbank Accession NM_009473), and human (GenBank Accession No. U07132) forms of the receptor.

As used herein "LXR" or "LXRs" refers to both LXRα and LXRβ.

The terms "obese" and "obesity" refers to a Body Mass Index (BMI) greater than 27.8 kg/m$^2$ for men and 27.3 kg/m$^2$ for women (BMI equals weight (kg)/(height)$^2$(m$^2$).

Use of the Compounds of the Invention

The compounds of the invention exhibit valuable pharmacological properties in mammals, and are particularly useful as selective LXR agonists, antagonists, inverse agonists, partial agonists and antagonists, for the treatment, or prevention of diseases associated with, or symptoms arising from the complications of, altered cholesterol transport, cholesterol reverse transport, fatty acid metabolism, cholesterol absorption, cholesterol re-absorption, cholesterol secretion, cholesterol excretion, or cholesterol metabolism.

These diseases include, for example, hyperlipidemia, dyslipidemia, hypercholesterolemia, atherosclerosis, atherosclerotic cardiovascular diseases, hyperlipoproteinemia, (see, e.g., Patent Application Publication Nos. WO 00/57915 and WO 00/37077), hyperglycemia, insulin resistance, diabetes, lipodystrophy, obesity, syndrome X (US Patent Application No. 20030073614, International Patent Application Publication No. WO 01/82917), excess lipid deposition in peripheral tissues such as skin (xanthomas) (see, e.g., U.S. Pat. Nos. 6,184,215 and 6,187,814), stroke, peripheral occlusive disease, memory loss (*Brain Research* (1997), Vol. 752, pp. 189-196), optic nerve and retinal pathologies (i.e., macular degeneration, retinitis pigmentosa), repair of traumatic damage to the central or peripheral nervous system (*Trends in Neurosciences* (1994), Vol. 17, pp. 525-530), prevention of the degenerative process due to aging (*American Journal of Pathology* (1997), Vol. 151, pp. 1371-1377), Parkinson's disease or Alzheimer's disease (see, e.g., International Patent Application Publication No. WO 00/17334; *Trends in Neurosciences* (1994), Vol. 17, pp. 525-530), prevention of degenerative neuropathies occurring in diseases such as diabetic neuropathies (see, e.g., International Patent Application Publication No. WO 01/82917), multiple sclerosis (*Annals of Clinical Biochem.* (1996), Vol. 33, No. 2, pp. 148-150), and autoimmune diseases (*J Lipid Res.* (1998), Vol. 39, pp. 1740-1743).

Also provided, are methods of increasing the expression of ATP-Binding Cassette (ABCA1), (see, e.g., International Patent Application Publication No. WO 00/78972) thereby increasing reverse cholesterol transport in mammalian cells using the claimed compounds and compositions.

Accordingly in another aspect, the invention also includes methods to remove cholesterol from tissue deposits such as atherosclerotic plaques or xanthomas in a patient with atherosclerosis or atherosclerotic cardiovascular disease manifest by clinical signs of such disease, wherein the methods comprise administering to the patient a therapeutically effective amount of a compound or composition of the present invention. Additionally, the instant invention also provides a method for preventing or reducing the risk of a first or subsequent occurrence of an atherosclerotic cardiovascular disease event including ischemic heart disease, ischemic stroke, multi-infarct dementia, and intermittent claudication comprising the administration of a prophylactically effective amount of a compound or composition of the present invention to a patient at risk for such an event. The patient may already have atherosclerotic cardiovascular disease at the time of administration, or may be at risk for developing it.

Risk factors for developing atherosclerotic cardiovascular disease events include increasing age (65 and over), male gender, a family history of atherosclerotic cardiovascular disease events, high blood cholesterol (especially LDL or "bad" cholesterol over 100 mg/dL), cigarette smoking and exposure to tobacco smoke, high blood pressure, diabetes, obesity and physical inactivity.

Also contemplated herein is the use of a compound of the invention, or a pharmaceutically acceptable derivative thereof, in combination with one or more of the following therapeutic agents in treating atherosclerosis: antihyperlipidemic agents, plasma HDL-raising agents, antihypercholesterolemic agents, cholesterol biosynthesis inhibitors (such as HMG CoA reductase inhibitors, such as lovastatin, simvastatin, pravastatin, fluvastatin, atorvastatin and rivastatin), acyl-coenzyme A:cholesterol acytransferase (ACAT) inhibitors, probucol, raloxifene, nicotinic acid, niacinamide, cholesterol absorption inhibitors, bile acid sequestrants (such as anion exchange resins, or quaternary amines (e.g., cholestyramine or colestipol)), low density lipoprotein receptor inducers, clofibrate, fenofibrate, benzofibrate, cipofibrate, gemfibrizol, vitamin $B_6$, vitamin $B_{12}$, anti-oxidant vitamins, β-blockers, anti-diabetes agents, angiotensin II antagonists, angiotensin converting enzyme inhibitors, platelet aggregation inhibitors, fibrinogen receptor antagonists, aspirin or fibric acid derivatives.

In one embodiment compounds of the invention are used in combination with a cholesterol biosynthesis inhibitor, particularly an HMG-CoA reductase inhibitor. The term HMG-CoA reductase inhibitor is intended to include all pharmaceutically acceptable salt, ester, free acid and lactone forms of compounds which have HMG-CoA reductase inhibitory activity and, therefore, the use of such salts, esters, free acids and lactone forms is included within the scope of this invention. Compounds which have inhibitory activity for HMG-CoA reductase can be readily identified using assays well-known in the art. For instance, suitable assays are described or disclosed in U.S. Pat. No. 4,231,938 and WO 84/02131. Examples of suitable HMG-CoA reductase inhibitors include, but are not limited to, lovastatin (MEVACOR®; see, U.S. Pat. No. 4,231,938); simvastatin (ZOCOR®; see, U.S. Pat. No. 4,444,784); pravastatin sodium (PRAVACHOL®; see, U.S. Pat. No. 4,346,227); fluvastatin sodium (LESCOL®; see, U.S. Pat. No. 5,354,772); atorvastatin calcium (LIPITOR®; see, U.S. Pat. No. 5,273,995) and rivastatin (also known as cerivastatin; see, U.S. Pat. No. 5,177,080). The structural formulas of these and additional HMG-CoA reductase inhibitors that can be used in combination with the compounds of the invention are described at page 87 of M. Yalpani, "Cholesterol Lowering Drugs," *Chemistry & Industry*, pp. 85-89 (5 Feb. 1996). In presently preferred embodiments, the HMG-CoA reductase inhibitor is selected from lovastatin and simvastatin.

The compounds of the present invention can also be used in methods for decreasing hyperglycemia and insulin resistance, i.e., in methods for treating diabetes (International Patent Application Publication No. WO 01/82917), and in methods of treatment, prevention, or amelioration of disorders related to, or arising as complications of diabetes, hyperglycemia or insulin resistance including the cluster of disease states, conditions or disorders that make up "Syndrome X" (See US Patent Application 20030073614) comprising the administration of a therapeutically effective amount of a compound or composition of the present invention to a patient in need of such treatment. Additionally, the instant invention also provides a method for preventing or reducing the risk of developing hyperglycemia, insulin resistance, diabetes or syndrome X in a patient, comprising the administration of a prophylactically effective amount of a compound or composition of the present invention to a patient at risk for such an event.

Diabetes mellitus, commonly called diabetes, refers to a disease process derived from multiple causative factors and characterized by elevated levels of plasma glucose, referred to as hyperglycemia. See, e.g., LeRoith, D. et al., (eds.), DIABETES MELLITUS (Lippincott-Raven Publishers, Philadelphia, Pa. U.S.A. 1996). According to the American Diabetes Association, diabetes mellitus is estimated to affect approximately 6% of the world population. Uncontrolled hyperglycemia is associated with increased and premature mortality due to an increased risk for macrovascular and macrovascular diseases, including nephropathy, neuropathy, retinopathy, hypertension, cerebrovascular disease and coronary heart disease. Therefore, control of glucose homeostasis is a critically important approach for the treatment of diabetes.

There are two major forms of diabetes: type 1 diabetes (formerly referred to as insulin-dependent diabetes or IDEM); and type 2 diabetes (formerly referred to as nonin-sulin dependent diabetes or NIDDM).

Type 2 diabetes is a disease characterized by insulin resistance accompanied by relative, rather than absolute, insulin deficiency. Type 2 diabetes can range from predominant insulin resistance with relative insulin deficiency to predominant insulin deficiency with some insulin resistance. Insulin resistance is the diminished ability of insulin to exert its biological action across a broad range of concentrations. In insulin resistant individuals, the body secretes abnormally high amounts of insulin to compensate for this defect. When inadequate amounts of insulin are present to compensate for insulin resistance and adequate control of glucose, a state of impaired glucose tolerance develops. In a significant number of individuals, insulin secretion declines further and the plasma glucose level rises, resulting in the clinical state of diabetes. Type 2 diabetes can be due to a profound resistance to insulin stimulating regulatory effects on glucose and lipid metabolism in the main insulin-sensitive tissues: muscle, liver and adipose tissue. This resistance to insulin responsiveness results in insufficient insulin activation of glucose uptake, oxidation and storage in muscle and inadequate insulin repression of lipolysis in adipose tissue and of glucose production and secretion in liver. In Type 2 diabetes, free fatty acid levels are often elevated in obese and some non-obese patients and lipid oxidation is increased.

Premature development of atherosclerosis and increased rate of cardiovascular and peripheral vascular diseases are characteristic features of patients with diabetes. Hyperlipidemia is an important precipitating factor for these diseases. Hyperlipidemia is a condition generally characterized by an abnormal increase in serum lipids, e.g., cholesterol and triglyceride, in the bloodstream and is an important risk factor in developing atherosclerosis and heart disease. For a review of disorders of lipid metabolism, see, e.g., Wilson, J. et al., (ed.), Disorders of Lipid Metabolism, Chapter 23, Textbook of Endocrinology, 9th Edition, (W. B. Sanders Company, Philadelphia, Pa. U.S.A. 1998). Hyperlipidemia is usually classified as primary or secondary hyperlipidemia. Primary hyperlipidemia is generally caused by genetic defects, while secondary hyperlipidemia is generally caused by other factors, such as various disease states, drugs, and dietary factors. Alternatively, hyperlipidemia can result from both a combination of primary and secondary causes of hyperlipidemia.

Elevated cholesterol levels are associated with a number of disease states, including coronary artery disease, angina pectoris, carotid artery disease, strokes, cerebral arteriosclerosis, and xanthoma.

Dyslipidemia, or abnormal levels of lipoproteins in blood plasma, is a frequent occurrence among diabetics, and has been shown to be one of the main contributors to the increased incidence of coronary events and deaths among diabetic subjects (see, e.g., Joslin, E. Ann. Chim. Med. (1927), Vol. 5, pp. 1061-1079). Epidemiological studies since then have confirmed the association and have shown a several-fold increase in coronary deaths among diabetic subjects when compared with non-diabetic subjects (see, e.g., Garcia, M. J. et al., Diabetes (1974), Vol. 23, pp. 105-11 (1974); and Laakso, M. and Lehto, S., Diabetes Reviews (1997), Vol. 5, No. 4, pp. 294-315). Several lipoprotein abnormalities have been described among diabetic subjects (Howard B., et al., Arteriosclerosis (1978), Vol. 30, pp. 153-162).

The compounds of the invention can also be used effectively in combination with one or more additional active diabetes agents depending on the desired target therapy (see, e.g., Turner, N. et al., Prog. Drug Res. (1998), Vol. 51, pp. 33-94; Haffner, S., Diabetes Care (1998), Vol. 21, pp. 160-178; and DeFronzo, R. et al. (eds.), Diabetes Reviews (1997), Vol. 5, No. 4). A number of studies have investigated the benefits of combination therapies with oral agents (see, e.g., Mahler, R, J. Clin. Endocrinol. Metab. (1999), Vol. 84, pp. 1165-71; United Kingdom Prospective Diabetes Study Group: UKPDS 28, Diabetes Care (1998), Vol. 21, pp. 87-92; Bardin, C. W. (ed.), CURRENT THERAPY IN ENDOCRINOLOGY AND METABOLISM, 6th Edition (Mosby—Year Book, Inc., St. Louis, Mo. 1997); Chiasson, J. et al., Ann. Intern. Med. (1994), Vol. 121, pp. 928-935; Coniff, R. et al., Clin. Ther. (1997), Vol. 19, pp. 16-26; Coniff, R. et al., Am. J. Med. (1995), Vol. 98, pp. 443-451; Iwamoto, Y. et al., Diabet. Med. (1996), Vol. 13, pp. 365-370; Kwiterovich, P., Am. J. Cardiol (1998), Vol. 82 (12A), pp. 3U-17U). These studies indicate that diabetes and hyperlipidemia modulation can be further improved by the addition of a second agent to the therapeutic regimen.

Accordingly, the compounds of the invention may be used in combination with one or more of the following therapeutic agents in treating diabetes: sulfonylureas (such as chlorpropamide, tolbutamide, acetohexamide, tolazamide, glyburide, gliclazide, glynase, glimepiride, and glipizide), biguanides (such as metformin), thiazolidinediones (such as ciglitazone, pioglitazone, troglitazone, and rosiglitazone), and related insulin sensitizers, such as selective and non-selective activators of PPARα, PPARδ and PPARγ; dehydroepiandrosterone (also referred to as DHEA or its conjugated sulphate ester, DHEA-SO4); antiglucocorticoids; TNFαinhibitors; α-glucosidase inhibitors (such as acarbose, miglitol, and voglibose), pramlintide (a synthetic analog of the human hormone amylin), other insulin secretogogues (such as repaglinide, gliquidone, and nateglinide), insulin, as well as the therapeutic agents discussed above for treating atherosclerosis.

Further provided by this invention are methods of using the compounds of the invention to treat obesity, as well as the complications of obesity. Obesity is linked to a variety of medical conditions including diabetes and hyperlipidemia. Obesity is also a known risk factor for the development of type 2 diabetes (See, e.g., Barrett-Conner, E., Epidemol. Rev. (1989), Vol. 11, pp. 172-181; and Knowler, et al., Am. J. Clin. Nutr. (1991), Vol. 53, pp. 1543-1551).

In addition, the compounds of the invention can be used in combination with agents used in treated obesity or obesity-related disorders. Such agents, include, but are not limited to, phenylpropanolamine, phentermine, diethylpropion, mazindol, fenfluramine, dexfenfluramine, phentiramine, $β_3$ adrenoceptor agonist agents; sibutramine, gastrointestinal lipase inhibitors (such as orlistat), and leptins. Other agents used in treating obesity or obesity-related disorders include neuropeptide Y, enterostatin, cholecytokinin, bombesin, amylin, histamine $H_3$ receptors, dopamine $D_2$ receptor modulators, melanocyte stimulating hormone, corticotrophin releasing factor, galanin and gamma amino butyric acid (GABA).

Evaluation of the Use of the Compounds of the Invention

Standard physiological, pharmacological and biochemical procedures are available for testing the compounds to identify those that possess biological activities that modulate the activity or nuclear receptors, including the LXRs (LXRα and LXRβ). Such assays include, for example, biochemical assays such as binding assays, fluorescence polarization assays, FRET based coactivator recruitment assays (see, generally, Glickman et al., J. Biomolecular Screening (2002), Vol. 7, No. 1, pp. 3-10, as well as cell based assays including the co-transfection assay, the use of LBD-Gal 4 chimeras and protein-protein interaction assays, (see, Lehmann. et al., J. Biol. Chem. (1997), Vol. 272, No. 6, pp. 3137-3140.

High throughput screening systems are commercially available (see, e.g., Zymark Corp., Hopkinton, Mass.; Air Technical Industries, Mentor, Ohio; Beckman Instruments Inc., Fullerton, Calif.; Precision Systems, Inc., Natick, Mass.) that enable these assays to be run in a high throughput mode. These systems typically automate entire procedures, including all sample and reagent pipetting, liquid dispensing timed incubations, and final readings of the microplate in detector(s) appropriate for the assay. These configurable systems provide high throughput and rapid start up as well as a high degree of flexibility and customization. The manufacturers of such systems provide detailed protocols for various high throughput systems. Thus, for example, Zymark Corp. provides technical bulletins describing screening systems for detecting the modulation of gene transcription, ligand binding, and the like.

Assays that do not require washing or liquid separation steps are preferred for such high throughput screening systems and include biochemical assays such as fluorescence polarization assays (see, for example, Owicki, J., Biomol. Screen (2000 October), Vol. 5, No. 5, pp. 297), scintillation proximity assays (SPA) (see, for example, Carpenter et al., Methods Mol. Biol. (2002), Vol 190, pp. 31-49) and fluorescence resonance energy transfer energy transfer (FRET) or time resolved FRET based coactivator recruitment assays (Mukherjee et al., J. Steroid Biochem. Mol. Biol. (2002 July); Vol. 81, No. 3, pp. 217-25; (Zhou et al., Mol. Endocrinol. (1998 October), Vol. 12, No. 10, pp. 1594-604).

Generally such assays can be preformed using either the full length receptor, or isolated ligand binding domain (LBD). In the case of LXRα, the LBD comprises amino acids 188-447, for LXRβ the LDB comprises amino acids 198-461, and for FXR, the LBD comprises amino acids 244 to 472 of the full length sequence.

If a fluorescently labeled ligand is available, fluorescence polarization assays provide a way of detecting binding of compounds to the nuclear receptor of interest by measuring changes in fluorescence polarization that occur as a result of the displacement of a trace amount of the label ligand by the compound. Additionally this approach can also be used to monitor the ligand dependent association of a fluorescently labeled coactivator peptide to the nuclear receptor of interest to detect ligand binding to the nuclear receptor of interest.

The ability of a compound to bind to a receptor, or heterodimer complex with RXR, can also be measured in a homogeneous assay format by assessing the degree to which the compound can compete off a radiolabelled ligand with known affinity for the receptor using a scintillation proximity assay (SPA). In this approach, the radioactivity emitted by a radiolabelled compound (for example, [$^3$H]24,25 Epoxycholesterol) generates an optical signal when it is brought into close proximity to a scintillant such as a YSI-copper containing bead, to which the nuclear receptor is bound. If the radiolabelled compound is displaced from the nuclear receptor the amount of light emitted from the nuclear receptor bound scintillant decreases, and this can be readily detected using standard microplate liquid scintillation plate readers such as, for example, a Wallac MicroBeta reader.

The heterodimerization of LXR with RXRα can also be measured by fluorescence resonance energy transfer (FRET), or time resolved FRET, to monitor the ability of the compounds provided herein to bind to LXR or other nuclear receptors. Both approaches rely upon the fact that energy transfer from a donor molecule to an acceptor molecule only occurs when donor and acceptor are in close proximity. Typically the purified LBD of the nuclear receptor of interest is labeled with biotin then mixed with stoichiometric amounts of europium labeled streptavidin (Wallac Inc.), and the purified LBD of RXRα is labeled with a suitable fluorophore such as CY5™. Equimolar amounts of each modified LBD are mixed together and allowed to equilibrate for at least 1 hour prior to addition to either variable or constant concentrations of the sample for which the affinity is to be determined. After equilibration, the time-resolved fluorescent signal is quantitated using a fluorescent plate reader. The affinity of the compound can then be estimated from a plot of fluorescence versus concentration of compound added.

This approach can also be exploited to measure the ligand dependent interaction of a co-activator peptide with a nuclear receptor in order to characterize the agonist or antagonist activity of the compounds disclosed herein. Typically the assay in this case involves the use a recombinant Glutathione-5-transferase (GST)-nuclear receptor ligand binding domain (LBD) fusion protein and a synthetic biotinylated peptide sequenced derived from the receptor interacting domain of a co-activator peptide such as the steroid receptor coactivator 1 (SRC-1). Typically GST-LBD is labeled with a europium chelate (donor) via a europium-tagged anti-GST antibody, and the coactivator peptide is labeled with allophycocyanin via a streptavidin-biotin linkage.

In the presence of an agonist for the nuclear receptor, the peptide is recruited to the GST-LBD bringing europium and allophycocyanin into close proximity to enable energy transfer from the europium chelate to the allophycocyanin. Upon excitation of the complex with light at 340 nm excitation energy absorbed by the europium chelate is transmitted to the allophycocyanin moiety resulting in emission at 665 nm. If the europium chelate is not brought in to close proximity to the allophycocyanin moiety there is little or no energy transfer and excitation of the europium chelate results in emission at 615 nm. Thus the intensity of light emitted at 665 nm gives an indication of the strength of the protein-protein interaction. The activity of a nuclear receptor antagonist can be measured by determining the ability of a compound to competitively inhibit (i.e., $IC_{50}$) the activity of an agonist for the nuclear receptor In addition, a variety of cell based assay methodologies may be successfully used in screening assays to identify and profile the specificity of compounds of the present invention. These approaches include the co-transfection assay, translocation assays, complementation assays and the use of gene activation technologies to over express endogenous nuclear receptors.

Three basic variants of the co-transfection assay strategy exist, co-transfection assays using full-length nuclear receptor, co transfection assays using chimeric nuclear receptors comprising the ligand binding domain of the nuclear receptor of interest fused to a heterologous DNA binding domain, and assays based around the use of the mammalian two hybrid assay system.

The basic co-transfection assay is based on the co-transfection into the cell of an expression plasmid to express the nuclear receptor of interest in the cell with a reporter plasmid comprising a reporter gene whose expression is under the control of DNA sequence that is capable of interacting with that nuclear receptor (see, for example, U.S. Pat. Nos. 5,071,773; 5,298,429 and 6,416,957). Treatment of the transfected cells with an agonist for the nuclear receptor increases the transcriptional activity of that receptor which is reflected by an increase in expression of the reporter gene which may be measured by a variety of standard procedures.

For those receptors that function as heterodimers with RXR, such as the LXRs, the co-transfection assay typically includes the use of expression plasmids for both the nuclear receptor of interest and RXR . Typical co-transfection assays require access to the full length nuclear receptor and suitable response elements that provide sufficient screening sensitivity and specificity to the nuclear receptor of interest.

Typically, the expression plasmid comprises: (1) a promoter, such as an SV40 early region promoter, HSV tk promoter or phosphoglycerate kinase (pgk) promoter, CMV promoter, Srac promoter or other suitable control elements known in the art, (2) a cloned polynucleotide sequence, such as a cDNA encoding a receptor, co-factor, or fragment thereof, ligated to the promoter in sense orientation so that transcription from the promoter will produce a RNA that encodes a functional protein, and (3) a polyadenylation sequence. For example and not limitation, an expression cassette of the invention may comprise the cDNA expression cloning vectors, or other preferred expression vectors known and commercially available from vendors such as Invitrogen, (CA), Stratagene, (CA) or Clontech, (CA). Alternatively expression vectors developed by academic groups such as the pCMX vectors originally developed in the Evans lab (Willey et al. Genes & Development 9 1033-1045 (1995)) may also be used.

The transcriptional regulatory sequences in an expression cassette are selected by the practitioner based on the intended application; depending upon the specific use, transcription regulation can employ inducible, repressible, constitutive, cell-type specific, developmental stage-specific, sex-specific, or other desired type of promoter or control sequence.

Alternatively, the expression plasmid may comprise an activation sequence to activate or increase the expression of an endogenous chromosomal sequence. Such activation sequences include for example, a synthetic zinc finger motif (for example, see U.S. Pat. Nos. 6,534,261 and 6,503,7171) or a strong promoter or enhancer sequence together with a targeting sequence to enable homologous or non-homologous recombination of the activating sequence upstream of the gene of interest.

Genes encoding the following full-length previously described proteins, which are suitable for use in the co-transfection studies and profiling the compounds described herein, include human LXRα (accession U22662), human LXRβ (accession U07132), rat FXR (accession U18374), human FXR (accession NM_005123), human RXRα (accession NM 002957), human RXRβ (accession XM_042579), human RXRγ (accession XM_053680), human PPARα (accession X57638) and human PPARδ (accession U10375). All accession numbers in this application refer to GenBank accession numbers.

Reporter plasmids may be constructed using standard molecular biological techniques by placing cDNA encoding for the reporter gene downstream from a suitable minimal promoter. For example luciferase reporter plasmids may be constructed by placing cDNA encoding firefly luciferase (typically with SV40 small t intron and poly-A tail, (de Wet et al., (1987) Mol. Cell. Biol. 7 725-735) down stream from the herpes virus thymidine kinase promoter (located at nucleotides residues -105 to +51 of the thymidine kinase nucleotide sequence, obtained for example, from the plasmid pBLCAT2 (Luckow & Schutz (1987) Nucl. Acid. Res. 15 5490-5494)) which is linked in turn to the appropriate response element ($R^E$).

The choice of hormone response element is dependent upon the type of assay to be used. In the case of the use of the full-length LXRα or LXRβ a reporter plasmid comprising a known LXR RE would typically be used, such as for example in a reporter plasmid such as LXREx1-tk-luciferase, (see U.S. Pat. No. 5,747,661, which is hereby incorporated by reference). In the case of a LXRα or LXRβ-LBD-Gal4 fusion, GAL4 Upstream Activating Sequences (UAS) would be used. Typically the GAL4 UAS would comprise the sequence 5'CGGRNNRCYNYNCNCCG-3', where Y=C or T, $R^{11}$=A or G, and N=A, C, T or G, and would be present as a tandem repeat of 4 copies.

Numerous methods of co-transfecting the expression and reporter plasmids are known to those of skill in the art and may be used for the co-transfection assay to introduce the plasmids into a suitable cell type. Typically such a cell will not endogenously express nuclear receptors that interact with the response elements used in the reporter plasmid.

Numerous reporter gene systems are known in the art and include, for example, alkaline phosphatase (see, Berger, J., et al., Gene (1988), Vol. 66, pp. 1-10; and Kain, S. R., Methods. Mol. Biol. (1997), Vol. 63, pp. 49-60), β-galactosidase (See, U.S. Pat. No. 5,070,012, issued Dec. 3, 1991 to Nolan et al., and Bronstein, I., et al., J. Chemilum. Biolum. (1989), Vol. 4, pp. 99-111), chloramphenicol acetyltransferase (See, Gorman et al., Mol. Cell. Biol. (1982), Vol. 2, pp. 1044-51), β-glucuronidase, peroxidase, β-lactamase (U.S. Pat. Nos. 5,741,657 and 5,955,604), catalytic antibodies, luciferases (U.S. Pat. Nos. 5,221,623; 5,683,888; 5,674,713; 5,650,289; and 5,843,746) and naturally fluorescent proteins (Tsien, R. Y., Annu. Rev. Biochem. (1998), Vol. 67, pp. 509-44).

The use of chimeras comprising the ligand binding domain (LBD) of the nuclear receptor of interest to a heterologous DNA binding domain (DBD) expands the versatility of cell based assays by directing activation of the nuclear receptor in question to defined DNA binding elements recognized by defined DNA binding domain (see WO95/18380). This assay expands the utility of cell based co-transfection assays in cases where the biological response or screening window using the native DNA binding domain is not satisfactory.

In general the methodology is similar to that used with the basic co-transfection assay, except that a chimeric construct is used in place of the full length nuclear receptor. As with the full length nuclear receptor, treatment of the transfected cells with an agonist for the nuclear receptor LBD increases the transcriptional activity of the heterologous DNA binding domain which is reflected by an increase in expression of the reporter gene as described above. Typically for such chimeric constructs, the DNA binding domains from defined nuclear receptors, or from yeast or bacterially derived transcriptional regulators such as members of the GAL 4 and Lex A/Umud super families are used.

A third cell based assay of utility for screening compounds of the present invention is a mammalian two-hybrid assay that measures the ability of the nuclear hormone receptor to interact with a cofactor in the presence of a ligand (see, for example, U.S. Pat. Nos. 5,667,973, 5,283,173 and 5,468, 614). The basic approach is to create three plasmid constructs that enable the interaction of the nuclear receptor with the interacting protein to be coupled to a transcriptional readout within a living cell. The first construct is an expression plasmid for expressing a fusion protein comprising the interacting protein, or a portion of that protein containing the interacting domain, fused to a GAL4 DNA binding domain. The second expression plasmid comprises DNA encoding the nuclear receptor of interest fused to a strong transcription activation domain such as VP16, and the third construct comprises the reporter plasmid comprising a reporter gene with a minimal promoter and GAL4 upstream activating sequences.

Once all three plasmids are introduced into a cell, the GAL4 DNA binding domain encoded in the first construct allows for specific binding of the fusion protein to GAL4 sites upstream of a minimal promoter. However because the GAL4 DNA binding domain typically has no strong transcriptional activation properties in isolation, expression of the reporter gene occurs only at a low level. In the presence of a ligand, the nuclear receptor-VP16 fusion protein can bind to the GAL4-interacting protein fusion protein bringing the strong transcriptional activator VP16 in close proximity to the GAL4 binding sites and minimal promoter region of the reporter gene. This interaction significantly enhances the transcription of the reporter gene which can be measured for various reporter genes as described above. Transcription of the reporter gene is thus driven by the interaction of the interacting protein and nuclear receptor of interest in a ligand dependent fashion.

Any compound which is a candidate for activation of LXRα or LXRβ may be tested by these methods. Generally, compounds are tested at several different concentrations to optimize the chances that activation of the receptor will be detected and recognized if present. Typically assays are performed in triplicate and vary within experimental error by less than 15%. Each experiment is typically repeated three or more times with similar results.

Activity of the reporter gene can be conveniently normalized to the internal control and the data plotted as fold activation relative to untreated cells. A positive control compound (agonist) may be included along with DMSO as high and low controls for normalization of the assay data. Similarly, antagonist activity can be measured by determining the ability of a compound to competitively inhibit the activity of an agonist.

Additionally the compounds and compositions can be evaluated for their ability to increase or decrease the expression of genes known to be modulated by LXRα or LXRβ and other nuclear receptors in vivo, using Northern-blot, RT PCR or oligonucleotide microarray analysis to analyze RNA levels. Western-blot analysis can be used to measure expression of proteins encoded by LXR target genes. Genes that are known to be regulated by the LXRs include the ATP binding cassette transporters ABCA1, ABCG1, ABCG5, ABCG8, the sterol response element binding protein 1c (SREBP1c) gene, stearoyl CoA desaturase 1 (SCD-1) and the apolipoprotein apoE gene (ApoE).

Established animal models exist for a number of diseases of direct relevance to the claimed compounds and these can be used to further profile and characterize the claimed compounds. These model systems include diabetic dislipidemia using Zucker (fa/fa) rats or (db/db) mice, spontaneous hyperlipidemia using apolipoprotein E deficient mice (ApoE$^{-/-}$), diet-induced hyperlipidemia, using low density lipoprotein receptor deficient mice (LDLR$^{-/-}$) and atherosclerosis using both the Apo E($^{-/-}$) and LDLR($^{-/-}$) mice fed a western diet. (21% fat, 0.05% cholesterol). Additionally LXR or FXR animal models (e.g., knockout mice) can be used to further evaluate the present compounds and compositions in vivo (see, for example, Peet, et al., Cell (1998), Vol. 93, pp. 693-704, and Sinal, et al., Cell (2000), Vol. 102, pp. 731-744).

Administration of the Compounds of the Invention

Administration of the compounds of the invention, or their pharmaceutically acceptable salts, in pure form or in an appropriate pharmaceutical composition, can be carried out via any of the accepted modes of administration of agents for serving similar utilities. The pharmaceutical compositions of the invention can be prepared by combining a compound of the invention with an appropriate pharmaceutically acceptable carrier, diluent or excipient, and may be formulated into preparations in solid, semi-solid, liquid or gaseous forms, such as tablets, capsules, powders, granules, ointments, solutions, suppositories, injections, inhalants, gels, microspheres, and aerosols. Typical routes of administering such pharmaceutical compositions include, without limitation, oral, topical, transdermal, inhalation, parenteral, sublingual, rectal, vaginal, and intranasal. The term parenteral as used herein includes subcutaneous injections, intravenous, intramuscular, intrasternal injection or infusion techniques. Pharmaceutical compositions of the invention are formulated so as to allow the active ingredients contained therein to be bioavailable upon administration of the composition to a patient. Compositions that will be administered to a subject or patient take the form of one or more dosage units, where for example, a tablet may be a single dosage unit, and a container of a compound of the invention in aerosol form may hold a plurality of dosage units. Actual methods of preparing such dosage forms are known, or will be apparent, to those skilled in this art; for example, see Remington's Pharmaceutical Sciences, 18th Ed., (Mack Publishing Company, Easton, Pa., 1990). The composition to be administered will, in any event, contain a therapeutically effective amount of a compound of the invention, or a pharmaceutically acceptable salt thereof, for treatment of a disease-state associated with the activity of a nuclear receptor in accordance with the teachings of this invention.

A pharmaceutical composition of the invention may be in the form of a solid or liquid. In one aspect, the carrier(s) are particulate, so that the compositions are, for example, in tablet or powder form.

The carrier(s) may be liquid, with the compositions being, for example, an oral syrup, injectable liquid or an aerosol, which is useful in, e.g., inhalatory administration.

When intended for oral administration, the pharmaceutical composition is preferably in either solid or liquid form, where semi-solid, semi-liquid, suspension and gel forms are included within the forms considered herein as either solid or liquid.

As a solid composition for oral administration, the pharmaceutical composition may be formulated into a powder, granule, compressed tablet, pill, capsule, chewing gum, wafer or the like form. Such a solid composition will typically contain one or more inert diluents or edible carriers. In addition, one or more of the following may be present: binders such as carboxymethylcellulose, ethyl cellulose, microcrystalline cellulose, gum tragacanth or gelatin; excipients such as starch, lactose or dextrins, disintegrating agents such as alginic acid, sodium alginate, Primogel, com starch and the like; lubricants such as magnesium stearate or Sterotex; glidants such as colloidal silicon dioxide; sweetening agents such as sucrose or saccharin; a flavoring agent such as peppermint, methyl salicylate or orange flavoring; and a coloring agent.

When the pharmaceutical composition is in the form of a capsule, e.g., a gelatin capsule, it may contain, in addition to materials of the above type, a liquid carrier such as polyethylene glycol or oil.

The pharmaceutical composition may be in the form of a liquid, e.g., an elixir, syrup, solution, emulsion or suspension. The liquid may be for oral administration or for delivery by injection, as two examples. When intended for oral administration, preferred composition contain, in addition to the present compounds, one or more of a sweetening agent, preservatives, dye/colorant and flavor enhancer. In a composition intended to be administered by injection, one or more of a surfactant, preservative, wetting agent, dispersing agent, suspending agent, buffer, stabilizer and isotonic agent may be included.

The liquid pharmaceutical compositions of the invention, whether they be solutions, suspensions or other like form, may include one or more of the following adjuvants: sterile diluents such as water for injection, saline solution, preferably physiological saline, Ringer's solution, isotonic sodium chloride, fixed oils such as synthetic mono or diglycerides which may serve as the solvent or suspending medium, polyethylene glycols, glycerin, propylene glycol or other solvents; antibacterial agents such as benzyl alcohol or methyl paraben; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parenteral preparation can be enclosed in ampoules, disposable syringes or multiple dose vials made of glass or plastic. Physiological saline is a preferred adjuvant. An injectable pharmaceutical composition is preferably sterile.

A liquid pharmaceutical composition of the invention intended for either parenteral or oral administration should contain an amount of a compound of the invention such that a suitable dosage will be obtained. Typically, this amount is at least 0.01% of a compound of the invention in the composition. When intended for oral administration, this amount may be varied to be between 0.1 and about 70% of the weight of the composition. Preferred oral pharmaceutical compositions contain between about 4% and about 50% of the compound of the invention. Preferred pharmaceutical compositions and preparations according to the present invention are prepared so that a parenteral dosage unit contains between 0.01 to 1% by weight of the compound of the invention.

The pharmaceutical composition of the invention may be intended for topical administration, in which case the carrier may suitably comprise a solution, emulsion, ointment or gel base. The base, for example, may comprise one or more of the following: petrolatum, lanolin, polyethylene glycols, bee wax, mineral oil, diluents such as water and alcohol, and emulsifiers and stabilizers. Thickening agents may be present in a pharmaceutical composition for topical administration. If intended for transdermal administration, the composition may include a transdermal patch or iontophoresis device. Topical formulations may contain a concentration of the compound of the invention from about 0.1 to about 10% w/v (weight per unit volume).

The pharmaceutical composition of the invention may be intended for rectal administration, in the form, e.g., of a suppository, which will melt in the rectum and release the drug. The composition for rectal administration may contain an oleaginous base as a suitable nonirritating excipient. Such bases include, without limitation, lanolin, cocoa butter and polyethylene glycol.

The pharmaceutical composition of the invention may include various materials, which modify the physical form of a solid or liquid dosage unit. For example, the composition may include materials that form a coating shell around the active ingredients. The materials that form the coating shell are typically inert, and may be selected from, for example, sugar, shellac, and other enteric coating agents. Alternatively, the active ingredients may be encased in a gelatin capsule.

The pharmaceutical composition of the invention in solid or liquid form may include an agent that binds to the compound of the invention and thereby assists in the delivery of the compound. Suitable agents that may act in this capacity include a monoclonal or polyclonal antibody, a protein or a liposome.

The pharmaceutical composition of the invention may consist of dosage units that can be administered as an aerosol. The term aerosol is used to denote a variety of systems ranging from those of colloidal nature to systems consisting of pressurized packages. Delivery may be by a liquefied or compressed gas or by a suitable pump system that dispenses the active ingredients. Aerosols of compounds of the invention may be delivered in single phase, bi-phasic, or tri-phasic systems in order to deliver the active ingredient(s). Delivery of the aerosol includes the necessary container, activators, valves, subcontainers, and the like, which together may form a kit. One skilled in the art, without undue experimentation may determine preferred aerosols.

The pharmaceutical compositions of the invention may be prepared by methodology well known in the pharmaceutical art. For example, a pharmaceutical composition intended to be administered by injection can be prepared by combining a compound of the invention with sterile, distilled water so as to form a solution. A surfactant may be added to facilitate the formation of a homogeneous solution or suspension. Surfactants are compounds that non-covalently interact with the compound of the invention so as to facilitate dissolution or homogeneous suspension of the compound in the aqueous delivery system.

The compounds of the invention, or their pharmaceutically acceptable salts, are administered in a therapeutically effective amount, which will vary depending upon a variety of factors including the activity of the specific compound employed; the metabolic stability and length of action of the compound; the age, body weight, general health, sex, and diet of the patient; the mode and time of administration; the rate of excretion; the drug combination; the severity of the particular disorder or condition; and the subject undergoing therapy. Generally, a therapeutically effective daily dose is from about 0.1 mg to about 20 mg/kg of body weight per day of a compound of the invention, or a pharmaceutically acceptable salt thereof; preferably, from about 0.1 mg to about 10 mg/kg of body weight per day; and most preferably, from about 0.1 mg to about 7.5 mg/kg of body weight per day.

Compounds of the invention, or pharmaceutically acceptable derivatives thereof, may also be administered simultaneously with, prior to, or after administration of one or more of the therapeutic agents described above in the Utility of the Compounds of the Invention. Such combination therapy includes administration of a single pharmaceutical dosage formulation which contains a compound of the invention and one or more additional active agents, as well as administration of the compound of the invention and each active agent in its own separate pharmaceutical dosage formulation. For example, a compound of the invention and an HMG-CoA reductase inhibitor can be administered to the patient together in a single oral dosage composition such as a tablet or capsule, or each agent administered in separate oral dosage formulations. Where separate dosage formulations are used, the compounds of the invention and one or more additional active agents can be administered at essentially the same time, i.e., concurrently, or at separately staggered times, i.e., sequentially; combination therapy is understood to include all these regimens.

Dosage information for HMG-CoA reductase inhibitors is well known in the art, since several HMG-CoA reductase inhibitors are marketed in the U.S. In particular, the daily dosage amounts of the HMG-CoA reductase inhibitor may be the same or similar to those amounts which are employed for anti-hypercholesterolemic treatment and which are described in the Physicians' Desk Reference (PDR). For example, see the 50th Ed. of the PDR, 1996 (Medical Economics Co); in particular, see at page 216 the heading "Hypolipidemics," sub-heading "HMG-CoA Reductase Inhibitors," and the reference pages cited therein. Preferably, the oral dosage amount of HMG-CoA reductase inhibitor is from about 1 to 200 mg/day and, more preferably, from about 5 to 160 mg/day. However, dosage amounts will vary depending on the potency of the specific HMG-CoA reductase inhibitor used as well as other factors as noted above. An HMG-CoA reductase inhibitor which has sufficiently greater potency may be given in sub-milligram daily dosages.

As examples, the daily dosage amount for simvastatin may be selected from 5 mg, 10 mg, 20 mg, 40 mg, 80 mg and 160 mg for lovastatin, 10 mg, 20 mg, 40 mg and 80 mg; for fluvastatin sodium, mg, 40 mg and 80 mg; and for pravastatin sodium, 10 mg, 20 mg, and 40 mg. The daily dosage amount for atorvastatin calcium may be in the range of from 1 mg to 160 mg and, more particularly, from 5 mg to 80 mg. Oral administration may be in a single or divided doses of two, three, or four times daily, although a single daily dose of the HMG-CoA reductase inhibitor is preferred.

Preparation of the Compounds of the Invention

It is understood that in the following description, combinations of substituents and/or variables of the depicted formulae are permissible only if such contributions result in stable compounds.

It will also be appreciated by those skilled in the art that in the processes described below the functional groups of intermediate compounds may need to be protected by suitable protecting groups. Such functional groups include hydroxy, amino, mercapto and carboxylic acid. Suitable protecting groups for hydroxy include trialkylsilyl or diarylalkylsilyl (e.g., t-butyldimethylsilyl, t-butyldiphenylsilyl or trimethylsilyl), tetrahydropyranyl, benzyl, and the like. Suitable protecting groups for 1,2-dihydroxys include ketal- and acetal-forming groups. Suitable protecting groups for amino, amidino and guanidino include t-butoxycarbonyl, benzyloxycarbonyl, and the like. Suitable protecting groups for mercapto include —C(O)—R (where R is alkyl, aryl or aralkyl), p-methoxybenzyl, trityl and the like. Suitable protecting groups for carboxylic acid include alkyl, aryl or aralkyl esters.

Protecting groups may be added or removed in accordance with standard techniques, which are well-known to those skilled in the art and as described herein. The use of protecting groups is described in detail in Green, T. W. and P. G. M. Wutz, Protective Groups in Organic Synthesis (1991), 2nd Ed., Wiley-Interscience. The protecting group may also be a polymer resin such as a Wang resin or a 2-chlorotrityl chloride resin.

It will also be appreciated by those skilled in the art, although such protected derivatives of compounds of the invention, as described above in the First aspect of the invention, may not possess pharmacological activity as such, they may be administered to a mammal having a disease associated with defects in cholesterol transport, glucose metabolism, fatty acid metabolism and cholesterol metabolism, and thereafter metabolized in the body to form compounds of the invention which are pharmacologically active. Such derivatives may therefore be described as "prodrugs". All prodrugs of compounds of the invention are included within the scope of the invention.

It is understood that one of ordinary skill in the art would be able to make the compounds of the invention not specifically prepared herein in light of the following disclosure, including the Preparations and Examples, and information known to those of ordinary skill in the chemical synthesis field.

Starting materials in the synthesis examples provided herein are either available from commercial sources or via literature procedures or by methods disclosed herein. All commercially available compounds were used without further purification unless otherwise indicated. Deuterated solvents such as DMSO or CDCl$_3$ (99.8% D, Cambridge Isotope Laboratories) were used in all experiments as indicated. $^1$H NMR spectra were recorded on a Bruker Avance 400 MHz NMR spectrometer. Significant peaks are tabulated and typically include: number of protons, multiplicity (s, singlet; d, double; t, triplet; q, quartet; m, multiplet; br s, broad singlet) and coupling constant(s) in Hertz. Chemical shifts are reported as parts per million (5) relative to tetramethylsilane. Mass spectra were recorded on a Perkin-Elmer SCIEX HPLC/MS instrument using reverse-phase conditions (acetonitrile/water, 0.05% trifluoroacetic acid) and electrospray (ES) ionization. Abbreviations used in the examples below have their accepted meanings in the chemical literature. For example, CH$_2$Cl$_2$ (dichloromethane), C$_6$H$_6$ (benzene), TFA (trifluoroacetic acid), EtOAc (Ethyl Acetate), Et$_2$O (diethyl ether), DMAP (4-dimethylaminopyridine), DMF (N,N-dimethylformamide) and THF (tetrahydrofuran). Flash chromatography was performed using Merck Silica Gel 60 (230-400 mesh).

For purposes of illustration only, most of the formulae in the following Reaction Schemes are directed to specific embodiments of the compounds of invention. However, one of ordinary skill in the art, in view of the teachings of this specification would reasonably be expected to be able to prepare all the compounds of the invention in the First aspect of the invention utilizing the appropriately-substituted starting materials and methods known to one skilled in the art.

In the general descriptions immediately following each Reaction Scheme, the phrase "standard isolation procedures" is meant to include one or more of the following techniques familiar to one schooled in the art of organic chemistry: organic extraction, washing of organic solutions with dilute aqueous acid or base, use of drying agents, filtration, concentration in vacuo, followed by purification using distillation, crystallization, or solid-liquid phase chromatography. The phrase "elevated temperature" refers to a temperature above ambient temperature and the phrase "reduced temperature" refers to a temperature below ambient temperature.

The following specific Preparations (for intermediates) and Examples (for compounds, pharmaceutical compositions and methods of use of the invention) are provided as a guide to assist in the practice of the invention, and are not intended as a limitation on the scope of the invention. Without further description, it is believed that one of ordinary skill in the art can, using the preceding description and the following illustrative examples, make and utilize the compounds of the present invention and practice the claimed methods. It should be understood that the foregoing discussion and examples merely present a detailed description of certain preferred embodiments. It will be apparent to one of ordinary skill in the art that various modifications and equivalents can be made without departing from the spirit and scope of the invention.

Unless otherwise indicated, all compounds associated with NMR and/or mass spectra data were prepared and the NMR and mass spectra measured.

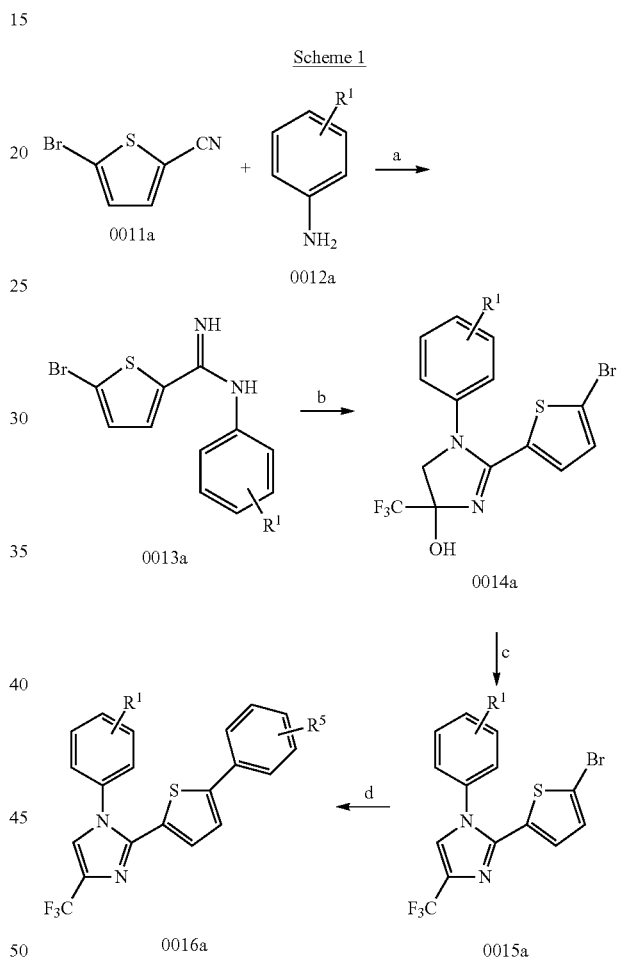

Scheme 1

Reaction and conditions: (a) NaHMDS, THF; 0° C.-rt; (b) 3-bromo-1,1,1-trifluoroacetone, NaHCO$_3$, 2-PrOH, 80° C.; (c) TSA, toluene, reflux; (d) ArB(OH)$_2$, K$_2$CO$_3$, PdCl$_2$(dppf), DME/H$_2$O, 80° C.

In general, compounds of formula (0016a) are prepared by first reacting an aniline of formula (0012a) with aryl nitriles (0011a), such as 5-bromo-thiophene-2-carbonitrile, in the presence of base to give compounds of formula (0013a) after standard isolation procedures. In a subsequent step, exposure of amidine (0013a) to haloketone, such as 1-bromo-3,3,3-trifluoroacetone, under basic condition at elevated temperature provides 1H-imidazol-4-ol of formula (0014a) after standard isolation procedures. Conversion of compounds of formula (0014a) to compounds of formula (0015a) is then accomplished by treating the compounds of formula (0014a) with a catalyst acid such as p-toluenesulfonic acid at reflux. In a palladium-mediated coupling reaction, for example, a Suzuki reaction, compounds of formula (0015a) are then reacted with a boronate or boronic acid reagent to give compounds of formula (0016a) after standard isolation procedures.

EXAMPLE 1

1-(2,5-Dichloro-phenyl)-2-[5-(3-methanesulfonyl-phenyl)-thiophen-2-yl]-4-trifluoromethyl-1H-imidazole

EXAMPLE 1a

Preparation of 5-Bromo-N-(2,5-dichloro-phenyl)-thiophene-2-carboxamidine

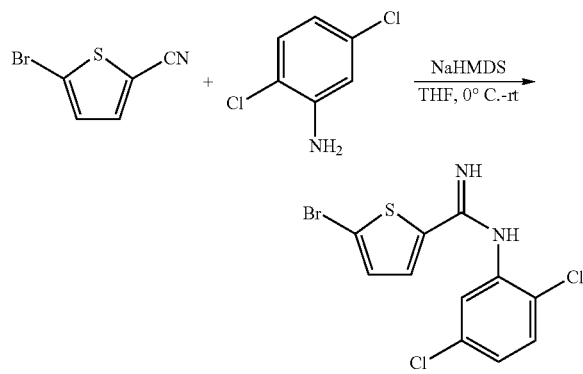 [SMILES: N#Cc1ccc(Br)s1 ; Nc1cc(Cl)ccc1Cl ; N=C(Nc1cc(Cl)ccc1Cl)c1ccc(Br)s1]

Under N$_2$ atmosphere, to a solution of 2,5-dichloroaniline (341 mg, 2.1 mmol) in 2 mL dry THF was added sodium bis(trimethylsilyl)amide (2.1 mL, 1M solution in THF, 2.1 mmol). After the mixture was stirred at ambient temperature for 40 min, a solution of 5-bromo-thiophene-2-carbonitrile (376 mg, 2 mmol) in 2 mL dry THF was added dropwise. The reaction mixture was stirred overnight, and then poured into 100 mL ice water. The orange precipitate was collected by filtration, washed with a solution of ether and hexane (3/7, v/v), and air dried to give a light orange solid (653 mg, 94% yield). $^1$H-NMR (400 MHz, MeOH-d$_4$): δ 6.94 (d, 1H), 6.99 (dd, 1H), 7.06 (d, 1H), 7.32 (d, 1H), 7.37 (d, 1H).

EXAMPLE 1b

Preparation of 2-(5-Bromo-thiophen-2-yl)-1-(2,5-dichloro-phenyl)-4-trifluoromethyl-4,5-dihydro-1H-imidazol-4-ol

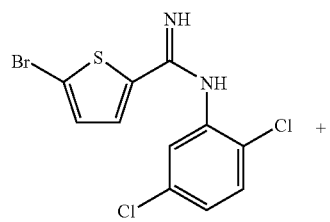

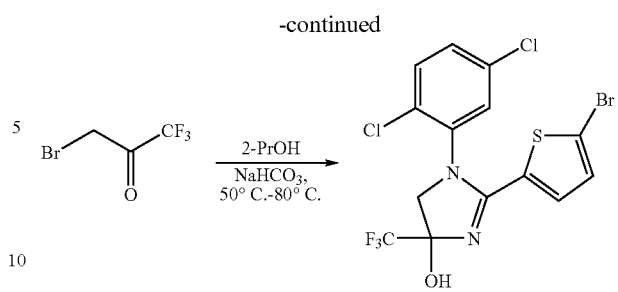

To a suspension of 5-bromo-N-(2,5-dichloro-phenyl)-thiophene-2-carboxamidine (634 mg, 1.8 mmol) and sodium bicarbonate (227 mg, 2.7 mmol) in 8 mL 2-proponal was added 3-bromo-1,1,1-trifluoroacetone (520 mg, 2.7 mmol). The reaction mixture was heated at 50° C. for 1.5 hrs, then at 80° C. for 4 hrs. After cooling to room temperature, the residue was filtered out and washed with dichloromethane. The filtrate and washings were combined together and concentrated under vacuum to give a light pink solid that was used directly for the next step (820 mg, 99% yield). $^1$H-NMR (400 MHz, DMSO-d$_6$): δ 3.09 (d, 1H), 3.95 (dd, 1H), 6.31 (d, 1H), 6.91 (d, 1H), 7.15 (m, 1H), 7.33 (dd, 1H), 7.44 (m, 2H).

EXAMPLE 1c

Preparation of 2-(5-Bromo-thiophen-2-yl)-1-(2,5-dichloro-phenyl)-4-trifluoromethyl-1H-imidazole

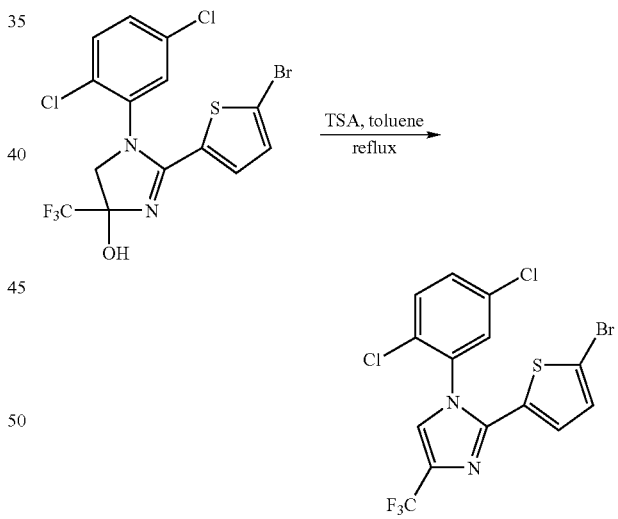

The mixture of 2-(5-bromo-thiophen-2-yl)-1-(2,5-dichloro-phenyl)-4-trifluoromethyl-4,5-dihydro-1H-imidazol-4-ol (822 mg, 1.8 mmol) and p-toluenesulfonic acid monohydrate (172 mg, 0.9 mmol) in 10 mL toluene was heated at 120° C. for 6 hrs. The solvent was removed, and the residue was redissolved into dichloromethane, then washed with saturated NaHCO$_3$ and brine, dried over Na$_2$SO$_4$, and concentrated in vacuo. The crude product was purified by chromatography on silica gel (hexane/EtOAc 85/15) to give an off-white solid (512 mg, 64% yield). $^1$H-NMR (400 MHz, CDCl$_3$): δ 6.68 (d, 1H), 6.89 (d, 1H), 7.31 (dd, 1H), 7.47 (dd, 1H), 7.55 (d, 1H), 7.56 (s, 1H).

EXAMPLE 1d

Preparation of 1-(2,5-Dichloro-phenyl)-2-[5-(3-methanesulfonyl-phenyl)-thiophen-2-yl]-4-trifluoromethyl-1H-imidazole

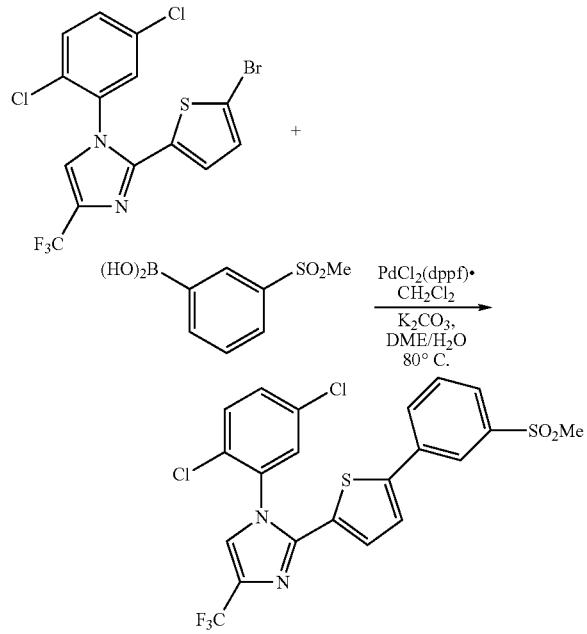

2-(5-Bromo-thiophen-2-yl)-1-(2,5-dichloro-phenyl)-4-trifluoromethyl-1H-imidazole (90 mg, 0.2 mmol), (3-methylsulfonyl)phenylboronic acid (60 mg, 0.3 mmol), potassium carbonate (110 mg, 0.8 mmol), and $PdCl_2$ (dppf).$CH_2Cl_2$ (16 mg, 0.02 mmol) were mixed with 2 mL 9:1 DME/$H_2O$ (v/v), then heated at 80° C. overnight. All solvent was removed in vacuo. The crude product was purified by chromatography on silica gel (Hexane/EtOAc, 6/4) to give a white solid (76 mg, 74% yield). $^1$H-NMR (400 MHz, $CDCl_3$): δ 3.08 (s, 3H), 6.79 (d, 1H), 7.22 (d, 1H), 7.36 (d, 1H), 7.52 (d, 1H), 7.58 (m, 3H), 7.78 (m, 1H), 7.86 (m, 1H), 8.10 (t, 1H).

All the following compounds were prepared in similar manner as described in Scheme 1 and mass and NMR spectra measured. The boronic acid or boronate reagents for Suzuki coupling, if not commercially available, were made using standard techniques that are readily apparent to one skilled in the art.

1-(2,5-dichlorophenyl)-2-{5-[3-(methylsulfonyl)phenyl]-2-thienyl}-4-(trifluoromethyl)-1H-imidazole; MS (ES): 517.3 $[M+H]^+$;

5-{5-[1-(2,5-dichlorophenyl)-4-(trifluoromethyl)-1H-imidazol-2-yl]-2-thienyl}-3-methyl-2-(methylthio)pyridine; MS (ES): 500.4 $[M+H]^+$;

5-{5-[1-(2,5-dichlorophenyl)-4-(trifluoromethyl)-1H-imidazol-2-yl]-2-thienyl}-2-(ethylthio)-3-methylpyridine; MS (ES): 514.2 $[M+H]^+$;

4-(5-{5-[1-(2,5-dichlorophenyl)-4-(trifluoromethyl)-1H-imidazol-2-yl]-2-thienyl}pyridin-2-yl)morpholine; MS (ES): 525.4, 527.3 $[M+H]^+$;

1,1-dimethylethyl 4-(5-{5-[1-(2,5-dichlorophenyl)-4-(trifluoromethyl)-1H-imidazol-2-yl]-2-thienyl}pyridin-2-yl)piperazine-1-carboxylate; MS (ES): 624.5, 626.3 $[M+H]^+$;

1-(2-chlorophenyl)-2-{5-[3-(methylsulfonyl)phenyl]-2-thienyl}-4-(trifluoromethyl)-1H-imidazole; MS (ES): 483.2 $[M+H]^+$;

5-{5-[1-(2-chlorophenyl)-4-(trifluoromethyl)-1H-imidazol-2-yl]-2-thienyl}-3-methyl-2-(methylthio)pyridine; MS (ES): 466.2 $[M+H]^+$;

5-{5-[1-(2-chlorophenyl)-4-(trifluoromethyl)-1H-imidazol-2-yl]-2-thienyl}-2-(ethylthio)-3-methylpyridine; MS (ES): 480.2 $[M+H]^+$;

methyl (4-{5-[1-(2-chlorophenyl)-4-(trifluoromethyl)-1H-imidazol-2-yl]-2-thienyl}-3-methylphenyl)acetate; MS (ES): 491.2 $[M+H]^+$;

3-{5-[1-(2-chlorophenyl)-4-(trifluoromethyl)-1H-imidazol-2-yl]-2-thienyl}benzenesulfonamide; MS (ES): 484.0 $[M+H]^+$;

4-{5-[1-(2-chlorophenyl)-4-(trifluoromethyl)-1H-imidazol-2-yl]-2-thienyl}benzenesulfonamide; MS (ES): 484.1 $[M+H]^+$;

Scheme 2

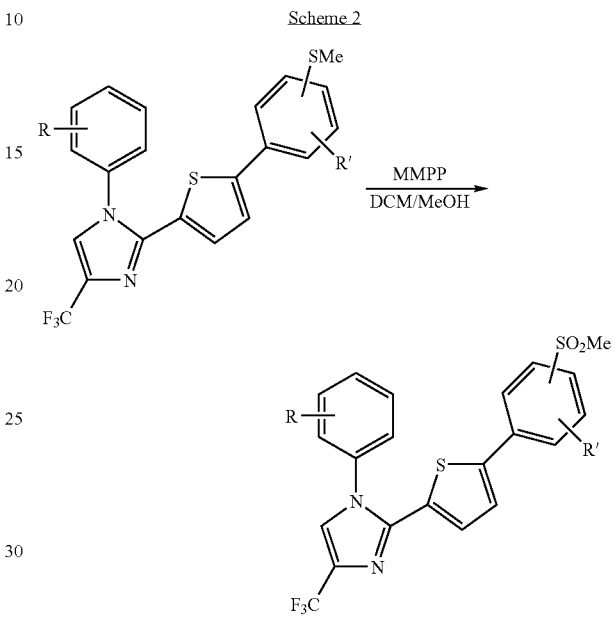

The starting materials were prepared in similar manner as Scheme 1, followed by further transformations to make the final products as described in Scheme 2.

EXAMPLE 2

Preparation of 5-{5-[1-(2,5-dichlorophenyl)-4-(trifluoromethyl)-1H-imidazol-2-yl]-2-thienyl}-2-(methylsulfonyl)-3-methylpyridine

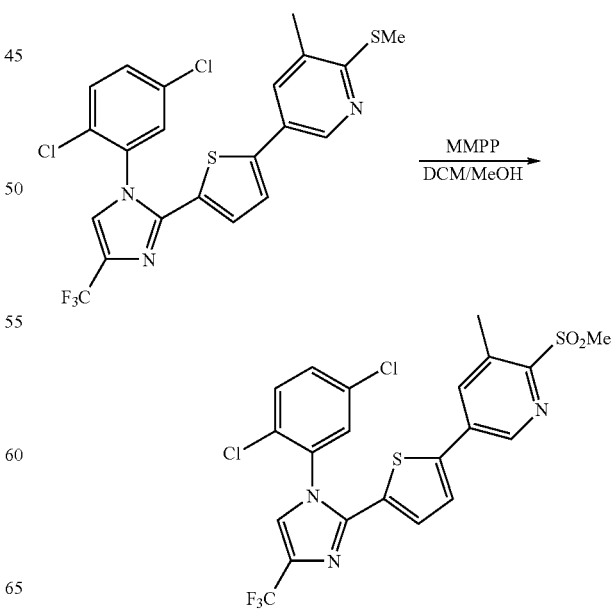

5-{5-[1-(2,5-Dichloro-phenyl)-4-trifluoromethyl-1H-imidazol-2-yl]-thiophen-2-yl}-3-methyl-2-methylsulfanyl-pyridine (80 mg, 0.16 mmol) was dissolved in 8 mL mixture of dichloromethane and methanol (5:1, V/V). MMPP (magnesium monoperoxyphthalate hexahydrate, 200 mg, 0.35 mmol, 80% tech.) was added then. The mixture was stirred at room temperature for 2 hrs, then diluted with dichloromethane, and filtered. The filtrate was washed with saturated $NaHCO_3$, and brine, dried over $Na_2SO_4$, and concentrated in vacuo. The crude product was purified by column chromatography on silica gel (15→60% EtOAc/Hexane) to give a white solid (52 mg, 61% yield). 1H-NMR (400 MHz, DMSO-$d_6$): δ 2.61 (s, 3H), 3.37 (s, 3H), 6.58 (d, J=4.0, 1H), 7.63 (d, J=4.0, 1H), 7.86-7.79 (m, 2H), 8.20-8.17 (m, 2H), 8.31-8.30 (m, 1H), 8.80 (m, 1H). MS (ES): 532.2, 536.2 [M+H]$^+$ The following compounds were made in similar manner by oxidation of appropriate sulfides.

5-{5-[1-(2,5-dichlorophenyl)-4-(trifluoromethyl)-1H-imidazol-2-yl]-2-thienyl}-2-(ethylsulfonyl)-3-methylpyridine; MS (ES): 546.2 [M+H]$^+$ 5-{5-[1-(2,5-dichlorophenyl)-4-(trifluoromethyl)-1H-imidazol-2-yl]-2-thienyl}-3-methyl-2-(methylsulfonyl)pyridine; MS (ES): 532.2 [M+H]$^+$ 5-{5-[1-(2-chlorophenyl)-4-(trifluoromethyl)-1H-imidazol-2-yl]-2-thienyl}-3-methyl-2-(methylsulfonyl)pyridine; MS (ES): 498.4 [M+H]$^+$ 5-{5-[1-(2-chlorophenyl)-4-(trifluoromethyl)-1H-imidazol-2-yl]-2-thienyl}-2-(ethylsulfonyl)-3-methylpyridine; MS (ES): 512.2 [M+H]$^+$ Scheme 3

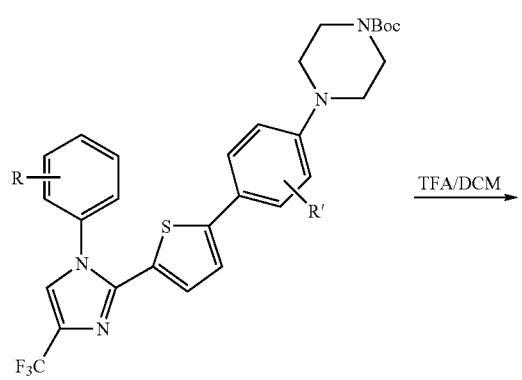

The starting materials were prepared in similar manner as Scheme 1, followed by further transformations to make the final products as described in Scheme 3.

EXAMPLE 3

1-(5-{5-[1-(2,5-Dichloro-phenyl)-4-trifluoromethyl-1H-imidazol-2-yl]-thiophen-2-yl}-pyridin-2-yl)-piperazine

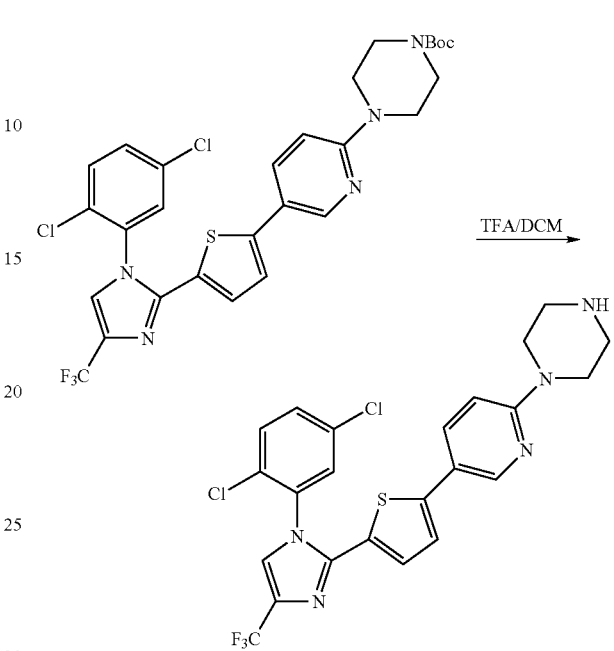

4-(5-{5-[1-(2,5-Dichloro-phenyl)-4-trifluoromethyl-1H-imidazol-2-yl]-thiophen-2-yl}-pyridin-2-yl)-piperazine-1-carboxylic acid tert-butyl ester (104 mg, 0.17 mmol) was mixed with 4 mL 50% trifluoromethylacetic acid in dichloromethane, and stirred at room temperature for 2 hrs. All solvent was removed; the residue was redissolved in dichloromethane and neutralized to pH 7 by saturated $NaHCO_3$. The organic layer was washed with brine, dried over $Na_2SO_4$, and concentrated in vacuo. The residue was precipitated from dichloromethane/Hexane mixture, then filtered and washed several times with dichloromethane to give yellow solid (50 mg, 57% yield). 1H-NMR (400 MHz, CDCl$_3$): δ 3.30-2.97 (m, 4H), 3.57-3.54 (m, 4H), 6.63 (d, J=8.7, 1H), 6.78 (d, J=4.0, 1), 6.96 (d, J=4.0, 1H), 7.31 (s, 1H), 7.60-7.50 (m, 4H), 8.37 (m, 1H). MS (ES): 524.3, 526.5. [M+]$^+$ Scheme 4

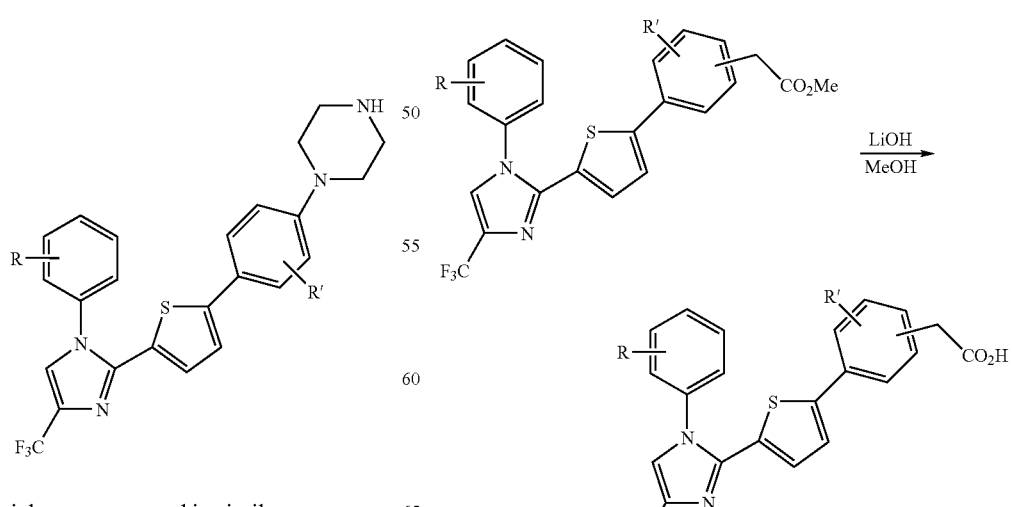

The starting materials were prepared in similar manner as Scheme 1, followed by further transformations to make the final products as described in Scheme 4.

EXAMPLE 4

(4-{5-[1-(2-Chloro-phenyl)-4-trifluoromethyl-1H-imidazol-2-yl]-thiophen-2-yl}-3-methyl-phenyl)-acetic acid

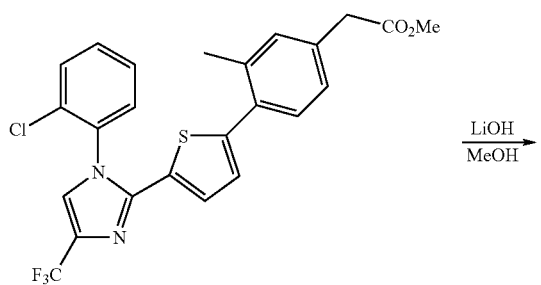

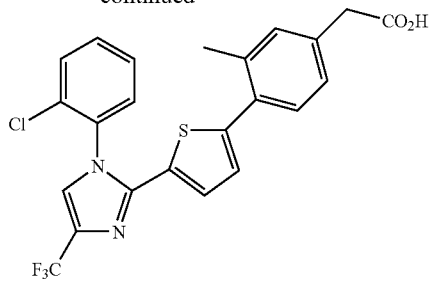

(4-{5-[1-(2-Chloro-phenyl)-4-trifluoromethyl-1H-imidazol-2-yl]-thiophen-2-yl}-3-methyl-phenyl)-acetic acid methyl ester (123 mg, 0.25 mmol) was dissolved in 6 mL mixture of THF and water (3:1, V/V). Lithium hydroxide monohydrate (2.3 mg, 0.55 mmol) was added then. The mixture was stirred at room temperature for 3 hrs. The mixture was neutralized to pH 7 by 1N HCl, and then extracted with ethyl acetate. The combined organic layers were washed with brine, dried over $Na_2SO_4$, and concentrated in vacuo. The crude product was purified by column chromatography on silica gel (0→5% MeOH/DCM) to give a white solid (47 mg, 39% yield). 1H-NMR (400 MHz, $CDCl_3$): δ 2.35 (s, 3H), 3.64 (s, 2H), 6.83 (s, 2H), 7.13-7.10 (m, 1H), 7.16 (m, 1H), 7.29-7.27 (m, 1H), 7.35 (m, 1H), 7.47-7.46 (m, 2H), 7.57-7.52 (m, 1H), 7.64-7.62 (m, 1H). MS (ES): 477.1, $[M+H]^+$ Scheme 5

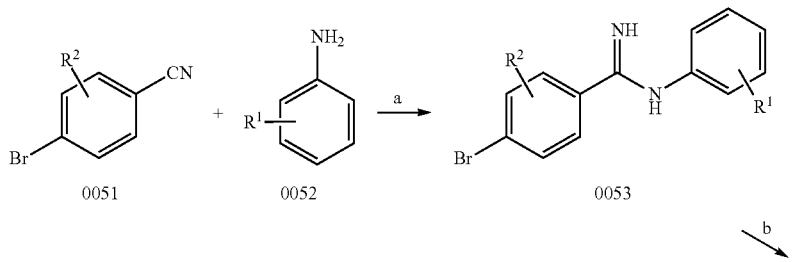

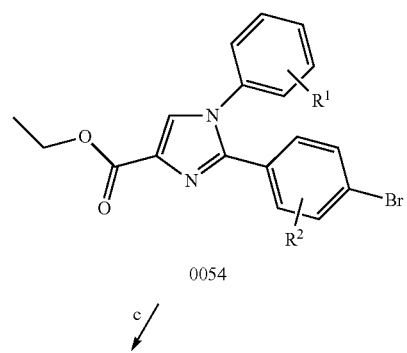

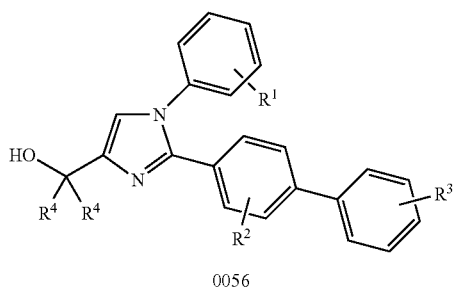

0056

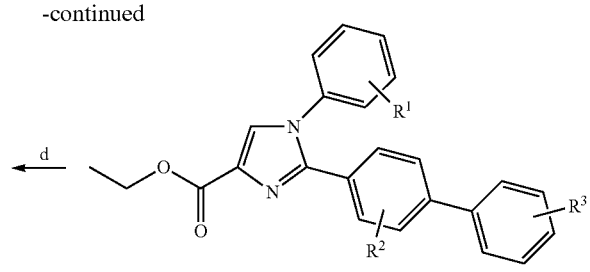

0055

(a) Me₃Al, PhMe, 90° C.;
(b) ethyl bromopyruvate, NaHCO₃, 2-PrOH, 95° C.;
(c) ArB(OH)₂, Cl₂Pd(dppf), K₂CO₃, H₂O/DME, 80° C.;
(d) R⁴MgBr, THF, 0° C.-rt.

In general, compounds of formula (0056) can be prepared as depicted in Scheme 5. An arylnitrile (0051) and an arylamine (0052) can react in the presence of a Lewis acid, such as trimethylaluminum, to give the corresponding amidine (0053). Heteroarylnitriles 0051 and/or heteroarylamines 0052 also can be utilized for the syntheses of their respective amidines 0053. Intermediate 0053 then can react with ethyl bromopyruvate in the presence of a weak base, such as sodium bicarbonate, followed by dehydration at elevated temperature to yield the corresponding imidazole (0054). This intermediate 0054 can undergo cross-coupling reactions, such as with an arylboronic acid under typical Suzuki conditions, to afford the corresponding 2-biaryl-imidazole (0055). 0055 can react with a Grignard reagent, such as an alkylmagnesium bromide, to afford the desired product 0056.

EXAMPLE 5

2-{1-(2,6-dichlorophenyl)-2-[5-(3-methanesulfonyl-phenyl)-thiophen-2-yl]-1H-imidazol-4-yl}-propan-2-ol

EXAMPLE 5a

Preparation of 5-bromo-N-(2,6-dichlorophenyl)-thiophene-2-carboxamidine

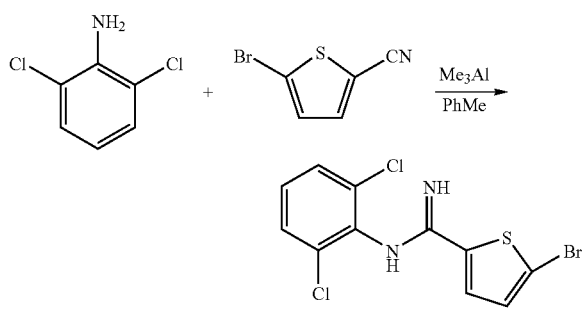

To a stirred solution of 2,6-dichloroaniline (1.75 g, 10.8 mmol) in toluene (25 mL, anhyd) was added dropwise a 2.0M solution of trimethylaluminum in toluene (8.0 mL, 16 mmol). After 90 min the reaction mixture was charged with a solution of 5-bromothiophene-2-carbonitrile (3.00 g, 16 mmol) in toluene (20 mL, anhyd) and then heated at 90° C. After 5 h the reaction mixture was allowed to cool to ambient temperature and quenched by addition to a stirred slurry of silica (25 g) in 3:1 CHCl₃/MeOH (100 mL). After 30 min the resulting mixture was filtered and the solids rinsed with MeOH and DCM. The combined filtrates were concentrated to afford the title compound (3.9 g, quant) as a pale yellow solid, which was used in the next step without purification. GC-MS (EI): 348, 350, 352.

EXAMPLE 5b

Preparation of 2-(5-bromothiophen-2-yl)-1-(2,6-dichlorophenyl)-1H-imidazole-4-carboxylic acid ethyl ester

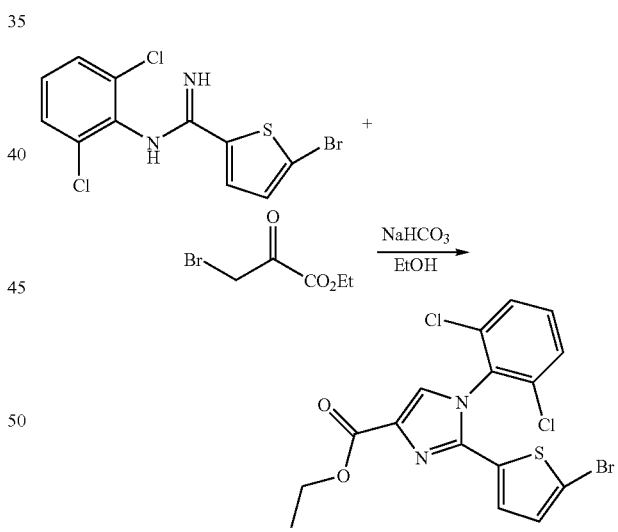

A stirred mixture of 5-bromo-N-(2,6-dichlorophenyl)-thiophene-2-carboxamidine (3.9 g, 11 mmol) and sodium bicarbonate (1.85 g, 22 mmol) in isopropanol (55 mL) was charged with ethyl bromopyruvate (2.5 mL, 20 mmol) and then heated at 95° C. After 17 h the reaction mixture was allowed to cool to ambient temperature, filtered and the solids rinsed with EtOAc. The combined filtrates were concentrated under reduced pressure and purified by chromatography (silica, EtOAc/Hex, 15:85 to 65:35) to give the title compound (3.3 g, 67%) as a tacky yellow solid, which was used in the next step without further purification. ¹H-NMR (DCM-d$_2$): δ 7.60 (s, 1H), 7.49-7.59 (m, 3H), 6.89 (d, 1H), 6.56 (d, 1H), 4.37 (q, 2H), 1.38 (t, 3H).

EXAMPLE 5c

Preparation of 1-(2,6-dichlorophenyl)-2-[5-(3-methanesulfonyl-phenyl)-thiophen-2-yl]-1H-imidazole-4-carboxylic acid ethyl ester

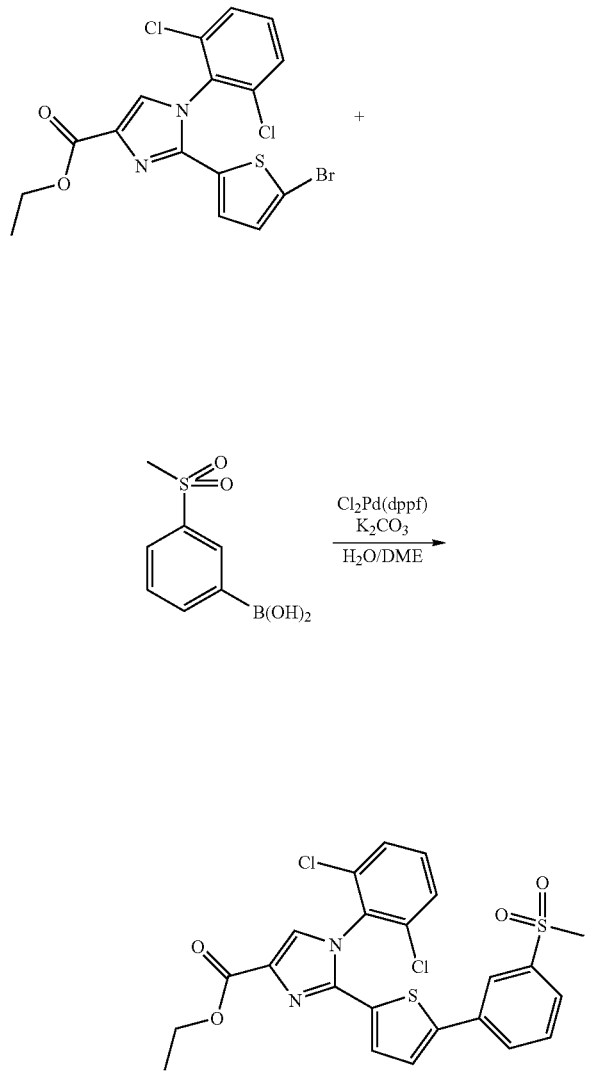

A mixture of 2-(5-bromothiophen-2-yl)-1-(2,6-dichlorophenyl)-1H-imidazole-4-carboxylic acid ethyl ester (335 mg, 0.75 mmol), 3-methanesulfonyl-phenylboronic acid (180 mg, 0.90 mmol), K$_2$CO$_3$ (0.32 g, 2.3 mmol), Cl$_2$Pd(dppf)-DCM (30 mg, 5 mol %) and H$_2$O (0.4 mL) in DME (4 mL) was sparged with Argon for 5 min and then heated at 80° C. as a sealed flask. After 2 h the reaction mixture was allowed to cool to ambient temperature, filtered (Celite™) and the filter agent rinsed with EtOAc. The combined filtrates were concentrated under reduced pressure and purified by chromatography (silica, EtOAc/Hex, 30:70 to 80:20) to give the title compound (313 mg, 80%) as a pale yellow solid, which was used in the next step without further purification. $^1$H-NMR (DCM-d$_2$): δ 8.08 (m, 1H), 7.82 (m, 2H), 7.64 (s, 1H), 7.51-7.62 (m, 4H), 724 (d, 1H), 6.72 (d, 1H), 4.38 (q, 2H), 3.05 (s, 3H), 1.40 (t, 3H).

EXAMPLE 5d

Preparation of 2-{1-(2,6-dichlorophenyl)-2-[5-(3-methanesulfonyl-phenyl)-thiophen-2-yl]-1H-imidazol-4-yl}-propan-2-ol

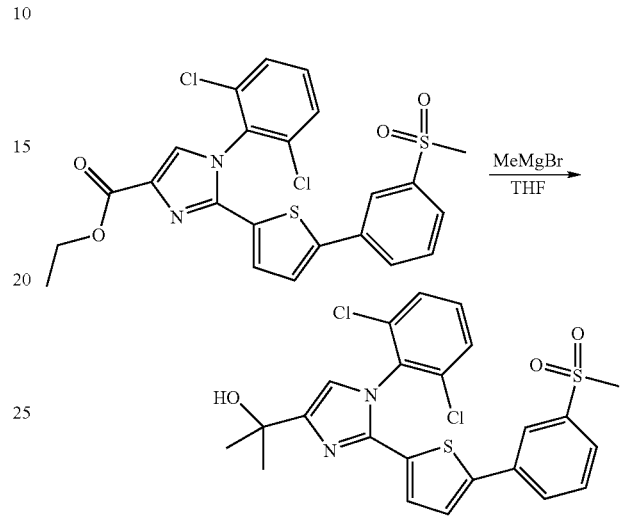

To a stirred solution of 1-(2,6-dichlorophenyl)-2-[5-(3-methanesulfonyl-phenyl)-thiophen-2-yl]-1H-imidazole-4-carboxylic acid ethyl ester (300 mg, 0.58 mmol) in THF (3 mL) at 0° C. was added a 3.0M solution of methylmagnesium bromide in Et$_2$O (0.80 mL, 2.4 mmol). After addition was completed the flask was removed from the ice-water bath and allowed to warm to ambient temperature.

At 40 min the reaction mixture was quenched by addition of satd NH$_4$Cl, extracted with EtOAc, dried (Na$_2$SO$_4$), concentrated and purified by chromatography (silica, EtOAc/Hex, 40:60 to 90:10) to give the title compound (0.17 g, 59%) as a white solid. $^1$H-NMR (DCM-d$_2$): δ 8.07 (m, 1H), 7.81 (m, 2H), 7.46-7.60 (m, 4H), 7.21 (d, 1H), 6.85 (s, 1H), 6.62 (d, 1H), 3.05 (s, 3H), 2.68 (br s, 1H), 1.61 (s, 6H); MS (ES): 507, 509 [M+H]$^+$.

In a similar manner, the following imidazoles were prepared from appropriate reagents. Optionally the order of Suzuki cross-coupling and addition of Grignard reagent was switched.

2-(1-(2,6-dichlorophenyl)-2-(5-(3-(ethylsulfonyl)phenyl) thiophen-2-yl)-1H-imidazol-4-yl)propan-2-ol; MS (ES): 521, 523 [M+H]$^+$ 2-(1-(2,6-dichlorophenyl)-2-(3-methyl-3'-(methylsulfonyl) biphenyl-4-yl)-1H-imidazol-4-yl)propan-2-ol; MS (ES): 515,517 [M+H]$^+$ 2-(1-(2,6-dichlorophenyl)-2-(3'-(ethylsulfonyl)-3-methylbiphenyl-4-yl)-1H-imidazol-4-yl)propan-2-ol; MS (ES): 529, 531 [M+H]$^+$ 2-(1-(2-isopropyl-6-methylphenyl)-2-(3-methyl-3'-(methylsulfonyl)biphenyl-4-yl)-1H-imidazol-4-yl)propan-2-ol; MS (ES): 503 [M+H]$^+$ 2-(2-(3'-(ethylsulfonyl)-3-methylbiphenyl-4-yl)-1-(2-isopropyl-6-methylphenyl)-1H-imidazol-4-yl)propan-2-ol; MS (ES): 517 [M+H]$^+$ 2-(1-(2-isopropylphenyl)-2-(3-methyl-3'-(methylsulfonyl) biphenyl-4-yl)-1H-imidazol-4-yl)propan-2-ol; MS (ES): 489 [M+H]$^+$ 2-(2-(3'-(ethylsulfonyl)-3-methylbiphenyl-4-yl)-1-(2-isopropylphenyl)-1H-imidazol-4-yl)propan-2-ol; MS (ES): 503 [M+H]+

2-(1-(2,6-dichlorophenyl)-2-(3'-(methylsulfonyl)biphenyl-4-yl)-1H-imidazol-4-yl)propan-2-ol; MS (ES): 501, 503 [M+H]+

2-(1-(2,6-dichlorophenyl)-2-(3'-(ethylsulfonyl)biphenyl-4-yl)-1H-imidazol-4-yl)propan-2-ol; MS (ES): 515, 517 [M+H]

2-(2-(3-chloro-3'-(methylsulfonyl)biphenyl-4-yl)-1-(2,6-dichlorophenyl)-1H-imidazol-4-yl)propan-2-ol; MS (ES): 535, 537 [M+H]+

2-(2-(3-chloro-3'-(ethylsulfonyl)biphenyl-4-yl)-1-(2,6-dichlorophenyl)-1H-imidazol-4-yl)propan-2-ol; MS (ES): 549, 551 [M+H]+

EXAMPLE 6

2-[5-chloro-2-(3-chloro-3'-methanesulfonyl-biphenyl-4-yl)-1-(2,6-dichlorophenyl)-1H-imidazol-4-yl]-propan-2-ol

EXAMPLE 6a

Preparation of 2-[2-(4-bromo-2-chlorophenyl)-1-(2,6-dichlorophenyl)-1H-imidazol-4-yl]-propan-2-ol

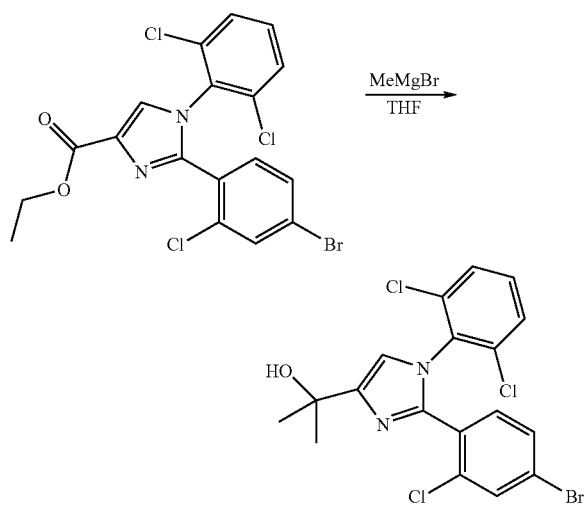

To a 3.0 M solution of MeMgBr in Et₂O (7.0 mL, 21.0 mmol) at 0° C. added slowly a solution of 2-(4-bromo-2-chlorophenyl)-1-(2,6-dichlorophenyl)-1H-imidazole-4-carboxylic acid ethyl ester (2.80 g, 5.90 mmol) in THF (30 mL, anhyd). After addition was completed the flask was removed from the ice-water bath and allowed to warm to ambient temperature. At 50 min the reaction mixture was quenched by addition of satd NH₄Cl, extracted with EtOAc, dried (Na₂SO₄), concentrated and purified by chromatography (silica, EtOAc/Hex, 15:85 to 55:45) to give the title compound (2.1 g, 77%) as a white solid. ¹H-NMR (DCM-d₂): δ 7.58 (d, 1H), 7.37-7.41 (m, 2H), 7.26-7.32 (m, 2H), 7.11 (d, 1H), 6.93 (s, 1H), 2.73 (br s, 1H), 1.61 (s, 6H).

EXAMPLE 6b

Preparation of 2-[2-(4-bromo-2-chlorophenyl)-5-chloro-1-(2,6-dichlorophenyl)-1H-imidazol-4-yl]-propan-2-ol

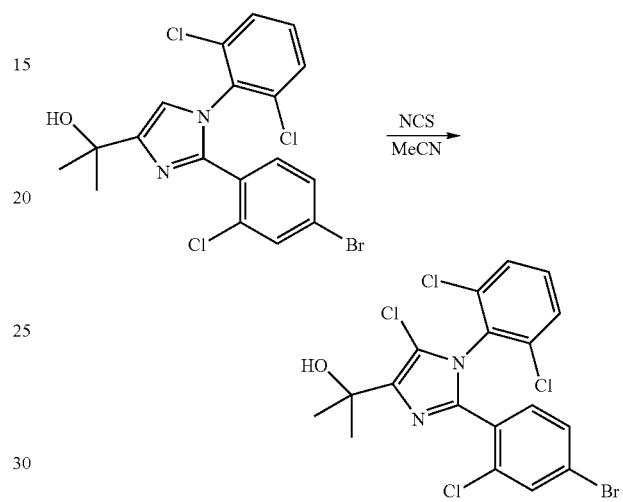

A suspension of 2-[2-(4-bromo-2-chlorophenyl)-1-(2,6-dichlorophenyl)-1H-imidazol-4-yl]-propan-2-ol (230 mg, 0.50 mmol) in MeCN (4 mL, anhyd) was charged with N-chlorosuccinimide (70 mg, 0.52 mg) and then heated at 70 C. After 22 h the reaction mixture was charged with additional N-chlorosuccinimide (67 mg, 0.50 mmol) and heated at 85 C. After 40 h (total reaction time) the reaction mixture was allowed to cool to ambient temperature, concentrated and purified by chromatography (silica, EtOAc/Hex, 0:100 to 30:70) to give the title compound (0.19 g, 77%) as a white solid. ¹H-NMR (DCM-d₂): δ 7.61 (d, 1H), 7.42-7.45 (m, 2H), 7.36 (m, 1H), 7.27 (dd, 1H), 7.10 (d, 1H), 3.33 (s, 1H), 1.65 (s, 6H).

EXAMPLE 6c

Preparation of 2-[5-chloro-2-(3-chloro-3'-methanesulfonyl-biphenyl-4-yl)-1-(2,6-dichlorophenyl)-1H-imidazol-4-yl]-propan-2-ol

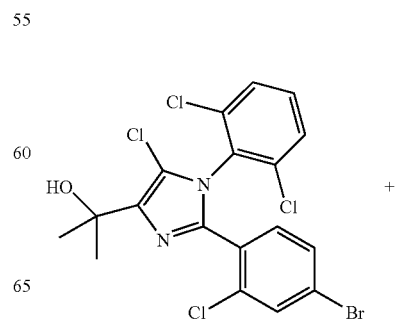
+

111

-continued

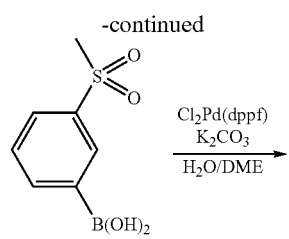

112

A mixture of 2-[2-(4-bromo-2-chlorophenyl)-5-chloro-1-(2,6-dichlorophenyl)-1H-imidazol-4-yl]-propan-2-ol (184 mg, 0.37 mmol), 3-methanesulfonyl-phenylboronic acid (90 mg, 0.45 mmol), $K_2CO_3$ (0.15 g, 1.1 mmol), $Cl_2$ Pd(dppf)-DCM (15 mg, 5 mol %) and $H_2O$ (0.2 mL) in DME (2 mL) was sparged with Argon for 5 min and then heated at 60° C. as a sealed flask. After 70 min the reaction mixture was allowed to cool to ambient temperature, filtered (Celite™) and the filter agent rinsed with EtOAc. The combined filtrates were concentrated under reduced pressure and purified by chromatography (silica, EtOAc/Hex, 20:80 to 60:40) to give the title compound (165 mg, 78%) as a white solid. $^1$H-NMR (DCM-$d_2$): δ 8.08 (m, 1H), 7.93 (m, 1H), 7.84 (m, 1H), 7.73 (d, 1H), 7.67 (m, 1H), 7.33-7.47 (m, 5H), 3.42 (br s, 1H), 3.06 (s, 3H), 1.68 (s, 6H); MS (ES): 591, 593, 595 [M+Na]$^+$.

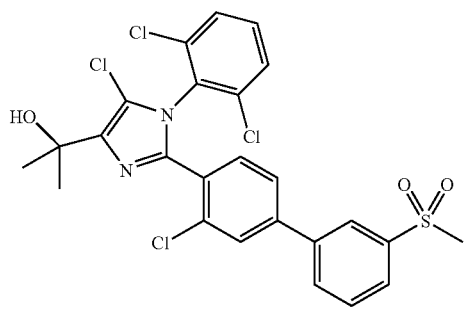

Scheme 6

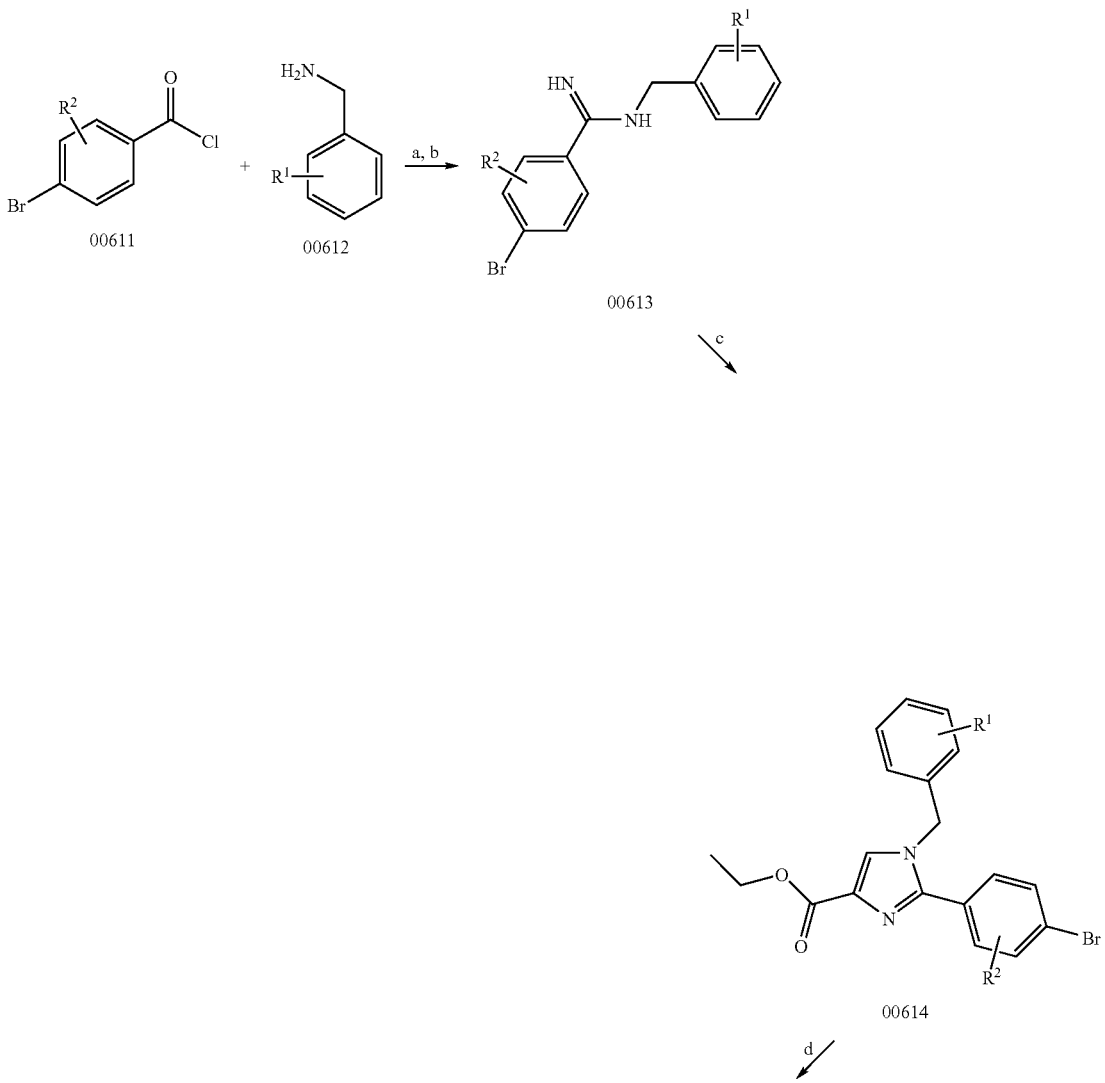

-continued

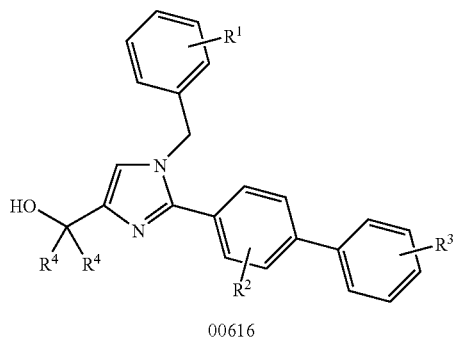

00616

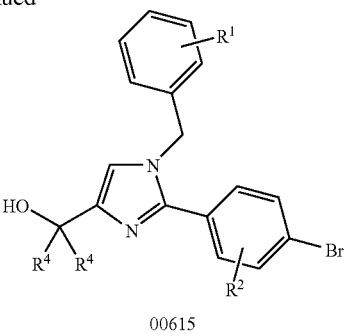

00615

(a) Et₃N, THF;
(b) SOCl₂, 90° C.; concentrate and add to NH₃/MeOH;
(c) ethyl bromopyruvate, NaHCO₃, EtOH, μW 175° C.;
(d) R⁴MgBr, THF, 0° C.-rt;
(e) ArB(OH)₂, Cl₂Pd(dppf), K₂CO₃, H₂O/DME, μW 120° C..

In general, compounds of formula 00616 can be prepared as shown in Scheme 6. First, an amide can be generated from reacting a benzoyl chloride (00611) and a benzylamine (00612) under basic conditions. The resulting amide can be treated with thionyl chloride at elevated temperature to give an imidoyl chloride, which can be converted directly to its corresponding amidine (00613) upon addition to a solution of ammonia. Amidine 00613 and ethyl bromopyruvate can react under basic conditions and at elevated temperature to yield the corresponding imidazole (00614). This intermediate ester 00614 can react with a Grignard reagent, such as an alkyl-magnesium bromide, to afford the respective carbinol (00615). Last intermediate 00615 can undergo cross-couplings reactions, such as a Suzuki-Miyaura reaction with boronic acids (esters), to yield the target imidazole 00616.

EXAMPLE 7

2-[1-(2-chlorobenzyl)-2-(3'-methanesulfonyl-biphenyl-4-yl)-1H-imidazol-4-yl]-propan-2-ol EXAMPLE 7a Preparation of 4-bromo-N-(2-chlorobenzyl)-benzamide

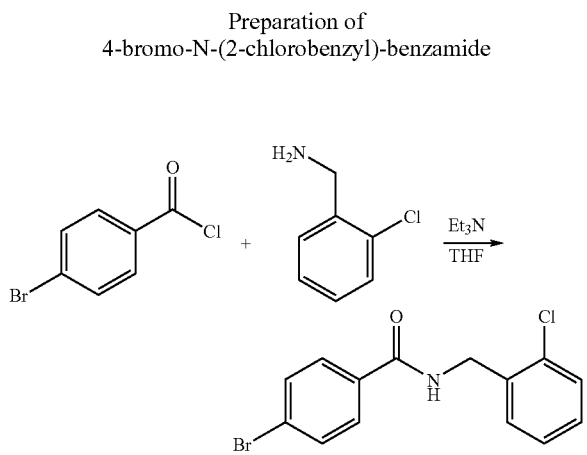

To a stirred solution of 2-chlorobenzylamine (2.42 mL, 20 mmol) in THF (80 mL, anhyd) at 0° C. added a solution of 4-bromobenzoyl chloride (4.39 g, 20 mmol) in THF (20 mL, anhyd.) and then triethylamine (2.93 mL, 21 mmol). After 12 h the resulting mixture was filtered and the solids rinsed with EtOAc. The combined filtrates were diluted with EtOAc (100 mL), washed with 1N HCl, satd NaHCO₃ and brine, then dried (anhyd Na₂SO₄) and concentrated to afford the title compound (6.36 g, 98%) as a white solid, which was used in the next step without purification. GC-MS (EI): 322, 324.

EXAMPLE 7b

Preparation of 4-bromo-N-(2-chlorobenzyl)-benzamidine

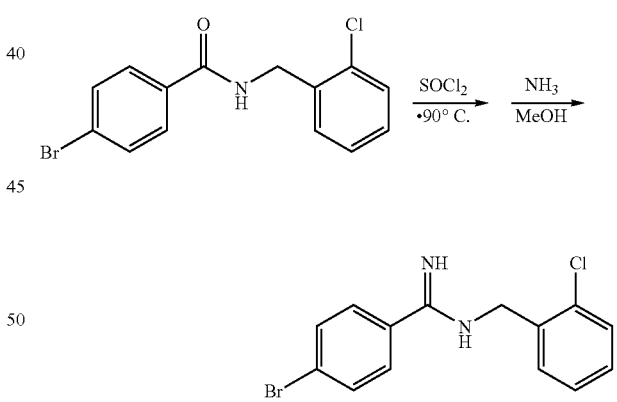

A mixture of 4-bromo-N-(2-chlorobenzyl)-benzamide (1.62 g, 5.0 mmol) and thionyl chloride (0.73 mL, 10 mmol) was heated at 90° C. After 150 min the reaction mixture was cooled and concentrated under reduced pressure. The resulting residue was diluted with toluene (10 mL, anhyd) and concentrated to give the corresponding imidoyl chloride [conversion confirmed by NMR] as a pale yellow solid. To a stirred 2M solution of NH₃ in MeOH (8 mL, 16 mmol) was added this intermediate in small portions. After 12 h the reaction mixture was added to satd NaHCO₃ and extracted with EtOAc (2×50 mL). The combined extracts were washed with brine, dried (Na₂SO₄) and concentrated under reduced pressure to afford the title compound (1.5 g, 93%), which was used in the next step without purification. GC-MS (EI): 321, 323.

EXAMPLE 7c

Preparation of 2-(4-bromophenyl)-1-(2-chlorobenzyl)-1H-imidazole-4-carboxylic acid ethyl ester

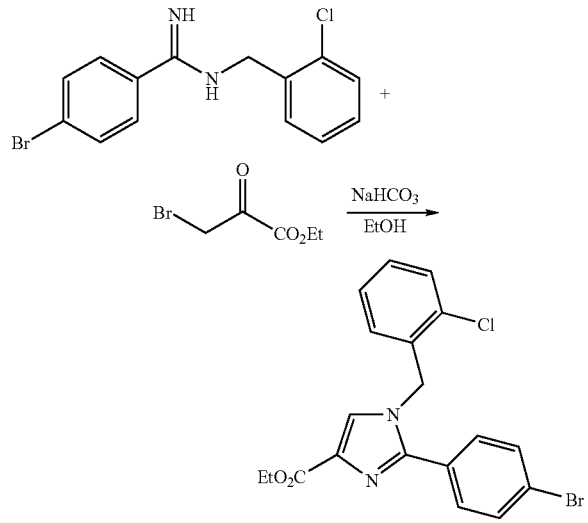

A mixture of 4-bromo-N-(2-chlorobenzyl)-benzamidine (1.4 g, 4.3 mmol), sodium bicarbonate (0.72 g, 8.6 mmol) and ethyl bromopyruvate (0.98 mL, 7.8 mmol) in EtOH (14 mL) was heated in a microwave unit (Biotage Initiator™) at 175° C. for 12 min. The resulting mixture was decanted and the solids rinsed with EtOAc. The combined filtrates were concentrated and purified by chromatography (silica, EtOAc/Hex, 0:100 to 40:60) to give the title compound (0.24 g, 13%) as a pale brown residue. $^1$H-NMR (DCM-d$_2$): δ 7.58-7.62 (m, 3H), 7.43-7.49 (m, 3H), 7.34 (m, 1H), 7.28 (m, 1H), 6.96 (d, 1H), 5.30 (s, 2H), 4.32 (q, 2H), 1.35 (t, 3H); MS (ES): 419, 421 [M+H].

EXAMPLE 7d

Preparation of 2-[2-(4-bromophenyl)-1-(2-chlorobenzyl)-1H-imidazol-4-yl]-propan-2-ol

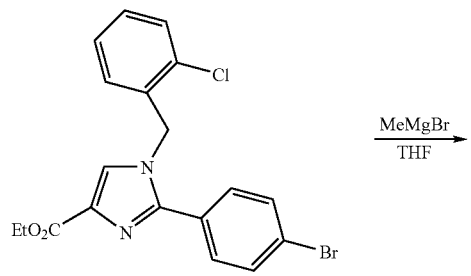

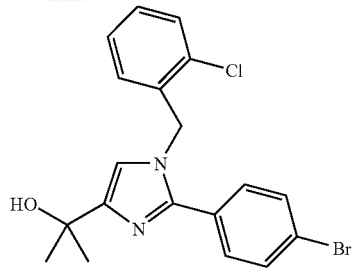

To a 3.0 M solution of MeMgBr in Et$_2$O (1.0 mL, 3.0 mmol) at 0° C. added slowly a solution of 2-(4-bromophenyl)-1-(2-chlorobenzyl)-1H-imidazole-4-carboxylic acid ethyl ester (235 mg, 0.56 mmol) in THF (3 mL, anhyd). After addition was completed the flask was removed from the ice-water bath and allowed to warm to ambient temperature. At 40 min the reaction mixture was quenched by addition of satd NH$_4$Cl, extracted with EtOAc, dried (MgSO$_4$), concentrated and purified by chromatography (silica, EtOAc/Hex, 20:80 to 60:40) to give the title compound (135 mg, 59%) as a pale amber solid. $^1$H-NMR (DCM-d$_2$): δ 7.54 (d, 2H), 7.38-7.45 (m, 3H), 7.24-7.33 (m, 2H), 6.89 (d, 1H), 6.82 (s, 1H), 5.25 (s, 2H), 2.86 (br s, 1H), 1.54 (s, 6H); MS (ES): 405, 407 [M+H]$^+$.

EXAMPLE 7e

Preparation of 2-[1-(2-chlorobenzyl)-2-(3'-methanesulfonyl-biphenyl-4-yl)-H-imidazol-4-yl]-propan-2-ol

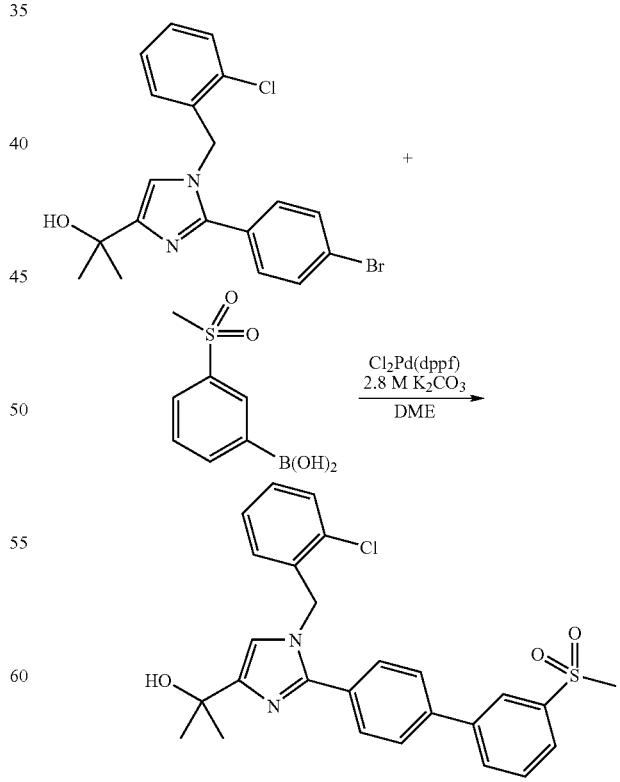

A mixture of 2-[2-(4-bromophenyl)-1-(2-chlorobenzyl)-1H-imidazol-4-yl]-propan-2-ol (130 mg, 0.32 mmol), 3-methanesulfonyl-phenylboronic acid (80 mg, 0.40 mmol), $Cl_2$ Pd(dppf)-DCM (13 mg, 5 mol %) and a 2.8M aqueous solution of $K_2CO_3$ (0.35 mL, 0.98 mmol) in DME (2 mL) was heated in a microwave unit (Biotage Initiator™) at 120° C. for 4 min. The reaction mixture was concentrated and purified by chromatography (silica, EtOAc/Hex, 45:55 to 90:10) to give the title compound (118 mg, 77%) as a white solid. $^1$H-NMR (DCM-$d_2$): δ 8.08 (m, 1H), 7.84 (dd, 2H), 7.55-7.64 (m, 5H), 7.36 (m, 1H), 7.17-7.26 (m, 2H), 6.85 (d, 1H), 6.77 (s, 1H), 5.24 (s, 21H), 3.00 (s, 3H), 2.86 (br s, 1H), 1.49 (s, 6H); MS (ES): 481 [M+H]$^+$.

In a similar manner 2-[1-(2,3-dichlorobenzyl)-2-(3'-methanesulfonyl-biphenyl-4-yl)-1H-imidazol-4-yl]-propan-2-ol was prepared by replacing 2-chlorobenzylamine with 2,3-dichlorobenzylamine. MS (ES): 515, 517 [M+H]$^+$.

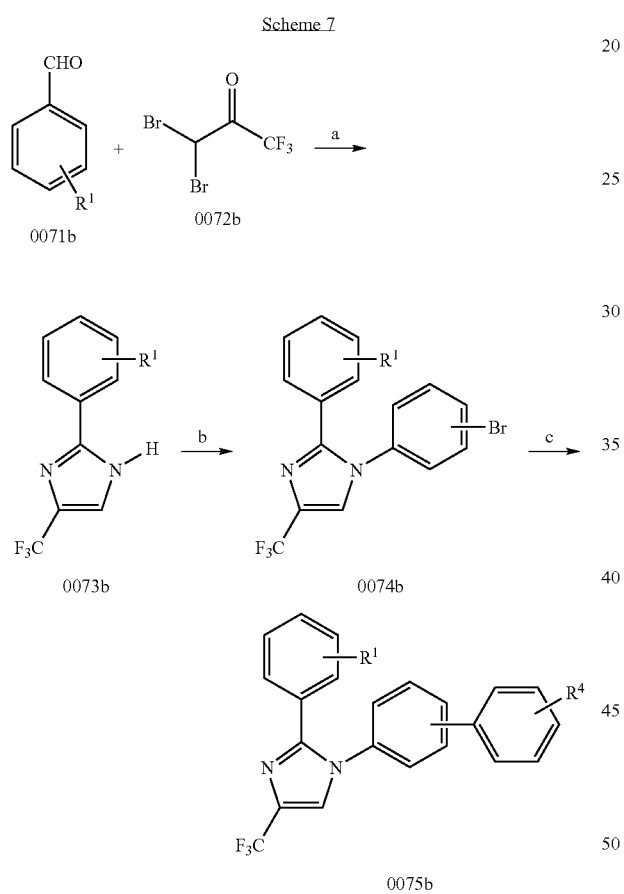

Scheme 7

Reaction and conditions: (a) NaOAc, NH$_4$OH, MeOH; (b) ArB(OH)$_2$, [Cu(OH)·TMEDA]$_2$Cl$_2$, DCM; (c) ArB(OH)$_2$, K$_2$CO$_3$, PdCl$_2$(dppf), DME/H$_2$O, 80° C.

In general, compounds of formula (0075b) are prepared by first reacting 3,3-dihaloketone such as 3,3-dibromo-1,1,1-trifluoromethylacetone with aqueous sodium acetate to generate a glyoxal which react in situ with aldehyde of formula (0071b) and ammonia to yield an imidazole of formula (0073b). Conversion of compounds of formula (0073b) to compounds of formula (0074b) is then accomplished by means of N-arylation such as a Buchwald reaction or Cu(II) catalyzed coupling with boronic acid regents. In a palladium mediated coupling reaction, for example a Suzuki reaction, compounds of formula (0074b) are then reacted with a boronate or boronic acid to give compounds of formula (0075b) after standard isolation procedures.

EXAMPLE 8

2-(2-Chloro-phenyl)-1-(3'-methanesulfonyl-biphenyl-4-yl)-4-trifluoromethyl-1H-imidazole EXAMPLE 8a Preparation of 2-(2-Chloro-phenyl)-4-trifluoromethyl-1H-imidazole

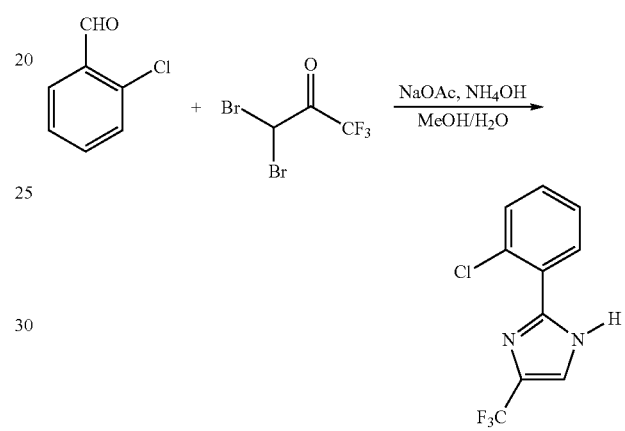

3,3-Dibromo-1,1,1-trifluoroacetone (6.75 g, 25 mmol) was added to a solution of NaOAc (4.11 g, 50 mmol) in 15 mL water, and the mixture was heated at 100° C. for 60 min. After cooling to room temperature, 2-chlorobenzaldehyde (2.8 g, 20 mmol) dissolved in MeOH (45 mL) was added, followed by conc. NH$_4$ OH (10 mL). The mixture was stirred at room temperature overnight. After methanol was removed by evaporation, water was added. The precipitate was collected by filtration and washed with water, and dried under vacuum to give a light yellow solid (4.7 g, 76%). $^1$H-NMR (400 MHz, CDCl$_3$): δ 7.37 (dd, 1H), 7.40 (dd, 1H), 7.46 (dd, 1H), 7.50 (m, 1H), 8.33 (dd, 1H).

EXAMPLE 8b

Preparation of 1-(4-Bromo-phenyl)-2-(2-chloro-phenyl)-4-trifluoromethyl-1H-imidazole

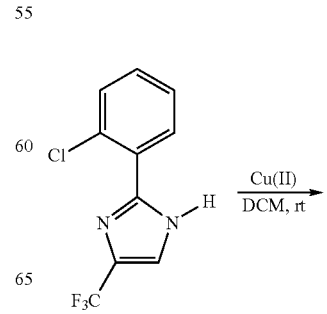

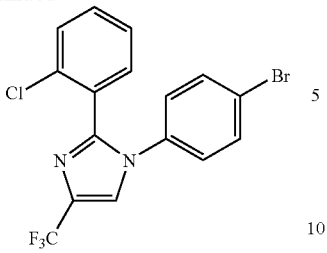

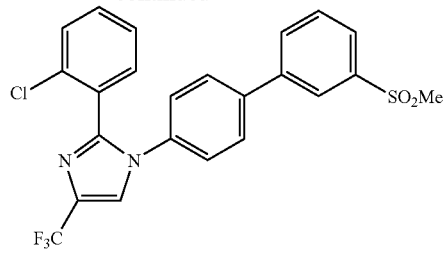

2-(2-Chloro-phenyl)-4-trifluoromethyl-1H-imidazole (370 mg, 1.5 mmol), 4-bromo-phenylboronic acid (600 mg, 3 mmol), and [Cu(OH).TMEDA]$_2$Cl$_2$ (140 mg, 0.3 mmol) were mixed with 6 mL dry dichloromethane, and stirred at room temperature under atmosphere of dioxygen for 2 days. The reaction mixture was diluted with dichloromethane and filtered through celite. The filtrate was concentrated under vacuum, and the residue was purified by chromatography on silica gel (Hexane/EtOAc 8/2) to give a solid (151 mg, 25% yield). $^1$H-NMR (400 MHz, CDCl$_3$): δ 7.02 (d, 2H), 7.34 (m, 3H), 7.47 (d, 2H), 7.53 (dd, 1H), 7.56 (dd, 1H).

EXAMPLE 8c

Preparation of 2-(2-Chloro-phenyl)-1-(3'-methane-sulfonyl-biphenyl-4-yl)-4-fluoromethyl-1H-imidazole

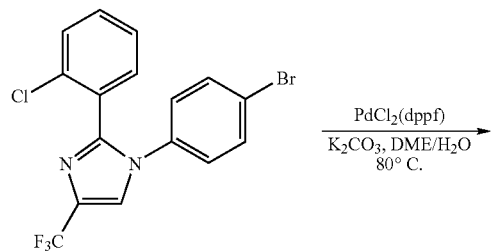

1-(4-Bromo-phenyl)-2-(2-chloro-phenyl)-4-trifluoromethyl-1H-imidazole (100 mg, 0.25 mmol), (3-methylsulfonyl)phenylboronic acid (100 mg, 0.5 mmol), potassium carbonate (155 mg, 1.13 mmol), and PdCl$_2$ (dppf).CH$_2$Cl$_2$ (20 mg, 0.025 mmol) were mixed with 3 mL 9:1 DME/H$_2$O (v/v), then heated at 80° C. overnight. All solvent was removed in vacuo. The residue was purified by chromatography on silica gel (Hexane/EtOAc, 6/4), then by reverse phase HPLC (30% acetonitrile in water) to give a white solid (55 mg, 46% yield). $^1$H-NMR (400 MHz, CDCl$_3$): δ 3.10 (s, 3H), 7.26 (m, 2H), 7.37 (m, 3H), 7.62 (m, 5H), 7.84 (m, 1H), 7.94 (m, 1H), 8.12 (t, 1H).

In similar manner, all the following compounds were prepared using appropriate aldehydes and boronic acid reagents.
2-(2-chlorophenyl)-1-[3'-(methylsulfonyl)biphenyl-4-yl]-4-(trifluoromethyl) 1H-imidazole; MS (ES): 477.0 [M+H]$^+$;
4'-[2-(2-chlorophenyl)-4-(trifluoromethyl)-1H-imidazol-1-yl]biphenyl-3-sulfonamide; MS (ES): 478.0 [M+H]$^+$;
1-(4-bromophenyl)-4-(trifluoromethyl)-2-[2-(trifluoromethyl)phenyl]-1H-imidazole; MS (ES): 435.0 [M+H]$^+$;
1-[3'-(methylsulfonyl)biphenyl-4-yl]-4-(trifluoromethyl)-2-[2-(trifluoromethyl)phenyl]-1H-imidazole; MS (ES): 511.3 [M+H]$^+$;
4'-{4-(trifluoromethyl)-2-[2-(trifluoromethyl)phenyl]-1H-imidazol-1-yl}biphenyl-3-sulfonamide; MS (ES): 512.3 [M+H]$^+$;

The following compounds were prepared in similar manner as described in Scheme 7, except Cu (II) catalyzed coupling reaction to make compounds of formula (0074b) was replaced by base, like sodium hydride, catalyzed replacement reaction with aryl bromides bearing appropriate leaving groups, such as 2,5-dibromopyridine.
5-[3-(methylsulfonyl)phenyl]-2-{4-(trifluoromethyl)-2-[2-(trifluoromethyl)phenyl]-1H-imidazol-1-yl}pyridine; MS (ES): 512.3 [M+H]$^+$;
2-[2-(2-chlorophenyl)-4-(trifluoromethyl)-1H-imidazol-1-yl]-5-[3-(methylsulfonyl)phenyl]pyridine; MS (ES): 478.0 [M+H]$^+$;

Scheme 8

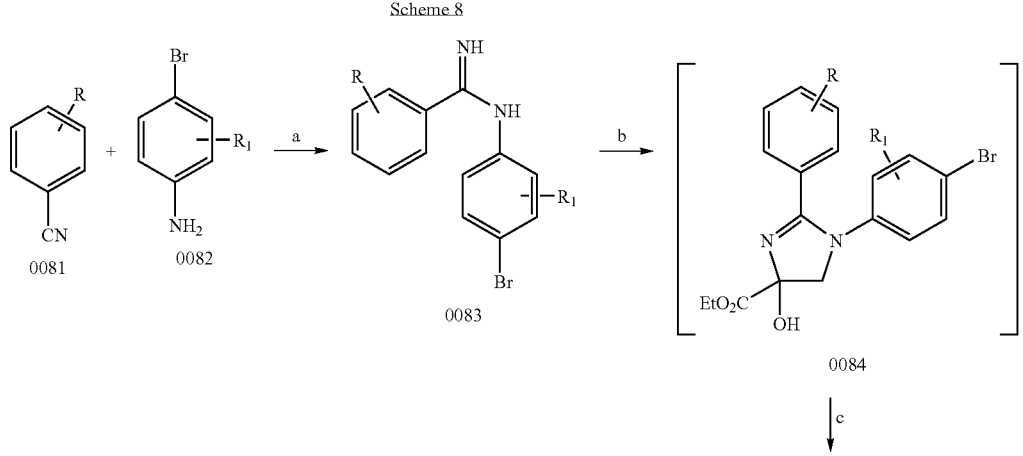

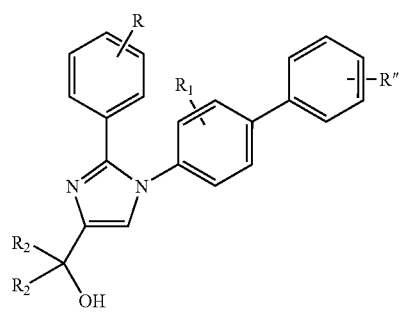

0087

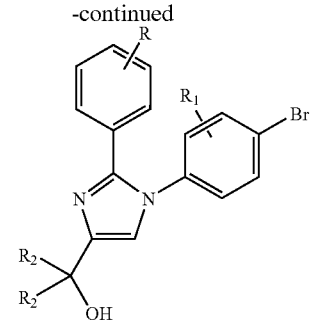

0086

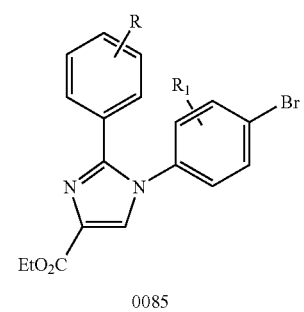

0085

(a) Method A: Me₃Al, Toluene, 0° C.-80° C.; Method B: NaHMDS, THF; 0° C.-rt; (b) Ethyl bromopyruvate, NaHCO₃, 2-PrOH, 80° C.; (c) NaHCO₃/2-PrOH or HOAc/2-PrOH, reflux; (d) R₂MgBr, THF, 0° C.-rt; (e) ArB(OH)₂, K₂CO₃, PdCl₂(dppf), DME/H₂O, 80° C.

In general, compounds of formula (0087) are prepared by first reacting aniline of formula (0082) with aryl nitriles (0081), in the presence of either Lewis Acid (Method A) or base (Method B), to give compounds of formula (0083) after standard isolation procedures. In a subsequent step, exposure of amidine (0083) to haloester, such as Ethyl α-bromopyruvate, under basic condition at elevated temperature provides intermediate 1H-imidazol-4-ol of formula (0084), which can be converted to compounds of formula (0085) in situ, or by means of acid catalyzed dehydration. Compounds of formula (0085) are then subjected to functionality transformation, such as from ester to carbinol. In a palladium mediated coupling reaction, for example Suzuki reactions, compounds of formula (0086) are then reacted with a diboronate or boronic acid reagent to give compounds of formula (0087) after standard isolation procedures.

EXAMPLE 9

2-[2-(2,6-Difluoro-phenyl)-1-(3'-methanesulfonyl-biphenyl-4-yl)-1H-imidazo-4-yl]-propan-2-ol

EXAMPLE 9a

Method A

Preparation of N-(4-bromophenyl)-2,6-difluorobenzimidamide

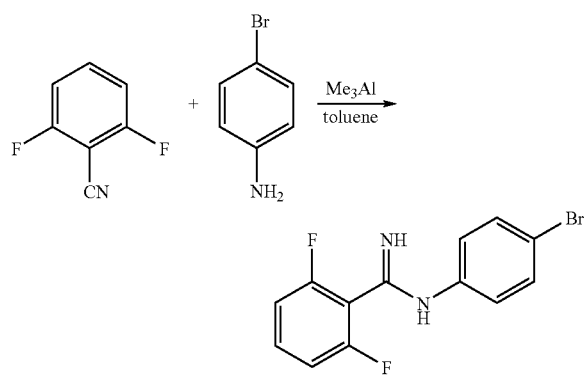

N-(4-Bromo-phenyl)-2,6-difluoro-benzamidine: 4-bromoaniline (1.72 g, 10 mmol) was placed into a three-neck reactor, and the reactor was flushed with argon for 20 min. 50 mL anhydrous toluene was added. After cooling to 0° C., trimethylaluminum (7.5 mL, 2.0M solution in toluene, 15 mmol) was added slowly to keep the inner temperature below 18° C. After addition, the reaction mixture was warmed to room temperature and then stirred for additional 2 hrs. A solution of 2,6-difluorobenzonitirle (2.78 g, 20 mmol) in 50 mL anhydrous toluene was added, and the reaction mixture was heated to 80° C. After 18 hrs, the reaction mixture was cooled to room temperature and poured over a slurry of silica gel in CHCl₃/MeOH (4/1, V/V). After being stirring for 20 min, the mixture was filtered and the residue was washed with a mixture of CHCl₃/MeOH (4/1, V/V). The combined filtrates were concentrated in vacuo, and the resulting solid was stirred with a solution of Hexane/Ether (3/1, V/V). The intermediate was filtered and washed with additional Hexane/Ether (3/1, V/V) to give a white solid (2.4 g, 79% yield), which was used directly for the next step without further purification.

EXAMPLE 9aa

Method B

Preparation of N-(4-bromophenyl)-2-chloro-6-methylbenzimidamide

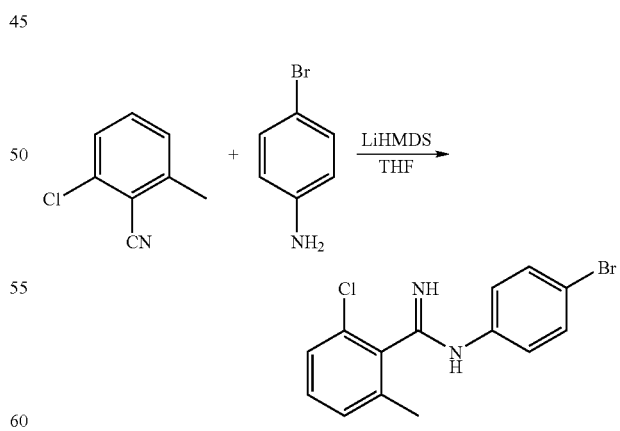

N-(4-Bromo-phenyl)-2-chloro-6-methyl-benzamidine: Under N₂ atmosphere at room temperature to a solution of lithium bis(trimethylsilyl)amide (9.7 mL, 1.0 M solution in THF, 9.7 mmol) was added a solution of 4-bromoaniline (1.67 g, 9.7 mmol) in 10 mL anhydrous THF. After the mixture was stirred at ambient temperature for 40 min, a solution of 2-chloro-6-methylbezonitrile (1.55 mg, 10.2 mmol) in 10 mL anhydrous THF was added. The reaction mixture was stirred at room temperature overnight, and then poured into 300 mL ice water. The orange precipitate was collected by filtration, washed with hexane and air dried to give a light orange solid (2.19 g, 66% yield), which was used directly for the next step without further purification.

EXAMPLE 9b

Preparation of ethyl 1-(4-bromophenyl)-2-(2,6-difluorophenyl)-1H-imidazole-4-carboxylate

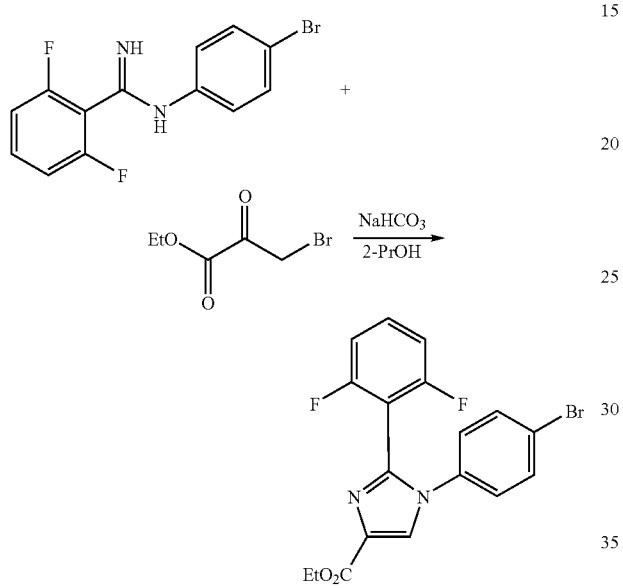

To a mixture of N-(4-Bromo-phenyl)-2,6-difluorobenzamidine (2.4 g, 7.7 mmol) and sodium bicarbonate (1.3 g, 15.4 mmol) in 40 mL 2-proponal was added ethyl α-bromopyruvate (3.34 g, 15.4 mmol, 90% tech). The mixture was heated at 80-85° C. overnight. After cooling to room temperature, the solvent was removed and the residue was redissolved into dichloromethane. The precipitate was filtered out, and the filtrate was concentrated down. The crude product was purified by column chromatography on silica gel (30→50% EtOAc/Hexane) to give a yellow solid (1.82 g, 58% yield).

EXAMPLE 9c

Preparation of 2-(1-(4-bromophenyl)-2-(2,6-difluorophenyl)-1H-imidazol-4-yl)propan-2-ol

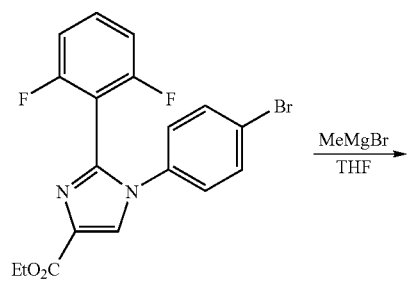

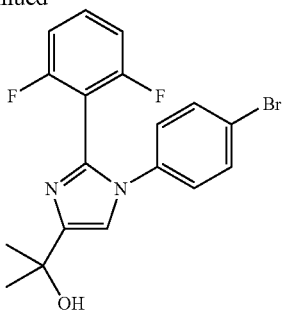

Methylmagnesium bromide (11.2 ml, 15.7 mmol, 1.4M in toluene/THF 75:25) was placed into a three-neck flask. Under nitrogen at 0° C. to it was added a solution of 1-(4-Bromophenyl)-2-(2,6-difluoro-phenyl)-1H-imidazole-4-carboxylic acid ethyl ester in 15 mL THF. After the addition, the ice bath was removed and the reaction mixture was stirred at room temperature for 2.5 hrs. The reaction was quenched with sat. Ammonium chloride. Two layers were separated, and the aqueous layer was extracted three times with ethyl acetate. The combined organic layers were washed with brine, dried over Na₂SO₄, and concentrated in vacuo. The crude product was purified by column chromatography on silica gel (30→50% EtOAc/Hexane) to give an off-white solid (0.9 g, 51% yield).

EXAMPLE 9d

Preparation of 2-(2-(2,6-difluorophenyl)-1-(3'-(methylsulfonyl)biphenyl-4-yl)-1H-imidazo-4-yl)propan-2-ol

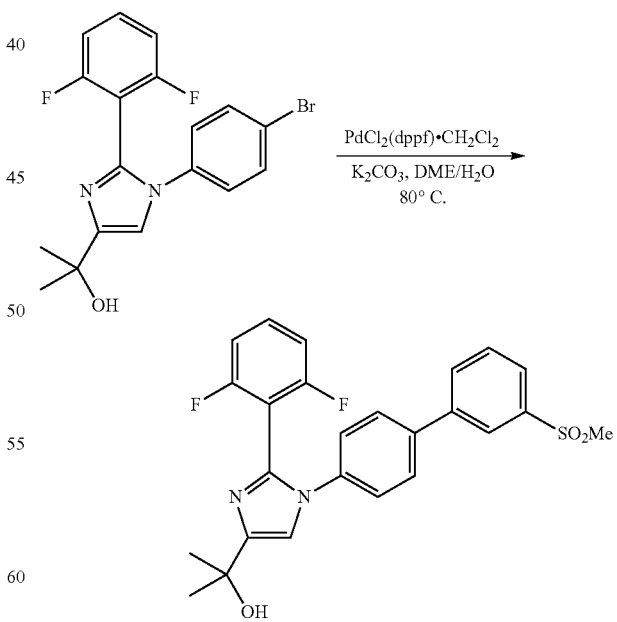

2-[1-(4-Bromo-phenyl)-2-(2,6-difluoro-phenyl)-1H-imidazol-4-yl]-propan-2-ol (250 mg, 0.64 mmol), (3-methylsulfonylphenyl)boronic acid (254 mg, 1.27 mmol), and potassium carbonate (398 mg, 2.88 mmol) were placed into a flask.

6 mL of mixture of DME (1,2-dimethoxyethane) and water (9:1, V/V) was added. The flask was flushed with argon for 15 min, and then Pd catalyst (Dichloro[1,1'-bis (diphenylphosphino)ferrocene]palladium (II) dichloromethane adduct, 52 mg, 0.064 mmol) was added.

The mixture was heated to 80° C. overnight. After cooling to room temperature, all solvent was removed. The crude product was purified by column chromatography on silica gel (45→99% EtOAc/Hexane) to give an off-white solid (230 mg, 77% yield). 1H-NMR (400 MHz, CDCl$_3$): δ 1.70 (s, 6H), 2.71 (s, 1H), 3.09 (s, 3H), 6.92-6.88 (m, 2H), 7.21 (s, 1H), 7.39-7.28 (m, 3H), 7.59-7.57 (m, 2H), 7.66 (t, 1H, J=7.8), 7.86-7.83 (M, 1H), 7.95-7.92 (m, 1H), 8.12 (t, 1H, J=1.7). MS (ES): 491.4 [M+Na]$^+$ In similar manner, all the following compounds were made using either Method A (Example 9a) or Method B (Example 9aa) to prepare amidines. The order of last two steps of Grignard addition and Suzuki coupling were switched in some cases. The boronic acid or boronate reagents for Suzuki coupling, if not commercially available, were made using standard techniques that are readily apparent to one skilled in the art.

ethyl 1-[3'-(methylsulfonyl)biphenyl-4-yl]-2-[2-(trifluoromethyl)phenyl]-1H-imidazole-4-carboxylate; MS (ES): 515.3 [M+H]$^+$;

2-{1-[3'-(methylsulfonyl)biphenyl-4-yl]-2-[2-(trifluoromethyl)phenyl]-1H-imidazol-4-yl}propan-2-ol; MS (ES): 501.4 [M+H]$^+$, 523.3[M+Na]$^+$;

5-{3-[(1-methylethyl)sulfonyl]phenyl}-2-{4-(trifluoromethyl)-2-[2-(trifluoromethyl)phenyl]-1H-imidazol-1-yl}pyridine; MS (ES): 540.3 [M+H]$^+$;

1-{3'-[(1-methylethyl)sulfonyl]biphenyl-4-yl}-4-(trifluoromethyl)-2-[2-(trifluoromethyl)phenyl]-1H-imidazole; MS (ES): 539.3 [M+H]$^+$;

N-(4'-{4-(trifluoromethyl)-2-[2-(trifluoromethyl)phenyl]-1H-imidazol-1-yl}biphenyl-3-yl)methanesulfonamide; MS (ES): 526.5 [M+H]$^+$;

ethyl 1-[3'-(methylsulfonyl)biphenyl-4-yl]-2-phenyl-1H-imidazole-4-carboxylate; MS (ES): 447.3 [M+H]$^+$;

2-{1-[3'-(methylsulfonyl)biphenyl-4-yl]-2-phenyl-1H-imidazol-4-yl}propan-2-ol;

2-{2-(2-chlorophenyl)-1-[3'-(methylsulfonyl)biphenyl-4-yl]-1H-imidazol-4-yl}propan-2-ol; MS (ES): 467.4 [M+H]$^+$;

2-{2-(2-fluorophenyl)-1-[3'-(methylsulfonyl)biphenyl-4-yl]-1H-imidazol-4-yl}propan-2-ol; MS (ES): 451.1 [M+H]$^+$;

1-{2-(2-fluorophenyl)-1-[3'-(methylsulfonyl)biphenyl-4-yl]-1H-imidazol-4-yl}ethanone; MS (ES): 457.1 [M+Na]$^+$;

2-{2-(4-fluorophenyl)-1-[3'-(methylsulfonyl)biphenyl-4-yl]-1H-imidazol-4-yl}propan-2-ol; MS (ES): 451.3 [M+H]$^+$;

2-{2-(2-chloro-6-methylphenyl)-1-[3'-(methylsulfonyl)biphenyl-4-yl]-1H-imidazol-4-yl}propan-2-ol; MS (ES): 481.1 [M+H]$^+$;

2-{1-[4'-(methylsulfonyl)biphenyl-4-yl]-2-[2-(trifluoromethyl)phenyl]-1H-imidazol-4-yl}propan-2-ol; MS (ES): 501.5 [M+H]$^+$;

2-{1-[3'-(ethylsulfonyl)biphenyl-4-yl]-2-[2-(trifluoromethyl)phenyl]-1H-imidazol-4-yl}propan-2-ol; MS (ES): 515.5 [M+H]$^+$;

2-{1-[3'-(methylsulfonyl)biphenyl-3-yl]-2-[2-(trifluoromethyl)phenyl]-1H-imidazol-4-yl}propan-2-ol; MS (ES): 501.4 [M+H]$^+$;

2-{1-[4'-(methylsulfonyl)biphenyl-3-yl]-2-[2-(trifluoromethyl)phenyl]-1H-imidazol-4-yl}propan-2-ol; MS (ES): 501.4 [M+H]$^+$;

2-{2-(2,6-difluorophenyl)-1-[3'-(methylsulfonyl)biphenyl-4-yl]-1H-imidazol-4-yl}propan-2-ol; MS (ES): 491.4 [M+Na]$^+$;

2-(1-{3'-[(1-methylethyl)sulfonyl]biphenyl-4-yl}-2-[2-(trifluoromethyl)phenyl]-1H-imidazol-4-yl)propan-2-ol; MS (ES): 529.3 [M+H]$^+$;

2-(1-{3'-[(1-methylethyl)sulfonyl]biphenyl-3-yl}-2-[2-(trifluoromethyl)phenyl]-1H-imidazol-4-yl)propan-2-ol; MS (ES): 529.3 [M+H]$^+$;

2-{2-(2-chlorophenyl)-1-[3'-(ethylsulfonyl)biphenyl-4-yl]-1H-imidazol-4-yl}propan-2-ol; MS (ES): 481.3 [M+H]$^+$;

2-{2-(2-chloro-6-fluorophenyl)-1-[3'-(methylsulfonyl)biphenyl-4-yl]-1H-imidazol-4-yl}propan-2-ol; MS (ES): 485.3 [M+H]$^+$;

2-{2-(2,6-difluorophenyl)-1-[3'-(ethylsulfonyl)biphenyl-4-yl]-1H-imidazol-4-yl}propan-2-ol; MS (§ES): 483.4 [M+H];

2-(1-{5-[3-(methylsulfonyl)phenyl]pyridin-2-yl}-2-[2-(trifluoromethyl)phenyl]-1H-imidazol-4-yl)propan-2-ol; MS (ES): 502.5 [M+H]$^+$;

2-(1-{6-[3-(methylsulfonyl)phenyl]pyridin-3-yl}-2-[2-(trifluoromethyl)phenyl]-1H-imidazol-4-yl)propan-2-ol; MS (ES): 502.3 [M+H]$^+$;

2-{2-(2,6-dichlorophenyl)-1-[3'-(methylsulfonyl)biphenyl-4-yl]-1H-imidazo-4-yl}propan-2-ol; MS (ES): 523.3 [M+Na]$^+$;

2-{2-[2-fluoro-6-(trifluoromethyl)phenyl]-1-[3'-(methylsulfonyl)biphenyl-4-yl]-1H-imidazol-4-yl}propan-2-ol; MS (ES): 541.3 [M+Na]$^+$;

2-{2-(2-methylphenyl)-1-[3'-(methylsulfonyl)biphenyl-4-yl]-1H-imidazol-4-yl}propan-2-o; MS (ES): 447.0 [M+H]$^+$;

2-(1-[3'-(methylsulfonyl)biphenyl-4-yl]-2-{2-[(trifluoromethyl)oxy]phenyl}-1H-imidazol-4-yl) propan-2-ol; MS (§ES): 517.3 [M+H]$^+$, 539.3 [M+Na]$^+$;

2-{2-[2-(dimethylamino)-6-fluorophenyl]-1-[3'-(methylsulfonyl)biphenyl-4-yl]-1H-imidazol-4-yl}propan-2-ol; MS (§ES): 516.3 [M+Na]$^+$;

2-{2-(2,6-dichlorophenyl)-1-[3'-(ethylsulfonyl)biphenyl-4-yl]-1H-imidazol-4-yl}propan-2-ol; MS (ES): 515.2 [M+H]$^+$;

2-{2-(2-cloro-6-fluorophenyl)-1-[3'-(ethylsulfonyl)biphenyl-4-yl]-1H-imidazol-4-yl}propan-2-ol; MS (ES): 499.5 I[M+H]$^+$, 521.3 [M+Na]$^+$;

2-{2-(2,6-dichlorophenyl)-1-[4'-(hydroxymethyl)-3'-(methylsulfonyl)biphenyl-4-yl]-1H-imidazo-4-yl}propan-2-ol; MS (ES): 531.1, 533.3 [M+H]$^+$;

2-{2-(2-chloro-6-fluorophenyl)-1-[4'-(hydroxymethyl)-3'-(methylsulfonyl)biphenyl-4-yl]-1H-imidazol-4-yl}propan-2-ol; MS (ES): 515.7, 517.3 [M+H]$^+$;

2-(2-(3-chloro-3'-(methylsulfonyl)biphenyl-2-yl)-1-(3'-(methylsulfonyl)biphenyl-4-yl)-1H-imidazol-4-yl)propan-2-ol; MS (ES): 621.5 [M+H]$^+$.

2-{2-(2,3-dichlorophenyl)-1-[3'-(hydroxymethyl)biphenyl-4-yl]-1H-imidazol-4-yl}propan-2-ol; MS (ES): 453 [M+H]$^+$.

2-{2-(2,3-dichlorophenyl)-1-[4-(hydroxymethyl)biphenyl-4-yl]-1H-imidazo-4-yl}propan-2-o; MS (ES): 453 [M+H]$^+$.

2-{1-[3-methyl-3'-(methylsulfonyl)biphenyl-4-yl]-2-(3-thienyl)-1H-imidazol-4-yl}propan-2-ol; MS (ES): 453 [M+H]$^+$.

2-{1-[3-chloro-3'-(ethylsulfonyl)biphenyl-4-yl]-2-(2-chloro-6-fluorophenyl)-1H-imidazol-4-yl}propan-2-ol; MS (ES): 535 [M+H]$^+$.

2-{1-[3-chloro-3'-(methylsulfonyl)biphenyl-4-yl]-2-(2,6-dichlorophenyl)-1H-imidazol-4-yl}propan-2-ol; MS (ES): 537 [M+H]+.

2-{1-[3'-(ethylsulfonyl)-3-methylbiphenyl-4-yl]-2-isoquinolin-5-yl-1H-imidazol-4-yl}propan-2-ol; MS (ES): 512 [M+H]+.

2-{2-isoquinolin-5-yl-1-[3-methyl-3'-(methylsulfonyl)biphenyl-4-yl]-1H-imidazol-4-yl}propan-2-ol; MS (ES): 498 [M+H]+.

2-{2-(1,5-dimethyl-1H-pyrrol-2-yl)-1-[3-methyl-3'-(methylsulfonyl)biphenyl-4-yl]-1H-imidazol-4-yl}propan-2-ol; MS (ES): 464 [M+H]+.

2-{1-[3-methyl-3'-(methylsulfonyl)biphenyl-4-yl]-2-(2-thienyl)-1H-imidazol-4-yl}propan-2-ol; MS (ES): 453 [M+H]+.

2-{1-[3-chloro-3'-(ethylsulfonyl)biphenyl-4-yl]-2-isoquinolin-1-yl-1H-imidazol-4-yl}propan-2-ol; MS (ES): 529 [M+H]+.

2-{1-[3-chloro-3'-(methylsulfonyl)biphenyl-4-yl]-2-isoquinolin-1-yl-1H-imidazol-4-yl}propan-2-ol; MS (ES): 518 [M+H]+.

2-{2-(3-chloro-2-methylphenyl)-1-[3'-(ethylsulfonyl)-3-fluorobiphenyl-4-yl]-1H-imidazol-4-yl}propan-2-ol; MS (ES): 513 [M+H]+.

2-{2-(3-chloro-2-methyl-phenyl)-1-[3-fluoro-3'-(methylsulfonyl)biphenyl-4-yl]-1H-imidazo-4-yl}propan-2-ol; MS (ES): 499 [M+H]+.

2-{2-(3-chloro-2-methylphenyl)-1-[3'-(ethylsulfonyl)-3-methylbiphenyl-4-yl]-1H-imidazol-4-yl}propan-2-ol; MS (ES): 509 [M+H]+.

2-{2-(3-chloro-2-methylphenyl)-1-[3-methyl-3'-(methylsulfonyl)biphenyl-4-yl]-1H-imidazol-4-yl}propan-2-ol; MS (ES): 495 [M+H]+.

2-{1-[3'-(methylsulfonyl)biphenyl-4-yl]-2-[2-(trifluoromethyl)phenyl]-1H-imidazol-4-yl}propan-2-ol; MS (ES): 501 [M+H]+.

2-{1-[3-chloro-3'-(ethylsulfonyl)biphenyl-4-yl]-2-naphthalen-1-yl-1H-imidazol-4-yl}propan-2-ol; MS (ES): 531 [M+H]+.

2-{1-[3'-(ethylsulfonyl)-3-methylbiphenyl-4-yl]-2-[2-(trifluoromethyl)phenyl]-1H-imidazol-4-yl}propan-2-ol; MS (ES): 529 [M+H]+.

2-{1-[3-chloro-3-yl-(ethylsulfonyl)biphenyl-4-yl]-2-(3-chloro-2-methylphenyl)-1H-imidazol-4-yl}propan-2-ol; MS (ES): 529 [M+H]+.

2-{2-(3-chloro-2-methylphenyl)-1-[3-chloro-3'-(methylsulfonyl)biphenyl-4-yl]-1H-imidazol-4-yl}propan-2-ol; MS (ES): 515 [M+H]+.

2-{1-[3-methyl-3'-(methylsulfonyl)biphenyl-4 yl]2-[2-(trifluoromethyl)phenyl]-1H-imidazol-4-yl}propan-2-ol; MS (ES): 515 [M+H]+.

2-{1-[3-chloro-3'-(methylsulfonyl)biphenyl-4-yl]-2-naphthalen-1-yl-1H-imidazol-4-yl}propan-2-ol; MS (ES): 517 [M+H]+.

2-{1-[3-chloro-3'-(ethylsulfonyl)biphenyl-4-yl]-2-(2-chlorophenyl)-1H-imidazol-4-yl}propan-2-ol; MS (ES): 515 [M+H]+.

2-{1-[3-chloro-3'-(ethylsulfonyl)biphenyl-4-yl]-2-[2-(trifluoromethyl)phenyl]-1H-imidazol-4-yl}propan-2-ol; MS (ES): 549 [M+H]+.

2-{1-[3-chloro-3'-(methylsulfonyl)biphenyl-4-yl]-2-[2-(trifluoromethyl)phenyl]-1H-imidazol-4-yl}propan-2-ol; MS (ES): 535 [M+H]+.

2-{1-[3'-(ethylsulfonyl)-2-fluorobiphenyl-4-yl]-2-[2-(trifluoromethyl)phenyl]-1H-imidazol-4-yl}propan-2-ol; MS (ES): 533 [M+H]+.

2-{1-[2-fluoro-3'-(methylsulfonyl)biphenyl-4-yl]-2-[2-(trifluoromethyl)phenyl]-1H-imidazol-4-yl}propan-2-ol; MS (ES): 519 [M+H]+.

2-{1-[3'-(ethylsulfonyl)-3-fluorobiphenyl-4-yl]-2-[2-(trifluoromethyl)phenyl]-1H-imidazol-4-yl}propan-2-ol; MS (ES): 533 [M+H]+.

2-{1-[3-fluoro-3'-(methylsulfonyl)biphenyl-4-yl]-2-[2-(trifluoromethyl)phenyl]-1H-imidazol-4-yl}propan-2-ol; MS (ES): 519 [M+H]+.

2-(2-(2-chloro-6-methylphenyl)-1-(3-fluoro-3'-(methylsulfonyl)biphenyl-4-yl)-1H-imidazol-4-yl)propan-2-ol; MS (ES): 499.3 [M+H]+

2-(2-(2-chloro-6-methylphenyl)-1-(3'-(ethylsulfonyl)-3-fluorobiphenyl-4-yl)-1H-imidazol-4-yl)propan-2-ol; MS (ES): 513.3 [M+H]+

2-(2-(2,6-dichlorophenyl)-1-(3-methyl-3'-(methylsulfonyl)biphenyl-4-yl)-1H-imidazol-4-yl)propan-2-ol; MS (ES): 515.3, 517.3 [M+H]+

2-(2-(2,6-dichlorophenyl)-1-(3'-(ethylsulfonyl)-3-methylbiphenyl-4-yl)-1H-imidazol-4-yl)propan-2-ol; MS (ES): 529.3, 531.3 [M+H]+

2-(1-(3-chloro-3'-(ethylsulfonyl)biphenyl-4-yl)-2-(2,6-dichlorophenyl)-1H-imidazol-4-yl)propan-2-ol; MS (ES): 549.3, 551.3, 553.3 [M+H]+

2-(1-(3-chloro-4'-(hydroxymethyl)-3'-(methylsulfonyl)biphenyl-4-yl)-2-(2,6-dichlorophenyl)-1H-imidazol-4-yl)propan-2-ol; MS (ES): 565.0, 567.0, 569.2 [M+H]+

2-(1-(3-chloro-3'-(methylsulfonyl)biphenyl-4-yl)-2-(2-chloro-6-methylphenyl)-1H-imidazol-4-yl)propan-2-ol; MS (ES): 515.2, 517.3 [M+H]+

2-(1-(3-chloro-4-(hydroxymethyl)-3'-(methylsulfonyl)biphenyl-4-yl)-2-(2-chloro-6-methylphenyl)-1H-imidazol-4-yl)propan-2-ol; MS (ES): 545.3, 547.3 [M+H]+

2-(1-(3-chloro-3'-(ethylsulfonyl)biphenyl-4-yl)-2-(2-chloro-6-methylphenyl)-1H-imidazol-4-yl)propan-2-ol; MS (ES): 529.2, 531.2 [M+H]+

2-(2-(2,6-dichlorophenyl)-1-(3-fluoro-4'-(hydroxymethyl)-3'-(methylsulfonyl)biphenyl-4-yl)-1H-imidazol-4-yl)propan-2-ol; MS (ES): 549.3, 551.3 [M+H]+, 571.2, 573.2 [M+Na]+

2-(2-(2-chloro-6-methylphenyl)-1-(3'-(ethylsulfonyl)-3-methylbiphenyl-4-yl)-1H imidazol-4-yl)propan-2-ol; MS (ES): 509.3, 511.3 [M+H]+

2-(2-(2-chloro-6-methylphenyl)-1-(3-methyl-3'-(methylsulfonyl)biphenyl-4-yl)-H-1-imidazol-4-yl)propan-2-ol; MS (ES): 495.4, 497.4 [M+H]+

2-(2-(2-chloro-6-methylphenyl)-1-(3'-(ethylsulfonyl)biphenyl-4-yl)-1H-imidazol-4-yl)propan-2-o; MS (ES): 495.4 [M-H]+

2-(2-(2-chloro-6-methylphenyl)-1-(4'-(hydroxymethyl)-3'-(methylsulfonyl)biphenyl-4-yl)-1H-imidazol-4-yl)propan-2-ol; MS (ES): 511.3 [M+H]+

2-(2-(2,6-dichlorophenyl)-1-(3-fluoro-3'-(methylsulfonyl)biphenyl-4-yl)-1H-imidazol-4-yl)propan-2-ol; MS (ES): 519.3, 521.3 [M+H]+

2-(2-(2,6-dichlorophenyl)-1-(3'-(ethylsulfonyl)-3-methylbiphenyl-4-yl)-1H-imidazol-4-yl)propan-2-ol; MS (ES): 529.3, 531.3 [M+H]+, 551.3, 553.3 [M+Na]+

2-(1-(3-chloro-3'-(methylsulfonyl)biphenyl-4-yl)-2-(2,6-dichlorophenyl)-1H-imidazol-4-yl)propan-2-ol; MS (ES): 535.3, 537.3, 539.3 [M+H]+

2-(2-(2,6-dichlorophenyl)-1-(3-methyl-3'-(methylsulfonyl)biphenyl-4-yl)-1H-imidazol-4-yl)propan-2-ol; MS (ES): 537.0 [M+Na]+

2-(2-(2-chloro-6-methylphenyl)-1-(4'-(hydroxymethyl)-3-methyl-3'-(methylsulfonyl)biphenyl-4-yl)-1H-imidazol-4-yl)propan-2-ol; MS (ES): 525.5 [M+H]$^+$, 547.3 [M+Na]$^+$ 2-(2-(2-chloro-6-methylphenyl)-1-(3-fluoro-4'-(hydroxymethyl)-3'-(methylsulfonyl)biphenyl-4-yl)-1H-imidazol-4-yl)propan-2-ol; MS (ES): 529.3, 531.3 [M+H]$^+$ ethyl 1-(3-chloro-3'-(methylsulfonyl)biphenyl-4-yl)-2-(2,6-dichlorophenyl)-1H-imidazole-4-carboxylate; MS (ES): 549.0, 551.0, 553.0 [M+H]$^+$ 2-{1-[2'-(trifluoromethyl)biphenyl-4-yl]-2-[2-(trifluoromethyl)phenyl]-1H-imidazol-4-yl}propan-2-ol; MS (ES): 491 [M+H]$^+$;

2-{1-(2',3'-difluorobiphenyl-4-yl)-2-[2-(trifluoromethyl)phenyl]-1H-imidazol-4-yl}propan-2-ol; MS (ES): 459 [M+H]$^+$;

2-(1-{4'-([(1-methylethyl)oxy]biphenyl-4-yl}2-[2-(trifluoromethyl)phenyl]-1H-imidazol-4-yl)propan-2-ol; MS (ES): 481 [M+H]$^+$;

2-{1-(4'-fluoro-3'-methylbiphenyl-yl)-2-[2-(trifluoromethyl)phenyl]-1H-imidazol-4-yl}propan-2-ol; MS (ES): 455 [M+H]$^+$;

2-{1-(3'-fluorobiphenyl-4-yl)-2-[2-(trifluoromethyl)phenyl]-1H-imidazol-4-yl}propan-2-ol; MS (ES): 441 [M+H]$^+$;

2-{1-(2',4',5'-trifluorobiphenyl-4-yl)-2-[2-(trifluoromethyl)phenyl]-1H-imidazol-4-yl}propan-2-ol; MS (ES): 477 [M+]$^+$;

2-{1-[5'-fluoro-2'-(methyloxy)biphenyl-4-yl]-2-[2-(trifluoromethyl)phenyl]-1H-imidazol-4-yl}propan-2-ol; MS (ES): 471 [M+H]$^+$;

2-{1-(4'-chlorobiphenyl-4-yl)-2-[2-(trifluoromethyl)phenyl]-1H-imidazol-4-yl}propan-2-o; MS (ES): 457 [M+H]$^+$;

2-{1-(4 pyrimidin-5-ylphenyl)-2-[2-(trifluoromethyl)phenyl]-1H-imidazol-4-yl}propan-2-ol; MS (ES): 425 [M+H]$^+$;

2-{1-[4'-(hydroxymethyl)biphenyl-yl]-2-[2-(trifluoromethyl)phenyl]-1H-imidazo-4-yl}propan-2-ol; MS (ES): 453 [M+H]$^+$;

2-{1-[4'-(dimethylamino)biphenyl-4-yl]-2-[2-(trifluoromethyl)phenyl]-1H-imidazol-4-yl}propan-2-ol; MS (ES): 466 [M+H]$^+$;

2-{1-[4'-(trifluoromethyl)biphenyl-4-yl]-2-[2-(trifluoromethyl)phenyl]-1H-imidazol-4-yl}propan-2-ol; MS (ES): 491 [M+H]$^+$;

2-{1-[4'-(1-methylethyl)biphenyl-4-yl]-2-[2-(trifluoromethyl)phenyl]-1H-imidazol-4-yl}propan-2-ol; MS (ES): 465 [M+H]$^+$;

2-{1-[4'-chloro-2'-(trifluoromethyl)biphenyl-4-yl]-2-[2-(trifluoromethyl)phenyl]-1H-imidazo-4-yl}propan-2-ol; MS (ES): 525 [M+H]$^+$;

2-{1-(2',3',4'-trifluorobiphenyl-4-yl)-2-[2-(trifluoromethyl)phenyl]-1H-imidazol-4-yl}propan-2-ol; MS (ES): 477 [M+H]$^+$;

2-{1-(3',4-difluorobiphenyl-4-yl)-2-[2-(trifluoromethyl)phenyl]-1H-imidazol-4-yl}propan-2-ol; MS (ES): 459 [M+H]$^+$;

2-{1-(2'-chloro-6'-fluoro-3'-methylbiphenyl-4-yl)-2-[2-(trifluoromethyl)phenyl]-1H-imidazol-4-yl}propan-2-ol; MS (ES): 489 [M+H]$^+$;

2-{1-[5'-chloro-2'-(methyloxy)biphenyl-4-yl]-2-[2-(trifluoroethyl)phenyl]-1H-imidazol-4-yl}propan-2-ol; MS (ES): 487 [M+H]$^+$;

2-{1-[2'-fluoro-5'-(trifluoromethyl)biphenyl-4-yl]-2-[2-(trifluoromethyl)phenyl]-1H-imidazol-4-yl}propan-2-ol; MS (ES): 509 [M+H]$^+$;

2-{1-[2'-(methylthio)biphenyl-4-yl]-2-[2-(trifluoromethyl)phenyl]-1H-imidazol-4 yl}propan-2-o; MS (ES): 469 [M+H]$^+$;

4'-{4-(1-hydroxy-1-methylethyl)-2-[2-(trifluoromethyl)phenyl]-1H-imidazol-1-yl}biphenyl-4-carboxylic acid; MS (ES): 467 [M+H]$^+$;

2-{1-[4-(1,3-benzodioxol-5-yl)phenyl]-2-[2-(trifluoromethyl)phenyl]-1H-imidazol-4-yl}propane-2-ol; MS (ES): 467 [M+H]$^+$;

2-(1-{4-[6-(methyloxy)pyridin-3-yl]phenyl}-2-[2-(trifluoromethyl)phenyl]-1H-imidazol-4-yl)propan-2-ol; MS (ES): 454 [M+H]$^+$;

2-(1-{4-[(1E)-3,3-dimethylbut-1-en-1-yl]phenyl}-2-[2-(trifluoromethyl)phenyl]-1H-imidazol-yl)propan-2-ol; MS (ES): 429 [M+H]$^+$;

2-{1-(3'-chlorobiphenyl-4-yl)-2-[2-(trifluoromethyl)phenyl]-1H-imidazol-4 yl}propan-2-ol; MS (ES): 457 [M+H]$^+$;

2-{1-[2'-fluoro-5'-(methyloxy)biphenyl-4-yl]-2-[2-(trifluoromethyl)phenyl]-1H-imidazol-4-yl}propan-2-ol; MS (ES): 471 [M+H]$^+$;

ethyl 4'-{4-(1-hydroxy-1-methylethyl)-2-[2-(trifluoromethyl)phenyl]-1H-imidazol-1-yl}biphenyl-4-carboxylate; MS (ES): 495 [M+H]$^+$;

2-{1-(4-{2-[(1-methylethyl)oxy]pyridin-3-yl}phenyl)-2-[2-(trifluoromethyl)phenyl]-1H-imidazol-4-yl}propan-2-ol; MS (ES): 482 [M+H]$^+$;

2-{1-[3'-chloro-4'-(methyoxy)biphenyl-4-yl]-2-[2-(trifluoromethyl)phenyl]-1H-imidazol-4-yl}propan-2-ol; MS (ES): 487 [M+H]$^+$;

2-{1-[2'-fluoro-3'-(methyloxy)biphenyl-4-yl]-2-[2-(trifluoromethyl)phenyl]-1H-imidazol-4-yl}propan-2-ol; MS (ES): 471 [M+H]$^+$;

4'-{4-(1-hydroxy-1-methylethyl)-2-[2-(trifluoromethyl)phenyl]-1H-imidazol-1-yl}biphenyl-3-carboxamide; MS (ES): 466 [M+L$^1$]$^+$;

4'-{4-(1-hydroxy-1-methylethyl)-2-[2-(trifluoromethyl)phenyl]-1H-imidazol-1-yl}biphenyl-4-carboxamide; MS (ES): 466 [M+H]$^+$;

2-(1-{4-[(trifluoromethyl)oxy]biphenyl-4-yl}-2-[2-(trifluoromethyl)phenyl]-1H-imidazol-4-yl)propan-2-ol; MS (ES): 507 [M+H]$^+$;

2-{1-[4'-fluoro-3'-(trifluoromethyl)biphenyl-4-yl]-2-[2-(trifluoromethyl)phenyl]-1H-imidazol-4-yl}propan-2-ol; MS (ES): 509 [M+H]$^+$;

2-{1-(4'-propylbiphenyl-4-yl)-2-[2-(trifluoromethyl)phenyl]-1H-imidazol-4-yl}propan-2-ol; MS (ES): 465 [M+H]$^+$;

2-{1-[4'-(ethyloxy)-3'-(trifluoromethyl)biphenyl-4-yl]-2-[2-(trifluoromethyl)phenyl]-1H-imidazol-4-yl}propan-2-ol; MS (ES): 535 [M+H]$^+$;

2-(1-{2'-[(1-methylethyl)oxy]biphenyl-4-yl}-2-[2-(trifluoromethyl)phenyl]-1H-imidazol-4-yl)propan-2-ol; MS (ES): 481 [M+H]$^+$;

2-(1-{3'-chloro-4'-[(1-methylethyl)oxy]biphenyl-yl}-2-[2-(trifluoromethyl)phenyl]-1H-imidazol-4-yl)propan-2-ol; MS (ES): 515 [M+H]$^+$;

2-{1-[4-(1H-indol-4-yl)phenyl]-2-[2-(trifluoromethyl)phenyl]-1H-imidazol-4-yl}propan-2-ol; MS (ES): 462 [M+H]$^+$;

2-{1-[4'-(methylthio)biphenyl-4-yl]-2-[2-(trifluoromethyl)phenyl]-1H-imidazol-4-yl}propan-2-o; MS (ES): 469 [M+H]$^+$;

2-{1-[3'-(hydroxymethyl)biphenyl-4-yl]-2-[2-(trifluoromethyl)phenyl]-1H-imidazol-4-yl}propan-2-ol; MS (ES): 453 [M+H]$^+$;

2-{1-[3'-(ethyloxy)biphenyl-4-yl]-2-[2-(trifluoromethyl)phenyl]-1H-imidazol-4-yl}propan-2-ol; MS (ES): 467 [M+H]+;

2-{1-(4'-ethylbiphenyl-4-yl)-2-[2-(trifluoromethyl)phenyl]-1H-imidazol-4-yl}propan-2-ol; MS (ES): 451 [M+H]+;

2-{1-(2',4'-difluorobiphenyl-4-yl)-2-[2-(trifluoromethyl)phenyl]-1H-imidazol-4-yl}propan-2-ol; MS (ES): 459 [M+H]+;

2-{1-(3',4'-dichlorobiphenyl-4-yl)-2-[2-(trifluoromethyl)phenyl]-1H-imidazol-4-yl}propan-2-ol; MS (ES): 491 [M+H]+;

2-{1-[2'-chloro-4'-(trifluoromethyl)biphenyl-4-yl]-2-[2-(trifluoromethyl)phenyl]-1H-imidazol-4-yl}propan-2-ol; MS (ES): 525 [M+H]+;

2-{1-(4-naphthalen-2-ylphenyl)-2-[2-(trifluoromethyl)phenyl]-1H-imidazol-4-yl}propan-2-ol; MS (ES): 473 [M+H]+;

2-{1-[3'-(methyloxy)biphenyl-4-yl]-2-[2-(trifluoromethyl)phenyl]-1H-imidazol-4-yl}propan-2-ol; MS (ES): 453 [M+H]+;

4'-{4-(1-hydroxy-1-methylethyl)-2-[2-(trifluoromethyl)phenyl]-1H-imidazol-1-yl}biphenyl-3-ol; MS (ES): 439 [M+H]+;

2-{1-(3',4',5'-trifluorobiphenyl-4-yl)-2-[2-(trifluoromethyl)phenyl]-1H-imidazol-4-yl}propan-2-ol; MS (ES): 477 [M+H]+;

1-[5-(4-{4-(1-hydroxy-1-methylethyl)-2-[2-(trifluoromethyl)phenyl]-1H-imidazol-1-yl}phenyl)-2-thienyl]ethanone; MS (ES): 471 [M+H]+;

2-{1-(3',5'-difluorobiphenyl-4-yl)-2-[2-(trifluoromethyl)phenyl]-1H-imidazol-4-yl}propan-2-o; MS (ES): 459 [M+H]+;

2-{1-(3'-chloro-4'-fluorobiphenyl-4-yl)-2-[2-(trifluoromethyl)phenyl]-1H-imidazol-4-yl}propan-2-ol; MS (ES): 475 [M+H]+

2-{1-[5'-methyl-2'-(methyloxy)biphenyl-4-yl]-2-[2-(trifluoromethyl)phenyl]-1,1-imidazol-4-yl}propan-2-ol; MS (ES): 467 [M+H]+;

2-{1-(2',5'-difluorobiphenyl-4-yl)-2-[2-(trifluoromethyl)phenyl]-1H-imidazol-4-yl}propan-2-ol; MS (ES): 459 [M+H]+;

2-{1-[3'-(butyloxy)biphenyl-4-yl]-2-[2-(trifluoromethyl)phenyl]-1H imidazol-4-yl}propan-2-ol; MS (ES): 495 [M+H]+;

2-{1-[5'-chloro-2'-(ethyloxy)biphenyl-4-yl]-2-[2-(trifluoromethyl)phenyl]-1H-imidazol-4-yl}propan-2-ol; MS (ES): 501 [M+H]+;

2-(1-{3'-[(trifluoromethyl)oxy]biphenyl-4-yl}-2-[2-(trifluoromethyl)phenyl]-1H-imidazol-4-yl)propan-2-ol; MS (ES): 507 [M+H]+;

2-{1-(2',3',5'-trifluorobiphenyl-4-yl)-2-[2-(trifluoromethyl)phenyl]-1H-imidazo-4-yl}propan-2-o; MS (ES): 477 [M+H]+;

2-{1-[3'-(ethylthio)biphenyl-4-yl]-2-[2-(trifluoromethyl)phenyl]-1H-imidazol-4-yl}propan-2-ol; MS (ES): 483 [M+H]+;

2-(1-{3'-[(1-methylethyl)oxy]biphenyl-4-yl}-2-[2-(trifluoromethyl)phenyl]-1H-imidazol-4-yl)propan-2-ol; MS (ES): 481 [M+H]+;

2-{1-[4-(1-benzothien-3-yl)phenyl]-2-[2-(trifluoromethyl)phenyl]-1H-imidazol-4-yl}propan-2-ol; MS (ES): 479 [M+H]+;

2-{1-[4-(4-methylnaphthalen-1-yl)phenyl]-2-[2-(trifluoromethyl)phenyl]-1H-imidazol-4-yl}propan-2-ol; MS (ES): 487 [M+H]+;

2-{1-(2',4'-dichlorobiphenyl-4-yl)-2-[2-(trifluoromethyl)phenyl]-1H-imidazol-4-yl}propan-2-o; MS (ES): 491 [M+H]+;

2-{1-[3',4'-bis(methyloxy)biphenyl-4-yl]-2-[2-(trifluoromethyl)phenyl]-1H-imidazol-4-yl}propan-2-ol; MS (ES): 483 [M+H]+;

2-{2-[2-(trifluoromethyl)phenyl]-1-(2',4',5'-trimethylbiphenyl-4-yl)-1H-imidazol-4-yl}propan-2-ol; MS (ES): 465 [M+H]+;

4-fluoro-4'-{4-(1-hydroxy-1-methylethyl)-2-[2-(trifluoromethyl)phenyl]-1H-imidazol-1-yl}biphenyl-2-ol; MS (ES): 457 [M+H]+;

2-{1-[2'(hydroxymethyl)biphenyl-4-yl]-2-[2-(trifluoromethyl)phenyl]-1H-imidazol-4-yl}propan-2-ol; MS (ES): 453 [M+H]+;

2-{1-[3'-(trifluoromethyl)biphenyl-4-yl]-2-[2-(trifluoromethyl)phenyl]-1H-imidazol-4-yl}propan-2-ol; MS (ES): 491 [M+H]+;

2-{1-2'-chloro-6'-fluorobiphenyl-4-yl)-2-(trifluromethyl)phenyl]-1H-imidazol-4-yl}propan-2-ol; MS (ES): 475 [M+H]+;

2-{1-[3',5'-difluoro-2'-(methyloxy)biphenyl-yl]-2-[2-(trifluoromethyl)phenyl]-1H-imidazol-4-yl}propan-2-ol; MS (ES): 489 [M+H]+;

2-(1-{4-[2-(methyloxy)pyridin-3-yl]phenyl}-2-[2-(trifluoromethyl)phenyl]-1H-imidazol-4-yl)propan-2-ol; MS (ES): 454 [M+H]+;

2-{1-[2'-methyl-5'-(methyloxy)biphenyl-4-yl]-2-[2-(trifluoromethyl)phenyl]-1H-imidazol-4-yl}propan-2-ol; MS (ES): 467 [M+H]+;

2-{1-(2'-ethylbiphenyl-4-yl)-2-[2-(trifluoromethyl)phenyl]-1H-imidazol-4-Yl}propan-2-ol; MS (ES): 451 [M+H]+;

2-(1-{2'-methyl-4'-[(1-methylethy)oxy]biphenyl-4-yl}-2-[2-(trifluoromethyl)phenyl]-1H-imidazol-4-yl)propan-2-ol; MS (ES): 495 [M+H]+;

2-{1-[4'-(ethylsulfonyl)biphenyl-4-yl]-2-[2-(trifluoromethyl)phenyl]-1H-imidazol -4-yl}propan-2-ol; MS (ES): 515 [M+H]+;

2-{1-(5-fluoro-2'-methylbiphenyl-4-yl)-2-[2-(trifluoromethyl)phenyl]-1H-imidazol-4-yl}propan-2-ol; MS (ES): 455 [M+H]+;

2-{1-[3'-chloro-4'-(trifluoromethyl)biphenyl-4-yl]-2-[2-(trifluoromethyl)phenyl]-1H-imidazol-4-yl}propan-2-ol; MS (ES): 525 [M+H]+;

2-{1-(2',5'-dimethylbiphenyl-4-yl)-2-[2-(trifluoromethyl)phenyl]-1H-imidazol-4-yl}propan-2-ol; MS (ES): 451 [M+H]+;

2-{1-[2'-(ethyloxy)-5'-(trifluormethyl)biphenyl-4-yl]-2-[2-(trifluoromethyl)phenyl]-1H-imidazol-4-yl}propan-2-ol; MS (ES): 535 [M+H]+;

2-{1-(3'-fluoro-4'-methylbiphenyl-4 yl)-2-[2-(rifluoromethyl)phenyl]-1H-imidazol-4-yl}propan-2-ol; MS (ES): 455 [M+H]+;

methyl (2E)-3-(4'-{4-(1-hydroxy-1-methylethyl)-2-[2-(trifluoromethyl)phenyl]-1H-imidazol-1-yl}biphenyl-4-yl)prop-2-enoate; MS (ES): 507 [M+H]+;

N-ethyl-4'-{4-(1-hydroxy-1-methylethyl)-2-[2-(trifluoromethyl)phenyl]-1H-imidazol-1-yl}biphenyl-3-carboxamide; MS (ES): 494 [M+H]+;

2-{1-[4-(2,3-dihydro-1-benzofuran-5-yl)phenyl]-2-[2-(trifluoromethyl)phenyl]-1H-imidazol-4-yl}propan-2-ol; MS (ES): 465 [M+H]+;

N-butyl-4'-{4-(1-hydroxy-1-methylethyl)-2-[2-(trifluoromethyl)phenyl]-1H-imidazo-1-yl}biphenyl-3-sulfonamide; MS (ES): 558 [M+H]+;

N-(1,1-dimethylethyl)-4'-{4-(1-hydroxy-1-methylethyl)-2-[2-(trifluoromethyl)phenyl]-1H imidazol-1-yl}-6-methyl-biphenyl-3-sulfonamide; MS (ES): 572 [M+H]+;

4'-{4-(1-hydroxy-1-methylethyl)-2-[2-(trifluoromethyl)phenyl]-1H-imidazol-1-yl}N-methylbiphenyl-3-sulfonamide; MS (ES): 516 [M+H]+;

N-ethyl-4'-{4-(1-hydroxy-1-methylethyl)-2-[2-trifluoromethyl)phenyl]1H-imidazol-1-yl}biphenyl-3-sulfonamide; MS (ES): 530 [M+H]+;

N-(1,1-dimethylethyl)-4'-{4-(1-hydroxy-1-methylethyl)-2-[2-(rifluoromethyl)phenyl]-1H-imidazol-1-yl}biphenyl-3-sulfonamide; MS (ES): 558 [M+H]+;

2-{1-[2'-amino-5'-(trifluoromethyl)biphenyl-4-yl]-2-[2-(trifluoromethyl)phenyl]-1H-imidazol-4-yl}propan-2-ol; MS (ES): 506 [M+H]+;

2-{1-[3'-fluoro-5'-(trifluoromethyl)biphenyl-4-yl]-2-[2-(trifluoromethyl)phenyl]-1H-imidazol-4-yl}propan-2-ol; MS (ES): 509 [M+H]+;

2-{1-[4'-chloro-3'-(trifluoromethyl)biphenyl-4-yl]-2-[2-(trifluoromethyl)phenyl]-1H-imidazol-4-yl}propan-2-ol; MS (ES): 525 [M+H]+;

3-chloro-4'-{4-(1-hydroxy-1-methylethy)-2-[2-(trifluoromethyl)phenyl]-1H-imidazo-1-yl}biphenyl-4-carboxylic acid; MS (ES): 501 [M+H]+;

2-(2-[2-(trifluoromethyl)phenyl]-1-{3'-[(trifluoromethyl)thio]biphenyl-4-yl}-1H-imidazol-4-yl)propan-2-ol; MS (ES): 523 [M+H]+;

2-{1-[3'-(morpholin-4-ylsulfonyl)bipheny-4-yl]-2-[2-(trifluoromethyl)phenyl]-1H-imidazol-4-yl}propan-2-ol; MS (ES): 572 [M+H]+;

2-(1-{4-[5-(hydroxymethyl)-1,3-thiazol-2-yl]phenyl}-2-[2-(trifluoromethyl)phenyl]-1H-imidazol-4-yl)propan-2-ol; MS (ES): 460 [M+H]+;

2-{1-[2'-methyl-5'-(piperidin-1-ylsulfonyl)biphenyl-4-yl]-2-[2-(trifluoromethyl)phenyl]-1H-imidazol-4-yl}propan-2-ol; MS (ES): 584 [M+H]+;

1-[4-(4-{4-(1-hydroxy-1-methylethyl)-2-[2-(trifluoromethyl)phenyl]-1H-imidazol-1-yl}phenyl)-2-thienyl]ethanone; MS (ES): 471 [M+H]+;

2-(1-{4-[5-(hydroxymethyl)-3-thienyl]-phenyl}-2-[2-(trifluoromethyl)phenyl]-1H-imidazol-4-yl)propan-2-ol; MS (ES): 459 [M+H]+;

2-chloro-4'-[2-(2,6-dichlorophenyl)-4-(1-hydroxy-1-methylethyl)-1H-imidazol-1-yl]-3'-methylbiphenyl-4-carboxylic acid; MS (ES): 515 [M+H]+;

2-(1-{3-[6-(methyoxy)pyridin-3-yl]phenyl}-2-[2-(trifluoromethyl)phenyl]-1H-imidazol-4-yl)propan-2-ol; MS (ES): 454 [M+H]+;

3'-{4-(1-hydroxy-1-methylethy)-2-[2-(trifluoromethyl)phenyl]-1H-imidazo-1-yl}N-(1-methylethyl) biphenyl-3-sulfonamide; MS (ES): 544 [M+H]+;

3'-{4-(1-hydroxy-1-methylethy)-2-[2-(trifluoromethyl)phenyl]-1H-imidazo-1-yl}biphenyl-4-carboxamide; MS (ES): 466 [M+1H]+;

2-(1-{3-[2-(cyclopentyloxy)pyridin-3-yl]phenyl}-2-[2-(trifluoromethyl)phenyl]-1H-imidazol-4-yl)propan-2-ol; MS (ES): 508 [M+H]+;

2-{1-(3'-chlorobiphenyl-3-yl)-2-[2-(trifluoromethyl)phenyl]-1H-imidazol-4-yl}propan-2-ol; MS (ES): 457 [M+H]+;

2-{1-[2'-fluoro-5'-(methyloxy)biphenyl-3-yl]-2-[2-(trifluoromethyl)phenyl]-1H-imidazo-4-yl}propan-2-ol; MS (ES): 471 [M+H]+;

3'-{4-(1 hydroxyl-methylethyl)$_2$-[2-(trifluormethyl)phenyl]-1H-imidazol-1-yl}biphenyl-3-carboxamide; MS (ES): 466 [M+H]+;

2-{1-[3',4'-bis(methyloxy)biphenyl-3-yl]-2-[2-(trifluoromethyl)phenyl]-1H-imidazol-4-yl}propan 2-ol; MS (ES): 483 [M+H]+;

N-(3'-{4-(1-hydroxy-1-methylethyl)-2-[2-(trifluoromethyl)phenyl]-1H-imidazol-1-yl}biphenyl-2-yl)methanesulfonamide; MS (ES): 516 [M+H]+;

2-{1-[3'-(trifluoromethyl)biphenyl-3-yl]-2-[2-(trifluoromethyl)phenyl]-1H-imidazol-4-yl}propan-2-ol; MS (ES): 491 [M+H]+;

3-fluoro-3'-{4-(1-hydroxy-1-methylethyl)-2-[2-(trifluoromethyl)phenyl]-1H-imidazol-yl}biphenyl-4-carboxylic acid; MS (ES): 485 [M+H]+;

4-chloro-3'-{4-(1-hydroxy-1-methylethyl)-2-[2-(trifluoromethyl)phenyl]-1H-imidazol-1-yl}biphenyl-3-carboxamide; MS (ES): 500 [M+H]+;

2-{1-(3-{2-[(1-methylethy)oxy]pyridin-3-yl}phenyl)-2-[2-(trifluoromethyl)phenyl]1-imidazol-4-yl}propan-2-ol; MS (ES): 482 [M+H]+;

N-(3'-{4-(1-hydroxy-1-methylethyl)-2-[2-(trifluoromethyl)phenyl]-1H-imidazol-1-yl}biphenyl-3-yl)acetamide; MS (ES): 480 [M+H]+;

2-{1-[2'-methyl-5'-(methyloxy)biphenyl-3-yl]-2-[2-(trifluoromethyl)phenyl]-1H-imidazol-4-yl}propan-2-ol; MS (ES): 467 [M+H]+;

N-(3'-{4-(1-hydroxy-1-methylethyl)-2-[2-(trifluoromethyl)phenyl]-1H-imidazol-1-yl}biphenyl-4-yl)acetamide; MS (ES): 480 [M+H]+;

2-{1-(4'-chlorobiphenyl-3-yl)-2-[2-(trifluoromethyl)phenyl]-1H-imidazol-4-yl}propan-2-ol; MS (ES): 457 [M+H]+;

2-{1-[4'-(phenyloxy)biphenyl-3-yl]-2-[2-(trifluoromethyl)phenyl]-1H-imidazol-4-yl}propan-2-ol; MS (ES): 515 [M+H]+;

2-{-[5'-fluoro-2'-(methyloxy)biphenyl-3-yl]-2-[2-(trifluoromethyl)phenyl]-H-imidazol-4-yl}propan-2-ol; MS (ES): 471 [M+H]+;

2-{1-(2',3'-dichlorobiphenyl-3-yl)-2-[2-(trifluoromethyl)phenyl]-1H-imidazol-4-yl}propan-2-ol; MS (ES): 491 [M+H]+;

2-(1-{3'-[(trifluoromethyl)oxy]biphenyl-3-yl}-2-[2-(trifluoromethyl)phenyl]-1H-imidazol-4-yl}propan-2-ol; MS (ES): 507 [M+H]+;

3'-{4-(1-hydroxy-1-methylethyl)-2-[2-(trifluoromethyl)phenyl]-1H-imidazol-1-yl}biphenyl-3-sulfonamide; MS (ES): 502 [M+H]+;

2-{1-[3',5'-bis(trifluoromethyl)biphenyl-3-yl]-2-[2-(trifluoromethyl)phenyl]-1H-imidazol-4-yl}propan-2-ol; MS (ES): 559 [M+H]+;

2-{(1-(3',5'-dichlorobiphenyl-3-yl)-2-[2-(trifluoromethyl)phenyl]-1H-imidazol-4-yl}propan-2-ol; MS (ES): 491 [M+H]+;

3-chloro-3'-{4-(1-hydroxy-1-methylethyl)-2-[2-(trifluoromethyl)phenyl]-1H-imidazol-1-yl}-N-(1-methylethyl)biphenyl-4-carboxamide; MS (ES): 542 [M+H]+;

N,N-diethyl-3'-{4-(1-hydroxy-1-methylethyl)-2-[2-(trifluoromethyl)phenyl]-1H-imidazol-1-yl}biphenyl-3-carboxamide; MS (ES): 522 [M+H]+;

4-chloro-3'-{4-(1-hydroxy-1-methylethyl)-2-[2-(trifluoromethyl)phenyl]-1H-imidazol-1-yl}-N-(1-methylethyl)biphenyl-3-carboxamide; MS (ES): 542 [M+H]+;

2-{1-[3'-(methyloxy)biphenyl-3-yl]-2-[2-(rifluoromethyl)phenyl]-1H-imidazol-4-yl}propan-2-ol; MS (ES): 453 [M+H]+;

3'-{4-(1-hydroxy-1-methylethyl)-2-[2-(trifluoromethyl)phenyl]-1H-imidazol-1-yl}biphenyl-3-carboxylic acid; MS (ES): 467 [M+H]+;

N-ethyl-3'-{4-(1-hydroxy-1-methylethyl)-2-[2-(trifluormethyl)phenyl]-1H-imidazol-1-yl}biphenyl-3-carboxamide; MS (ES): 494 [M+H]$^+$;

4-chloro-N-ethyl-3'-{4-(1-hydroxy-1-methylethyl)-2-[2-(trifluoromethyl)phenyl]-1H-imidazol-1-yl}biphenyl-3-carboxamide; MS (ES): 528 [M+H]$^+$;

2-{1-(2',5'-difluorobiphenyl-3-yl)-2-[2-(trifluoromethyl)phenyl]-1H-imidazol-4-yl}propan-2-ol; MS (ES): 459 [M+H]$^+$;

2-(1-{3'-[(1-methylethyl)oxy]biphenyl-3-yl}-2-[2-(trifluoromethyl)phenyl]-1H-imidazol-4-yl)propan-2-ol; MS (ES): 481 [M+H]$^+$;

2-{1-[2'-fluoro-5'-(trifluoromethyl)biphenyl-3-yl]-2-[2-(trifluoromethyl)phenyl]-1H-imidazol-4-yl}propan-2-ol; MS (ES): 509 [M+H]$^+$;

2-{1-(3',4'-dichlorobiphenyl-3-yl)-2-[2-(trifluoromethyl)phenyl]-1H-imidazol-4-yl}propan-2-ol; MS (ES): 491 [M+H]$^+$;

2-{1-[3'-(ethyloxy)biphenyl-3-yl]-2-[2-(trifluoromethyl)phenyl]-1H-imidazol-4-yl}propan-2-o; MS (ES): 467 [M+H]$^+$;

2-(1-{2'-methyl-4-[(1-methylethyl)oxy]biphenyl-3-yl}-2-[2-(trifluoromethyl)phenyl]-1H-imidazol-4-yl)propan-2-ol; MS (ES): 495 [M+H]$^+$;

2-{1-[3-(1-methyl-1H-indol-5-yl)phenyl]-2-[2-(trifluoromethyl)phenyl]-1H-imidazol-4-yl}propan-2-ol; MS (ES): 476 [M+H]$^+$;

2-{1-[4'-(ethyloxy)-3'-(trifluoromethyl)biphenyl-3-yl]-2-[2-(trifluoromethyl)phenyl]-1H-imidazol-4-yl}propan-2-ol; MS (ES): 535 [M+H]$^+$;

2-{1-[3'-(ethylsulfonyl)biphenyl-3-yl]-2-[2-(trifluoromethyl)phenyl]-1H-imidazol-4-yl}propan-2-ol; MS (ES): 515 [M+H]$^+$;

2-{1-[2'-(trifluoromethyl)biphenyl-3-yl]-2-[2-(trifluoromethyl)phenyl]-1H-imidazol-4-yl}propan-2-ol; MS (ES): 491 [M+H]$^+$;

2-{1-[3'-(hydroxymethyl)biphenyl-3-yl]-2-[2-(trifluoromethyl)phenyl]-1H-imidazol-4-yl}propan-2-ol; MS (ES): 453 [M+H]$^+$;

2-{1-[3-(1H-indol-4-yl)phenyl]-2-[2-(trifluoromethyl)phenyl]-1H-imidazol-4-yl}propan-2-ol; MS (ES): 462 [M+H]$^+$;

3'-{4-(1-hydroxy-1-methylethyl)-2-[2-(trifluoromethyl)phenyl]-1H-imidazol-1-yl}biphenyl-4-carboxylic acid, MS (ES): 467 [M+H]$^+$;

1-[5-(3-{4-(1-hydroxy-1-methylethyl)-2-[2-(trifluoromethyl)phenyl]-1H-imidazol-1-yl}phenyl)-2-thienyl]ethanone; MS (ES): 471 [M+H]$^+$;

2-{1-(5'-chloro-2'-methylbiphenyl-3-yl)-2-[2-(trifluoromethyl)phenyl]-1H-imidazol-4-yl}propan-2-ol; MS (ES): 471 [M+H]$^+$;

2-(1-{4'-[(trifluoromethyl)oxy]biphenyl-3-yl}-2-[2-(trifluoromethyl)phenyl]-1H-imidazol-4-yl)propan-2-ol; MS (ES): 507 [M+H]$^+$;

2-{1-[2'-chloro-4'-(trifluoromethyl)biphenyl-3-yl]-2-[2-(trifluoromethyl)phenyl]-1H-imidazol-4-yl}propan-2-ol; MS (ES): 525 [M+H]$^+$;

2-{1-(2',5'-dichlorobiphenyl-3-yl)-2-[2-(trifluoromethyl)phenyl]-1H-imidazol-4-yl}propan-2-ol; MS (ES): 491 [M+H]$^+$;

2-{1-[2'-(ethyloxy)-5'-(trifluoromethyl)biphenyl-3-yl]-2-[2-(trifluoromethyl)phenyl]-1-imidazol-4-yl}propan-2-ol; MS (ES): 535 [M+H]$^+$;

3'-{4-(1-hydroxy-1-methylethyl)-2-[2-(trifluoromethyl)phenyl]-1H-imidazol-1-yl}-N-(1-methylethyl)biphenyl-4-carboxamide; MS (ES): 508 [M+H]$^+$;

2-{1-(2',4'-dichlorobiphenyl-3-yl)-2-[2-(trifluoromethyl)phenyl]-1H-imidazol-4-yl}propan-2-ol; MS (ES): 491 [M+H]$^+$;

2-{1-[4'-(ethylsulfonyl)biphenyl-3-yl]-2-[2-(trifluoromethyl)phenyl]-1H-imidazol-4-yl}propan-2-ol; MS (ES): 515 [M+H]$^+$;

2-{1-[4'-fluoro-3'-(trifluoromethyl)biphenyl-3-yl]-2-[2-(trifluoromethyl)phenyl]-1H-imidazol-4-yl}propan-2-ol; MS (ES): 509 [M+H]$^+$;

2-{1-(3'-fluoro-4'-methylbiphenyl-3-yl)-2-[2-(trifluoromethyl)phenyl]-1H-imidazol-4-yl}propan-2-ol; MS (ES): 455 [M+H]$^+$;

2-{2-(2-chloro-6-fluorophenyl)-1-[3'-(ethylsulfonyl)-3-fluorobiphenyl-4-yl]-1H-imidazol-4-yl}propan-2-ol; MS (ES): 539 (M+Na);

2-{2-(2-chloro-6-fluorophenyl)-1-[3-fluoro-4'-(hydroxymethyl)-3'-(methylsulfonyl)biphenyl-4-yl]-1H-imidazol-4-yl}propan-2-ol MS (ES): 533[M+H]$^+$ 2-{2-(2,6-difluorophenyl)-1-[3-fluoro-3'-(methylsulfonyl)biphenyl-4-yl]-1H-imidazol-4-yl}propan-2-ol; MS (ES): 487 [1+H]$^+$ 2-{2-(2,6-difluorophenyl)-1-[3'-(ethylsulfonyl)-3-fluorobiphenyl-4-yl]-1H-imidazol-4-yl}propan-2-ol; MS (ES): 501 [M+H]$^+$ 2-{2-(2,6-difluorophenyl)-1-[3-fluoro-4-(hydroxymethyl)-3'-(methylsulfonyl)biphenyl-4-yl]-1H-imidazol-4-yl}propan-2-ol MS (ES): δ 17[M+H]$^+$ 2-{2-(2-chloro-6-fluorophenyl)-1-[3-fluoro-3'-(methylsulfonyl)biphenyl-4-yl]-1H-imidazol-4-yl}propan-2-ol MS (ES): 503 [M+H]$^+$ 2-{2-(2,6-difluorophenyl)-1-[4'-(hydroxymethyl)-3'-(methylsulfonyl)biphenyl-4-yl]-1H-imidazol-4-yl}propan-2-ol MS (ES): 499[M+H]$^+$ 2-{2-(chloro-6-fluorophenyl)-1-[3-chloro-3'-(methylsulfonyl)biphenyl-4-yl]-1H-imidazol-4-yl}propan-2-ol MS (ES): 519[M+H]$^+$ 2-{1-[3-chloro-3'-(ethylsulfonyl)biphenyl-4-yl]-2-(2-chloro-6-fluorophenyl)-1H-imidazo-4-yl}propan-2-ol MS (ES): 533 [M+H]$^+$ 2-{1-[3-chloro-3'-(ethylsulfonyl)biphenyl-4 yl]-2-(2-chloro-6-fluorophenyl)-1H-imidazol-4-yl}propan-2-ol MS (ES): 533 [M+H]$^+$ 2-{2-(2-chloro-6-fluorophenyl)-1-[3-chloro-4'-(hydroxymethyl)-3'-(methylsulfonyl)biphenyl-4-yl]-1H-imidazol-4-yl}propan-2-ol MS (ES): 549[M+H]$^+$ 2-{2-(2-chloro-6-fluorophenyl)-1-[3-methyl-3'-(methylsulfonyl)biphenyl-4-yl]-1H-imidazol-4-yl}propan-2-ol MS (ES): 499 [M+H]$^+$ 2-{2-(2-chloro-6-fluorophenyl)-1-[Y-(ethylsulfonyl)-3-methylbiphenyl-4-yl]-1H-imidazol-4-yl}propan-2-ol MS (ES): δ 13 [M+H]$^+$ 2-{2-(2-chloro-6-fluorophenyl)-1-[4'-(hydroxymethyl)-3-methyl-3'-(methylsulfonyl)biphenyl-4-yl]-1H-imidazol-4-yl}propan-2-ol MS (ES): 529 [M+H]$^+$ 2-{1-[3'-(methylsulfonyl)biphenyl-4-yl]-2-[4-(trifluoromethyl)pyridin-3-yl]-1H-imidazol-4-yl}propan-2-ol MS (ES): 502[M+H]$^+$ 2-{1-[3'-(ethylsulfonyl)biphenyl-4-yl]-2-[4-trifluoromethyl)pyridin-3-yl]-1H-imidazol-4-yl}propan-2-ol MS (ES): 516[M+H]$^+$ 2-{1-[4'-(hydroxymethyl)-3'-(methylsulfonyl)biphenyl-4-yl]-2-[4-(trifluoromethyl)pyridin-3-yl]-1H-imidazol-4-yl}propan-2-ol MS (ES): 532[M+H]+

2-{1-[3'-(methylsulfonyl)biphenyl-4-yl]-2-(2-morpholin-4-ylethyl)-1H-imidazol-4-yl}propan-2-ol MS (ES): 470[M+H]$^+$ 2-{1-[3-chloro-(methylsulfonyl)biphenyl-4-yl]-2-(2,6-difluorophenyl)-1H-imidazol-4-yl}propan-2-ol MS (ES): 503 [1+H]⁺

2-{1-[3-chloro-3'-(ethylsulfonyl)biphenyl-4-yl]2-(2,6-difluorophenyl)-1-imidazol-4-yl}propan-2-ol MS (ES): 517 [M+H]⁺

2-{1-[3-chloro-4'-(hydroxymethyl)-3'-(methylsulfonyl)biphenyl-4-yl]-2-(2,6-difluorophenyl)-1H-imidazol-4-yl}propan-2-ol MS (ES): 533 [M+H]⁺

2-{2-(2,6-difluorophenyl)-1-[3-methyl-3'-(methylsulfonyl)biphenyl-4-yl]-1H-imidazol-4-yl}propan-2-ol MS (ES): 483 [M+H]⁺

2-{2-(2,6-difluorophenyl)-1-[3'-(ethylsulfonyl)-3-methylbiphenyl-4-yl]-1H-imidazol-4-yl}propan-2-ol MS (ES): 497[M+H]⁺

2-{2-(2,6-difluorophenyl)-1-[4'-(hydroxymethyl)-3-methyl-3'-(methylsulfonyl)biphenyl-4-yl]-1H-imidazol-4-yl}propan-2-ol MS (ES): 513 [M+H]⁺

2-{2-(2,3-dichlorophenyl)-1-[3'-(methylsulfonyl)biphenyl-4-yl]-1H-imidazol-4-yl}propan-2-ol; MS (ES): 501,503 [M+H]⁺

2-{2-(2-chloro-3-fluorophenyl)-1-[3'-(methylsulfonyl)biphenyl-4-yl]-1H-imidazol-4-yl}propan-2-ol; MS (ES): 485 [M+H]⁺

2-{2-(2-chlorophenyl)-1-[3-fluoro-3'-(methylsulfonyl)biphenyl-4-yl]-1H-imidazol-4-yl}propan-2-ol; MS (ES): 485 [M+H]⁺

2-{2-(2-chlorophenyl)-1-[2-fluoro-3'-(methylsulfonyl)biphenyl-4-yl]-1H-imidazol-4-yl}propan-2-ol; MS (ES): 485 [M+H]⁺

2-{1-[3'-(methylsulfonyl)biphenyl-4 yl]-2-[3-(trifluoromethyl)phenyl]-1H-imidazol-4-yl}propan-2-ol; MS (§ES): 501 [M+H]⁺

2-{2-(3-chlorophenyl)-1-[3'-(methylsulfonyl)biphenyl-4-yl]-1H-imidazol-4-yl}propan-2-ol; MS (ES): 467 [M+H]⁺

2-{1-[3-chloro-3'(methylsulfonyl)biphenyl-4-yl]-2-(2-chlorophenyl)-1H-imidazol-4-yl}propan-2-ol; MS (ES): 501, 503 [M+H]⁺

2-{2-(2-chlorophenyl)-1-[3-methyl-3'-(methylsulfonyl)biphenyl-4-yl]-1H-imidazol-4-yl}propan-2-ol; MS (ES): 481 [M+H]⁺

2-{2-(2,3-dichlorophenyl)-1-[3'-(ethylsulfonyl)biphenyl-4-yl]-1H-imidazol-4-yl}propan-2-ol; MS (ES): 515, 517 [M+H]⁺

2-{2-(2-chlorophenyl)-1-[3'-(ethylsulfonyl)-3-fluorobiphenyl-4-yl]-1H-imidazol-4-yl}propan-2-ol; MS (ES): 499 [M+H]⁺

2-{2-(2-chlorophenyl)-1-[3'-(ethylsulfonyl)-2-fluorobiphenyl-4-yl]-1H-imidazol-4-yl}propan-2-ol; MS (ES): 499 [M+H]⁺

2-{2-(3-chloro-2-methylphenyl)-1-[3'-(methylsulfonyl)biphenyl-4-yl]-1H-imidazol-4-yl}propan-2-ol; MS (ES): 481 [M+H]⁺

2-{2-(2-chlorophenyl)-1-[2-methyl-3'-(methylsulfonyl)biphenyl-4-yl]-1H-imidazol-4-yl}propan-2-ol; MS (ES): 481 [M+H]⁺

2-{2-(3-chloro-2-methylphenyl)-1-[3'-(ethylsulfonyl)biphenyl-4-yl]-1H-imidazol-4-yl}propan-2-ol; MS (ES): 495 [M+H]⁺

2-(2-(2-chlorophenyl)-1-(3-ethyl-3'-(methylsulfonyl)biphenyl-4-yl)-1H-imidazol-4-yl)propan-2-ol; MS (ES): 495 [M+H]⁺

2-(1-(3-chloro-3'-(methylsulfonyl)biphenyl-4-yl)-2-(2,3-dichlorophenyl)-1H-imidazol-4-yl)propan-2-ol; MS (ES): 535, 537 [M+H]⁺

2-(1-(3-chloro-3'-(ethylsulfonyl)biphenyl-4-yl)-2-(2,3-dichlorophenyl)-1H-imidazol-4-yl)propan-2-ol; MS (ES): 549, 551 [M+H]⁺

2-(2-(2,3-dichlorophenyl)-1-(3-methyl-3'-(methylsulfonyl)biphenyl-4-yl)-1H-imidazol-4-yl)propan-2-al; MS (ES): 515, 517 [M+H]⁺

2-(2-(2,3-dichlorophenyl)-1-(3'-(ethylsulfonyl)-3-methylbiphenyl-4-yl)-1H-imidazol-4-yl)propan-2-ol; MS (ES): 529, 531 [M+H]⁺

2-(2-(2,3-dichlorophenyl)-1-(3-fluoro-3'-(methylsulfonyl)biphenyl-4-yl)-1H-imidazol-4-yl)propan-2-ol; MS (ES): 519, 521 [M+H]⁺

2-(2-(2,3-dichlorophenyl)-1-(3'-(ethylsulfonyl)-3-fluorobiphenyl-4-yl)-1H-imidazol-4-yl)propan-2-ol; MS (ES): 533, 535 [M+H]⁺

2-(2-(2-chloro-3-fluorophenyl)-1-(3-methyl-3'-(methylsulfonyl)biphenyl-4-yl)-1H-imidazol-4-yl)propan-2-ol; MS (ES): 499 [1+H]⁺

2-(2-(2-chloro-3-fluorophenyl)-1-(3'-(ethylsulfonyl)-3-methylbiphenyl-4-yl)-1H-imidazol-4-yl)propan-2-ol; MS (ES): 513 [1+H]⁺

2-(2-(2,3-dichlorophenyl)-1-(4-hydrohyethyl)-3'-(methylsulfonyl)biphenyl-4-yl)-1H-imidazol-4-yl)propan-2-ol; MS (ES): 531, 533 [M+H]⁺

2-(2-(2,3-dichlorophenyl)-1-(3-fluoro-4-(hydroxymethyl)-3'-(methylsulfonyl)biphenyl-4-yl)-1H-imidazol-4-yl)propan-2-ol; MS (ES): 549, 551 [M+H]⁺

2-(2-(2-chloro-3-fluorophenyl)-1-(4'-(hydroxyethyl)-3-methyl-3'-(methylsulfonyl)biphenyl-4-yl)-1H-imidazol-4-yl)propan-2-ol; MS (§ES): 529 [M+H]⁺

2-(1-(3-chloro-4'-(hydroxymethyl)-3'-(methylsulfonyl)biphenyl-4-yl)-2-(2,3-dichlorophenyl)-1H-imidazol-4-yl)propan-2-ol; MS (ES): 565, 567 [M+H]⁺

2-(2-(2,3-dichlorophenyl)-1-(4'-(hydroxymethyl)-3-methyl-3'-(methylsulfonyl)biphenyl-4-yl)-1H-imidazol-4-yl)propan-2-ol; MS (ES): 545, 547 [M+H]⁺

2-(1-(3-chloro-5-methyl-3'-(methylsulfonyl)biphenyl-4-yl)-2-(2-chlorophenyl)-1H-imidazol-4-yl)propan-2-ol; MS (ES): 537, 539 [M+Na]⁺

2-(1-(3-chloro-3'-(ethylsulfonyl)-5-methylbiphenyl-4-yl)-2-(2-chlorophenyl)-1H-imidaZol-4-yl)propan-2-ol; MS (ES): 551, 553 [M+Na]⁺

2-(1-(3-chloro-3'-(methylsulfonyl)biphenyl-4-yl)-2-(2-chloro-3-fluorophenyl)-1H-imidazol-4-yl)propan-2-ol; MS (ES): 541, 543 [M+Na]⁺

2-(1-(3-chloro-3'-(ethylsulfonyl)biphenyl-4-yl)-2-(2-chloro-3-fluorophenyl)-1H-imidazol-4-yl)propan-2-ol; MS (ES): 555, 557 [M+Na]⁺

2-(2-(2-chloro-3-fluorophenyl)-1-(3-fluoro-3'-(methylsulfonyl)biphenyl-4-yl)-1H-imidazol-4-yl)propan-2-ol; MS (ES): 525 [M+Na]⁺

2-(2-(2-chloro-3-fluorophenyl)-1-(3'-(ethylsulfonyl)-3-fluorobiphenyl-4-yl)-1H-imidazol-4-yl)propan-2-ol; MS (ES): 517 [M+H]

2-(2-(2-chloro-3-fluorophenyl)-1-(3-fluoro-4'-(hydroxymethyl)-3'-(methylsulfonyl)biphenyl-4-yl)-1H-imidazol-4-yl)propan-2-ol; S(ES): 555 [M+Na]⁺

2-(2-(2-chloro-3-fluorophenyl)-1-(3-chloro-4'-(hydroxymethyl)-3'-(methylsulfonyl)biphenyl-4-yl)-1H-imidazol-4-yl)propan-2-ol; MS (ES): 571, 573 [M+Na]⁺

2-(2-(2-chloro-3-fluorophenyl)-1-(3'-(ethylsulfonyl)biphenyl-4-yl)-1H-imidazol-4-yl)propan-2-ol; MS (ES): 499 [M+H]⁺

In a similar manner, the following compounds were prepared by replacing methylmagnesium bromide with ethylmagnesium bromide:

3-(2-(2,3-dichlorophenyl)-1-(3'-(methylsulfonyl)biphenyl-4-yl)-1H-imidazol-4-yl)pentan-3-ol; MS (ES): 529, 531 [M+H]⁺;

3-(2-(2,3-dichlorophenyl)-1-(3'-(ethylsulfonyl)biphenyl-4-yl)-1H-imidazol-4-yl)pentan-3-ol; MS (ES): 543, 545 [M+H]⁺;

3-{2-(2,6-dichlorophenyl)-1-[3'-(methylsulfonyl)biphenyl-4-yl]-1H-imidazol-4-yl}pentan-3-ol; 529.3, [M+H]⁺.

In a similar manner, the following compound was prepared by replacing ethyl bromopyruvate with ethyl 3-bromo-2-ketobutyrate: 2-{5-methyl-1-[3'-(methylsulfonyl)biphenyl-4-yl]-2-[2-(trifluoromethyl)phenyl]-1H-imidazol-4-yl}propan-2-ol; MS (ES): 515 [M+H]⁺

EXAMPLE 10

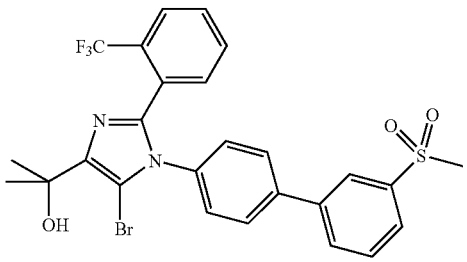 [SMILES: CC(C)(O)c1nc(-c2ccccc2C(F)(F)F)n(-c2ccc(-c3cccc(S(C)(=O)=O)c3)cc2)c1Br]

Preparation of 2-[5-bromo-1-(3'-methanesulfonyl-biphenyl-4-yl)-2-(2-trifluoromethyl-phenyl)-1H-imidazol-4-yl]-propan-2-ol To a solution of 2-[1-(3'-methanesulfonyl-biphenyl-4-yl)-2-(2-trifluoromethyl-phenyl)-1H-imidazol-4-yl]-propan-2-ol (100 mg, 0.20 mmol) in MeCN (2 mL, anhyd) was added N-bromosuccinimide (45 mg, 0.25 mmol). After 2 h, the reaction mixture was diluted with EtOAc, washed with saturated NaHCO₃, water (3×10 mL) and brine, then dried (Na₂SO₄) and concentrated. The residue was purified by chromatography (silica), eluting with EtOAc/hexanes (65:40 to 95:5) to yield the title compound (100 g, 86%) as a white solid. ¹H-NMR (CD₂Cl₂): δ 8.10 (1H, m), 7.92 (1H, m), 7.86 (1H, m), 7.60-7.74 (4H, m), 7.47 (2H, m), 7.25-7.31 (3H, m), 3.56 (1H, s), 3.06 (3H, s), 1.66 (6H, s); MS (ES): 579, 581 [M+H]⁺.

In a similar manner, the following compound was prepared by replacing N-bromosuccinimide with N-chlorosuccinimide: 2-{5-chloro-1-[3'-(methylsulfonyl)biphenyl-4-yl]-2-[2-(trifluoromethyl)phenyl]-1H-imidazol-4-yl}propan-2-ol; MS (ES): 535 [M+H]⁺

In a similar manner, the following compound was prepared by treating the appropriate imidazole-4-carboxylic acid ethyl ester intermediate with 1-chloromethyl-4-fluoro-1,4-diazoniabicyclo[2.2.2]octane bis(tetrafluoroborate) (Selectfluor™) followed by the previously described sequence of Suzuki cross-coupling and reaction with Grignard reagent: 2-{5-fluoro-1-[3'-(methylsulfonyl)biphenyl-4-yl]-2-[2-(trifluoromethyl)phenyl]-1H-imidazol-4-yl}propan-2-ol; MS (ES): 519 [M+H]⁺

The following compounds were made in a similar manner, except boronic acid or boronate reagents for Suzuki coupling were prepared as described in Examples 23-29.

6-{3-Chloro-4-[2-(2-chloro-6-fluorophenyl)-4-(1-hydroxy-1-methyl-ethyl)-imidazol-1-yl]-phenyl}-1,1-dioxo-2,3-dihydro-1H-1λ,*6*-benzo[b]thiophen-3-ol; MS (M+H)⁺: 547 [M+H]⁺.

2-{2-(2,3-dichlorophenyl)-1-[4'-(methyloxy)-3'-(methylsulfonyl)biphenyl-4-yl]-1H-imidazol-4-yl}propan-2-ol; MS (ES): 531, 533 each [M+H]⁺.

2-{2-(2-chloro-6-fluorophenyl)-1-[3-chloro-4'-(methyloxy)-3'-(methylsulfonyl)biphenyl-4-yl]-1H-imidazol-4-yl}propan-2-ol; MS (ES): 549, 551 each [M+H]⁺.

ethyl 3'-chloro-4'-[2-(2-chloro-6-fluorophenyl)-4-(1-hydroxy-1-methylethyl)-1H-imidazol-1-yl]-3-(methylsulfonyl)biphenyl-4-carboxylate; MS (ES): 591, 593 each [M+H]⁺.

2-{2-(2,3-dichlorophenyl)-1-[4'-(hydroxymethyl)-3'-(methylsulfonyl)biphenyl-4-yl]-1H-imidazol-4-yl}propan-2-ol; MS (ES): 531, 533 each [M+H]⁺.

2-{4'-[2-(2,3-dichlorophenyl)-4-(1-hydroxy-1-methylethyl)-1H-imidazol-1-yl]-3-(methylsulfonyl)biphenyl-4-yl}propan-2-ol; MS (ES): 559 [M+H]⁺.

2-{3'-chloro-4'-[2-(2-chloro-6-fluorophenyl)-4-(1-hydroxy-1-methylethyl)-1H-imidazol-1-yl]-3-(methylsulfonyl)biphenyl-4-yl}propan-2-ol; MS (ES): 577 [M+H]⁺.

2-{1-[3-chloro-4'-(1-hydroxy-1-methylethyl)-3'-(methylsulfonyl)biphenyl-4-yl]-2-[2-(trifluoromethyl)phenyl]-1H-imidazol-4-yl}propan-2-ol; MS (ES): 593[M+H]⁺.

2-{3'-chloro-4-[2-(2-chlorophenyl)-4-(1-hydroxy-1-methylethyl)-1H-imidazol-1-yl]-3-(methylsulfonyl)biphenyl-4-yl}propan-2-ol; MS (ES): 559 [M+H]⁺.

2-{2-(3-chloro-2-methylphenyl)-1-[4'-(hydroxymethyl)-3'-(methylsulfonyl)biphenyl-4-yl]-1H imidazol-4-yl}propan-2-ol; MS (ES): 511 [M+H]⁺.

2-{1-[3-chloro-4'-(hydroxymethyl)-3'-(methylsulfonyl)biphenyl-4-yl]-3-chloro-2-methylphenyl)-1H-imidazol-4-yl}propan-2-ol; MS (ES): 545 [M+N]⁺.

2-{1-[3-fluoro-4-(hydroxymethyl)-3'-(methylsulfonyl)biphenyl-4-yl]-2-[2-(trifluoromethyl)phenyl]-1H-imidazol-4-yl}propan-2-ol; MS (ES): 549 [M+H]⁺.

2-{2-(3-chloro-2-methylphenyl)-1-[3-fluoro-4'-(hydroxymethyl)-3'-(methylsulfonyl)biphenyl-4-yl]-1H-imidazol-4-yl}propan 2-ol; MS (ES): 529 [M+H]⁺.

2-{2-(3-chloro-2-methylphenyl)-1-[4'(hydroxymethyl)-3-methyl-3'-(methylsulfonyl)biphenyl-4-yl]-1H imidazol-4-yl}propan-2-ol; MS (ES): 525 [M+H]⁺.

2-{1-[3-chloro-4'-(hydroxymethyl)-3'-(methylsulfonyl)biphenyl-4-yl]-2-naphthalen-1-yl-1H-imidazol-4-yl}propan-2-ol; MS (ES): 547 [M+H]⁺.

2-{1-[4'-(hydroxymethyl)-3-methyl-3'-(methylsulfonyl)biphenyl-4-yl]-2-[2-(trifluoromethyl)phenyl]-1H-imidazol-4-yl}propan-2-ol; MS (ES): 545 [M+H]⁺.

2-{1-[3-chloro-4'-(hydroxymethyl)-3'-(methylsulfonyl)biphenyl-4-yl]-2-[2-(trifluoromethyl)phenyl]-1H-imidazol-4-yl}propan-2-ol; MS (ES): 565 [M+H]⁺.

2-{1-[3-chloro-4'-(hydroxymethyl)-3'-(methylsulfonyl)biphenyl-4-yl]-2-(2-chlorophenyl)-1H-imidazol-4-yl}propan-2-ol; MS (ES): 531 [M+H]⁺.

ethyl 4'-{4-(1-hydroxy-1-methylethyl)-2-[2-(trifluoromethyl)phenyl]-1H-imidazol-1-yl}-5-(methylsulfonyl)biphenyl-3-carboxylate; MS (ES): 573 [M+H]⁺.

2-{1-[4'-(hydroxymethyl)-3-(methylsulfonyl)biphenyl-4-yl]-2-[2-(trifluoromethyl)phenyl]-1H imidazol-4-yl}propan-2-ol; MS (ES): 531 [M+H]⁺.

2-{1-[4'-(methyloxy)-3'-(methylsulfonyl)biphenyl-4 yl]-2-[2-(trifluoromethyl)phenyl]-1H-imidazol-4-yl}propan-2-ol; MS (ES): 531 [M+H]⁺

2-(2-(2,6-dichlorophenyl)-1-(3'-methyl-5'-(methylsulfonyl)biphenyl-4-yl)-1H-imidazol-4-yl)propan-2-ol; MS (ES): 515, 517 [M+H]⁺

2-(1-(2'-chloro-5'-(methylsulfonyl)biphenyl-4-yl)-2-(2,6-dichlorophenyl)-1H-imidazol-4-yl)propan-2-ol; MS (ES): 535,537 [M+H]⁺

2-(1-(2',3-dichloro-5'-(methylsulfonyl)biphenyl-4-yl)-2-(2,6-dichlorophenyl)-1H-imidazol-4-yl)propan-2-ol; MS (ES): 591, 593, 595 [M+Na]⁺.

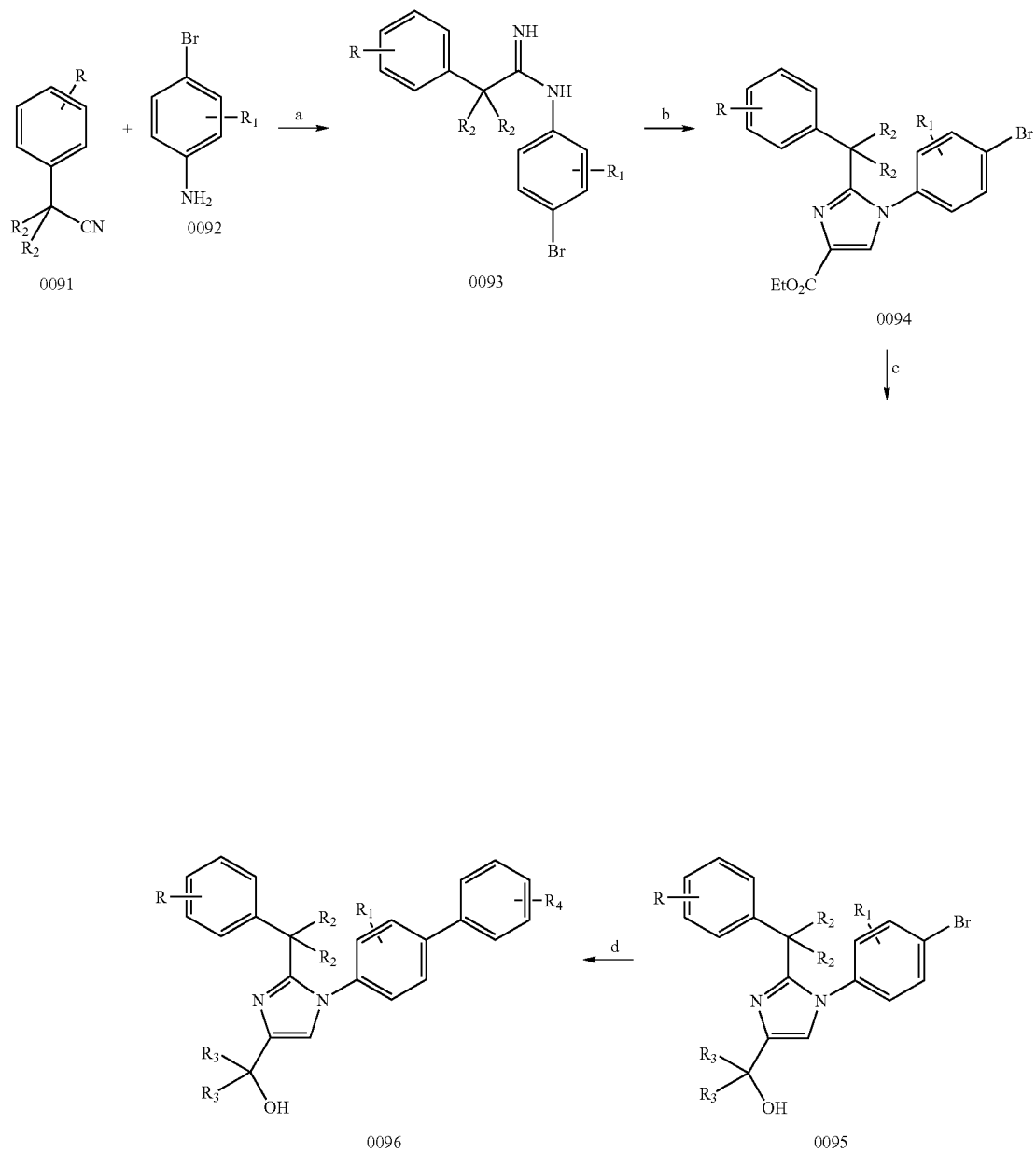
Scheme 9
(a) Me₃Al, Toluene, 0° C.-80° C.; (b) Ethyl bromopyruvate, NaHCO₃ EtOH, 80° C.; (c) R₃MgBr, THF, 0° C.-rt; (d) ArB(OH)₂, K₂CO₃, PdCl₂(dppf), DME/H₂O, 80° C.

In general, compounds of formula (0096) are prepared by first reacting aniline of formula (0092) with benzyl cyanide (0091), such as 2,3-dichlorobenzyl cyanide, in the presence of base to give compounds of formula (0093) after standard isolation procedures. In a subsequent step, exposure of amidine (0093) to haloester, such as ethyl α-bromopyruvate, under basic condition at elevated temperature provides 1H-imidazole of formula (0094) after standard isolation procedures. Compounds of formula (0094) are then subjected to functionality transformation, such as from ester to carbinol. In a palladium mediated coupling reaction, for example Suzuki reactions, compounds of formula (0095) are then reacted with a diboronate or boronic acid reagent to give compounds of formula (0096) after standard isolation procedures.

EXAMPLE 11

2-{2-[(2-fluorophenyl)methyl]-1-[3'-(methylsulfonyl)biphenyl-4-yl]-1H-imidazol-4-yl}propan-2-ol

EXAMPLE 11a

Preparation of N-(4-bromophenyl)-2-(2-chlorophenyl)acetimidamide

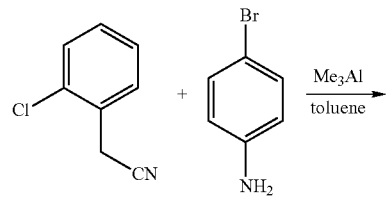

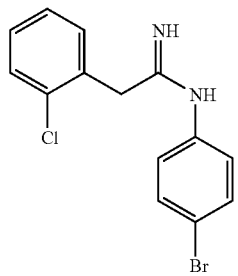

4-Bromoaniline (6.4 g, 37 mmol) was placed into a three-neck reactor, and the reactor was flushed with argon for 20 min. 60 mL anhydrous toluene was added. After cooling to 0° C., trimethylaluminum (28 mL, 2.0M solution in toluene, 56 mmol) was added slowly to keep the inner temperature below 20° C. Over 0.5 h, the addition was completed. Ice bath was removed, and the reaction mixture was warmed to room temperature and then stirred for additional 2.5 hrs. A solution of 2-chlorobenzyl cyanide (8.4 g, 55 mmol) in 35 mL anhydrous toluene was added, and the reaction mixture was heated to 80° C. After 18 hrs, the reaction mixture was cooled to room temperature and poured over a slurry of silica gel in CHCl$_3$/MeOH (4/1, 400 mL). After stirring for 30 min, the mixture was filtered and the residue was washed with a mixture of CHCl$_3$/MeOH (4/1). The combined filtrates were concentrated in vacuo, and the resulting solid was washed with hexane to give a light pink solid (5.78 g, 48% yield).

EXAMPLE 11b

Preparation of ethyl 1-(4-bromophenyl)-2-(2-chlorobenzyl)-1H-imidazole-4-carboxylate

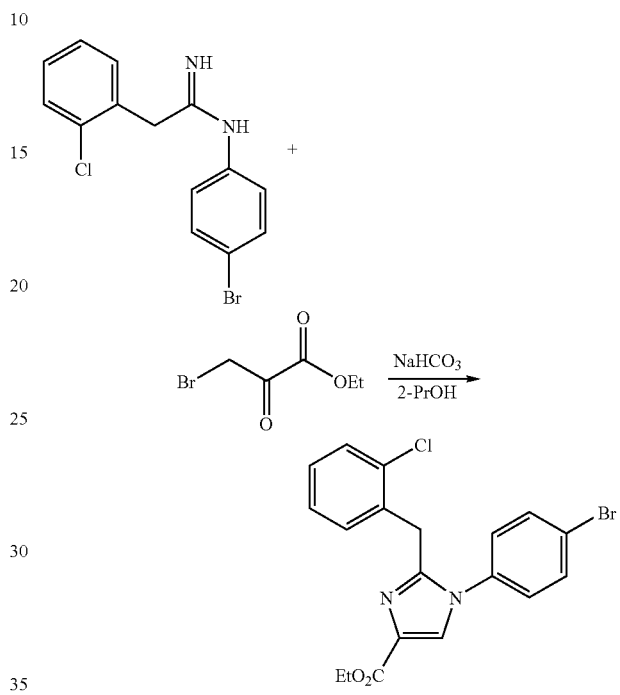

To a mixture of N-(4-Bromo-phenyl)-2-(2-chloro-phenyl)-acetamidine (5.78 g, 17.9 mmol, from above reaction) and sodium bicarbonate (3.0 g, 36 mmol) in 50 mL 2-proponal was added ethyl α-bromopyruvate (7.8 g, 36 mmol, 90% tech.). The mixture was heated to 80° C. overnight, and then cooled to room temperature. The supernatant was decanted and concentrated in vacuo. The residue was redissolved into dichloromethane, and then filtered. The precipitate was washed several times with dichloromethane. The combined filtrates were concentrated down. The crude product was purified by column chromatography on silica gel (30→50% EtOAc/Hexane) to give a brown solid (1.75 g, 23% yield).

EXAMPLE 11c

Preparation of 2-(1-(4-bromophenyl)-2-(2-chlorobenzyl)-1H-imidazol-4-yl)propan-2-ol

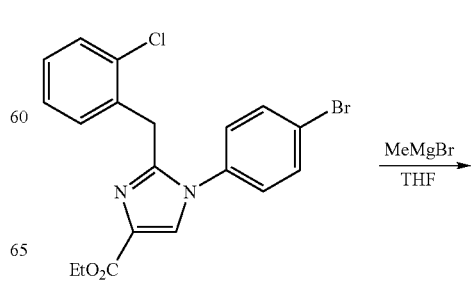

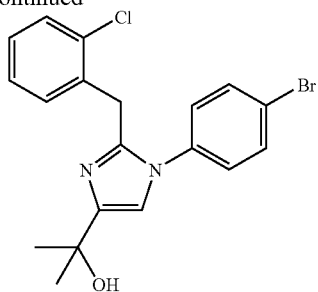

Methylmagnesium bromide (13 ml, 18.6 mmol, 1.4M in toluene/THF 75:25) was placed into a three-neck flask. Under nitrogen at 0° C. to it was added a solution of 1-(4-Bromophenyl)-2-(2-chloro-benzyl)-1H-imidazole-4-carboxylic acid ethyl ester (1.74 g, 4.1 mmol) in 15 mL THF. After the addition, the ice bath was removed and the reaction mixture was stirred at room temperature for 3 hrs. The reaction was quenched with sat. Ammonium chloride. Two layers were separated, and the aqueous layer was extracted three times with ethyl acetate. The combined organic layers were washed with brine, dried over $Na_2SO_4$, and concentrated in vacuo. The crude product was purified by column chromatography on silica gel (30→50% EtOAc/Hexane) to give a yellow solid (600 mg, 36% yield).

EXAMPLE 11d

Preparation of 2-(2-(2-chlorobenzyl)-1-(3'-(methylsulfonyl)biphenyl-4-yl)-1H-imidazol-4-yl)propan-2-ol

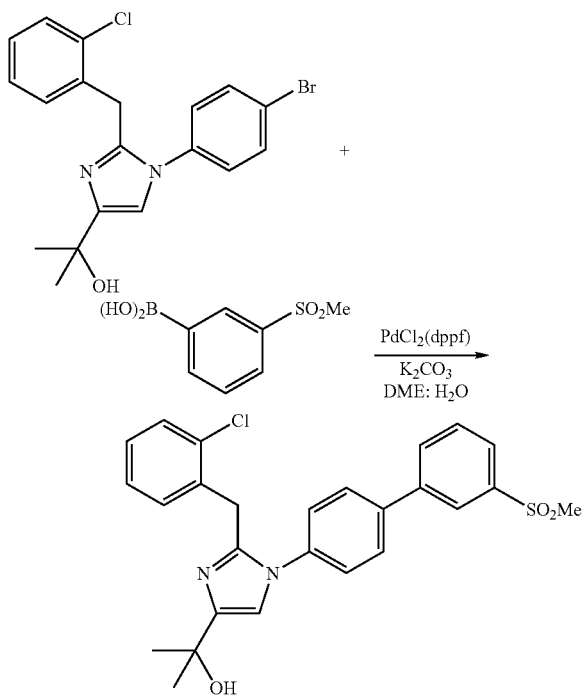

2-[1-(4-Bromo-phenyl)-2-(2-chloro-benzyl)-1H-imidazol-4-yl]-propan-2-ol (202 mg, 0.5 mmol), (3-methylsulfonyl)phenylboronic acid (200 mg, 1.0 mmol), potassium carbonate (311 mg, 2.3 mmol), and $PdCl_2$ (dppf).$CH_2Cl_2$ (42 mg, 0.05 mmol) were mixed with 5 mL 9:1 DME/$H_2O$ (v/v), then heated at 80° C. overnight. All solvent was removed in vacuo. The crude product was purified by chromatography on silica gel (50→95% EtOAc/Hexane) to give a white solid (158 mg, 66% yield). 1H-NMR (400 MHz, d-DMSO): δ 1.43 (s, 6H), 3.30 (s, 3H), 4.13 (s, 2H), 4.73 (s, 1H), 7.11-7.09 (m, 1H), 7.13 (m, 1H), 7.24-7.20 (m, 2H), 7.37-7.34 (m, 1H), 7.47 (m, 2H), 7.75 (t, 1H, J=7.8), 7.88-7.86 (m, 2H), 7.94-7.92 (m, 1H), 8.08-8.06 (m, 1H), 8.18 (t, 1H, J=1.9). MS (ES): 481.0 $[M+H]^+$.

All the following compounds were made in similar manner using appropriate nitriles and anilines. The boronic acid or boronate reagents for Suzuki coupling, if not commercially available, were made using standard techniques that are readily apparent to one skilled in the art.

2-{2-[(2-fluorophenyl)methyl]-1-[3'-(methylsulfonyl)biphenyl-4-yl]-1H-imidazol-4-yl}propan-2-ol; MS (ES): 465.0 $[M+H]^+$;

2-(1-[3'-(methylsulfonyl)biphenyl-4-yl]-2-{[2-(trifluoromethyl)phenyl]methyl}-1H-imidazol-4-yl)propan-2-ol; MS (ES): 515.3 $[M+H]^+$;

2-{2-[(2-chlorophenyl)methyl]-1-[3'-(methylsulfonyl)biphenyl-4-yl]-1H-imidazol-4-yl}propan-2-ol; MS (ES): 481.0 $[M+H]^+$;

2-{2-[(2-chlorophenyl)methyl]-1-[3'-(ethylsulfonyl)biphenyl-4-yl]-1H-imidazol-4-yl}propan-2-ol; MS (ES): 495.4 $[M+H]^+$;

2-{2-[(2-chlorophenyl)methyl]-1-[4'-(hydroxymethyl)-3'-(methylsulfonyl)biphenyl-4-yl]-1H-imidazol-4-yl}propan-2-ol; MS (ES): 511.4 $[M+H]^+$;

2-{2-[(2,6-dichlorophenyl)methyl]-1-[3'-(methylsulfonyl)biphenyl-4-yl]-1H-imidazol-4-yl}propan-2-ol; MS (ES): 515.3 $[M+H]^+$;

2-{2-[(2,6-dichlorophenyl)methyl]-1-[3'-(ethylsulfonyl)biphenyl-4-yl]-1H-imidazol-4-yl}propan-2-01; MS (ES): 529.3 $[M+H]^+$;

2-{2-[(2,6-dichlorophenyl)methyl]-1-[3'-(ethylsulfonyl)-4'-(hydroxymethyl)biphenyl-4-yl]-1H-imidazol-4-yl}propan-2-ol; MS (ES): 545.3 $[M+H]^+$;

2-{2-[(2-chloro-6-fluorophenyl)methyl]-1-[3'-(methylsulfonyl)biphenyl-4-yl]-1H-imidazol-4-yl}propan-2-ol; MS (ES): 499.5 $[M+H]^+$;

2-{2-[(2-chloro-6-fluorophenyl)methyl]-1-[3'-(ethylsulfonyl)biphenyl-4-yl]-1H-imidazol-4-yl}propan-2-ol; MS (ES): 513.5 $[M+H]^+$;

2-{2-[(2,3-dichlorophenyl)methyl]-1-[3'-(methylsulfonyl)biphenyl-4-yl]-1H-imidazol-4-yl}propan-2-ol; MS (ES): 15.3 $[M+H]^+$;

2-{2-[(2,3-dichlorophenyl)methyl]-1-[3'-(ethylsulfonyl)biphenyl-4-yl]-1H-imidazol-4-yl}propan-2-ol; MS (ES): 529.3 $[M+H]^+$;

3-{2-[(2-chlorophenyl)methyl]-1-[3'-(methylsulfonyl)biphenyl-4-yl]-1H-imidazol-4-yl}pentan-3-o; MS (ES): 509.3 $[M+H]^+$;

3-{2[(2-chlorophenyl)methyl]1-[3'-(methylsulfonyl)biphenyl-4-yl]-1H-imidazol-4-yl}pentan 3-ol; MS (ES): 523.3 $[M+H]^+$;

3-{2-[(2-chlorophenyl)methyl]-1-[4'-(hydroxymethyl)-3'-(methylsulfonyl)biphenyl-4-yl]-1H-imidazol-4-yl}pentan-3-ol; MS (ES): 539.2 $[M+H]^+$;

2-(2-(5-chloro-2-(trifluoromethyl)benzyl)-1-(3'-(methylsulfonyl)biphenyl-4-yl)-1H-imidazol-4-yl)propan-2-ol; MS (ES): 549.3 $[M+H]^+$;

2-(2-(5-chloro-2-(trifluoromethyl)benzyl)-1-(3'-(ethylsulfonyl)biphenyl-4-yl)-1H-imidazol-4-yl)propan-2-ol; MS (ES): 563.3 $[M+1H]^+$;

2-(2-(5-chloro-2-(trifluoromethyl)benzyl)-1-(4'-(hydroxymethyl)-3'-(methylsulfonyl)biphenyl-4-yl)-1H-imidazol-4-yl)propan-2-ol; MS (ES): 579.2 [M+H]+;

2-(2-(2-(2-chlorophenyl)propan-2-yl)-1-(3'-(methylsulfonyl)biphenyl-4-yl)-1H-imidazol-4-yl)propan-2-ol; MS (ES): 509.0 [M+H]+;

2-(2-(2-(2-chlorophenyl)propan-2-yl)-1-(3'-(ethylsulfonyl)biphenyl-4-yl)-1H-imidazol-4-yl)propan-2-ol; MS (ES): 523.3 [M+H]+;

2-(2-(2-(2,3-dichlorophenyl)propan-2-yl)-1-(3'-(methylsulfonyl)biphenyl-4-yl)-1H-imidazol-4-yl)propan-2-ol; MS (ES): 543.3 [M+H]+;

2-(2-(2-(2,3-dichlorophenyl)propan-2-yl)-1-(3'-(ethylsulfonyl)biphenyl-4-yl)-1H-imidazol-4-yl)propan-2-ol; MS (ES): 557.3 [M+H]+;

2-(2-(2,3-dichlorobenzyl)-1-(3-methyl-3'-(methylsulfonyl)biphenyl-4-yl)-1H-imidazol-4-yl)propan-2-ol; MS (ES): 529.3 [M+H]+;

2-(2-(2,3-dichlorobenzyl)-1-(3'-(ethylsulfonyl)-3-methylbiphenyl-4-yl)-1H-imidazol-4-yl)propan-2-ol; MS (ES): 543.3 [M+H]+;

2-(1-(3-chloro-3'-(methylsulfonyl)biphenyl-4-yl)-2-(2,3-dichlorobenzyl)-1H-imidazol-4-yl)propan-2-ol; MS (ES): 549.3 [M+H]+;

2-(1-(3-chloro-3'-(ethylsulfonyl)biphenyl-4-yl)-2-(2,3-dichlorobenzyl)-1H-imidazol-4-yl)propan-2-ol; MS (ES): 565.2 [M+H]+;

2-(2-(2,3-dichlorobenzyl)-1-(3-fluoro-3'-(methylsulfonyl)biphenyl-4-yl)-1H-imidazol-4-yl)propan-2-ol; MS (ES): 533.0 [M+H]+;

2-(2-(2,3-dichlorobenzyl)-1-(3'-(ethylsulfonyl)-3-fluorobiphenyl-4-yl)-1H-imidazol-4-yl)propan-2-ol; MS (ES): 547.3 [M+H]+;

2-(1-(3-chloro-3'-(methylsulfonyl)biphenyl-4-yl)-2-(2-(2,3-dichlorophenyl)propan-2-yl)-1H-imidazol-4-yl)propan-2-ol; MS (ES): 579.3 [M+H]+;

2-(1-(3-chloro-3'-(ethylsulfonyl)biphenyl-4-yl)-2-(2-(2,3-dichlorophenyl)propan-2-yl)-1H-imidazol-4-yl)propan-2-ol; MS (ES): 593.3, 595.3 [M+H];

2-(2-(5-chloro-2-fluorobenzyl)-1-(3'-(methylsulfonyl)biphenyl-4-yl)-1H-imidazol-4-yl)propan-2-ol; MS (ES): 499.3, [M+H]+; 521.3 [M+Na]+;

2-(2-(5-chloro-2-fluorobenzyl)-1-(3'-(ethylsulfonyl)biphenyl-4-yl)-1H-imidazol-4-yl)propan-2-ol; MS (ES): 535.0 [M+Na]+;

2-(1-(2'-chloro-3-methyl-5'-(methylsulfonyl)biphenyl-4-yl)-2-(2,3-dichlorobenzyl)-1H-imidazol-4-yl)propan-2-ol; MS (ES): 563, 565 [M+H]+.

The following compounds were made in a similar manner, except the boronic acid or boronate reagents for the Suzuki coupling were made as described in Examples 23-29.

2-{1-[3-chloro-4'-(methyloxy)-3'-(methylsulfonyl)biphenyl-4-yl]-2-[(2,3-dichlorophenyl)methyl]-1H-imidazol-4-yl}propan-2-ol; MS (ES): 579, 581, 583 each [M+H]+.

2-{2-[(2,3-dichlorophenyl)methyl]-1-[3-methyl-4'-(methyloxy)-3'-(methylsulfonyl)biphenyl-4-yl]-1H-imidazol-4-yl}propan-2-ol; MS (ES): 559, 561 [each [M+H]+.

2-(1-(2'-chloro-3-methyl-5'-(methylsulfonyl)biphenyl-4-yl)-2-(2,3-dichlorobenzyl)-1H-imidazol-4-yl)propan-2-ol; MS (ES): 563, 565 [M+H]+

The following compounds were made in similar manner, except appropriate propionitrile was used as starting material, instead of benzyl cyanide.

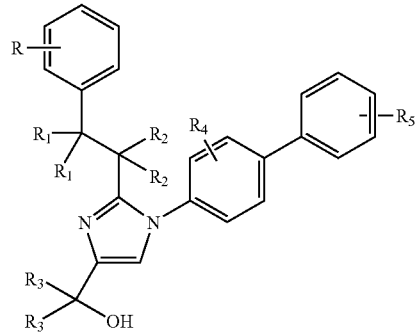

2-{2-[2-(2-chlorophenyl)ethyl]-1-[3'-(methylsulfonyl)biphenyl-4-yl]-1H-imidazol-4-yl}propan-2-ol; MS (ES): 495.4 [M+H]+;

2-{2-[2-(2-chlorophenyl)ethyl]-1-[3'-(ethylsulfonyl)biphenyl-4-yl]-1H-imidazol-4-yl}propan-2-ol; MS (ES): 509.3 [M+H]+;

2-{2-[2-(2-chlorophenyl)ethyl]-1-[4'-(hydroxymethyl)-3'-(methylsulfonyl)biphenyl-4-yl]-1H-imidazol-4-yl}propan-2-ol; MS (ES): 525.3 [M+H]+.

EXAMPLE 12

1,1,1-trifluoro-2-(1-(3'-(methylsulfonyl)biphenyl-4-yl)-2-(2-(trifluoromethyl)phenyl)-1H-imidazol-4-yl)propan-2-ol EXAMPLE 12a Preparation of 2-[1-(4-bromophenyl)-2-(2-trifluoromethyl-phenyl)-1H-imidazol-4-yl]-1,1-trifluoropropan-2-ol

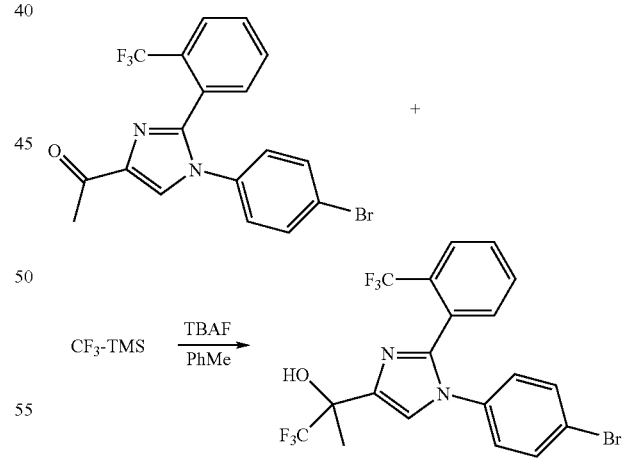

To a solution of 1-[1-(4-bromophenyl)-2-(2-trifluoromethyl-phenyl)-1H-imidazol-4-yl]-ethanone (0.24 g, 0.59 mmol) and trifluoromethyl-trimethylsilane (0.10 mL, 0.68 mmol) in toluene (3 mL, anhyd) at 0° C. was added a 1.0M solution of tetrabutylammonium fluoride (TBAF) in THF (0.12 mL, 20 mol %, dried over 4 Å molecular sieves). After 24 h the reaction mixture was charged with additional trifluoromethyl-trimethylsilane (0.10 mL) and 1.0M TBAF (0.12 mL) and then heated at 50° C. After 48 h (total) the reaction mixture was allowed to cool to ambient temperature, quenched with H₂O and extracted with DCM (2×30 mL). The combined extracts were dried (Na₂SO₄), concentrated and purified by chromatography (silica, EtOAc/Hex, 20:80 to 60:40) to yield the title compound (0.11 g, 39%) as a white solid. ¹H-NMR (DCM-d₂): δ 7.76 (d, 1H), 7.50-7.60 (m, 2H), 7.46 (d, 2H), 7.27 (m, 2H), 7.02 (d, 2H), 4.36 (s, 1H), 1.72 (s, 3H).

EXAMPLE 12b

Preparation of 1,1-trifluoro-2-(1-(3'-(methylsulfonyl)biphenyl-4-yl)-2-(2-(trifluoromethyl)phenyl)-1H-imidazol-4-yl)propan-2-ol

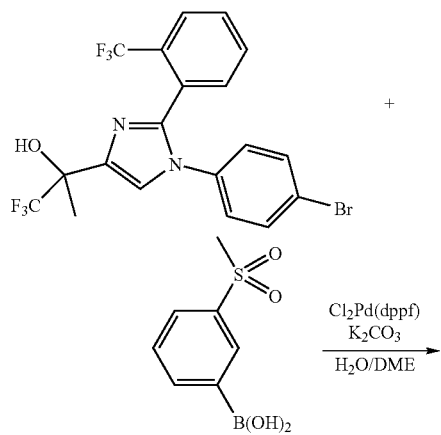

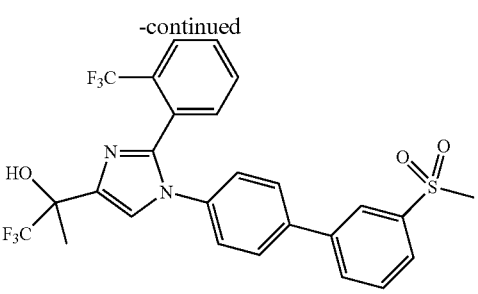

A mixture of 2-[1-(4-bromophenyl)-2-(2-trifluoromethyl-phenyl)-1H-imidazol-4-yl]-1,1,1-trifluoro-propan-2-ol (0.11 g, 0.23 mmol), 3-methanesulfonyl-phenylboronic acid (54 mg, 0.27 mmol), K₂CO₃ (95 mg, 0.69 mmol), Cl₂ Pd(dppf) .DCM (15 mg, 8 mol %) and H₂O (0.25 mL) in DME (2.5 mL) was sparged with Argon for 5 min and then heated at 80° C. as a sealed flask. After 90 min the reaction mixture was allowed to cool to ambient temperature, filtered (Celite™) and the filter agent rinsed with EtOAc. The combined filtrates were concentrated under reduced pressure and purified by chromatography (silica, EtOAc/Hex, 35:65 to 80:20) to give the title compound (116 mg, 89%) as a white solid. ¹H-NMR (DCM-d₂): δ 8.09 (m, 1H), 7.91 (m, 1H), 7.84 (m, 1H), 7.78 (d, 1H), 7.66 (m, 1H), 7.59 (d, 2H), 7.49-7.57 (m, 2H), 7.33 (m, 2H), 7.25 (d, 2H), 4.40 (s, 1H), 3.06 (s, 3H), 1.75 (s, 3H); MS (ES): 555 [M+H]⁺.

Scheme 10

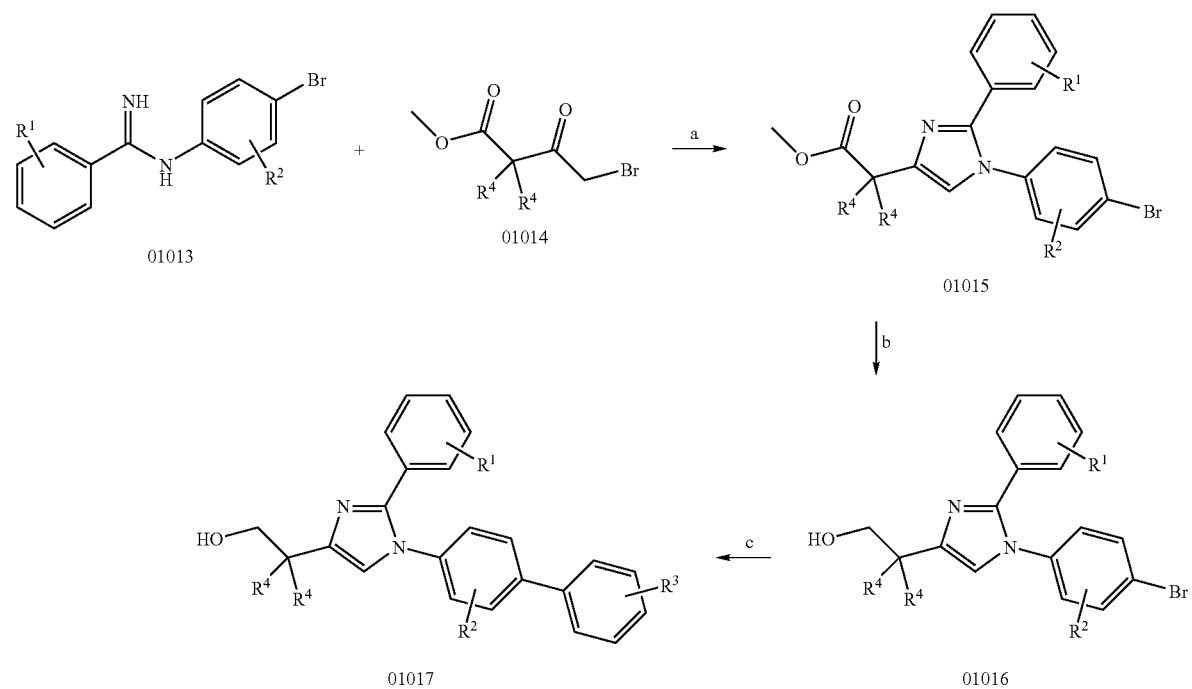

(a) NaHCO₃, 2-PrOH, μW 180° C.; (b) LiBH₄, 10-20 mol% B(OMe)₃, THF; (c) ArB(OH)₂, Cl₂Pd(dppf), K₂CO₃, H₂O/DME, μW 120° C.

In general, compounds of formula 01017 can be prepared as depicted in Scheme 10. First an amidine (01013) and a bromoketone (01014) can react under basic conditions and at elevated temperature to give the corresponding imidazole (01015). This intermediate ester 01015 can be reduced under standard conditions, such as with lithium borohydride and, optionally, catalytic trimethyl borate, to afford the corresponding carbinol (01016). Last intermediate 01016 can undergo cross-couplings reactions, such as a Suzuki-Miyaura reaction with boronic acids (esters), to yield the target imidazole 01017.

EXAMPLE 13

2-[2-(2,6-dichlorophenyl)-1-(3-methanesulfonyl-phenyl)-1-(3'-methanesulfonyl-biphenyl-4-yl)-1H-imidazol-4-yl]-2-met-propan-1-ol

EXAMPLE 13a

Preparation of 2-[1-(4-bromophenyl)-2-(2,6-dichlorophenyl)-1H-imidazol-4-yl]-2-methyl-propionic acid methyl ester

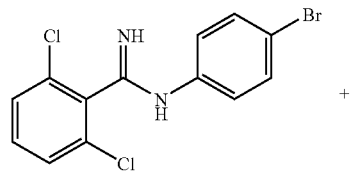

+

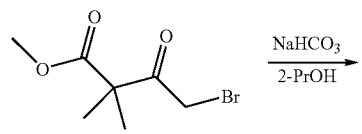

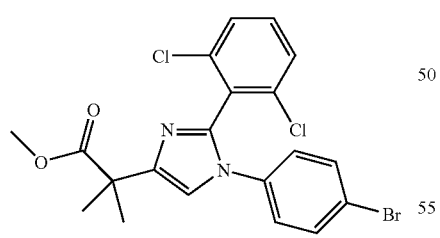

A mixture of N-(4-bromophenyl)-2,6-dichlorobenzamidine (1.03 g, 3.0 mmol), methyl 4-bromo-2,2-dimethylacetoacetate (1.78 g, 8.0 mmol) and NaHCO₃ (0.76 g, 9.0 mmol) in isopropanol (12 mL) was heated in a microwave unit (Biotage Initiator™) at 170° C. for 25 min. The resulting mixture was decanted and the solids rinsed with EtOAc. The combined filtrates were concentrated and purified by chromatography (silica, EtOAc/Hex, 15:85 to 50:50) to give the title compound (0.80 g, 57%) as a pale yellow solid. $^1$H-NMR (DCM-d₂): δ 7.44 (d, 2H), 7.27-7.34 (m, 3H), 7.09 (m, 2-1), 3.67 (s, 3H), 1.61 (s, 6H); MS (ES): 467, 469, 471 [M+H]⁺.

EXAMPLE 13b

Preparation of 2-[1-(4-bromophenyl)-2-(2,6-dichlorophenyl)-1H-imidazol-4-yl]-2-methyl-propan-1-ol

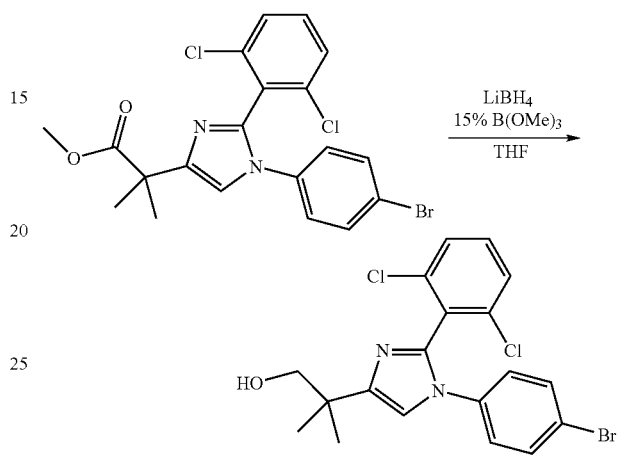

To a stirred suspension of 2-[1-(4-bromophenyl)-2-(2,6-dichlorophenyl)-1H-imidazol-4-yl]-2-methyl-propionic acid methyl ester (0.65 g, 1.4 mmol) in Et₂O (3.5 mL, anhyd) added dropwise 2.0M solution of lithium borohydride in THF (1.4 mL, 2.8 mmol) and then added trimethyl borate (22 L, 15 mol %). After 3 h the reaction mixture was quenched with 1N NaOH (4 mL) and extracted with EtOAc (2×20 mL). The combined extracts were washed with satd NH₄Cl and brine, dried (Na₂SO₄), concentrated and purified by chromatography (silica, EtOAc/Hex, 15:85 to 50:50) to yield a white solid (0.21 g) consisting of a 2:1 mixture of the title compound, MS (ES): 439, 441, 443 [M+H]⁺, and 2-[2-(2,6-dichlorophenyl)-1-phenyl-1H-imidazol-4-yl]-2-methyl-propan-1-ol, MS (ES): 361, 363 [M+H]⁺.

The latter resulted from over-reduction of the title compound under the given conditions. The isolated product was used in the next step without further purification.

EXAMPLE 13c

Preparation of 2-[2-(2,6-dichlorophenyl)-1-(3'-methanesulfonyl-biphenyl-4-yl)-1H-imidazol-4-yl]-2-methyl-propan-1-ol

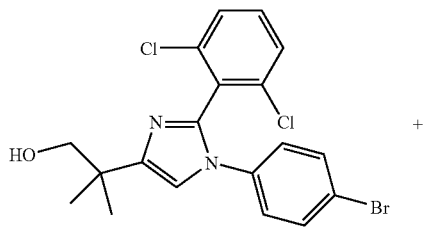 +

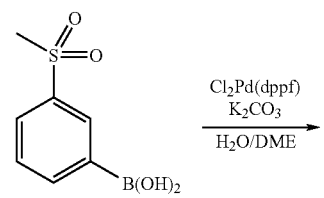

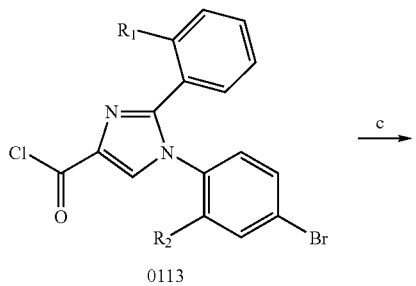

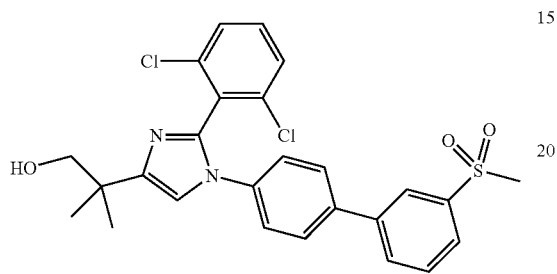

A stirred mixture of 2-[1-(4-bromophenyl)-2-(2,6-dichlorophenyl)-1H-imidazol-4-yl]-2-methyl-propan-1-ol (202 mg, 0.46 mmol), 3-methanesulfonyl-phenylboronic acid (92 mg, 0.46 mmol), potassium carbonate (0.19 g, 1.4 mmol), $Cl_2$Pd(dppf).DCM (19 mg, 5 mol %) and $H_2O$ (0.25 mL) in DME (2.5 mL) was sparged with Argon for 5 min and then heated at 60° C. as a sealed flask. After 30 min the reaction mixture was concentrated under reduced pressure and purified by chromatography (silica, EtOAc/Hex, 40:60 to 75:25) to give the title compound (35 mg) as a white solid. $^1$H-NMR (DCM-$d_2$): δ 8.10 (m, 1H), 7.91 (d, 1H), 7.85 (d, 1H), 7.66 (m, 1-1), 7.60 (d, 2H), 7.29-7.37 (m, 5H), 7.10 (s, 1H), 3.79 (br s, 1H), 3.62 (s, 2H), 3.06 (s, 3H), 1.36 (s, 6H); MS (ES): 515, 517 [M+H]$^+$.

Scheme 11.

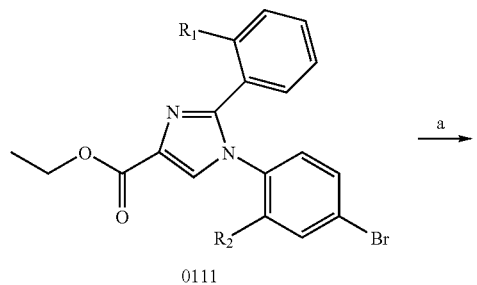

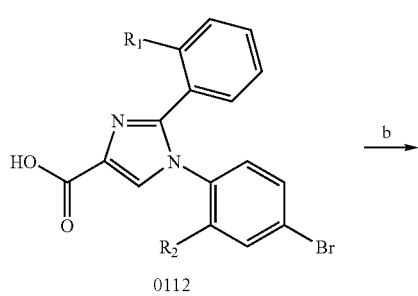

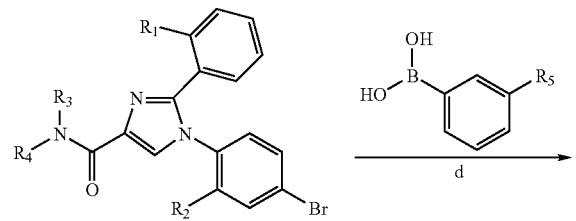

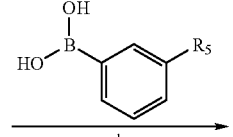

(a) aq NaOH, MeOH; (b) (COCl)$_2$, DCM, DMF; (c) R$_3$R$_4$NH, CHCl$_3$, DIEA; (d) PdCl$_2$dppf, K$_2$CO$_3$, DME, H$_2$O In general, amide containing compounds of formula (0115) can be synthesized following the methodology shown in Scheme 11. The ester group in compound (0111) can be hydrolyzed under aqueous basic conditions to give the carboxylic acid (0112). Acid (0112) can be converted to an acid chloride (0113) using known procedures followed by reaction with a primary or secondary amine to provide amide intermediate (0114). The amide intermediate (0114) can undergo cross coupling transformations to afford the corresponding 2-biaryl-imidazole (0115).

EXAMPLE 14

2-(2-Chloro-phenyl)-1-(3'-methanesulfonyl-biphenyl-4-yl)-1H-imidazole-4-carboxylic acid (2,2,2-trifluoro-ethyl)-amide

EXAMPLE 14a

Preparation of 1-(4-Bromo-phenyl)-2-(2-chloro-phenyl)-1H-imidazole-4-carboxylic acid

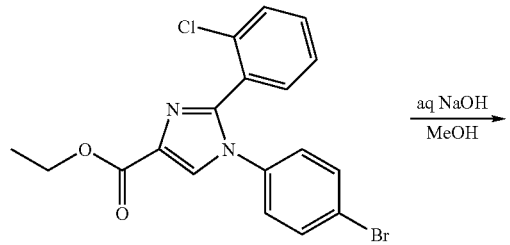

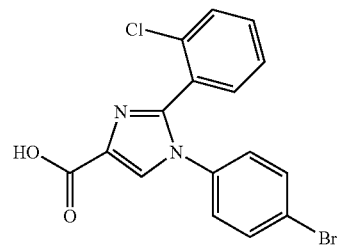

To a 100 mL round bottom flask was added 1-(4-Bromophenyl)-2-(2-chloro-phenyl)-1H-imidazole-4-carboxylic acid ethyl ester (1.03 g, 2.54 mmol), MeOH (20 mL), and 1N aq NaOH (10 mL). The reaction solution was allowed to stir at 45° C. for 1 hr prior to analysis by LCMS. The reaction solution was diluted with EtOAc (150 mL), poured into a separatory funnel and the organic phase was partitioned. The aqueous phase was neutralized by the addition of aq 1 N HCl and extracted with EtOAc (70 mL×2). The combined organic phase was dried over $Na_2SO_4$, filtered into a round bottom flask and concentrated on the Rotavapor. The crude residue was chromatographed thru a 25 g $SiO_2$ column using a mobile phase gradient of 100% Hx to 85% EtOAc to afford 845 mg (88% yield) carboxylic acid intermediate. MS (ES): 378 $[M+H]^+$.

EXAMPLE 14b

Preparation of 1-(4-Bromo-phenyl)-2-(2-chloro-phenyl)-1H-imidazole-4-carboxylic acid (2,2,2-trifluoroethyl)-amide

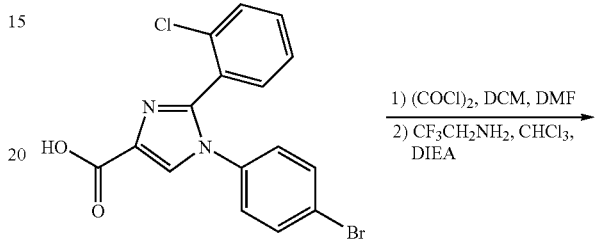

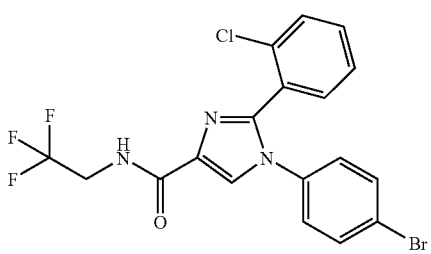

To a dry, $N_2$ purged 100 mL round bottom flask was added 1-(4-Bromo-phenyl)-2-(2-chloro-phenyl)-1H-imidazole-4-carboxylic acid (845 mg, 2.24 mmol), and (10 mL) anhydrous DCM. The solution was cooled to 0° C. prior to addition of oxalyl chloride (590 µL, 6.7 mmol) and several drops anhydrous DMF. The reaction solution was allowed to stir warming to rt over 2 hrs. The solvent and excess reagent was removed in vacuo. To the crude acid chloride residue was added anhydrous $CHCl_3$ (15 mL), 2,2,2-trifluoroethylamine (700 mg, 6.70 mmol) and DIEA (1.3 mL, 7.46 mmol). The reaction solution was allowed to stir at 40° C. for approx 1 hr. The reaction solution was diluted with DCM (70 mL) and transferred to a separatory funnel. The solution was washed with aq $NH_4Cl$ (50 mL×2) and with aq NaCl (50 mL). The organic phase was dried over $Na_2SO_4$, filtered, concentrated on the Rotavapor and chromatographed through a 25 g $SiO_2$ column using a mobile phase gradient of 100% Hx to 70% EtOAc to afford 840 mg (82% yield) of amide product. MS (ES): 461 [M+H]+.

EXAMPLE 14c

Preparation of 2-(2-Chloro-phenyl)-1-(3'-methanesulfonyl-biphenyl-4-yl)-1H-imidazole-4-carboxylic acid (2,2,2-trifluoro-ethyl)-amide

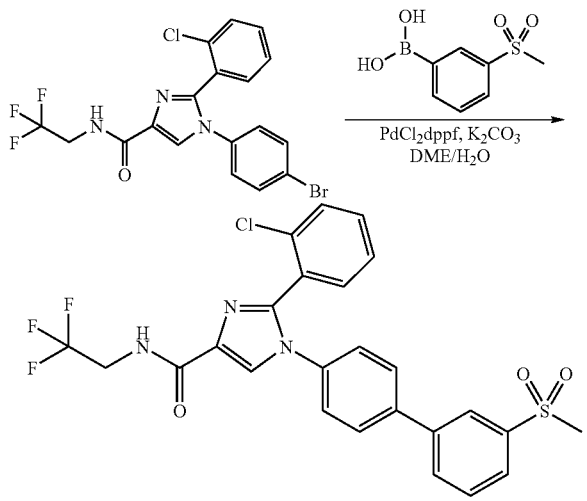

To a 50 mL round bottom flask attached with Vigreux column and magnetic stir bar was added 1-(4-Bromo-phenyl)-2-(2-chloro-phenyl)-1H-imidazole-4-carboxylic acid (2,2,2-trifluoro-ethyl)-amide (249 mg, 540 μmol), 3-methylsulfonylphenyl boronic acid (130 mg, 650 μmol), PdCl$_2$dppf (40 mg, 10 mol %), K$_2$CO$_3$ (260 mg, 1.90 mmol), 1,2-dimethoxyethane (14 mL) and H$_2$O (2 mL). The reaction solution was allowed to stir at 75° C. for 2 hrs. The reaction solution was diluted with EtOAc (150 mL) and filtered through a Celite padded Buchner funnel to remove spent Pd. The filtrate was transferred to a separatory funnel and washed with aq NH$_4$Cl (100 mL) and aq NaCl (100 mL). The organic phase was dried over Na$_2$SO$_4$, filtered, concentrated on the Rotavapor and chromatographed through a 25 g SiO$_2$ column using a mobile phase gradient of 2% EtOAc to 90% EtOAc to afford 212 mg (74% yield) of the title compound. MS (ES): 534 [M+H]+, 557 [M+Na]+. $^1$H NMR (400 MHz, CDCl$_3$): δ 8.13 (s, 1H), 7.99 (s, 1H), 7.92 (d, 1H), 7.65 (t, 1H), 7.57 (d, 2H), 7.52 (d, 2H), 7.41-7.34 (m, 3H), 7.24 (d, 2H), 4.11 (q, 2H), 3.08 (s, 3H); $^{19}$F NMR (400 MHz, CDCl$_3$) 6-72.4 ppm.

The following compounds were prepared in a manner similar to that described in experimental procedure Example 14:

2-(2-isopropylphenyl)-1-(3-methyl-3'-(methylsulfonyl)biphenyl-4-yl)-N-(2,2,2-trifluoroethyl)-1H-imidazole-4-carboxamide; MS (ES): 556.3 [M+H]+.

2-(2,6-dichlorophenyl)-1-(3-methyl-3'-(methylsulfonyl)biphenyl-4-yl)-N-(2,2,2-trifluoroethyl)-1H-imidazole-4-carboxamide; MS (ES): 582.2, 584.2 [M+H]+.

2-(2,6-dichlorophenyl)-1-(3'-(ethylsulfonyl)-3-methylbiphenyl-4-yl)-N-(2,2,2-trifluoroethyl)-1H-imidazole-4-carboxamide; MS (ES): 596.3, 598.3 [M+H]+.

2-(2,6-dichlorophenyl)-N,N-diethyl-1-(3-methyl-3'-(methylsulfonyl)biphenyl-4-yl)-1H-imidazole-4-carboxamide; MS (ES): 556.3, 558.3 [M+H]+.

2-(2,6-dichlorophenyl)-1-(3'-(methylsulfonyl)biphenyl-4-yl)-N-(2,2,2-trifluoroethyl)-1H-imidazole-4-carboxamide; MS (ES): 568.2, 570.2 [M+H]+.

2-(2,6-dichlorophenyl)-N-(2-fluoroethyl)-1-(3'-(methylsulfonyl)biphenyl-4-yl)-1H-imidazole-4-carboxamide; MS (ES): 532, 534 [M+H]+.

2-(2,6-dichlorophenyl)-N-ethyl-1-(3'-(methylsulfonyl)biphenyl-4-yl)-1H-imidazole-4-carboxamide; MS (ES): 514.3, 516.3 [M+H]+.

(2-(2,6-dichlorophenyl)-1-(3'-(methylsulfonyl)biphenyl-4-yl)-1H-imidazol-4-yl)(4-methylpiperazin-1-yl)methanone; MS (ES): 569.2, 571.3 [M+H]+.

2-(2,6-dichlorophenyl)-N-(2-hydroxyethyl)-1-(3'-(methylsulfonyl)biphenyl-4-yl)-1H-imidazole-4-carboxamide; MS (ES): 530.3, 5302.3 [M+H]+.

1-(3-chloro-3'-(methylsulfonyl)biphenyl-4-yl)-2-(2,6-dichlorophenyl)-N-(2,2,2-trifluoroethyl)-1H-imidazole-4-carboxamide; MS (ES): 602.0, 604.0, 606.3 [M+H]+.

1-(3-chloro-3'-(methylsulfonyl)biphenyl-4-yl)-2-(2,6-dichlorophenyl)-N-(2-fluoroethyl)-1H-imidazole-4-carboxamide; MS (ES): 566.3, 568.3, 570.2 [M+H]+.

2-(1-(3-chloro-3'-(methylsulfonyl)biphenyl-4-yl)-2-(2,6-dichlorophenyl)-1H-imidazole-4-carboxamido)acetic acid; MS (ES): 578.3, 580.3, 582.3 [M+H]+.

1-(3-chloro-3'-(ethylsulfonyl)biphenyl-4-yl)-2-(2,6-dichlorophenyl)-N-(2,2,2-trifluoroethyl)-1H-imidazole-4-carboxamide; MS (ES): 616.0, 618.0, 620.0 [M+H]+.

1-(3-chloro-3'-(methylsulfonyl)biphenyl-4-yl)-2-(2,6-dichlorophenyl) N (1-hydroxy-2-methylpropan-2-yl)-1H-imidazole-4-carboxamide; MS (ES): 592.0, 594.0, 596.2 [M+H]+

1-(3-chloro-3'-(ethylsulfonyl)biphenyl-4-yl)-2-(2,6-dichlorophenyl)-N-(1-hydroxy-2-methylpropan-2-yl)-1H-imidazole-4-carboxamide; MS (ES): 606.3, 608.3, 610.0 [M+H]+

N-tert-butyl-1-(3-chloro-3'-(methylsulfonyl)biphenyl-4-yl)-2-(2,6-dichlorophenyl)-1H-imidazole-4-carboxamide; MS (ES): 576.3, 578.3, 580.3 [M+H]+

1-(3-chloro-3'-(methylsulfonyl)biphenyl-4-yl)-2-(2,6-dichlorophenyl)-N-(2-hydroxyethyl)-1H-imidazole-4-carboxamide; MS (ES): 564.2, 566.2, 568.3 [M+H]+

1-(3-chloro-3'-(ethylsulfonyl)biphenyl-4-yl)-2-(2,6-dichlorophenyl)-N-(2-hydroxyethyl)-1H-imidazole-4-carboxamide; MS (ES): 578.3, 580.3, 582.2 [M+H]+

1-(3-chloro-3'-(methylsulfonyl)biphenyl-4-yl)-2-(2,6-dichlorophenyl)-N-(2-hydroxy-2-methylpropyl)-1H-imidazole-4-carboxamide; MS (ES): 592.3, 594.3, 596.0 [M+H]+

1-(3-chloro-3'-(ethylsulfonyl)biphenyl-4-yl)-2-(2,6-dichlorophenyl)-N-(2-hydroxy-2-methylpropyl)-1H-imidazole-4-carboxamide; MS (ES): 606.2, 608.2, 610.2 [M+H]+

2-(2,6-dichlorophenyl)-N-(1-hydroxy-2-methylpropan-2-yl)-1-(3'-(methylsulfonyl)biphenyl-4-yl)-1H-imidazole-4-carboxamide; MS (ES): 558.3, 560.3 [M+H]+

2-(2,6-dichlorophenyl)-1-(3'-(ethylsulfonyl)biphenyl-4-yl)-N-(1-hydroxy-2-methylpropan-2-yl)-1H-imidazole-4-carboxamide; MS (ES): 572.3, 574.3 [M+H]+

N-tert-butyl-2-(2,6-dichlorophenyl)-1-(3'-(methylsulfonyl)biphenyl-4-yl)-1H-imidazole-4-carboxamide; MS (ES): 542.3, 544.3 [M+H]+

Scheme 12

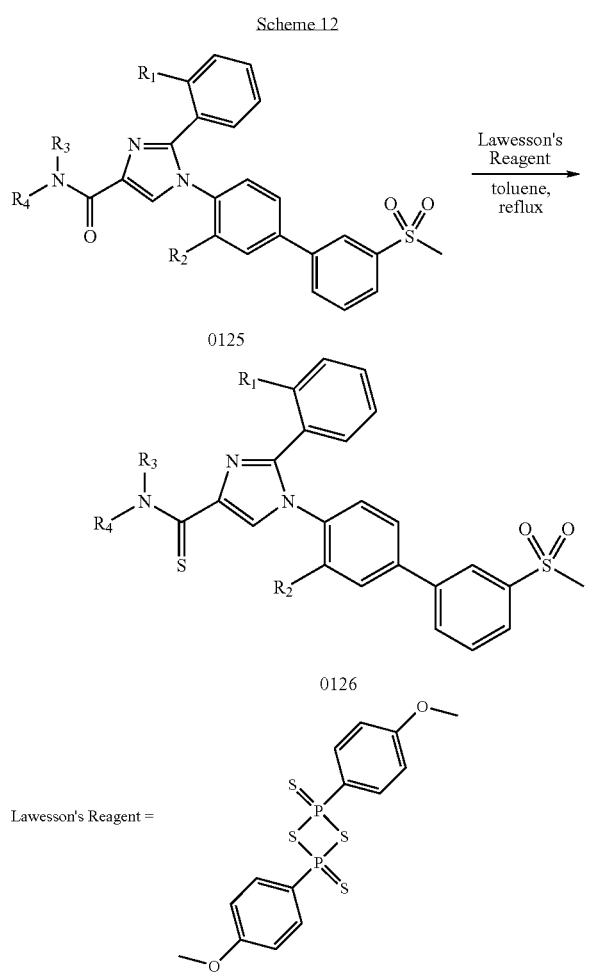

In general, carboxylic acid amides of formula (0125) can be converted to the thioamide derivative (0126) as shown in Scheme 12. The functional transformation can be carried out using a suitable thiation reagent, such as Lawesson's reagents or related compound.

EXAMPLE 15

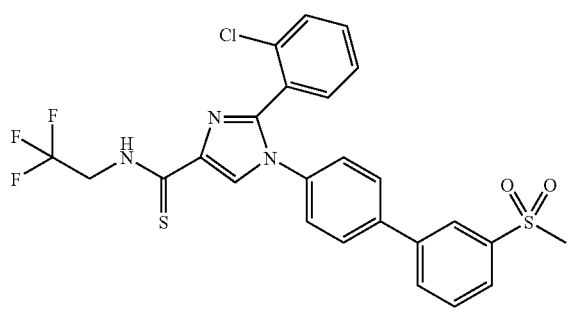 [SMILES: CS(=O)(=O)c1cccc(-c2ccc(-n3cc(C(=S)NCC(F)(F)F)nc3-c3ccccc3Cl)cc2)c1]

Preparation of 2-(2-Chloro-phenyl)-1-(3'-methanesulfonyl-biphenyl-4-yl)-1H-imidazole-4-carbothioic acid (2,2,2-trifluoro-ethyl)-amide To a 25 mL round bottom flask attached with Vigreux column and magnetic stir bar was added 2-(2-Chloro-phenyl)-1-(3'-methanesulfonyl-biphenyl-4-yl)-1H-imidazole-4-carboxylic acid (2,2,2-trifluoro-ethyl)-amide (65 mg, 127 μmol), Lawesson's Reagent (230 mg, 570 μmol), and anhydrous toluene (6 mL). The reaction solution was allowed to stir at reflux 5 hrs prior to TLC analysis showing full transformation of starting material. The reaction solution was allowed to cool to room temperature prior to addition of a 1:1 mixture of benzene and Et$_2$O. The resulting precipitate was removed by vacuum filtration through a Buchner funnel. The filtrate was concentrated on the Rotavapor and the crude residue was chromatographed through a 12 g SiO$_2$ column using a mobile phase gradient of 100% Hx to 50% EtOAc to afford 55 mg (79% yield) of the title compound. $^1$H NMR (400 MHz, CDCl$_3$) 9.21 (t, 1H), 8.11 (s, 1H), 8.04 (t, 1H), 7.85 (d, 1H), 7.75 (d, 1H), 7.59 (t, 1H), 7.53-7.46 (m, 4H), 7.34-7.311 (m, 3H), 7.18 (d, 2H), 4.56 (m, 2H), 3.02 (s, 3H); $^{19}$F NMR (400 MHz, CDCl$_3$) 6-70.8 ppm; MS (ES): 550.3, 552.3 [M+H]$^+$.

The following compounds were prepared in a manner similar to that described in experimental procedure Example 15:

2-(2-isopropylphenyl)-1-(3-methyl-3'-(methylsulfonyl)biphenyl-4-yl)-N-(2,2,2-trifluoroethyl)-1H-imidazole-4-carbothioamide; MS (ES): 572.2 [M+H]$^+$ 1-(4-bromophenyl)-2-(2-chlorophenyl)-N-(2,2,2-trifluoroethyl)-1H-imidazole-4-carbothioamide; MS (ES): 474.0, 476.0 [M+H]$^+$

Scheme 13

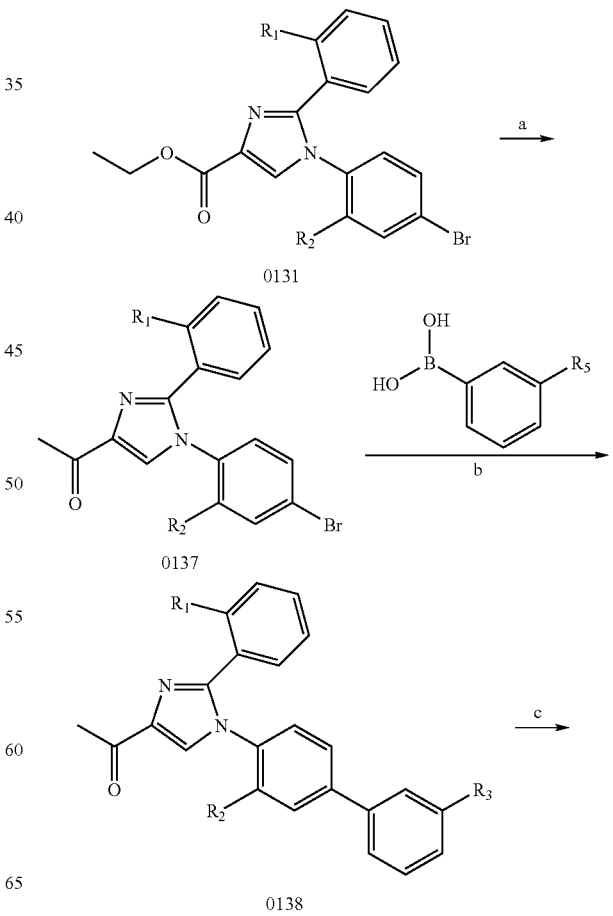

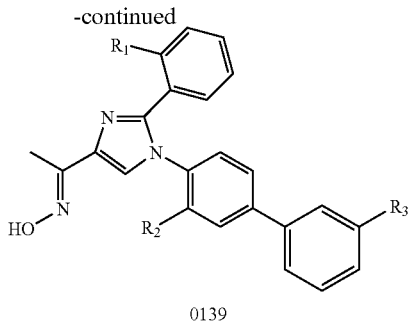

0139
1:1 mixture of
oxime isomers around
the C═N bond (a) (i)Me₃Al, toluene, MeNHCH₂CH₂NHMe, reflux, (ii) aq HCl; (b) PdCl₂dppf, K₂CO₃, DME/H₂O; (c) H₂NOH—HCl, 2:1 MeOH/H₂O, NaOAc, reflux In general, oxime containing compounds of formula (0139) can be prepared as shown in Scheme 13. The imidazole-ester intermediate (0131) can be converted to the methylketone substituted compound (0137) using trimethylaluminium and a diamine chelant, such as N,N,-dimethyl ethylenediamine. Compound (0137) can undergo cross-coupling to install the D-ring to yield final compound (0138). The oxime substituted product (0139) can be prepared by reaction with hydroxylamine under known conditions.

EXAMPLE 16

1-[2-(2-Chloro-phenyl)-1-(3'-methanesulfonyl-biphenyl-4-yl)-1H-imidazol-4-yl]-ethanone oxime

EXAMPLE 16a

Preparation of 1-[1-(4-Bromo-phenyl)-2-(2-chloro-phenyl)-1H-imidazol-4-yl]-ethanone

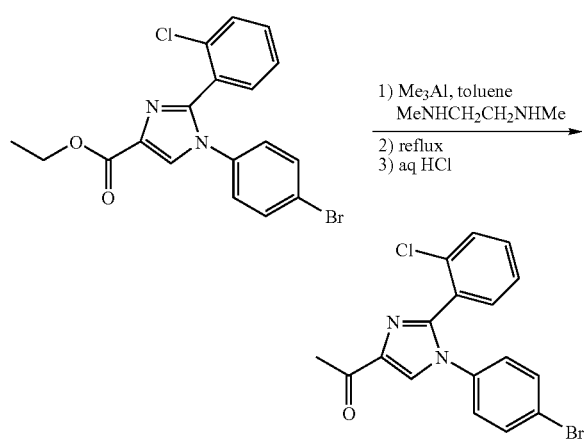

To a dried, N₂ purged 100 mL RB flask, attached with Vigreux column was added anh. toluene (20 mL) and N,N-dimethylethylenediamine (2.2 mL, 1.1 equiv). The solution was cooled to 0° C. prior to dropwise addition of a 2.0 M solution of Me₃Al in hexanes (28 mL, 3.1 equiv). The reaction solution was stirred at room temperature for 40 min prior to the addition of 1-(4-Bromo-phenyl)-2-(2-chloro-phenyl)-1H-imidazole-4-carboxylic acid ethyl ester (7.41 g, 18.3 mmol) in a solution of toluene (10 mL). The reaction solution was allowed to stir at reflux for 2 hrs. The reaction solution was cooled to room temperature and quenched by the addition of IN aq HCl (10 mL). The reaction solution was dilute with EtOAc, partitioned, washed with aq NaCl, dried over Na₂SO₄, filtered, concentrated on the Rotavapor and chromatographed through an 80 g SiO₂ column using a mobile phase gradient of 100% Hx to 75% EtOAc to afford 3.10 g (45% yield) of the methyl ketone intermediate. MS (ES): 376 [M+H]⁺.

EXAMPLE 16b

Preparation of 1-[2-(2-Chloro-phenyl)-1-(3'-methanesulfonyl-biphenyl-4-yl)-1H-imidazol-4-yl]-ethanone

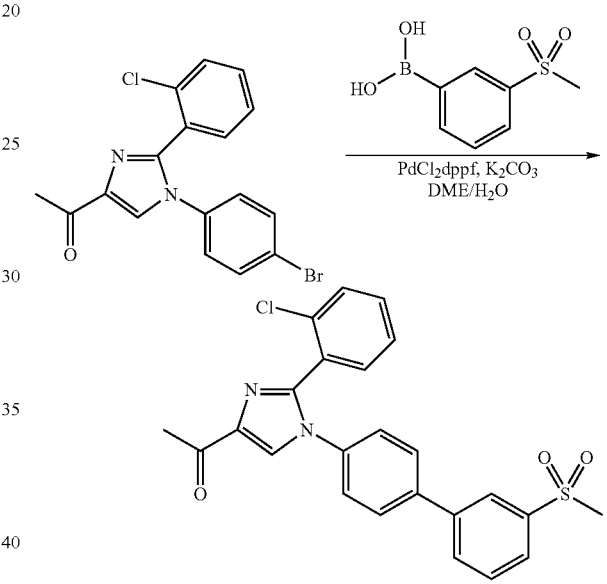

To a 50 mL round bottom flask attached with Vigreux column and magnetic stir bar was added 1-[1-(4-Bromo-phenyl)-2-(2-chloro-phenyl)-1H-imidazol-4-yl]-ethanone (270 mg, 719 mol), 3-methylsulfonylphenyl boronic acid (220 mg, 1.08 mmol), PdCl₂ dppf (55 mg, 10 mol %), K₂CO₃ (300 mg, 2.16 mmol), 1,2-dimethoxyethane (11 mL) and H₂O (1 mL). The reaction solution was allowed to stir at 70° C. for 14 hrs. The reaction solution was diluted with EtOAc (150 mL) and filtered through a Celite padded Buchner funnel to remove spent Pd. The filtrate was transferred to a separatory funnel and washed with aq NH₄Cl (100 mL) and aq NaCl (100 mL). The organic phase was dried over Na₂SO₄, filtered, concentrated on the Rotavapor and chromatographed through a 25 g SiO₂ column using a mobile phase gradient of 100% Hx to 75% EtOAc to afford 170 mg (52% yield) of product. MS (ES): 451 [M+H]⁺, 473 [M+Na]⁺.

The following compounds were synthesized in a manner similar to the above procedure:

1-{1-[3'-(methylsulfonyl)biphenyl-4-yl]-2-[2-(trifluoromethyl)phenyl]-1H-imidazol-4-yl}ethanone; MS (ES): 485.4 [M+H]

1-(2-(2,6-dichlorophenyl)-1-(3'-(methylsulfonyl)biphenyl-4-yl)-1H-imidazol-4-yl)ethanone; MS (ES): 485.3, 487.3 [M+H]$^+$

EXAMPLE 16c

Preparation of 1-[2-(2-Chloro-phenyl)-1-(3'-methanesulfonyl-biphenyl-H-imidazol-4-yl-1H-imidazoyl]-ethanone oxime

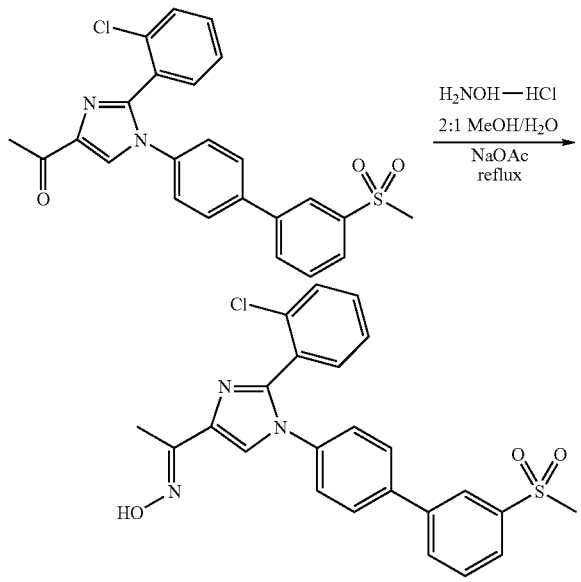

To a 50 mL RB flask attached with Vigreux column was added compound I-[2-(2-Chloro-phenyl)-1-(3'-methanesulfonyl-biphenyl-4-yl)-1H-imidazol-4-yl]-ethanone (162 mg, 359 µmol), hydroxylamine-HCl (200 mg, 2.87 mmol), sodium acetate (238 mg, 2.90 mmol), MeOH (12 mL) and H$_2$O (6 mL). The reaction solution was allowed to stir at reflux for 2 hrs prior to TLC analysis. The reaction solution was diluted with EtOAc (150 mL), washed with aq. NaCl (100 mL), partitioned, dried over Na$_2$SO$_4$, filtered, and concentrated on the Rotavapor. The crude product was chromatographed through a 25 g SiO$_2$ column using a mobile phase gradient of 100% Hx to 80% EtOAc to afford 85 mg (51% yield) of the title compound as a mixture of E and Z isomers. The isomers were separated by chromatography with a Reverse Phase HPLC using a C$_{18}$ Preparative column. Characterization for one single oxime isomer: $^1$H NMR (400 MHz, DMSO-d$_6$) δ 9.86 (s, 1H), 8.15 (t, 1H), 8.02 (d, 1H), 7.90 (d, 1H), 7.85 (s, 1H), 7.80 (d, 2H), 7.72 (t, 1H), 7.64 (d, 1H), 7.47-7.44 (m, 3H), 7.35 (d, 2H); MS (ES): 466.1 [M+H]$^+$.

The following compounds were prepared in a manner similar to that described in experimental procedure Example 16:

1-{1-[3'-(methylsulfonyl)biphenyl-4-yl]-2-[2-(trifluoromethyl)phenyl]-1H-imidazol-4-yl}ethanone oxime; MS (ES): 500.3 [M+H]$^+$ 1-{2-(2-chlorophenyl)-1-[3'-(ethylsulfonyl)biphenyl-4-yl]-1H-imidazol-4-yl}ethanone oxime; MS (ES): 480.0, 482.0 [M+H]$^+$ 1-{2-(2-chlorophenyl)-1-[3'-(ethylsulfonyl)biphenyl-4-yl]-1H-imidazol-4-yl}ethanone oxime; MS (ES): 480.0, 482.0 [M+H]$^+$ 1-{2-(2-chlorophenyl)-1-[3'-(1-methylethy)biphenyl-4-yl]-1H-imidazol-4-yl}ethanone oxime; MS (ES): 430.0, 432.0 [M+H]$^+$ 1-{2-(2-chlorophenyl)-1-[3'-(methylsulfonyl)biphenyl-4-yl]-1H-imidazol-4-yl}ethanone oxime; MS (ES): 466.0, 468.0 [M+H]$^+$ 1-{2-(2-chlorophenyl)-1-[3'-(methylsulfonyl)biphenyl-4-yl]-1H-imidazol-4-yl}ethanone oxime; MS (ES): 466.0, 468.0 [M+H]$^+$ 1-{2-(2-chlorophenyl)-1-[4'-(hydroxymethyl)-3'-(methylsulfonyl)biphenyl-4-yl]-1H-imidazol-4-yl}ethanone oxime; MS (ES): 495.3, 497.3 [M+H]$^+$ (E)-1-(2-(2,6-dichlorophenyl)-1-(3'-(methylsulfonyl)biphenyl-4-yl)-1H-imidazol-4-yl)ethanone oxime; MS (ES): 500.4, 502.3 [M+H]$^+$ (E)-1-(2-(2-ethylphenyl)-1-(3'-(methylsulfonyl)biphenyl-4-yl)-1H-imidazol-4-yl)ethanone oxime; MS (ES): 460.3 [M+H]$^+$ (E)-1-(2-(2-isopropylphenyl)-1-(3-methyl-3'-(methylsulfonyl)biphenyl-4-yl)-1H-imidazol-4-yl)ethanone oxime; MS (ES): 488.3 [M+H]$^+$ Scheme 14

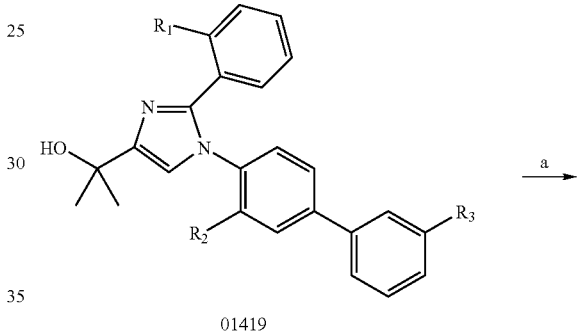

(a) HCl, dioxane, Δ or HOAc, toluene, Δ

In general, carbinol substituted imidazole compounds of formula (01419) can be dehydrated using known methods to provide the corresponding alkene (01420) (Scheme 14). The

EXAMPLE 17

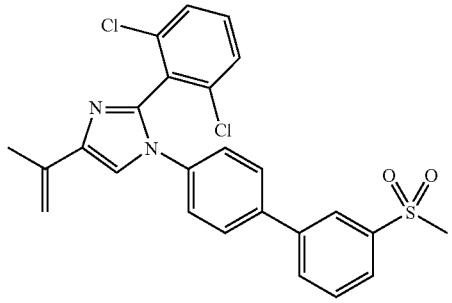 [SMILES: C=C(C)c1cn(-c2ccc(-c3cccc(S(C)(=O)=O)c3)cc2)c(-c2c(Cl)cccc2Cl)n1]

Preparation of 2-(2,6-Dichloro-phenyl)-4-isoprope-nyl-1-(3'-methanesulfonyl-biphenyl-4-yl)-1H-imidazole To a 25 mL round bottom flask attached with Vigreux column was added 2-[2-(2,6-Dichloro-phenyl)-1-(3'-methanesulfonyl-biphenyl-4-yl)-1H-imidazol-4-yl]-propan-2-ol (383 mg, 764 μmol), anhydrous toluene (8 mL) and acetic acid (3.5 mL). The reaction solution was allowed to stir at reflux for 1.5 hr. The cooled reaction solution was concentrated in vacuo, and the residue was taken into EtOAc (200 mL) and washed with aq NaHCO$_3$ (100 mL×2) and aq. NaCl (100 mL). The organic phase was partitioned, dried over Na$_2$SO$_4$, filtered and concentrated in vacuo. The crude product was chromatographed through a 25 g SiO$_2$ column using a mobile gradient of 100% Hx to 80% EtOAc to provide 288 mg (78% yield) of title compound. $^1$H NMR (400 MHz, DMSO-d$_6$): δ 8.15 (br s, 1H), 8.08-7.97 (m, 2H), 7.92 (d, 1H), 7.89 (d, 2H), 7.75 (t, 1H), 7.64-7.57 (m, 3H), 7.43 (d, 2H), 5.77 (br s, 1H), 5.10 (br s, 1H), 3.29 (s, 3H), 2.11 (s, 3H); MS (ES): 483.1, 485.1 [M+H]$^+$.

The following compound was made according to this scheme:
2-(2,3-dichlorophenyl)-1-(3'-(ethylsulfonyl)biphenyl-4-yl)-4-(prop-1-en-2-yl)-1H-imidazole; MS (ES): 497, 499 [M+H]$^+$ Scheme 15

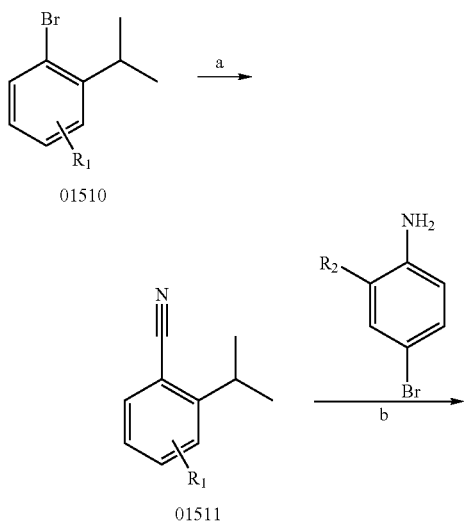

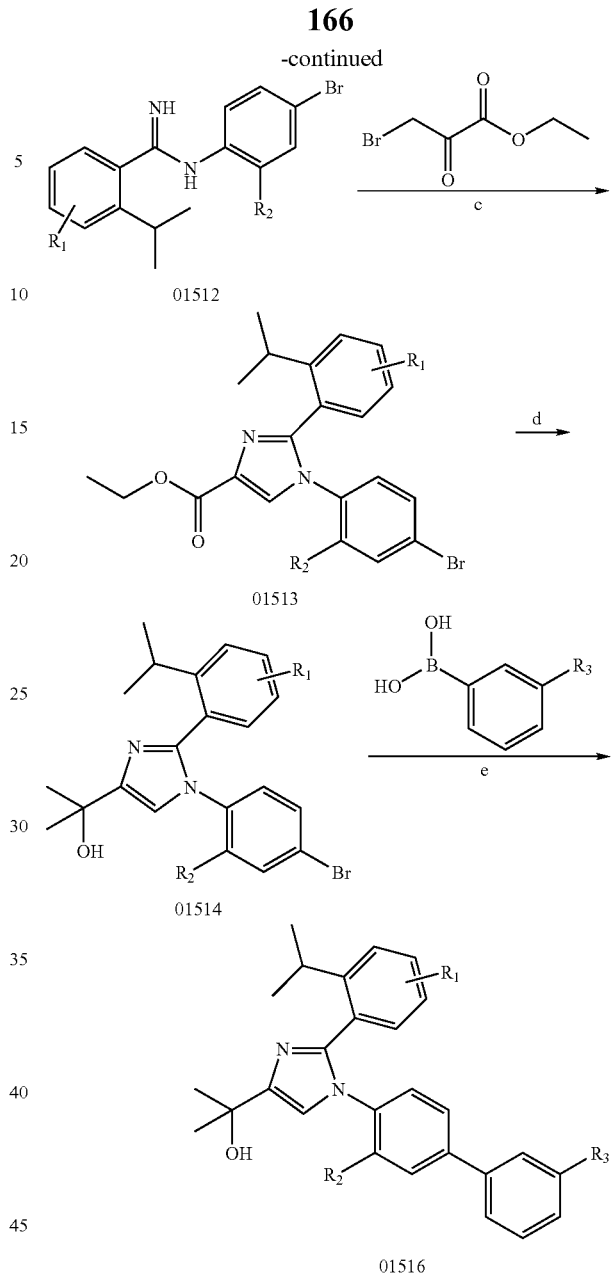

(a) CuCN, DMF, reflux;
(b) (i) Me$_3$Al, toluene, (ii) reflux 1d;
(c) (i) EtOH, NaHCO$_3$, (ii) HOAc, reflux;
(d) 4 equiv MeMgBr;
(e) PdCl$_2$dppf, K$_2$CO$_3$, DME/H$_2$O In general, compounds of formula (01515), with alkyl A-ring substituents larger than Me or Et, can be synthesized following the sequence shown in Scheme 15. By example, the methodology in Scheme 15 can afford imidazole compounds with 2-iso-propyl groups on the phenyl A-ring. In general, the methodology can also afford compounds with either mono- or disubstituted phenyl A-rings. An arylbromide (01510) can be converted to an arylnitrile (01511) by reaction with copper (I) cyanide. The arylnitrile can be reacted with aniline in the presence of a Lewis acid, such as trimethylaluminium, to give the corresponding amidine (01512). Amidine (01512) can be reacted with ethyl bromopyruvate in the presence of sodium bicarbonate, followed by dehydration to afford the cyclized imidazole intermediate (01513). Carbinol formation to provide (01514) and Suzuki cross coupling can be used to afford compound (01515) in a manner similar to that described in Scheme 8.

The following compound was made according to this scheme: 2-(2,3-dichlorophenyl)-1-(3'-(ethylsulfonyl)biphenyl-4-yl)-4-(prop-1-en-2-yl)-1H-imidazole; MS (ES): 497, 499 [M+H]$^+$

EXAMPLE 18

2-[2-(2-isopropyl-phenyl)-1-(3'-methanesulfonyl-biphenyl-4-yl)-1H-imidazol-4-yl]-propan-2-ol

EXAMPLE 18a

Preparation of 2-isopropylbenzonitrile

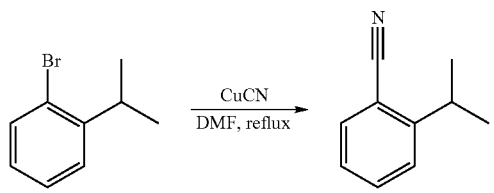

To a dry, N$_2$ purged 100 mL round bottom flask attached with condenser was added 1-bromo-2-isopropylbenzene (10.0 g, 50.2 mmol), anhydrous DMF (26 mL), and CuCN (5.85 g, 65.3 mmol).

The reaction slurry was stirred at reflux under N$_2$ for 4 hrs prior to analysis by GCMS. The reaction mixture was cooled to room temperature and poured into an ice/aq NH$_4$Cl solution. The resulting precipitates were removed by vacuum filtration through a Buchner funnel. The aqueous filtrate was extracted with EtOAc (150 mL×3). The combined organic phase was dried over Na$_2$SO$_4$, filtered and concentrated on the Rotavapor to afford 5.97 g (82% yield) of 2-isopropyl-benzonitrile. The product was used in the next step without further purification. GCMS m/z=145 [M$^+$].

EXAMPLE 18b

Preparation of N-(4-Bromo-phenyl)-2-isopropyl-benzamidine

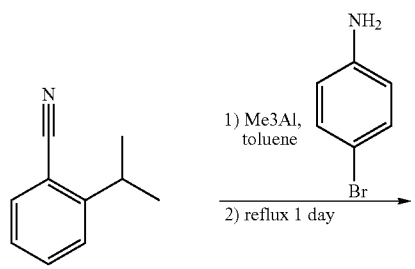

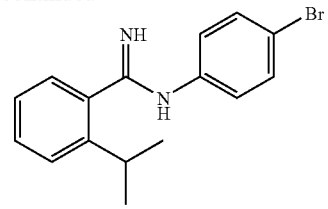

To a dry, N$_2$ purged 100 mL round bottom flask was added 4-bromo-aniline (2.73 g, 15.9 mmol) and anhydrous toluene (40 mL). To the solution at 0° C. was added, dropwise, a 2.0 M solution of Me$_3$Al in hexanes (9.4 mL). The solution was allowed to stir, warming to room temperature for approximately 1 hr. To the reaction solution was added 2-isopropyl-benzonitrile (3.00 g, 20.7 mmol) in a toluene solution (15 mL). The reaction solution was allowed to stir at 80° C. for approximately 24 hrs. The reaction solution was allowed to cool to room temperature prior to quenching by pouring the reaction solution into an Erlenmeyer containing a 2:1 CHCl$_3$/MeOH solution and 100 g of silica. The slurry was allowed to stir 30 min prior to filtration into a Buchner funnel under vacuum. The filtrate was concentrated on the Rotavapor and the resulting residue was reprecipitated using a 10:1 Hx/Et$_2$O mixture. The resulting white precipitates were isolated by vacuum filtration to afford 1.98 g (40% yield) of amidine product. GCMS m/z=317 [M$^+$].

EXAMPLE 18c

Preparation of 1-(4-Bromo-phenyl)-2-(2-isopropyl-phenyl)-1H-imidazole-4-carboxylic acid ethyl ester

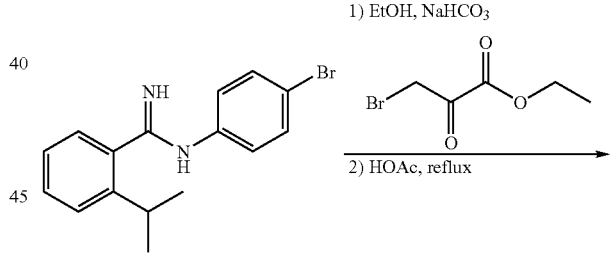

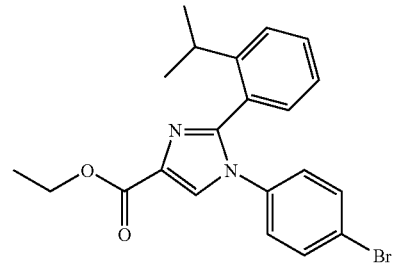

To a 250 mL round bottom flask attached with condenser was added N-(4-Bromo-phenyl)-2-isopropyl-benzamidine (1.94 g, 6.11 mmol), ethyl bromopyruvate (1.54 mL, 12.2 mmol), sodium bicarbonate (1.02 g, 12.2 mmol), and isopropanol (45 mL). The reaction slurry was allowed to stir at 80° C. for approximately 2 hrs. The reaction solution was decanted into a clean round bottom flask and concentrated in vacuo. The resulting residue was dissolved in acetic acid (25 mL), and the solution was allowed to stir at reflux for approximately 2 hrs. The solution was concentrated in vacuo, and the product residue was taken into EtOAc (200 mL) and washed with aq NaCl (200 mL×2) and aq NaHCO$_3$ (100 mL). The organic phase was partitioned, dried over Na$_2$SO$_4$, filtered, concentrated, and chromatographed through a 40 g SiO$_2$ column using a mobile gradient of 100% Hx to 70% EtOAc to afford 1.90 g (75% yield) of title compound. MS (ES): 414.0 [M+H]$^+$.

EXAMPLE 18d

Preparation of 2-[1-(4-Bromo-phenyl)-2-(2-isopropyl-phenyl)-1H-imidazol-4-yl]-propan-2-ol

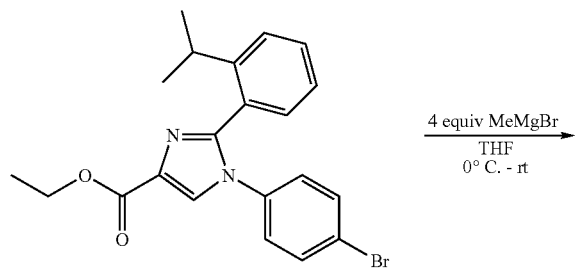

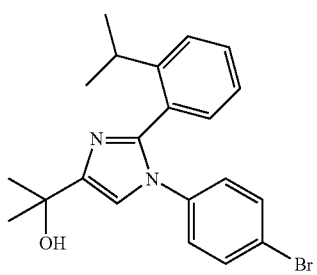

To a dry, N$_2$ purged round bottom flask containing 1-(4-Bromo-phenyl)-2-(2-isopropyl-phenyl)-1H-imidazole-4-carboxylic acid ethyl ester (1.87 g, 4.52 mmol) was added anhydrous THF (55 mL). The solution was cooled to 0° C. prior to the addition of a 3.0 M solution of methylmagnesium bromide (5.3 mL). The reaction was stirred 1 hr at room temperature prior to quenching with aq NH$_4$Cl (30 mL). The organic phase was partitioned, dried over Na$_2$SO$_4$, filtered, and concentrated in vacuo. The crude product was chromatographed through a SiO$_2$ column using a mobile gradient to 100% Hx to 80% EtOAc to afford 1.19 g (66% yield) of 369-45.

EXAMPLE 18e

Preparation of 2-[2-(2-Isopropyl-phenyl)-1-(3'-methanesulfonyl-biphenyl-4-yl)-1H-imidazol-4-yl]-propan-2-ol

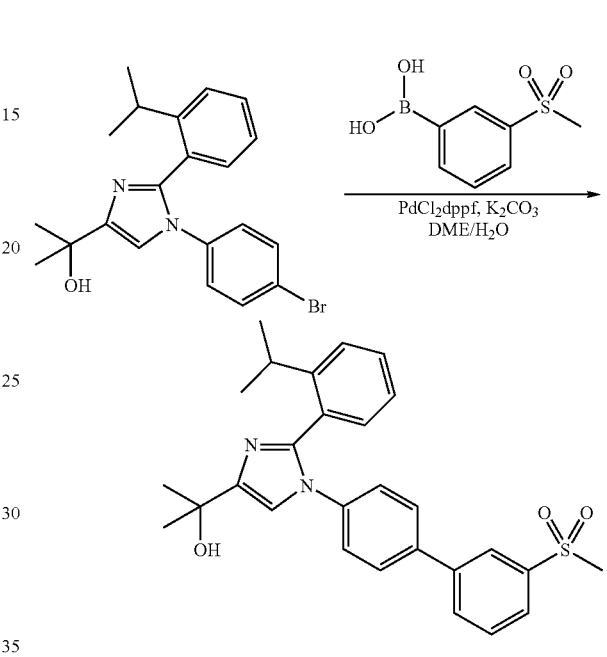

To a 50 mL round bottom flask attached with Vigreux column and magnetic stir bar was added 2-[1-(4-Bromo-phenyl)-2-(2-isopropyl-phenyl)-1H-imidazol-4-yl]-propan-2-ol (297 mg, 743 μmol), 3-methylsulfonylphenyl boronic acid (193 mg, 968 μmol), PdCl$_2$ dppf (60 mg, 10 mol %), K$_2$CO$_3$ (310 mg, 2.23 mmol), 1,2-dimethoxyethane (14 mL) and H$_2$O (4 mL). The reaction solution was allowed to stir at 80° C. for 2 hrs. The reaction solution was diluted with EtOAc (150 mL) and filtered through a Celite padded Buchner funnel to remove spent Pd. The filtrate was transferred to a separatory funnel and washed with aq NH$_4$Cl (100 mL) and aq NaCl (100 mL). The organic phase was dried over Na$_2$SO$_4$, filtered, concentrated on the Rotavapor and chromatographed through a 25 g SiO$_2$ column using a mobile phase gradient of 100% Hx to 90% EtOAc to afford 303 mg (86% yield) of the title compound. $^1$H NMR (400 MHz, DMSO-d$_6$): δ 8.14 (s, 1H), 8.02 (d, 1H), 7.89 (d, 1H), 7.89 (d, 1H), 7.78 (d, 2H), 7.72 (t, 1H), 7.37-7.34 (m, 3H), 7.26 (d, 2H), 7.18-7.16 (m, 2H), 4.84 (s, 1H), 3.26 (s, 3H), 2.85 (sept, 1H), 1.50 (6H), 0.96 (d, 6H); MS (ES): 475.4 [M+H]$^+$, 497.5 [M+Na].

The following compounds were prepared in a manner similar to that described in experimental procedure Example 18:

2-(1-(3'-(ethylsulfonyl)biphenyl-4-yl)-2-(2-isopropylphenyl)-1H-imidazol-4-yl)propan-2-ol; MS (ES): 489.4 [M+H], 511.4 [M+Na]$^+$ 2-(1-(3-chloro-3'-(methylsulfonyl)biphenyl-4-yl)-2-(2-isopropylphenyl)-1H-imidazol-4-yl)propan-2-ol; MS (ES): 509.3, 511.3 [M+H]$^+$ 2-(2-(2-isopropylphenyl)-1-(3-methyl-3'-(methylsulfonyl)biphenyl-4-yl)-1H-imidazol-4-yl)propan-2-ol; MS (ES): 489.3, 511.4 [M+Na]$^+$ 2-(1-(3'-(ethylsulfonyl)-3-methylbiphenyl-4-yl)-2-(2-isopropylphenyl)-1H-imidazol-4-yl)propan-2-ol; MS (ES): 503.4 [M+H]+

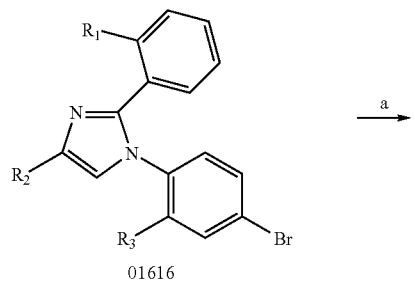

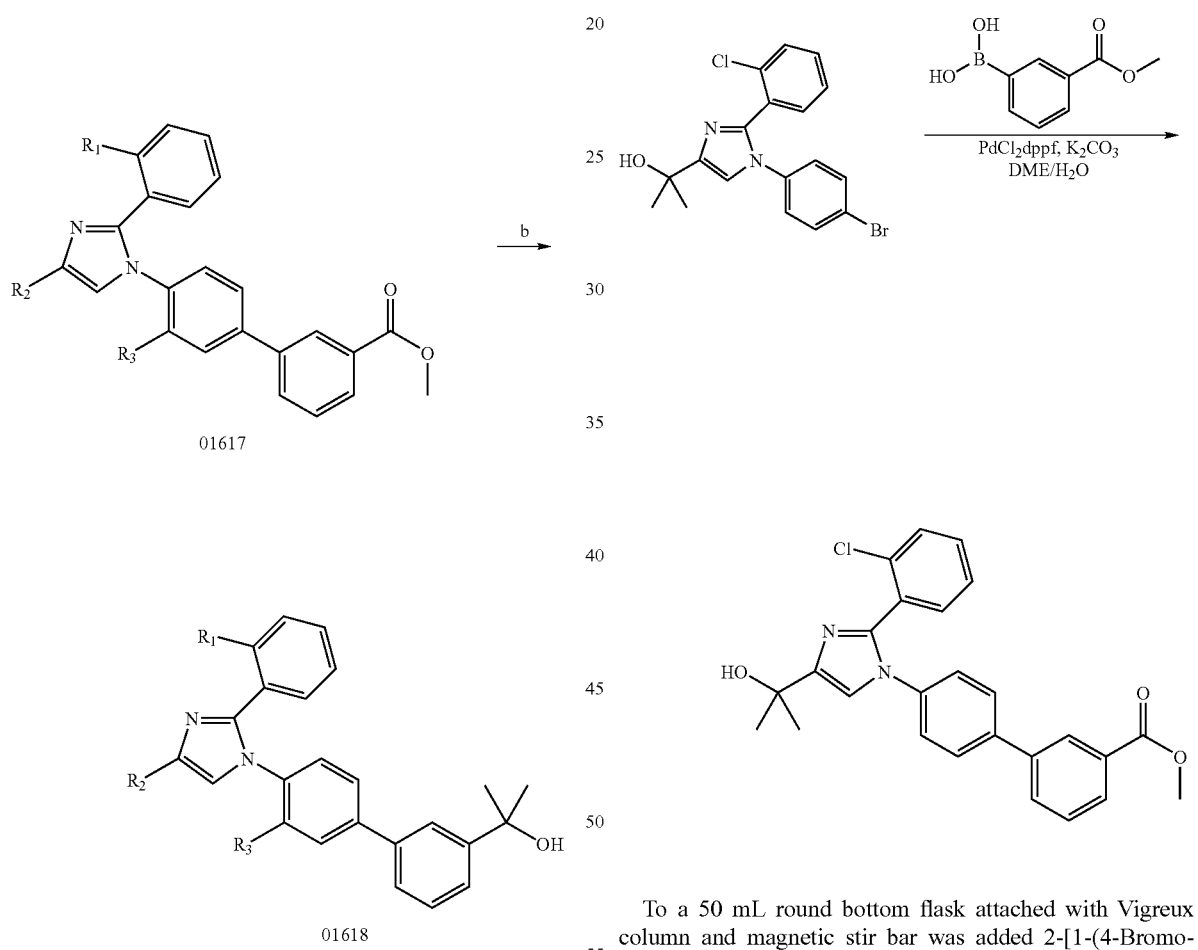

(a) Suzuki Coupling;
(b) 4 equiv MeMgBr, toluene

In general, compounds of formula (01618) can be synthesized as shown in Scheme 16. The method involves use of a methylester substituted D-ring compound, such as depicted with compound (01617). The D-ring ester (01617) can be converted to a dimethylcarbinol compound (01618) by reaction with a molar excess of methylmagnesium bromide. The transformation can be carried out when $R_2$ is either and ester group of carbinol. When $R_2$ is an ester group, four equivalents of methylmagnesium bromide can be used to prepare the bis-carbinol version of compound (01618).

EXAMPLE 19

2-{2-(2-Chloro-phenyl)-1-[3'-(1-hydroxy-1-methyl-ethyl)-biphenyl-4-yl]-1H-imidazol-4-yl}-propan-2-ol

EXAMPLE 19a

Preparation of 4'-[2-(2-Chloro-phenyl)-4-(1-hydroxy-1-methyl-ethyl)-imidazol-1-yl]-biphenyl-3-carboxylic acid methyl ester To a 50 mL round bottom flask attached with Vigreux column and magnetic stir bar was added 2-[1-(4-Bromo-phenyl)-2-(2-chloro-phenyl)-1H-imidazol-4-yl]-propan-2-ol (275 mg, 702 µmol), 3-methoxycarbonylphenyl boronic acid (164 mg, 913 µmol), PdCl$_2$dppf (51 mg, 10 mol %), K$_2$CO$_3$ (290 mg, 2.11 mmol), 1,2-dimethoxyethane (13 mL) and H$_2$O (1.5 mL). The reaction solution was allowed to stir at 70° C. for approximately 2 hrs. The reaction solution was diluted with EtOAc (150 mL) and filtered through a Celite padded Buchner funnel to remove spent Pd. The filtrate was transferred to a separatory funnel and washed with aq NH$_4$Cl (100 mL) and aq NaCl (100 mL). The organic phase was dried over Na$_2$SO$_4$, filtered, concentrated on the Rotavapor and chromatographed through a 25 g SiO$_2$ column using a mobile phase gradient of 100% Hx to 90% EtOAc to afford 122 mg (39% yield) of product. MS (ES): 446.3, 448.3 [M+H]+.

EXAMPLE 19b

Preparation of Preparation of 2-{2-(2-Chloro-phenyl)-1-[3'-(1-hydroxy-1-methyl-ethyl)-biphenyl-4-yl]-1H-imidazol-4-yl}-propan-2-ol

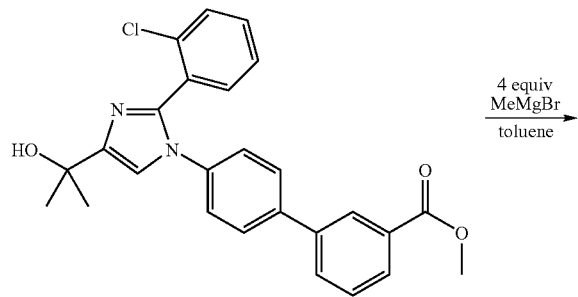

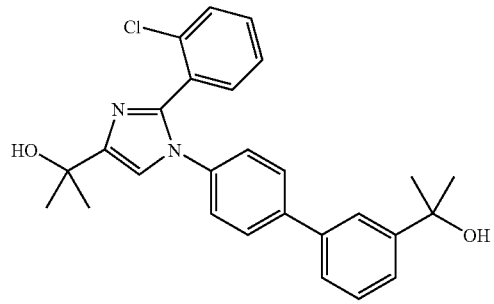

To a dry, N₂ purged 50 mL round bottom flask was added 4'-[2-(2-Chloro-phenyl)-4-(1-hydroxy-1-methyl-ethyl)-imidazol-1-yl]-biphenyl-3-carboxylic acid methyl ester (100 mg, 225 μmol), anhydrous and toluene (7 mL). To the solution at 0° C. was added a 1.4 M solution of methylmagnesium bromide (640 μL). The reaction solution was allowed to stir at room temperature for approximately 1 hr. The reaction was quenched by the addition of aq NH₄Cl (20 mL). The organic phase was partitioned, dried over Na₂SO₄, filtered, and concentrated in vacuo. The crude residue was chromatographed through a 12 g SiO₂ column using a gradient of 100% Hx to 100% EtOAc to afford 45 mg (45% yield) of title compound. $^1$H NMR (400 MHz, CDCl₃): δ 7.70 (s, 1H), 7.55 (d, 2H), 7.48-7.38 (m, 5H), 7.35 (s, 1H), 7.33 (m, 1H), 7.18 (d, 2H), 7.16 (s, 1H), 1.73 (s, 6H), 1.62 (s, 6H); MS (ES): 447.4 [M+H]+, 469.3 [M+Na]+

The following compounds were prepared in a manner similar to that described in experimental procedure Example 19:

1-(3-chloro-3'-(2-hydroxypropan-2-yl)biphenyl-4-yl)-2-(2,6-dichlorophenyl)-N-(1-hydroxy-2-methylpropan-2-yl)-1H-imidazole-4-carboxamide; MS (ES): 572.3, 574.3, 576.3 [M+H]+

2-{2-(2,3-dichlorophenyl)-1-[3'-(1-hydroxy-1-methylethyl)biphenyl-4-yl]-1H-imidazol-4-yl}propan-2-ol; MS (ES): 481 [M+H]+, 503 [M+Na]+.

EXAMPLE 20

Preparation of 3'-chloro-4'-[2-(2-chloro-6-fluorophenyl)-4-(1-hydroxy-1-methyl)-1H-imidazol-1-yl]-N-methyl-N-(methyloxy)-3-(methylsulfonyl)biphenyl-4-carboxamide

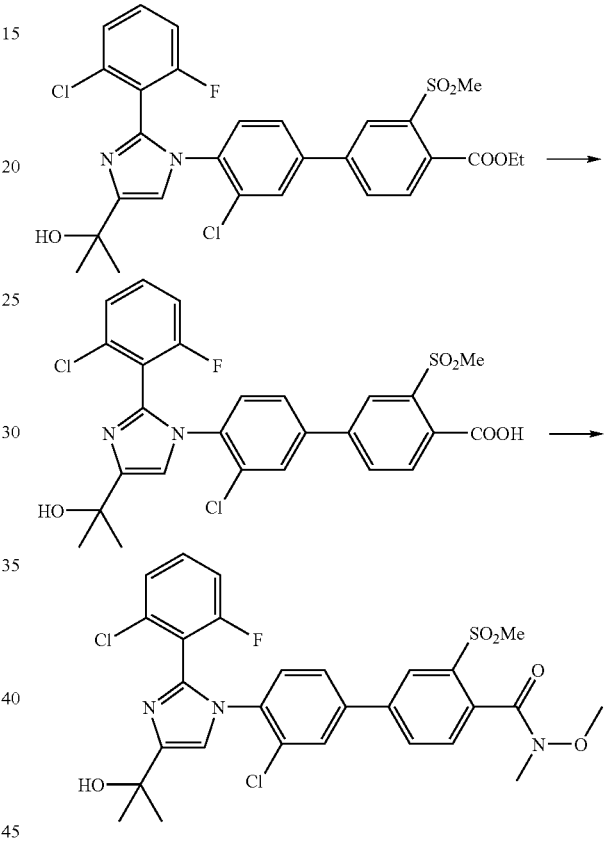

Ethyl 3'-chloro-4'-[2-(2-chloro-6-fluorophenyl)-4-(1-hydroxy-1-methylethyl)-1H-imidazol-1-yl]-3-(methylsulfonyl)biphenyl-4-carboxylate was prepared as described in Example 9. Into a 500 mL flask was weighed 11.19 g (18.92 mmol) of ester, 100 mL of THF, 100 mL of methanol, and 19.0 mL of 3.0 M LiOH—H₂O. The resulting suspension was stirred at room temperature for 21 h then was concentrated in vacuo. The residue was treated with ethyl acetate and 1.0 M HCl and the resulting suspension was filtered of solids. The filtrate was placed into a separatory funnel and the ethyl acetate was separated, washed with brine, was dried (Na₂SO₄), and concentrated in vacuo. The solids collected by filtration were added and the combined solids were dried under high vacuum to afford 3'-chloro-4'-[2-(2-chloro-6-fluorophenyl)-4-(1-hydroxy-1-methylethyl)-1H-imidazol-1-yl]-3-(methylsulfonyl)biphenyl-4-carboxylic acid as a colorless solid, yield: 7.36 g (69%); MS (ES): 563 [M+H]+.

Also recovered as a minor byproduct was 3'-chloro-4'-[2-(2-chloro-6-fluorophenyl)-4-(1-methylethenyl)-1H-imidazol-1-yl]-3-(methylsulfonyl)biphenyl-4-carboxylic acid; MS (ES): 545 and 547 each [M+H]+.

Into an 8 mL vial was weighed 68 mg (697 μmol) of N,O-Dimethyl-hydroxylamine hydrochloride, and 157 mg (279 μmol) of acid. The solids were then treated with 710 μL of a 0.5 M O-(Benzotriazol-1-yl)-N,N,N',N'-tetramethyluronium hexafluorophosphate solution in DMF and 200 μL of diisopropylethylamine was added. The reaction was stirred at room temperature for 20 h then was washed into a separatory funnel with ethyl acetate and 1 M HCl. The ethyl acetate was separated, washed with brine, was dried (Na$_2$SO$_4$), and was concentrated in vacuo. The product was purified by silica gel flash chromatography (Biotage, 12.5×150 mm SiO$_2$, gradient elution from 100% hexanes to 100% ethyl acetate over 0.5 h). Appropriate fractions were combined and concentrate in vacuo to afford the product as a colorless solid, yield: 85 mg (47%); $^1$H NMR (400 MHz, DMSO-d$_6$): δ 8.26 (s, 1H), 8.19 (d, J=8 Hz, 1H), 8.15 (s, 1H), 7.87 (d, J=6 Hz, 1H), 7.72 (d, J=8 Hz, 1H), 7.53 (q, J=6 Hz, 1H), 7.4-7.5 (m, 3H), 7.31 (t, J=8 Hz, 1H), 3.39 (s, 3H), 3.32 and 3.36 (each s, 3H), 2.75 (s, 3H), 1.58 (s, 6H); MS (ES): 606 [M+H]$^+$.

In a manner similar to that described, the following examples of the invention were prepared by substituting an appropriate reagent.

3'-Chloro-4'-[2-(2-chloro-6-fluorophenyl)-4-(1-hydroxy-1-methylethyl)-1H-imidazol-1-yl]-3-(methylsulfonyl)biphenyl-4-carboxamide; MS (ES): 562 [M+H]$^+$.

3'-Chloro-4'-[2-(2-chloro-6-fluorophenyl)-4-(1-hydroxy-1-methylethyl)-1H-imidazol-1-yl]-N,N-dimethyl-3-(methylsulfonyl)biphenyl-4-carboxamide; MS (ES): 590 [M+H]$^+$.

3'-Chloro-4'-[2-(2-chloro-6-fluorophenyl)-4-(1-hydroxy-1-methylethyl)-1H-imidazol-1-yl]-N-ethyl-3-(methylsulfonyl)biphenyl-4-carboxamide; MS (ES): 590 [M+H]$^+$.

2-{2-(2-Chloro-6-fluorophenyl)-1-[3-chloro-3'-(methylsulfonyl)-4'-(morpholin-4-ylcarbonyl)biphenyl-4-yl]-1H-imidazol-4-yl}propan-2-ol; MS (ES): 632 [M+H]$^+$.

3'-Chloro-4'-[2-(2-chloro-6-fluorophenyl)-4-(1-hydroxy-1-methylethyl)-1H-imidazol-1-yl]-3-(methylsulfonyl)-N-(phenylmethyl)biphenyl-4-carboxamide; MS (ES): 652 [M+H]$^+$.

Scheme 17

2,4,5-Trisubstituted imidazole (Isomer IIc and tautomer IId)

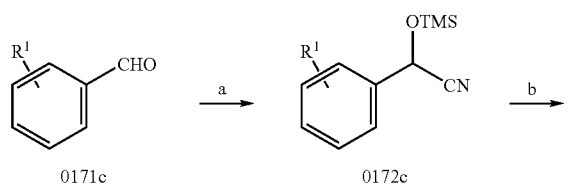

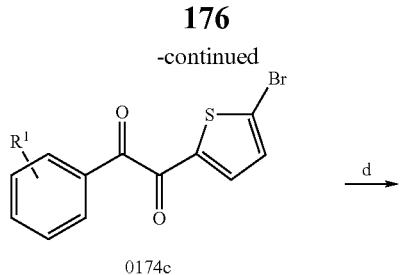

0174c

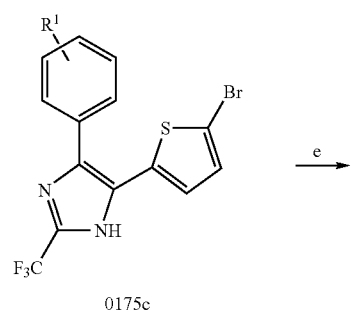

0175c

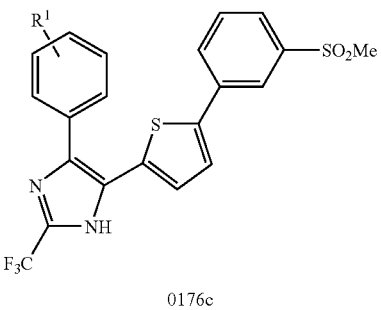

0176c

Reactions and conditions:
(a) TMSCN, ZnI$_2$, rt;
(b) 5-bromothiophen-2-carboxaldehyde, LiHMDS, THF, -78° C.;
(c) Bi$_2$O$_3$, HOAc, 90° C.;
(d) NH$_4$OAc, CF$_3$CH(OEt)(OH), AcOH, reflux;
(e) ArB(OH)$_2$, K$_2$CO$_3$, PdCl$_2$(dppf), DME/H$_2$O, 80° C..

The subject imidazole compounds of formula (0176c) are synthesized according to the sequence outlined in Scheme 3. Aldehyde (0171c) such as 2-chlorobenzaldehyde is converted to the protected cyanohydrin of formula (0172c) by reaction with trialkylsilyl cyanide, such as trimethylsilyl cyanide (TMSCN), in the presence of a catalyst such as zinc iodide. Reaction of cyanohydrin (0172c) with aldehyde such as 5-bromothiophene-2-carboxalhedyde, under strong base produces bezoin of formula (0173c). Oxidation of bezoin with a suitable oxidant such as bismuth oxide provides the diketone of formula (0174c), which subsequently reacts with ammonium acetate and appropriate aldehyde or its equivalent such as trifluoroacetaldehyde ethyl hemiacetal to give 1H-imidazole of formula (0175c). In a palladium mediated coupling reaction, for example a Suzuki reaction, compounds of formula (0175c) are then reacted with a boronate or boronic acid reagent to give compounds of formula (0176c) after standard isolation procedures.

EXAMPLE 21

4-(2-chlorophenyl)-5-(5-(3-(methylsulfonyl)phenyl)thiophen-2-yl)-2-(trifluoromethyl)-1H-imidazole

EXAMPLE 21a

Preparation of (2-Chloro-phenyl)-trimethylsilanyloxy-acetonitrile

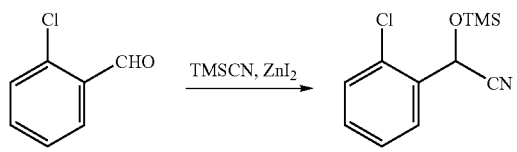

Under an atmosphere of nitrogen, anhydrous zinc iodide (30 mg, 0.1 mmol) was placed into a dry flask. At 0° C. trimethylsilylcyanide (5.2 g, 52.5 mmol) was added, followed by 2-chlorobenzaldehyde (7.0 g, 50 mmol). The mixture was stirred at 0° C. for 3 hrs, then at room temperature overnight. Ethyl ether was added, and the mixture was washed with water and brine, dried over $Na_2SO_4$, and concentrated in vacuo to give a brown oil (10.95 g, 91% yield), which wad used directly for the next step without further purification. $^1$H-NMR (400 MHz, $CDCl_3$): δ 5.80 (s, 1H), 7.38 (m, 3H), 7.73 (dd, 1H).

EXAMPLE 21b

Preparation of 2-(5-Bromo-thiophen-2-yl)-1-(2-chloro-phenyl)-2-hydroxy-ethanone

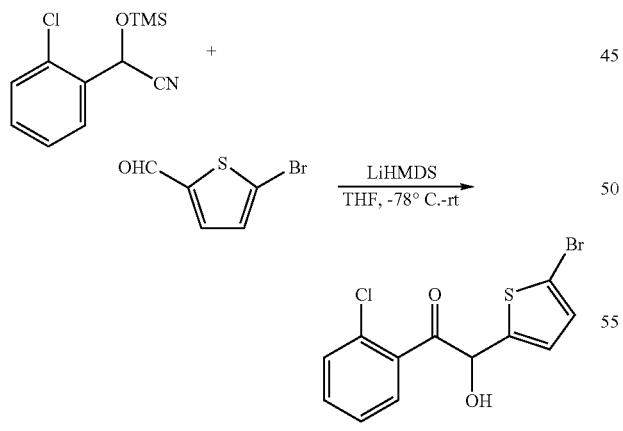

Under an atmosphere of nitrogen, to a clod (−78° C.) solution of lithium bis(trimethylsilyl)amide (8.05 mL, 1.0M solution in THF, 8.05 mmol) was added a solution of (2-chlorophenyl)-trimethylsilanyloxy-acetonitrile (1.69 g, 7 mmol) in tetrahydrofuran (10 mL) dropwise over 10 min. After stirring for another 30 min, a solution of 5-bromothiophen-2-carboxaldehyde in tetrahydrofuran (10 mL) was added dropwise. The reaction was stirred overnight from −78° C. to reach room temperature, then was quenched by adding 3N HCl (20 mL) and warming at 40° C. for 5 hrs. After cooling, the mixture was partitioned between ethyl ether and water. The organic layer was stirred with 1M NaOH (30 mL) for 2 hrs; and the layers were separated. The organic layer was washed with brine, dried over $Na_2SO_4$, and concentrated in vacuo. The crude product was purified by chromatography on silica gel (Hexane/EtOAc, 8/2) to give a brown oil (320 mg, 14% yield). $^1$H-NMR (400 MHz, $CDCl_3$): δ 4.35 (d, 1H), 6.12 (d, 1H), 7.02 (d, 1H), 7.26 (m, 2H), 7.41 (d, 1H), 7.44 (dd, 1H).

EXAMPLE 21c

Preparation of 1-(5-Bromo-thiophen-2-yl)-2-(2-chloro-phenyl)-ethane-1,2-dione

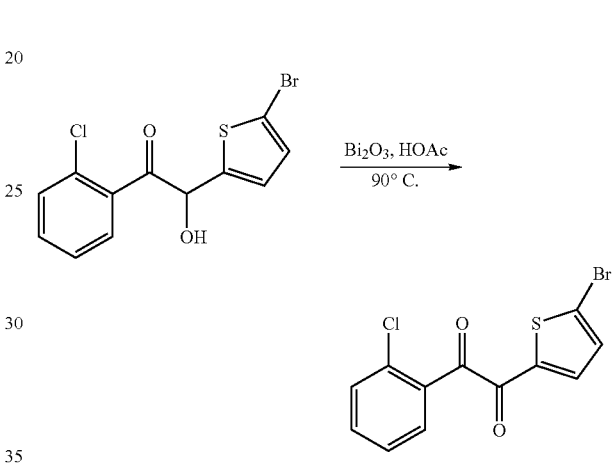

A mixture of benzoin prepared from above (316 mg, 0.95 mmol), and bismuth oxide (560 mg, 1.2 mmol) in acetic acid (5 mL) was heated at 90° C. for 5 hrs. The hot reaction mixture was filtered through celite and the filtrate was concentrated in vacuo. The brown residue was redissolved into hot methanol, and then filtered. The filtrate was evaporated to give a brown oil (311 mg, 99% yield), which is used directly for the next step without further purification. $^1$H-NMR (400 MHz, $CDCl_3$): δ 7.21 (d, 1H), 7.43 (m, 1H), 7.45 (m, 1H), 7.54 (m, 1H), 7.70 (d, 1H), 7.77 (dd, 1H).

EXAMPLE 21d

Preparation of 5-(5-Bromo-thiophen-2-yl)-4-(2-chloro-phenyl)-2-trifluoromethyl-1H-imidazole

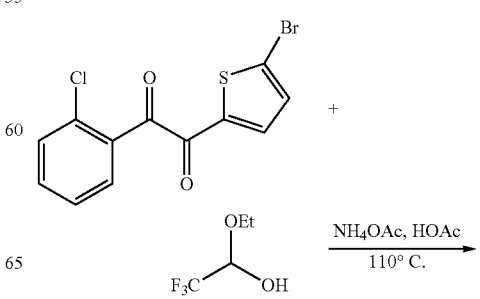

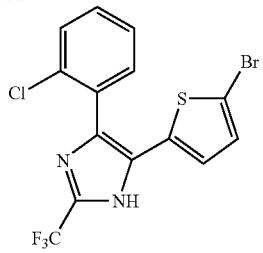

A mixture of diketone (311 mg, 0.95 mmol), ammonium acetate (366 mg, 4.75 mmol), and trifluoroacetaldehyde ethyl hemiacetal (684 mg, 4.75 mmol) in 5 mL acetic acid was heated at 110° C. for 10 hrs under nitrogen atmosphere. All solvent was removed under vacuo, and the residue was redissolved into dichloromethane and filtered. The filtrate was concentrated, and then purified by chromatography on silica gel (Hexane/EtOAc, 8/2) to give a light pink solid (141 mg, 36% yield). $^1$H-NMR (400 MHz, CDCl$_3$): δ 6.81 (d, 1H), 6.87 (d, 1H), 7.38 (t, 1H), 7.49 (m, 2H), 7.56 (d, 1H), 9.55 (s, 1H).

EXAMPLE 21e

Preparation of 4-(2-Chloro-phenyl)-5-[5-(3-methanesulfonylphenyl)-thiophen-2-yl]-2-trifluoromethyl-1H-imidazole

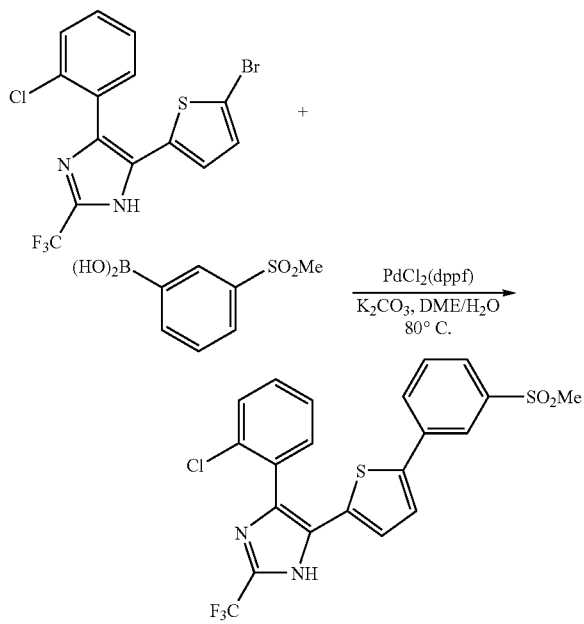

5-(5-Bromo-thiophen-2-yl)-4-(2-chloro-phenyl)-2-trifluoromethyl-1H-imidazole (70 mg, 0.17 mmol), (3-methylsulfonyl)phenylboronic acid (69 mg, 0.34 mmol), potassium carbonate (106 mg, 0.77 mmol), and PdCl$_2$ (dppf).CH$_2$Cl$_2$ (14 mg, 0.017 mmol) were mixed with 2 mL 9:1 (v/v) DME/H$_2$O, then heated at 80° C. overnight. All solvent was removed in vacuo. The residue was purified by chromatography on silica gel (Hexane/EtOAc, 6/4) to give a white solid (25 mg, 30% yield). $^1$H-NMR (400 MHz, CDCl$_3$): δ 3.07 (s, 3H), 7.00 (d, 1H), 7.12 (m, 1H), 7.51 (m, 5H), 7.81 (m, 2H), 8.10 (t, 1H), 9.65 (s, 1H).

All the following compounds were prepared in similar manner using appropriate aldehydes as starting materials
4-(2-chlorophenyl)-5-[3'-(methylsulfonyl)biphenyl-4-yl]-2-(trifluoromethyl)-H-imidazole; 477.1, 479.3 [M+H]$^+$;
4'-[4-(2-chlorophenyl)-2-(trifluoromethyl)-1H-imidazol-5-yl]biphenyl-3-sulfonamide; 478.0 [M+H]$^+$;
3-{5-[4-(2-chlorophenyl)-2-(trifluoromethyl)-1H-imidazol-5-yl]-2-thienyl}benzenesulfonamide; 484.0 [M+H]$^+$.

EXAMPLE 22

Preparation of 2-(4-methoxy-3-(methylsulfonyl)phenyl)-4,4,5,5-tetramethyl-1,3,2-dioxaborolane

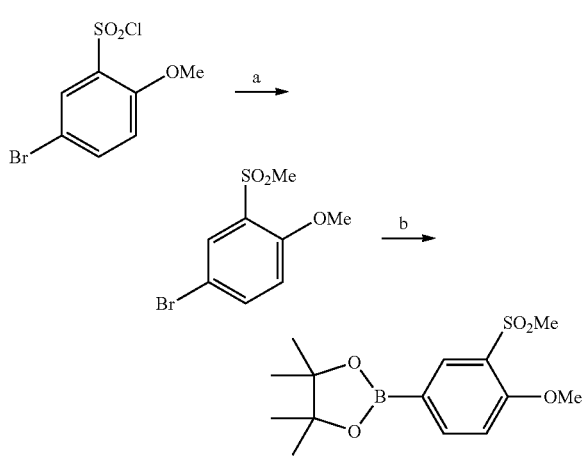

a) NaHCO$_3$, Na$_2$SO$_3$, H$_2$O, 85° C.;
b) Bis(pinacolato)diboron, Pd(dppf), KOAc, DMSO, 100° C..

Into a 1 L flask was weighed 41.4 g of sodium sulfite, 29 g of sodium bicarbonate, and 175 mL of water. The suspension was stirred at 80-85° C. and sulfonyl chloride (50 g) was added portionwise over 3 h. Heating was continued for 3 h then the reaction was allowed to stand at room temperature for 3 days. The intermediate sulfinate was collected by filtration with added water then was dried under high vacuum. The dry solids (45 g) were retuned to a 1 L flask along with 28.0 g of sodium bicarbonate, 25 mL of dimethylsulfate, and 63.75 mL of water. The resulting suspension was heated at 120-125° C., where it became a solution, for 20 h then was cooled and washed into a separatory funnel with ethyl acetate and water. The ethyl acetate was separated, washed with brine, was dried (Na$_2$SO$_4$), and concentrated in vacuo. The product was precipitated from dichloromethane with hexanes and was dried under high vacuum to afford the intermediate 4-Bromo-2-methanesulfonyl-1-methoxy-benzene as a colorless powder, yield: 31.1 g (67%). $^1$H NMR (400 MHz, CDCl$_3$): δ 8.08 (2, 1H), 7.69 (d, J=8 Hz, 1H), 6.96 (d, J=8 Hz, 1H), 4.00 (s, 3H), 3.21 (s, 3H).

Into a 500 mL flask was weighed 15.48 g (58.4 mmol) of bromide, 23 g of boronate, 21 g of potassium acetate, 5 g of dichloro[1,1'-bis(diphenylphosphino)ferrocene]palladium (II) dichloromethane adduct, and 150 mL of DMSO. The resulting suspension was heated at ~100° C. for 20 h then was cooled and diluted with 200 mL of ethyl acetate and 200 mL of water. The suspension was filtered through celite to remove solids and the filtrate was transferred to a separatory funnel. The aqueous phase was separated and washed with ethyl acetate. The ethyl acetate washings were combined, washed with brine, were dried (Na$_2$SO$_4$) and concentrated in vacuo.

The residue was purified by silica gel flash chromatography (Biotage, 65×200 mm SiO$_2$, gradient elution from 100% hexanes to 100% ethyl acetate over 1 h). Appropriate fractions were combined and concentrated in vacuo. The partially purified product was dissolved in ethyl acetate and was precipitated with hexanes. The 2-(3-Methanesulfonyl-4-methoxyphenyl)-4,4,5,5-tetramethyl-[1,3,2]dioxaborolane was recovered as a faintly yellow powder, yield: 12.56 g (77%). $^1$H NMR (400 MHz, CDCl$_3$): δ 8.43 (s, 1H), 8.01 (d, J=8 Hz, 1H), 7.03 (d, J=8 Hz, 1H), 4.02 (s, 3H), 3.20 (s, 3H), 1.33 (s, 12H).

EXAMPLE 23

Preparation of ethyl 2-(methylsulfonyl)-4-(4,4,5,5-tetramethyl-1,3,2-dioxaborolan-2-yl)benzoate

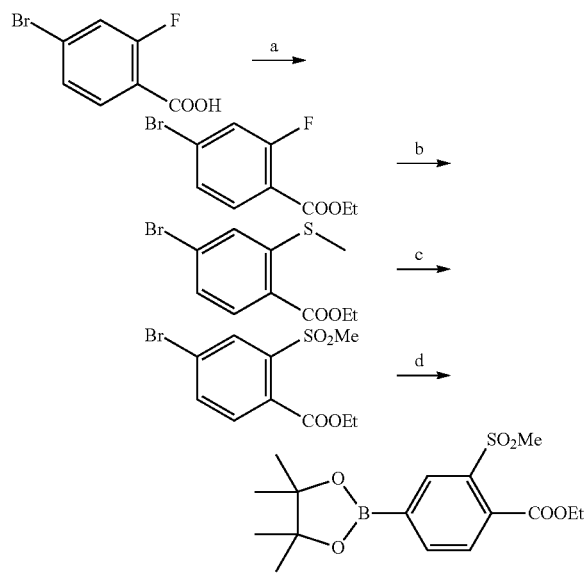

a) EDCI, DMAP, EtOH, CH$_2$Cl$_2$, 45° C.;
b) NaSMe, THF, 80° C.;
c) MCPBA, CH$_2$Cl$_2$, 25° C.;
d) Bis(pinacolato)diboron, Pd(dppf), KOAc, DMSO, 85° C.

Into a 1 L flask was weighed 24.66 g (113 mmol) of acid, 26.5 g (138 mmol) of EDCI, 1.7 g of DMAP, 425 mL of dichloromethane, and 25 mL of ethanol. The resulting solution was heated at 40-45° C. for 24 h then was concentrated in vacuo to remove dichloromethane. The residue was washed into a separatory funnel with ethyl acetate and 1 M HCl. The ethyl acetate was separated, washed with brine, was dried (Na$_2$SO$_4$) and was concentrated in vacuo. The intermediate 4-Bromo-2-fluoro-benzoic acid ethyl ester was recovered as a colorless oil, yield: 24.99 g (89.8%).

The ester was treated with 12.2 g of sodium thiomethoxide and 200 mL of THF and the resulting suspension was heated at 80-85° C. for 5 h. The reaction was then concentrated to remove THF and was washed into a separatory funnel with ethyl acetate and 1 M HCl. The ethyl acetate was separated, washed with brine, was dried (Na$_2$SO$_4$), and concentrated in vacuo affording the intermediate 4-Bromo-2-methylsulfanyl-benzoic acid ethyl ester as a light gray solid, yield: 27.5 g (99%). $^1$H NMR (400 MHz, CDCl$_3$): δ 7.86 (d, J=8 Hz, 1H), 7.36 (s, 1H), 7.28 (d, J=8 Hz, 1H), 4.38 (q, J=7 Hz, 2H), 2.45 (s, 3H), 1.39 (t, J=7 Hz, 3H).

Into a 1 L flask was weighed 15.0 g of 4-Bromo-2-methylsulfanyl-benzoic acid ethyl ester (54.5 mmol), 200 mL of dichloromethane, and 28.0 g of MCPBA (77% max., Aldrich) was added portionwise at room temperature. The resulting suspension was stirred at room temperature for three days then was concentrated in vacuo to remove dichloromethane. The residue was washed into a separatory funnel with ethyl acetate and 1.0 M NaOH. The ethyl acetate was separated, washed with brine, was dried (Na$_2$SO$_4$), and concentrated in vacuo. The intermediate 4-Bromo-2-methanesulfonyl-benzoic acid ethyl ester was recovered as a colorless oil which crystallized on standing, yield: 16.3 g (97%). $^1$H NMR (400 MHz, CDCl$_3$): δ 8.27 (s, 1H), 7.82 (d, J=8 Hz, 1H), 7.60 (d, J=8 Hz, 1H), 4.44 (q, J=7 Hz, 2H), 3.38 (s, 3H), 1.41 (t, J=7 Hz, 3H).

The 4-Bromo-2-methanesulfonyl-benzoic acid ethyl ester (16.3 g, 53 mmol) was weighed into a flask with 21 g of bis(pinacolato)diboron, 19 g of potassium acetate, 5 g of dichloro[1,1'-bis(diphenylphosphino)ferrocene]palladium (II) dichloromethane adduct, and 150 mL of DMSO. The resulting suspension was heated at 80-85° C. for 20 h then was diluted with 200 mL of water, 200 mL of ethyl acetate, and the reaction mixture was filtered through celite to remove solids. The filtrate was transferred to a separatory funnel and the aqueous phase was separated and washed with ethyl acetate.

The ethyl acetate washings were combined, washed with brine, were dried (Na$_2$SO$_4$) and concentrated in vacuo. The residue was purified by silica gel flash chromatography (Biotage, 65×200 mm SiO$_2$, gradient elution from 100% hexanes to 40% ethyl acetate over 1 h). Appropriate fractions were combined and concentrated in vacuo affording the product as a colorless solid, yield: 12.65 g (67%). $^1$H-NMR (400 MHz, CDCl$_3$): δ 8.52 (s, 1H), 8.08 (d, J=8 Hz, 1H), 7.65 (d, J=8 Hz, 1H), 4.45 (q, J=7 Hz, 2H), 3.33 (s, 3H), 1.42 (t, J=7 Hz, 3H), 1.35 (s, 12H).

EXAMPLE 24

Preparation of 2-(methylsulfonyl)-4-(4,4,5,5-tetramethyl-1,3,2-dioxaborolan-2-yl)phenyl)methanol

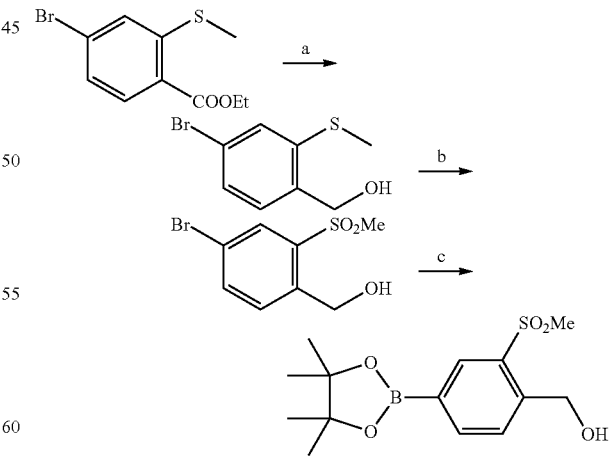

a) LiBH$_4$, THF, 85° C.;
b) MCPBA, CH$_2$C$_2$, 25° C.;
c) Bis(pinacolato)diboron, Pd(dppf), KOAc, DMSO, 100° C..

The 4-Bromo-2-methanesulfonyl-benzoic acid ethyl ester was prepared as described in Example 23. Into a 1 L flask was weighed 27.5 g of ester (99.9 mmol) and 150 mL of THF. A solution of 2.0 M LiBH₄ in THF (50 mL, 100 mmol) was then added and the reaction was heated to 80-85° C. where it remained for 23 h. The reaction was then removed from heat and was cooled in an ice bath as it was quenched by addition of acetone. The reaction was then concentrated in vacuo and was washed into a separatory funnel with ethyl acetate and 1 M HCl. The ethyl acetate was separated, washed with brine, was dried (Na₂SO₄), and concentrated in vacuo. The intermediate (4-Bromo-2-methylsulfanyl-phenyl)-methanol was recovered as a colorless oil that solidified on standing, yield: 25.5 g (100+%). ¹H NMR (400 MHz, CDCl₃): δ 7.24-7.34 (m, 3H), 4.69 (s, 2H), 2.50 (s, 3H).

The alcohol was then dissolved in 250 mL of dichloromethane, was cooled to 0-3° C. in an ice bath, and 44 g of 3-chloroperbenzoic acid (77% max., Aldrich) was added portionwise. The reaction was then allowed to warm to room temperature where it remained for 22 h. The reaction was then concentrated in vacuo to remove dichloromethane and the residue was washed into a separatory funnel with ethyl acetate and 1 M NaOH. The ethyl acetate was separated, washed with 1 M NaOH, was dried (Na₂SO₄), and concentrated in vacuo. The residue was purified by silica gel flash chromatography (Biotage, 65×200 mm SiO₂, gradient elution from 100% hexanes to 100% ethyl acetate over 1 h).

Appropriate fractions were combined and concentrated in vacuo to afford the intermediate (4-Bromo-2-methanesulfonyl-phenyl)-methanol as a colorless, semi-crystalline solid, yield: 17.13 g (65%). ¹H NMR (400 MHz, CDCl₃): δ 8.18 (s, 1H), 7.77 (d, J=8 Hz, 1H), 7.46 (d, J=8 Hz, 1H), 4.92 (s, 2H), 3.19 (s, 3H), 2.94 (br s, 1H).

Into a 1 L flask was weighed 17.13 g of bromide, 25 g of bis(pinacolato)diboron, 5.0 g of dichloro[1,1'-bis(diphenylphosphino)ferrocene]palladium (II) dichloromethane adduct, 23 g of potassium acetate, and 175 mL of DMSO. The resulting suspension was heated at 98-102° C. for 18 h then was diluted with 200 mL of ethyl acetate and 200 mL of water. The resulting suspension was filtered through celite to remove solids and the filtrate was transferred to a separatory funnel. The aqueous phase was separated and washed with ethyl acetate. The ethyl acetate washings were combined, washed with brine, were dried (Na₂SO₄) and concentrated in vacuo. The residue was purified by silica gel flash chromatography (Biotage, 65×200 mm SiO₂, gradient elution from 100% hexanes to 40% ethyl acetate over 1 h). Appropriate fractions were combined and concentrated in vacuo. The partially purified product was dissolved in dichloromethane and was precipitated with hexanes. The [2-Methanesulfonyl-4-(4,4,5,5-tetramethyl-[1,3,2]dioxaborolan-2-yl)-phenyl]-methanol was recovered as an off-white powder, yield: 8.78 g (43%). ¹H NMR (400 MHz, CDCl₃): δ 8.45 (s, 1H), 8.04 (d, J=8 Hz, 1H), 7.57 (d, J=8 Hz, 1H), 4.96 (s, 1H), 3.17 (s, 3H), 1.35 (s, 6H), 1.24 (s, 61H).

EXAMPLE 25

Preparation of 6-(4,4,5,5-tetramethyl-1,3,2-dioxaborolan-2-yl)-2,3-dihydro-1-benzothiophene-3-ol 1,1-dioxide

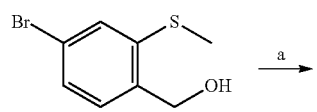

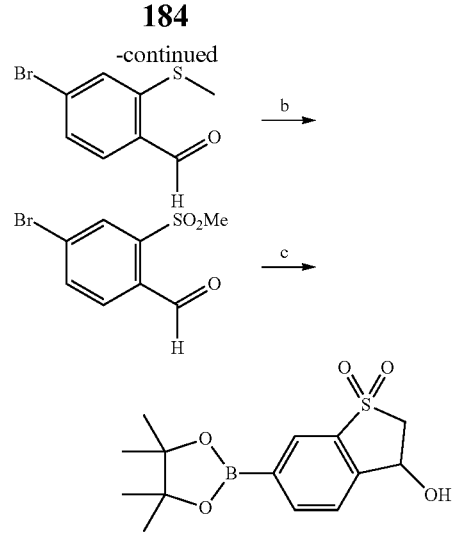

a) DMSO, oxalyl chloride, CH₂C₂, -78° C.;
b) MCPBA, CH₂C₂, 25° C.;
c) Bis(pinacolato)diboron, Pd(dppf), KOAc, DMSO, 100° C..

The (4-Bromo-2-methylsulfanyl-phenyl)-methanol was prepared as described in Example 24. Into a 500 mL flask was placed 220 mL of dichloromethane and 5.66 mL of oxalyl chloride under nitrogen. The solution was cooled to -70 to -78° C. and 9.80 mL of DMSO was added dropwise. The resulting suspension was stirred at -78° C. for 15 minutes. A solution of alcohol (10.0 g, 42.9 mmol) in mL of dichloromethane was prepared and was added to the suspension via cannula. The reaction was stirred at -78° C. for 0.5 h then 30 mL of triethylamine was added via syringe. The reaction was stirred at -78° C. for 30 minutes then was quenched by addition of saturated ammonium chloride. The mixture was washed into a separatory funnel with added water and dichloromethane. The dichloromethane was separated, dried (Na₂SO₄), and concentrated in vacuo. The residue was purified by silica gel flash chromatography (Biotage, 65×200 mm SiO₂, gradient elution from 100% hexanes to 20% ethyl acetate over 1 h). Appropriate fractions were combined and concentrated in vacuo to afford the product as a lemon yellow solid, yield: 6.78 g (88% based on recovered starting material). ¹H NMR (400 MHz, CDCl₃): δ 10.19 (s, 1H), 7.65 (d, J=8 Hz, 1H), 7.40-7.45 (m, 2H), 2.50 (s, 3H).

Into a 250 mL flask was weighed 6.78 g (25.8 mmol) of aldehyde and 60 mL of dichloromethane. The reaction was cooled to 0-3° C. in an ice bath and 10 g of MCPBA (77% max., Aldrich) was added portionwise. The reaction was allowed to warm to room temperature where it remained for 21 h. The reaction was then concentrated in vacuo to remove dichloromethane and was washed into a separatory funnel with ethyl acetate and 1 M NaOH. The ethyl acetate was separated, washed with 1.0 M NaOH, brine, was dried (Na₂SO₄), and was concentrated in vacuo. The residue was purified by silica gel flash chromatography (Biotage, 45×150 mm SiO₂, gradient elution from 100% hexanes to 20% ethyl acetate over 1 h). Appropriate fractions were combined and concentrated in vacuo to afford the product as a colorless solid, yield: 5.32 g (89%). ¹H NMR (400 MHz, CDCl₃): δ 10.71 (s, 1H), 8.30 (s, 1H), 7.95 (s, 2H), 3.29 (s, 3H).

Into a 250 mL flask was weighed 5.32 g (20.2 mmol) of aldehyde, 7.13 g of potassium acetate, 7.85 g of bis(pinacolato)diboron, 1.88 g of dichloro[1,1'-bis(diphenylphosphino)ferrocene]palladium (II) dichloromethane adduct, and 55 mL of DMSO. The resulting suspension was heated at 98-102° C. for 20 h then was diluted with 100 mL of ethyl acetate and 100 mL of water. The resulting suspension was filtered through celite to remove solids and the filtrate was transferred to a separatory funnel. The aqueous phase was separated and washed with ethyl acetate. The ethyl acetate washings were combined, washed with brine, were dried (Na$_2$SO$_4$) and concentrated in vacuo. The residue was purified by silica gel flash chromatography (Biotage, 65×200 mm SiO$_2$, gradient elution from 100% hexanes to 40% ethyl acetate over 0.5 h). Appropriate fractions were combined and concentrated in vacuo. The partially purified product was dissolved in dichloromethane and was precipitated with hexanes. The 1,1-Dioxo-6-(4,4,5,5-tetramethyl-[1,3,2]dioxaborolan-2-yl)-2,3-dihydro-1H-1λ*6*-benzo[b]thiophen-3-ol was recovered as a tan powder, yield: 1.88 g (30%). $^1$H NMR (400 MHz, CDCl$_3$): δ 8.21 (s, 1H), 8.08 (d, J=8 Hz, 1H), 7.64 (d, J=8 Hz, 1H), 5.49 (m, 1H), 3.80 (dd, J=7, 13 Hz, 1H), 3.45 (dd, J=5, 13 Hz, 1H), 2.79 (d, J=8 Hz, 1H), 1.34 (s, 12H).

EXAMPLE 26

Preparation of 2-(2-(methylsulfonyl)-4-(4,4,5,5-tetramethyl-1,3,2-dioxaborolan-2-yl)phenyl)propan-2-ol

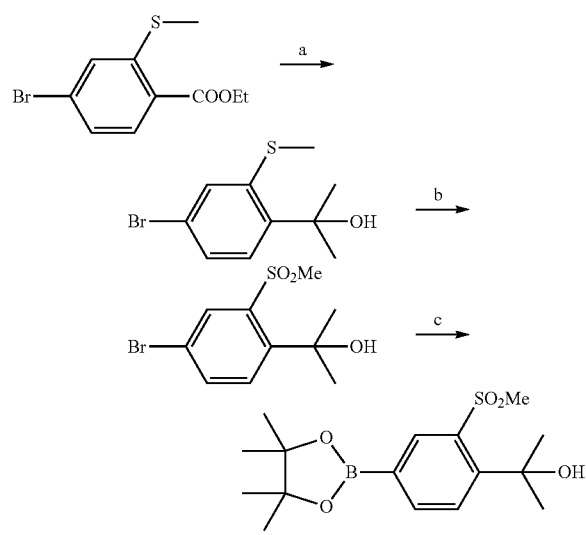

a) MeMgBr, THF, -78° C.;
b) MCPBA, CH$_2$C$_2$, 50° C.;
c) Bis(pinacolato)diboron, Pd(dppf), KOAc, DMSO, 100° C..

The 4-Bromo-2-methanesulfonyl-benzoic acid ethyl ester was prepared as described in Example 25. Into a 500 mL flask was weighed 10.2 g (37.1 mmol) of ester and 100 mL of anhydrous THF. The resulting solution was cooled to −78° C. and 80 mL of 1.4 M MeMgBr in THF (Aldrich) was added portionwise. The reaction was allowed to warm to room temperature where it remained for 3 h. The reaction was then quenched by addition of saturated ammonium chloride and the mixture was washed into a separatory funnel with ethyl acetate and saturated ammonium chloride. The ethyl acetate was separated, washed with brine, was dried (Na$_2$SO$_4$), and concentrated in vacuo. The intermediate 2-(4-Bromo-2-methylsulfanyl-phenyl)-propan-2-ol was carried into the subsequent step without additional purification.

The crude alcohol was dissolved in 100 mL of dichloromethane, was cooled to 0-3° C. in an ice bath, and 20 g of MCPBA (77% max., Aldrich) was added portionwise. The reaction was then removed to an oil bath where it was heated at ~50° C. for 18 h. The reaction was then cooled and concentrated in vacuo to remove dichloromethane. The residue was washed into a separatory funnel with ethyl acetate and 1.0 M NaOH. The ethyl acetate was separated, washed with 1.0 M NaOH, brine, was dried (Na$_2$SO$_4$), and concentrated in vacuo. The residue was purified by silica gel flash chromatography (Biotage 45×150 mm SiO$_2$, gradient elution from 100% hexanes to 40% ethyl acetate over 1 h). Appropriate fractions were combined and concentrated in vacuo affording the intermediate 2-(4-Bromo-2-methanesulfonyl-phenyl)-propan-2-ol as a colorless solid, yield: 10.02 g (92% for both steps). $^1$H NMR (400 MHz, CDCl$_3$): δ 8.33 (s, 1H), 7.68 (d, J=8 Hz, 1H), 7.33 (d, J=8 Hz, 1H), 3.41 (s, 3H), 1.76 (s, 1H), 1.69 (s, 6H).

Into a 500 mL flask was weighed 9.88 g (33.7 mmol) of bromide, 12 g of potassium acetate, 13.1 g of bis(pinacolato) diboron, 3.0 g of dichloro[1,1'-bis(diphenylphosphino)ferrocene]palladium (II) dichloromethane adduct, and 90 mL of DMSO. The resulting suspension was heated at 98-102° C. for 20 h then was diluted with 200 mL of ethyl acetate and 200 mL of water. The resulting suspension was filtered through celite to remove solids and the filtrate was transferred to a separatory funnel. The aqueous phase was separated and washed with ethyl acetate. The ethyl acetate washings were combined, washed with brine, were dried (Na$_2$SO$_4$) and concentrated in vacuo. The residue was purified by silica gel flash chromatography (Biotage, 65×200 mm SiO$_2$, gradient elution from 100% hexanes to 100% ethyl acetate over 1 h). Appropriate fractions were combined and concentrated in vacuo affording the 2-[2-Methanesulfonyl-4-(4,4,5,5-tetramethyl-[1,3,2]dioxaborolan-2-yl)-phenyl]-propan-2-ol as a gray solid, yield: 10.0 g (87%). $^1$H NMR (400 MHz, CDCl$_3$): δ 8.61 (s, 1H), 7.96 (d, J=8 Hz, 1H), 7.45 (d, J=8 Hz, 1H), 3.39 (s, 3H), 1.70 (s, 6H), 1.34 (s, 12H).

Several different boronates can by synthesized by the general methods outlined in Scheme 18 and exemplified in Example 27. A suitable aromatic substrate, such as a 2-halopyridine, can react to produce an intermediate with an 'directing' group attached. Such a system can then be halogenated to afford a para-disposed halogen. Such a system can then be converted to a boronate using methods such as those described below. Alternatively, several commercially available intermediates could be used such as 2,4-Dibromo-3-methylpyridine, 4-Bromo-2-chlorpyrimidine, and several substituted benzene rings.

Scheme 18

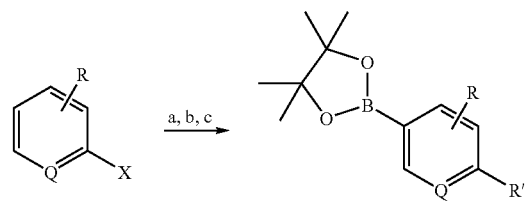

Q = Used to identify any aromatic ring system that can be suitably functionalized as would be readily apparent to one skilled in the art
X = halogen or prexisting 'directing' group
R' = 'directing group'
R = any suitable functionality that will not interfere with the directing effect of the R' group

EXAMPLE 27

Preparation of 2-(methylthio)-5-(4,4,5,5-tetramethyl-1,3,2-dioxaborolan-2-yl)pyridine

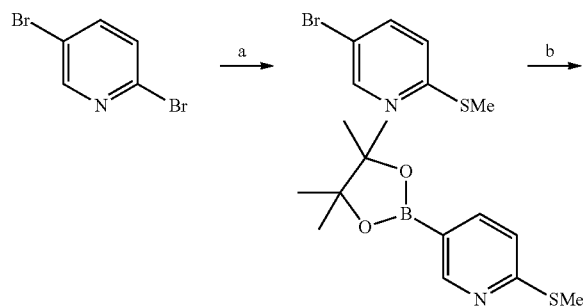

Reaction condition
a) NaSMe, DMF, 160° C.;
b) Bis(pinacolato)diboron, Pd(dppf), KOAc, DMSO, 80° C..

2,5-Dibromo-pyridine (3.0 g, 12.7 mmol) and sodium thiomethoxide (0.84 g, 12 mmol) were dissolved in 18 ml anhydrous N N-dimethylformamide. The mixture was heated at 160° C. under nitrogen for 6 hrs. After cooling to room temperature, water and ethyl acetate were added to the reaction mixture. The aqueous layer was extracted with ethyl acetate several times. The combined extract was washed with brine, dried over sodium sulfate, and concentrated in vacuo. The crude product was purified by column chromatography on silica gel (0→6% EtOAC/Hexane) to give 5-Bromo-2-methylsulfanyl-pyridine as a white solid (2.18 g, 84% yield). 1H-NMR (400 MHz, CDCl$_3$): δ 2.55 (s, 3H), 7.09 (dd, 1H, J=0.7, J=8.6), 7.59 (dd, 1H, J=2.4, J=8.6), 8.50 (m, 1H).

Palladium catalyst ([1,1'-bis(diphenylphosphino)ferrocene]dichloropalladium (II) complex with dichloromethane (1:1), 167 mg, 0.21 mmol), potassium acetate (1.81 g, 18.5 mmol, Aldrich), and bis(pinacolato)diboron (1.56 g, 6.1 mmol) were placed into a vial and degassed with stream of nitrogen for 20 min. In a separate vial, 5-bromo-2-methylsulfanylpyridine (no. (2)) (836 mg, 4.1 mmol) was dissolved in 8 ml anhydrous DMSO and degassed with stream of nitrogen for 20 min. This DMSO solution was added to the "catalyst" vial, and then heated at 80° C. overnight. After cooling to room temperature, water and ethyl acetate were added to the reaction mixture. The aqueous layer was extracted with ethyl acetate. The combined organic layers were washed with brine, dried over sodium sulfate, and concentrated in vacuo. The crude product was purified by column chromatography on silica gel (10→30% EtOAC/Hexane, 025% Et$_3$N in hexane) to give the 2-Methylsulfanyl-5-(4,4,5,5-tetramethyl-[1,3,2]dioxaborolan-2-yl)pyridine as a colorless oil (1.00 g, 97% yield). 1H NMR (400 MHz, CDCl$_3$): δ 1.35 (s, 12H), 2.58 (s, 3H), 7.16 (dd, 1H, J=1.0, J=8.0), 7.83 (dd, 1H, J=1.8, J=8.0), 8.50 (dd, 1H, J=1.7, J=1.0)

In a manner similar to that stated the following examples of the invention were prepared by substituting an appropriate reagent.

2-Methylsulfanyl-3-methyl-5-(4,4,5,5-tetramethyl-[1,3,2]dioxaborolan-2-yl)pyridine. 1H-NMR (400 MHz, CDCl$_3$): δ 1.35 (s, 12H), 2.24 (s, 3H), 2.59 (s, 3H), 7.64 (d, J=0.8, 1H), 8.63 (d, J=1.0, 1H).

2-Ethylsulfanyl-3-methyl-5-(4,4,5,5-tetramethyl-[1,3,2]dioxaborolan-2-yl)pyridine. 1H-NMR (400 MHz, CDCl$_3$): δ 1.35 (s, 12H), 1.38 (t, J=7.4, 3H), 2.22 (s, 3H), 3.23 (q, J=7.4, 2H), 7.64 (d, J=0.8, 1H,), 8.61 (d, J=1.0, 1H). MS (ES): 280.2, 282.1 [M+H]$^+$.

Scheme 19

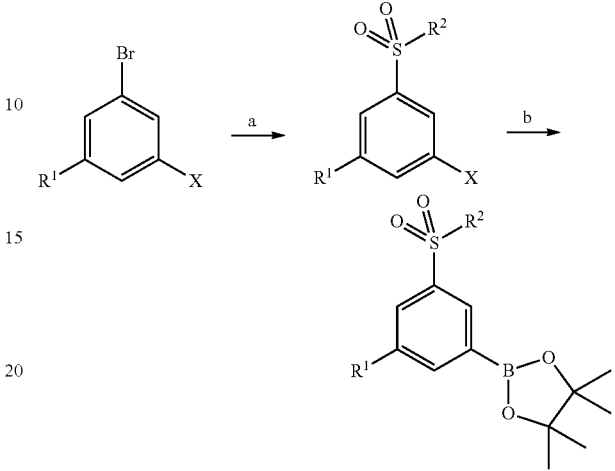

R$^1$ = any functionality that will not prevent the described chemistry from occuring
R$^2$ = alkyl, aryl, or other appropriate attachments
X = halogen a) NaO$_2$SR$^2$, 10 mol % CuI, 20 mol % proline, 20 mol % NaOH, DMSO, μW 210° C.;
b) bis(pinacolato)diboron, KOAc, Cl$_2$Pd(dppf), DMSO, μW 130° C..

In general, compounds of formula 1,3- (or 3,5-) disubstituted aryl systems can be prepared as depicted in Scheme 19. A dibromoarene can react with a sulfinic acid sodium salt (NaO$_2$SR$^2$) in the presence of catalytic copper iodide and the sodium salt of proline at elevated temperature to give the corresponding sulfone. This intermediate then can be converted into the corresponding arylboronate or boronic acid under standard conditions apparent to one skilled in the art.

EXAMPLE 28

Preparation of 1-bromo-3-methanesulfonyl-5-methyl-benzene

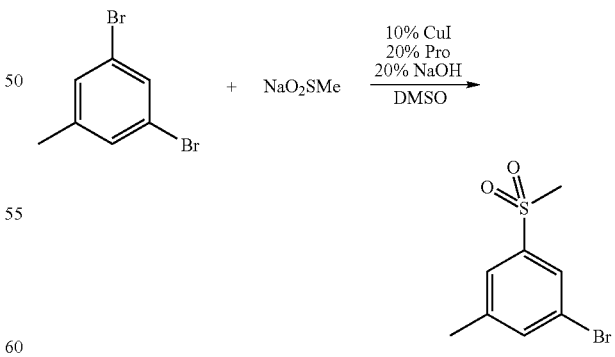

A mixture of 3,5-dibromotoluene (2.0 g, 8.0 mmol), sodium methanesulfinate (0.92 g, 9.0 mmol), copper(I) iodide (152 mg, 0.8 mmol), proline (0.18 g, 1.6 mmol) and sodium hydroxide (64 mg, 1.6 mmol) in DSMO (15 mL, anhyd) was heated in a microwave unit (Biotage Initiator™) at 210° C. for min. The reaction was repeated two more times and the reaction mixtures were combined, diluted with H₂O and extracted with EtOAc. The combined extracts were washed with H₂O and brine, then dried (Na₂SO₄), concentrated and purified by chromatography (silica, EtOAc/Hex, 0:100 to 40:60) to give the title compound (1.2 g, 20% combined yield) as a white solid. GC-MS (EI): 248, 250.

2-(3-Methanesulfonyl-5-methyl-phenyl)-4,4,5,5-tetramethyl-[1,3,2]dioxaborolane was prepared from 1-bromo-3-methanesulfonyl-5-methyl-benzene in a similar manner as other boronate syntheses previously described.

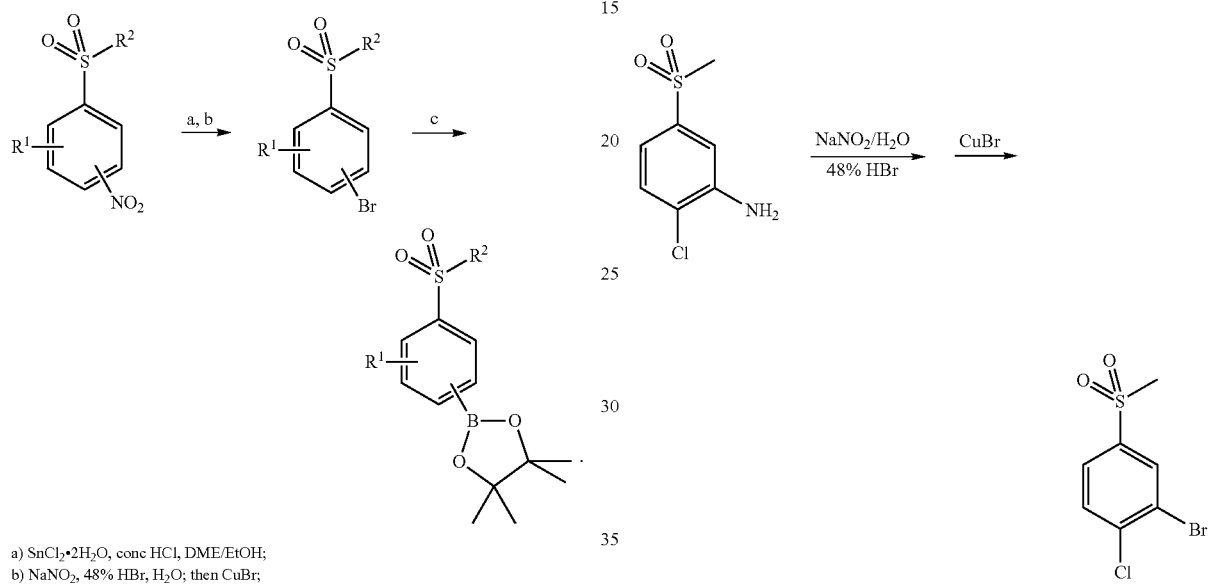

a) SnCl₂•2H₂O, conc HCl, DME/EtOH;
b) NaNO₂, 48% HBr, H₂O; then CuBr;
c) bis(pinacolato)diboron, KOAc, Cl₂Pd(dppf), DMSO, μW 130° C..

In general, several different boronates can be prepared as depicted in Scheme 20 A nitroarene can be reduced under standard conditions, such as with tin chloride, to yield the corresponding arylamine, which can be converted to the corresponding bromoarene via the Sandmeyer reaction. Aryl bromides can easily be converted to boronates using conditions apparent to one skilled in the art.

EXAMPLE 29

Preparation of 2-bromo-1-chloro-4-methanesulfonyl-benzene

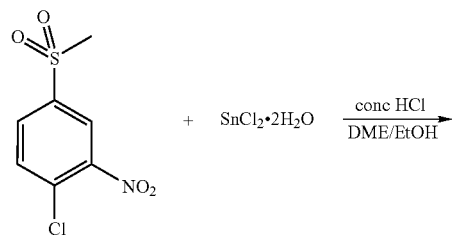

To a stirred mixture of 1-chloro-4-methanesulfonyl-2-nitrobenzene (5.2 g, 22 mmol) and 3:4 DME/EtOH (77 mL) was added dropwise a solution of tin(II) chloride dihydrate (15.3 g, 68 mmol) in 9N HCl (36 mL). After 3 h the reaction mixture was poured onto ice and treated with 10% NaOH until pH 11 had been achieved. The resulting mixture was extracted with EtOAc (4×75 mL) and the combined extracts were washed with brine, dried (Na₂SO₄) and concentrated to afford the title compound (4.5 q, quant) as a white solid, which was used without purification in the next step. GC-MS (EI): 205.

To a slurry of 2-chloro-5-methanesulfonyl-aniline (4.50 g, 21.9 mmol) in 48% HBr (12 mL) at 0° C. was added dropwise a solution of sodium nitrite (2.28 g, 33 mmol) in H₂O (8 mL) at such a rate that the temperature never exceeds 5° C. The resulting yellow mixture was allowed to stir 20 min at 0° C. and then charged with copper(I) bromide (3.3 g, 23 mmol). After 30 min the resulting mixture was extracted with EtOAc (2×100 mL) and the combined extracts were washed successively with satd NH₄Cl, 3N HCl and brine, then dried (Na₂SO₄) and concentrated under reduced pressure. The resulting residue was purified by chromatography (silica, EtOAc/Hex, 0:100 to 50:50) to give the title compound (4.92 g, 83%) as a white solid. GC-MS (EI): 268, 270.

2-(2-Chloro-5-methanesulfonyl-phenyl)-4,4,5,5-tetramethyl-[1,3,2]dioxaborolane was prepared from 2-bromo-1-chloro-4-methanesulfonyl-benzene in a similar manner as other boronate syntheses previously described.

EXAMPLE 30

The following compounds of the invention, in Tables 1 and 2, were prepared according to one of the previous Example 1-29.

TABLE 1

| Cpd # | Structure | Name |
|---|---|---|
| 1 | 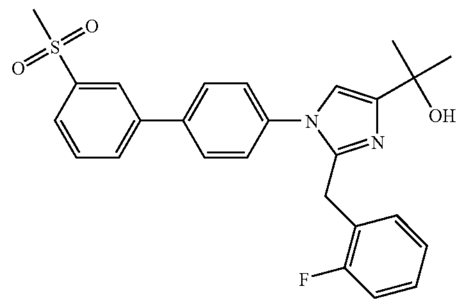 [SMILES: CC(C)(O)c1cn(-c2ccc(-c3cccc(S(C)(=O)=O)c3)cc2)c(Cc2ccccc2F)n1] | 2-(2-(2-fluorobenzyl-1-(3'-(methylsulfonyl)biphenyl-4-yl)-1H-imidazol-4-yl)propan-2-ol; |
| 2 | 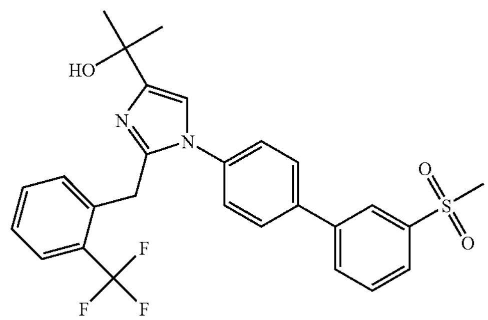 [SMILES: CC(C)(O)c1cn(-c2ccc(-c3cccc(S(C)(=O)=O)c3)cc2)c(Cc2ccccc2C(F)(F)F)n1] | 2-(1-(3'-(methylsulfonyl)biphenyl-4-yl)-2-(2-(trifluoromethyl)benzyl)-1H-imidazol-4-yl)propan-2-ol; |
| 3 | 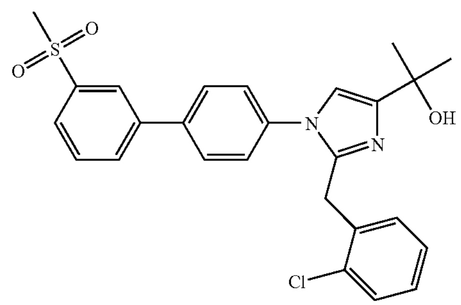 | 2-(2-(2-chlorobenzyl)-1-(3'-(methylsulfonyl)biphenyl-4-yl)-1H-imidazol-4-yl)propan-2-ol; |
| 4 | 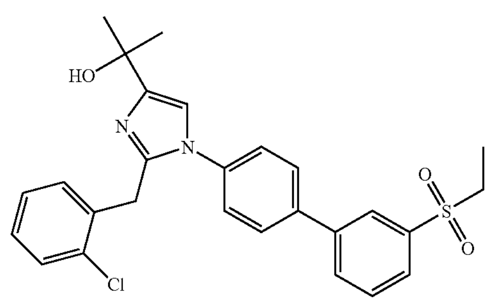 [SMILES: CCS(=O)(=O)c1cccc(-c2ccc(-n3cc(C(C)(C)O)nc3Cc3ccccc3Cl)cc2)c1] | 2-(2-(2-chlorobenzyl)-1-(3'-(ethylsulfonyl)biphenyl-4-yl)-1H-imidazol-4-yl)propan-2-ol; |

TABLE 1-continued

| Cpd # | Structure | Name |
|---|---|---|
| 5 | 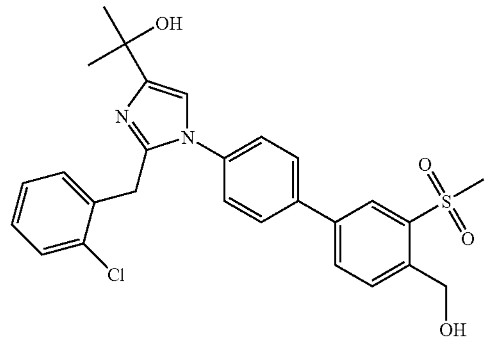 [SMILES: CC(C)(O)c1cn(-c2ccc(-c3ccc(CO)c(S(C)(=O)=O)c3)cc2)c(Cc2ccccc2Cl)n1] | 2-(2-(2-chlorobenzyl)-1-(4'-(hydroxymethyl)-3'-(methylsulfonyl)biphenyl-4-yl)-1H-imidazol-4-yl)propan-2-ol; |
| 6 | 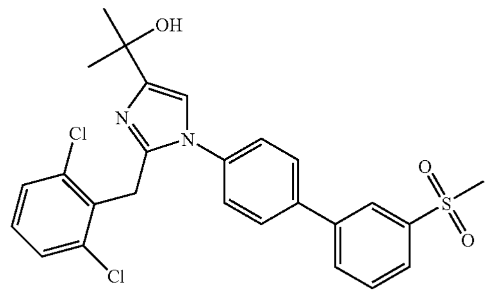 | 2-(2-(2,6-dichlorobenzyl)-1-(3'-(methylsulfonyl)biphenyl-4-yl)-1H-imidazol-4-yl)propan-2-ol; |
| 7 | 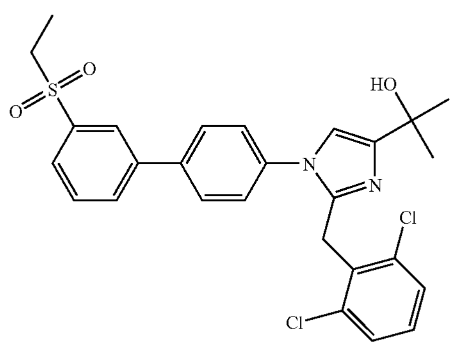 | 2-(2-(2,6-dichlorobenzyl)-1-(3'-(ethylsulfonyl)biphenyl-4-yl)-1H-imidazol-4-yl)propan-2-ol; |
| 8 | 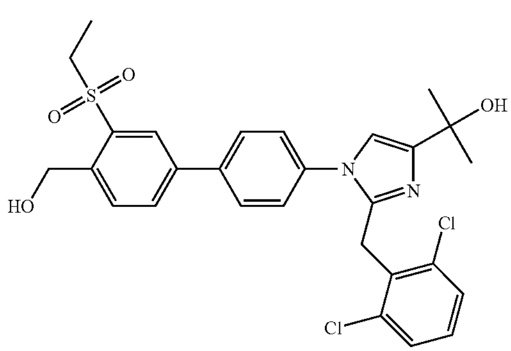 [SMILES: CCS(=O)(=O)c1cc(-c2ccc(-n3cc(C(C)(C)O)nc3Cc3c(Cl)cccc3Cl)cc2)ccc1CO] | 2-(2-(2,6-dichlorobenzyl)-1-(3'-(ethylsulfonyl)-4'-(hydroxymethyl)biphenyl-4-yl)-1H-imidazol-4-yl)propan-2-ol; |

TABLE 1-continued

| Cpd # | Structure | Name |
|---|---|---|
| 9 | 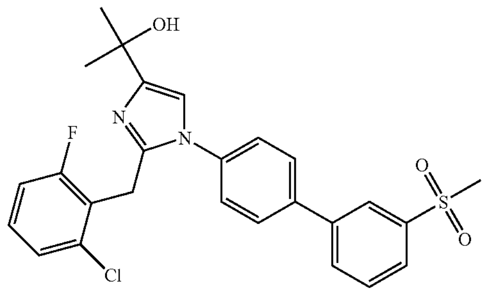 | 2-(2-(2-chloro-6-fluorobenzyl)-1-(3'-(methylsulfonyl)biphenyl-4-yl)-1H-imidazol-4-yl)propan-2-ol; |
| 10 | 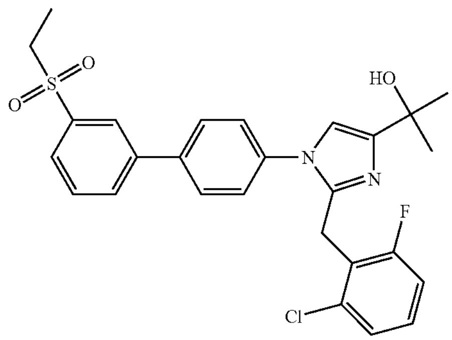 | 2-(2-(2-chloro-6-fluorobenzyl)-1-(3'-(ethylsulfonyl)biphenyl-4-yl)-1H-imidazol-4-yl)propan-2-ol; |
| 11 | 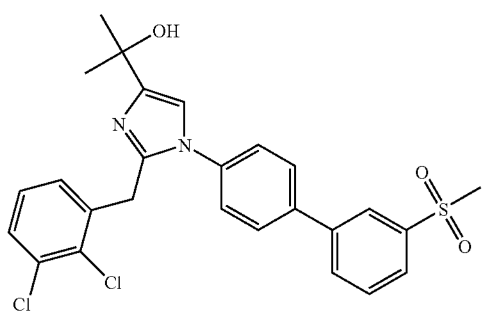 [SMILES: CC(C)(O)c1cn(-c2ccc(-c3cccc(S(C)(=O)=O)c3)cc2)c(Cc2cccc(Cl)c2Cl)n1] | 2-(2-(2,3-dichlorobenzyl)-1-(3'-(methylsulfonyl)biphenyl-4-yl)-1H-imidazol-4-yl)propan-2-ol; |
| 12 | 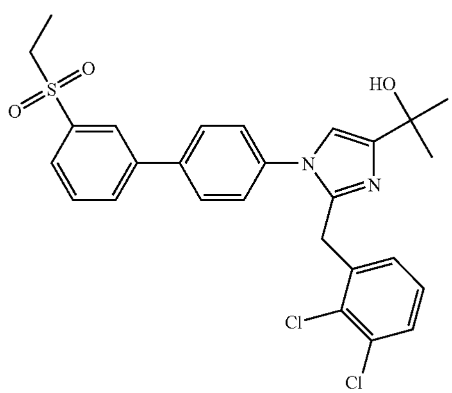 [SMILES: CCS(=O)(=O)c1cccc(-c2ccc(-n3cc(C(C)(C)O)nc3Cc3cccc(Cl)c3Cl)cc2)c1] | 2-(2-(2,3-dichlorobenzyl)-1-(3'-(ethylsulfonyl)biphenyl-4-yl)-1H-imidazol-4-yl)propan-2-ol; |

TABLE 1-continued

| Cpd # | Structure | Name |
|---|---|---|
| 13 | 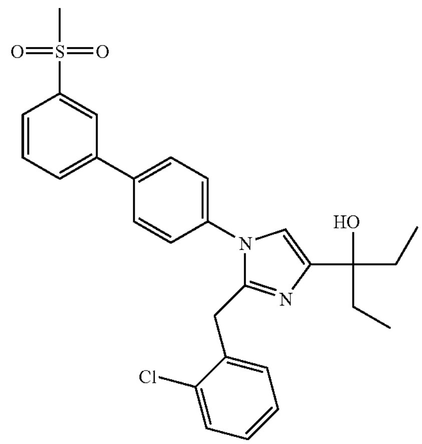 [SMILES: CCC(O)(CC)c1cn(-c2ccc(-c3cccc(S(C)(=O)=O)c3)cc2)c(Cc2ccccc2Cl)n1] | 3-(2-(2-chlorobenzyl)-1-(3'-(methylsulfonyl)biphenyl-4-yl)-1H-imidazol-4-yl)pentan-3-ol; |
| 14 | 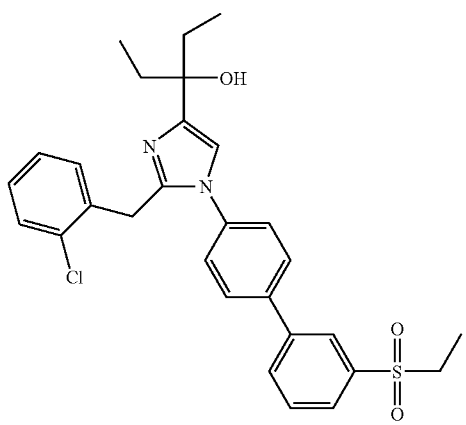 [SMILES: CCC(O)(CC)c1cn(-c2ccc(-c3cccc(S(=O)(=O)CC)c3)cc2)c(Cc2ccccc2Cl)n1] | 3-(2-(2-chlorobenzyl)-1-(3'-(ethylsulfonyl)biphenyl-4-yl)-1H-imidazol-4-yl)pentan-3-ol; |
| 15 | 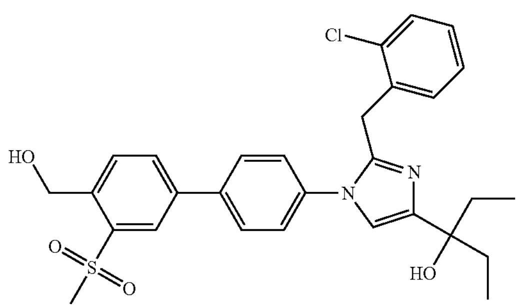 [SMILES: CCC(O)(CC)c1cn(-c2ccc(-c3ccc(CO)c(S(C)(=O)=O)c3)cc2)c(Cc2ccccc2Cl)n1] | 3-(2-(2-chlorobenzyl)-1-(4'-(hydroxymethyl)-3'-(methylsulfonyl)biphenyl-4-yl)-1H-imidazol-4-yl)pentan-3-ol; |
| 16 | 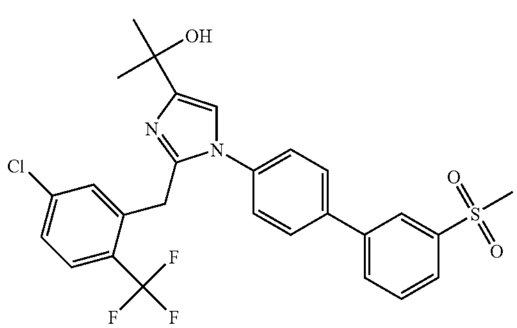 [SMILES: CC(C)(O)c1cn(-c2ccc(-c3cccc(S(C)(=O)=O)c3)cc2)c(Cc2cc(Cl)ccc2C(F)(F)F)n1] | 2-(2-(5-chloro-2-(trifluoromethyl)benzyl)-1-(3'-(methylsulfonyl)biphenyl-4-yl)-1H-imidazol-4-yl)propan-2-ol; |

TABLE 1-continued

| Cpd # | Structure | Name |
|---|---|---|
| 17 | 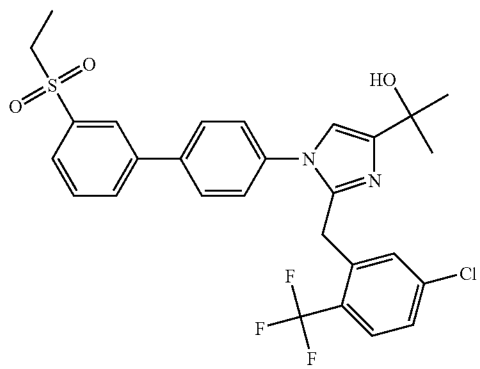 [SMILES: CCS(=O)(=O)c1cccc(-c2ccc(-n3cc(C(C)(C)O)nc3Cc3cc(Cl)ccc3C(F)(F)F)cc2)c1] | 2-(2-(5-chloro-2-(trifluoromethyl)benzyl)-1-(3'-(ethylsulfonyl)biphenyl-4-yl)-1H-imidazol-4-yl)propan-2-ol; |
| 18 | 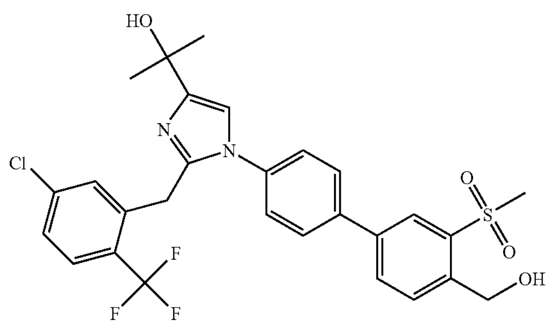 [SMILES: CC(C)(O)c1cn(-c2ccc(-c3ccc(CO)c(S(C)(=O)=O)c3)cc2)c(Cc2cc(Cl)ccc2C(F)(F)F)n1] | 2-(2-(5-chloro-2-(trifluoromethyl)benzyl)-1-(4'-(hydroxymethyl)-3'-(methylsulfonyl)biphenyl-4-yl)-1H-imidazol-4-yl)propan-2-ol; |
| 19 | 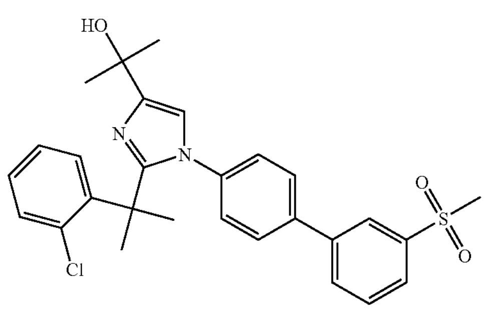 [SMILES: CC(C)(O)c1cn(-c2ccc(-c3cccc(S(C)(=O)=O)c3)cc2)c(C(C)(C)c2ccccc2Cl)n1] | 2-(2-(2-(2-chlorophenyl)propan-2-yl)-1-(3'-(methylsulfonyl)biphenyl-4-yl)-1H-imidazol-4-yl)propan-2-ol; |
| 20 | 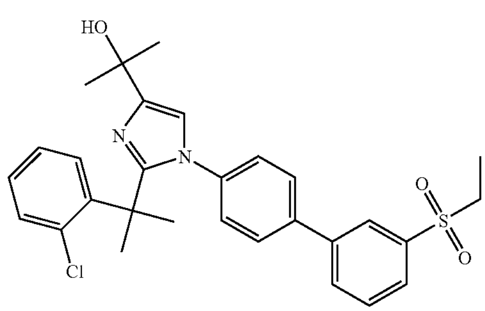 | 2-(2-(2-(2-chlorophenyl)propan-2-yl)-1-(3'-(ethylsulfonyl)biphenyl-4-yl)-1H-imidazol-4-yl)propan-2-ol; |

TABLE 1-continued

| Cpd # | Structure | Name |
|---|---|---|
| 21 | 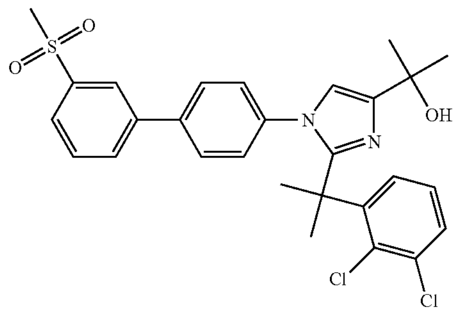 [SMILES: CC(C)(O)c1cn(-c2ccc(-c3cccc(S(C)(=O)=O)c3)cc2)c(C(C)(C)c2cccc(Cl)c2Cl)n1] | 2-(2-(2-(2,3-dichlorophenyl)propan-2-yl)-1-(3'-(methylsulfonyl)biphenyl-4-yl)-1H-imidazol-4-yl)propan-2-ol; |
| 22 | 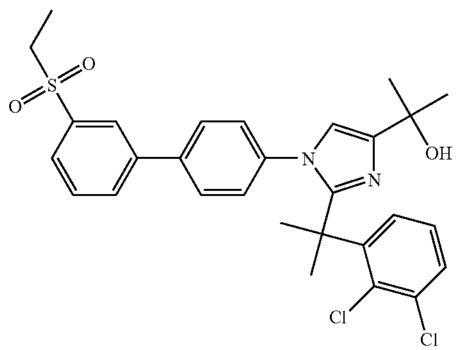 [SMILES: CCS(=O)(=O)c1cccc(-c2ccc(-n3cc(C(C)(C)O)nc3C(C)(C)c3cccc(Cl)c3Cl)cc2)c1] | 2-(2-(2-(2,3-dichlorophenyl)propan-2-yl)-1-(3'-(ethylsulfonyl)biphenyl-4-yl)-1H-imidazol-4-yl)propan-2-ol; |
| 23 | 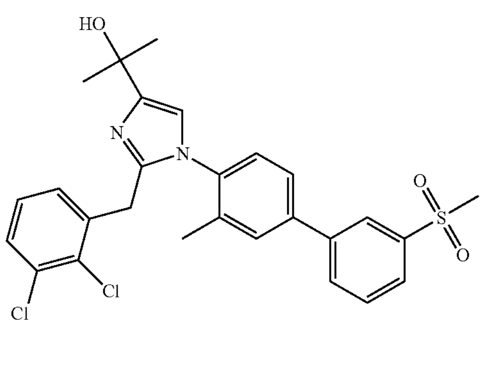 [SMILES: Cc1cc(-c2cccc(S(C)(=O)=O)c2)ccc1-n1cc(C(C)(C)O)nc1Cc1cccc(Cl)c1Cl] | 2-(2-(2,3-dichlorobenzyl)-1-(3-methyl-3'-(methylsulfonyl)biphenyl-4-yl)-1H-imidazol-4-yl)propan-2-ol; |
| 24 | 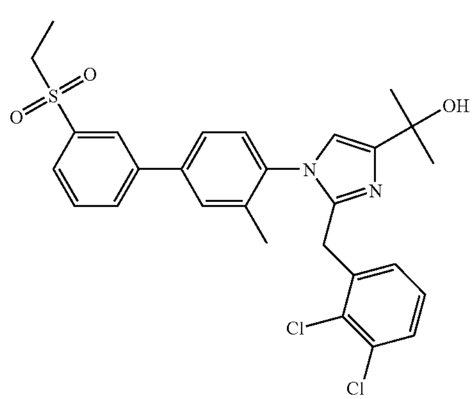 [SMILES: CCS(=O)(=O)c1cccc(-c2ccc(-n3cc(C(C)(C)O)nc3Cc3cccc(Cl)c3Cl)c(C)c2)c1] | 2-(2-(2,3-dichlorobenzyl)-1-(3'-(ethylsulfonyl)-3-methylbiphenyl-4-yl)-1H-imidazol-4-yl)propan-2-ol; |

TABLE 1-continued

| Cpd # | Structure | Name |
|---|---|---|
| 25 | 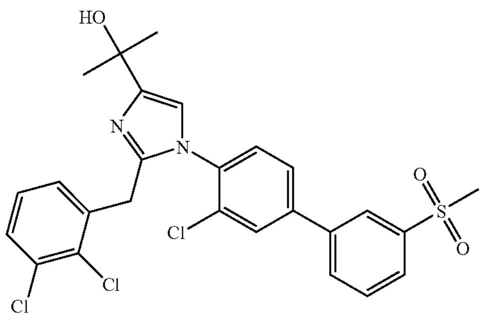 [SMILES: CC(C)(O)c1cn(-c2ccc(-c3cccc(S(C)(=O)=O)c3)cc2Cl)c(Cc2cccc(Cl)c2Cl)n1] | 2-(1-(3-chloro-3'-(methylsulfonyl)biphenyl-4-yl)-2-(2,3-dichlorobenzyl)-1H-imidazol-4-yl)propan-2-ol; |
| 26 | 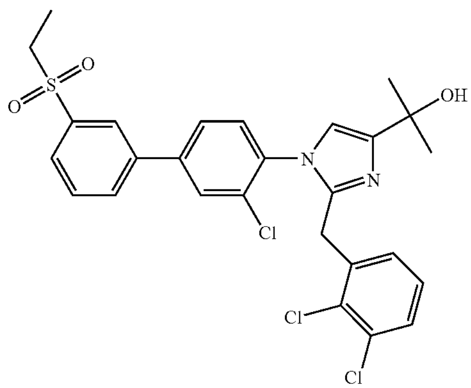 [SMILES: CCS(=O)(=O)c1cccc(-c2ccc(-n3cc(C(C)(C)O)nc3Cc3cccc(Cl)c3Cl)c(Cl)c2)c1] | 2-(1-(3-chloro-3'-(ethylsulfonyl)biphenyl-4-yl)-2-(2,3-dichlorobenzyl)-1H-imidazol-4-yl)propan-2-ol; |
| 27 | 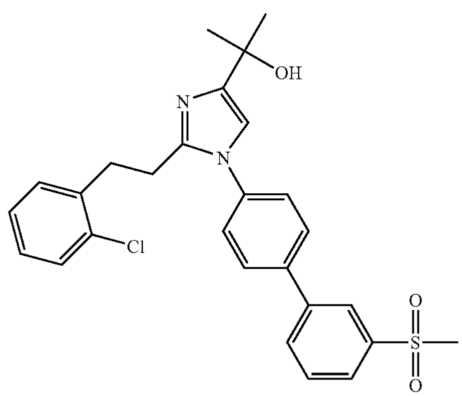 [SMILES: CC(C)(O)c1cn(-c2ccc(-c3cccc(S(C)(=O)=O)c3)cc2)c(CCc2ccccc2Cl)n1] | 2-(2-(2-chlorophenethyl)-1-(3'-(methylsulfonyl)biphenyl-4-yl)-1H-imidazol-4-yl)propan-2-ol; |
| 28 | 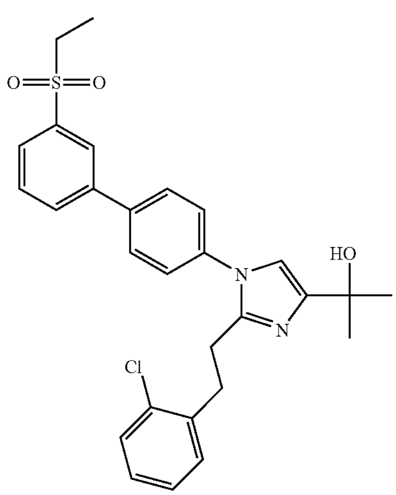 [SMILES: CCS(=O)(=O)c1cccc(-c2ccc(-n3cc(C(C)(C)O)nc3CCc3ccccc3Cl)cc2)c1] | 2-(2-(2-chlorophenethyl)-1-(3'-(ethylsulfonyl)biphenyl-4-yl)-1H-imidazol-4-yl)propan-2-ol; |

TABLE 1-continued

| Cpd # | Structure | Name |
|---|---|---|
| 29 | 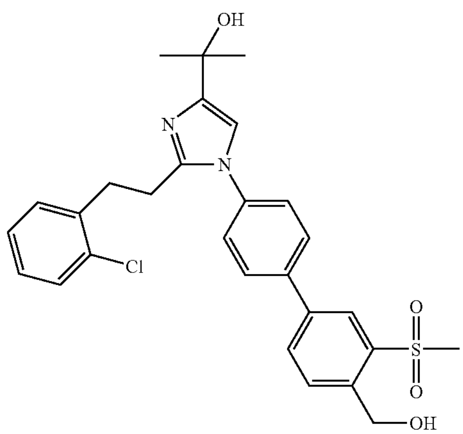 [SMILES: CC(C)(O)c1cn(-c2ccc(-c3ccc(CO)c(S(C)(=O)=O)c3)cc2)c(CCc2ccccc2Cl)n1] | 2-(2-(2-chlorophenethyl)-1-(4'-(hydroxymethyl)-3'-(methylsulfonyl)biphenyl-4-yl)-1H-imidazol-4-yl)propan-2-ol; |
| 30 | 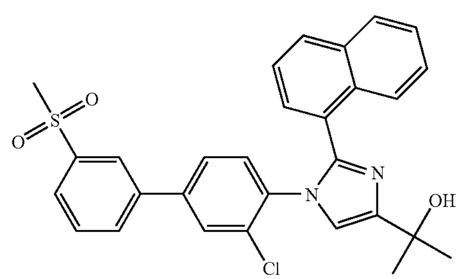 [SMILES: CC(C)(O)c1cn(-c2ccc(-c3cccc(S(C)(=O)=O)c3)cc2Cl)c(-c2cccc3ccccc23)n1] | 2-(1-(3-chloro-3'-(methylsulfonyl)biphenyl-4-yl)-2-(naphthalen-1-yl)-1H-imidazol-4-yl)propan-2-ol; |
| 31 | 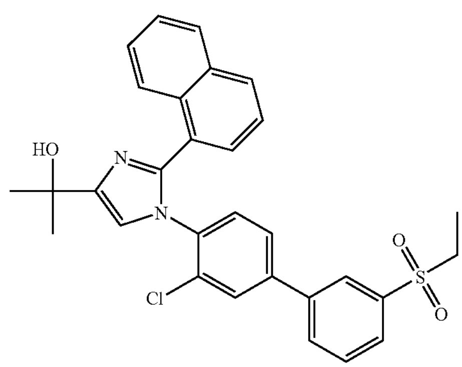 [SMILES: CCS(=O)(=O)c1cccc(-c2ccc(-n3cc(C(C)(C)O)nc3-c3cccc4ccccc34)c(Cl)c2)c1] | 2-(1-(3-chloro-3'-(ethylsulfonyl)biphenyl-4-yl)-2-(naphthalen-1-yl)-1H-imidazol-4-yl)propan-2-ol; |
| 32 | 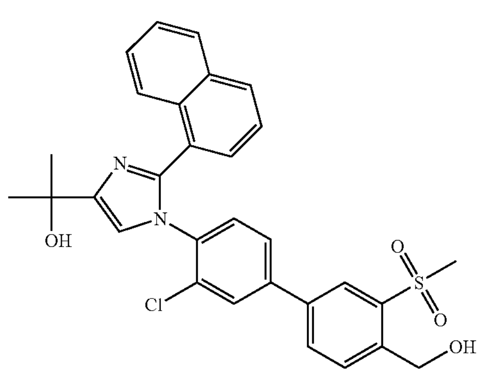 [SMILES: CC(C)(O)c1cn(-c2ccc(-c3ccc(CO)c(S(C)(=O)=O)c3)cc2Cl)c(-c2cccc3ccccc23)n1] | 2-(1-(3-chloro-4'-(hydroxymethyl)-3'-(methylsulfonyl)biphenyl-4-yl)-2-(napthalen-1-yl)-1H-imidazol-4-yl)propan-2-ol; |

TABLE 1-continued

| Cpd # | Structure | Name |
|---|---|---|
| 33 | 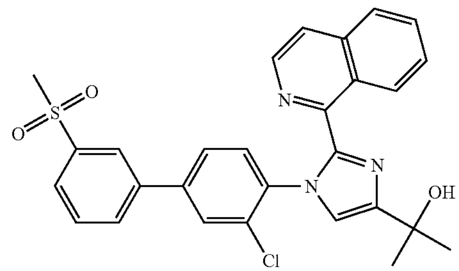 [SMILES: CC(C)(O)c1cn(-c2ccc(-c3cccc(S(C)(=O)=O)c3)cc2Cl)c(-c2nccc3ccccc23)n1] | 2-(1-(3-chloro-3'-(methylsulfonyl)biphenyl-4-yl)-2-(isoquinolin-1-yl)-1H-imidazol-4-yl)propan-2-ol; |
| 34 | 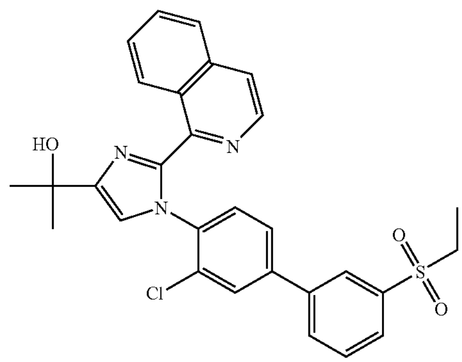 [SMILES: CCS(=O)(=O)c1cccc(-c2ccc(-n3cc(C(C)(C)O)nc3-c3nccc4ccccc34)c(Cl)c2)c1] | 2-(1-(3-chloro-3'-(ethylsulfonyl)biphenyl-4-yl)-2-(isoquinolin-1-yl)-1H-imidazol-4-yl)propan-2-ol; |
| 35 | 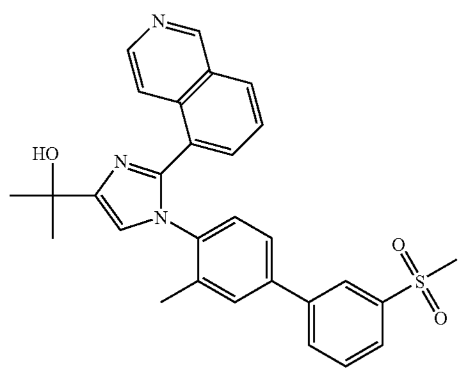 [SMILES: Cc1cc(-c2cccc(S(C)(=O)=O)c2)ccc1-n1cc(C(C)(C)O)nc1-c1cccc2cnccc12] | 2-(2-(isoquinolin-5-yl)-1-(3-methyl-3'-(methylsulfonyl)biphenyl-4-yl)-1H-imidazol-4-yl)propan-2-ol; |
| 36 | 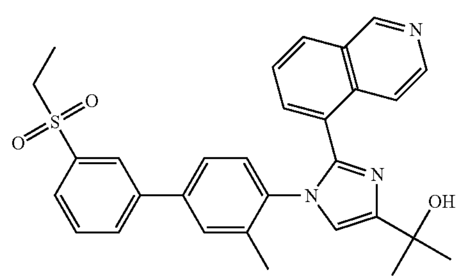 [SMILES: CCS(=O)(=O)c1cccc(-c2ccc(-n3cc(C(C)(C)O)nc3-c3cccc4cnccc34)c(C)c2)c1] | 2-(1-(3'-(ethylsulfonyl)-3-methylbiphenyl-4-yl)-2-(isoquinolin-5-yl)-1H-imidazol-4-yl)propan-2-ol; |
| 37 | 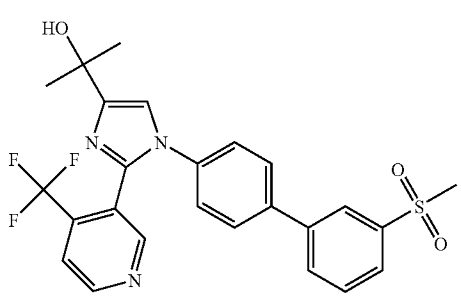 | 2-(1-(3'-(methylsulfonyl)biphenyl-4-yl)-2-(4-(trifluoromethyl)pyridin-3-yl)-1H-imidazol-4-yl)propan-2-ol; |

TABLE 1-continued

| Cpd # | Structure | Name |
|---|---|---|
| 38 | 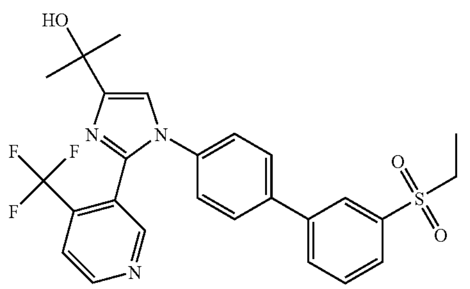 [SMILES: CCS(=O)(=O)c1cccc(-c2ccc(-n3cc(C(C)(C)O)nc3-c3cnccc3C(F)(F)F)cc2)c1] | 2-(1-(3'-(ethylsulfonyl)biphenyl-4-yl)-2-(4-(trifluoromethyl)pyridin-3-yl)-1H-imidazol-4-yl)propan-2-ol; |
| 39 | 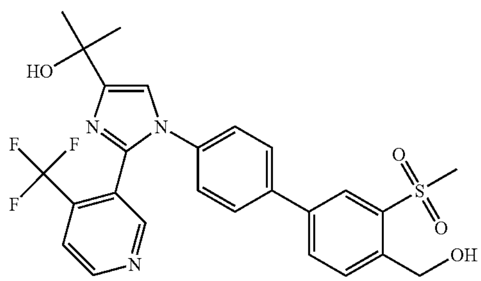 [SMILES: CC(C)(O)c1cn(-c2ccc(-c3ccc(CO)c(S(C)(=O)=O)c3)cc2)c(-c2cnccc2C(F)(F)F)n1] | 2-(1-(4'-(hydroxymethyl)-3'-(methylsulfonyl)biphenyl-4-yl)-2-(4-(trifluoromethyl)pyridin-3-yl)-1H-imidazol-4-yl)propan-2-ol; |
| 40 | 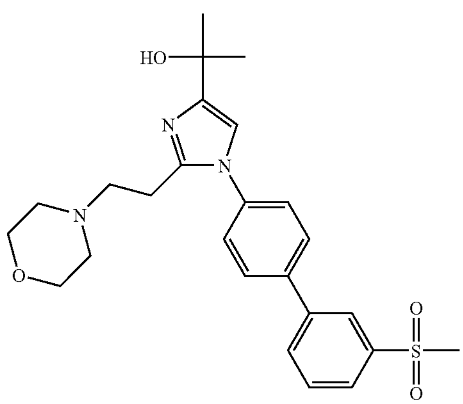 [SMILES: CC(C)(O)c1cn(-c2ccc(-c3cccc(S(C)(=O)=O)c3)cc2)c(CCN2CCOCC2)n1] | 2-(1-(3'-(methylsulfonyl)biphenyl-4-yl)-2-(2-morpholinoethyl)-1H-imidazol-4-yl)propan-2-ol; |
| 41 | 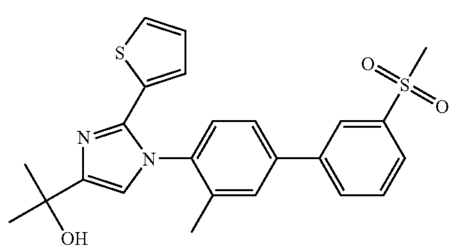 [SMILES: Cc1cc(-c2cccc(S(C)(=O)=O)c2)ccc1-n1cc(C(C)(C)O)nc1-c1cccs1] | 2-(1-(3-methyl-3'-(methylsulfonyl)biphenyl-4-yl)-2-(thiophen-2-yl)-1H-imidazol-4-yl)propan-2-ol; |
| 42 | 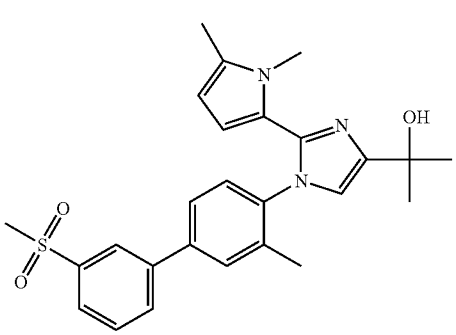 [SMILES: Cc1cc(-c2cccc(S(C)(=O)=O)c2)ccc1-n1cc(C(C)(C)O)nc1-c1ccc(C)n1C] | 2-(2-(1,5-dimethyl-1H-pyrrol-2-yl)-1-(3-methyl-3'-(methylsulfonyl)biphenyl-4-yl)-1H-imidazol-4-yl)propan-2-ol; |

TABLE 1-continued

| Cpd # | Structure | Name |
|---|---|---|
| 43 | 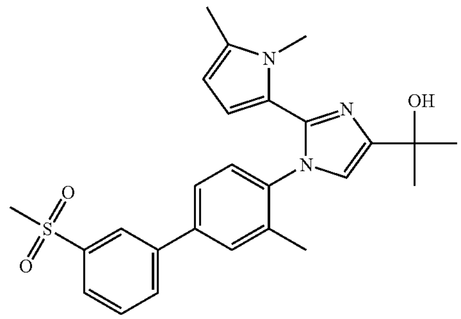 [SMILES: Cc1cc(-c2cccc(S(C)(=O)=O)c2)ccc1-n1cc(C(C)(C)O)nc1-c1ccc(C)n1C] | 2-(2-(1,5-dimethyl-1H-pyrrol-2-yl)-1-(3-methyl-3'-(methylsulfonyl)biphenyl-4-yl)-1H-imidazol-4-yl)propan-2-ol; |
| 44 | 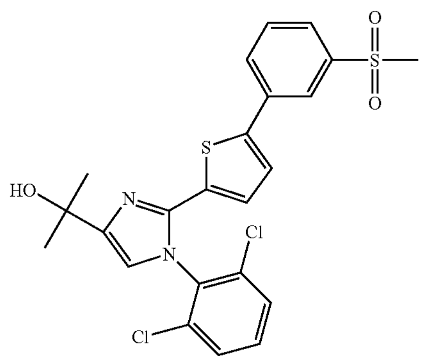 [SMILES: CC(C)(O)c1cn(-c2c(Cl)cccc2Cl)c(-c2ccc(-c3cccc(S(C)(=O)=O)c3)s2)n1] | 2-(1-(2,6-dichlorophenyl)-2-(5-(3-(methylsulfonyl)phenyl)thiophen-2-yl)-1H-imidazol-4-yl)propan-2-ol; |
| 45 | 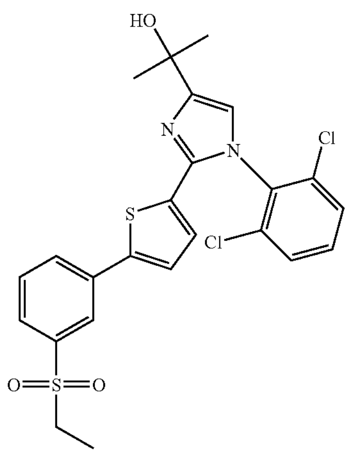 [SMILES: CCS(=O)(=O)c1cccc(-c2ccc(-c3nc(C(C)(C)O)cn3-c3c(Cl)cccc3Cl)s2)c1] | 2-(1-(2,6-dichlorophenyl)-2-(5-(3-(ethylsulfonyl)phenyl)thiophen-2-yl)-1H-imidazol-4-yl)propan-2-ol; |
| 46 | 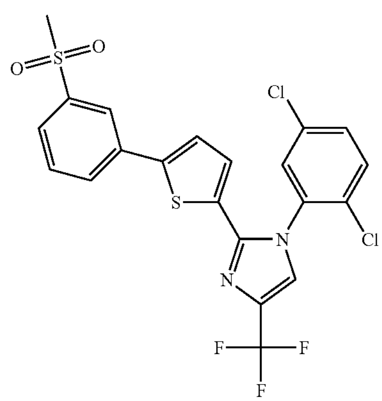 [SMILES: CS(=O)(=O)c1cccc(-c2ccc(-c3nc(C(F)(F)F)cn3-c3cc(Cl)ccc3Cl)s2)c1] | 1-(2,5-dichlorophenyl)-2-{5-[3-(methylsulfonyl)phenyl]-2-thienyl}-4-(trifluoromethyl)-1H-imidazole; |

TABLE 1-continued

| Cpd # | Structure | Name |
|---|---|---|
| 47 | 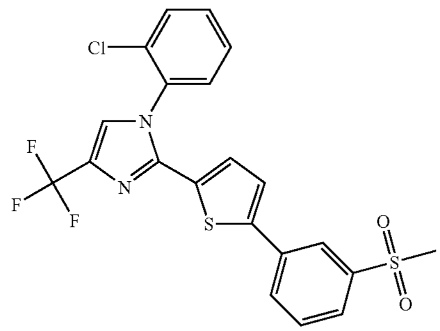 [SMILES: CS(=O)(=O)c1cccc(-c2ccc(-c3nc(C(F)(F)F)cn3-c3ccccc3Cl)s2)c1] | 1-(2-chlorophenyl)-2-{5-[3-(methylsulfonyl)phenyl]-2-thienyl}-4-(trifluoromethyl)-1H-imidazole; |
| 48 | 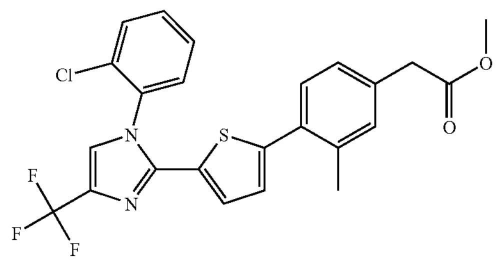 [SMILES: COC(=O)Cc1ccc(-c2ccc(-c3nc(C(F)(F)F)cn3-c3ccccc3Cl)s2)c(C)c1] | methyl (4-{5-[1-(2-chlorophenyl)-4-(trifluoromethyl)-1H-imidazol-2-yl]-2-thienyl}-3-methylphenyl)acetate |
| 49 | 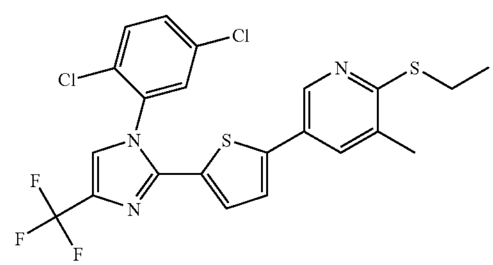 [SMILES: CCSc1ncc(-c2ccc(-c3nc(C(F)(F)F)cn3-c3cc(Cl)ccc3Cl)s2)cc1C] | 5-{5-[1-(2,5-dichlorophenyl)-4-(trifluoromethyl)-1H-imidazol-2-yl]-2-thienyl}-2-(ethylthio)-3-methylpyridine; |
| 50 | 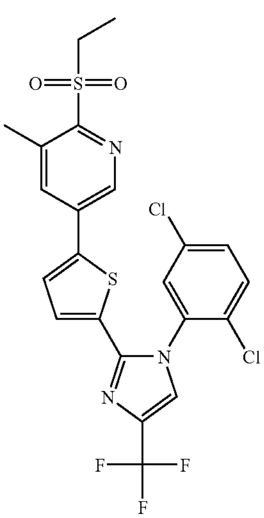 [SMILES: CCS(=O)(=O)c1ncc(-c2ccc(-c3nc(C(F)(F)F)cn3-c3cc(Cl)ccc3Cl)s2)cc1C] | 5-{5-[1-(2,5-dichlorophenyl)-4-(trifluoromethyl)-1H-imidazol-2-yl]-2-thienyl}-2-(ethylsulfonyl)-3-methylpyridine; |

TABLE 1-continued

| Cpd # | Structure | Name |
|---|---|---|
| 51 | 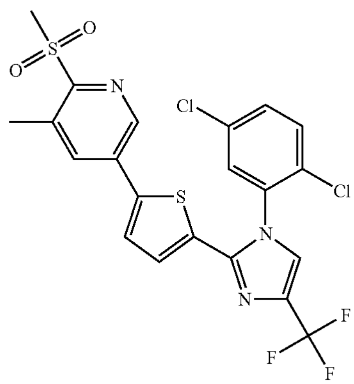 [SMILES: Cc1cc(-c2ccc(-c3nc(C(F)(F)F)cn3-c3cc(Cl)ccc3Cl)s2)cnc1S(C)(=O)=O] | 5-{5-[1-(2,5-dichlorophenyl)-4-(trifluoromethyl)-1H-imidazol-2-yl]-2-thienyl}-3-methyl-2-(methylsulfonyl)pyridine; |
| 52 | 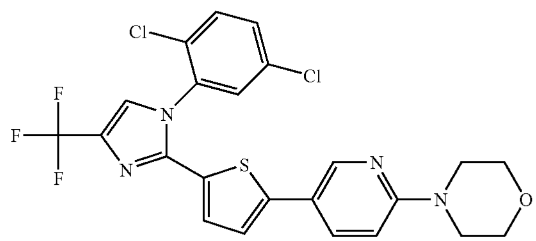 [SMILES: FC(F)(F)c1cn(-c2cc(Cl)ccc2Cl)c(-c2ccc(-c3ccc(N4CCOCC4)nc3)s2)n1] | 4-(5-{5-[1-(2,5-dichlorophenyl)-4-(trifluoromethyl)-1H-imidazol-2-yl]-2-thienyl}pyridin-2-yl)morpholine; |
| 53 | 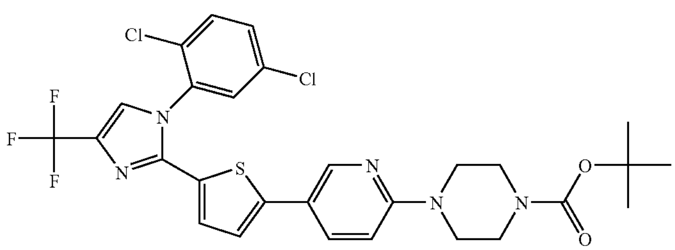 [SMILES: CC(C)(C)OC(=O)N1CCN(c2ccc(-c3ccc(-c4nc(C(F)(F)F)cn4-c4cc(Cl)ccc4Cl)s3)cn2)CC1] | 1,1-dimethylethyl 4-(5-{5-[1-(2,5-dichlorophenyl)-4-(trifluoromethyl)-1H-imidazol-2-yl]-2-thienyl}pyridin-2-yl)piperazine-1-carboxylate; |
| 54 | 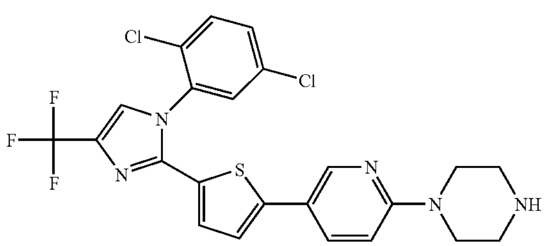 [SMILES: FC(F)(F)c1cn(-c2cc(Cl)ccc2Cl)c(-c2ccc(-c3ccc(N4CCNCC4)nc3)s2)n1] | 1-(5-{5-[1-(2,5-dichlorophenyl)-4-(trifluoromethyl)-1H-imidazol-2-yl]-2-thienyl}pyridin-2-yl)piperazine; |
| 55 | 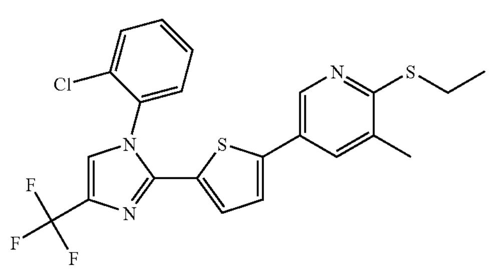 [SMILES: CCSc1ncc(-c2ccc(-c3nc(C(F)(F)F)cn3-c3ccccc3Cl)s2)cc1C] | 5-{5-[1-(2-chlorophenyl)-4-(trifluoromethyl)-1H-imidazol-2-yl]-2-thienyl}-2-(ethylthio)-3-methylpyridine; |

TABLE 1-continued

| Cpd # | Structure | Name |
|---|---|---|
| 56 | 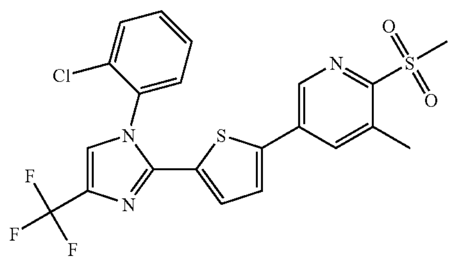 [SMILES: Cc1cc(-c2ccc(-c3nc(C(F)(F)F)cn3-c3ccccc3Cl)s2)cnc1S(C)(=O)=O] | 5-{5-[1-(2-chlorophenyl)-4-(trifluoromethyl)-1H-imidazol-2-yl]-2-thienyl}-3-methyl-2-(methylsulfonyl)pyridine; |
| 57 | 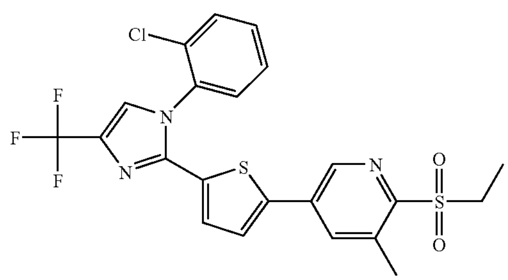 [SMILES: CCS(=O)(=O)c1ncc(-c2ccc(-c3nc(C(F)(F)F)cn3-c3ccccc3Cl)s2)cc1C] | 5-{5-[1-(2-chlorophenyl)-4-(trifluoromethyl)-1H-imidazol-2-yl]-2-thienyl}-2-(ethylsulfonyl)-3-methylpyridine; |
| 58 | 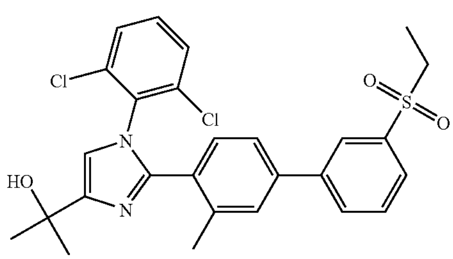 [SMILES: CCS(=O)(=O)c1cccc(-c2ccc(-c3nc(C(C)(C)O)cn3-c3c(Cl)cccc3Cl)c(C)c2)c1] | 2-(1-(2,6-dichlorophenyl)-2-(3'-(ethylsulfonyl)-3-methylbiphenyl-4-yl)-1H-imidazol-4-yl)propan-2-ol; |
| 59 | 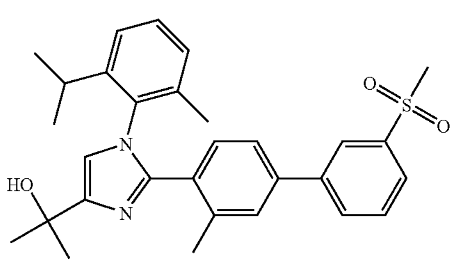 [SMILES: Cc1cc(-c2cccc(S(C)(=O)=O)c2)ccc1-c1nc(C(C)(C)O)cn1-c1c(C)cccc1C(C)C] | 2-(1-(2-isopropyl-6-methylphenyl)-2-(3-methyl-3'-(methylsulfonyl)biphenyl-4-yl)-1H-imidazol-4-yl)propan-2-ol; |
| 60 | 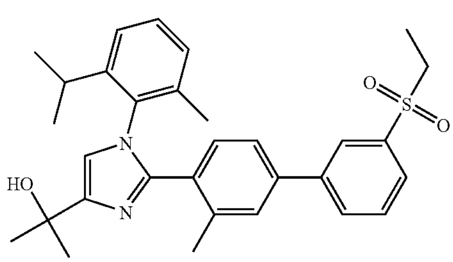 | 2-(2-(3'-(ethylsulfonyl)-3-methylbiphenyl-4-yl)-1-(2-isopropyl-6-methylphenyl)-1H-imidazol-4-yl)propan-2-ol; |

TABLE 1-continued

| Cpd # | Structure | Name |
|---|---|---|
| 61 | 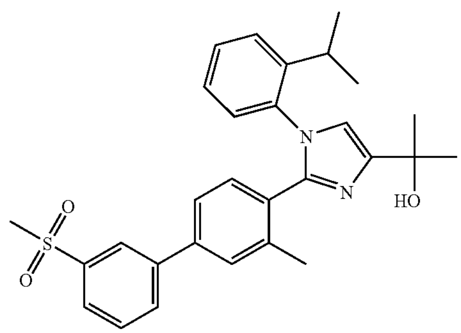 [SMILES: Cc1cc(-c2cccc(S(C)(=O)=O)c2)ccc1-c1nc(C(C)(C)O)cn1-c1ccccc1C(C)C] | 2-(1-(2-(isopropylphenyl)-2-(3-methyl-3'-(methylsulfonyl)biphenyl-4-yl)-1H-imidazol-4-yl)propan-2-ol; |
| 62 | 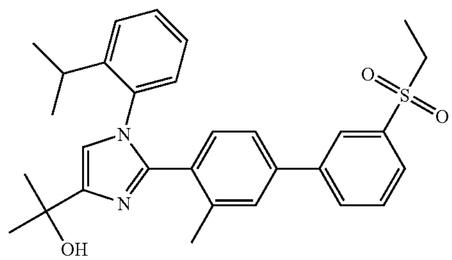 [SMILES: CCS(=O)(=O)c1cccc(-c2ccc(-c3nc(C(C)(C)O)cn3-c3ccccc3C(C)C)c(C)c2)c1] | 2-(2-(3'-(ethylsulfonyl)-3-methylbiphenyl-4-yl)-1-(2-isopropylphenyl)-1H-imidazol-4-yl)propan-2-ol; |
| 63 | 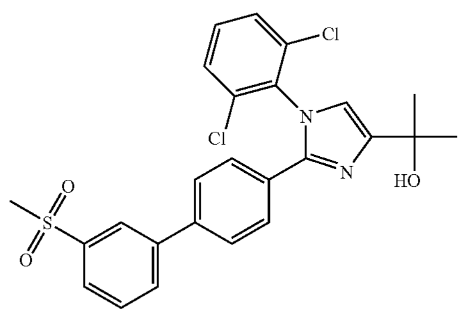 [SMILES: CC(C)(O)c1cn(-c2c(Cl)cccc2Cl)c(-c2ccc(-c3cccc(S(C)(=O)=O)c3)cc2)n1] | 2-(1-(2,6-dichlorophenyl)-2-(3'-(methylsulfonyl)biphenyl-4-yl)-1H-imidazol-4-yl)propan-2-ol; |
| 64 | 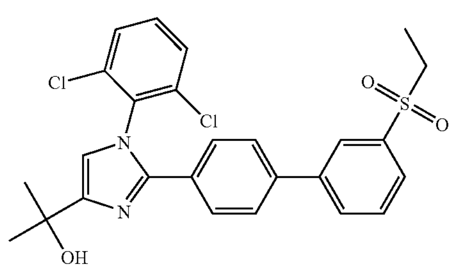 [SMILES: CCS(=O)(=O)c1cccc(-c2ccc(-c3nc(C(C)(C)O)cn3-c3c(Cl)cccc3Cl)cc2)c1] | 2-(1-(2,6-dichlorophenyl)-2-(3'-(ethylsulfonyl)biphenyl-4-yl)-1H-imidazol-4-yl)propan-2-ol; |
| 65 | 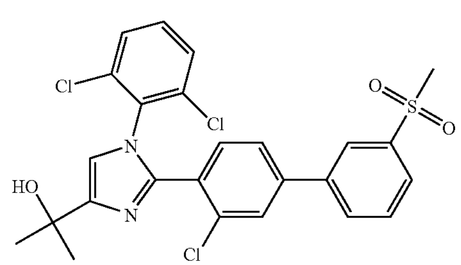 | 2-(2-(3-chloro-3'-(methylsulfonyl)biphenyl-4-yl)-1-(2,6-dichlorophenyl)-1H-imidazol-4-yl)propan-2-ol; |

TABLE 1-continued

| Cpd # | Structure | Name |
|---|---|---|
| 66 | 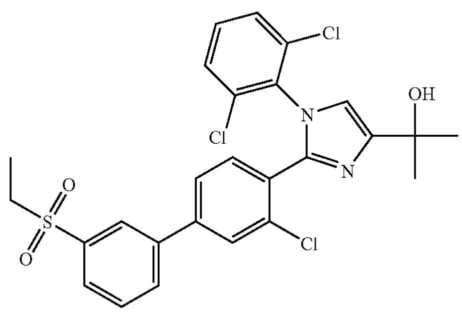 [SMILES: CCS(=O)(=O)c1cccc(-c2ccc(-c3nc(C(C)(C)O)cn3-c3c(Cl)cccc3Cl)c(Cl)c2)c1] | 2-(2-(3-chloro-3'-(ethylsulfonyl)biphenyl-4-yl)-1-(2,6-dichlorophenyl)-1H-imidazol-4-yl)propan-2-ol; |
| 67 | 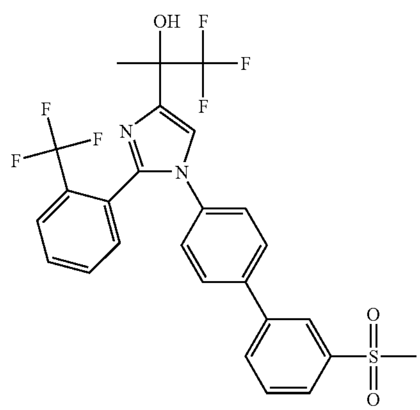 [SMILES: CC(O)(c1cn(-c2ccc(-c3cccc(S(C)(=O)=O)c3)cc2)c(-c2ccccc2C(F)(F)F)n1)C(F)(F)F] | 1,1,1-trifluoro-2-(1-(3'-(methylsulfonyl)biphenyl-4-yl)-2-(2-(trifluoromethyl)phenyl)-1H-imidazol-4-yl)propan-2-ol; |
| 68 | 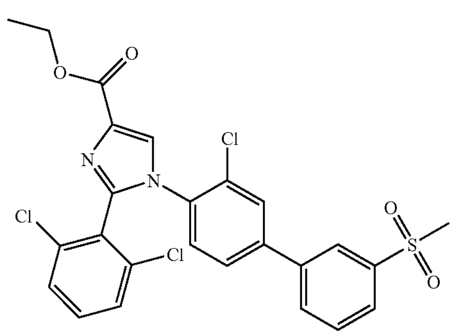 [SMILES: CCOC(=O)c1cn(-c2ccc(-c3cccc(S(C)(=O)=O)c3)cc2Cl)c(-c2c(Cl)cccc2Cl)n1] | ethyl 1-(3-chloro-3'-(methylsulfonyl)biphenyl-4-yl)-2-(2,6-dichlorophenyl)-1H-imidazol-4-carboxylate; |
| 69 | 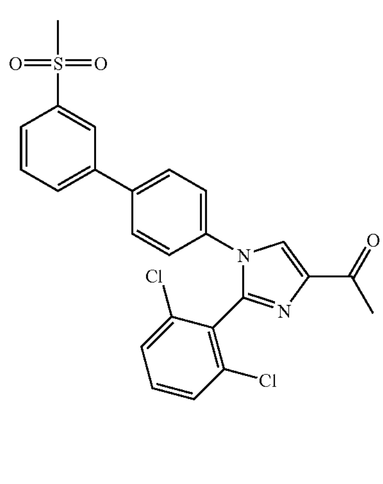 [SMILES: CC(=O)c1cn(-c2ccc(-c3cccc(S(C)(=O)=O)c3)cc2)c(-c2c(Cl)cccc2Cl)n1] | 1-(2-(2,6-dichlorophenyl)-1-(3'-(methylsulfonyl)biphenyl-4-yl)-1H-imidazol-4-yl)ethanone; |

TABLE 1-continued

| Cpd # | Structure | Name |
|---|---|---|
| 70 | 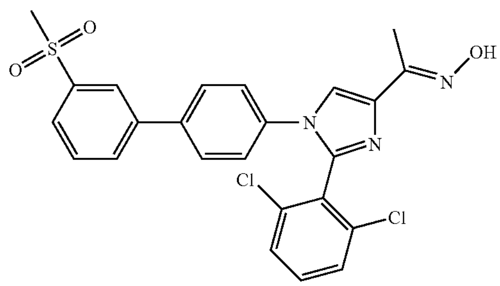 [SMILES: C/C(=N\O)c1cn(-c2ccc(-c3cccc(S(C)(=O)=O)c3)cc2)c(-c2c(Cl)cccc2Cl)n1] | (E)-1-(2-(2,6-dichlorophenyl)-1-(3'-(methylsulfonyl)biphenyl-4-yl)-1H-imidazol-4-yl)ethanone oxime; |
| 71 | 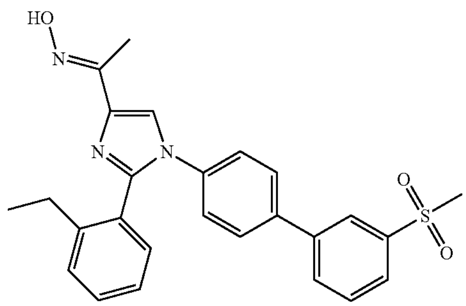 [SMILES: CCc1ccccc1-c1nc(/C(C)=N/O)cn1-c1ccc(-c2cccc(S(C)(=O)=O)c2)cc1] | (E)-1-(2-(2-ethylphenyl)-1-(3'-(methylsulfonyl)biphenyl-4-yl)-1H-imidazol-4-yl)ethanone oxime; |
| 72 | 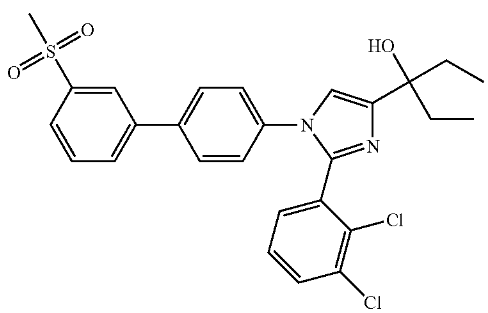 [SMILES: CCC(O)(CC)c1cn(-c2ccc(-c3cccc(S(C)(=O)=O)c3)cc2)c(-c2cccc(Cl)c2Cl)n1] | 3-(2-(2,3-dichlorophenyl)-1-(3'-(methylsulfonyl)biphenyl-4-yl)-1H-imidazol-4-yl)pentan-3-ol; |
| 73 | 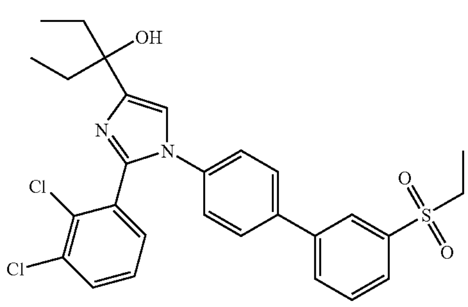 [SMILES: CCC(O)(CC)c1cn(-c2ccc(-c3cccc(S(=O)(=O)CC)c3)cc2)c(-c2cccc(Cl)c2Cl)n1] | 3-(2-(2,3-dichlorophenyl)-1-(3'-(ethylsulfonyl)biphenyl-4-yl)-1H-imidazol-4-yl)pentan-3-ol; |

TABLE 1-continued

| Cpd # | Structure | Name |
|---|---|---|
| 74 | 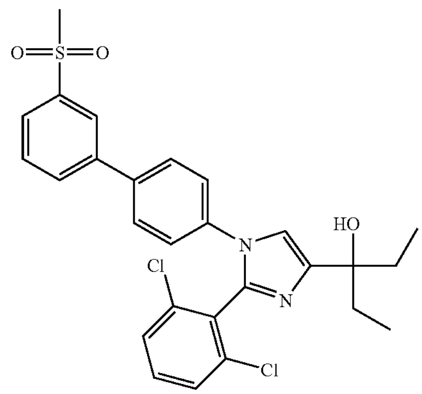 | 3-(2-(2,6-dichlorophenyl)-1-(3'-(methylsulfonyl)biphenyl-4-yl)-1H-imidazol-4-yl)pentan-3-ol; |
| 75 | 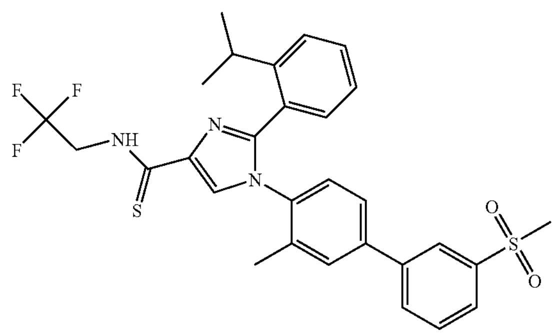 | 2-(2-isopropylphenyl)-1-(3-methyl-3'-(methylsulfonyl)biphenyl-4-yl)-N-(2,2,2-trifluoroethyl)-1H-imidazole-4-carbothioamide; |
| 76 | 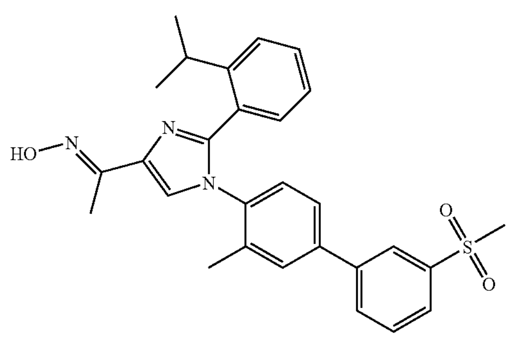 [SMILES: C/C(=N\O)c1cn(-c2ccc(-c3cccc(S(C)(=O)=O)c3)cc2C)c(-c2ccccc2C(C)C)n1] | (E)-1-(2-(2-isopropylphenyl)-1-(3-methyl-3'-(methylsuflonyl)biphenyl-4-yl)-1H-imidazol-4-yl)ethanone oxime; |
| 77 | 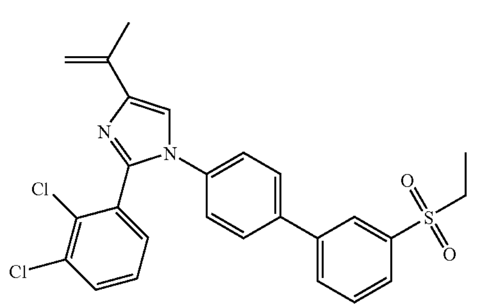 [SMILES: C=C(C)c1cn(-c2ccc(-c3cccc(S(=O)(=O)CC)c3)cc2)c(-c2cccc(Cl)c2Cl)n1] | 2-(2,3-dichlorophenyl)-1-(3'-(ethylsulfonyl)biphenyl-4-yl)-4-(prop-1-en-2-yl)-1H-imidazole; |

TABLE 1-continued

| Cpd # | Structure | Name |
|---|---|---|
| 78 | 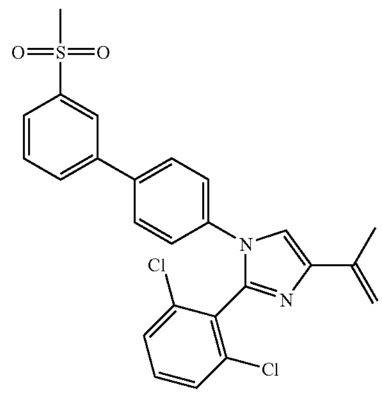 [SMILES: C=C(C)c1cn(-c2ccc(-c3cccc(S(C)(=O)=O)c3)cc2)c(-c2c(Cl)cccc2Cl)n1] | 2-(2,6-dichlorophenyl)-1-(3'-(methylsulfonyl)biphenyl-4-yl)-4-(prop-1-en-2-yl)-1H-imidazole; |
| 79 | 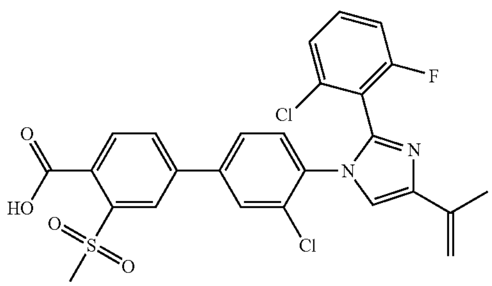 [SMILES: C=C(C)c1cn(-c2ccc(-c3ccc(C(=O)O)c(S(C)(=O)=O)c3)cc2Cl)c(-c2c(F)cccc2Cl)n1] | 3'-chloro-4'-(2-(2-chloro-6-fluorophenyl)-4-(prop-1-en-2-yl)-1H-imidazol-1-yl)-3-(methylsulfonyl)biphenyl-4-carboxylic acid; |
| 80 | 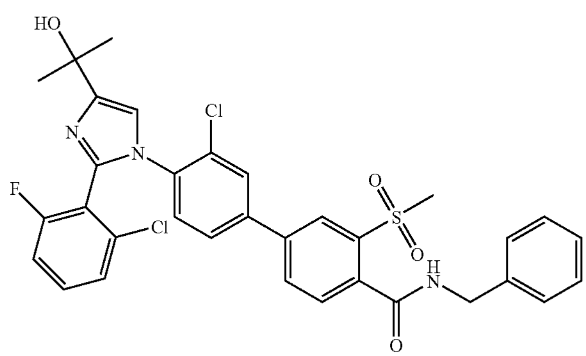 [SMILES: CC(C)(O)c1cn(-c2ccc(-c3ccc(C(=O)NCc4ccccc4)c(S(C)(=O)=O)c3)cc2Cl)c(-c2c(F)cccc2Cl)n1] | N-benzyl-3'-chloro-4'-(2-(2-chloro-6-fluorophenyl)-4-(2-hydroxypropan-2-yl)-1H-imidazaol-1-yl)-3-(methylsulfonyl)biphenyl-4-carboxamide; |
| 81 | 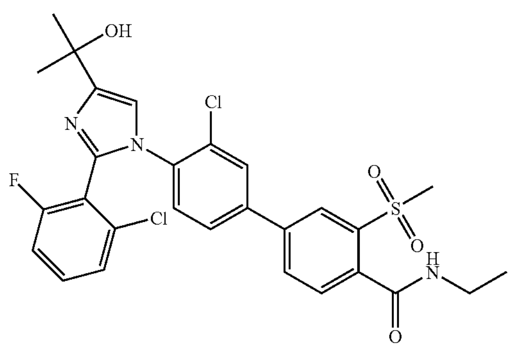 [SMILES: CCNC(=O)c1ccc(-c2ccc(-n3cc(C(C)(C)O)nc3-c3c(F)cccc3Cl)c(Cl)c2)cc1S(C)(=O)=O] | 3'-chloro-4'-(2-(2-chloro-6-fluorophenyl)-4-(2-hydroxypropan-2-yl)-1H-imidazol-1-yl)-N-ethyl-3-(methylsulfonylbiphenyl-4-carboxamide; |

TABLE 1-continued

| Cpd # | Structure | Name |
|---|---|---|
| 82 | 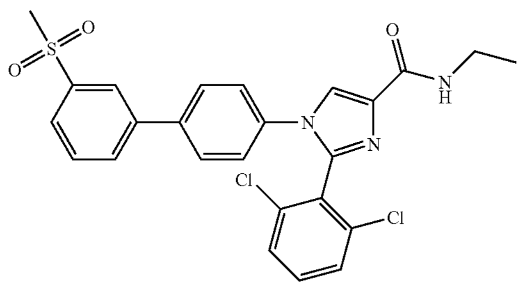 [SMILES: CCNC(=O)c1cn(-c2ccc(-c3cccc(S(C)(=O)=O)c3)cc2)c(-c2c(Cl)cccc2Cl)n1] | 2-(2,6-dichlorophenyl)-N-ethyl-1-(3'-(methylsulfonyl)biphenyl-4-yl)-1H-imidazole-4-carboxamide; |
| 83 | 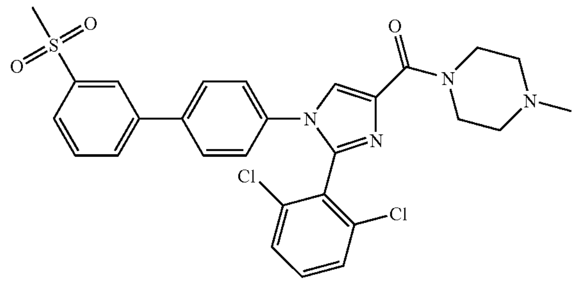 [SMILES: CN1CCN(C(=O)c2cn(-c3ccc(-c4cccc(S(C)(=O)=O)c4)cc3)c(-c3c(Cl)cccc3Cl)n2)CC1] | 2-(2,6-dichlorophenyl)-1-(3'-(methylsulfonyl)biphenyl-4-yl)-1H-imidazol-4-yl)(4-methylpiperazin-1-yl)methanone; |
| 84 | 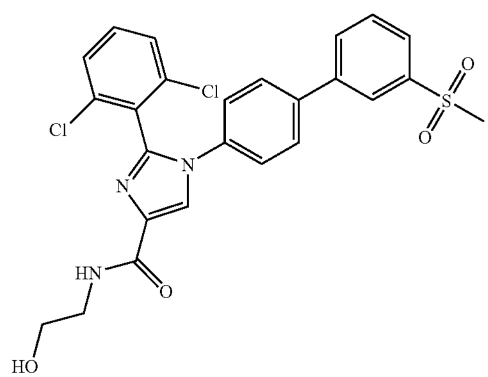 [SMILES: CS(=O)(=O)c1cccc(-c2ccc(-n3cc(C(=O)NCCO)nc3-c3c(Cl)cccc3Cl)cc2)c1] | 2-(2,6-dichlorophenyl)-N-(2-hydroxyethyl)-1-(3'-(methylsulfonyl)biphenyl-4-yl)-1H-imidazole-4-carboxamide; |
| 85 | 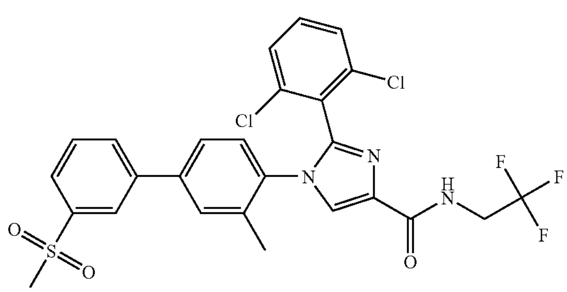 [SMILES: Cc1cc(-c2cccc(S(C)(=O)=O)c2)ccc1-n1cc(C(=O)NCC(F)(F)F)nc1-c1c(Cl)cccc1Cl] | 2-(2,6-dichlorophenyl)-1-(3-methyl-3'-(methylsulfonyl)biphenyl-4-yl)-N-(2,2,2-trifluoroethyl)-1H-imidazole-4-carboxamide; |
| 86 | 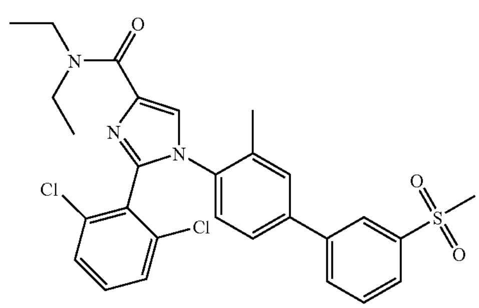 [SMILES: CCN(CC)C(=O)c1cn(-c2ccc(-c3cccc(S(C)(=O)=O)c3)cc2C)c(-c2c(Cl)cccc2Cl)n1] | 2-(2,6-dichlorophenyl)-N,N-diethyl-1-(3-methyl-3'-(methylsulfonyl)biphenyl-4-yl)-1H-imidazole-4-carboxamide |

TABLE 1-continued

| Cpd # | Structure | Name |
|---|---|---|
| 87 | 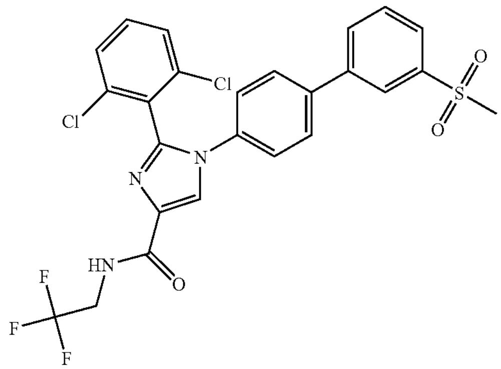 [SMILES: CS(=O)(=O)c1cccc(-c2ccc(-n3cc(C(=O)NCC(F)(F)F)nc3-c3c(Cl)cccc3Cl)cc2)c1] | 2-(2,6-dichlorophenyl)-1-(3'-(methylsulfonyl)biphenyl-4-yl)-N-(2,2,2-trifluoroethyl)-1H-imidazole-4-carboxamide; |
| 88 | 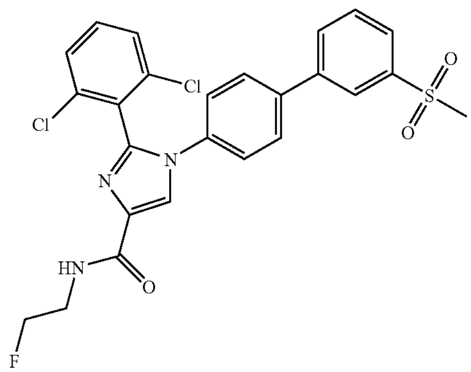 [SMILES: CS(=O)(=O)c1cccc(-c2ccc(-n3cc(C(=O)NCCF)nc3-c3c(Cl)cccc3Cl)cc2)c1] | 2-(2,6-dichlorophenyl)-N-(2-fluoroethyl)-1-(3'-(methylsulfonyl)biphenyl-4-yl)-1H-imidazole-4-carboxamide; |
| 89 | 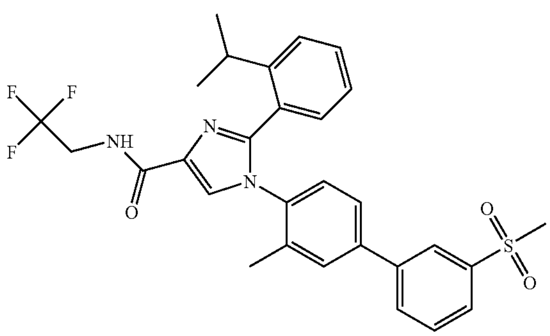 [SMILES: Cc1cc(-c2cccc(S(C)(=O)=O)c2)ccc1-n1cc(C(=O)NCC(F)(F)F)nc1-c1ccccc1C(C)C] | 2-(2-isopropylphenyl)-1-(3-methyl-3'-(methylsulfonyl)biphenyl-4-yl)-N-(2,2,2-trifluoroethyl)-1H-imidazole-4-carboxamide; |
| 90 | 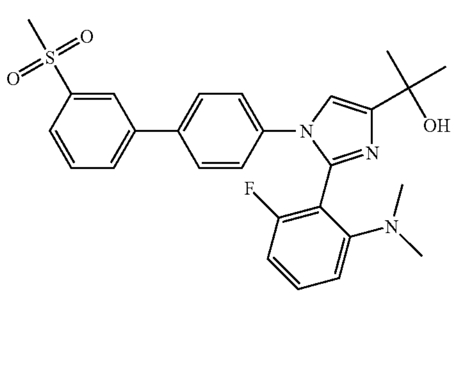 [SMILES: CN(C)c1cccc(F)c1-c1nc(C(C)(C)O)cn1-c1ccc(-c2cccc(S(C)(=O)=O)c2)cc1] | 2-(2-(2-dimethylamino)-6-fluorophenyl)-1-(3'-(methylsulfonyl)biphenyl-4-yl)-1H-imidazol-4-yl)propan-2-ol; |

TABLE 1-continued

| Cpd # | Structure | Name |
|---|---|---|
| 91 | 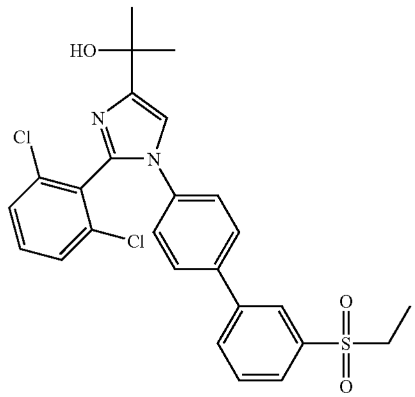 [SMILES: CCS(=O)(=O)c1cccc(-c2ccc(-n3cc(C(C)(C)O)nc3-c3c(Cl)cccc3Cl)cc2)c1] | 2-(2-(2,6-dichlorophenyl)-1-(3'-(ethylsulfonyl)biphenyl-4-yl)-1H-imidazol-4-yl)propan-2-ol; |
| 92 | 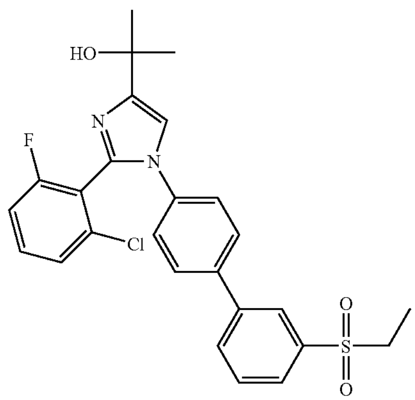 [SMILES: CCS(=O)(=O)c1cccc(-c2ccc(-n3cc(C(C)(C)O)nc3-c3c(F)cccc3Cl)cc2)c1] | 2-(2-(2-chloro-6-fluorophenyl)-1-(3'-(ethylsulfonyl)biphenyl-4-yl)-1H-imidazol-4-yl)propan-2-ol; |
| 93 | 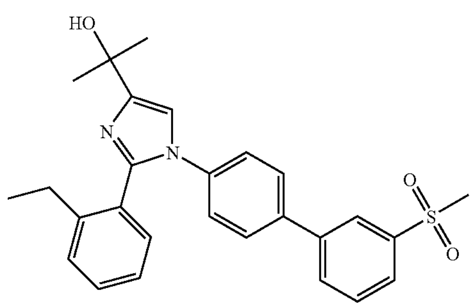 [SMILES: CCc1ccccc1-c1nc(C(C)(C)O)cn1-c1ccc(-c2cccc(S(C)(=O)=O)c2)cc1] | 2-(2-(2-ethylphenyl)-1-(3'-(methylsulfonyl)biphenyl-4-yl)-1H-imidazol-4-yl)propan-2-ol; |
| 94 | 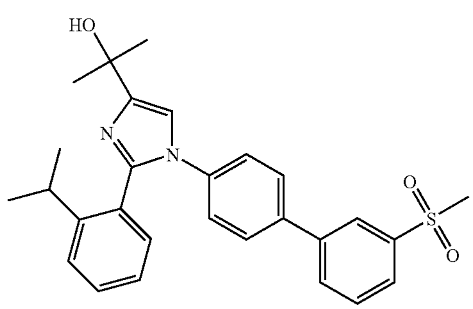 | 2-(2-(2-isopropylphenyl)-1-(3'-(methylsulfonyl)biphenyl-4-yl)-1H-imidazol-4-yl)propan-2-ol; |

TABLE 1-continued

| Cpd # | Structure | Name |
|---|---|---|
| 95 | 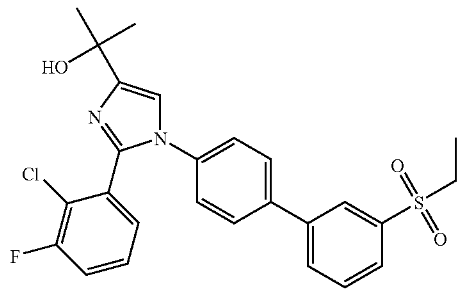 [SMILES: CCS(=O)(=O)c1cccc(-c2ccc(-n3cc(C(C)(C)O)nc3-c3cccc(F)c3Cl)cc2)c1] | 2-(2-(2-chloro-3-fluorophenyl)-1-(3'-(ethylsulfonyl)biphenyl-4-yl)-1H-imidazol-4-yl)propan-2-ol; |
| 96 | 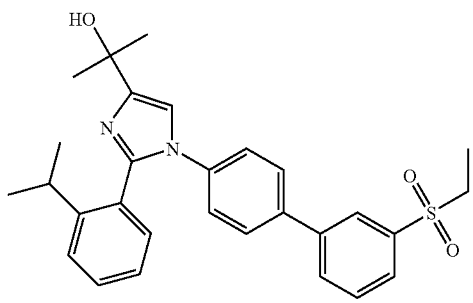 [SMILES: CCS(=O)(=O)c1cccc(-c2ccc(-n3cc(C(C)(C)O)nc3-c3ccccc3C(C)C)cc2)c1] | 2-(1-(3'-(ethylsulfonyl)biphenyl-4-yl)-2-(2-isopropylphenyl)-1H-imidazol-4-yl)propan-2-ol; |
| 97 | 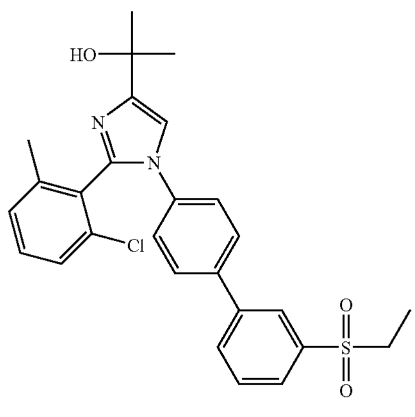 [SMILES: CCS(=O)(=O)c1cccc(-c2ccc(-n3cc(C(C)(C)O)nc3-c3c(C)cccc3Cl)cc2)c1] | 2-(2-(2-chloro-6-methylphenyl)-1-(3'-(ethylsulfonyl)biphenyl-4-yl)-1H-imidazol-4-yl)propan-2-ol; |
| 98 | 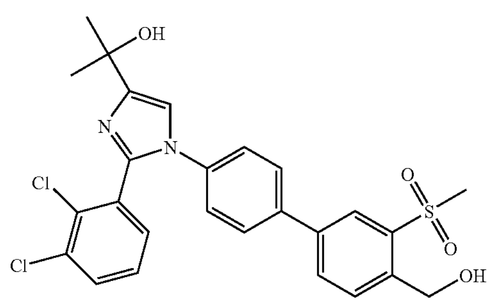 | 2-(2-(2,3-dichlorophenyl)-1-(4'-(hydroxymethyl)-3'-(methylsulfonyl)biphenyl-4-yl)-1H-imidazol-4-yl)propan-2-ol; |

TABLE 1-continued

| Cpd # | Structure | Name |
|---|---|---|
| 99 | 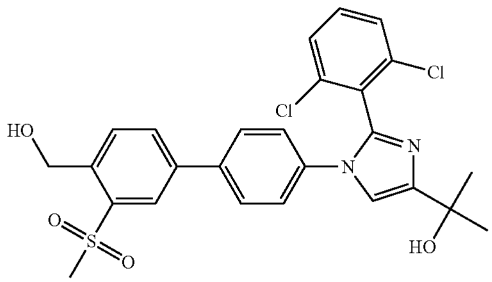 | 2-(2-(2,6-dichlorophenyl)-1-(4'-(hydroxymethyl)-3'-(methylsulfonyl)biphenyl-4-yl)-1H-imidazol-4-yl)propan-2-ol; |
| 100 | 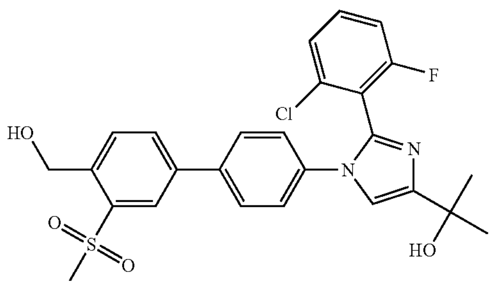 | 2-(2-(2-chloro-6-fluorophenyl)-1-(4'-(hydroxymethyl)-3'-(methylsulfonyl)biphenyl-4-yl)-1H-imidazol-4-yl)propan-2-ol; |
| 101 | 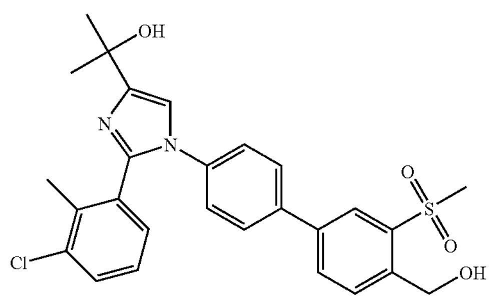 [SMILES: Cc1c(Cl)cccc1-c1nc(C(C)(C)O)cn1-c1ccc(-c2ccc(CO)c(S(C)(=O)=O)c2)cc1] | 2-(2-(3-chloro-2-methylphenyl)-1-(4'-(hydroxymethyl)-3'-(methylsulfonyl)biphenyl-4-yl)-1H-imidazol-4-yl)propan-2-ol; |
| 102 | 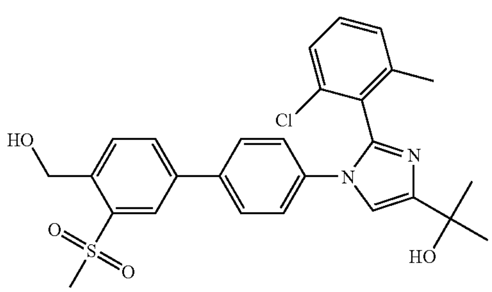 [SMILES: Cc1cccc(Cl)c1-c1nc(C(C)(C)O)cn1-c1ccc(-c2ccc(CO)c(S(C)(=O)=O)c2)cc1] | 2-(2-(2-chloro-6-methylphenyl)-1-(4'-(hydroxymethyl)-3'-(methylsulfonyl)biphenyl-4-yl)-1H-imidazol-4-yl)propan-2-ol; |
| 103 | 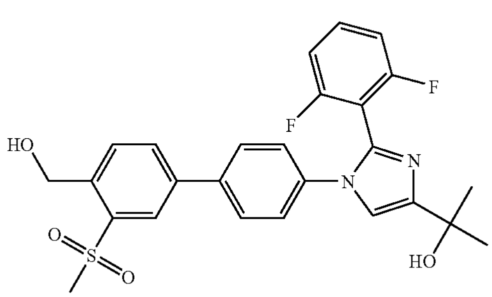 | 2-(2-(2,6-difluorophenyl)-1-(4'-(hydroxymethyl)-3'-(methylsulfonyl)biphenyl-4-yl)-1H-imidazol-4-yl)propan-2-ol; |

| Cpd # | Structure | Name |
|---|---|---|
| 104 | 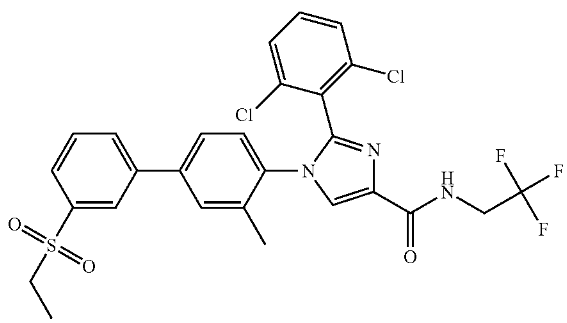 [SMILES: CCS(=O)(=O)c1cccc(-c2ccc(-n3cc(C(=O)NCC(F)(F)F)nc3-c3c(Cl)cccc3Cl)c(C)c2)c1] | 2-(2,6-dichlorophenyl)-1-(3'-(ethylsulfonyl)-3-methylbiphenyl-4-yl)-N-(2,2,2-trifluoroethyl)-1H-imidazole-4-carboxamide; |
| 105 | 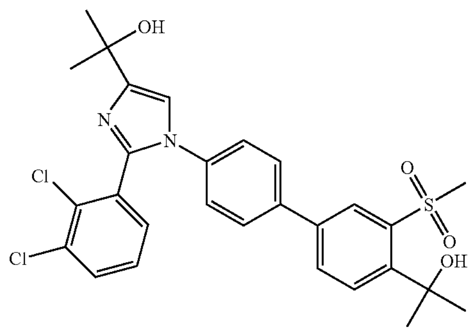 [SMILES: CC(C)(O)c1cn(-c2ccc(-c3ccc(C(C)(C)O)c(S(C)(=O)=O)c3)cc2)c(-c2cccc(Cl)c2Cl)n1] | 2-(2-(2,3-dichlorophenyl)-1-(4'-(2-hydroxypropan-2-yl)-3'-(methylsulfonyl)biphenyl-4-yl)-1H-imidazol-4-yl)propan-2-ol; |
| 106 | 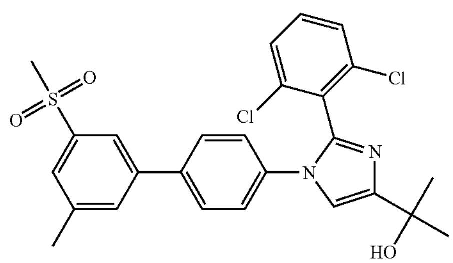 [SMILES: Cc1cc(-c2ccc(-n3cc(C(C)(C)O)nc3-c3c(Cl)cccc3Cl)cc2)cc(S(C)(=O)=O)c1] | 2-(2-(2,6-dichlorophenyl)-1-(3'-methyl-5'-(methylsulfonyl)biphenyl-4-yl)-1H-imidazol-4-yl)propan-2-ol; |
| 107 | 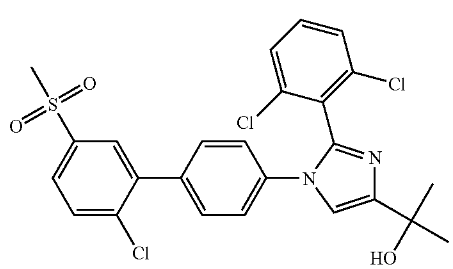 [SMILES: CC(C)(O)c1cn(-c2ccc(-c3cc(S(C)(=O)=O)ccc3Cl)cc2)c(-c2c(Cl)cccc2Cl)n1] | 2-(1-(2'-chloro-5'-(methylsulfonyl)biphenyl-4-yl)-2-(2,6-dichlorophenyl)-1H-imidazol-4-yl)propan-2-ol; |

TABLE 1-continued

| Cpd # | Structure | Name |
|---|---|---|
| 108 | 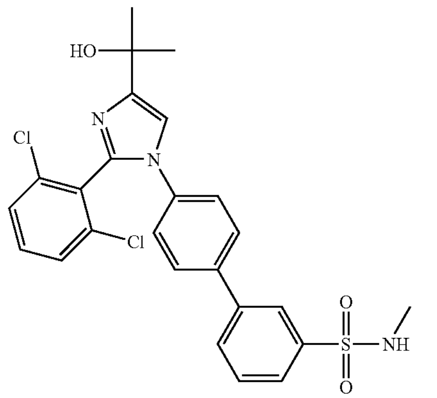 [SMILES: CNS(=O)(=O)c1cccc(-c2ccc(-n3cc(C(C)(C)O)nc3-c3c(Cl)cccc3Cl)cc2)c1] | 4'-(2-(2,6-dichlorophenyl)-4-(2-hydroxypropan-2-yl)-1H-imidazol-4-yl)-N-methylbiphenyl-3-sulfonamide; |
| 109 | 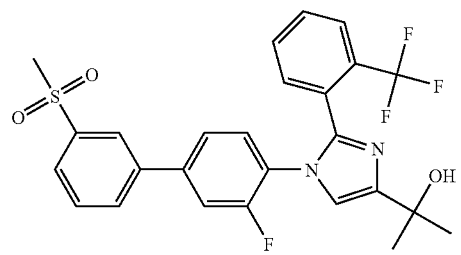 | 2-(1-(3-fluoro-3'-(methylsulfonyl)biphenyl-4-yl)-2-(2-(trifluoromethyl)phenyl)-1H-imidazol-4-yl)propan-2-ol; |
| 110 | 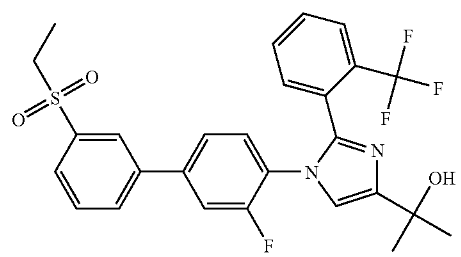 | 2-(1-(3'-(ethylsulfonyl)-3-fluorobiphenyl-4-yl)-2-(2-(trifluoromethyl)-1H-imidazol-4-yl)propan-2-ol; |
| 111 | 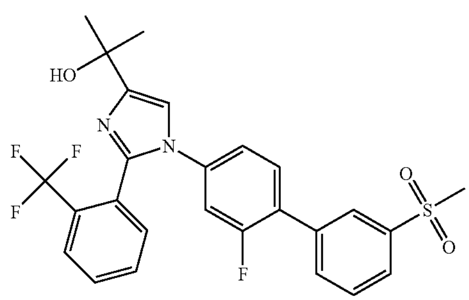 [SMILES: CC(C)(O)c1cn(-c2ccc(-c3cccc(S(C)(=O)=O)c3)c(F)c2)c(-c2ccccc2C(F)(F)F)n1] | 2-(1-(2-fluoro-(3'-(methylsulfonyl)biphenyl-4-yl)-2-(2-(trifluoromethyl)phenyl-1H-imidazol-4-yl)propan-2-ol; |
| 112 | 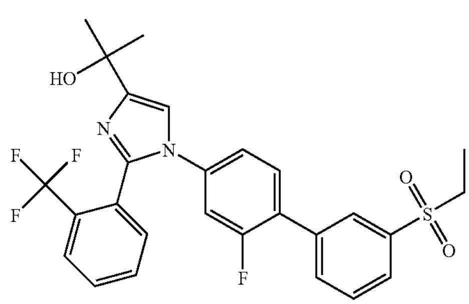 [SMILES: CCS(=O)(=O)c1cccc(-c2ccc(-n3cc(C(C)(C)O)nc3-c3ccccc3C(F)(F)F)cc2F)c1] | 2-(1-(3'-(ethylsulfonyl)-2-fluorobiphenyl-4-yl)-2-(2-(trifluoromethyl)phenyl)-1H-imidazol-4-yl)propan-2-ol; |

TABLE 1-continued

| Cpd # | Structure | Name |
|---|---|---|
| 113 | 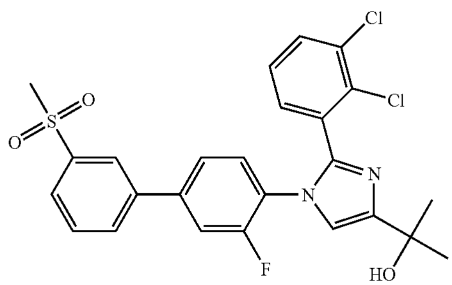 | 2-(2-(2,3-dichlorophenyl)-1-(3-fluoro-3'-(methylsulfonyl)biphenyl-4-yl)-1H-imidazol-4-yl)propan-2-ol; |
| 114 | 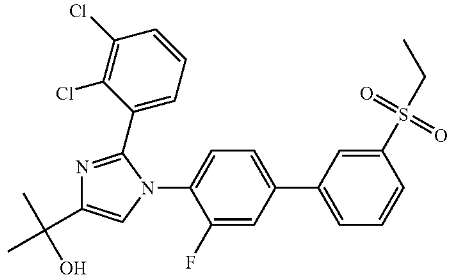 | 2-(2-(2,3-dichlorophenyl)-1-(3'-(ethylsulfonyl)-3-fluorobiphenyl-4-yl)-1H-imidazol-4-yl)propan-2-ol; |
| 115 | 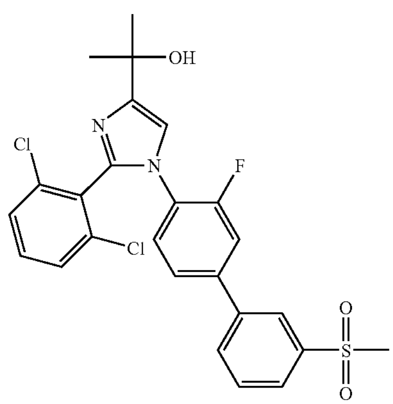 [SMILES: CC(C)(O)c1cn(-c2ccc(-c3cccc(S(C)(=O)=O)c3)cc2F)c(-c2c(Cl)cccc2Cl)n1] | 2-(2-(2,6-dichlorophenyl)-1-(3-fluoro-3'-(methylsulfonyl)biphenyl-4-yl)-1H-imidazol-4-yl)propan-2-ol; |
| 116 | 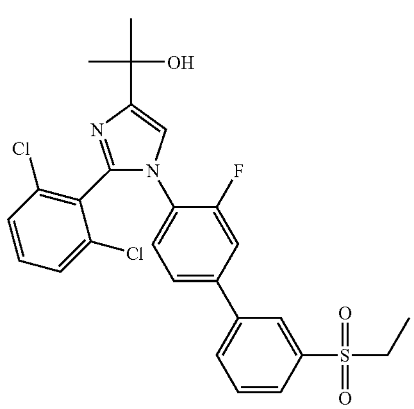 | 2-(2-(2,6-dichlorophenyl)-1-(3'-(ethylsulfonyl)-3-fluorobiphenyl-4-yl)-1H-imidazol-4-yl)propan-2-ol; |

TABLE 1-continued

| Cpd # | Structure | Name |
|---|---|---|
| 117 | 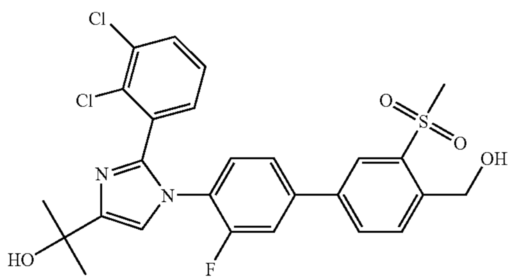 [SMILES: CC(C)(O)c1cn(-c2ccc(-c3ccc(CO)c(S(C)(=O)=O)c3)cc2F)c(-c2cccc(Cl)c2Cl)n1] | 2-(2-(2,3-dichlorophenyl)-1-(3-fluoro-4'-(hydroxymethyl)-3'-(methylsulfonyl)biphenyl-4-yl)-1H-imidazol-4-yl)propan-2-ol; |
| 118 | 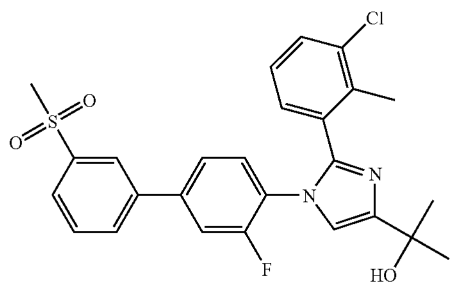 [SMILES: Cc1c(Cl)cccc1-c1nc(C(C)(C)O)cn1-c1ccc(-c2cccc(S(C)(=O)=O)c2)cc1F] | 2-(2-(3-chloro-2-methylphenyl)-1-(3-fluoro-3'-(methylsulfonyl)biphenyl-4-yl)-1H-imidazol-4-yl)propan-2-ol; |
| 119 | 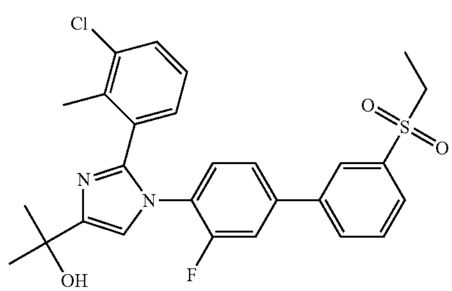 | 2-(2-(3-chloro-2-methylphenyl)-1-(3'-(ethylsulfonyl)-3-fluorobiphenyl-4-yl)-1H-imidazol-4-yl)propan-2-ol; |
| 120 | 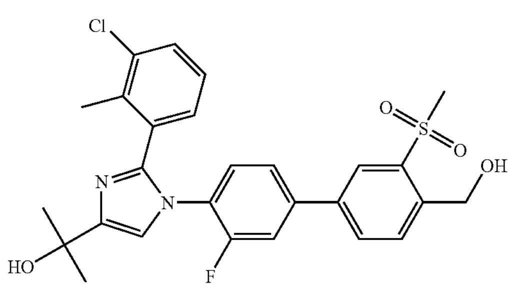 [SMILES: Cc1c(Cl)cccc1-c1nc(C(C)(C)O)cn1-c1ccc(-c2ccc(CO)c(S(C)(=O)=O)c2)cc1F] | 2-(2-(3-chloro-2-methylphenyl)-1-(3-fluoro-4'-(hydroxymethyl)-3'-(methylsulfonyl)biphenyl-4-yl)-1H-imidazol-4-yl)propan-2-ol; |
| 121 | 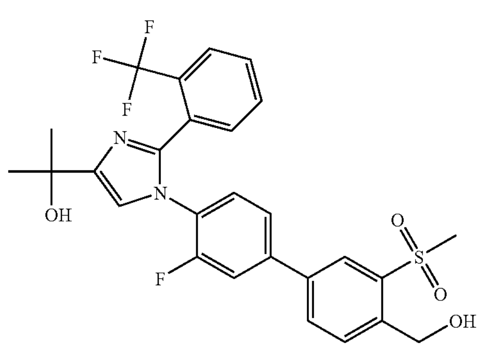 | 2-(1-(3-fluoro-4'-(hydroxymethyl)-3'-(methylsulfonyl)biphenyl-4-yl)-2-(2-(trifluoromethyl)phenyl)-1H-imidazol-4-yl)propan-2-ol; |

TABLE 1-continued

| Cpd # | Structure | Name |
|---|---|---|
| 122 | 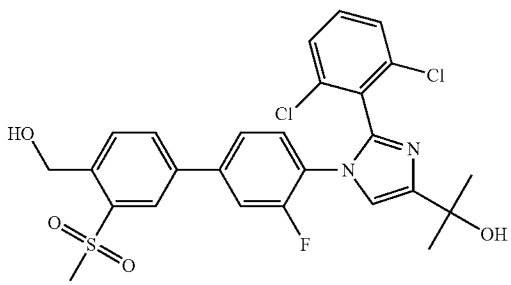 | 2-(2-(2,6-dichlorophenyl)-1-(3-fluoro-4'-(hydroxymethyl)-3'-(methylsulfonyl)biphenyl-4-yl)-1H-imidazol-4-yl)propan-2-ol; |
| 123 | 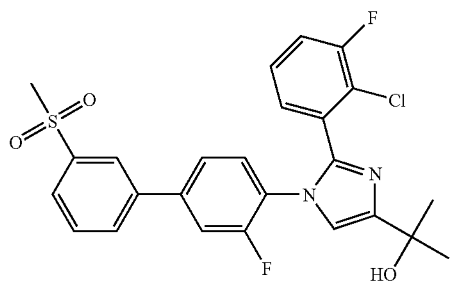 | 2-(2-(2-chloro-3-fluorophenyl)-1-(3-fluoro-3'-(methylsulfonyl)biphenyl-4-yl)-1H-imidazol-4-yl)propan-2-ol; |
| 124 | 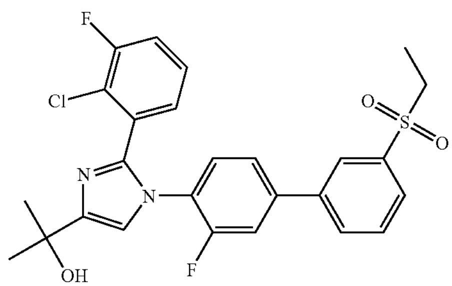 | 2-(2-(2-chloro-3-fluorophenyl)-1-(3'-(ethylsulfonyl)-3-fluorobiphenyl-4-yl)-1H-imidazol-4-yl)propan-2-ol; |
| 125 | 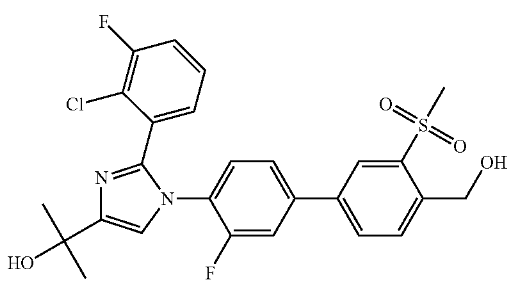 [SMILES: CC(C)(O)c1cn(-c2ccc(-c3ccc(CO)c(S(C)(=O)=O)c3)cc2F)c(-c2cccc(F)c2Cl)n1] | 2-(2-(2-chloro-3-fluorophenyl)-1-(3-fluoro-4'-(hydroxymethyl)-3'-(methylsulfonyl)biphenyl-4-yl)-1H-imidazol-4-yl)propan-2-ol; |
| 126 | 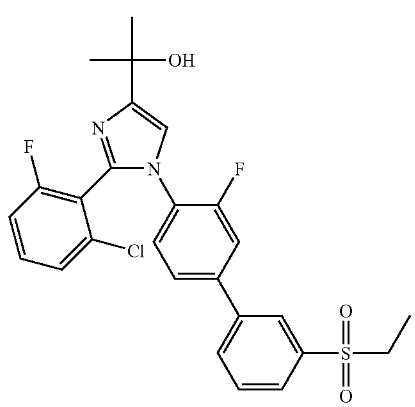 [SMILES: CCS(=O)(=O)c1cccc(-c2ccc(-n3cc(C(C)(C)O)nc3-c3c(F)cccc3Cl)c(F)c2)c1] | 2-(2-(2-chloro-6-fluorophenyl)-1-(3'-(ethylsulfonyl)-3-fluorobiphenyl-4-yl)-1H-imidazol-4-yl)propan-2-ol; |

TABLE 1-continued

| Cpd # | Structure | Name |
|---|---|---|
| 127 | 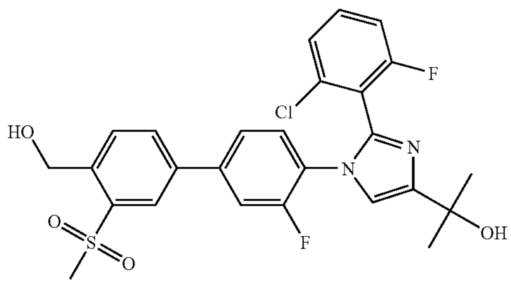 | 2-(2-(2-chloro-6-fluorophenyl)-1-(3-fluoro-4'-(hydroxymethyl)-3'-(methylsulfonyl)biphenyl-4-yl)-1H-imidazol-4-yl)propan-2-ol; |
| 128 | 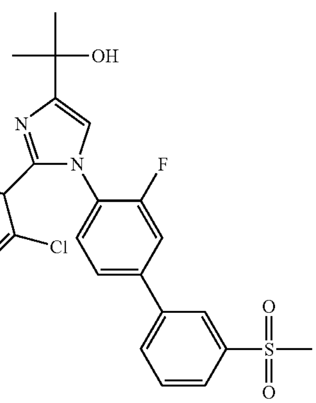 | 2-(2-(2-chloro-6-methylphenyl)-1-(3-fluoro-3'-(methylsulfonyl)biphenyl-4-yl)-1H-imidazol-4-yl)propan-2-ol; |
| 129 | 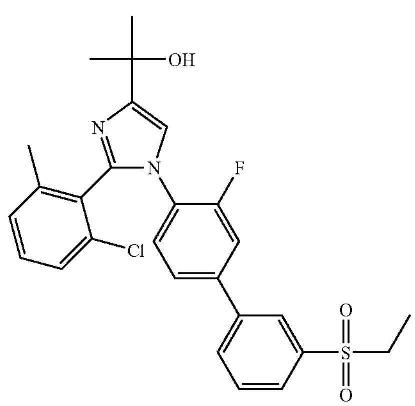 | 2-(2-(2-chloro-6-methylphenyl)-1-(3'-(ethylsulfonyl)-3-fluorobiphenyl-4-yl)-1H-imidazol-4-yl)propan-2-ol; |
| 130 | 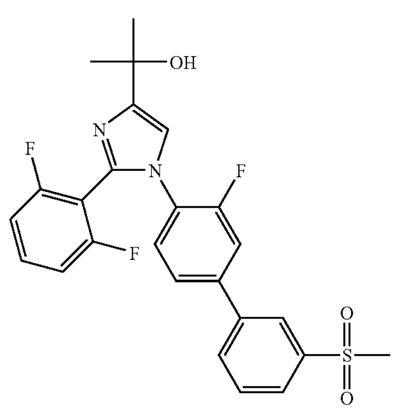 [SMILES: CC(C)(O)c1cn(-c2ccc(-c3cccc(S(C)(=O)=O)c3)cc2F)c(-c2c(F)cccc2F)n1] | 2-(2-(2,6-difluorophenyl)-1-(3-fluoro-3'-(methylsulfonyl)biphenyl-4-yl)-1H-imidazol-4-yl)propan-2-ol; |

TABLE 1-continued

| Cpd # | Structure | Name |
|---|---|---|
| 131 | 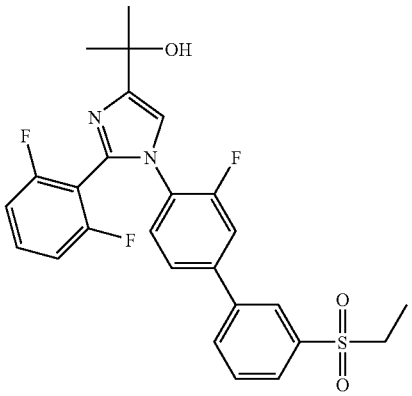 | 2-(2-(2,6-difluorophenyl)-1-(3'-(ethylsulfonyl)-3-fluorobiphenyl-4-yl)-1H-imidazol-4-yl)propan-2-ol; |
| 132 | 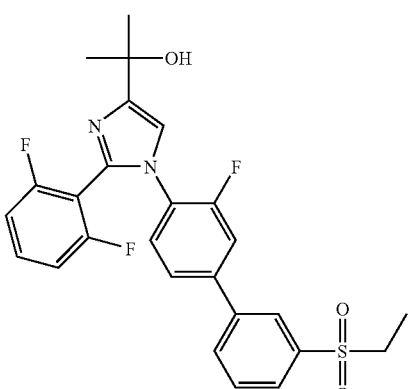 | 2-(2-(2,6-dichlorophenyl)-1-(3'-(ethylsulfonyl)-3-fluorobiphenyl-4-yl)-1H-imidazol-4-yl)propan-2-ol; |
| 133 | 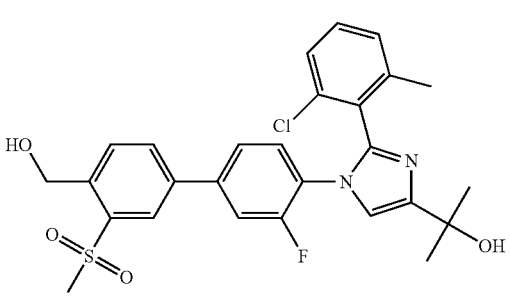 [SMILES: Cc1cccc(Cl)c1-c1nc(C(C)(C)O)cn1-c1ccc(-c2ccc(CO)c(S(C)(=O)=O)c2)cc1F] | 2-(2-(2-chloro-6-methylphenyl)-1-(3-fluoro-4'-(hydroxymethyl)-3'-(methylsulfonyl)biphenyl-4-yl)-1H-imidazol-4-yl)propan-2-ol; |
| 134 | 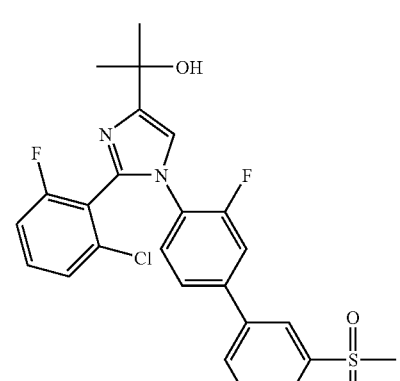 | 2-(2-(2-chloro-6-fluorophenyl)-1-(3-fluoro-3'-(methylsulfonyl)biphenyl-4-yl)-1H-imidazol-4-yl)propan-2-ol; |

| Cpd # | Structure | Name |
|---|---|---|
| 135 | 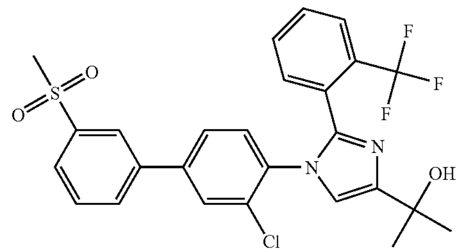 | 2-(1-(3-chloro-3'-(methylsulfonyl)biphenyl-4-yl)-2-(2-(trifluoromethyl)phenyl)-1H-imidazol-4-yl)propan-2-ol; |
| 136 | 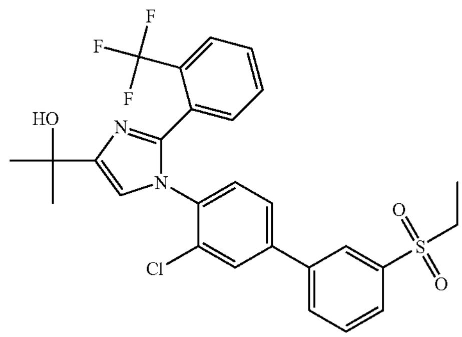 [SMILES: CCS(=O)(=O)c1cccc(-c2ccc(-n3cc(C(C)(C)O)nc3-c3ccccc3C(F)(F)F)c(Cl)c2)c1] | 2-(1-(3-chloro-3'-(ethylsulfonyl)biphenyl-4-yl)-2-(2-(trifluoromethyl)phenyl)-1H-imidazol-4-yl)propan-2-ol; |
| 137 | 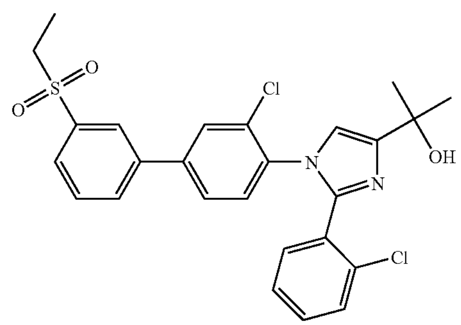 [SMILES: CCS(=O)(=O)c1cccc(-c2ccc(-n3cc(C(C)(C)O)nc3-c3ccccc3Cl)c(Cl)c2)c1] | 2-(1-(3-chloro-(3'-(ethylsulfonyl)biphenyl-4-yl)-2-(2-chlorophenyl)-1H-imidazol-4-yl)propan-2-ol; |
| 138 | 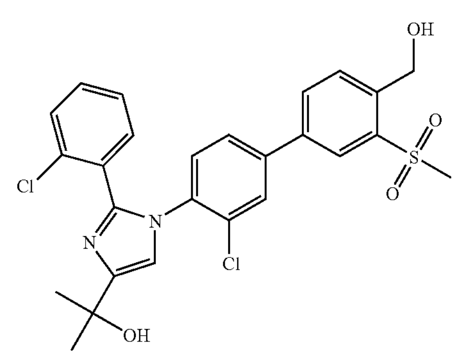 [SMILES: CC(C)(O)c1cn(-c2ccc(-c3ccc(CO)c(S(C)(=O)=O)c3)cc2Cl)c(-c2ccccc2Cl)n1] | 2-(1-(3-chloro-4'-(hydroxymethyl)-3'-(methylsulfonyl)biphenyl-4-yl)-2-(2-chlorophenyl)-1H-imidazol-4-yl)propan-2-ol; |

TABLE 1-continued

| Cpd # | Structure | Name |
|---|---|---|
| 139 | 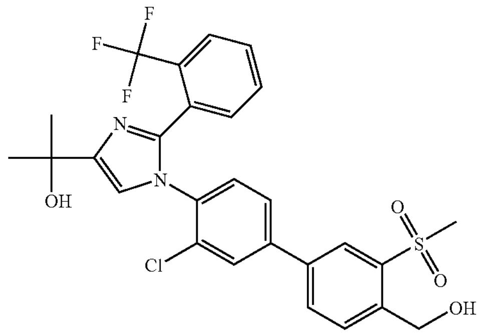 | 2-(1-(3-chloro-4'-(hydroxymethyl)-3'-(methylsulfonyl)biphenyl-4-yl)-2-(2-trifluoromethyl)phenyl-1H-imidazol-4-yl)propan-2-ol; |
| 140 | 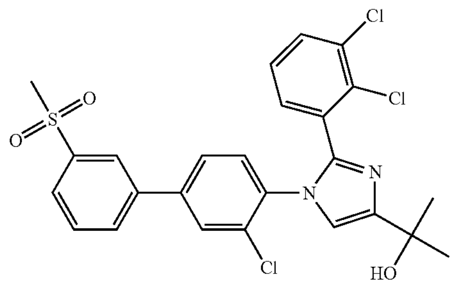 | 2-(1-(3-chloro-3'-(methylsulfonyl)biphenyl-4-yl)-2-(2,3-dichlorophenyl)-1H-imidazol-4-yl)propan-2-ol; |
| 141 | 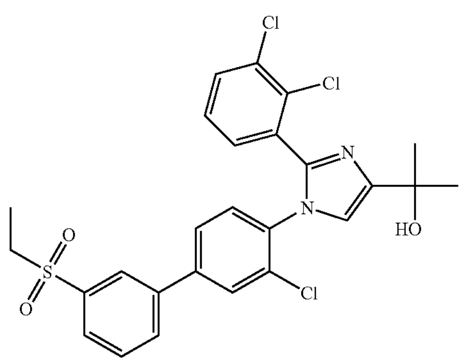 | 2-(1-(3-chloro-3'-(ethylsulfonyl)biphenyl-4-yl)-2-(2,3-dichlorophenyl)-1H-imidazol-4-yl)propan-2-ol; |
| 142 | 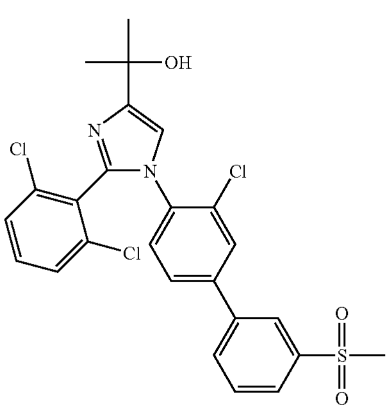 [SMILES: CC(C)(O)c1cn(-c2ccc(-c3cccc(S(C)(=O)=O)c3)cc2Cl)c(-c2c(Cl)cccc2Cl)n1] | 2-(1-(3-chloro-3'-(methylsulfonyl)biphenyl-4-yl)-2-(2,6-dichlorophenyl)-1H-imidazol-4-yl)propan-2-ol; |

TABLE 1-continued

| Cpd # | Structure | Name |
|---|---|---|
| 143 | 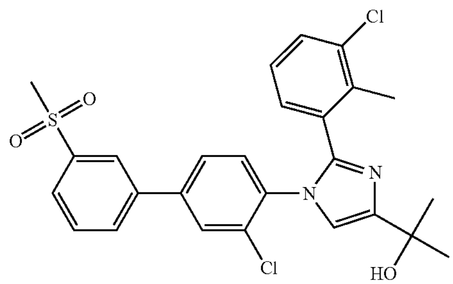 | 2-(2-(3-chloro-2-methylphenyl)-1-(3-chloro-3'-(methylsulfonyl)biphenyl-4-yl)-1H-imidazol-4-yl)propan-2-ol; |
| 144 | 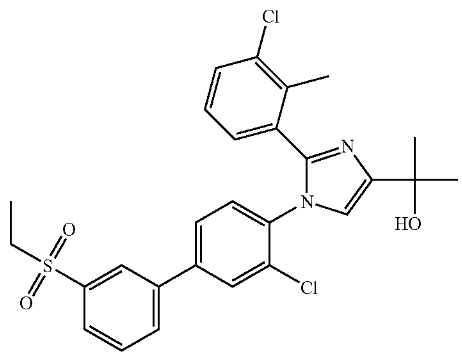 | 2-(2-(3-chloro-2-methylphenyl)-1-(3-chloro-3'-(ethylsulfonyl)biphenyl-4-yl)-1H-imidazol-4-yl)propan-2-ol; |
| 145 | 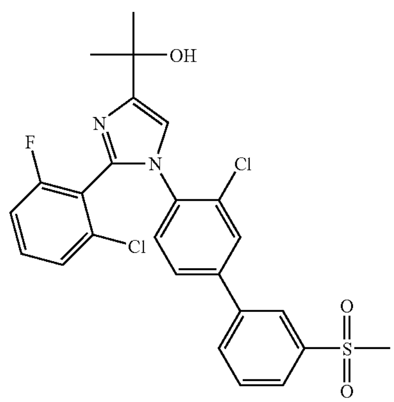 | 2-(1-(3-chloro-3'-(methylsulfonyl)biphenyl-4-yl)-2-(2-chloro-6-fluorophenyl)-1H-imidazol-4-yl)propan-2-ol; |
| 146 | 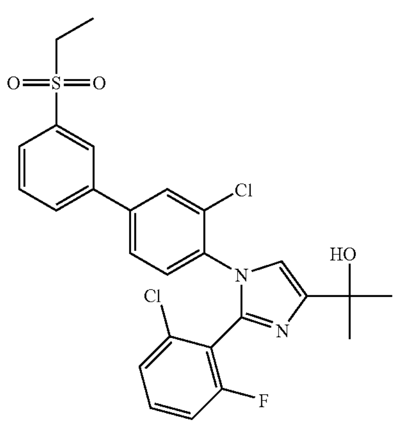 | 2-(1-(3-chloro-3'-(ethylsulfonyl)biphenyl-4-yl)-2-(2-chloro-6-fluorophenyl)-1H-imidazol-4-yl)propan-2-ol; |

TABLE 1-continued

| Cpd # | Structure | Name |
|---|---|---|
| 147 | 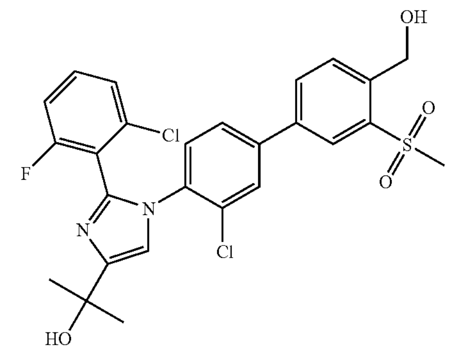 [SMILES: CC(C)(O)c1cn(-c2ccc(-c3ccc(CO)c(S(C)(=O)=O)c3)cc2Cl)c(-c2c(F)cccc2Cl)n1] | 2-(1-(3-chloro-4'-(hydroxymethyl)-3'-(methylsulfonyl)biphenyl-4-yl)-2-(2-chloro-6-fluorophenyl)-1H-imidazol-4-yl)propan-2-ol; |
| 148 | 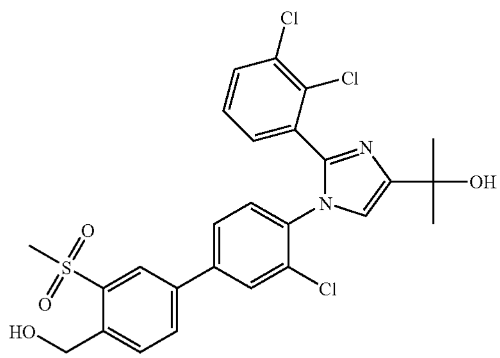 [SMILES: CC(C)(O)c1cn(-c2ccc(-c3ccc(CO)c(S(C)(=O)=O)c3)cc2Cl)c(-c2cccc(Cl)c2Cl)n1] | 2-(1-(3-chloro-4'-(hydroxymethyl)-3'-(methylsulfonyl)biphenyl-4-yl)-2-(2,3-dichlorophenyl)-1H-imidazol-4-yl)propan-2-ol; |
| 149 | 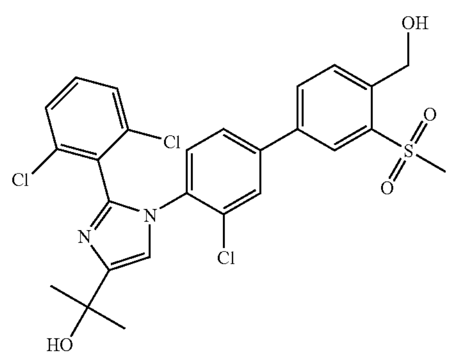 [SMILES: CC(C)(O)c1cn(-c2ccc(-c3ccc(CO)c(S(C)(=O)=O)c3)cc2Cl)c(-c2c(Cl)cccc2Cl)n1] | 2-(1-(3-chloro-4'-(hydroxymethyl)-3'-(methylsulfonyl)biphenyl-4-yl)-2-(2,6-dichlorophenyl)-1H-imidazol-4-yl)propan-2-ol; |
| 150 | 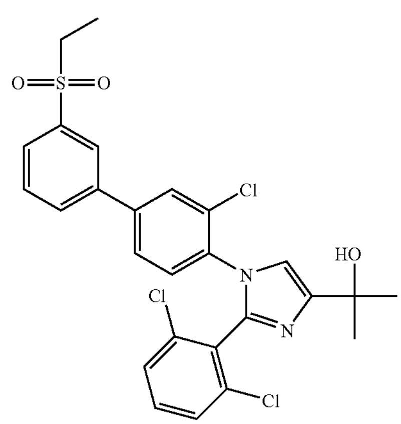 | 2-(1-(3-chloro-3'-(ethylsulfonyl)biphenyl-4-yl)-2-(2,6-dichlorophenyl)-1H-imidazol-4-yl)propan-2-ol; |

TABLE 1-continued

| Cpd # | Structure | Name |
|---|---|---|
| 151 | 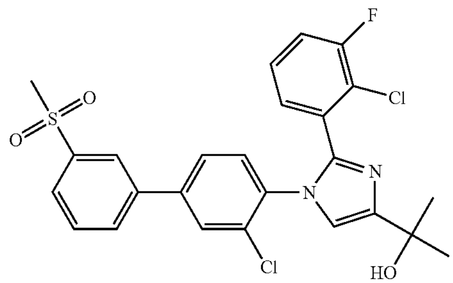 | 2-(1-(3-chloro-3'-(methylsulfonyl)biphenyl-4-yl)-2-(2-chloro-3-fluorophenyl)-1H-imidazol-4-yl)propan-2-ol; |
| 152 | 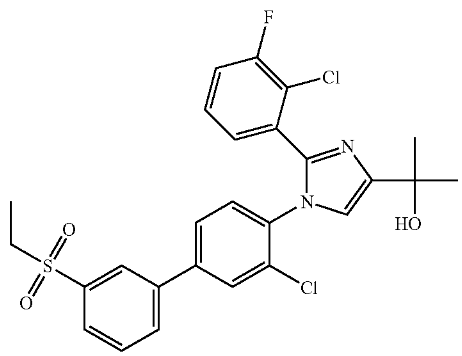 | 2-(1-(3-chloro-3'-(ethylsulfonyl)biphenyl-4-yl)-2-(2-chloro-3-fluorophenyl)-1H-imidazol-4-yl)propan-2-ol; |
| 153 | 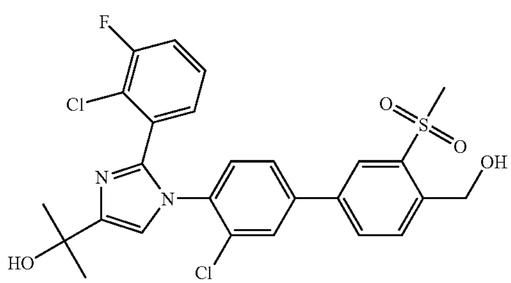 [SMILES: CC(C)(O)c1cn(-c2ccc(-c3ccc(CO)c(S(C)(=O)=O)c3)cc2Cl)c(-c2cccc(F)c2Cl)n1] | 2-(2-(2-chloro-3-fluorophenyl)-1-(3-chloro-4'-(hydroxymethyl)-3'-(methylsulfonyl)biphenyl-4-yl)-1H-imidazol-4-yl)propan-2-ol; |
| 154 | 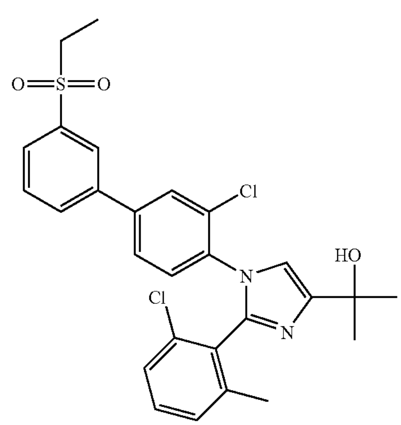 [SMILES: CCS(=O)(=O)c1cccc(-c2ccc(-n3cc(C(C)(C)O)nc3-c3c(C)cccc3Cl)c(Cl)c2)c1] | 2-(1-(3-chloro-3'-(ethylsulfonyl)biphenyl-4-yl)-2-(2-chloro-6-methylphenyl)-1H-imidazol-4-yl)propan-2-ol; |

TABLE 1-continued

| Cpd # | Structure | Name |
|---|---|---|
| 155 | 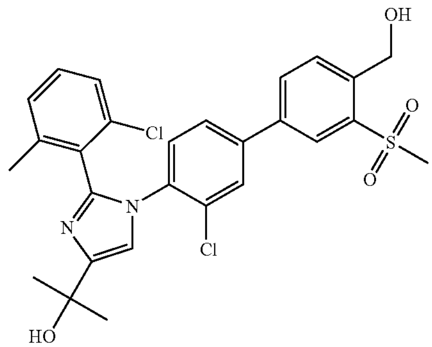 | 2-(1-(3-chloro-4'-(hydroxymethyl)-3'-(methylsulfonyl)biphenyl-4-yl)-2-(2-chloro-6-methylphenyl)-1H-imidazol-4-yl)propan-2-ol; |
| 156 | 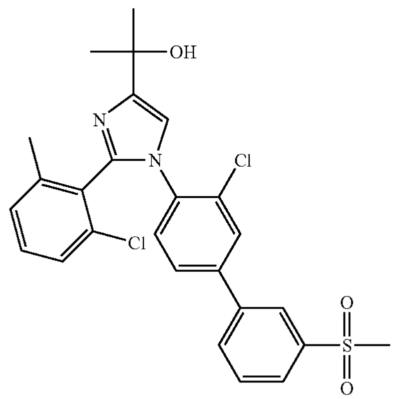 [SMILES: Cc1cccc(Cl)c1-c1nc(C(C)(C)O)cn1-c1ccc(-c2cccc(S(C)(=O)=O)c2)cc1Cl] | 2-(1-(3-chloro-3'-(methylsulfonyl)biphenyl-4-yl)-2-(2-chloro-6-methylphenyl)-1H-imidazol-4-yl)propan-2-ol; |
| 157 | 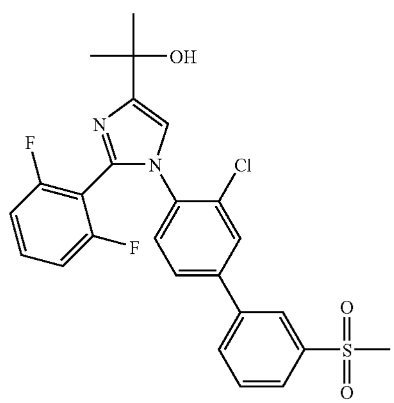 | 2-(1-(3-chloro-3'-(methylsulfonyl)biphenyl-4-yl)-2-(2,6-difluorophenyl)-1H-imidazol-4-yl)propan-2-ol; |
| 158 | 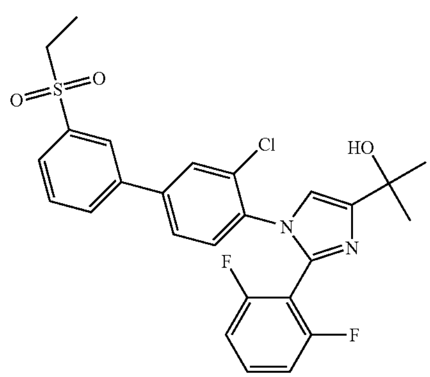 [SMILES: CCS(=O)(=O)c1cccc(-c2ccc(-n3cc(C(C)(C)O)nc3-c3c(F)cccc3F)c(Cl)c2)c1] | 2-(1-(3-chloro-3'-(ethylsulfonyl)biphenyl-4-yl)-2-(2,6-difluorophenyl)-1H-imidazol-4-yl)propan-2-ol; |

TABLE 1-continued

| Cpd # | Structure | Name |
|---|---|---|
| 159 | 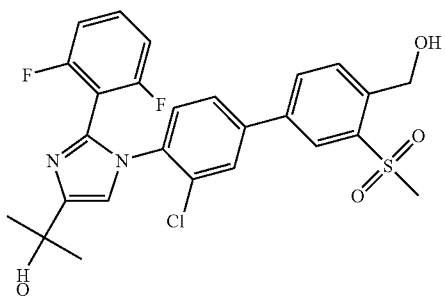 [SMILES: CC(C)(O)c1cn(-c2ccc(-c3ccc(CO)c(S(C)(=O)=O)c3)cc2Cl)c(-c2c(F)cccc2F)n1] | 2-(1-(3-chloro-4'-(hydroxymethyl)-3'-(methylsulfonyl)biphenyl-4-yl)-2-(2,6-difluorophenyl)-1H-imidazol-4-yl)propan-2-ol; |
| 160 | 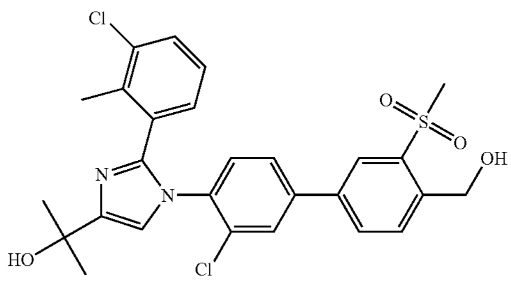 [SMILES: Cc1c(Cl)cccc1-c1nc(C(C)(C)O)cn1-c1ccc(-c2ccc(CO)c(S(C)(=O)=O)c2)cc1Cl] | 2-(2-(3-chloro-2-methylphenyl)-1-(3-chloro-4'-(hydroxymethyl)-3'-(methylsulfonyl)biphenyl-4-yl)-1H-imidazol-4-yl)propan-2-ol; |
| 161 | 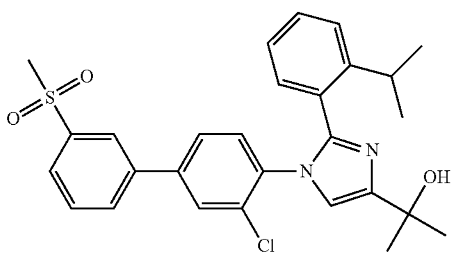 [SMILES: CC(C)c1ccccc1-c1nc(C(C)(C)O)cn1-c1ccc(-c2cccc(S(C)(=O)=O)c2)cc1Cl] | 2-(1-(3-chloro-3'-(methylsulfonyl)biphenyl-4-yl)-2-(2-isopropylphenyl)-1H-imidazol-4-yl)propan-2-ol; |
| 162 | 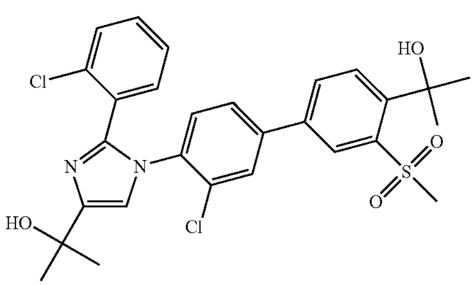 [SMILES: CC(C)(O)c1cn(-c2ccc(-c3ccc(C(C)(C)O)c(S(C)(=O)=O)c3)cc2Cl)c(-c2ccccc2Cl)n1] | 2-(3'-chloro-4'-(2-(2-chlorophenyl)-4-(2-hydroxypropan-2-yl)-1H-imidazol-1-yl)-3-(methylsulfonyl)biphenyl-4-yl)propan-2-ol; |
| 163 | 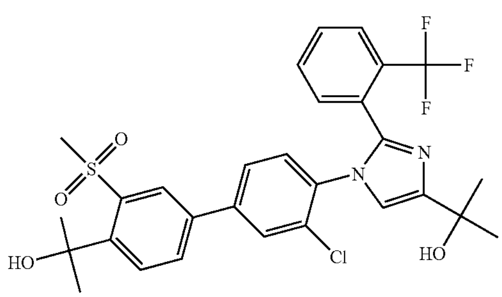 [SMILES: CC(C)(O)c1cn(-c2ccc(-c3ccc(C(C)(C)O)c(S(C)(=O)=O)c3)cc2Cl)c(-c2ccccc2C(F)(F)F)n1] | 2-(1-(3-chloro-4'-(2-hydroxypropan-2-yl)-3'-(methylsulfonyl)biphenyl-4-yl)-2-(2-(trifluoromethyl)phenyl)-1H-imidazol-4-yl)propan-2-ol; |

TABLE 1-continued

| Cpd # | Structure | Name |
|---|---|---|
| 164 | 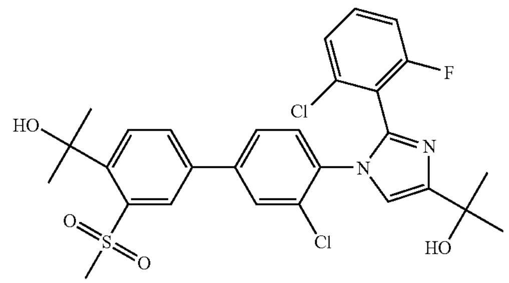 [SMILES: CC(C)(O)c1cn(-c2ccc(-c3ccc(C(C)(C)O)c(S(C)(=O)=O)c3)cc2Cl)c(-c2c(F)cccc2Cl)n1] | 2-(3'-chloro-4'-(2-(2-chloro-6-fluorophenyl)-4-(2-(hydroxypropan-2-yl)-1H-imidazol-1-yl)-3-(methylsulfonyl)biphenyl-4-yl)propan-2-ol; |
| 165 | 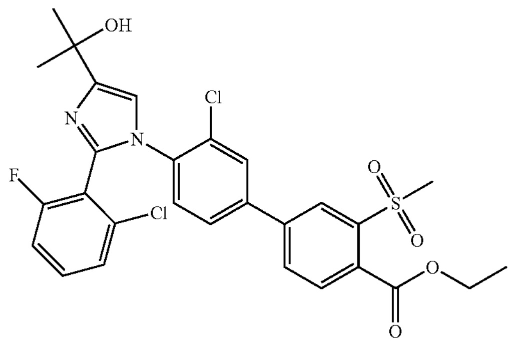 | ethyl 3'-chloro-4'-(2-(2-chloro-6-fluorophenyl)-4-(2-hydroxypropan-2-yl)-1H-imidazol-1-yl)-3-(methylsulfonyl)biphenyl-4-carboxylate; |
| 166 | 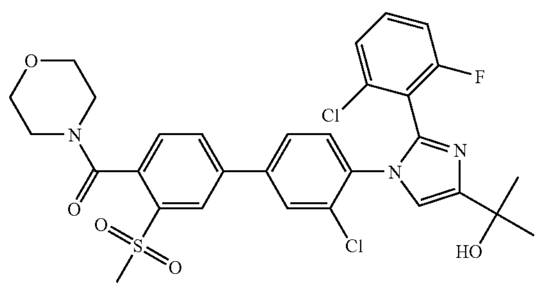 [SMILES: CC(C)(O)c1cn(-c2ccc(-c3ccc(C(=O)N4CCOCC4)c(S(C)(=O)=O)c3)cc2Cl)c(-c2c(F)cccc2Cl)n1] | (3'-chloro-4'-(2-(2-chloro-6-fluorophenyl)-4-(2-hydroxypropan-2-yl)-1H-imidazol-1-yl)-3-(methylsulfonyl)biphenyl-4-yl)(morpholino)methanone; |
| 167 | 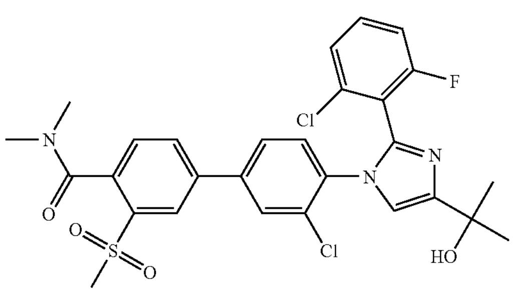 [SMILES: CN(C)C(=O)c1ccc(-c2ccc(-n3cc(C(C)(C)O)nc3-c3c(F)cccc3Cl)c(Cl)c2)cc1S(C)(=O)=O] | 3'-chloro-4'-(2-(2-chloro-6-fluorophenyl)-4-(2-hydroxypropan-2-yl)-1H-imidazol-1-yl)-N,N-dimethyl-3-(methylsulfonyl)biphenyl-4-carboxamide; |
| 168 | 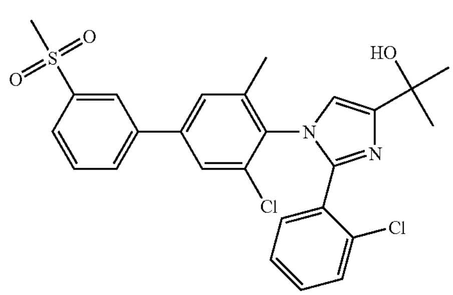 [SMILES: Cc1cc(-c2cccc(S(C)(=O)=O)c2)cc(Cl)c1-n1cc(C(C)(C)O)nc1-c1ccccc1Cl] | 2-(1-(3-chloro-5-methyl-3'-(methylsulfonyl)biphenyl-4-yl)-2-(2-chlorophenyl)-1H-imidazol-4-yl)propan-2-ol; |

TABLE 1-continued

| Cpd # | Structure | Name |
|---|---|---|
| 169 | 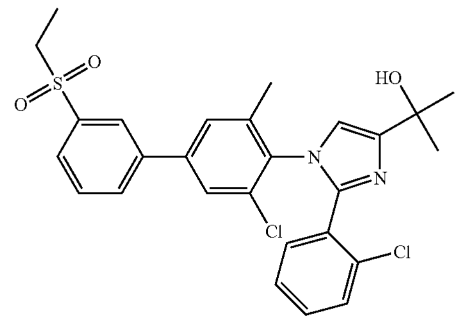 [SMILES: CCS(=O)(=O)c1cccc(-c2cc(C)c(-n3cc(C(C)(C)O)nc3-c3ccccc3Cl)c(Cl)c2)c1] | 2-(1-(3-chloro-3'-(ethylsulfonyl)-5-methylbiphenyl-4-yl)-2-(2-chlorophenyl)-1H-imidazol-4-yl)propan-2-ol; |
| 170 | 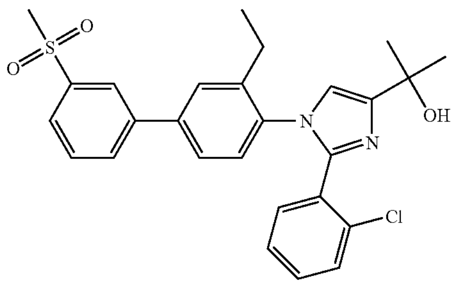 [SMILES: CCc1cc(-c2cccc(S(C)(=O)=O)c2)ccc1-n1cc(C(C)(C)O)nc1-c1ccccc1Cl] | 2-(2-(2-chlorophenyl)-1-(3-ethyl-3'-(methylsulfuonyl)biphenyl-4-yl)-1H-imidazol-4-yl)propan-2-ol; |
| 171 | 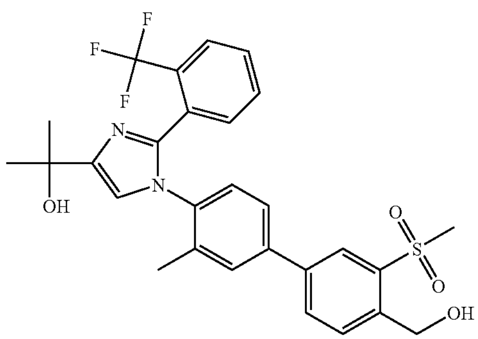 | 2-(1-(4'-(hydroxymethyl)-3-methyl-3'-(methylsulfonyl)biphenyl-4-yl)-2-(2-trifluoromethyl)phenyl)-1H-imidazol-4-yl)propan-2-ol; |
| 172 | 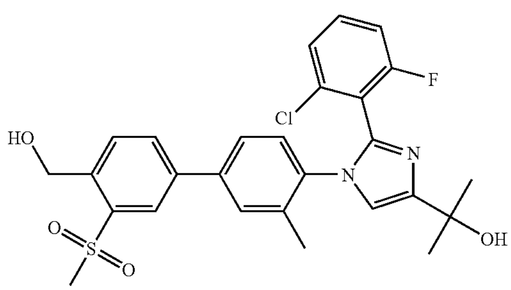 | 2-(2-(2-chloro-6-fluorophenyl)-1-(4'-(hydroxymethyl)-3-methyl-3'-(methylsulfonyl)biphenyl-4-yl)-1H-imidazol-4-yl)propan-2-ol; |
| 173 | 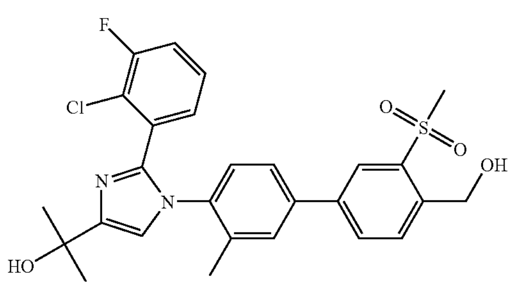 | 2-(2-(2-chloro-3-fluorophenyl)-1-(4'-(hydroxymethyl)-3-methyl-3'-(methylsulfonyl)biphenyl-4-yl)-1H-imidazol-4-yl)propan-2-ol; |

TABLE 1-continued

| Cpd # | Structure | Name |
|---|---|---|
| 174 | 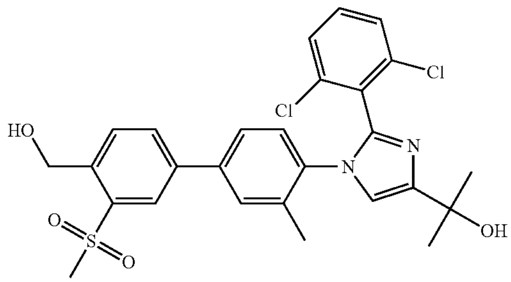 [SMILES: Cc1cc(-c2ccc(CO)c(S(C)(=O)=O)c2)ccc1-n1cc(C(C)(C)O)nc1-c1c(Cl)cccc1Cl] | 2-(2-(2,6-dichlorophenyl)-1-(4'-(hydroxymethyl)-3-methyl-3'-(methylsulfonyl)biphenyl-4-yl)-1H-imidazol-4-yl)propan-2-ol; |
| 175 | 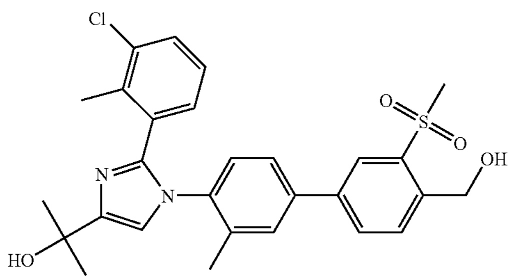 | 2-(2-(3-chloro-2-methylphenyl)-1-(4'-(hydroxymethyl)-3-methyl-3'-(methylsulfonyl)biphenyl-4-yl)-1H-imidazol-4-yl)propan-2-ol; |
| 176 | 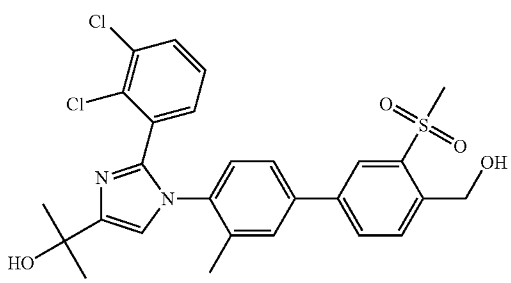 | 2-(2-(2,3-dichlorophenyl)-1-(4'-(hydroxymethyl)-3-methyl-3'-(methylsulfonyl)biphenyl-4-yl)-1H-imidazol-4-yl)propan-2-ol; |
| 177 | 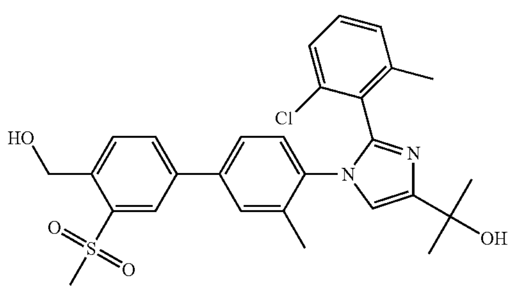 [SMILES: Cc1cc(-c2ccc(CO)c(S(C)(=O)=O)c2)ccc1-n1cc(C(C)(C)O)nc1-c1c(C)cccc1Cl] | 2-(2-(2-chloro-6-methylphenyl)-1-(4'-(hydroxymethyl)-3-methyl-3'-(methylsulfonyl)biphenyl-4-yl)-1H-imidazol-4-yl)propan-2-ol; |
| 178 | 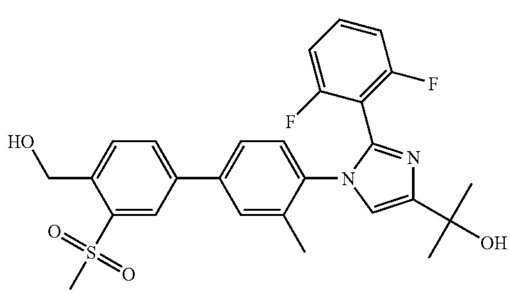 [SMILES: Cc1cc(-c2ccc(CO)c(S(C)(=O)=O)c2)ccc1-n1cc(C(C)(C)O)nc1-c1c(F)cccc1F] | 2-(2-(2,6-difluorophenyl)-1-(4'-(hydroxymethyl)-3-methyl-3'-(methylsulfonyl)biphenyl-4-yl)-1H-imidazol-4-yl)propan-2-ol; |

TABLE 1-continued

| Cpd # | Structure | Name |
|---|---|---|
| 179 | 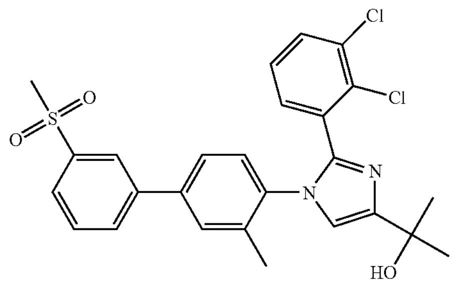 | 2-(2-(2,3-dichlorophenyl)-1-(3-methyl-3'-(methylsulfonyl)biphenyl-4-yl)-1H-imidazol-4-yl)propan-2-ol; |
| 180 | 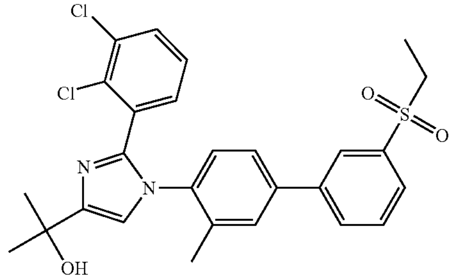 [SMILES: CCS(=O)(=O)c1cccc(-c2ccc(-n3cc(C(C)(C)O)nc3-c3cccc(Cl)c3Cl)c(C)c2)c1] | 2-(2-(2,3-dichlorophenyl)-1-(3'-(ethylsulfonyl)-3-methylbiphenyl-4-yl)-1H-imidazol-4-yl)propan-2-ol; |
| 181 | 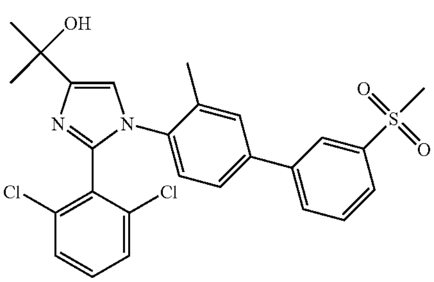 [SMILES: Cc1cc(-c2cccc(S(C)(=O)=O)c2)ccc1-n1cc(C(C)(C)O)nc1-c1c(Cl)cccc1Cl] | 2-(2-(2,6-dichlorophenyl)-1-(3-methyl-3'-(methylsulfonyl)biphenyl-4-yl)-1H-imidazol-4-yl)propan-2-ol; |
| 182 | 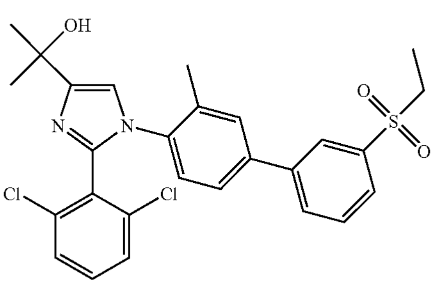 [SMILES: CCS(=O)(=O)c1cccc(-c2ccc(-n3cc(C(C)(C)O)nc3-c3c(Cl)cccc3Cl)c(C)c2)c1] | 2-(2-(2,6-dichlorophenyl)-1-(3'-(ethylsulfonyl)-3-methylbiphenyl-4-yl)-1H-imidazol-4-yl)propan-2-ol; |
| 183 | 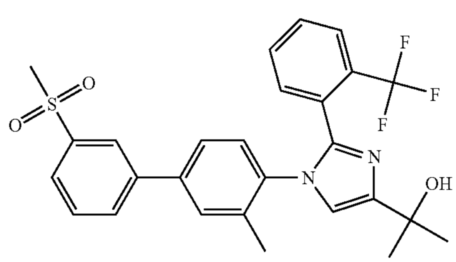 | 2-(1-(3-methyl-3'-(methylsulfonyl)biphenyl-4-yl)-2-(2-(trifluoromethyl)phenyl)-1H-imidazol-4-yl)propan-2-ol; |

TABLE 1-continued

| Cpd # | Structure | Name |
|---|---|---|
| 184 | 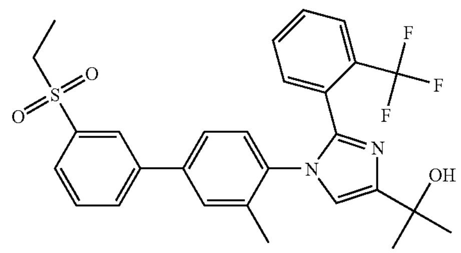 [SMILES: CCS(=O)(=O)c1cccc(-c2ccc(-n3cc(C(C)(C)O)nc3-c3ccccc3C(F)(F)F)c(C)c2)c1] | 2-(1-(3'-(ethylsulfonyl)-3-methylbiphenyl-4-yl)-2-(2-(trifluoromethyl)phenyl)-1H-imidazol-4-yl)propan-2-ol; |
| 185 | 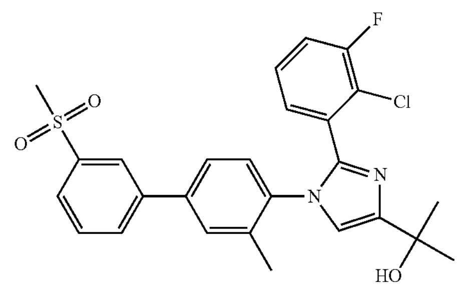 [SMILES: Cc1cc(-c2cccc(S(C)(=O)=O)c2)ccc1-n1cc(C(C)(C)O)nc1-c1cccc(F)c1Cl] | 2-(2-(2-chloro-3-fluorophenyl)-1-(3-methyl-3'-(methylsulfonyl)biphenyl-4-yl)-1H-imidazol-4-yl)propan-2-ol; |
| 186 | 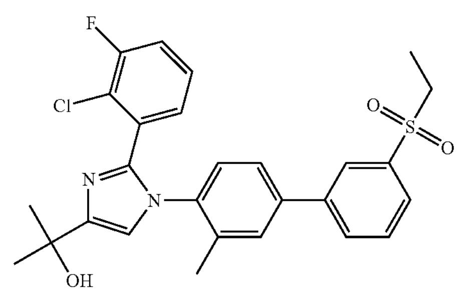 | 2-(2-(2-chloro-3-fluorophenyl)-1-(3'-(ethylsulfonyl)-3-methylbiphenyl-4-yl)-1H-imidazol-4-yl)propan-2-ol; |
| 187 | 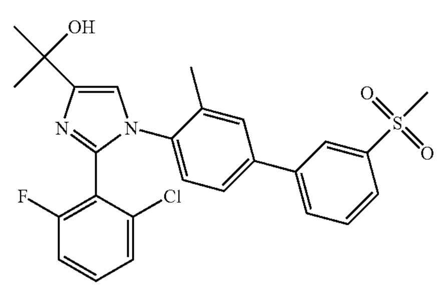 [SMILES: Cc1cc(-c2cccc(S(C)(=O)=O)c2)ccc1-n1cc(C(C)(C)O)nc1-c1c(F)cccc1Cl] | 2-(2-(2-chloro-6-fluorophenyl)-1-(3-methyl-3'-(methylsulfonyl)biphenyl-4-yl)-1H-imidazol-4-yl)propan-2-ol; |
| 188 | 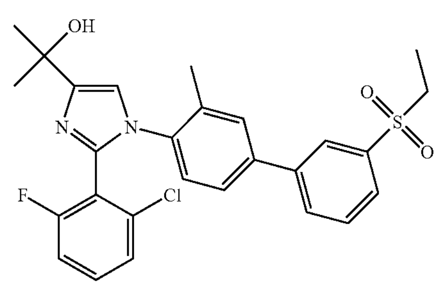 [SMILES: CCS(=O)(=O)c1cccc(-c2ccc(-n3cc(C(C)(C)O)nc3-c3c(F)cccc3Cl)c(C)c2)c1] | 2-(2-(2-chloro-6-fluorophenyl)-1-(3'-(ethylsulfonyl)-3-methylbiphenyl-4-yl)-1H-imidazol-4-yl)propan-2-ol; |

TABLE 1-continued

| Cpd # | Structure | Name |
|---|---|---|
| 189 | 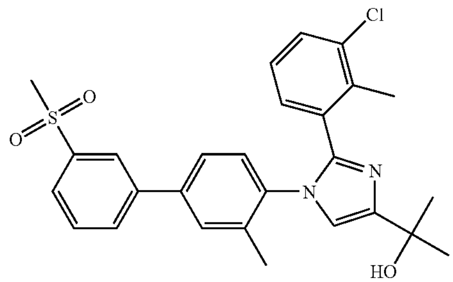 | 2-(2-(3-chloro-2-methylphenyl)-1-(3-methyl-3'-(methylsulfonyl)biphenyl-4-yl)-1H-imidazol-4-yl)propan-2-ol; |
| 190 | 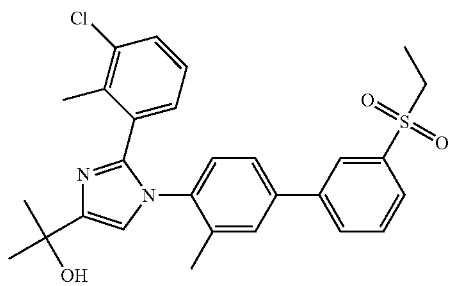 [SMILES: CCS(=O)(=O)c1cccc(-c2ccc(-n3cc(C(C)(C)O)nc3-c3cccc(Cl)c3C)c(C)c2)c1] | 2-(2-(3-chloro-2-methylphenyl)-1-(3'-(ethylsulfonyl)-3-methylbiphenyl-4-yl)-1H-imidazol-4-yl)propan-2-ol; |
| 191 | 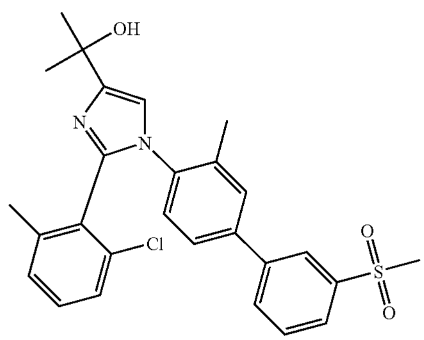 | 2-(2-(2-chloro-6-methylphenyl)-1-(3-methyl-3'-(methylsulfonyl)biphenyl-4-yl)-1H-imidazol-4-yl)propan-2-ol; |
| 192 | 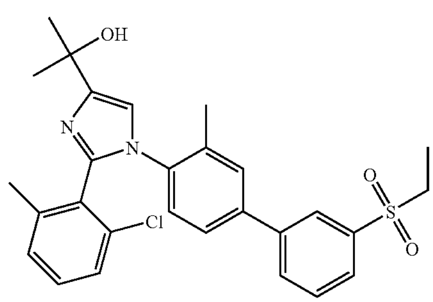 [SMILES: CCS(=O)(=O)c1cccc(-c2ccc(-n3cc(C(C)(C)O)nc3-c3c(C)cccc3Cl)c(C)c2)c1] | 2-(2-(2-chloro-6-methylphenyl)-1-(3'-(ethylsulfonyl)-3-methylbiphenyl-4-yl)-1H-imidazol-4-yl)propan-2-ol; |
| 193 | 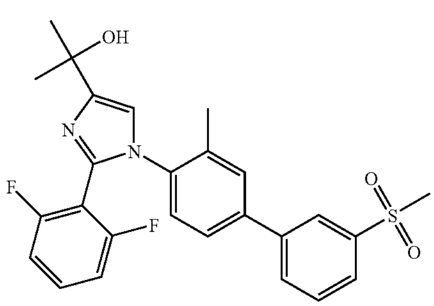 [SMILES: Cc1cc(-c2cccc(S(C)(=O)=O)c2)ccc1-n1cc(C(C)(C)O)nc1-c1c(F)cccc1F] | 2-(2-(2,6-difluorophenyl)-1-(3-methyl-3'-(methylsulfonyl)biphenyl-4-yl)-1H-imidazol-4-yl)propan-2-ol; |

TABLE 1-continued

| Cpd # | Structure | Name |
|---|---|---|
| 194 | 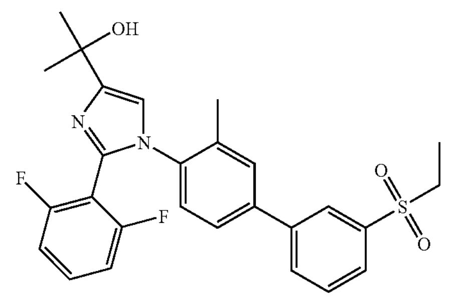 [SMILES: CCS(=O)(=O)c1cccc(-c2ccc(-n3cc(C(C)(C)O)nc3-c3c(F)cccc3F)c(C)c2)c1] | 2-(2-(2,6-difluorophenyl)-1-(3'-(ethylsulfonyl)-3-methylbiphenyl-4-yl)-1H-imidazol-4-yl)propan-2-ol; |
| 195 | 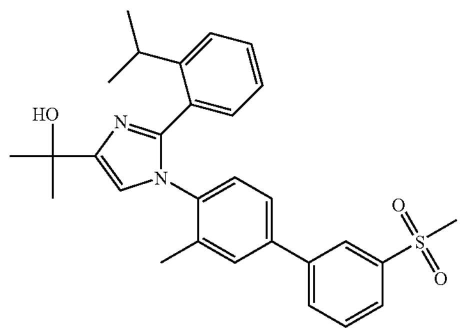 [SMILES: Cc1cc(-c2cccc(S(C)(=O)=O)c2)ccc1-n1cc(C(C)(C)O)nc1-c1ccccc1C(C)C] | 2-(2-(2-isopropylphenyl)-1-(3-methyl-3'-(methylsulfonyl)biphenyl-4-yl)-1H-imidazol-4-yl)propan-2-ol; |
| 196 | 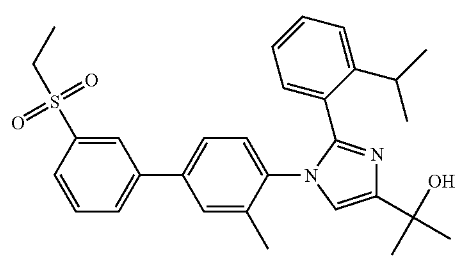 [SMILES: CCS(=O)(=O)c1cccc(-c2ccc(-n3cc(C(C)(C)O)nc3-c3ccccc3C(C)C)c(C)c2)c1] | 2-(1-(3'-(ethylsulfonyl)-3-methylbiphenyl-4-yl)-2-(2-isopropylphenyl)-1H-imidazol-4-yl)propan-2-ol; |
| 197 | 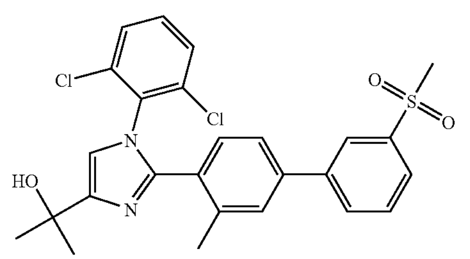 | 2-(1-(2,6-dichlorophenyl)-2-(3-methyl-3'-(methylsulfonyl)biphenyl-4-yl)-1H-imidazol-4-yl)propan-2-ol; |
| 198 | 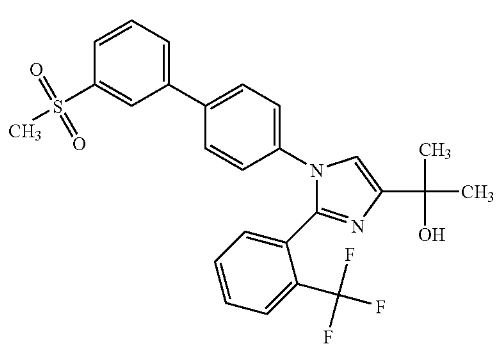 [SMILES: CC(C)(O)c1cn(-c2ccc(-c3cccc(S(C)(=O)=O)c3)cc2)c(-c2ccccc2C(F)(F)F)n1] | 2-{1-[3'-(methylsulfonyl)biphenyl-4-yl]-2-[2-(trifluoromethyl)phenyl]-1H-imidazol-4-yl}propan-2-ol; |

TABLE 1-continued

| Cpd # | Structure | Name |
|---|---|---|
| 199 | 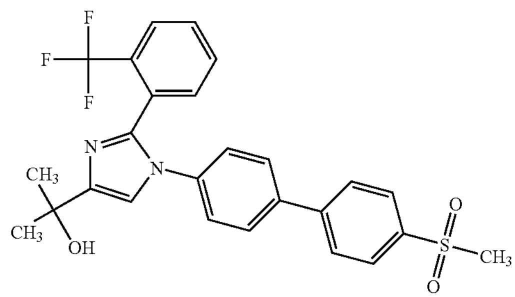 [SMILES: CC(C)(O)c1cn(-c2ccc(-c3ccc(S(C)(=O)=O)cc3)cc2)c(-c2ccccc2C(F)(F)F)n1] | 2-{1-[4'-(methylsulfonyl)biphenyl-4-yl]-2-[2-(trifluoromethyl)phenyl]-1H-imidazol-4-yl}propan-2-ol; |
| 200 | 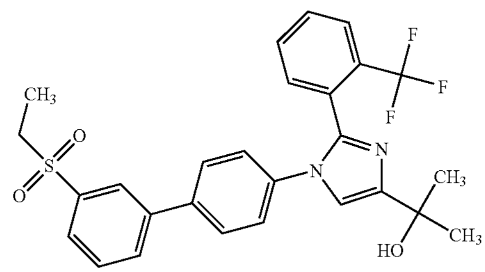 [SMILES: CCS(=O)(=O)c1cccc(-c2ccc(-n3cc(C(C)(C)O)nc3-c3ccccc3C(F)(F)F)cc2)c1] | 2-{1-[3'-(ethylsulfonyl)biphenyl-4-yl]-2-[2-(trifluoromethyl)phenyl]-1H-imidazol-4-yl}propan-2-ol; |
| 201 | 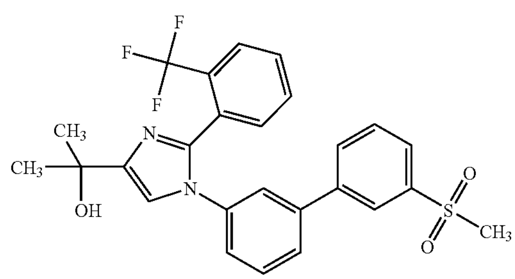 [SMILES: CC(C)(O)c1cn(-c2cccc(-c3cccc(S(C)(=O)=O)c3)c2)c(-c2ccccc2C(F)(F)F)n1] | 2-{1-[3'-(methylsulfonyl)biphenyl-3-yl]-2-[2-(trifluoromethyl)phenyl]-1H-imidazol-4-yl}propan-2-ol; |
| 202 | 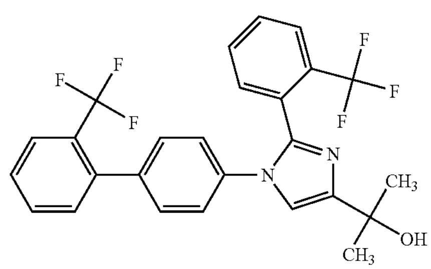 [SMILES: CC(C)(O)c1cn(-c2ccc(-c3ccccc3C(F)(F)F)cc2)c(-c2ccccc2C(F)(F)F)n1] | 2-{1-[2'-(trifluoromethyl)phenyl-4-yl]-2-[2-(trifluoromethyl)phenyl]-1H-imidazol-4-yl}propan-2-ol; |
| 203 | 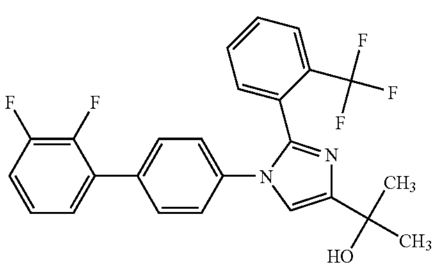 [SMILES: CC(C)(O)c1cn(-c2ccc(-c3cccc(F)c3F)cc2)c(-c2ccccc2C(F)(F)F)n1] | 2-{1-(2',3'-difluorobiphenyl-4-yl)-2-[2-(trifluoromethyl)phenyl]-1H-imidazol-4-yl}propan-2-ol; |

TABLE 1-continued

| Cpd # | Structure | Name |
|---|---|---|
| 204 | 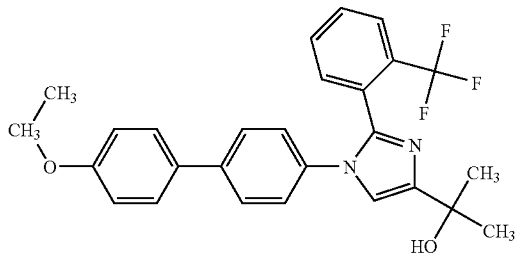 [SMILES: CCOc1ccc(-c2ccc(-n3cc(C(C)(C)O)nc3-c3ccccc3C(F)(F)F)cc2)cc1] | 2-(1-{4'-[(1-methylethyl)oxy]biphenyl-4-yl}-2-[2-(trifluoromethyl)phenyl]-1H-imidazol-4-yl)propan-2-ol; |
| 205 | 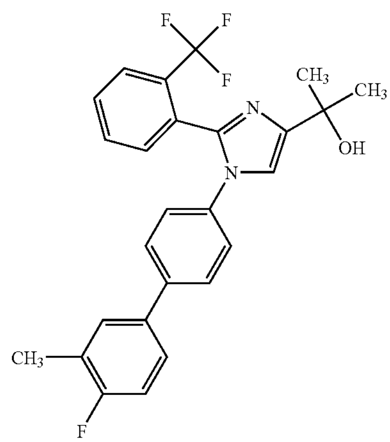 [SMILES: Cc1cc(-c2ccc(-n3cc(C(C)(C)O)nc3-c3ccccc3C(F)(F)F)cc2)ccc1F] | 2-{1-(4'-fluoro-3'-methylbiphenyl-4-yl)-2-[2-(trifluoromethyl)phenyl]-1H-imidazol-4-yl}propan-2-ol; |
| 206 | 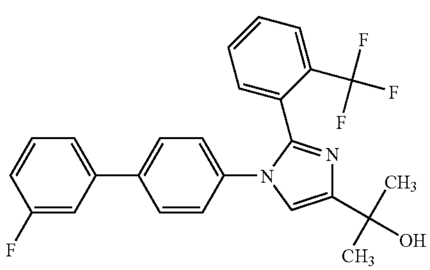 [SMILES: CC(C)(O)c1cn(-c2ccc(-c3cccc(F)c3)cc2)c(-c2ccccc2C(F)(F)F)n1] | 2-{1-(3'-fluorobiphenyl-4-yl)-2-[2-(trifluoromethyl)phenyl]-1H-imidazol-4-yl}propan-2-ol; |
| 207 | 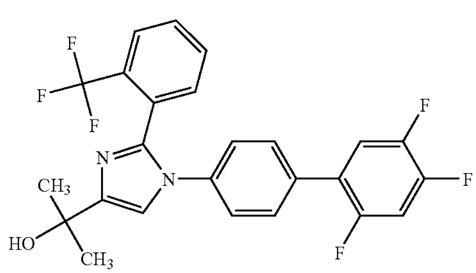 [SMILES: CC(C)(O)c1cn(-c2ccc(-c3cc(F)c(F)cc3F)cc2)c(-c2ccccc2C(F)(F)F)n1] | 2-{1-(2',4',5'-trifluorobiphenyl-4-yl)-2-[2-(trifluoromethyl)phenyl]-1H-imidazol-4-yl}propan-2-ol; |

TABLE 1-continued

| Cpd # | Structure | Name |
|---|---|---|
| 208 | 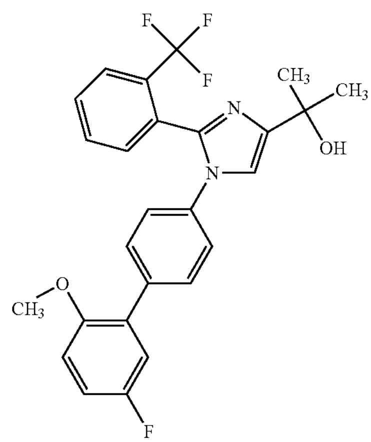 [SMILES: COc1ccc(F)cc1-c1ccc(-n2cc(C(C)(C)O)nc2-c2ccccc2C(F)(F)F)cc1] | 2-{1-[5'-fluoro-2'-(methyloxy)biphenyl-4-yl]-2-[2-(trifluoromethyl)phenyl]-1H-imidazol-4-yl}propan-2-ol; |
| 209 | 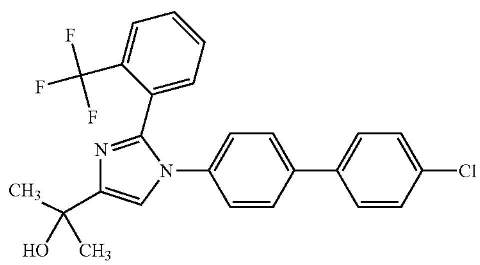 | 2-{1-(4'-chlorobiphenyl-4-yl)-2-[2-(trifluoromethyl)phenyl]-1H-imidazol-4-yl}propan-2-ol; |
| 210 | 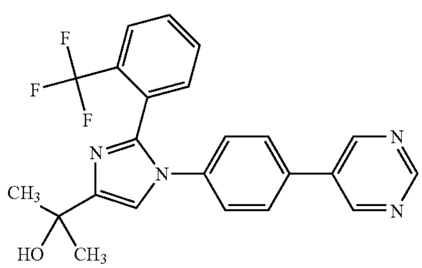 [SMILES: CC(C)(O)c1cn(-c2ccc(-c3cncnc3)cc2)c(-c2ccccc2C(F)(F)F)n1] | 2-{1-(4-pyridmin-5-ylphenyl)-2-[2-(trifluoromethyl)phenyl]-1H-imidazol-4-yl}propan-2-ol; |
| 211 | 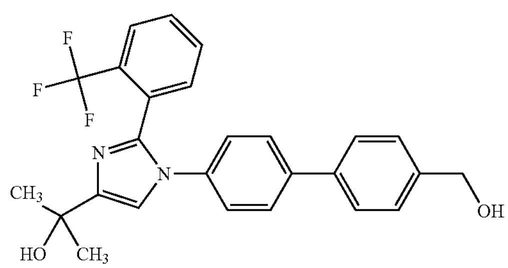 [SMILES: CC(C)(O)c1cn(-c2ccc(-c3ccc(CO)cc3)cc2)c(-c2ccccc2C(F)(F)F)n1] | 2-{1-[4'-(hydroxymethyl)biphenyl-4-yl]-2-[2-(trifluoromethyl)phenyl]-1H-imidazol-4-yl}propan-2-ol; |
| 212 | 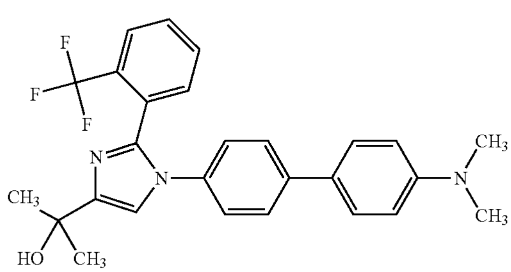 [SMILES: CN(C)c1ccc(-c2ccc(-n3cc(C(C)(C)O)nc3-c3ccccc3C(F)(F)F)cc2)cc1] | 2-{1-[4'-(dimethylamino)biphenyl-4-yl]-2-[2-(trifluoromethyl)phenyl]-1H-imidazol-4-yl}propan-2-ol; |

TABLE 1-continued

| Cpd # | Structure | Name |
|---|---|---|
| 213 | 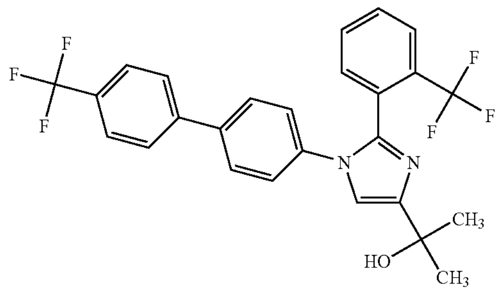 [SMILES: CC(C)(O)c1cn(-c2ccc(-c3ccc(C(F)(F)F)cc3)cc2)c(-c2ccccc2C(F)(F)F)n1] | 2-{1-[4'-(trifluoromethyl)biphenyl-4-yl]-2-[2-(trifluoromethyl)phenyl]-1H-imidazol-4-yl}propan-2-ol; |
| 214 | 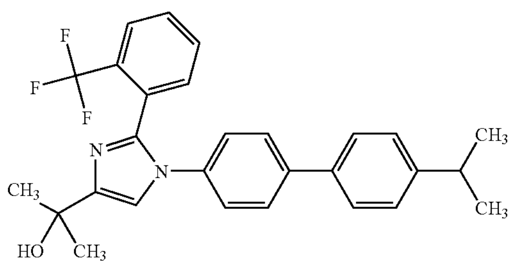 [SMILES: CC(C)c1ccc(-c2ccc(-n3cc(C(C)(C)O)nc3-c3ccccc3C(F)(F)F)cc2)cc1] | 2-{1-[4'-(1-methylethyl)biphenyl-4-yl]-2-[2-(trifluoromethyl)phenyl]-1H-imidazol-4-yl}propan-2-ol; |
| 215 | 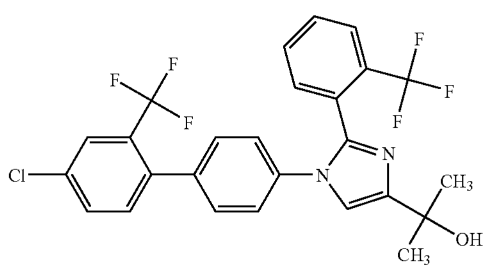 [SMILES: CC(C)(O)c1cn(-c2ccc(-c3ccc(Cl)cc3C(F)(F)F)cc2)c(-c2ccccc2C(F)(F)F)n1] | 2-{1-[4'-(chloro-2'-(trifluoromethyl)biphenyl-4-yl]-2-[2-(trifluoromethyl)phenyl]-1H-imidazol-4-yl}propan-2-ol; |
| 216 | 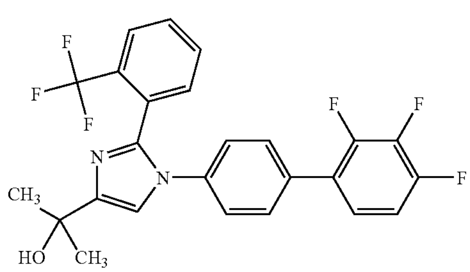 [SMILES: CC(C)(O)c1cn(-c2ccc(-c3ccc(F)c(F)c3F)cc2)c(-c2ccccc2C(F)(F)F)n1] | 2-{1-(2',3',4'-trifluorobiphenyl-4-yl)-2-[2-(trifluoromethyl)phenyl]-1H-imidazol-4-yl}propan-2-ol; |
| 217 | 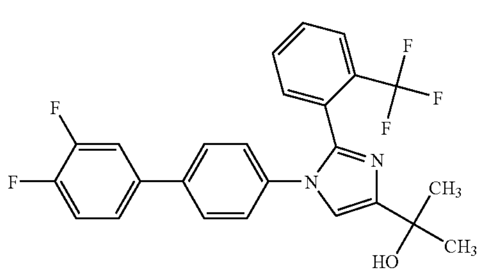 [SMILES: CC(C)(O)c1cn(-c2ccc(-c3ccc(F)c(F)c3)cc2)c(-c2ccccc2C(F)(F)F)n1] | 2-{1-(3', 4'-difluorobiphenyl-4-yl)-2-[2-(trifluoromethyl)phenyl]-1H-imidazol-4-yl}propan-2-ol; |

TABLE 1-continued

| Cpd # | Structure | Name |
|---|---|---|
| 218 | 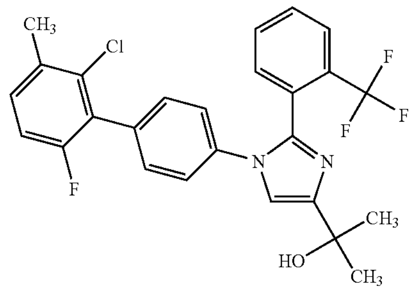 [SMILES: Cc1ccc(F)c(-c2ccc(-n3cc(C(C)(C)O)nc3-c3ccccc3C(F)(F)F)cc2)c1Cl] | 2-{1-(2'-chloro-6'-fluoro-3'-methylbiphenyl-4-yl)-2-[2-(trifluoromethyl)phenyl]-1H-imidazol-4-yl}propan-2-ol; |
| 219 | 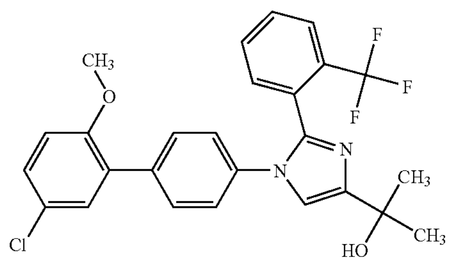 [SMILES: COc1ccc(Cl)cc1-c1ccc(-n2cc(C(C)(C)O)nc2-c2ccccc2C(F)(F)F)cc1] | 2-{1-[5'-chloro-2'-(methoxy)biphenyl-4-yl]-2-[2-(trifluoromethyl)phenyl]-1H-imidazol-4-yl}propan-2-ol; |
| 220 | 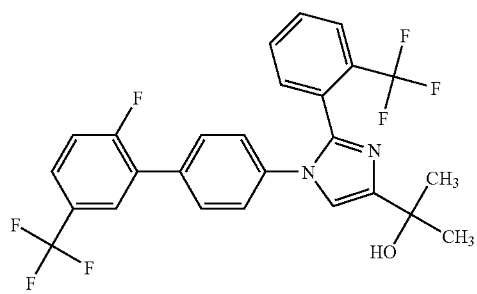 [SMILES: CC(C)(O)c1cn(-c2ccc(-c3cc(C(F)(F)F)ccc3F)cc2)c(-c2ccccc2C(F)(F)F)n1] | 2-{1-[2'-fluoro-5'-(trifluoromethyl)biphenyl-4-yl]-2-[2-(trifluoromethyl)phenyl]-1H-imidazol-4-yl}propan-2-ol; |
| 221 | 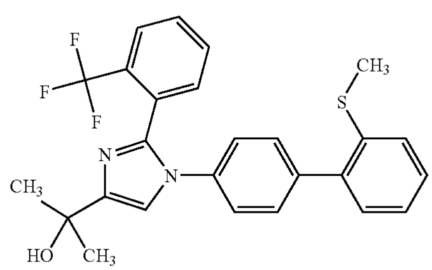 [SMILES: CSc1ccccc1-c1ccc(-n2cc(C(C)(C)O)nc2-c2ccccc2C(F)(F)F)cc1] | 2-{1-[2'-(methylthio)biphenyl-4-yl]-2-[2-(trifluoromethyl)phenyl]-1H-imidazol-4-yl}propan-2-ol; |
| 222 | 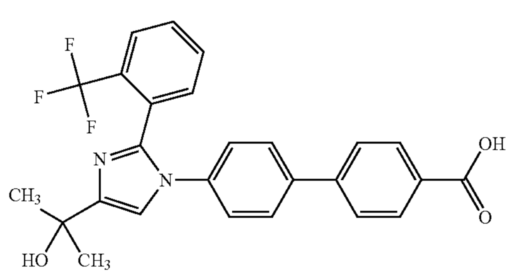 [SMILES: CC(C)(O)c1cn(-c2ccc(-c3ccc(C(=O)O)cc3)cc2)c(-c2ccccc2C(F)(F)F)n1] | 4'-{4-(1-hydroxy-1-methylethyl)-2-[2-(trifluoromethyl)phenyl]-1H-imidazol-1-yl}biphenyl-4-carboxylic acid; |

TABLE 1-continued

| Cpd # | Structure | Name |
|---|---|---|
| 223 | 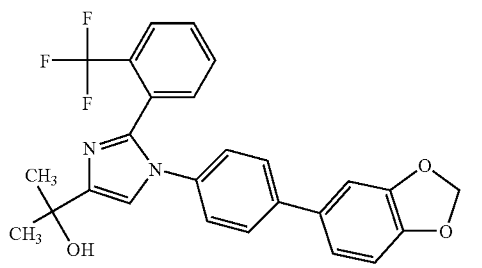 [SMILES: CC(C)(O)c1cn(-c2ccc(-c3ccc4c(c3)OCO4)cc2)c(-c2ccccc2C(F)(F)F)n1] | 2-{1-[4-(1,3-benzodioxol-5-yl)phenyl]-2-[2-(trifluoromethyl)phenyl]-1H-imidazol-4-yl}propan-2-ol; |
| 224 | 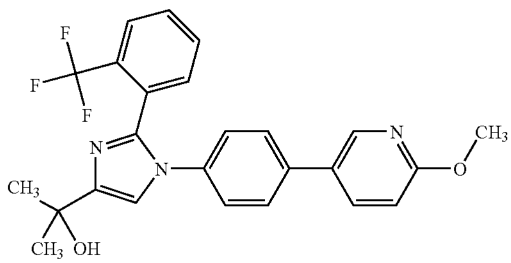 [SMILES: COc1ccc(-c2ccc(-n3cc(C(C)(C)O)nc3-c3ccccc3C(F)(F)F)cc2)cn1] | 2-(1-{4-[6-(methyloxy)pyridin-3-yl]phenyl}-2-[2-(trifluoromethyl)phenyl]-1H-imidazol-4-yl)propan-2-ol; |
| 225 | 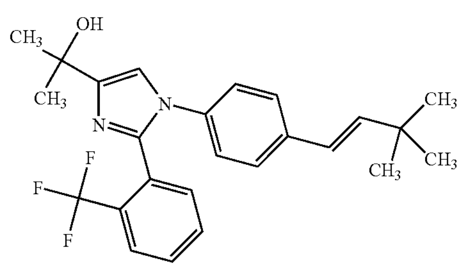 [SMILES: CC(C)(C)/C=C/c1ccc(-n2cc(C(C)(C)O)nc2-c2ccccc2C(F)(F)F)cc1] | 2-(1-{4-[(1E)-3,3-dimethylbut-1-en-1-yl]phenyl}-2-[2-(trifluoromethyl)phenyl]-1H-imidazol-4-yl)propan-2-ol; |
| 226 | 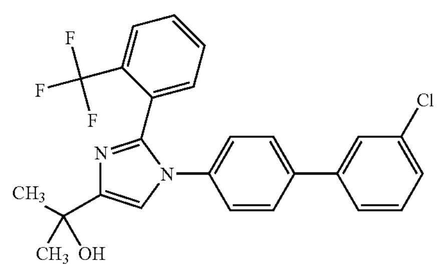 [SMILES: CC(C)(O)c1cn(-c2ccc(-c3cccc(Cl)c3)cc2)c(-c2ccccc2C(F)(F)F)n1] | 2-{1-(3'-chlorobiphenyl-4-yl)-2-[2-(trifluoromethyl)phenyl]-1H-imidazol-4-yl}propan-2-ol; |
| 227 | 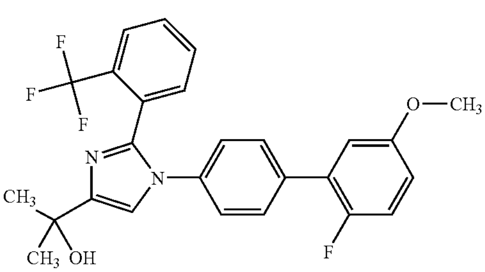 [SMILES: COc1ccc(F)c(-c2ccc(-n3cc(C(C)(C)O)nc3-c3ccccc3C(F)(F)F)cc2)c1] | 2-{1-[2'-fluoro-5'-(methyloxy)biphenyl-4-yl]-2-[2-(trifluoromethyl)phenyl]-1H-imidazol-4-yl}propan-2-ol; |

TABLE 1-continued

| Cpd # | Structure | Name |
|---|---|---|
| 228 | 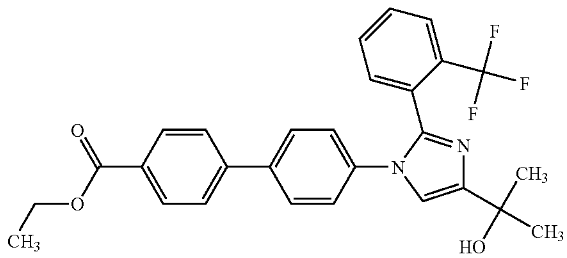 [SMILES: CCOC(=O)c1ccc(-c2ccc(-n3cc(C(C)(C)O)nc3-c3ccccc3C(F)(F)F)cc2)cc1] | ethyl 4'-{4-(1-hydroxy-1-methylethyl)-2-[2-(trifluoromethyl)phenyl]-1H-imidazol-1-yl}biphenyl-4-carboxylate; |
| 229 | 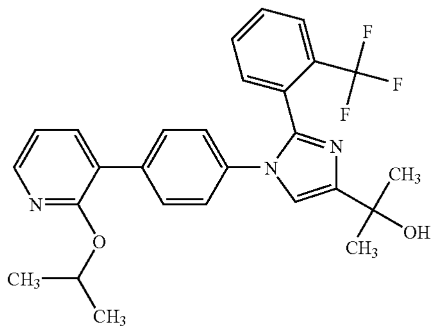 [SMILES: CC(C)Oc1ncccc1-c1ccc(-n2cc(C(C)(C)O)nc2-c2ccccc2C(F)(F)F)cc1] | 2-{1-(4-{2-[(1-methylethyl)oxy]pyridin-3-yl}phenyl)-2-[2-(trifluoromethyl)phenyl]-1H-imidazol-4-yl}propan-2-ol; |
| 230 | 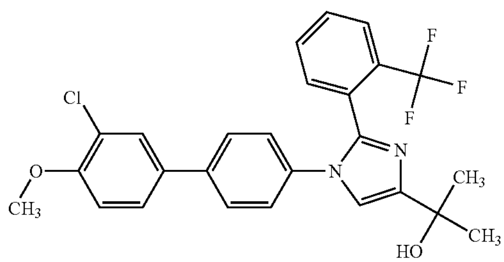 [SMILES: COc1ccc(-c2ccc(-n3cc(C(C)(C)O)nc3-c3ccccc3C(F)(F)F)cc2)cc1Cl] | 2-{1-[3'-chloro-4'-(methyloxy)biphenyl-4-yl]-2-[2-(trifluoromethyl)phenyl]-1H-imidazol-4-yl}propan-2-ol; |
| 232 | 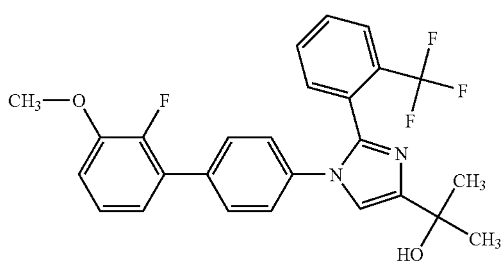 [SMILES: COc1cccc(-c2ccc(-n3cc(C(C)(C)O)nc3-c3ccccc3C(F)(F)F)cc2)c1F] | 2-{1-[2'-fluoro-3'-(methyloxy)biphenyl-4-yl]-2-[2-(trifluoromethyl)phenyl]-1H-imidazol-4-yl}propan-2-ol; |
| 233 | 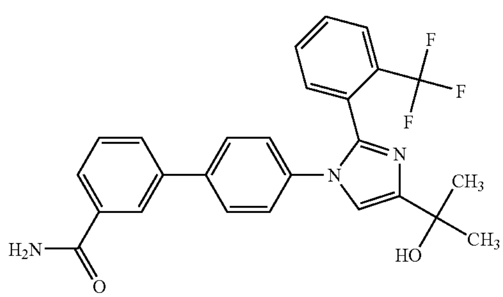 [SMILES: CC(C)(O)c1cn(-c2ccc(-c3cccc(C(N)=O)c3)cc2)c(-c2ccccc2C(F)(F)F)n1] | 4'-{4-(1-hydroxy-1-methylethyl)-2-[2-(trifluoromethyl)phenyl]-1H-imidazol-1-yl}biphenyl-3-carboxamide; |

TABLE 1-continued

| Cpd # | Structure | Name |
|---|---|---|
| 234 | 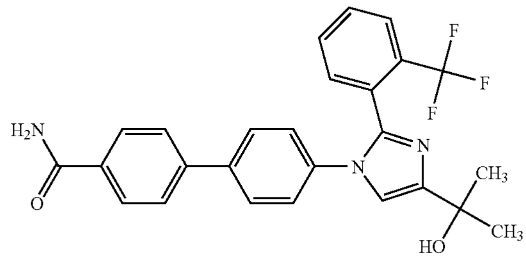 [SMILES: CC(C)(O)c1cn(-c2ccc(-c3ccc(C(N)=O)cc3)cc2)c(-c2ccccc2C(F)(F)F)n1] | 4'-{4-(1-hydroxy-1-methylethyl)-2-[2-(trifluoromethyl)phenyl]-1H-imidazol-1-yl}biphenyl-4-carboxamide; |
| 235 | 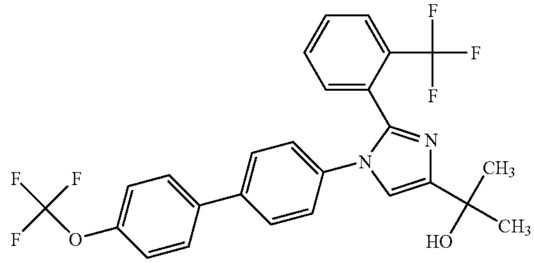 [SMILES: CC(C)(O)c1cn(-c2ccc(-c3ccc(OC(F)(F)F)cc3)cc2)c(-c2ccccc2C(F)(F)F)n1] | 2-(1-{4'-[(trifluoromethyl)oxy]biphenyl-4-yl}-2-[2-(trifluoromethyl)phenyl]-1H-imidazol-4-yl)propan-2-ol; |
| 236 | 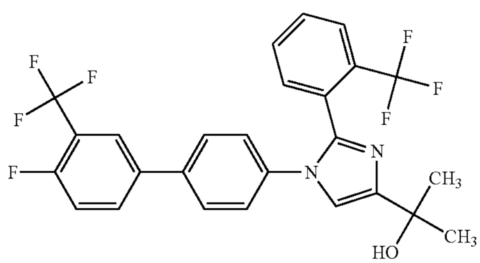 [SMILES: CC(C)(O)c1cn(-c2ccc(-c3ccc(F)c(C(F)(F)F)c3)cc2)c(-c2ccccc2C(F)(F)F)n1] | 2-{1-[4'-fluoro-3'-(trifluoromethyl)biphenyl-4-yl]-2-[2-(trifluoromethyl)phenyl]-1H-imidazol-4-yl}propan-2-ol; |
| 237 | 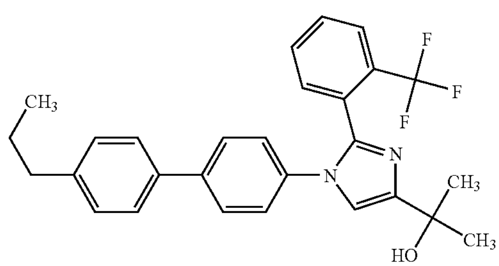 [SMILES: CCCc1ccc(-c2ccc(-n3cc(C(C)(C)O)nc3-c3ccccc3C(F)(F)F)cc2)cc1] | 2-{1-(4'-propylbiphenyl-4-yl)-2-[2-(trifluoromethyl)phenyl]-1H-imidazol-4-yl}propan-2-ol; |
| 238 | 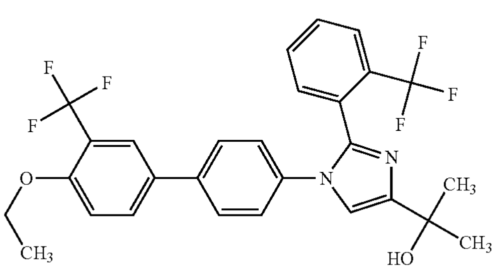 [SMILES: CCOc1ccc(-c2ccc(-n3cc(C(C)(C)O)nc3-c3ccccc3C(F)(F)F)cc2)cc1C(F)(F)F] | 2-{1-[4'-(ethyloxy)-3'-(trifluoromethyl)biphenyl-4-yl]-2-[2-(trifluoromethyl)phenyl]-1H-imidazol-4-yl}propan-2-ol; |

TABLE 1-continued

| Cpd # | Structure | Name |
|---|---|---|
| 239 | 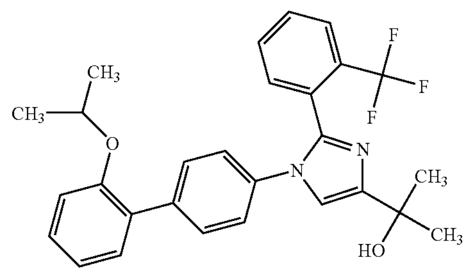 [SMILES: CC(C)Oc1ccccc1-c1ccc(-n2cc(C(C)(C)O)nc2-c2ccccc2C(F)(F)F)cc1] | 2-(1-{2'-[(1-methylethyl)oxy]biphenyl-4-yl}-2-[2-(trifluoromethyl)phenyl]-1H-imidazol-4-yl)propan-2-ol; |
| 240 | 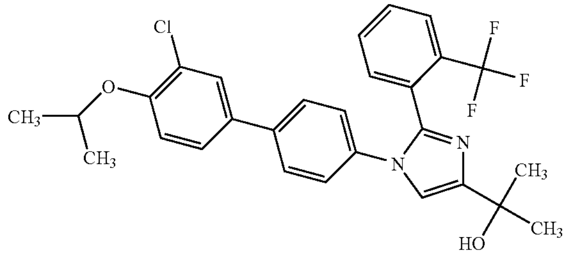 [SMILES: CC(C)Oc1ccc(-c2ccc(-n3cc(C(C)(C)O)nc3-c3ccccc3C(F)(F)F)cc2)cc1Cl] | 2-(1-{3'-chloro-4'-[(1-methylethyl)oxy]biphenyl-4-yl}-2-[2-(trifluoromethyl)phenyl]-1H-imidazol-4-yl)propan-2-ol; |
| 241 | 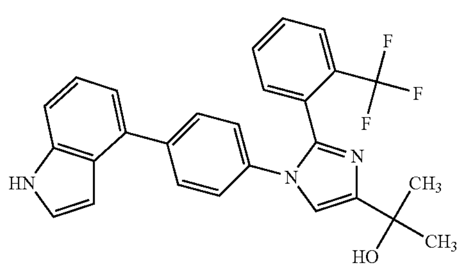 [SMILES: CC(C)(O)c1cn(-c2ccc(-c3cccc4[nH]ccc34)cc2)c(-c2ccccc2C(F)(F)F)n1] | 2-{1-[4-(1H-indol-4-yl)phenyl]-2-[2-(trifluoromethyl)phenyl]-1H-imidazol-4-yl}propan-2-ol; |
| 242 | 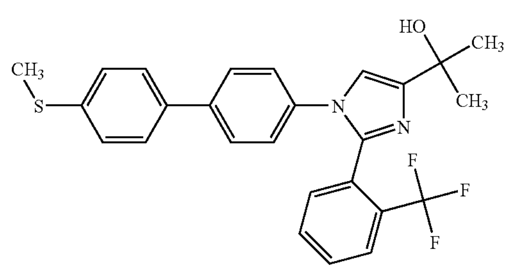 [SMILES: CSc1ccc(-c2ccc(-n3cc(C(C)(C)O)nc3-c3ccccc3C(F)(F)F)cc2)cc1] | 2-{1-[4'-(methylthio)biphenyl-4-yl]-2-[2-(trifluoromethyl)phenyl]-1H-imidazol-4-yl}propan-2-ol; |
| 243 | 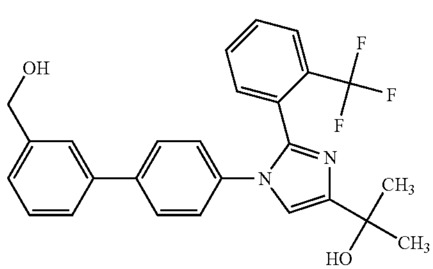 [SMILES: CC(C)(O)c1cn(-c2ccc(-c3cccc(CO)c3)cc2)c(-c2ccccc2C(F)(F)F)n1] | 2-{1-[3'-(hydroxymethyl)biphenyl-4-yl]-2-[2-(trifluoromethyl)phenyl]-1H-imidazol-4-yl}propan-2-ol; |

TABLE 1-continued

| Cpd # | Structure | Name |
|---|---|---|
| 244 | 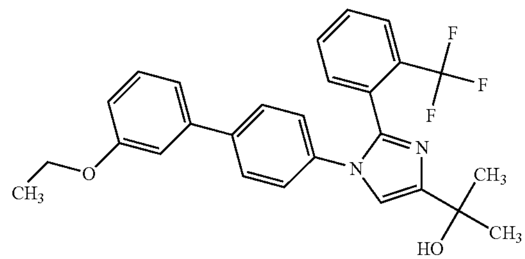 [SMILES: CCOc1cccc(-c2ccc(-n3cc(C(C)(C)O)nc3-c3ccccc3C(F)(F)F)cc2)c1] | 2-{1-[3'-(ethyloxy)biphenyl-4-yl]-2-[2-(trifluoromethyl)phenyl]-1H-imidazol-4-yl}propan-2-ol; |
| 245 | 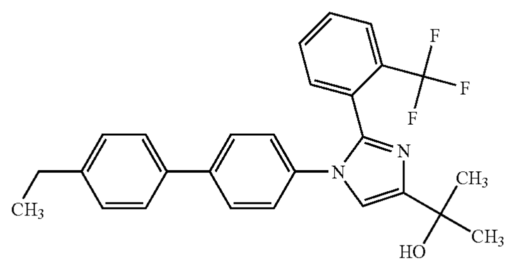 | 2-{1-(4'-ethylbiphenyl-4-yl)-2-[2-(trifluoromethyl)phenyl]-1H-imidazol-4-yl}propan-2-ol; |
| 246 | 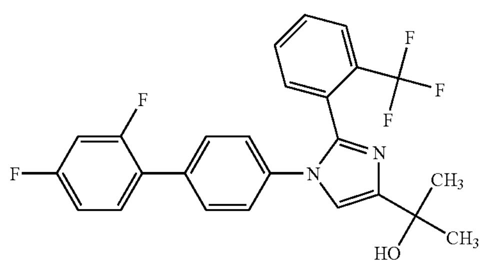 [SMILES: CC(C)(O)c1cn(-c2ccc(-c3ccc(F)cc3F)cc2)c(-c2ccccc2C(F)(F)F)n1] | 2-{1-(2',4'-difluorobiphenyl-4-yl)-2-[2-(trifluoromethyl)phenyl]-1H-imidazol-4-yl}propan-2-ol; |
| 247 | 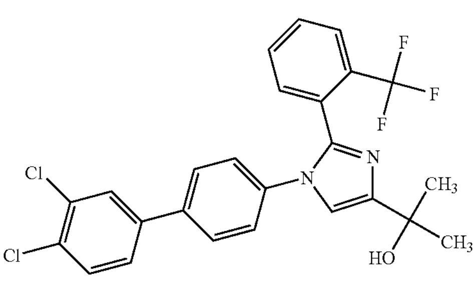 [SMILES: CC(C)(O)c1cn(-c2ccc(-c3ccc(Cl)c(Cl)c3)cc2)c(-c2ccccc2C(F)(F)F)n1] | 2-{1-(3',4'-dichlorobiphenyl-4-yl)-2-[2-(trifluoromethyl)phenyl]-1H-imidazol-4-yl}propan-2-ol; |
| 248 | 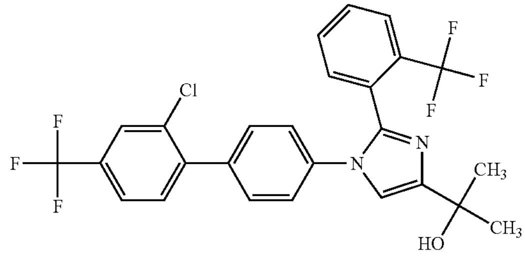 [SMILES: CC(C)(O)c1cn(-c2ccc(-c3ccc(C(F)(F)F)cc3Cl)cc2)c(-c2ccccc2C(F)(F)F)n1] | 2-{1-[2'-chloro-4'-(trifluoromethyl)biphenyl-4-yl]-2-[2-(trifluoromethyl)phenyl]-1H-imidazol-4-yl}propan-2-ol; |

TABLE 1-continued

| Cpd # | Structure | Name |
|---|---|---|
| 249 | 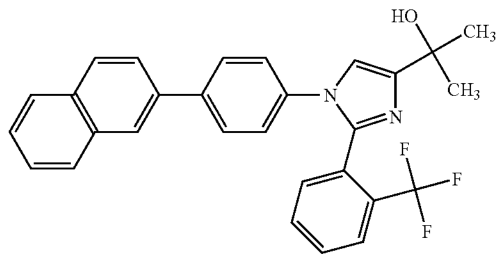 [SMILES: CC(C)(O)c1cn(-c2ccc(-c3ccc4ccccc4c3)cc2)c(-c2ccccc2C(F)(F)F)n1] | 2-{1-(4-naphthalen-2-ylphenyl)-2-[2-(trifluoromethyl)phenyl]-1H-imidazol-4-yl}propan-2-ol; |
| 250 | 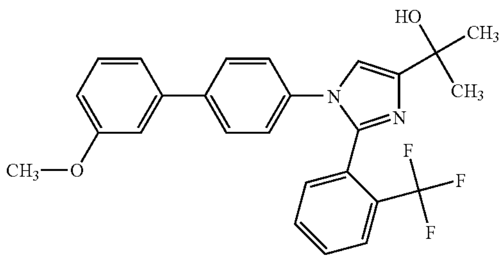 [SMILES: COc1cccc(-c2ccc(-n3cc(C(C)(C)O)nc3-c3ccccc3C(F)(F)F)cc2)c1] | 2-{1-[3'-(methyloxy)biphenyl-4-yl]-2-[2-(trifluoromethyl)phenyl]-1H-imidazol-4-yl}propan-2-ol |
| 251 | 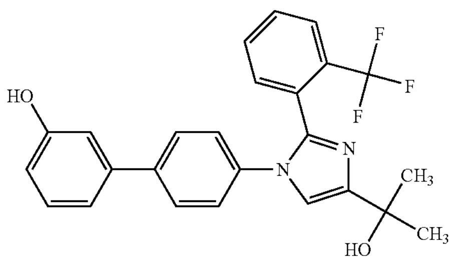 [SMILES: CC(C)(O)c1cn(-c2ccc(-c3cccc(O)c3)cc2)c(-c2ccccc2C(F)(F)F)n1] | 4'-{4-(1-hydroxy-1-methylethyl)-2-[2-(trifluoromethyl)phenyl]-1H-imidazol-1-yl}biphenyl-3-ol; |
| 252 | 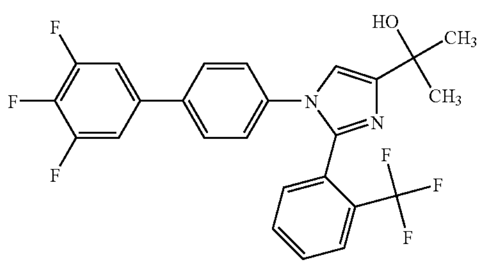 [SMILES: CC(C)(O)c1cn(-c2ccc(-c3cc(F)c(F)c(F)c3)cc2)c(-c2ccccc2C(F)(F)F)n1] | 2-{1-(3',4',5'-trifluorobiphenyl-4-yl)-2-[2-(trifluoromethyl)phenyl]-1H-imidazol-4-yl}propan-2-ol; |
| 253 | 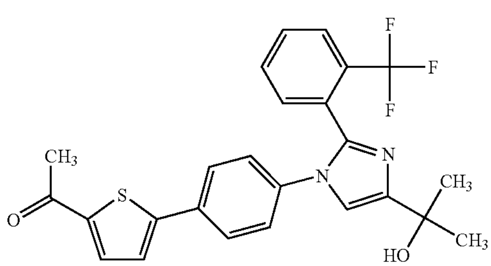 [SMILES: CC(=O)c1ccc(-c2ccc(-n3cc(C(C)(C)O)nc3-c3ccccc3C(F)(F)F)cc2)s1] | 1-[5-(4-{4-(1-hydroxy-1-methylethyl)-2-[2-(trifluoromethyl)phenyl]-1H-imidazol-1-yl}phenyl)-2-thienyl]ethanone; |
| 254 | 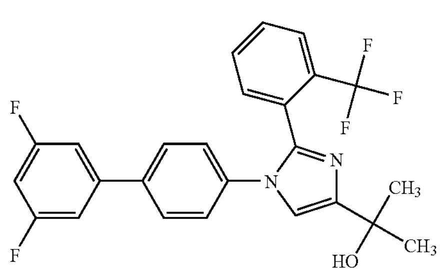 [SMILES: CC(C)(O)c1cn(-c2ccc(-c3cc(F)cc(F)c3)cc2)c(-c2ccccc2C(F)(F)F)n1] | 2-{1-(3',5'-difluorobiphenyl-4-yl)-2-[2-(trifluoromethyl)phenyl]-1H-imidazol-4-yl}propan-2-ol; |

TABLE 1-continued

| Cpd # | Structure | Name |
|---|---|---|
| 255 | 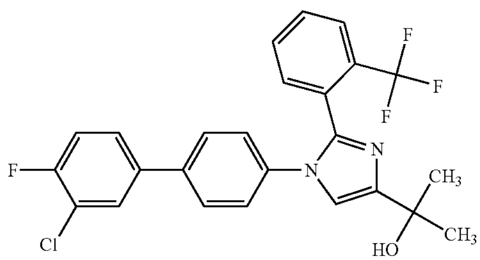 [SMILES: CC(C)(O)c1cn(-c2ccc(-c3ccc(F)c(Cl)c3)cc2)c(-c2ccccc2C(F)(F)F)n1] | 2-{1-(3'-chloro-4'-fluorobiphenyl-4-yl)-2-[2-(trifluoromethyl)phenyl]-1H-imidazol-4-yl}propan-2-ol; |
| 256 | 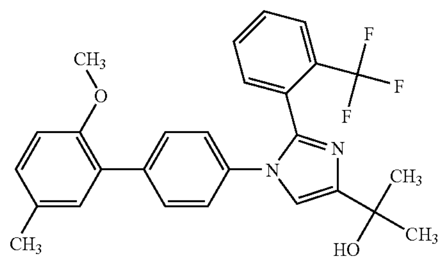 [SMILES: COc1ccc(C)cc1-c1ccc(-n2cc(C(C)(C)O)nc2-c2ccccc2C(F)(F)F)cc1] | 2-{1-[5'-methyl-2'-(methyloxy)biphenyl-4-yl]-2-[2-(trifluoromethyl)phenyl]-1H-imidazol-4-yl}propan-2-ol; |
| 257 | 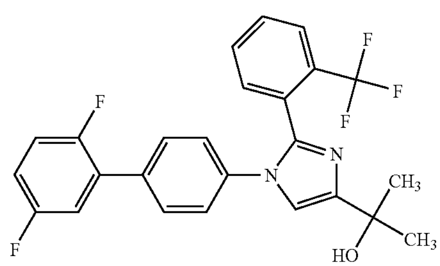 [SMILES: CC(C)(O)c1cn(-c2ccc(-c3cc(F)ccc3F)cc2)c(-c2ccccc2C(F)(F)F)n1] | 2-{1-(2',5'-difluorobiphenyl-4-yl)-2-[2-(trifluoromethyl)phenyl]-1H-imidazol-4-yl}propan-2-ol; |
| 258 | 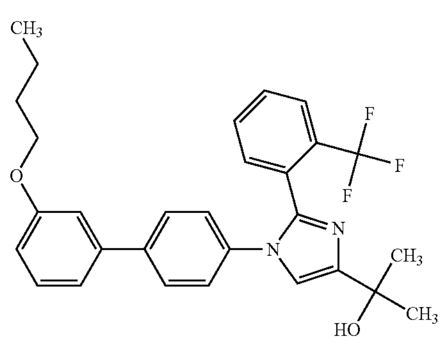 [SMILES: CCCCOc1cccc(-c2ccc(-n3cc(C(C)(C)O)nc3-c3ccccc3C(F)(F)F)cc2)c1] | 2-{1-[3'-(butyloxy)biphenyl-4-yl]-2-[2-(trifluoromethyl)phenyl]-1H-imidazol-4-yl}propan-2-ol; |
| 259 | 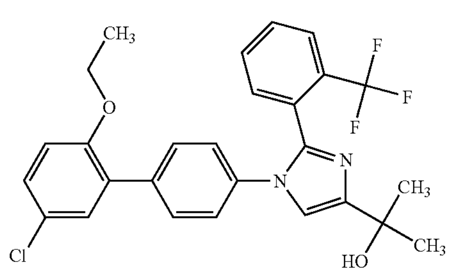 [SMILES: CCOc1ccc(Cl)cc1-c1ccc(-n2cc(C(C)(C)O)nc2-c2ccccc2C(F)(F)F)cc1] | 2-{1-[5'-chloro-2'-(ethyloxy)biphenyl-4-yl]-2-[2-(trifluoromethyl)phenyl]-1H-imidazol-4-yl}propan-2-ol; |

TABLE 1-continued

| Cpd # | Structure | Name |
|---|---|---|
| 260 | 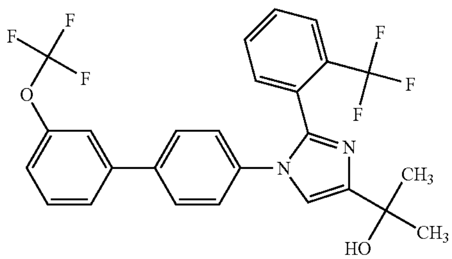 [SMILES: CC(C)(O)c1cn(-c2ccc(-c3cccc(OC(F)(F)F)c3)cc2)c(-c2ccccc2C(F)(F)F)n1] | 2-(1-{3'-[(trifluoromethyl)oxy]biphenyl-4-yl}-2-[2-(trifluoromethyl)phenyl]-1H-imidazol-4-yl)propan-2-ol; |
| 261 | 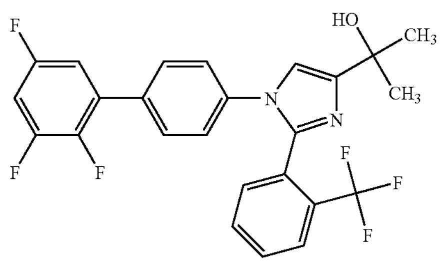 [SMILES: CC(C)(O)c1cn(-c2ccc(-c3cc(F)cc(F)c3F)cc2)c(-c2ccccc2C(F)(F)F)n1] | 2-{1-(2',3',5'-trifluorobiphenyl-4-yl)-2-[2-(trifluoromethyl)phenyl]-1H-imidazol-4-yl}propan-2-ol; |
| 262 | 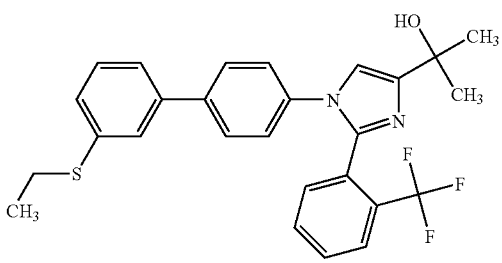 [SMILES: CCSc1cccc(-c2ccc(-n3cc(C(C)(C)O)nc3-c3ccccc3C(F)(F)F)cc2)c1] | 2-{1-[3'-(ethylthio)biphenyl-4-yl]-2-[2-(trifluoromethyl)phenyl]-1H-imidazol-4-yl}propan-2-ol; |
| 263 | 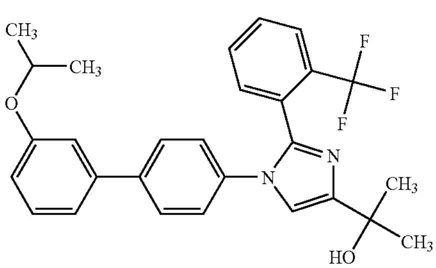 [SMILES: CC(C)Oc1cccc(-c2ccc(-n3cc(C(C)(C)O)nc3-c3ccccc3C(F)(F)F)cc2)c1] | 2-(1-{3'-[(1-methylethyl)oxy]biphenyl-4-yl}-2-[2-(trifluoromethyl)phenyl]-1H-imidazol-4-yl)propan-2-ol; |
| 264 | 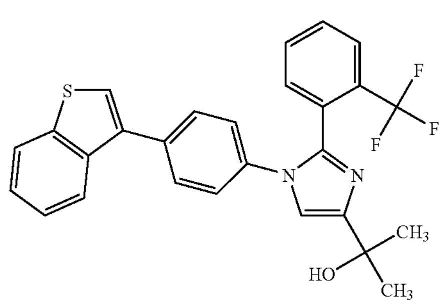 [SMILES: CC(C)(O)c1cn(-c2ccc(-c3csc4ccccc34)cc2)c(-c2ccccc2C(F)(F)F)n1] | 2-{1-[4-(1-benzothien-3-yl)phenyl]-2-[2-(trifluoromethyl)phenyl]-1H-imidazol-4-yl}propan-2-ol; |

TABLE 1-continued

| Cpd # | Structure | Name |
|---|---|---|
| 265 | 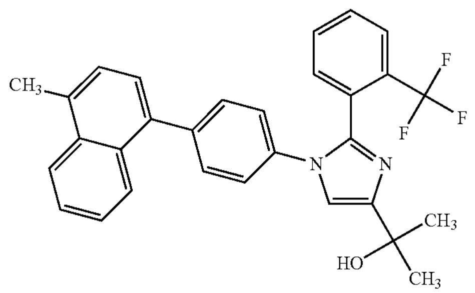 [SMILES: Cc1ccc(-c2ccc(-n3cc(C(C)(C)O)nc3-c3ccccc3C(F)(F)F)cc2)c2ccccc12] | 2-{1-[4-(4-methylnaphthalen-1-yl)phenyl]-2-[2-(trifluoromethyl)phenyl]-1H-imidazol-4-yl}propan-2-ol; |
| 266 | 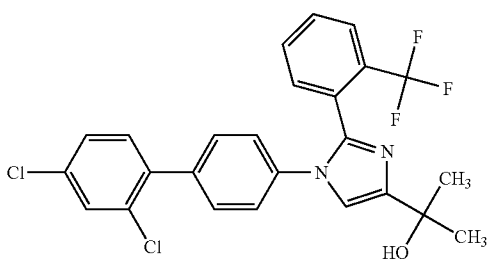 [SMILES: CC(C)(O)c1cn(-c2ccc(-c3ccc(Cl)cc3Cl)cc2)c(-c2ccccc2C(F)(F)F)n1] | 2-{1-(2',4'-dichlorobiphenyl-4-yl)-2-[2-(trifluoromethyl)phenyl]-1H-imidazol-4-yl}propan-2-ol; |
| 267 | 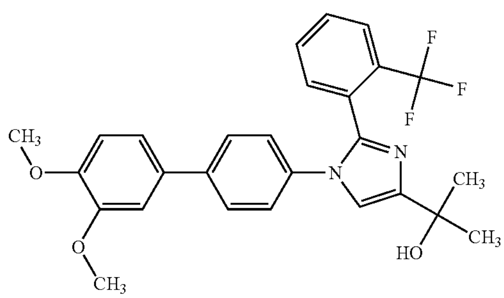 [SMILES: COc1ccc(-c2ccc(-n3cc(C(C)(C)O)nc3-c3ccccc3C(F)(F)F)cc2)cc1OC] | 2-{1-[3',4'-bis(methyloxy)biphenyl-4-yl]-2-[2-(trifluoromethyl)phenyl]-1H-imidazol-4-yl}propan-2-ol; |
| 268 | 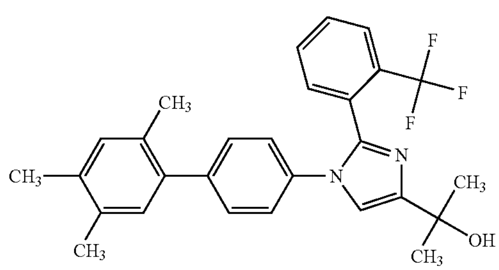 [SMILES: Cc1cc(C)c(-c2ccc(-n3cc(C(C)(C)O)nc3-c3ccccc3C(F)(F)F)cc2)cc1C] | 2-{2-[2-(trifluoromethyl)phenyl]-1-(2',4',5'-trimethylbiphenyl-4-yl)-1H-imidazol-4-yl}propan-2-ol; |
| 269 | 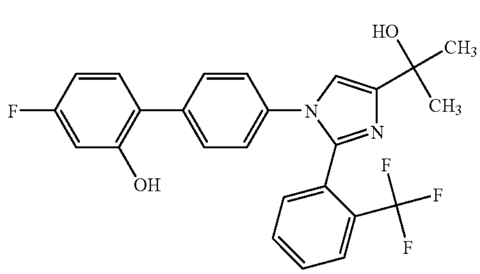 [SMILES: CC(C)(O)c1cn(-c2ccc(-c3ccc(F)cc3O)cc2)c(-c2ccccc2C(F)(F)F)n1] | 4-fluoro-4'-{4-(1-hydroxy-1-methylethyl)-2-[2-(trifluoromethyl)phenyl]-1H-imidazol-1-yl}biphenyl-2-ol; |

TABLE 1-continued

| Cpd # | Structure | Name |
|---|---|---|
| 270 | 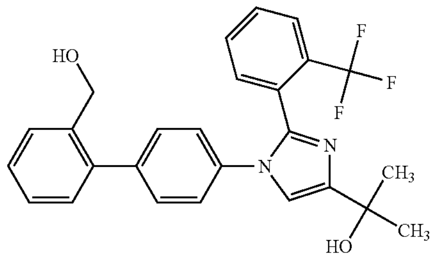 [SMILES: CC(C)(O)c1cn(-c2ccc(-c3ccccc3CO)cc2)c(-c2ccccc2C(F)(F)F)n1] | 2-{1-[2'-(hydroxymethyl)biphenyl-4-yl]-2-[2-(trifluoromethyl)phenyl]-1H-imidazol-4-yl}propan-2-ol; |
| 271 | 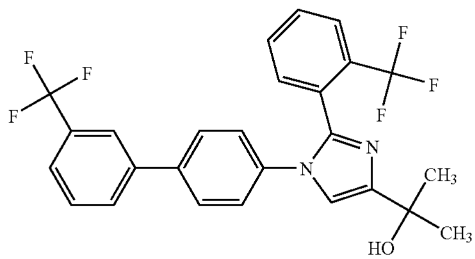 [SMILES: CC(C)(O)c1cn(-c2ccc(-c3cccc(C(F)(F)F)c3)cc2)c(-c2ccccc2C(F)(F)F)n1] | 2-{1-[3'-(trifluoromethyl)biphenyl-4-yl]-2-[2-(trifluoromethyl)phenyl]-1H-imidazol-4-yl}propan-2-ol; |
| 272 | 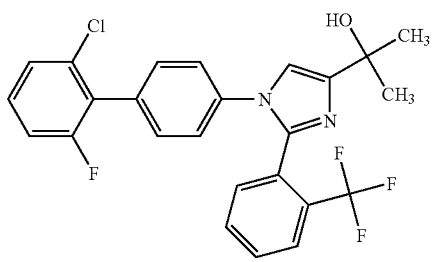 [SMILES: CC(C)(O)c1cn(-c2ccc(-c3c(F)cccc3Cl)cc2)c(-c2ccccc2C(F)(F)F)n1] | 2-{1-(2'-chloro-6'-fluorobiphenyl-4-yl)-2-[2-(trifluoromethyl)phenyl]-1H-imidazol-4-yl}propan-2-ol; |
| 273 | 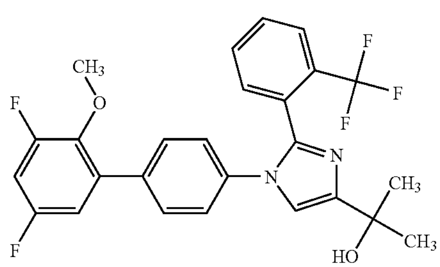 [SMILES: COc1c(F)cc(F)cc1-c1ccc(-n2cc(C(C)(C)O)nc2-c2ccccc2C(F)(F)F)cc1] | 2-{1-[3',5'-difluoro-2'-(methyloxy)biphenyl-4-yl]-2-[2-(trifluoromethyl)phenyl]-1H-imidazol-4-yl}propan-2-ol; |
| 274 | 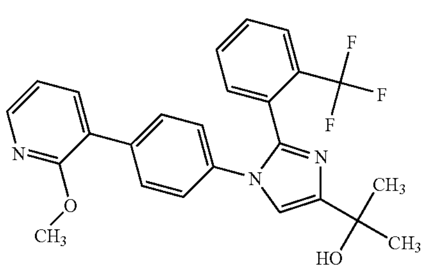 [SMILES: COc1ncccc1-c1ccc(-n2cc(C(C)(C)O)nc2-c2ccccc2C(F)(F)F)cc1] | 2-(1-{4-[2-(methyloxy)pyridin-3-yl]phenyl}-2-[2-(trifluoromethyl)phenyl]-1H-imidazol-4-yl)propan-2-ol; |

TABLE 1-continued

| Cpd # | Structure | Name |
|---|---|---|
| 275 | 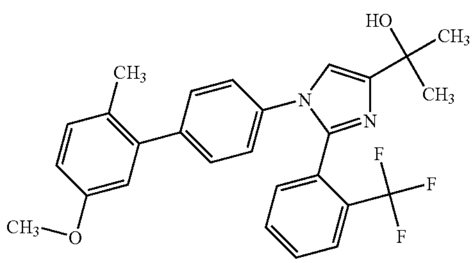 [SMILES: COc1ccc(C)c(-c2ccc(-n3cc(C(C)(C)O)nc3-c3ccccc3C(F)(F)F)cc2)c1] | 2-{1-[2'-methyl-5'-(methyloxy)biphenyl-4-yl]-2-[2-(trifluoromethyl)phenyl]-1H-imidazol-4-yl}propan-2-ol; |
| 276 | 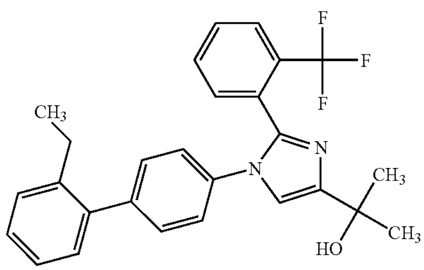 [SMILES: CCc1ccccc1-c1ccc(-n2cc(C(C)(C)O)nc2-c2ccccc2C(F)(F)F)cc1] | 2-{1-(2'-ethylbiphenyl-4-yl)-2-[2-(trifluoromethyl)phenyl]-1H-imidazol-4-yl}propan-2-ol; |
| 277 | 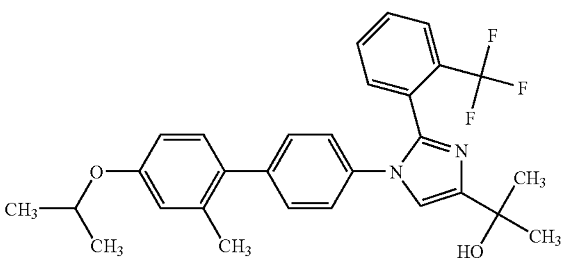 [SMILES: Cc1cc(OC(C)C)ccc1-c1ccc(-n2cc(C(C)(C)O)nc2-c2ccccc2C(F)(F)F)cc1] | 2-(1-{2'-methyl-4'-[(1-methylethyl)oxy]biphenyl-4-yl}-2-[2-(trifluoromethyl)phenyl]-1H-imidazol-4-yl)propan-2-ol; |
| 278 | 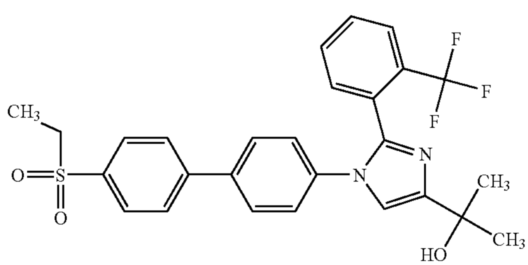 [SMILES: CCS(=O)(=O)c1ccc(-c2ccc(-n3cc(C(C)(C)O)nc3-c3ccccc3C(F)(F)F)cc2)cc1] | 2-{1-[4'-(ethylsulfonyl)biphenyl-4-yl]-2-[2-(trifluoromethyl)phenyl]-1H-imidazol-4-yl}propan-2-ol; |
| 279 | 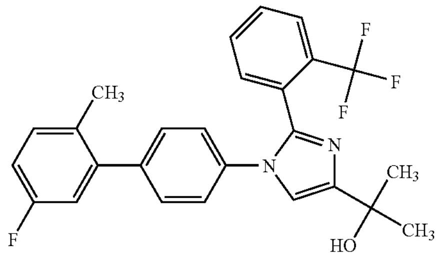 [SMILES: Cc1ccc(F)cc1-c1ccc(-n2cc(C(C)(C)O)nc2-c2ccccc2C(F)(F)F)cc1] | 2-{1-(5'-fluoro-2'-methylbiphenyl-4-yl)-2-[2-(trifluoromethyl)phenyl]-1H-imidazol-4-yl}propan-2-ol; |

TABLE 1-continued

| Cpd # | Structure | Name |
|---|---|---|
| 280 | 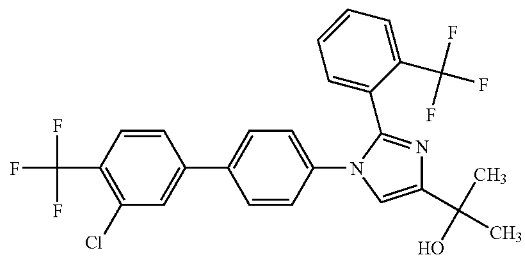 [SMILES: CC(C)(O)c1cn(-c2ccc(-c3ccc(C(F)(F)F)c(Cl)c3)cc2)c(-c2ccccc2C(F)(F)F)n1] | 2-{1-[3'-chloro-4'-(trifluoromethyl)biphenyl-4-yl]-2-[2-(trifluoromethyl)phenyl]-1H-imidazol-4-yl}propan-2-ol; |
| 281 | 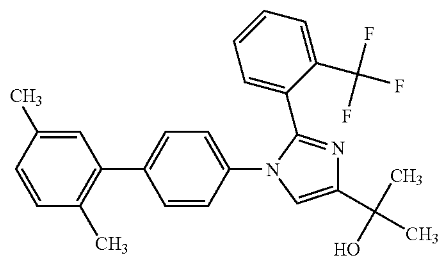 [SMILES: Cc1ccc(C)c(-c2ccc(-n3cc(C(C)(C)O)nc3-c3ccccc3C(F)(F)F)cc2)c1] | 2-{1-(5'-chloro-2'-methylbiphenyl-4-yl)-2-[2-(trifluoromethyl)phenyl]-1H-imidazol-4-yl}propan-2-ol; |
| 282 | 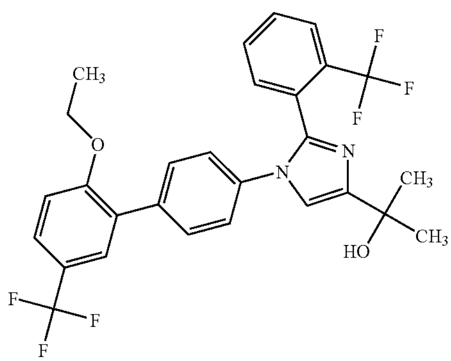 [SMILES: CCOc1ccc(C(F)(F)F)cc1-c1ccc(-n2cc(C(C)(C)O)nc2-c2ccccc2C(F)(F)F)cc1] | 2-{1-[2'-(ethyloxy)-5'-(trifluoromethyl)biphenyl-4-yl]-2-[2-(trifluoromethyl)phenyl]-1H-imidazol-4-yl}propan-2-ol; |
| 283 | 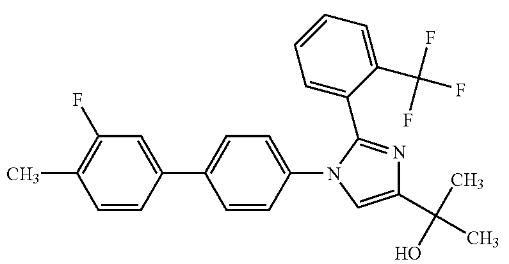 [SMILES: Cc1ccc(-c2ccc(-n3cc(C(C)(C)O)nc3-c3ccccc3C(F)(F)F)cc2)cc1F] | 2-{1-(3'-fluoro-4'-methylbiphenyl-4-yl)-2-[2-(trifluoromethyl)phenyl]-1H-imidazol-4-yl}propan-2-ol; |
| 284 | 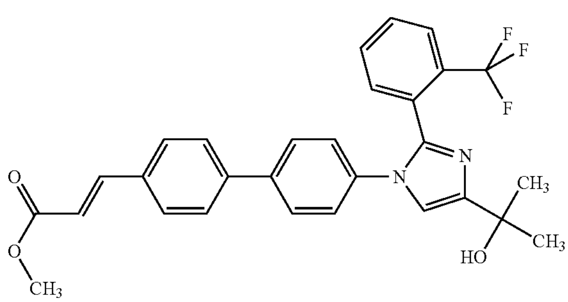 [SMILES: COC(=O)/C=C/c1ccc(-c2ccc(-n3cc(C(C)(C)O)nc3-c3ccccc3C(F)(F)F)cc2)cc1] | methyl (2E)-3-(4'-{4-(1-hydroxy-1-methylethyl)-2-[2-(trifluoromethyl)phenyl]-1H-imidazol-1-yl}biphenyl-4-yl)prop-2-enoate; |

TABLE 1-continued

| Cpd # | Structure | Name |
|---|---|---|
| 285 | 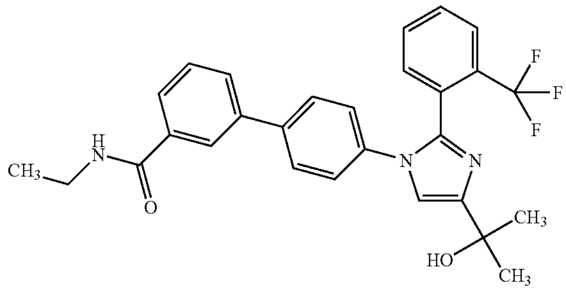 [SMILES: CCNC(=O)c1cccc(-c2ccc(-n3cc(C(C)(C)O)nc3-c3ccccc3C(F)(F)F)cc2)c1] | N-ethyl-4'-{4-(1-hydroxy-1-methylethyl)-2-[2-(trifluoromethyl)phenyl]-1H-imidazol-1-yl}biphenyl-3-carboxamide; |
| 286 | 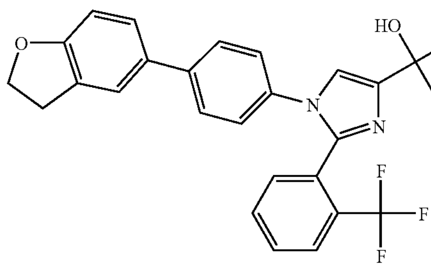 | 2-{1-[4-(2,3-dihydro-1-benzofuran-5-yl)phenyl]-2-[2-(trifluoromethyl)phenyl]-1H-imidazol-4-yl}propan-2-ol; |
| 287 | 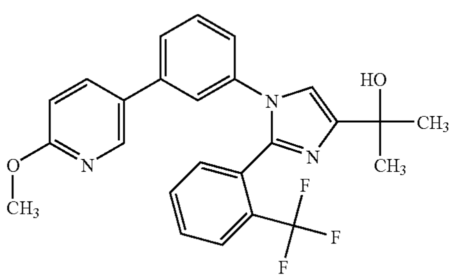 [SMILES: COc1ccc(-c2cccc(-n3cc(C(C)(C)O)nc3-c3ccccc3C(F)(F)F)c2)cn1] | 2-(1-{3-[6-(methyloxy)pyridin-3-yl]phenyl}-2-[2-(trifluoromethyl)phenyl]-1H-imidazol-4-yl)propan-2-ol; |
| 288 | 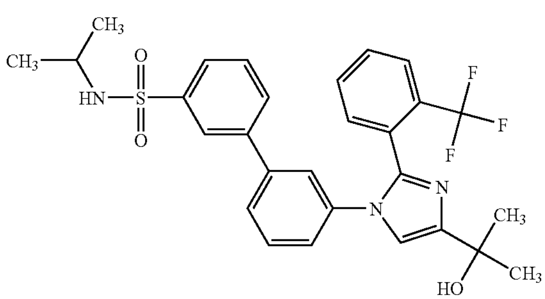 [SMILES: CC(C)NS(=O)(=O)c1cccc(-c2cccc(-n3cc(C(C)(C)O)nc3-c3ccccc3C(F)(F)F)c2)c1] | 3'-{4-(1-hydroxy-1-methylethyl)-2-[2-(trifluoromethyl)phenyl]-1H-imidazol-1-yl}-N-(1-methylethyl)biphenyl-3-sulfonamide; |
| 289 | 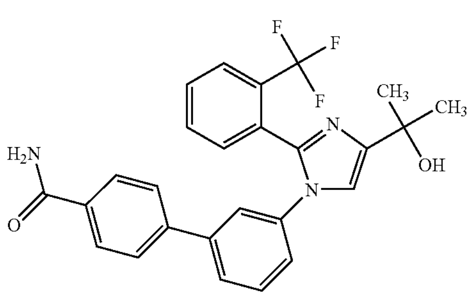 [SMILES: CC(C)(O)c1cn(-c2cccc(-c3ccc(C(N)=O)cc3)c2)c(-c2ccccc2C(F)(F)F)n1] | 3'-{4-(1-hydroxy-1-methylethyl)-2-[2-(trifluoromethyl)phenyl]-1H-imidazol-1-yl}biphenyl-4-carboxamide; |

TABLE 1-continued

| Cpd # | Structure | Name |
|---|---|---|
| 290 | 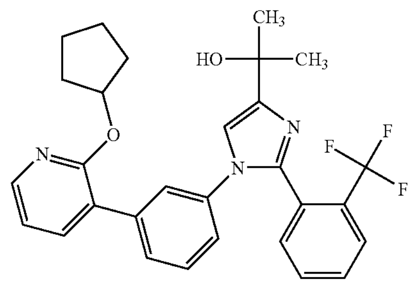 [SMILES: CC(C)(O)c1cn(-c2cccc(-c3cccnc3OC3CCCC3)c2)c(-c2ccccc2C(F)(F)F)n1] | 2-(1-{3-[2-(cyclopentyloxy) pyridin-3-yl]phenyl}-2-[2-(trifluoromethyl)phenyl]-1H-imidazol-4-yl)propan-2-ol; |
| 291 | 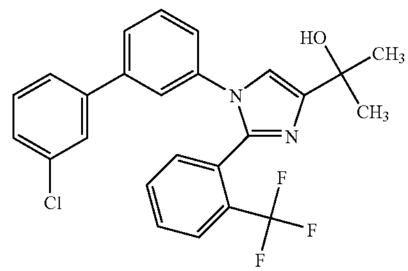 [SMILES: CC(C)(O)c1cn(-c2cccc(-c3cccc(Cl)c3)c2)c(-c2ccccc2C(F)(F)F)n1] | 2-{1-(3'-chlorobiphenyl-3-yl)-2-[2-(trifluoromethyl)phenyl]-1H-imidazol-4-yl}propan-2-ol; |
| 292 | 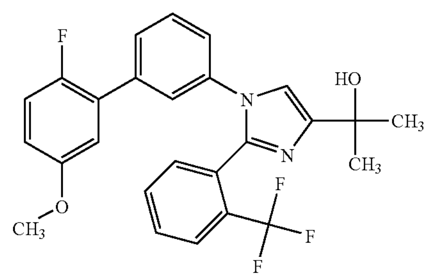 [SMILES: COc1ccc(F)c(-c2cccc(-n3cc(C(C)(C)O)nc3-c3ccccc3C(F)(F)F)c2)c1] | 2-{1-[2'-fluoro-5'-(methyloxy)biphenyl-3-yl]-2-[2-(trifluoromethyl)phenyl]-1H-imidazol-4-yl}propan-2-ol; |
| 293 | 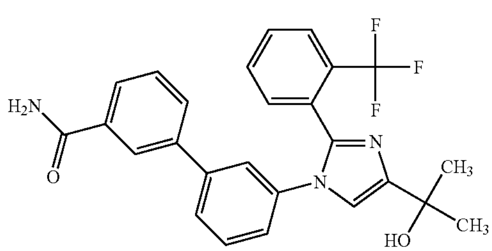 [SMILES: CC(C)(O)c1cn(-c2cccc(-c3cccc(C(N)=O)c3)c2)c(-c2ccccc2C(F)(F)F)n1] | 3'-{4-(1-hydroxy-1-methyethyl)-2-[2-(trifluoromethyl)phenyl]-1H-imidazol-1-yl}biphenyl-3-carboxamide; |
| 294 | 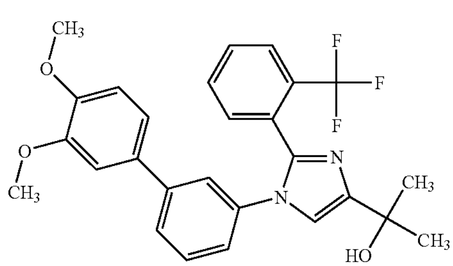 [SMILES: COc1ccc(-c2cccc(-n3cc(C(C)(C)O)nc3-c3ccccc3C(F)(F)F)c2)cc1OC] | 2-{1-[3',4'-bis(methyloxy)biphenyl-3-yl]-2-[2-(trifluoromethyl)phenyl]-1H-imidazol-4-yl}propan-2-ol; |

| Cpd # | Structure | Name |
|---|---|---|
| 295 | 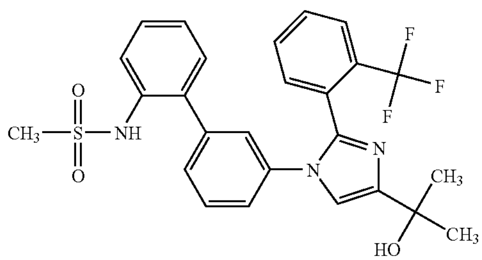 [SMILES: CC(C)(O)c1cn(-c2cccc(-c3ccccc3NS(C)(=O)=O)c2)c(-c2ccccc2C(F)(F)F)n1] | N-(3'-{4-(1-hydroxy-1-methylethyl)-2-[2-(trifluoromethyl)phenyl]-1H-imidazol-1-yl}biphenyl-2-yl)methanesulfonamide; |
| 296 | 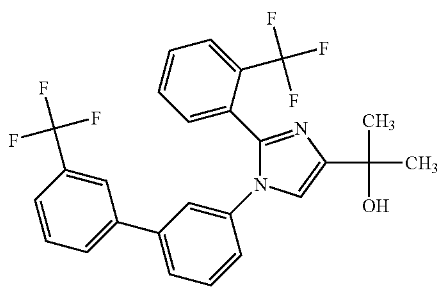 [SMILES: CC(C)(O)c1cn(-c2cccc(-c3cccc(C(F)(F)F)c3)c2)c(-c2ccccc2C(F)(F)F)n1] | 2-{1-[3'-(trifluoromethyl)biphenyl-3-yl]-2-[2-(trifluoromethyl)phenyl]-1H-imidazol-4-yl}propan-2-ol; |
| 297 | 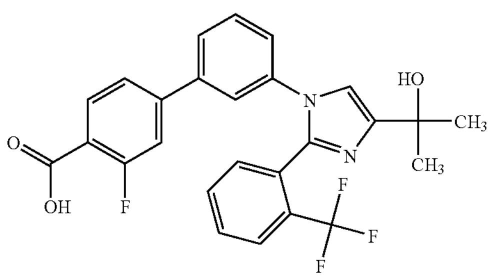 [SMILES: CC(C)(O)c1cn(-c2cccc(-c3ccc(C(=O)O)c(F)c3)c2)c(-c2ccccc2C(F)(F)F)n1] | 3-fluoro-3'-{4-(1-hydroxy-1-methylethyl)-2-[2-(trifluoromethyl)phenyl]-1H-imidazol-1-yl}biphenyl-4-carboxylic acid; |
| 298 | 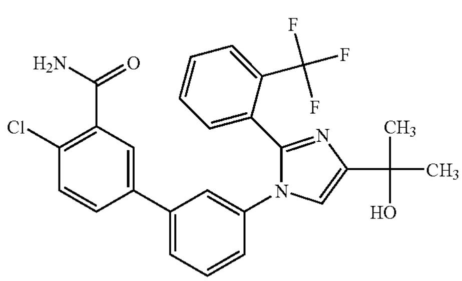 [SMILES: CC(C)(O)c1cn(-c2cccc(-c3ccc(Cl)c(C(N)=O)c3)c2)c(-c2ccccc2C(F)(F)F)n1] | 4-chloro-3'-{4-(1-hydroxy-1-methylethyl)-2-[2-(trifluoromethyl)phenyl]-1H-imidazol-1-yl}biphenyl-3-carboxamide; |
| 299 | 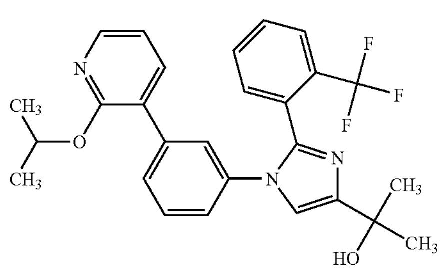 [SMILES: CC(C)Oc1ncccc1-c1cccc(-n2cc(C(C)(C)O)nc2-c2ccccc2C(F)(F)F)c1] | 2-{1-(3-{2-[(1-methylethyl)oxy]pyridin-3-yl}phenyl)-2-[2-(trifluoromethyl)phenyl]-1H-imidazol-4-yl}propan-2-ol; |

TABLE 1-continued

| Cpd # | Structure | Name |
|---|---|---|
| 300 | 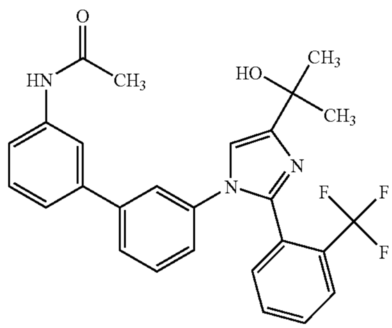 [SMILES: CC(=O)Nc1cccc(-c2cccc(-n3cc(C(C)(C)O)nc3-c3ccccc3C(F)(F)F)c2)c1] | N-(3'-{4-(1-hydroxy-1-methylethyl)-2-[2-(trifluoromethyl)phenyl]-1H-imidazol-1-yl}biphenyl-3-yl)acetamide; |
| 301 | 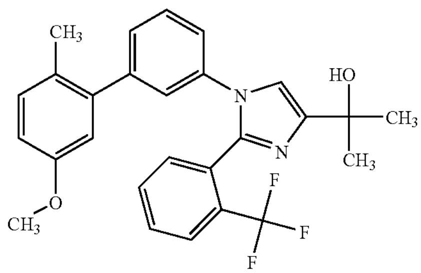 [SMILES: COc1ccc(C)c(-c2cccc(-n3cc(C(C)(C)O)nc3-c3ccccc3C(F)(F)F)c2)c1] | 2-{1-[2'-methyl-5'-(methyloxy)biphenyl-3-yl]-2-[2-(trifluoromethyl)phenyl]-1H-imidazol-4-yl}propan-2-ol; |
| 302 | 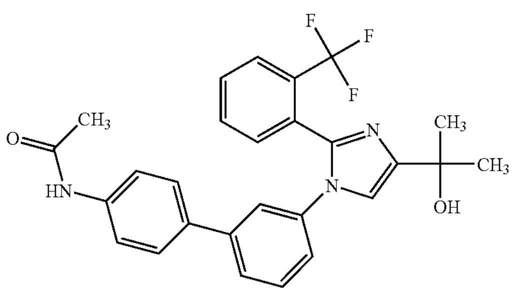 [SMILES: CC(=O)Nc1ccc(-c2cccc(-n3cc(C(C)(C)O)nc3-c3ccccc3C(F)(F)F)c2)cc1] | N-(3'-{4-(1-hydroxy-1-methylethyl)-2-[2-(trifluoromethyl)phenyl]-1H-imidazol-1-yl}biphenyl-4-yl)acetamide; |
| 303 | 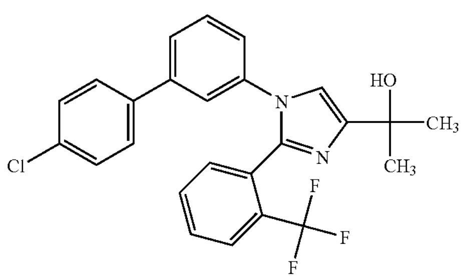 [SMILES: CC(C)(O)c1cn(-c2cccc(-c3ccc(Cl)cc3)c2)c(-c2ccccc2C(F)(F)F)n1] | 2-{1-(4'-chlorobiphenyl-3-yl)-2-[2-(trifluoromethyl)phenyl]-1H-imidazol-4-yl}propan-2-ol; |
| 304 | 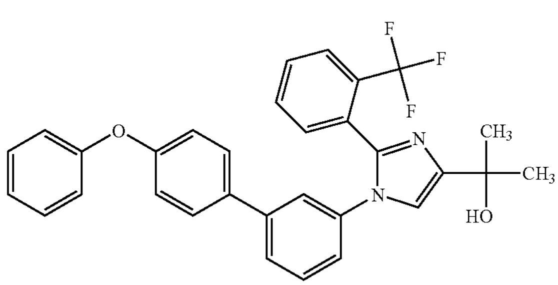 [SMILES: CC(C)(O)c1cn(-c2cccc(-c3ccc(Oc4ccccc4)cc3)c2)c(-c2ccccc2C(F)(F)F)n1] | 2-{1-[4'-(phenyloxy)biphenyl-3-yl]-2-[2-(trifluoromethyl)phenyl]-1H-imidazol-4-yl}propan-2-ol; |

TABLE 1-continued

| Cpd # | Structure | Name |
|---|---|---|
| 305 | 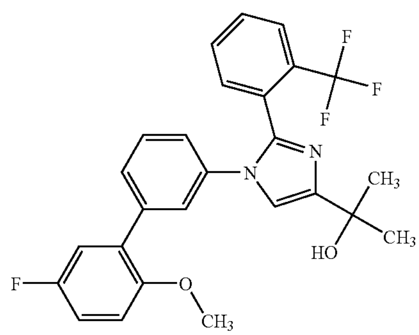 [SMILES: COc1ccc(F)cc1-c1cccc(-n2cc(C(C)(C)O)nc2-c2ccccc2C(F)(F)F)c1] | 2-{1-[5'-fluoro-2'-(methyloxy)biphenyl-3-yl]-2-[2-(trifluoromethyl)phenyl]-1H-imidazol-4-yl}propan-2-ol; |
| 306 | 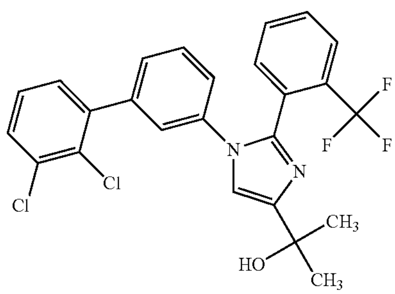 [SMILES: CC(C)(O)c1cn(-c2cccc(-c3cccc(Cl)c3Cl)c2)c(-c2ccccc2C(F)(F)F)n1] | 2-{1-(2',3'-dichlorobiphenyl-3-yl)-2-[2-(trifluoromethyl)phenyl]-1H-imidazol-4-yl}propan-2-ol; |
| 307 | 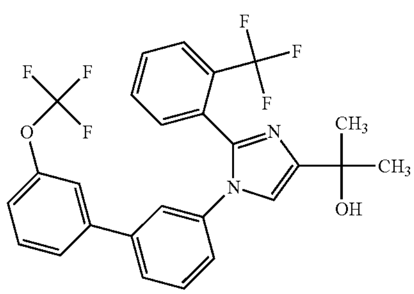 [SMILES: CC(C)(O)c1cn(-c2cccc(-c3cccc(OC(F)(F)F)c3)c2)c(-c2ccccc2C(F)(F)F)n1] | 2-(1-{3'-[(trifluoromethyl)oxy]biphenyl-3-yl}-2-[2-(trifluoromethyl)phenyl]-1H-imidazol-4-yl)propan-2-ol; |
| 308 | 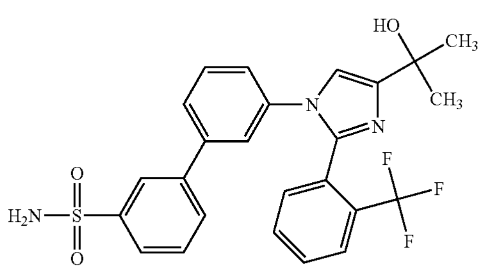 [SMILES: CC(C)(O)c1cn(-c2cccc(-c3cccc(S(N)(=O)=O)c3)c2)c(-c2ccccc2C(F)(F)F)n1] | 3'-{4-(1-hydroxy-1-methylethyl)-2-[2-(trifluoromethyl)phenyl]-1H-imidazol-1-yl}biphenyl-3-sulfonamide; |
| 309 | 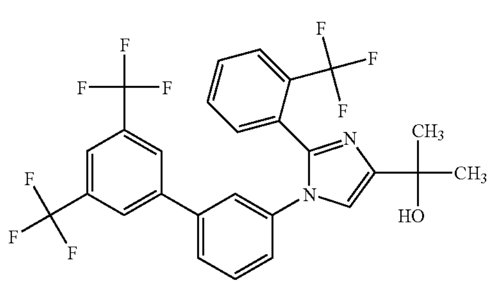 [SMILES: CC(C)(O)c1cn(-c2cccc(-c3cc(C(F)(F)F)cc(C(F)(F)F)c3)c2)c(-c2ccccc2C(F)(F)F)n1] | 2-{1-[3',5'-bis(trifluoromethyl)biphenyl-3-yl]-2-[2-(trifluoromethyl)phenyl]-1H-imidazol-4-yl}propan-2-ol; |

TABLE 1-continued

| Cpd # | Structure | Name |
|---|---|---|
| 310 | 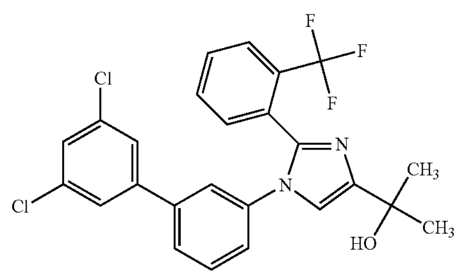 [SMILES: CC(C)(O)c1cn(-c2cccc(-c3cc(Cl)cc(Cl)c3)c2)c(-c2ccccc2C(F)(F)F)n1] | 2-{1-(3',5'-dichlorobiphenyl-3-yl)-2-[2-(trifluoromethyl)phenyl]-1H-imidazol-4-yl}propan-2-ol; |
| 311 | 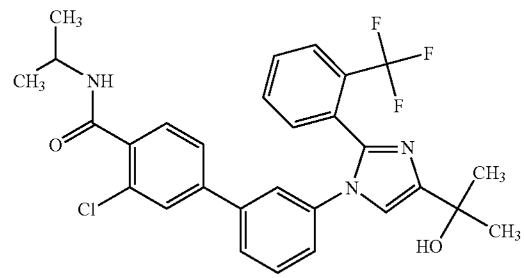 [SMILES: CC(C)NC(=O)c1ccc(-c2cccc(-n3cc(C(C)(C)O)nc3-c3ccccc3C(F)(F)F)c2)cc1Cl] | 3-chloro-3'-{4-(1-hydroxy-1-methylethyl)-2-[2-(trifluoromethyl)phenyl]-1H-imidazol-1-yl}-N-(1-methylethyl)biphenyl-4-carboxamide; |
| 312 | 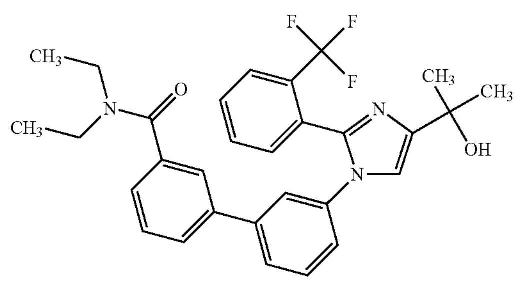 [SMILES: CCN(CC)C(=O)c1cccc(-c2cccc(-n3cc(C(C)(C)O)nc3-c3ccccc3C(F)(F)F)c2)c1] | N,N-diethyl-3'-{4-(1-hydroxy-1-methylethyl)-2-[2-(trifluoromethyl)phenyl]-1H-imidazol-1-yl}biphenyl-3-carboxamide; |
| 313 | 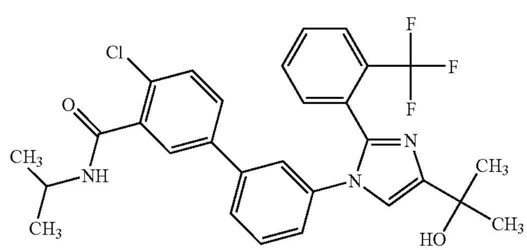 [SMILES: CC(C)NC(=O)c1cc(-c2cccc(-n3cc(C(C)(C)O)nc3-c3ccccc3C(F)(F)F)c2)ccc1Cl] | 4-chloro-3'-{4-(1-hydroxy-1-methylethyl)-2-[2-(trifluoromethyl)phenyl]-1H-imidazol-1-yl}-N-(1-methyethyl)biphenyl-3-carboxamide; |
| 314 | 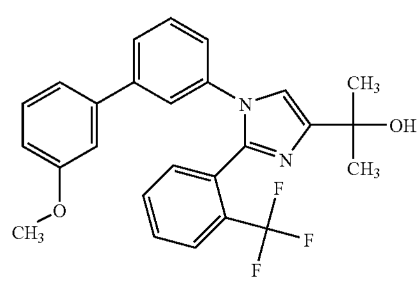 [SMILES: COc1cccc(-c2cccc(-n3cc(C(C)(C)O)nc3-c3ccccc3C(F)(F)F)c2)c1] | 2-{1-[3'-(methyloxy)biphenyl-3-yl]-2-[2-(trifluoromethyl)phenyl]-1H-imidazol-4-yl}propan-2-ol; |

TABLE 1-continued

| Cpd # | Structure | Name |
|---|---|---|
| 315 | 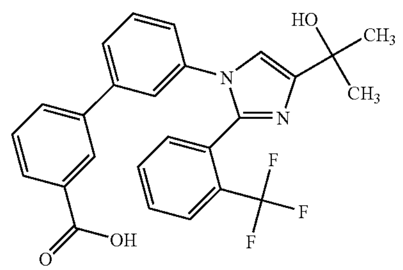 [SMILES: CC(C)(O)c1cn(-c2cccc(-c3cccc(C(=O)O)c3)c2)c(-c2ccccc2C(F)(F)F)n1] | 3'-{4-(1-hydroxy-1-methylethyl)-2-[2-(trifluoromethyl)phenyl]-1H-imidazol-1-yl}biphenyl-3-carboxylic acid; |
| 316 | 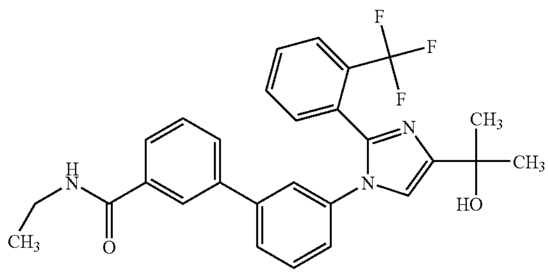 [SMILES: CCNC(=O)c1cccc(-c2cccc(-n3cc(C(C)(C)O)nc3-c3ccccc3C(F)(F)F)c2)c1] | N-ethyl-3'-{4-(1-hydroxy-1-methylethyl)-2-[2-(trifluoromethyl)phenyl]-1H-imidazol-1-yl}biphenyl-3-carboxamide; |
| 317 | 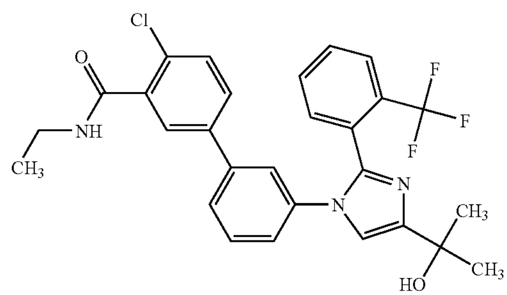 [SMILES: CCNC(=O)c1cc(-c2cccc(-n3cc(C(C)(C)O)nc3-c3ccccc3C(F)(F)F)c2)ccc1Cl] | 4-chloro-N-ethyl-3'-{4-(1-hydroxy-1-methylethyl)-2-[2-(trifluoromethyl)phenyl]-1H-imidazol-1-yl}biphenyl-3-carboxamide; |
| 318 | 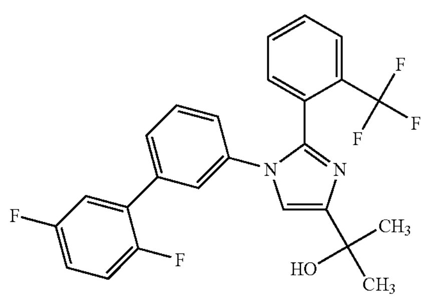 [SMILES: CC(C)(O)c1cn(-c2cccc(-c3cc(F)ccc3F)c2)c(-c2ccccc2C(F)(F)F)n1] | 2-{1-(2',5'-difluorobiphenyl-3-yl)-2-[2-(trifluoromethyl)phenyl]-1H-imidazol-4-yl}propan-2-ol; |
| 319 | 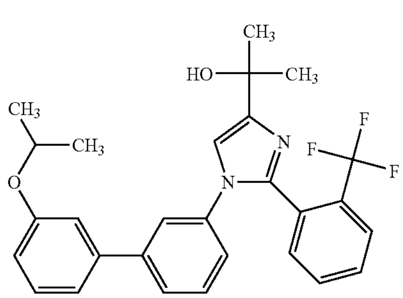 [SMILES: CC(C)Oc1cccc(-c2cccc(-n3cc(C(C)(C)O)nc3-c3ccccc3C(F)(F)F)c2)c1] | 2-(1-{3'-[(1-methylethyl)oxy]biphenyl-3-yl}-2-[2-(trifluoromethyl)phenyl]-1H-imidazol-4-yl)propan-2-ol; |

TABLE 1-continued

| Cpd # | Structure | Name |
|---|---|---|
| 320 | 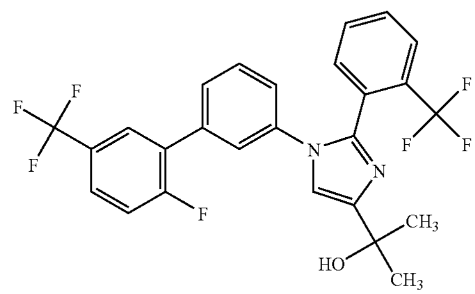 [SMILES: CC(C)(O)c1cn(-c2cccc(-c3cc(C(F)(F)F)ccc3F)c2)c(-c2ccccc2C(F)(F)F)n1] | 2-{1-[2'-fluoro-5'-(trifluoromethyl)biphenyl-3-yl]-2-[2-(trifluoromethyl)phenyl]-1H-imidazol-4-yl}propan-2-ol; |
| 321 | 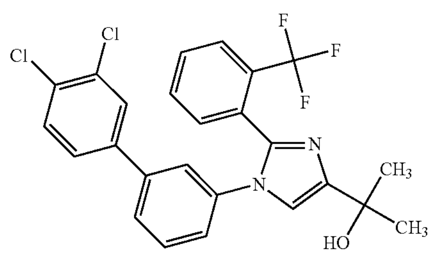 [SMILES: CC(C)(O)c1cn(-c2cccc(-c3ccc(Cl)c(Cl)c3)c2)c(-c2ccccc2C(F)(F)F)n1] | 2-{1-(3',4'-dichlorobiphenyl-3-yl)-2-[2-(trifluoromethyl)phenyl]-1H-imidazol-4-yl}propan-2-ol; |
| 322 | 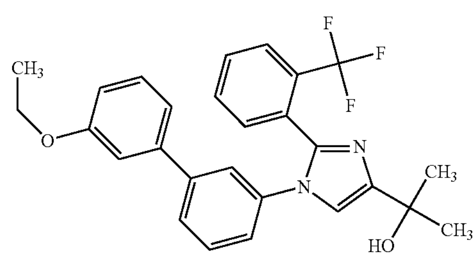 [SMILES: CCOc1cccc(-c2cccc(-n3cc(C(C)(C)O)nc3-c3ccccc3C(F)(F)F)c2)c1] | 2-{1-[3'-(ethyloxy)biphenyl-3-yl]-2-[2-(trifluoromethyl)phenyl]-1H-imidazol-4-yl}propan-2-ol; |
| 323 | 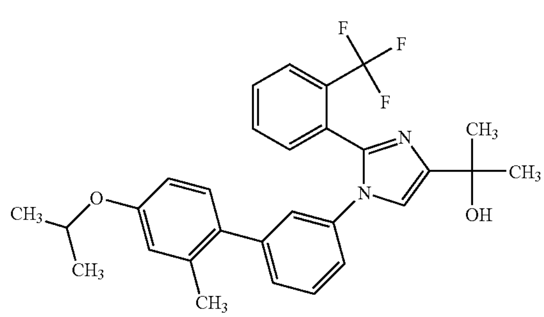 [SMILES: Cc1cc(OC(C)C)ccc1-c1cccc(-n2cc(C(C)(C)O)nc2-c2ccccc2C(F)(F)F)c1] | 2-(1-{2'-methyl-4'-[(1-methylethyl)oxy]biphenyl-3-yl}-2-[2-(trifluoromethyl)phenyl]-1H-imidazol-4-yl)propan-2-ol; |
| 324 | 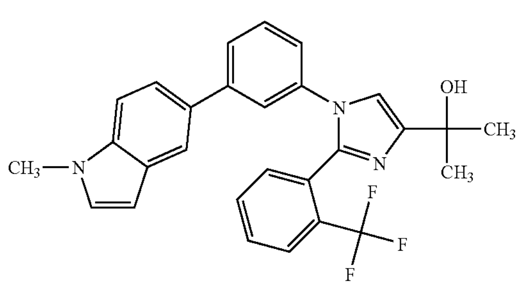 [SMILES: Cn1ccc2cc(-c3cccc(-n4cc(C(C)(C)O)nc4-c4ccccc4C(F)(F)F)c3)ccc21] | 2-{1-[3-(1-methyl-1H-indol-5-yl)phenyl]-2-[2-(trifluoromethyl)phenyl]-1H-imidazol-4-yl}propan-2-ol; |

TABLE 1-continued

| Cpd # | Structure | Name |
|---|---|---|
| 325 | 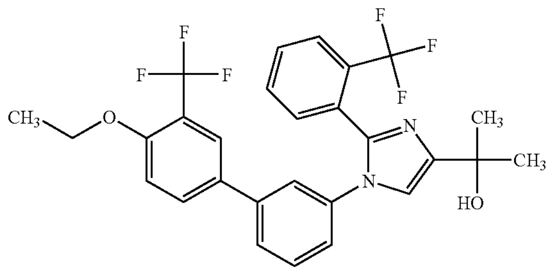 [SMILES: CCOc1ccc(-c2cccc(-n3cc(C(C)(C)O)nc3-c3ccccc3C(F)(F)F)c2)cc1C(F)(F)F] | 2-{1-[4'-(ethyloxy)-3'-(trifluoromethyl)biphenyl-3-yl]-2-[2-(trifluoromethyl)phenyl]-1H-imidazol-4-yl}propan-2-ol; |
| 326 | 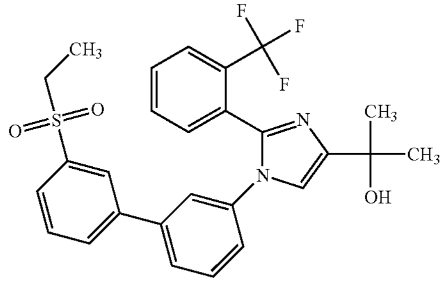 [SMILES: CCS(=O)(=O)c1cccc(-c2cccc(-n3cc(C(C)(C)O)nc3-c3ccccc3C(F)(F)F)c2)c1] | 2-{1-[3'-(ethylsulfonyl)biphenyl-3-yl]-2-[2-(trifluoromethyl)phenyl]-1H-imidazol-4-yl}propan-2-ol; |
| 327 | 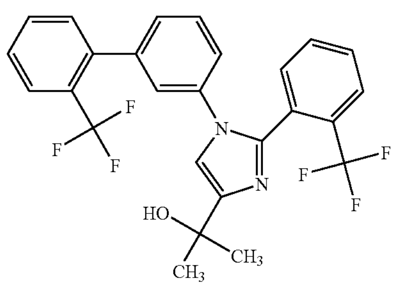 [SMILES: CC(C)(O)c1cn(-c2cccc(-c3ccccc3C(F)(F)F)c2)c(-c2ccccc2C(F)(F)F)n1] | 2-{1-[2'-(trifluoromethyl)biphenyl-3-yl]-2-[2-(trifluoromethyl)phenyl]-1H-imidazol-4-yl}propan-2-ol; |
| 328 | 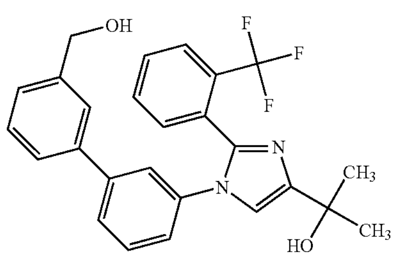 [SMILES: CC(C)(O)c1cn(-c2cccc(-c3cccc(CO)c3)c2)c(-c2ccccc2C(F)(F)F)n1] | 2-{1-[3'-(hydroxymethyl)biphenyl-3-yl]-2-[2-(trifluoromethyl)phenyl]-1H-imidazol-4-yl}propan-2-ol; |
| 329 | 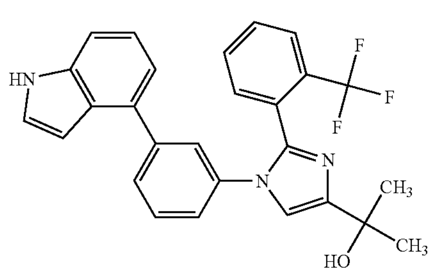 [SMILES: CC(C)(O)c1cn(-c2cccc(-c3cccc4[nH]ccc34)c2)c(-c2ccccc2C(F)(F)F)n1] | 2-{1-[3-(1H-indol-4-yl)phenyl]-2-[2-(trifluoromethyl)phenyl]-1H-imidazol-4-yl}propan-2-ol; |

TABLE 1-continued

| Cpd # | Structure | Name |
|---|---|---|
| 330 | 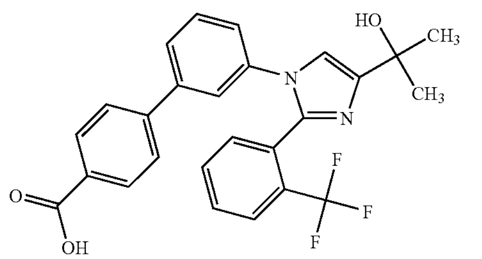 [SMILES: CC(C)(O)c1cn(-c2cccc(-c3ccc(C(=O)O)cc3)c2)c(-c2ccccc2C(F)(F)F)n1] | 3'-{4-(1-hydoxy-1-methylethyl)-2-[2-(trifluoromethyl)phenyl]-1H-imidazol-1-yl}biphenyl-4-carboxylic acid; |
| 331 | 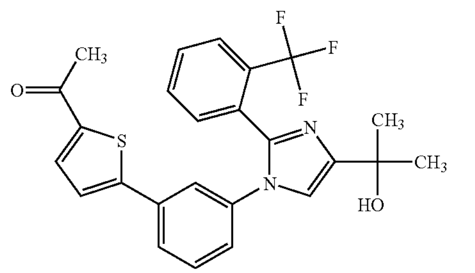 [SMILES: CC(=O)c1ccc(-c2cccc(-n3cc(C(C)(C)O)nc3-c3ccccc3C(F)(F)F)c2)s1] | 1-[5-(3-{4-(1-hydroxy-1-methylethyl)-2-[2-(trifluoromethyl)phenyl]-1H-imidazol-1-yl}phenyl)-2-thienyl]ethanone; |
| 332 | 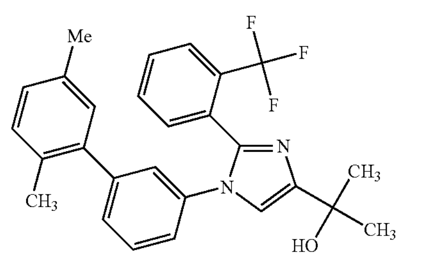 [SMILES: Cc1ccc(C)c(-c2cccc(-n3cc(C(C)(C)O)nc3-c3ccccc3C(F)(F)F)c2)c1] | 2-{1-(5'-chloro-2'-methylbiphenyl-3-yl)-2-[2-(trifluoromethyl)phenyl]-1H-imidazol-4-yl}propan-2-ol; |
| 333 | 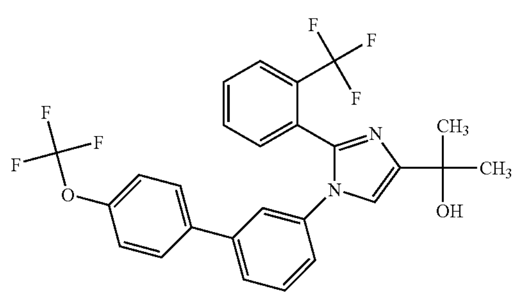 [SMILES: CC(C)(O)c1cn(-c2cccc(-c3ccc(OC(F)(F)F)cc3)c2)c(-c2ccccc2C(F)(F)F)n1] | 2-(1-{4'-[(trifluoromethyl)oxy]biphenyl-3-yl}-2-[2-(trifluoromethyl)phenyl]-1H-imidazol-4-yl)propan-2-ol; |
| 334 | 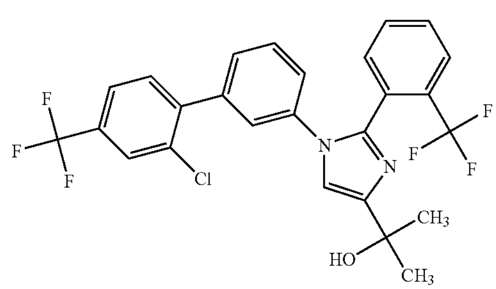 [SMILES: CC(C)(O)c1cn(-c2cccc(-c3ccc(C(F)(F)F)cc3Cl)c2)c(-c2ccccc2C(F)(F)F)n1] | 2-{1-[2'-chloro-4'-(trifluoromethyl)biphenyl-3-yl]-2-[2-(trifluoromethyl)phenyl]-1H-imidazol-4-yl}propan-2-ol; |

TABLE 1-continued

| Cpd # | Structure | Name |
|---|---|---|
| 335 | 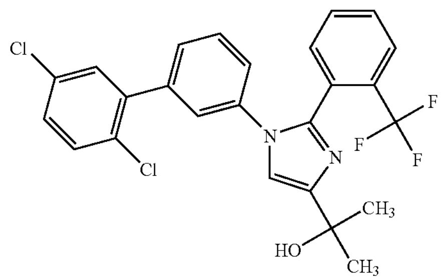 [SMILES: CC(C)(O)c1cn(-c2cccc(-c3cc(Cl)ccc3Cl)c2)c(-c2ccccc2C(F)(F)F)n1] | 2-{1-(2',5'-dichlorobiphenyl-3-yl)-2-[2-(trifluoromethyl)phenyl]-1H-imidazol-4-yl}propan-2-ol; |
| 336 | 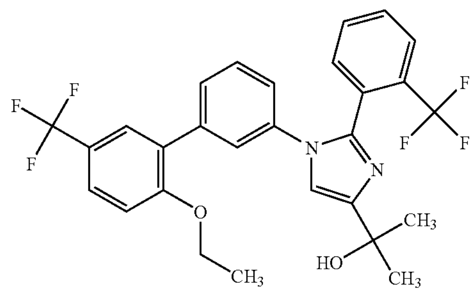 [SMILES: CCOc1ccc(C(F)(F)F)cc1-c1cccc(-n2cc(C(C)(C)O)nc2-c2ccccc2C(F)(F)F)c1] | 2-{1-[2'-(ethyloxy)-5'-(trifluoromethyl)biphenyl-3-yl]-2-[2-(trifluoromethyl)phenyl]-1H-imidazol-4-yl}propan-2-ol; |
| 337 | 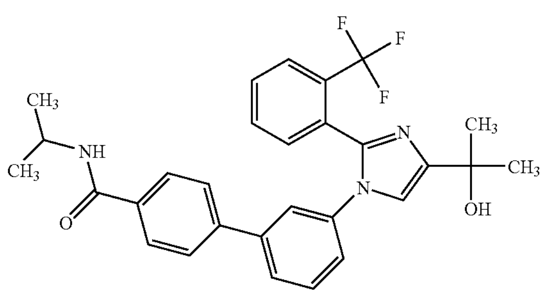 [SMILES: CC(C)NC(=O)c1ccc(-c2cccc(-n3cc(C(C)(C)O)nc3-c3ccccc3C(F)(F)F)c2)cc1] | 3'-{4-(1-hydroxy-1-methylethyl)-2-[2-(trifluoromethyl)phenyl]-1H-imidazol-1-yl}-N-(1-methylethyl)biphenyl-4-carboxamide; |
| 338 | 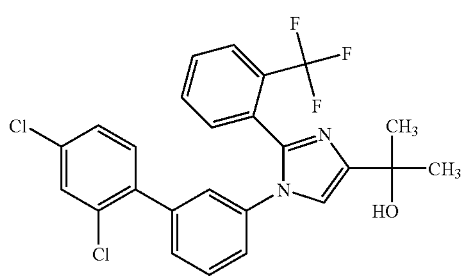 [SMILES: CC(C)(O)c1cn(-c2cccc(-c3ccc(Cl)cc3Cl)c2)c(-c2ccccc2C(F)(F)F)n1] | 2-{1-(2',4'-dichlorobiphenyl-3-yl)-2-[2-(trifluoromethyl)phenyl]-1H-imidazol-4-yl}propan-2-ol; |
| 339 | 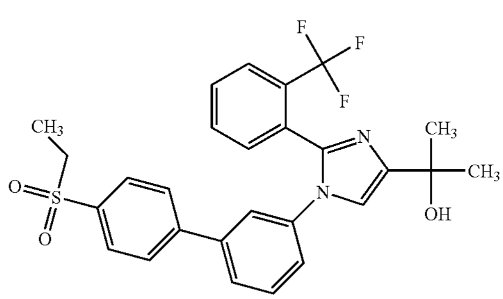 [SMILES: CCS(=O)(=O)c1ccc(-c2cccc(-n3cc(C(C)(C)O)nc3-c3ccccc3C(F)(F)F)c2)cc1] | 2-{1-[4'-(ethylsulfonyl)biphenyl-3-yl]-2-[2-(trifluoromethyl)phenyl]-1H-imidazol-4-yl}propan-2-ol; |

TABLE 1-continued

| Cpd # | Structure | Name |
|---|---|---|
| 340 | 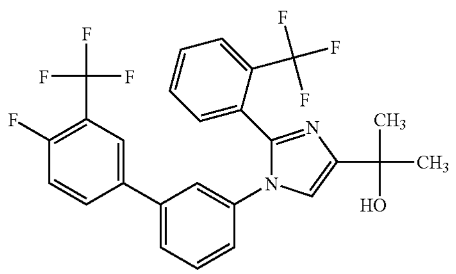 [SMILES: CC(C)(O)c1cn(-c2cccc(-c3ccc(F)c(C(F)(F)F)c3)c2)c(-c2ccccc2C(F)(F)F)n1] | 2-{1-[4'-fluoro-3'-(trifluoromethyl)biphenyl-3-yl]-2-[2-(trifluoromethyl)phenyl]-1H-imidazol-4-yl}propan-2-ol; |
| 341 | 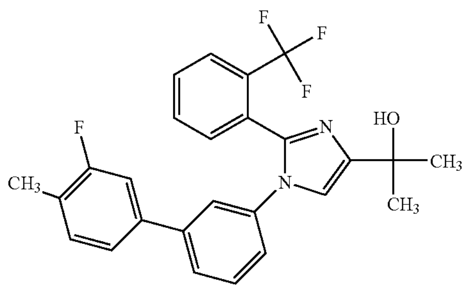 [SMILES: Cc1ccc(-c2cccc(-n3cc(C(C)(C)O)nc3-c3ccccc3C(F)(F)F)c2)cc1F] | 2-{1-(3'-fluoro-4'-methylbiphenyl-3-yl)-2-[2-(trifluoromethyl)phenyl]-1H-imidazol-4-yl}propan-2-ol; |
| 342 | 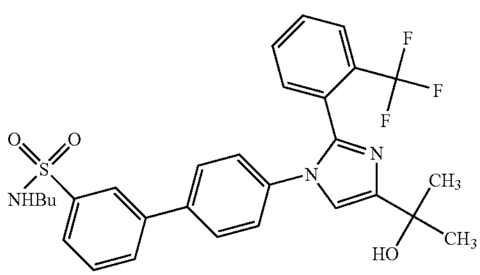 | N-butyl-4'-{4-(1-hydroxy-1-methylethyl)-2-[2-(trifluoromethyl)phenyl]-1H-imidazol-1-yl}biphenyl-3-sulfonamide; |
| 343 | 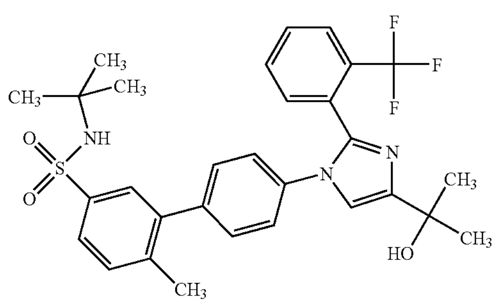 [SMILES: Cc1ccc(S(=O)(=O)NC(C)(C)C)cc1-c1ccc(-n2cc(C(C)(C)O)nc2-c2ccccc2C(F)(F)F)cc1] | N-(1,1-dimethylethyl)-4'-{4-(1-hydroxy-1-methylethyl)-2-[2-(trifluoromethyl)phenyl]-1H-imidazol-1-yl}-6-methylbiphenyl-3-sulfonamide; |
| 344 | 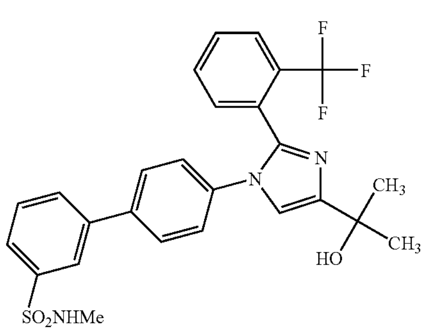 | 4'-{4-(1-hydroxy-1-methylethyl)-2-[2-(trifluoromethyl)phenyl]-1H-imidazol-1-yl}-N-methylbiphenyl-3-sulfonamide; |

TABLE 1-continued

| Cpd # | Structure | Name |
|---|---|---|
| 345 | 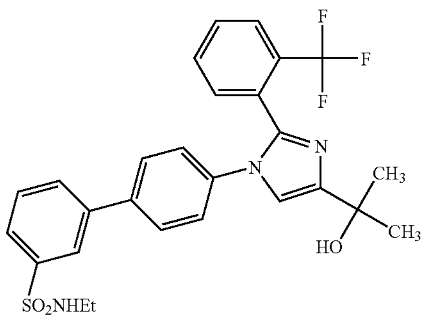 | N-ethyl-4'-{4-(1-hydroxy-1-methylethyl)-2-[2-(trifluoromethyl)phenyl]-1H-imidazol-1-yl}biphenyl-3-sulfonamide; |
| 346 | 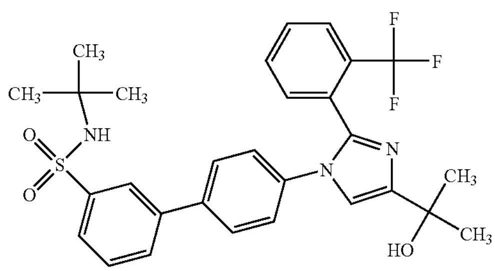 [SMILES: CC(C)(C)NS(=O)(=O)c1cccc(-c2ccc(-n3cc(C(C)(C)O)nc3-c3ccccc3C(F)(F)F)cc2)c1] | N-(1,1-dimethylethyl)-4'-{4-(1-hydroxy-1-methylethyl)-2-[2-(trifluoromethyl)phenyl]-1H-imidazol-1-yl}biphenyl-3-sulfonamide; |
| 347 | 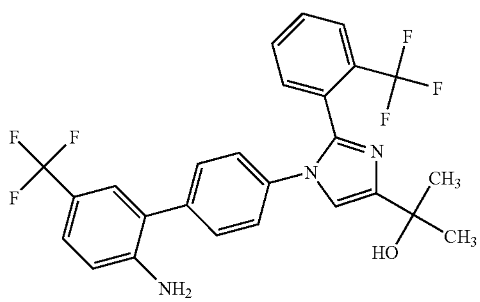 [SMILES: CC(C)(O)c1cn(-c2ccc(-c3cc(C(F)(F)F)ccc3N)cc2)c(-c2ccccc2C(F)(F)F)n1] | 2-{1-[2'-amino-5'-(trifluoromethyl)biphenyl-4-yl]-2-[2-(trifluoromethyl)phenyl]-1H-imidazol-4-yl}propan-2-ol; |
| 348 | 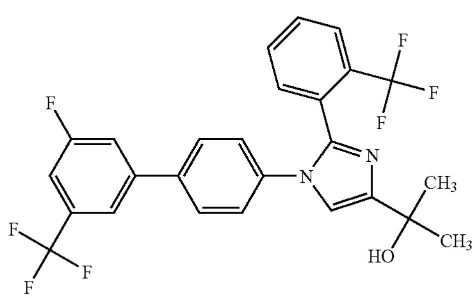 [SMILES: CC(C)(O)c1cn(-c2ccc(-c3cc(F)cc(C(F)(F)F)c3)cc2)c(-c2ccccc2C(F)(F)F)n1] | 2-{1-[3'-fluoro-5'-(trifluoromethyl)biphenyl-4-yl]-2-[2-(trifluoromethyl)phenyl]-1H-imidazol-4-yl}propan-2-ol; |
| 349 | 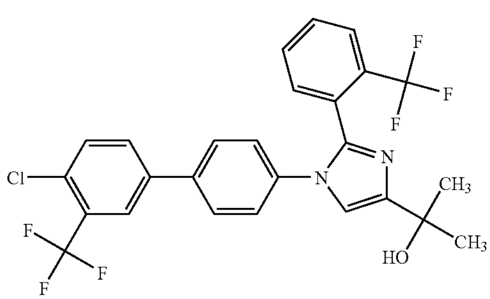 [SMILES: CC(C)(O)c1cn(-c2ccc(-c3ccc(Cl)c(C(F)(F)F)c3)cc2)c(-c2ccccc2C(F)(F)F)n1] | 2-{1-[4'-chloro-3'-(trifluoromethyl)biphenyl-3-yl]-2-[2-(trifluoromethyl)phenyl]-1H-imidazol-4-yl}propan-2-ol; |

TABLE 1-continued

| Cpd # | Structure | Name |
|---|---|---|
| 350 | 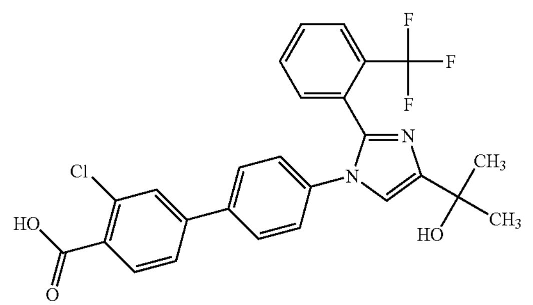 [SMILES: CC(C)(O)c1cn(-c2ccc(-c3ccc(C(=O)O)c(Cl)c3)cc2)c(-c2ccccc2C(F)(F)F)n1] | 3-chloro-4'-{4-(1-hydroxy-1-methylethyl)-2-[2-(trifluoromethyl)phenyl]-1H-imidazol-1-yl}biphenyl-4-carboxylic acid; |
| 351 | 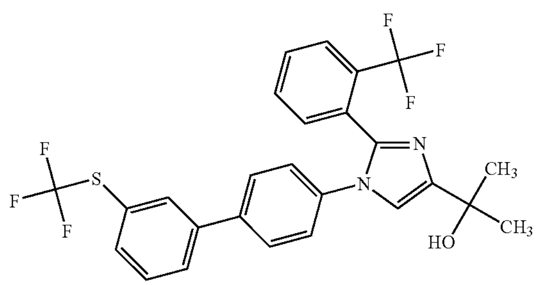 [SMILES: CC(C)(O)c1cn(-c2ccc(-c3cccc(SC(F)(F)F)c3)cc2)c(-c2ccccc2C(F)(F)F)n1] | 2-(2-[2-(trifluoromethyl)phenyl]-1-{3'-[(trifluoromethyl)thio]biphenyl-4-yl}-1H-imidazol-4-yl)propan-2-ol; |
| 352 | 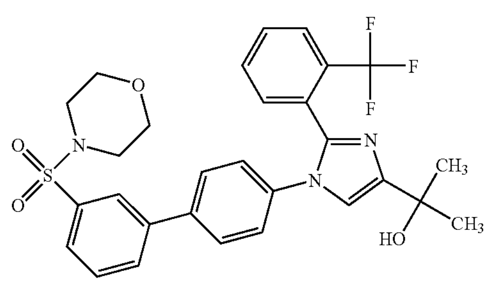 [SMILES: CC(C)(O)c1cn(-c2ccc(-c3cccc(S(=O)(=O)N4CCOCC4)c3)cc2)c(-c2ccccc2C(F)(F)F)n1] | 2-{1-[3'-(morpholin-4-ylsulfonyl)biphenyl-4-yl]-2-[2-(trifluoromethyl)phenyl]-1H-imidazol-4-yl}propan-2-ol; |
| 353 | 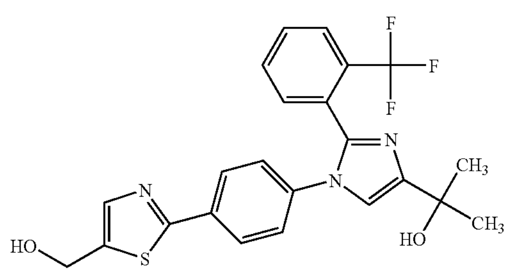 [SMILES: CC(C)(O)c1cn(-c2ccc(-c3ncc(CO)s3)cc2)c(-c2ccccc2C(F)(F)F)n1] | 2-(1-{4-[5-(hydroxymethyl)-1,3-thiazol-2-yl]phenyl}-2-[2-(trifluoromethyl)phenyl]-1H-imidazol-4-yl)propan-2-ol; |
| 354 | 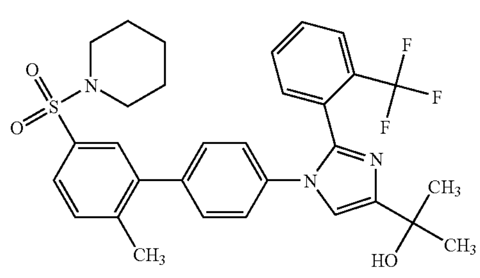 [SMILES: Cc1ccc(S(=O)(=O)N2CCCCC2)cc1-c1ccc(-n2cc(C(C)(C)O)nc2-c2ccccc2C(F)(F)F)cc1] | 2-{1-[2'-methyl-5'-(piperidin-1-ylsulfonyl)biphenyl-4-yl]-2-[2-(trifluoromethyl)phenyl]-1H-imidazol-4-yl}propan-2-ol; |

TABLE 1-continued

| Cpd # | Structure | Name |
|---|---|---|
| 355 | 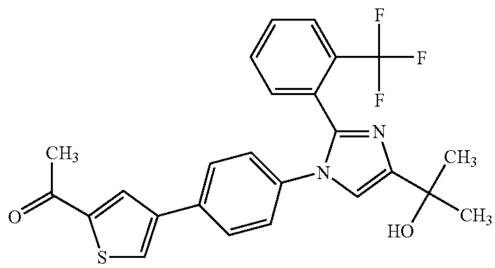 [SMILES: CC(=O)c1cc(-c2ccc(-n3cc(C(C)(C)O)nc3-c3ccccc3C(F)(F)F)cc2)cs1] | 1-[4-(4-{4-(1-hydroxy-1-methylethyl)-2-[2-(trifluoromethyl)phenyl]-1H-imidazol-1-yl}phenyl)-2-thienyl]ethanone; |
| 356 | 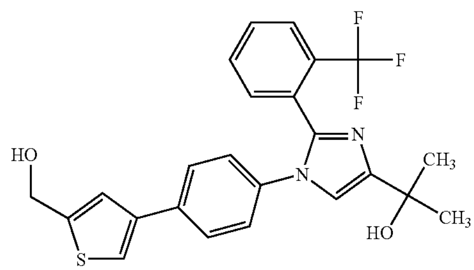 [SMILES: CC(C)(O)c1cn(-c2ccc(-c3csc(CO)c3)cc2)c(-c2ccccc2C(F)(F)F)n1] | 2-(1-{4-[5-(hydroxymethyl)-3-thienyl]phenyl}-2-[2-(trifluoromethyl)phenyl]-1H-imidazol-4-yl)propan-2-ol; |
| 357 | 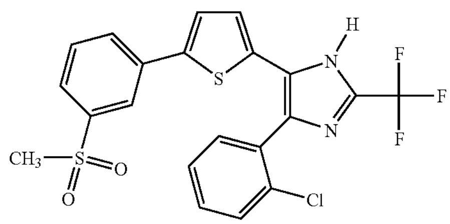 [SMILES: CS(=O)(=O)c1cccc(-c2ccc(-c3[nH]c(C(F)(F)F)nc3-c3ccccc3Cl)s2)c1] | 4-(2-chlorophenyl)-5-{5-[3-(methylsulfonyl)phenyl]-2-thienyl}-2-(trifluoromethyl)-1H-imidazole; |
| 358 | 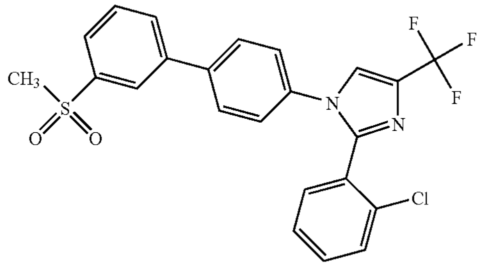 [SMILES: CS(=O)(=O)c1cccc(-c2ccc(-n3cc(C(F)(F)F)nc3-c3ccccc3Cl)cc2)c1] | 2-(2-chlorophenyl)-1-[3'-(methylsulfonyl)biphenyl-4-yl]-4-(trifluoromethyl)-1H-imidazole; |
| 359 | 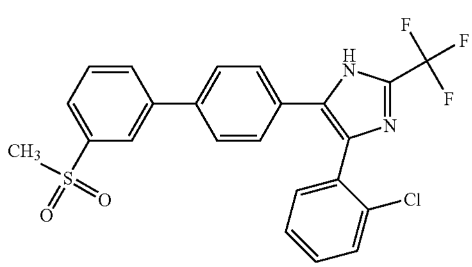 [SMILES: CS(=O)(=O)c1cccc(-c2ccc(-c3[nH]c(C(F)(F)F)nc3-c3ccccc3Cl)cc2)c1] | 4-(2-chlorophenyl)-5-[3'-(methylsulfonyl)biphenyl-4-yl]-2-(trifluoromethyl)-1H-imidazole; |
| 360 | 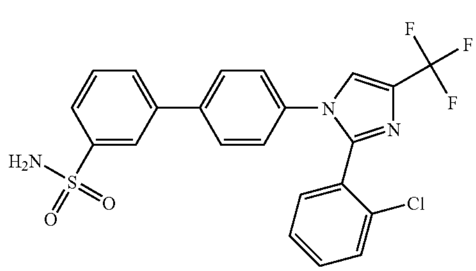 [SMILES: NS(=O)(=O)c1cccc(-c2ccc(-n3cc(C(F)(F)F)nc3-c3ccccc3Cl)cc2)c1] | 4'-[2-(2-chlorophenyl)-4-(trifluoromethyl)-1H-imidazol-1-yl]biphenyl-3-sulfonamide; |

TABLE 1-continued

| Cpd # | Structure | Name |
|---|---|---|
| 361 | 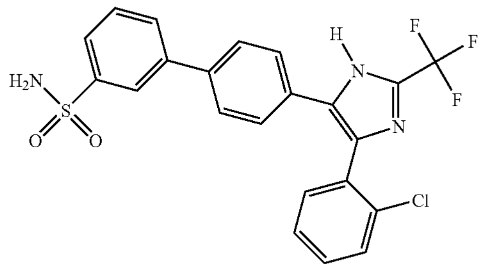 [SMILES: NS(=O)(=O)c1cccc(-c2ccc(-c3[nH]c(C(F)(F)F)nc3-c3ccccc3Cl)cc2)c1] | 4'-[4-(2-chlorophenyl)-2-(trifluoromethyl)-1H-imidazol-5-yl]biphenyl-3-sulfonamide; |
| 362 | 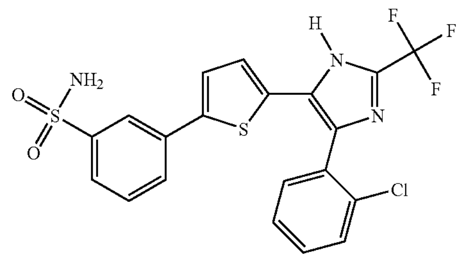 [SMILES: NS(=O)(=O)c1cccc(-c2ccc(-c3[nH]c(C(F)(F)F)nc3-c3ccccc3Cl)s2)c1] | 3-{5-[4-(2-chlorophenyl)-2-(trifluoromethyl)-1H-imidazol-5-yl]-2-thienyl}benzenesulfonamide; |
| 364 | 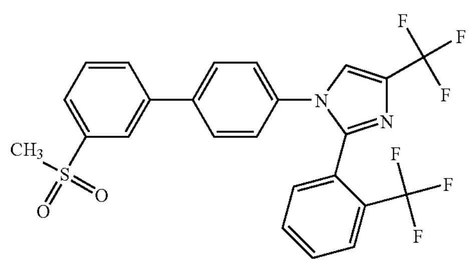 | 1-[3'-(methylsulfonyl)biphenyl-4-yl]-4-(trifluoromethyl)-2-[2-(trifluoromethyl)phenyl]-1H-imidazole; |
| 365 | 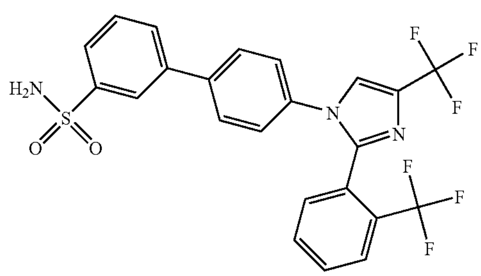 [SMILES: NS(=O)(=O)c1cccc(-c2ccc(-n3cc(C(F)(F)F)nc3-c3ccccc3C(F)(F)F)cc2)c1] | 4'-{4-(trifluoromethyl)-2-[2-(trifluoromethyl)phenyl]-1H-imidazol-1-yl}biphenyl-3-sulfonamide; |
| 366 | 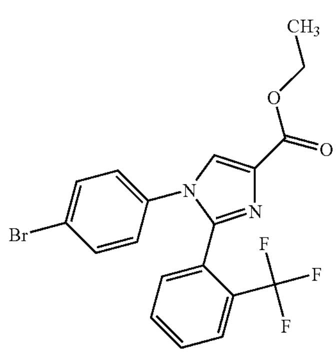 [SMILES: CCOC(=O)c1cn(-c2ccc(Br)cc2)c(-c2ccccc2C(F)(F)F)n1] | ethyl 1-(4-bromophenyl)-2-[2-(trifluoromethyl)phenyl]-1H-imidazole-4-carboxylate; |

TABLE 1-continued

| Cpd # | Structure | Name |
|---|---|---|
| 367 | 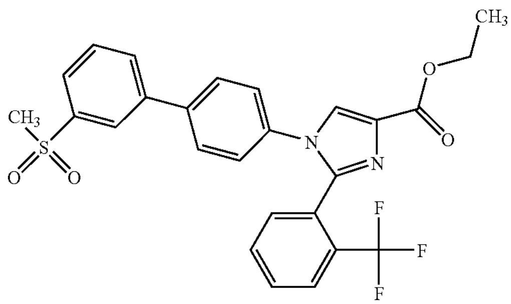 [SMILES: CCOC(=O)c1cn(-c2ccc(-c3cccc(S(C)(=O)=O)c3)cc2)c(-c2ccccc2C(F)(F)F)n1] | ethyl 1-[3'-(methylsulfonyl)biphenyl-4-yl]-2-[2-(trifluoromethyl)phenyl]-1H-imidazole-4-carboxylate; |
| 369 | 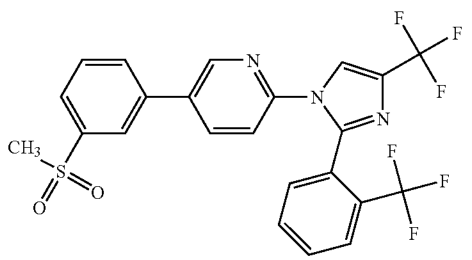 [SMILES: CS(=O)(=O)c1cccc(-c2ccc(-n3cc(C(F)(F)F)nc3-c3ccccc3C(F)(F)F)nc2)c1] | 5-[3-(methylsulfonyl)phenyl]-2-{4-(trifluoromethyl)-2-[2-(trifluoromethyl)phenyl]-1H-imidazol-1-yl}pyridine; |
| 370 | 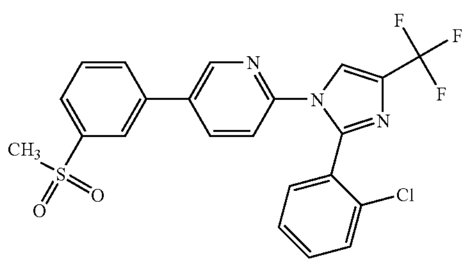 [SMILES: CS(=O)(=O)c1cccc(-c2ccc(-n3cc(C(F)(F)F)nc3-c3ccccc3Cl)nc2)c1] | 2-[2-(2-chlorophenyl)-4-(trifluoromethyl)-1H-imidazol-1-yl]-5-[3-(methylsulfonyl)phenyl]pyridine; |
| 371 | 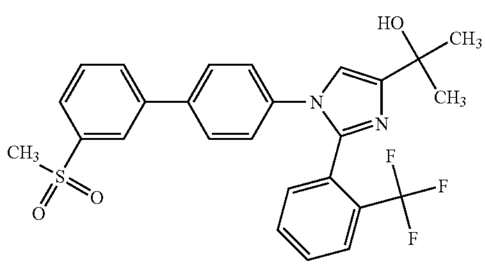 [SMILES: CC(C)(O)c1cn(-c2ccc(-c3cccc(S(C)(=O)=O)c3)cc2)c(-c2ccccc2C(F)(F)F)n1] | 2-{1-[3'-(methylsulfonyl)biphenyl-4-yl]-2-[2-(trifluoromethyl)phenyl]-1H-imidazol-4-yl}propan-2-ol; |
| 372 | 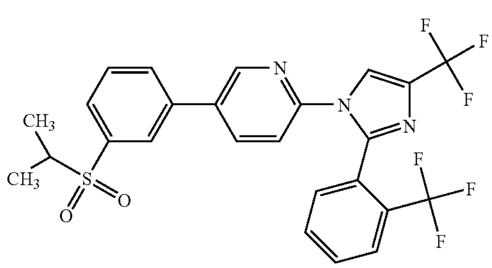 [SMILES: CC(C)S(=O)(=O)c1cccc(-c2ccc(-n3cc(C(F)(F)F)nc3-c3ccccc3C(F)(F)F)nc2)c1] | 5-{3-[(1-methylethyl)sulfonyl]phenyl}-2-{4-(trifluoromethyl)-2-[2-(trifluoromethyl)phenyl]-1H-imidazol-1-yl}pyridine; |

TABLE 1-continued

| Cpd # | Structure | Name |
|---|---|---|
| 373 | 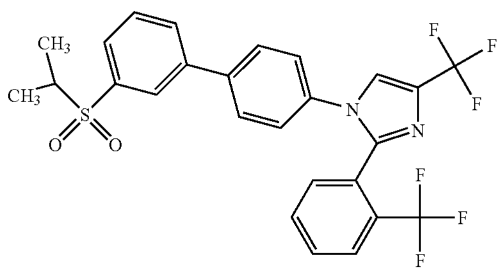 [SMILES: CC(C)S(=O)(=O)c1cccc(-c2ccc(-n3cc(C(F)(F)F)nc3-c3ccccc3C(F)(F)F)cc2)c1] | 1-{3'-[(1-methylethyl)sulfonyl]biphenyl-4-yl}-4-(trifluoromethyl)-2-[2-(trifluoromethyl)phenyl]-1H-imidazole; |
| 375 | 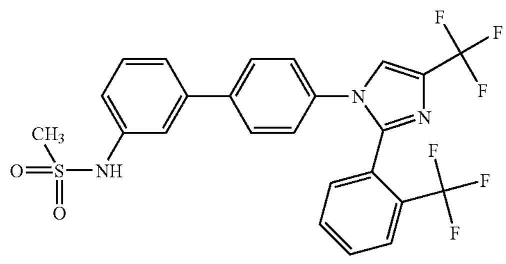 [SMILES: CS(=O)(=O)Nc1cccc(-c2ccc(-n3cc(C(F)(F)F)nc3-c3ccccc3C(F)(F)F)cc2)c1] | N-(4'-{4-(trifluoromethyl)-2-[2-(trifluoromethyl)phenyl]-1H-imidazol-1-yl}biphenyl-3-yl)methanesulfonamide; |
| 376 | 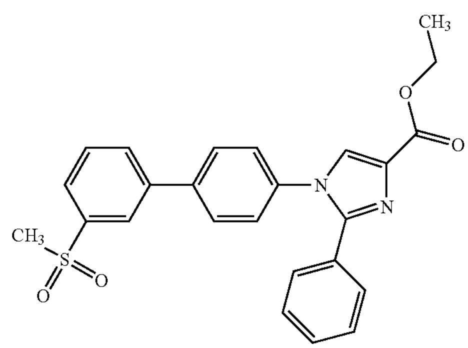 [SMILES: CCOC(=O)c1cn(-c2ccc(-c3cccc(S(C)(=O)=O)c3)cc2)c(-c2ccccc2)n1] | ethyl 1-[3'-(methylsulfonyl)biphenyl-4-yl]-2-phenyl-1H-imidazole-4-carboxylate; |
| 378 | 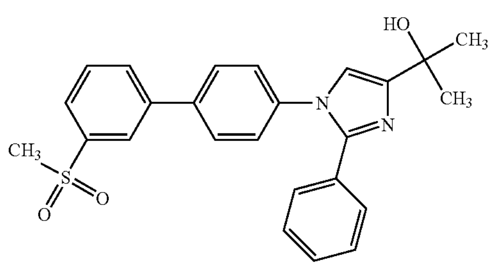 [SMILES: CC(C)(O)c1cn(-c2ccc(-c3cccc(S(C)(=O)=O)c3)cc2)c(-c2ccccc2)n1] | 2-{1-[3'-(methylsulfonyl)biphenyl-4-yl]-2-phenyl-1H-imidazol-4-yl}propan-2-ol; |
| 379 | 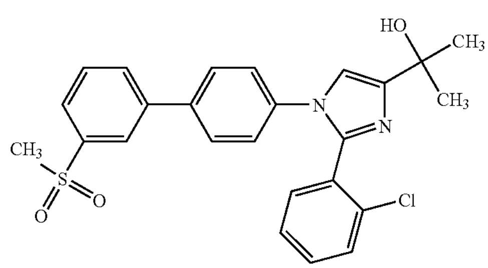 [SMILES: CC(C)(O)c1cn(-c2ccc(-c3cccc(S(C)(=O)=O)c3)cc2)c(-c2ccccc2Cl)n1] | 2-{2-(2-chlorophenyl)-1-[3'-(methylsulfonyl)biphenyl-4-yl]-1H-imidazol-4-yl}propan-2-ol; |

TABLE 1-continued

| Cpd # | Structure | Name |
|---|---|---|
| 380 | 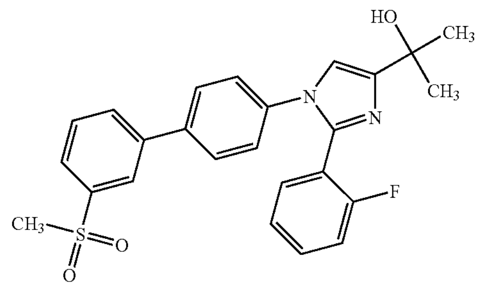 [SMILES: CC(C)(O)c1cn(-c2ccc(-c3cccc(S(C)(=O)=O)c3)cc2)c(-c2ccccc2F)n1] | 2-{2-(2-fluorophenyl)-1-[3'-(methylsulfonyl)biphenyl-4-yl]-1H-imidazol-4-yl}propan-2-ol; |
| 381 | 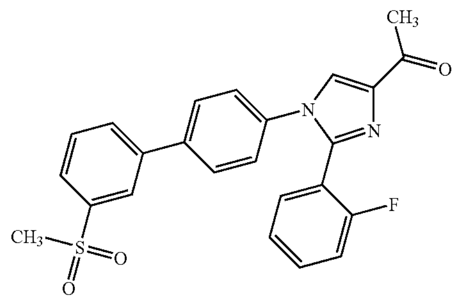 [SMILES: CC(=O)c1cn(-c2ccc(-c3cccc(S(C)(=O)=O)c3)cc2)c(-c2ccccc2F)n1] | 1-{2-(2-fluorophenyl)-1-[3'-(methylsulfonyl)biphenyl-4-yl]-1H-imidazol-4-yl}ethanone; |
| 382 | 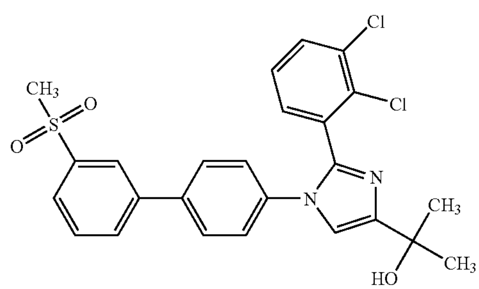 [SMILES: CC(C)(O)c1cn(-c2ccc(-c3cccc(S(C)(=O)=O)c3)cc2)c(-c2cccc(Cl)c2Cl)n1] | 2-{2-(2,3-dichlorophenyl)-1-[3'-(methylsulfonyl)biphenyl-4-yl]-1H-imidazol-4-yl}propan-2-ol; |
| 383 | 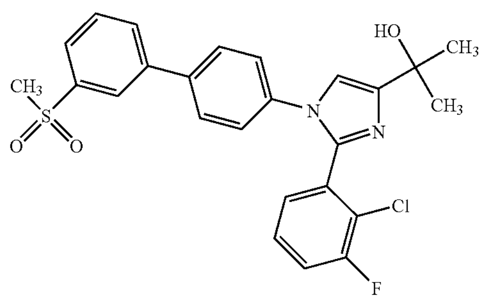 [SMILES: CC(C)(O)c1cn(-c2ccc(-c3cccc(S(C)(=O)=O)c3)cc2)c(-c2cccc(F)c2Cl)n1] | 2-{2-(2-chloro-3-fluorophenyl)-1-[3'-(methylsulfonyl)biphenyl-4-yl]-1H-imidazol-4-yl}propan-2-ol; |
| 384 | 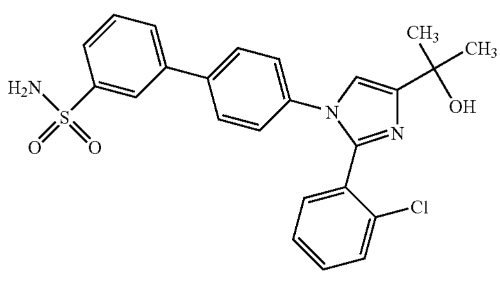 [SMILES: CC(C)(O)c1cn(-c2ccc(-c3cccc(S(N)(=O)=O)c3)cc2)c(-c2ccccc2Cl)n1] | 4'-[2-(2-chlorophenyl)-4-(1-hydroxy-1-(methylethyl)-1H-imidazol-1-yl]biphenyl-3-sulfonamide; |

TABLE 1-continued

| Cpd # | Structure | Name |
|---|---|---|
| 385 | 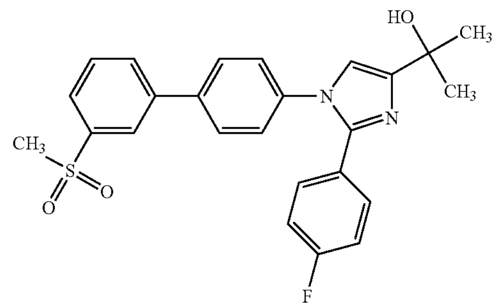 [SMILES: CC(C)(O)c1cn(-c2ccc(-c3cccc(S(C)(=O)=O)c3)cc2)c(-c2ccc(F)cc2)n1] | 2-{2-(4-fluorophenyl)-1-[3'-(methylsulfonyl)biphenyl-4-yl]-1H-imidazol-4-yl}propan-2-ol; |
| 386 | 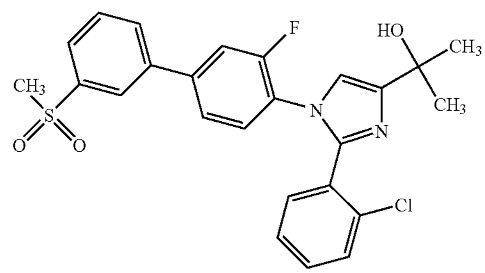 [SMILES: CC(C)(O)c1cn(-c2ccc(-c3cccc(S(C)(=O)=O)c3)cc2F)c(-c2ccccc2Cl)n1] | 2-{2-(2-chlorophenyl)-1-[3-fluoro-3'-(methylsulfonyl)biphenyl-4-yl]-1H-imidazol-4-yl}propan-2-ol; |
| 387 | 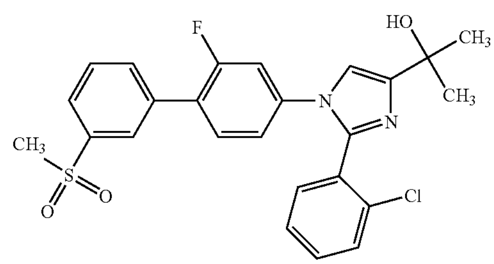 [SMILES: CC(C)(O)c1cn(-c2ccc(-c3cccc(S(C)(=O)=O)c3)c(F)c2)c(-c2ccccc2Cl)n1] | 2-{2-(2-chlorophenyl)-1-[2-fluoro-3'-(methylsulfonyl)biphenyl-4-yl]-1H-imidazol-4-yl}propan-2-ol; |
| 388 | 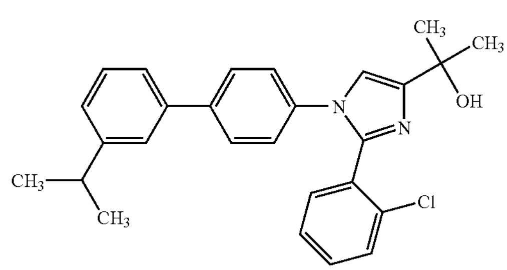 [SMILES: CC(C)c1cccc(-c2ccc(-n3cc(C(C)(C)O)nc3-c3ccccc3Cl)cc2)c1] | 2-{2-(2-chlorophenyl)-1-[3'-(1-methylethyl)biphenyl-4-yl]-1H-imidazol-4-yl}propan-2-ol; |
| 389 | 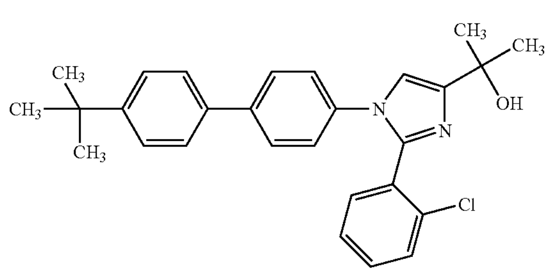 [SMILES: CC(C)(C)c1ccc(-c2ccc(-n3cc(C(C)(C)O)nc3-c3ccccc3Cl)cc2)cc1] | 2-{2-(2-chlorophenyl)-1-[4'-(1,1-dimethylethyl)biphenyl-4-yl]-1H-imidazol-4-yl}propan-2-ol; |

TABLE 1-continued

| Cpd # | Structure | Name |
|---|---|---|
| 390 | 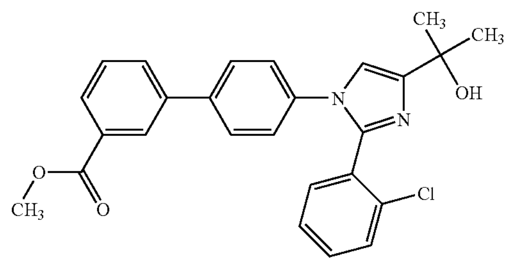 [SMILES: COC(=O)c1cccc(-c2ccc(-n3cc(C(C)(C)O)nc3-c3ccccc3Cl)cc2)c1] | methyl 4'-[2-(2-chlorophenyl)-4-(1-hydroxy-1-methylethyl)-1H-imidazol-1-yl]biphenyl-3-carboxylate; |
| 391 | 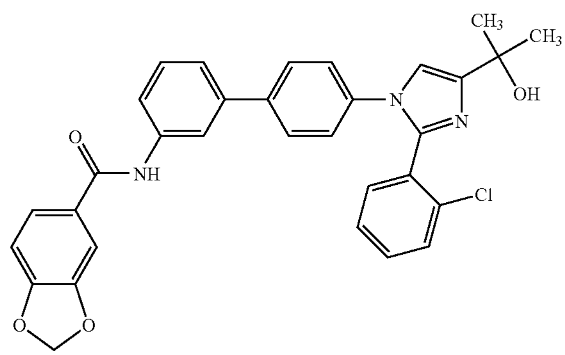 [SMILES: CC(C)(O)c1cn(-c2ccc(-c3cccc(NC(=O)c4ccc5c(c4)OCO5)c3)cc2)c(-c2ccccc2Cl)n1] | N-{4'-[2-(2-chlorophenyl)-4-(1-hydroxy-1-methylethyl)-1H-imidazol-1-yl]biphenyl-3-yl}-1,3-benzodioxole-5-carboxamide; |
| 392 | 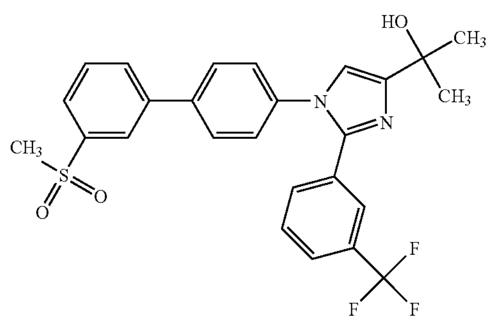 [SMILES: CC(C)(O)c1cn(-c2ccc(-c3cccc(S(C)(=O)=O)c3)cc2)c(-c2cccc(C(F)(F)F)c2)n1] | 2-{1-[3'-(methylsulfonyl)biphenyl-4-yl]-2-[3-(trifluoromethyl)phenyl]-1H-imidazol-4-yl}propan-2-ol; |
| 393 | 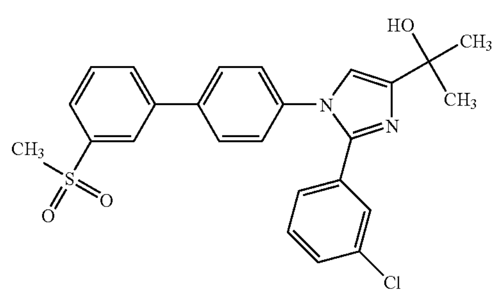 [SMILES: CC(C)(O)c1cn(-c2ccc(-c3cccc(S(C)(=O)=O)c3)cc2)c(-c2cccc(Cl)c2)n1] | 2-{2-(3-chlorophenyl)-1-[3'-(methylsulfonyl)biphenyl-4-yl]-1H-imidazol-4-yl}propan-2-ol; |
| 394 | 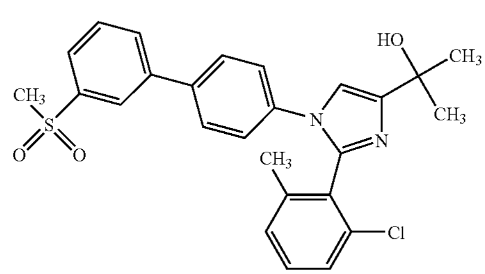 [SMILES: Cc1cccc(Cl)c1-c1nc(C(C)(C)O)cn1-c1ccc(-c2cccc(S(C)(=O)=O)c2)cc1] | 2-{2-(2-chloro-6-methylphenyl)-1-[3'-(methylsulfonyl)biphenyl-4-yl]-1H-imidazol-4-yl}propan-2-ol; |

| Cpd # | Structure | Name |
|---|---|---|
| 395 | 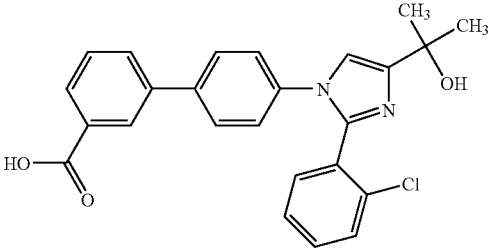 [SMILES: CC(C)(O)c1cn(-c2ccc(-c3cccc(C(=O)O)c3)cc2)c(-c2ccccc2Cl)n1] | 4'-[2-(2-chlorophenyl)-4-(1-hydroxy-1-methylethyl)-1H-imidazol-1-yl]biphenyl-3-carboxylic acid; |
| 397 | 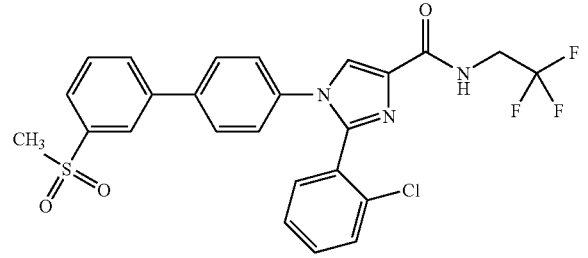 [SMILES: CS(=O)(=O)c1cccc(-c2ccc(-n3cc(C(=O)NCC(F)(F)F)nc3-c3ccccc3Cl)cc2)c1] | 2-(2-chlorophenyl)-1-[3'-(methylsulfonyl)biphenyl-4-yl]-N-(2,2,2-trifluoroethyl-1H-imidazole-4-carboxamide; |
| 398 | 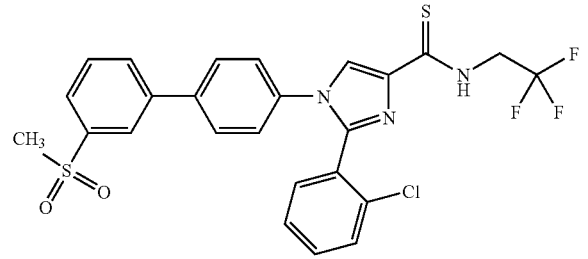 [SMILES: CS(=O)(=O)c1cccc(-c2ccc(-n3cc(C(=S)NCC(F)(F)F)nc3-c3ccccc3Cl)cc2)c1] | 2-(2-chlorophenyl)-1-[3'-(methylsulfonyl)biphenyl-4-yl]-N-(2,2,2-trifluoroethyl)-1H-imidazole-4-carbothioamide; |
| 399 | 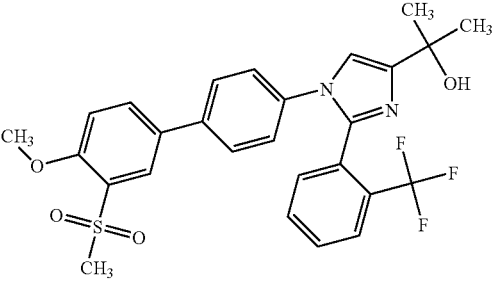 [SMILES: COc1ccc(-c2ccc(-n3cc(C(C)(C)O)nc3-c3ccccc3C(F)(F)F)cc2)cc1S(C)(=O)=O] | 2-{1-[4'-(methyloxy)-3'-(methylsulfonyl)biphenyl-4-yl]-2-[2-(trifluoromethyl)phenyl]-1H-imidazol-4-yl}propan-2-ol; |
| 400 | 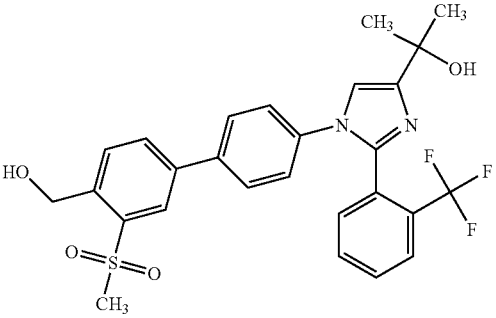 [SMILES: CC(C)(O)c1cn(-c2ccc(-c3ccc(CO)c(S(C)(=O)=O)c3)cc2)c(-c2ccccc2C(F)(F)F)n1] | 2-{1-[4'-(hydroxymethyl)-3'-(methylsulfonyl)biphenyl-4-yl]-2-[2-(trifluoromethyl)phenyl]-1H-imidazol-4-yl}propan-2-ol; |

TABLE 1-continued

| Cpd # | Structure | Name |
|---|---|---|
| 401 | 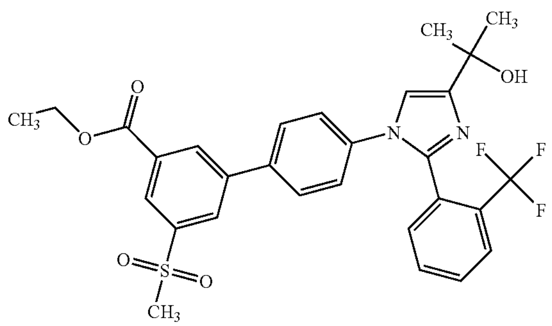 [SMILES: CCOC(=O)c1cc(-c2ccc(-n3cc(C(C)(C)O)nc3-c3ccccc3C(F)(F)F)cc2)cc(S(C)(=O)=O)c1] | ethyl 4'-{4-(1-hydroxy-1-methylethyl)-2-[2-(trifluoromethyl)phenyl]-1H-imidazol-1-yl}-5-(methylsulfonyl)biphenyl-3-carboxylate; |
| 402 | 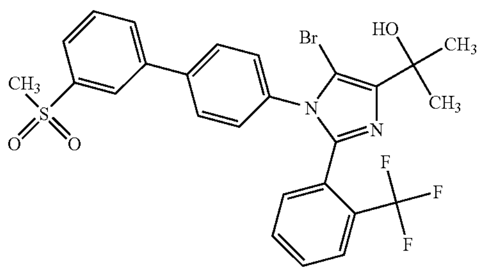 [SMILES: CC(C)(O)c1nc(-c2ccccc2C(F)(F)F)n(-c2ccc(-c3cccc(S(C)(=O)=O)c3)cc2)c1Br] | 2-{5-bromo-1-[3'-(methylsulfonyl)biphenyl-4-yl]-2-[2-(trifluoromethyl)phenyl]-1H-imidazol-4-yl}propan-2-ol; |
| 403 | 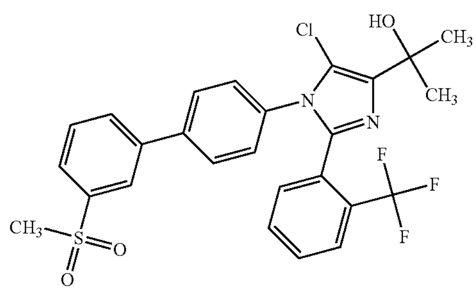 [SMILES: CC(C)(O)c1nc(-c2ccccc2C(F)(F)F)n(-c2ccc(-c3cccc(S(C)(=O)=O)c3)cc2)c1Cl] | 2-{5-chloro-1-[3'-(methylsulfonyl)biphenyl-4-yl]-2-[2-(trifluoromethyl)phenyl]-1H-imidazol-4-yl}propan-2-ol; |
| 404 | 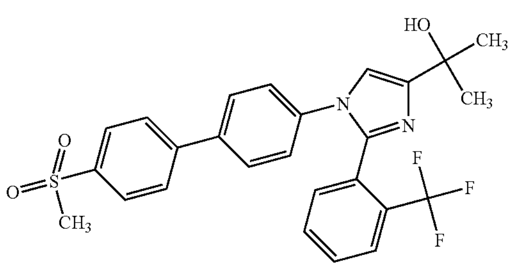 [SMILES: CC(C)(O)c1cn(-c2ccc(-c3ccc(S(C)(=O)=O)cc3)cc2)c(-c2ccccc2C(F)(F)F)n1] | 2-{1-[4'-(methylsulfonyl)biphenyl-4-yl]-2-[2-(trifluoromethyl)phenyl]-1H-imidazol-4-yl}propan-2-ol; |
| 405 | 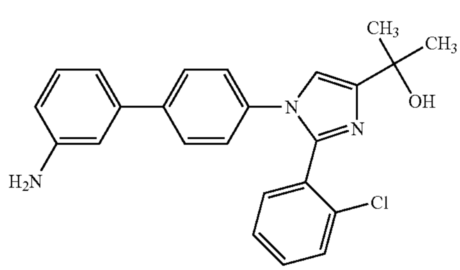 [SMILES: CC(C)(O)c1cn(-c2ccc(-c3cccc(N)c3)cc2)c(-c2ccccc2Cl)n1] | 2-[1-(3'-aminobiphenyl-4-yl)-2-(2-chlorophenyl)-1H-imidazol-4-yl]propan-2-ol; |

TABLE 1-continued

| Cpd # | Structure | Name |
|---|---|---|
| 406 | 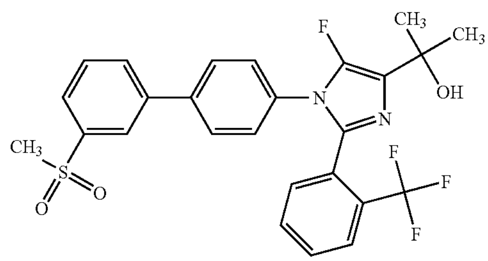 [SMILES: CC(C)(O)c1nc(-c2ccccc2C(F)(F)F)n(-c2ccc(-c3cccc(S(C)(=O)=O)c3)cc2)c1F] | 2-{5-fluoro-1-[3'-(methylsulfonyl)biphenyl-4-yl]-2-[2-(trifluoromethyl)phenyl]-1H-imidazol-4-yl}propan-2-ol; |
| 407 | 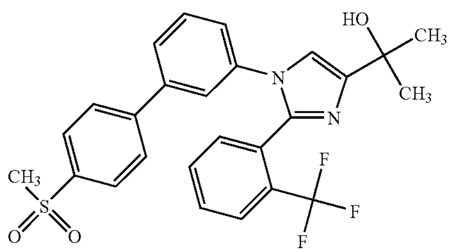 [SMILES: CC(C)(O)c1cn(-c2cccc(-c3ccc(S(C)(=O)=O)cc3)c2)c(-c2ccccc2C(F)(F)F)n1] | 2-{1-[4'-(methylsulfonyl)biphenyl-3-yl]-2-[2-(trifluoromethyl)phenyl]-1H-imidazol-4-yl}propan-2-ol; |
| 408 | 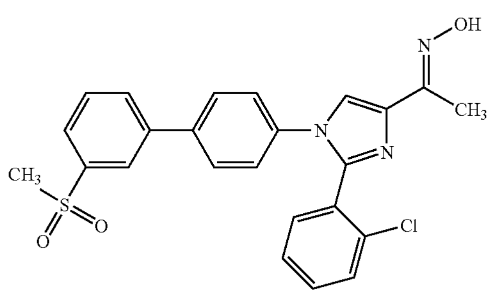 [SMILES: C/C(=N\O)c1cn(-c2ccc(-c3cccc(S(C)(=O)=O)c3)cc2)c(-c2ccccc2Cl)n1] | 1-{2-(2-chlorophenyl)-1-[3'-(methylsulfonyl)biphenyl-4-yl]-1H-imidazol-4-yl}ethanone oxime; |
| 409 | 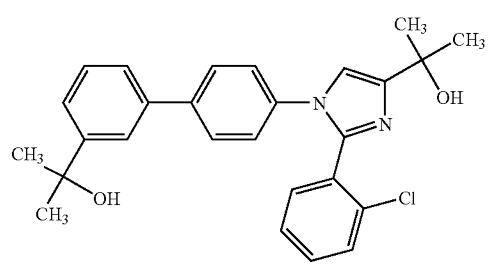 [SMILES: CC(C)(O)c1cccc(-c2ccc(-n3cc(C(C)(C)O)nc3-c3ccccc3Cl)cc2)c1] | 2-{2-(2-chlorophenyl)-1-[3'-(1-hydroxy-1-methylethyl)biphenyl-4-yl]-1H-imidazol-4-yl}propan-2-ol; |
| 410 | 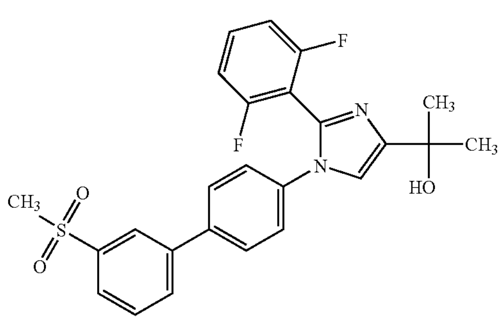 [SMILES: CC(C)(O)c1cn(-c2ccc(-c3cccc(S(C)(=O)=O)c3)cc2)c(-c2c(F)cccc2F)n1] | 2-{2-(2,6-difluorophenyl)-1-[3'-(methylsulfonyl)biphenyl-4-yl]-1H-imidazol-4-yl}propan-2-ol; |

TABLE 1-continued

| Cpd # | Structure | Name |
|---|---|---|
| 411 | 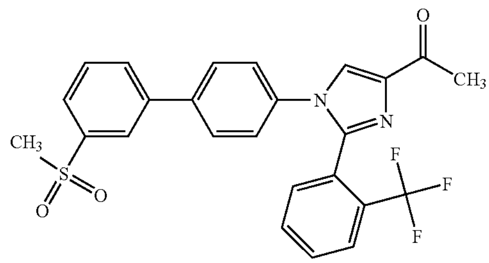 [SMILES: CC(=O)c1cn(-c2ccc(-c3cccc(S(C)(=O)=O)c3)cc2)c(-c2ccccc2C(F)(F)F)n1] | 1-{1-[3'-(methylsulfonyl)biphenyl-4-yl]-2-[2-(trifluoromethyl)phenyl]-1H-imidazol-4-yl}ethanone; |
| 412 | 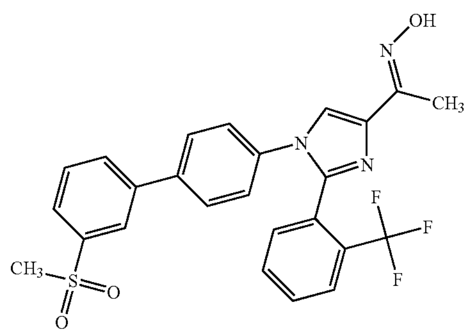 [SMILES: C/C(=N\O)c1cn(-c2ccc(-c3cccc(S(C)(=O)=O)c3)cc2)c(-c2ccccc2C(F)(F)F)n1] | 1-{1-[3'-(methylsulfonyl)biphenyl-4-yl]-2-[2-(trifluoromethyl)phenyl]-1H-imidazol-4-yl}ethanone oxime; |
| 413 | 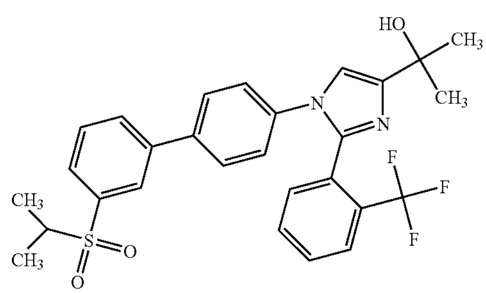 [SMILES: CC(C)S(=O)(=O)c1cccc(-c2ccc(-n3cc(C(C)(C)O)nc3-c3ccccc3C(F)(F)F)cc2)c1] | 2-(1-{3'-[(1-methylethyl)sulfonyl]biphenyl-4-yl}-2-[2-(trifluoromethyl)phenyl]-1H-imidazol-4-yl)propan-2-ol; |
| 414 | 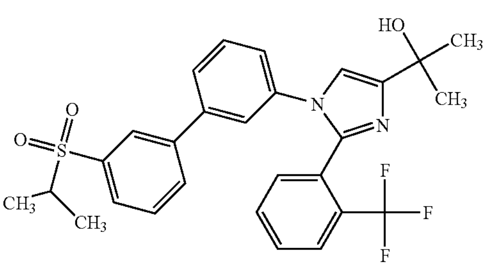 [SMILES: CC(C)S(=O)(=O)c1cccc(-c2cccc(-n3cc(C(C)(C)O)nc3-c3ccccc3C(F)(F)F)c2)c1] | 2-(1-{3'-[(1-methylethyl)sulfonyl]biphenyl-3-yl}-2-[2-(trifluoromethyl)phenyl]-1H-imidazol-4-yl)propan-2-ol; |
| 415 | 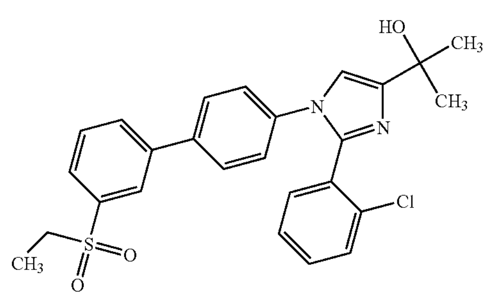 [SMILES: CCS(=O)(=O)c1cccc(-c2ccc(-n3cc(C(C)(C)O)nc3-c3ccccc3Cl)cc2)c1] | 2-{2-(2-chlorophenyl)-1-[3'-(ethylsulfonyl)biphenyl-4-yl]-1H-imidazol-4-yl}propan-2-ol; |

TABLE 1-continued

| Cpd # | Structure | Name |
|---|---|---|
| 416 | 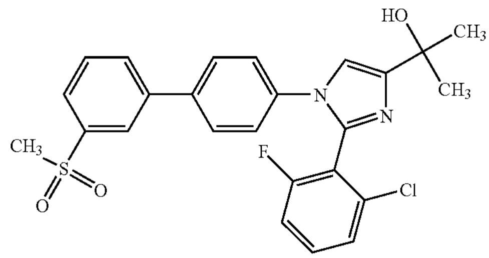 [SMILES: CC(C)(O)c1cn(-c2ccc(-c3cccc(S(C)(=O)=O)c3)cc2)c(-c2c(F)cccc2Cl)n1] | 2-{2-(2-chloro-6-fluorophenyl)-1-[3'-(methylsulfonyl)biphenyl-4-yl]-1H-imidazol-4-yl}propan-2-ol; |
| 417 | 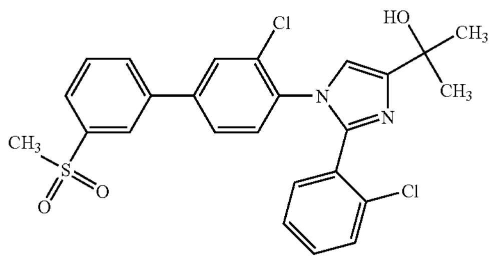 [SMILES: CC(C)(O)c1cn(-c2ccc(-c3cccc(S(C)(=O)=O)c3)cc2Cl)c(-c2ccccc2Cl)n1] | 2-{1-[3-chloro-3'-(methylsulfonyl)biphenyl-4-yl]-2-(2-chlorophenyl)-1H-imidazol-4-yl}propan-2-ol; |
| 418 | 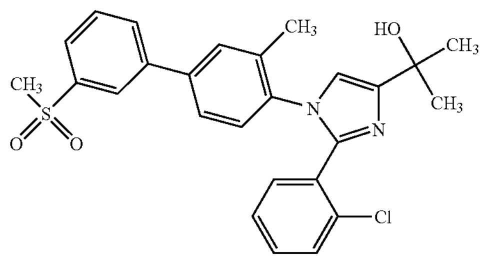 [SMILES: Cc1cc(-c2cccc(S(C)(=O)=O)c2)ccc1-n1cc(C(C)(C)O)nc1-c1ccccc1Cl] | 2-{2-(2-chlorophenyl)-1-[3-methyl-3'-(methylsulfonyl)biphenyl-4-yl]-1H-imidazol-4-yl}propan-2-ol; |
| 419 | 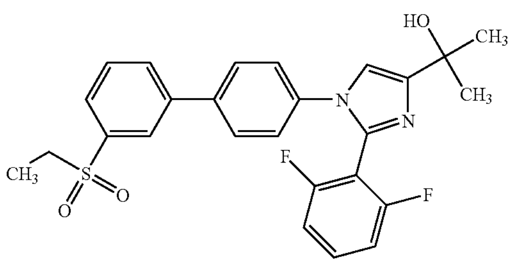 [SMILES: CCS(=O)(=O)c1cccc(-c2ccc(-n3cc(C(C)(C)O)nc3-c3c(F)cccc3F)cc2)c1] | 2-{2-(2,6-difluorophenyl)-1-[3'-(ethylsulfonyl)biphenyl-4-yl]-1H-imidazol-4-yl}propan-2-ol; |
| 420 | 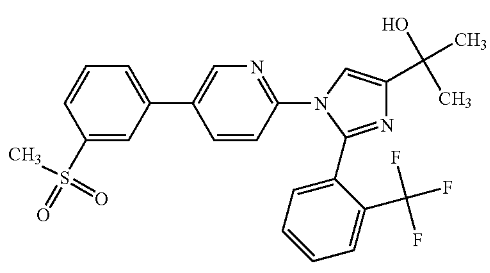 [SMILES: CC(C)(O)c1cn(-c2ccc(-c3cccc(S(C)(=O)=O)c3)cn2)c(-c2ccccc2C(F)(F)F)n1] | 2-(1-{5-[3-(methylsulfonyl)phenyl]pyridin-2-yl}-2-[2-(trifluoromethyl)phenyl]-1H-imidazol-4-yl)propan-2-ol; |

TABLE 1-continued

| Cpd # | Structure | Name |
|---|---|---|
| 421 | 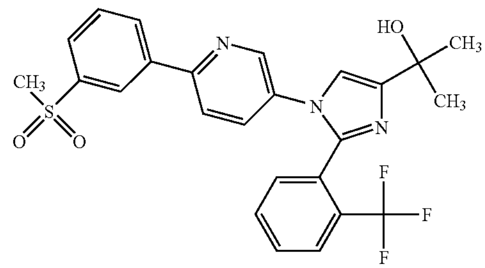 [SMILES: CC(C)(O)c1cn(-c2ccc(-c3cccc(S(C)(=O)=O)c3)nc2)c(-c2ccccc2C(F)(F)F)n1] | 2-(1-{6-[3-(methylsulfonyl) phenyl]pyridin-3-yl}-2-[2-(trifluoromethyl)phenyl]-1H-imidazol-4-yl)propan-2-ol; |
| 422 | 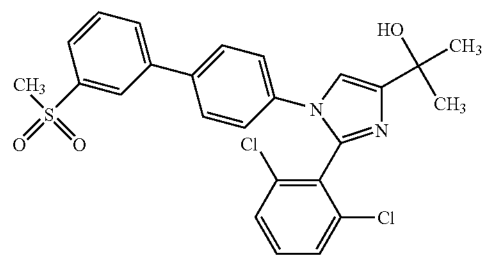 [SMILES: CC(C)(O)c1cn(-c2ccc(-c3cccc(S(C)(=O)=O)c3)cc2)c(-c2c(Cl)cccc2Cl)n1] | 2-{2-(2,6-dichlorophenyl)-1-[3'-(methylsulfonyl)biphenyl-4-yl]-1H-imidazol-4-yl}propan-2-ol; |
| 424 | 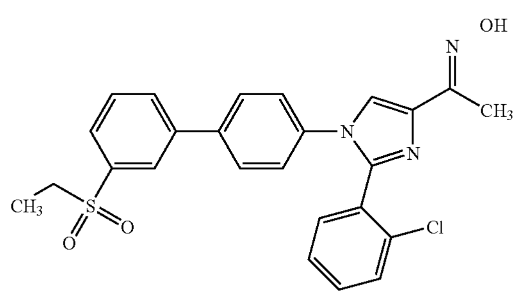 | 1-{2-(2-chlorophenyl)-1-[3'-(ethylsulfonyl)biphenyl-4-yl]-1H-imidazol-4-yl}ethanone oxime; |
| 425 | 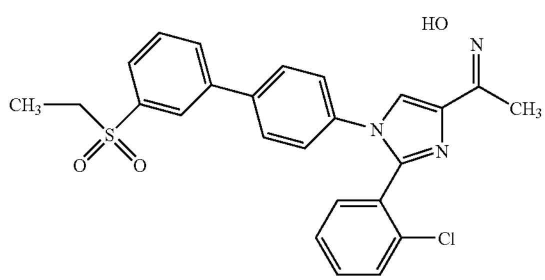 | 1-{2-(2-chlorophenyl)-1-[3'-(ethylsulfonyl)biphenyl-4-yl]-1H-imidazol-4-yl}ethanone oxime; |
| 426 | 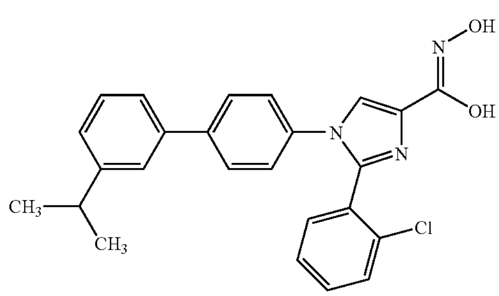 [SMILES: CC(C)c1cccc(-c2ccc(-n3cc(/C(O)=N/O)nc3-c3ccccc3Cl)cc2)c1] | 1-{2-(2-chlorophenyl)-1-[3'-(1-methylethyl)biphenyl-4-yl]-1H-imidazol-4-yl}ethanone oxime; |

TABLE 1-continued

| Cpd # | Structure | Name |
|---|---|---|
| 427 | 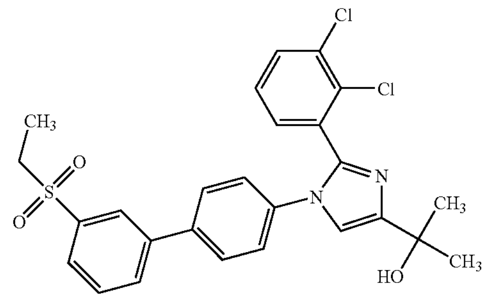 [SMILES: CCS(=O)(=O)c1cccc(-c2ccc(-n3cc(C(C)(C)O)nc3-c3cccc(Cl)c3Cl)cc2)c1] | 2-{2-(2,3-dichlorophenyl)-1-[3'-(ethylsulfonyl)biphenyl-4-yl]-1H-imidazol-4-yl}propan-2-ol; |
| 428 | 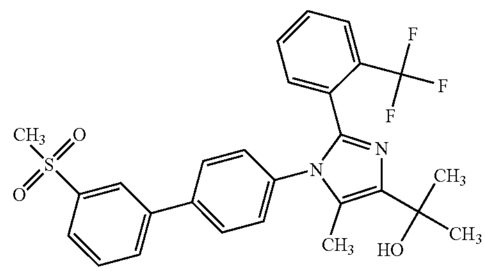 [SMILES: Cc1c(C(C)(C)O)nc(-c2ccccc2C(F)(F)F)n1-c1ccc(-c2cccc(S(C)(=O)=O)c2)cc1] | 2-{5-methyl-1-[3'-(methylsulfonyl)biphenyl-4-yl]-2-[2-(trifluoromethyl)phenyl]-1H-imidazol-4-yl}propan-2-ol; |
| 429 | 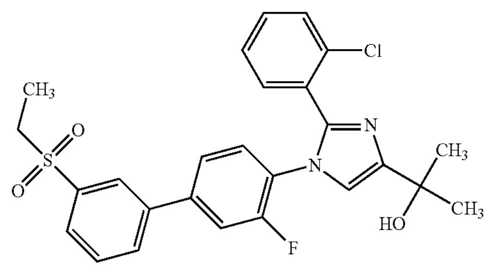 [SMILES: CCS(=O)(=O)c1cccc(-c2ccc(-n3cc(C(C)(C)O)nc3-c3ccccc3Cl)c(F)c2)c1] | 2-{2-(2-chlorophenyl)-1-[3'-(ethylsulfonyl)-3-fluorobiphenyl-4-yl]-1H-imidazol-4-yl}propan-2-ol; |
| 430 | 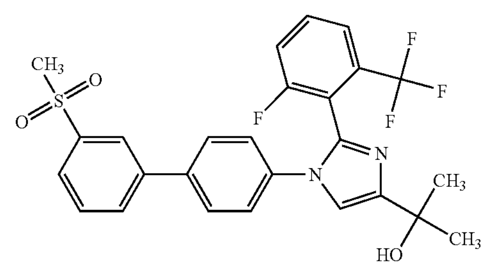 [SMILES: CC(C)(O)c1cn(-c2ccc(-c3cccc(S(C)(=O)=O)c3)cc2)c(-c2c(F)cccc2C(F)(F)F)n1] | 2-{2-[2-fluoro-6-(trifluoromethyl)phenyl]-1-[3'-(methylsulfonyl)biphenyl-4-yl]-1H-imidazol-4-yl}propan-2-ol; |
| 431 | 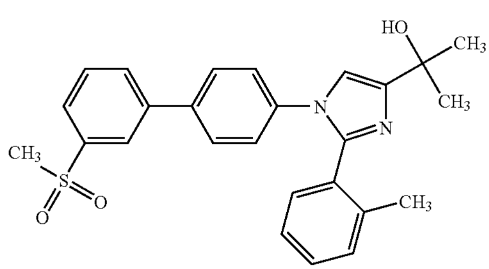 [SMILES: Cc1ccccc1-c1nc(C(C)(C)O)cn1-c1ccc(-c2cccc(S(C)(=O)=O)c2)cc1] | 2-{2-(2-methylphenyl)-1-[3'-(methylsulfonyl)biphenyl-4-yl]-1H-imidazol-4-yl}propan-2-ol; |

TABLE 1-continued

| Cpd # | Structure | Name |
|---|---|---|
| 432 | 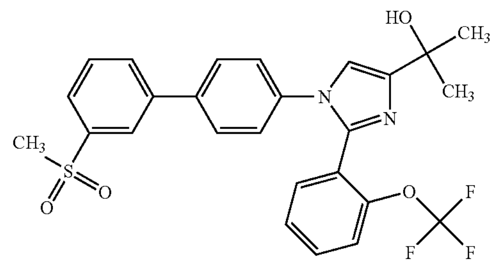 [SMILES: CC(C)(O)c1cn(-c2ccc(-c3cccc(S(C)(=O)=O)c3)cc2)c(-c2ccccc2OC(F)(F)F)n1] | 2-(1-[3'-(methylsulfonyl)biphenyl-4-yl]-2-{2-[(trifluoromethyl)oxy]phenyl}-1H-imidazol-4-yl)propan-2-ol; |
| 433 | 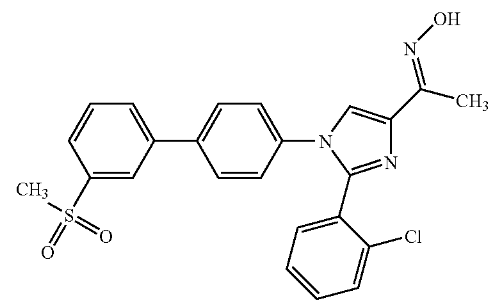 [SMILES: C/C(=N\O)c1cn(-c2ccc(-c3cccc(S(C)(=O)=O)c3)cc2)c(-c2ccccc2Cl)n1] | 1-{2-(2-chlorophenyl)-1-[3'-(methylsulfonyl)biphenyl-4-yl]-1H-imidazol-4-yl}ethanone oxime; |
| 434 | 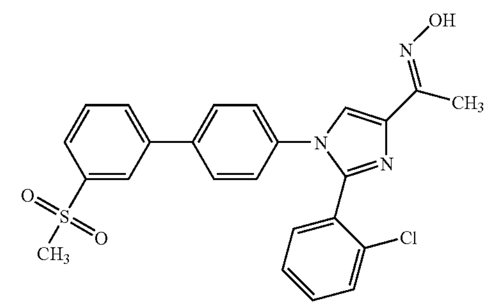 [SMILES: C/C(=N\O)c1cn(-c2ccc(-c3cccc(S(C)(=O)=O)c3)cc2)c(-c2ccccc2Cl)n1] | 1-{2-(2-chlorophenyl)-1-[3'-(methylsulfonyl)biphenyl-4-yl]-1H-imidazol-4-yl}ethanone oxime; |
| 435 | 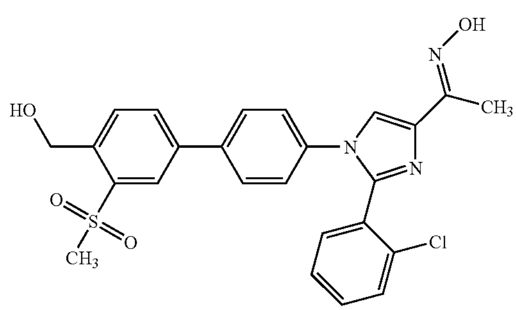 [SMILES: C/C(=N\O)c1cn(-c2ccc(-c3ccc(CO)c(S(C)(=O)=O)c3)cc2)c(-c2ccccc2Cl)n1] | 1-{2-(2-chlorophenyl)-1-[4'-(hydroxymethyl)-3'-(methylsulfonyl)biphenyl-4-yl]-1H-imidazol-4-yl}ethanone oxime; |
| 436 | 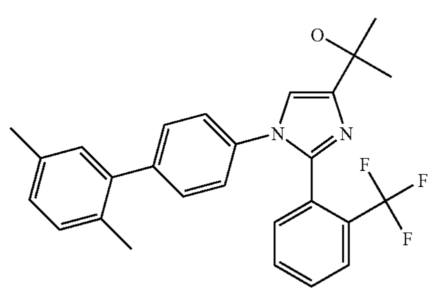 [SMILES: Cc1ccc(C)c(-c2ccc(-n3cc(C(C)(C)O)nc3-c3ccccc3C(F)(F)F)cc2)c1] | 2-(1-(2',5'-dimethylbiphenyl-4-yl-2-(2-trifluoromethyl)phenyl)1H-imidazol-4-yl)propan-2-ol; |

TABLE 1-continued

| Cpd # | Structure | Name |
|---|---|---|
| 437 | 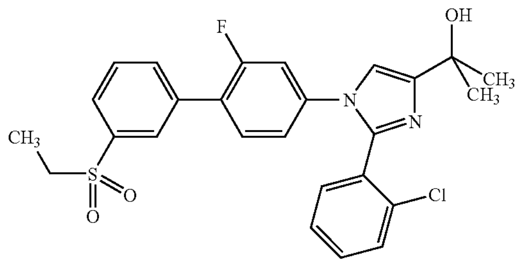 [SMILES: CCS(=O)(=O)c1cccc(-c2ccc(-n3cc(C(C)(C)O)nc3-c3ccccc3Cl)cc2F)c1] | 2-{2-(2-chlorophenyl)-1-[3'-(ethylsulfonyl)-2-fluorobiphenyl-4-yl]-1H-imidazol-4-yl}propan-2-ol; |
| 438 | 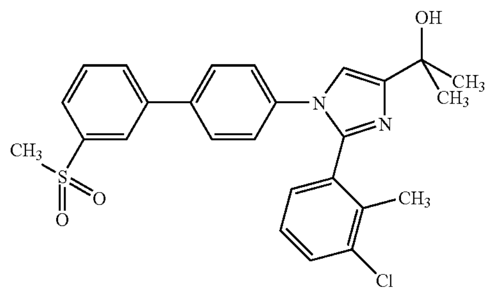 [SMILES: Cc1c(Cl)cccc1-c1nc(C(C)(C)O)cn1-c1ccc(-c2cccc(S(C)(=O)=O)c2)cc1] | 2-{2-(3-chloro-2-methylphenyl)-1-[3'-(methylsulfonyl)biphenyl-4-yl]-1H-imidazol-4-yl}propan-2-ol; |
| 439 | 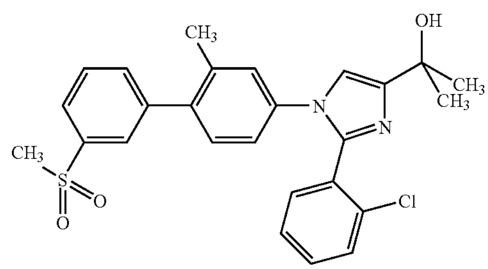 [SMILES: Cc1cc(-n2cc(C(C)(C)O)nc2-c2ccccc2Cl)ccc1-c1cccc(S(C)(=O)=O)c1] | 2-{2-(2-chlorophenyl)-1-[2-methyl-3'-(methylsulfonyl)biphenyl-4-yl]-1H-imidazol-4-yl}propan-2-ol; |
| 440 | 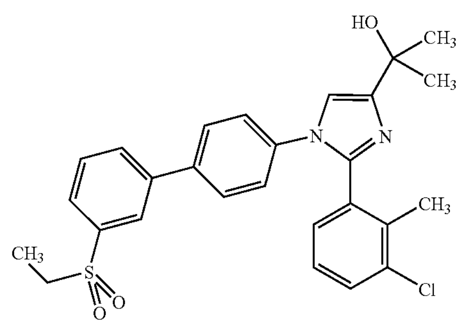 [SMILES: CCS(=O)(=O)c1cccc(-c2ccc(-n3cc(C(C)(C)O)nc3-c3cccc(Cl)c3C)cc2)c1] | 2-{2-(3-chloro-2-methylphenyl)-1-[3'-(ethylsulfonyl)biphenyl-4-yl]-1H-imidazol-4-yl}propan-2-ol; |
| 443 | 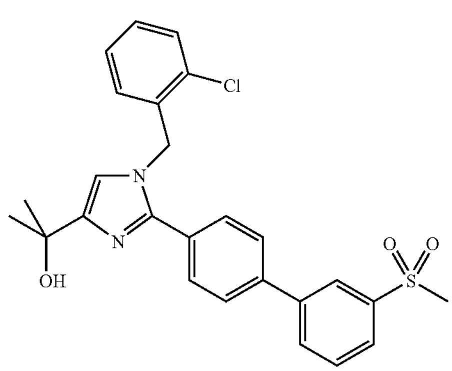 [SMILES: CC(C)(O)c1cn(Cc2ccccc2Cl)c(-c2ccc(-c3cccc(S(C)(=O)=O)c3)cc2)n1] | 2-(1-(2-chlorobenzyl)-2-(3'-(methylsulfonyl)biphenyl-4-yl)-1H-imidazol-4-yl)propan-2-ol |

TABLE 1-continued

| Cpd # | Structure | Name |
|---|---|---|
| 444 | 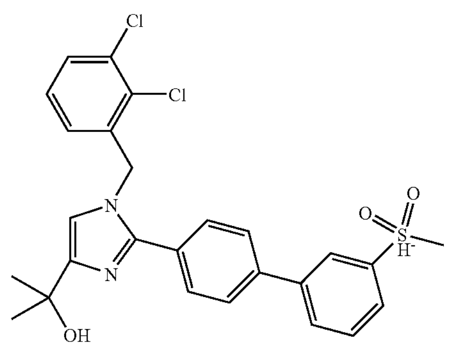 | 2-(1-(2,3-dichlorobenzyl)-2-(3'-(methylsulfonyl)biphenyl-4-yl)-1H-imidazol-4-yl)propan-2-ol |
| 445 | 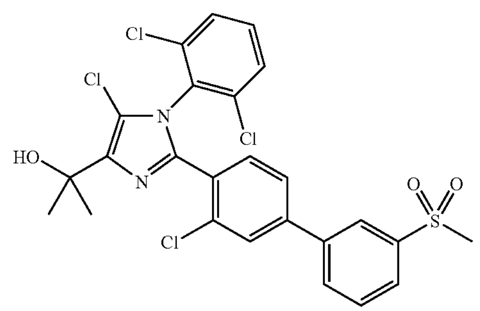 [SMILES: CC(C)(O)c1nc(-c2ccc(-c3cccc(S(C)(=O)=O)c3)cc2Cl)n(-c2c(Cl)cccc2Cl)c1Cl] | 2-(5-chloro-2-(3-chloro-3'-(methylsulfonyl)biphenyl-4-yl)-1-(2,6-dichlorophenyl)-1H-imidazol-4-yl)propan-2-ol |
| 446 | 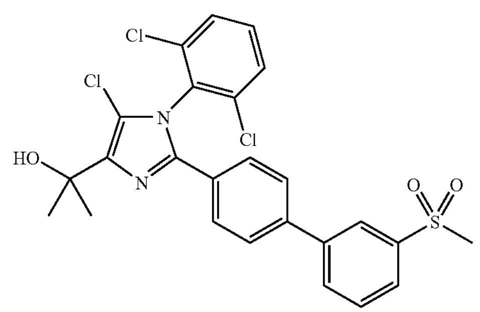 [SMILES: CC(C)(O)c1nc(-c2ccc(-c3cccc(S(C)(=O)=O)c3)cc2)n(-c2c(Cl)cccc2Cl)c1Cl] | 2-(5-chloro-1-(2,6-dichlorophenyl)-2-(3'-(methylsulfonyl)biphenyl-4-yl)-1H-imidazol-4-yl)propan-2-ol |
| 447 | 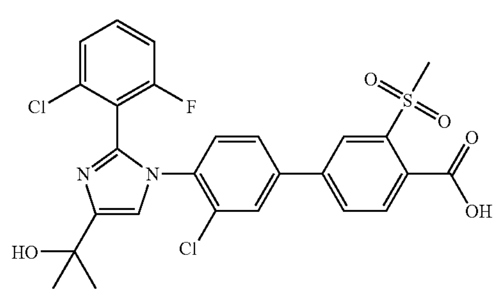 [SMILES: CC(C)(O)c1cn(-c2ccc(-c3ccc(C(=O)O)c(S(C)(=O)=O)c3)cc2Cl)c(-c2c(F)cccc2Cl)n1] | 3'-chloro-4'-(2-(2-chloro-6-fluorophenyl)-4-(2-hydroxypropan-2-yl)-1H-imidazol-1-yl)-3-(methylsulfonyl)biphenyl-4-carboxylic acid |
| 448 | 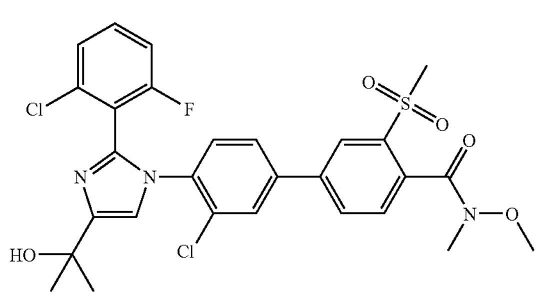 [SMILES: CON(C)C(=O)c1ccc(-c2ccc(-n3cc(C(C)(C)O)nc3-c3c(F)cccc3Cl)c(Cl)c2)cc1S(C)(=O)=O] | 3'-chloro-4'-(2-(2-chloro-6-fluorophenyl)-4-(2-hydroxypropan-2-yl)-1H-imidazol-1-yl)-N-methoxy-N-methyl-3-(methylsulfonyl)biphenyl-4-carboxamide |

TABLE 1-continued

| Cpd # | Structure | Name |
|---|---|---|
| 449 | 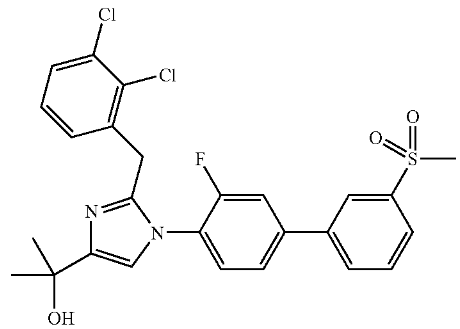 [SMILES: CC(C)(O)c1cn(-c2ccc(-c3cccc(S(C)(=O)=O)c3)cc2F)c(Cc2cccc(Cl)c2Cl)n1] | 2-(2-(2,3-dichlorobenzyl)-1-(3-fluoro-3'-(methylsulfonyl)biphenyl-4-yl)-1H-imidazol-4-yl)propan-2-ol |
| 450 | 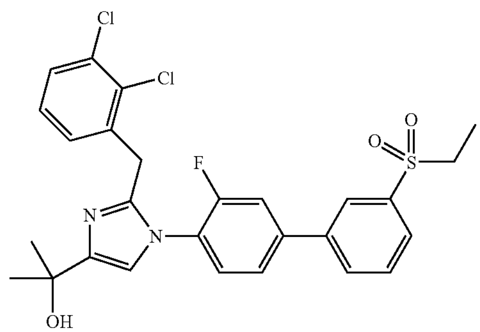 [SMILES: CCS(=O)(=O)c1cccc(-c2ccc(-n3cc(C(C)(C)O)nc3Cc3cccc(Cl)c3Cl)c(F)c2)c1] | 2-(2-(2,3-dichlorobenzyl)-1-(3'-(ethylsulfonyl)-3-fluorobiphenyl-4-yl)-1H-imidazol-4-yl)propan-2-ol |
| 451 | 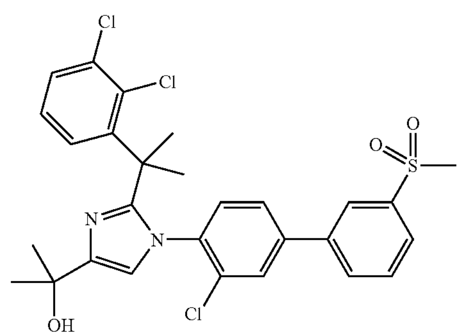 [SMILES: CC(C)(O)c1cn(-c2ccc(-c3cccc(S(C)(=O)=O)c3)cc2Cl)c(C(C)(C)c2cccc(Cl)c2Cl)n1] | 2-(1-(3-chloro-3'-(methylsulfonyl)biphenyl-4-yl)-2-(2-(2,3-dichlorophenyl)propan-2-yl)-1H-imidazol-4-yl)propan-2-ol |
| 452 | 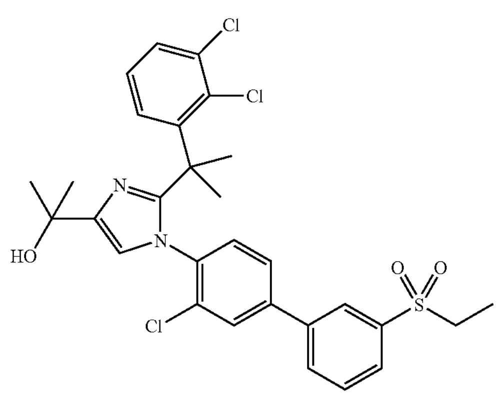 [SMILES: CCS(=O)(=O)c1cccc(-c2ccc(-n3cc(C(C)(C)O)nc3C(C)(C)c3cccc(Cl)c3Cl)c(Cl)c2)c1] | 2-(1-(3-chloro-3'-(ethylsulfonyl)biphenyl-4-yl)-2-(2-(2,3-dichlorophenyl)propan-2-yl)-1H-imidazol-4-yl)propan-2-ol |

TABLE 1-continued

| Cpd # | Structure | Name |
|---|---|---|
| 453 | 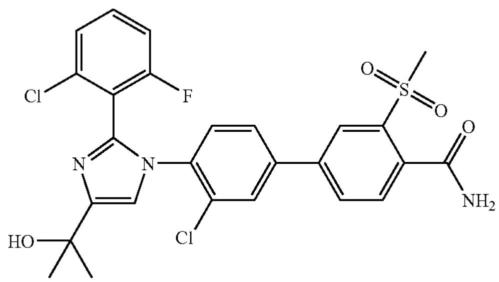 [SMILES: CC(C)(O)c1cn(-c2ccc(-c3ccc(C(N)=O)c(S(C)(=O)=O)c3)cc2Cl)c(-c2c(F)cccc2Cl)n1] | 3'-chloro-4'-(2-(2-chloro-6-fluorophenyl)-4-(2-hydroxypropan-2-yl)-1H-imidazol-1-yl)-3-(methylsulfonyl)biphenyl-4-carboxamide |
| 454 | 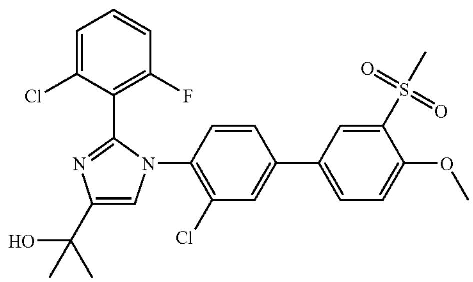 [SMILES: COc1ccc(-c2ccc(-n3cc(C(C)(C)O)nc3-c3c(F)cccc3Cl)c(Cl)c2)cc1S(C)(=O)=O] | 2-(1-(3-chloro-4'-methoxy-3'-(methylsulfonyl)biphenyl-4-yl)-2-(2-chloro-6-fluorophenyl)-1H-imidazol-4-yl)propan-2-ol |
| 455 | 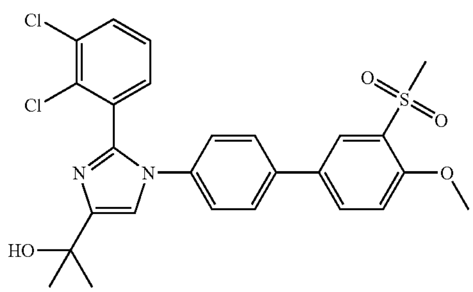 [SMILES: COc1ccc(-c2ccc(-n3cc(C(C)(C)O)nc3-c3cccc(Cl)c3Cl)cc2)cc1S(C)(=O)=O] | 2-(2-(2,3-dichlorophenyl)-1-(4'-methoxy-3'-(methylsulfonyl)biphenyl-4-yl)-1H-imidazol-4-yl)propan-2-ol |
| 456 | 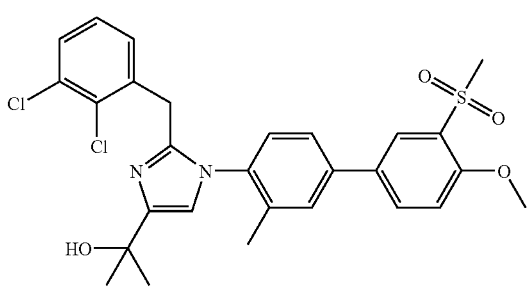 [SMILES: COc1ccc(-c2ccc(-n3cc(C(C)(C)O)nc3Cc3cccc(Cl)c3Cl)c(C)c2)cc1S(C)(=O)=O] | 2-(2-(2,3-dichlorobenzyl)-1-(4'-methoxy-3-methyl-3'-(methylsulfonyl)biphenyl-4-yl)-1H-imidazol-4-yl)propan-2-ol |
| 457 | 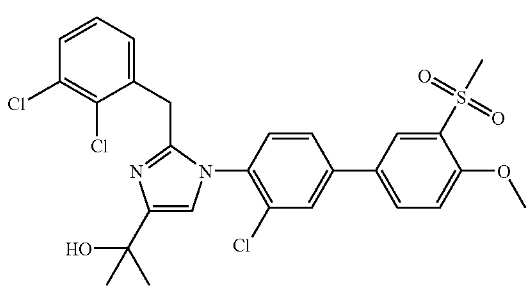 [SMILES: COc1ccc(-c2ccc(-n3cc(C(C)(C)O)nc3Cc3cccc(Cl)c3Cl)c(Cl)c2)cc1S(C)(=O)=O] | 2-(1-(3-chloro-4'-methoxy-3'-(methylsulfonyl)biphenyl-4-yl)-2-(2,3-dichlorobenzyl)-1H-imidazol-4-yl)propan-2-ol |

TABLE 1-continued

| Cpd # | Structure | Name |
|---|---|---|
| 458 | 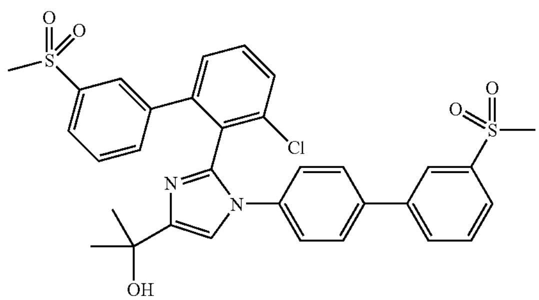 | 2-(2-(3-chloro-3'-(methylsulfonyl)biphenyl-2-yl)-1-(3'-(methylsulfonyl)biphenyl-4-yl)-1H-imidazol-4-yl)propan-2-ol |
| 459 | 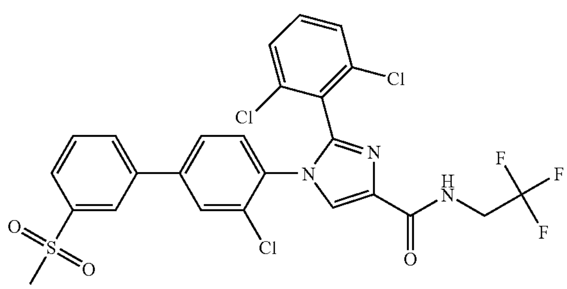 | 1-(3-chloro-3'-(methylsulfonyl)biphenyl-4-yl)-2-(2,6-dichlorophenyl)-N-(2,2,2-trifluoroethyl)-1H-imidazole-4-carboxamide |
| 460 | 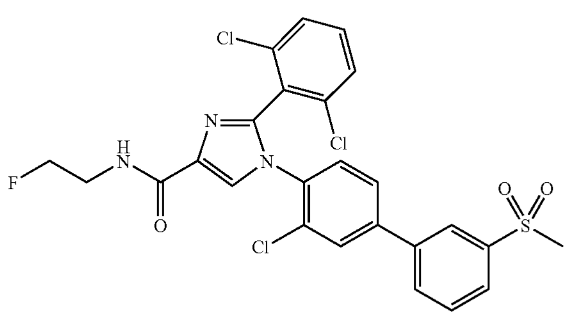 [SMILES: CS(=O)(=O)c1cccc(-c2ccc(-n3cc(C(=O)NCCF)nc3-c3c(Cl)cccc3Cl)c(Cl)c2)c1] | 1-(3-chloro-3'-(methylsulfonyl)biphenyl-4-yl)-2-(2,6-dichlorophenyl)-N-(2-fluoroethyl)-1H-imidazole-4-carboxamide |
| 461 | 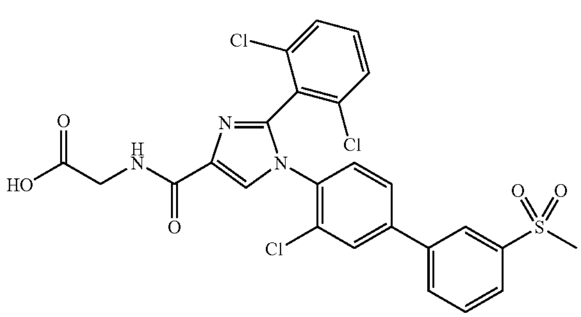 | 2-(1-(3-chloro-3'-(methylsulfonyl)biphenyl-4-yl)-2-(2,6-dichlorophenyl)-1H-imidazole-4-carboxamido)acetic acid |
| 462 | 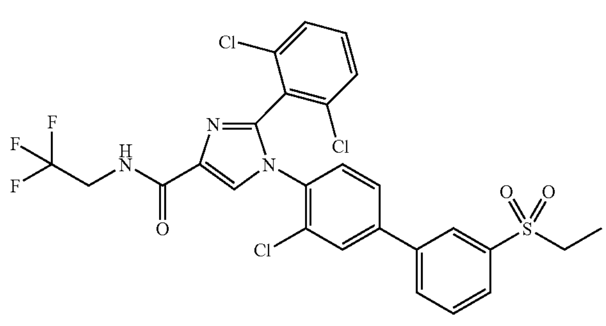 [SMILES: CCS(=O)(=O)c1cccc(-c2ccc(-n3cc(C(=O)NCC(F)(F)F)nc3-c3c(Cl)cccc3Cl)c(Cl)c2)c1] | 1-(3-chloro-3'-(ethylsulfonyl)biphenyl-4-yl)-2-(2,6-dichlorophenyl)-N-(2,2,2-trifluoroethyl)-1H-imidazole-4-carboxamide |

TABLE 1-continued

| Cpd # | Structure | Name |
|---|---|---|
| 463 | 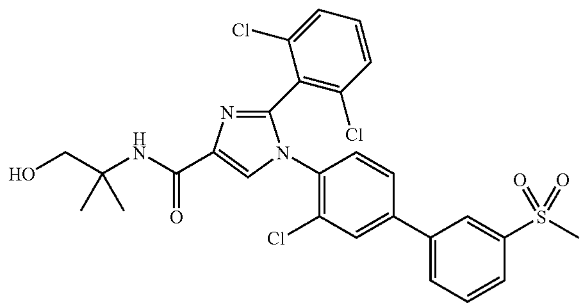 | 1-(3-chloro-3'-(methylsulfonyl)biphenyl-4-yl)-2-(2,6-dichlorophenyl)-N-(1-hydroxy-2-methylpropan-2-yl)-1H-imidazole-4-carboxamide |
| 464 | 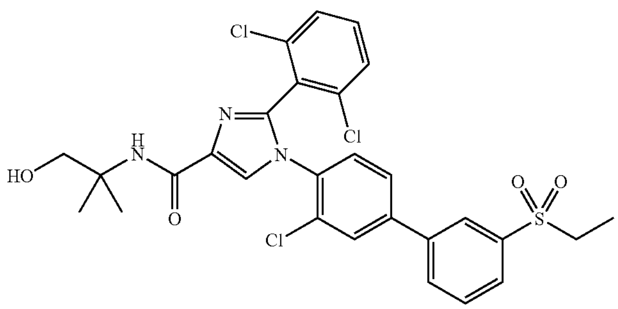 [SMILES: CCS(=O)(=O)c1cccc(-c2ccc(-n3cc(C(=O)NC(C)(C)CO)nc3-c3c(Cl)cccc3Cl)c(Cl)c2)c1] | 1-(3-chloro-3'-(ethylsulfonyl)biphenyl-4-yl)-2-(2,6-dichlorophenyl)-N-(1-hydroxy-2-methylpropan-2-yl)-1H-imidazole-4-carboxamide |
| 465 | 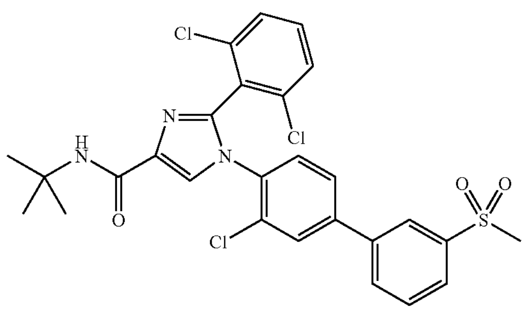 | N-tert-butyl-1-(3-chloro-3'-(methylsulfonyl)biphenyl-4-yl)-2-(2,6-dichlorophenyl)-1H-imidazole-4-carboxamide |
| 466 | 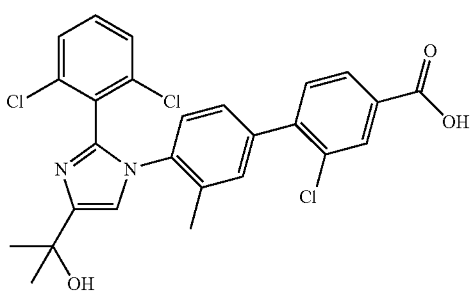 [SMILES: Cc1cc(-c2ccc(C(=O)O)cc2Cl)ccc1-n1cc(C(C)(C)O)nc1-c1c(Cl)cccc1Cl] | 2-chloro-4'-(2-(2,6-dichlorophenyl)-4-(2-hydroxypropan-2-yl)-1H-imidazol-1-yl)-3'-methylbiphenyl-4-carboxylic acid |
| 467 | 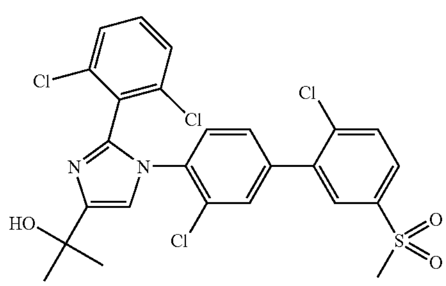 [SMILES: CC(C)(O)c1cn(-c2ccc(-c3cc(S(C)(=O)=O)ccc3Cl)cc2Cl)c(-c2c(Cl)cccc2Cl)n1] | 2-(1-(2',3-dichloro-5'-(methylsulfonyl)biphenyl-4-yl)-2-(2,6-dichlorophenyl)-1H-imidazol-4-yl)propan-2-ol |

TABLE 1-continued

| Cpd # | Structure | Name |
|---|---|---|
| 468 | 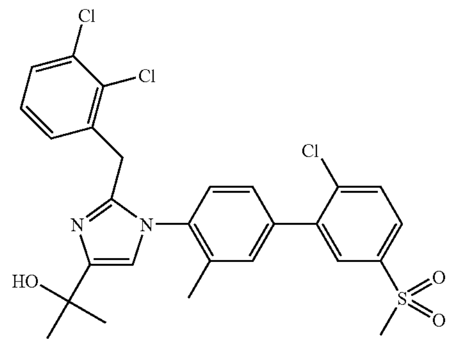 [SMILES: Cc1cc(-c2cc(S(C)(=O)=O)ccc2Cl)ccc1-n1cc(C(C)(C)O)nc1Cc1cccc(Cl)c1Cl] | 2-(1-(2'-chloro-3-methyl-5'-(methylsulfonyl)biphenyl-4-yl)-2-(2,3-dichlorobenzyl)-1H-imidazol-4-yl)propan-2-ol |
| 469 | 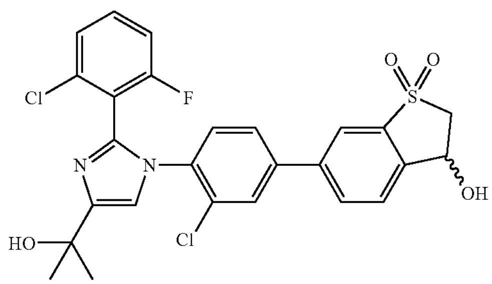 [SMILES: CC(C)(O)c1cn(-c2ccc(-c3ccc4c(c3)S(=O)(=O)CC4O)cc2Cl)c(-c2c(F)cccc2Cl)n1] | 6-{3-chloro-4-[2-(2-chloro-6-fluorophenyl)-4-(1-hydroxy-1-methylethyl)-1H-imidazol-1-yl]phenyl}-2,3-dihydro-1-benzothiophene-3-ol 1,1-dioxide |
| 470 | 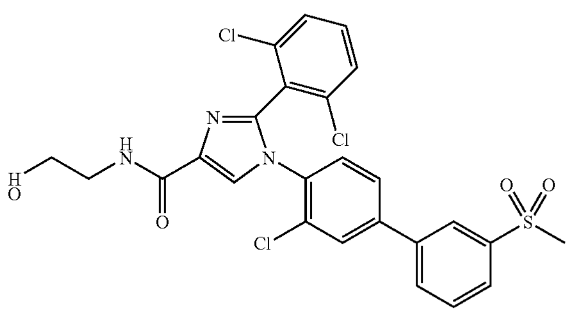 [SMILES: CS(=O)(=O)c1cccc(-c2ccc(-n3cc(C(=O)NCCO)nc3-c3c(Cl)cccc3Cl)c(Cl)c2)c1] | 1-(3-chloro-3'-(methylsulfonyl)biphenyl-4-yl)-2-(2,6-dichlorophenyl)-N-(2-hydroxyethyl)-1H-imidazole-4-carboxamide |
| 471 | 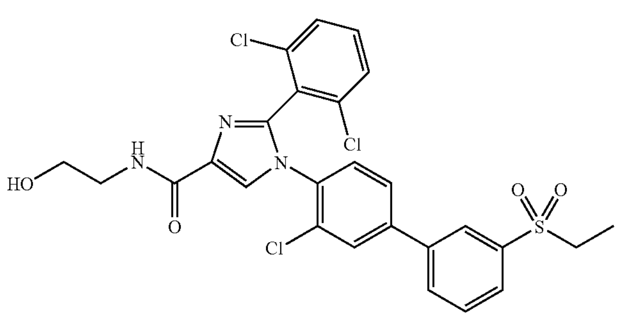 [SMILES: CCS(=O)(=O)c1cccc(-c2ccc(-n3cc(C(=O)NCCO)nc3-c3c(Cl)cccc3Cl)c(Cl)c2)c1] | 1-(3-chloro-3'-(ethylsulfonyl)biphenyl-4-yl)-2-(2,6-dichlorophenyl)-N-(2-hydroxyethyl)-1H-imidazole-4-carboxamide |
| 472 | 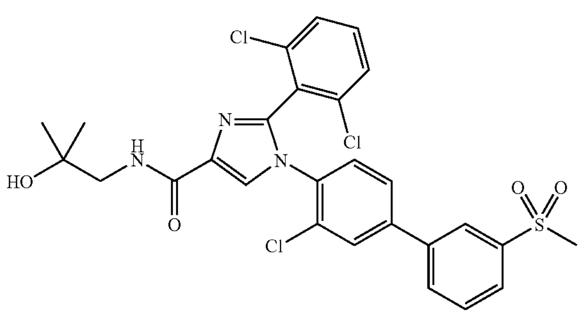 [SMILES: CC(C)(O)CNC(=O)c1cn(-c2ccc(-c3cccc(S(C)(=O)=O)c3)cc2Cl)c(-c2c(Cl)cccc2Cl)n1] | 1-(3-chloro-3'-(methylsulfonyl)biphenyl-4-yl)-2-(2,6-dichlorophenyl)-N-(2-hydroxy-2-methylpropyl)-1H-imidazole-4-carboxamide |

TABLE 1-continued

| Cpd # | Structure | Name |
|---|---|---|
| 473 | 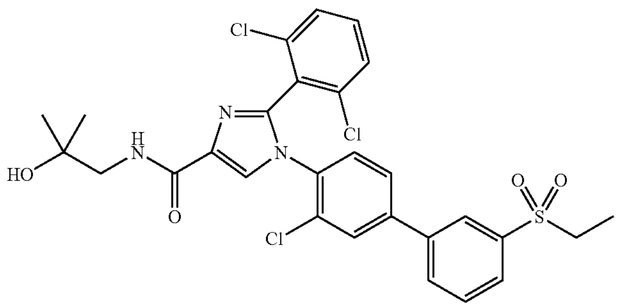 [SMILES: CCS(=O)(=O)c1cccc(-c2ccc(-n3cc(C(=O)NCC(C)(C)O)nc3-c3c(Cl)cccc3Cl)c(Cl)c2)c1] | 1-(3-chloro-3'-(ethylsulfonyl)biphenyl-4-yl)-2-(2,6-dichlorophenyl)-N-(2-hydroxy-2-methylpropyl)-1H-imidazole-4-carboxamide |
| 474 | 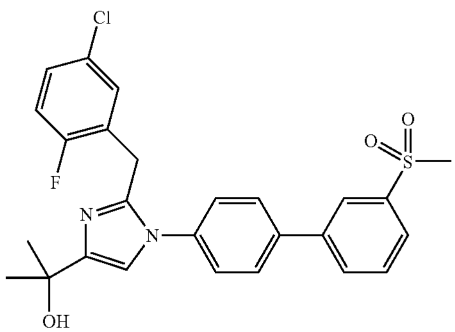 [SMILES: CC(C)(O)c1cn(-c2ccc(-c3cccc(S(C)(=O)=O)c3)cc2)c(Cc2cc(Cl)ccc2F)n1] | 2-(2-(5-chloro-2-fluorobenzyl)-1-(3'-(methylsulfonyl)biphenyl-4-yl)-1H-imidazol-4-yl)propan-2-ol |
| 475 | 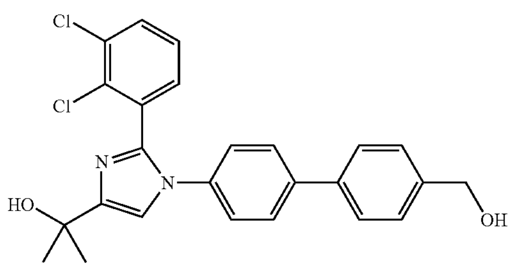 [SMILES: CC(C)(O)c1cn(-c2ccc(-c3ccc(CO)cc3)cc2)c(-c2cccc(Cl)c2Cl)n1] | 2-(2-(2,3-dichlorophenyl)-1-(4'-(hydroxymethyl)biphenyl-4-yl)-1H-imidazol-4-yl)propan-2-ol |
| 476 | 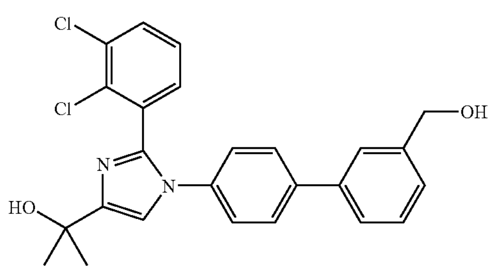 [SMILES: CC(C)(O)c1cn(-c2ccc(-c3cccc(CO)c3)cc2)c(-c2cccc(Cl)c2Cl)n1] | 2-(2-(2,3-dichlorophenyl)-1-(3'-(hydroxymethyl)biphenyl-4-yl)-1H-imidazol-4-yl)propan-2-ol |
| 477 | 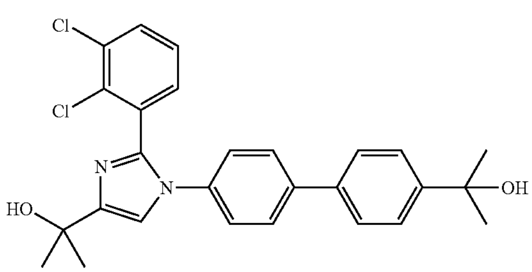 [SMILES: CC(C)(O)c1ccc(-c2ccc(-n3cc(C(C)(C)O)nc3-c3cccc(Cl)c3Cl)cc2)cc1] | 2-(2-(2,3-dichlorophenyl)-1-(4'-(2-hydroxypropan-2-yl)biphenyl-4-yl)-1H-imidazol-4-yl)propan-2-ol |

TABLE 1-continued

| Cpd # | Structure | Name |
|---|---|---|
| 478 | 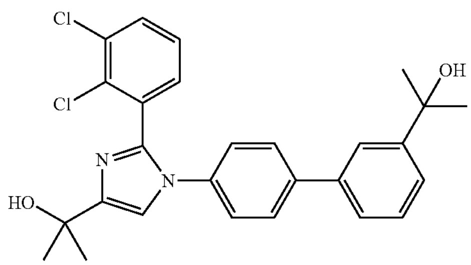 [SMILES: CC(C)(O)c1cccc(-c2ccc(-n3cc(C(C)(C)O)nc3-c3cccc(Cl)c3Cl)cc2)c1] | 2-(2-(2,3-dichlorophenyl)-1-(3'-(2-hydroxypropan-2-yl)biphenyl-4-yl)-1H-imidazol-4-yl)propan-2-ol |
| 479 | 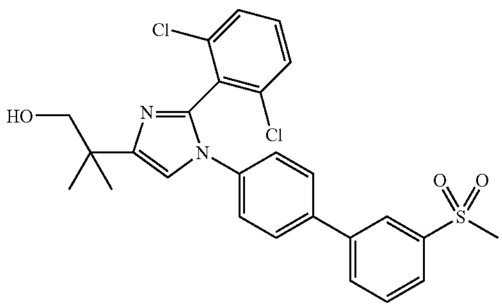 [SMILES: CC(C)(CO)c1cn(-c2ccc(-c3cccc(S(C)(=O)=O)c3)cc2)c(-c2c(Cl)cccc2Cl)n1] | 2-(2-(2,6-dichlorophenyl)-1-(3'-(methylsulfonyl)biphenyl-4-yl)-1H-imidazol-4-yl)-2-methylpropan-1-ol |
| 480 | 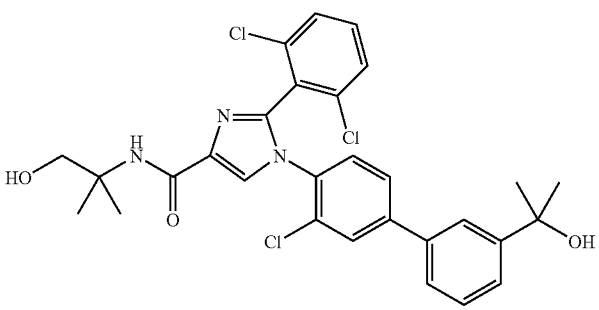 [SMILES: CC(C)(CO)NC(=O)c1cn(-c2ccc(-c3cccc(C(C)(C)O)c3)cc2Cl)c(-c2c(Cl)cccc2Cl)n1] | 1-(3-chloro-3'-(2-hydroxypropan-2-yl)biphenyl-4-yl)-2-(2,6-dichlorophenyl)-N-(1-hydroxy-2-methylpropan-2-yl)-1H-imidazole-4-carboxamide |
| 481 | 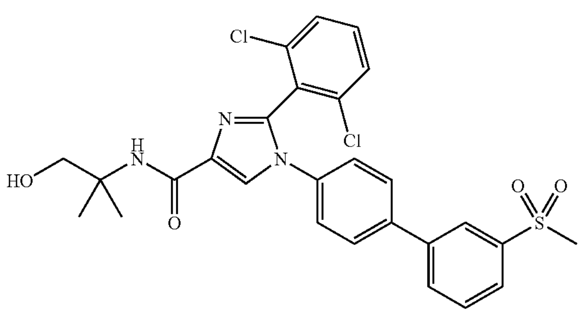 [SMILES: CC(C)(CO)NC(=O)c1cn(-c2ccc(-c3cccc(S(C)(=O)=O)c3)cc2)c(-c2c(Cl)cccc2Cl)n1] | 2-(2,6-dichlorophenyl)-N-(1-hydroxy-2-methylpropan-2-yl)-1-(3'-(methylsulfonyl)biphenyl-4-yl)-1H-imidazole-4-carboxamide |
| 482 | 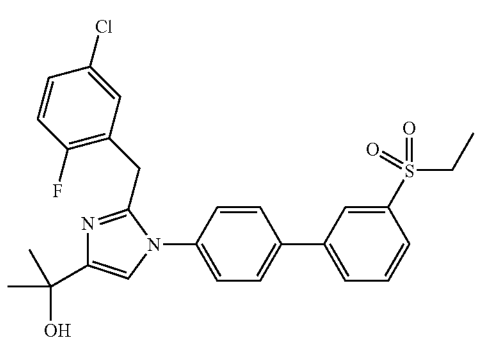 [SMILES: CCS(=O)(=O)c1cccc(-c2ccc(-n3cc(C(C)(C)O)nc3Cc3cc(Cl)ccc3F)cc2)c1] | 2-(2-(5-chloro-2-fluorobenzyl)-1-(3'-(ethylsulfonyl)biphenyl-4-yl)-1H-imidazol-4-yl)propan-2-ol |

TABLE 1-continued

| Cpd # | Structure | Name |
|---|---|---|
| 483 | 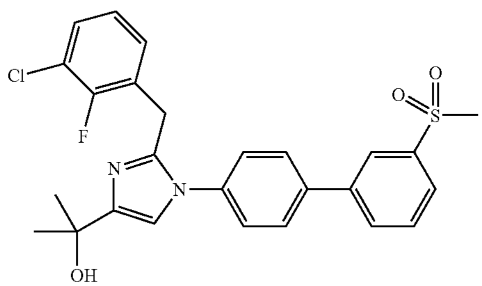 [SMILES: CC(C)(O)c1cn(-c2ccc(-c3cccc(S(C)(=O)=O)c3)cc2)c(Cc2cccc(Cl)c2F)n1] | 2-(2-(3-chloro-2-fluorobenzyl)-1-(3'-(methylsulfonyl)biphenyl-4-yl)-1H-imidazol-4-yl)propan-2-ol |
| 484 | 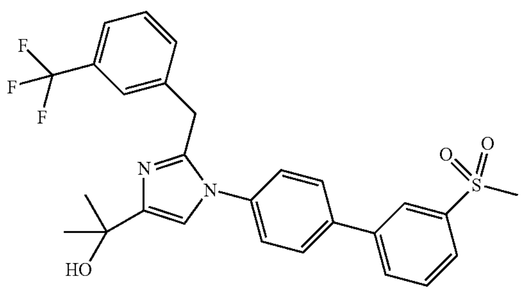 [SMILES: CC(C)(O)c1cn(-c2ccc(-c3cccc(S(C)(=O)=O)c3)cc2)c(Cc2cccc(C(F)(F)F)c2)n1] | 2-(1-(3'-(methylsulfonyl)biphenyl-4-yl)-2-(3-trifluoromethyl)benzyl)-1H-imidazol-4-yl)propan-2-ol |
| 485 | 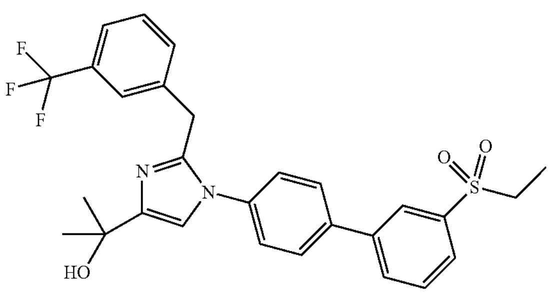 [SMILES: CCS(=O)(=O)c1cccc(-c2ccc(-n3cc(C(C)(C)O)nc3Cc3cccc(C(F)(F)F)c3)cc2)c1] | 2-(1-(3'-(ethylsulfonyl)biphenyl-4-yl)-2-(3-(trifluoromethyl)benzyl)-1H-imidazol-4-yl)propan-2-ol |
| 486 | 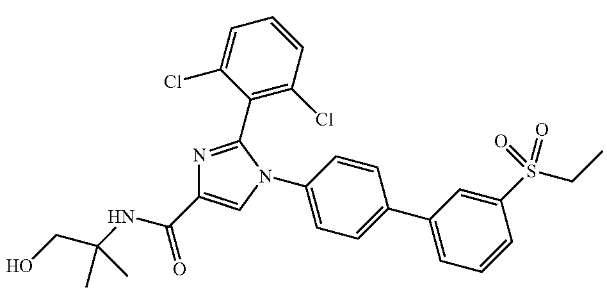 [SMILES: CCS(=O)(=O)c1cccc(-c2ccc(-n3cc(C(=O)NC(C)(C)CO)nc3-c3c(Cl)cccc3Cl)cc2)c1] | 2-(2,6-dichlorophenyl)-1-(3'-(ethylsulfonyl)biphenyl-4-yl)-N-(1-hydroxy-2-methylpropan-2-yl)-1H-imidazole-4-carboxamide |
| 487 | 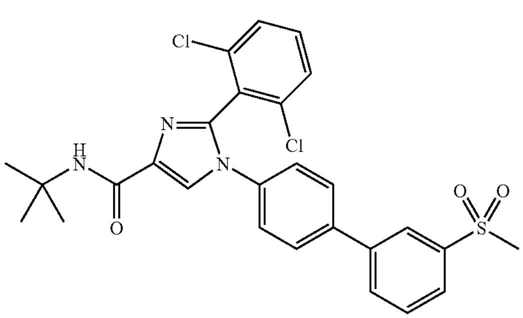 [SMILES: CC(C)(C)NC(=O)c1cn(-c2ccc(-c3cccc(S(C)(=O)=O)c3)cc2)c(-c2c(Cl)cccc2Cl)n1] | N-tert-butyl-2-(2,6-dichlorophenyl)-1-(3'-(methylsulfonyl)biphenyl-4-yl)-1H-imidazole-4-carboxamide |

TABLE 2

| | | |
|---|---|---|
| 363 | 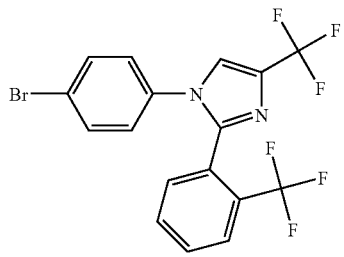 [SMILES: FC(F)(F)c1cn(-c2ccc(Br)cc2)c(-c2ccccc2C(F)(F)F)n1] | 1-(4-bromophenyl)-4-(trifluoromethyl)-2-[2-(trifluoromethyl)phenyl]-1H-imidazole; |
| 368 | 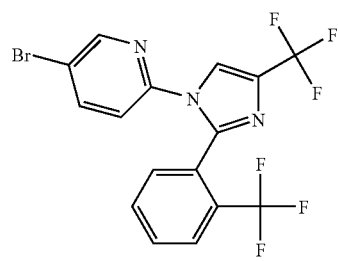 [SMILES: FC(F)(F)c1cn(-c2ccc(Br)cn2)c(-c2ccccc2C(F)(F)F)n1] | 5-bromo-2-{4-(trifluoromethyl)-2-[2-(trifluoromethyl)phenyl]-1H-imidazol-1-yl}pyridine; |
| 374 | 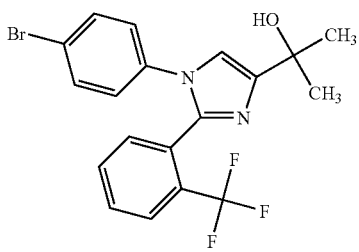 [SMILES: CC(C)(O)c1cn(-c2ccc(Br)cc2)c(-c2ccccc2C(F)(F)F)n1] | 2-{1-(4-bromophenyl)-2-[2-(trifluoromethyl)phenyl]-1H-imidazol-4-yl}propan-2-ol; |
| 377 | 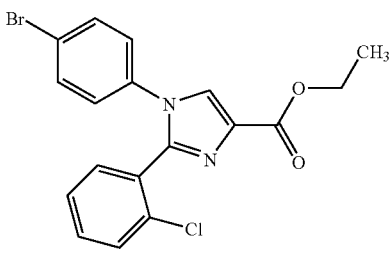 [SMILES: CCOC(=O)c1cn(-c2ccc(Br)cc2)c(-c2ccccc2Cl)n1] | ethyl 1-(4-bromophenyl)-2-(2-chlorophenyl)-1H-imidazole-4-carboxylate; |
| 396 | 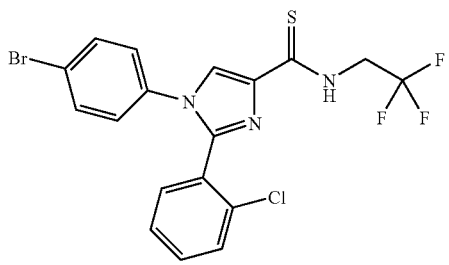 [SMILES: FC(F)(F)CNC(=S)c1cn(-c2ccc(Br)cc2)c(-c2ccccc2Cl)n1] | 1-(4-bromophenyl)-2-(2-chlorophenyl)-N-(2,2,2-trifluoroethyl)-1H-imidazole-4-carbothioamide; |
| 423 | 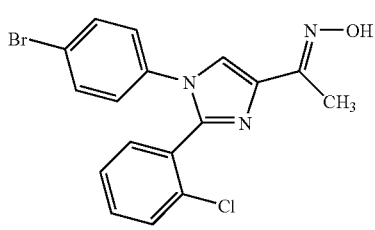 [SMILES: C/C(=N\O)c1cn(-c2ccc(Br)cc2)c(-c2ccccc2Cl)n1] | 1-[1-(4-bromophenyl)-2-(2-chlorophenyl)-1H-imidazol-4-yl]ethanone oxime; |

TABLE 2-continued

| | | |
|---|---|---|
| 441 | [structure] | 2-(5-bromo-2-thienyl)-1-(2,5-dichlorophenyl)-4-(trifluoromethyl)-1H-imidazole; |
| 442 | [structure] | 2-(5-bromo-2-thienyl)-1-(2-chlorophenyl)-4-(trifluoromethyl)-1H-imidazole; |

EXAMPLE 31

FRET Coactivator Assay

The FRET coactivator assay measures the ability of LXR ligands to promote protein-protein interactions between the ligand binding domain (LBD) of LXR and transcriptional coactivator proteins. The assay involves the use a recombinant Glutathione-5-transferase (GST)-nuclear receptor ligand binding domain (LBD) fusion protein and a synthetic biotinylated peptide sequence derived from the receptor interacting domain of a co-activator peptide such as the steroid receptor coactivator 1 (SRC-1). Typically GST-LBD is labeled with a europium chelate (donor) via a europium-tagged anti-GST antibody, and the coactivator peptide is labeled with allophycocyanin via a streptavidin-biotin linkage.

In the presence of an agonist for the nuclear receptor, the peptide is recruited to the GST-LBD bringing europium and allophycocyanin into close proximity to enable energy transfer from the europium chelate to the allophycocyanin. Upon excitation of the complex with light at 340 nm excitation energy absorbed by the europium chelate is transmitted to the allophycocyanin moiety resulting in emission at 665 nm. If the europium chelate is not brought into close proximity to the allophycocyanin moiety there is little or no energy transfer and excitation of the europium chelate results in emission at 615 nm. Thus the intensity of light emitted at 665 nm gives an indication of the strength of the protein-protein interaction.

Required Materials:

Partially purified recombinant protein comprising glutathione-5-transferase fused in frame to the LXR-ligand binding domain (comprising amino acids 188-447 of human LXRα, or amino acids 198-461 of human LXRβ). Biotinylated peptide containing a SRC-1 LXXLL receptor interaction motif (B-SRC-1). Anti-GST antibody conjugated to a Europium chelate (αGST-K) (From Wallac/PE Life Sciences Cat#AD0064). Streptavidin linked allophycocyanin (SA-APC) (From Wallac/PE Life Sciences CAT#AD0059A).

1×FRET Buffer: (20 mM $KH_2PO_4/K_2HPO_4$ pH 7.3, 150 mM NaCl, 2.5 mM CHAPS, 2 mM EDTA, 1 mM DTT (add fresh)). 96 well or 384 well black multiwell plates (from LJL) Stock Solutions:

0.5 M $KH_2PO_4/K_2HPO_4$: pH 7.3; 5 M NaCl; 80 mM (5%) CHAPS; 0.5 M EDTA pH 8.0; 1 M DTT (keep at −20° C.)

Preparation of Screening Reagents:

Prepare reaction mixture for the appropriate number of wells by combining the following reagents 5 nM/well GST-hLXRαLBD, 5 nM/well GST-hLXRβLBD, 5 nM/well Anti-GST antibody (Eu), 12 nM/well biotin-SRC-1 peptide, 12 nM/well APC-SA adjust the volume to 10 µL/well with 1×-FRET buffer.

Procedure:

Add 0.5 µL of a 1 mM stock compound (for approx. 10 µM final concentration) or solvent to each well in a 96 well or 384 well black plate (LJL). Add 10 µl reaction mixture (prepared above) to each well of the multiwell plate. Incubate covered or in the dark (the APC is light sensitive) at ambient temperature for 1-4 hours. After this time if reactions are not read they can be stored at 4° C. for several more hours without too much loss of signal.

Read the plate using an LJL Analyst, or similar instrument, using the following conditions: Channel 1: Excitation is 330 nm and emission is 615. This is for Eu chelate; Channel 2: Excitation is 330 nm and emission is 665. This is for APC; For channel 1: Flashes per well=100; Integration time=1000 µs; interval between flashes=1×10 ms; Delay after flash=200 µs; For channel 2: Flashes per well=100; Integration time=100 µs; interval between flashes=1×10 ins; Delay after flashes=65 µs.

EXAMPLE 32

Scintillation Proximity Assay (SPA)

The SPA assay measures the radioactive signal generated by the binding of $^3H$-24,25-epoxycholesterol to LXRα or LXRβ. The basis of the assay is the use of SPA beads containing a scintillant, such that when binding to the receptor brings the labeled ligand into proximity with the bead, the energy from the label stimulates the scintillant to emit light.

The light is measured using a standard microplate scintillation reader. The ability of a ligand to bind to a receptor can be measured by assessing the degree to which the compound can compete off a radiolabelled ligand with known affinity for the receptor.

Required Materials:
Label: $^3$H-24,25-epoxy-cholesterol (Amersham)
LXRα lysate: Baculovirus expressed LXRα/RXR heterodimer with RXR having a 6-HIS tag produced as a crude lysate
LXRβ lysate: Baculovirus expressed LXRβ/RXR heterodimer with RXR having a 6-HIS tag produced as a crude lysate
SPA beads: Ysi copper His-tag SPA beads (Amersham)
Plates: Non-binding surface 96-well plate (Corning)
Protein lysate dilution buffer: (20 mM Tris-HCl pH 7.9, 500 mM NaCl, 5 mM Imidazole). 2×SPA
Buffer: (40 mM $K_2$ $HPO_4$/$KH_2$ $PO_4$ pH7.3, 100 mM NaCl, 0.05% Tween 20, 20% Glycerol, 4 mM EDTA) 2×SPA Buffer w/o EDTA: (40 mM $K_2$ $HPO_4$/$KH_2$ $PO_4$ pH7.3, 100 mM NaCl, 0.05% Tween 20, 20% Glycerol)
Stock Solutions
0.5 M $K_2$ $HPO_4$/$KH_2$ $PO_4$ pH 7.3; 0.5 M EDTA pH 8.0; 5 M NaCl; 10% Tween-20; Glycerol
Preparation of Protein Lysates Baculovirus expression plasmids for human RXR α_accession No NM_002957)LXRα accession No U22662), LXRβ accession No U07132) were made by cloning the appropriate full-length cDNAs into the pBacPakhis1 vector (Clontech, CA) following standard procedures. Insertion of the cDNAs into the pBAcPakhis1 vector polylinker created an in frame fusion to the cDNA to an N-terminal poly-His tag present in pBacPakhis1. Correct cloning was confirmed by restriction mapping, and/or sequencing.

Cell lysates were prepared by infecting healthy, Sf9 insect cells at a density of approximately 1.25×10$^6$/ml at 27° C., in a total volume of 500 mL per 1 L sized spinner flasks, cultured under standard conditions. To prepare LXRα lysate, insect cells were co-transfected with the LXRα expression cassette at an M.O.I of 0.5 to 0.8 and with the RXR expression cassette at a M.O.I. of approximately 1.6. To prepare LXRβ lysate, insect cells were co-transfected with the LXRβ expression cassette at an M.O.I of approximately 1.6 and with the RXR expression cassette at a M.O.I. of approximately 1.6. In both cases cells were incubated for 48 hours at 27° C. with constant shaking prior to harvesting.

After incubation, cells were harvested by centrifugation and pelleted. Cell pellets were resuspended in two volumes of ice-cold freshly prepared extraction buffer (20 mM Tris pH 8.0, 10 mM Imidazole, 400 mM NaCl, containing one EDTA free protease inhibitor tablet (Roche Catalog No: 1836170) per 10 ml of extraction buffer). Cells were homogenized slowly on ice using a Douncer to achieve 80-90% cell lysis. The homogenate was centrifuged in a pre-chilled rotor (Ti50 or Ti70, or equivalent) at 45,000 rpm for 30 minutes at 4° C. Aliquots of the supernatant were frozen on dry ice and stored frozen at −80° C. until quantification and quality control. Aliquots of the lysates were tested in the SPA assay to ensure lot to lot consistency, and via SDS-PAGE analysis after purification using Ni-NTA Resin (Qiagen) and adjusted for protein concentration and expression level prior to use in screening assays.

Preparation of Screening Reagents

[$^3$H] 24,25 Epoxycholesterol (EC) solution: For a single 384-well plate (or 400 wells), 21 μL of [$^3$H] EC (specific activity 76.5 Ci/mmol, concentration 3.2 mCi/mL) was added to 4.4 mL of 2×SPA buffer to provide for a final concentration of 200 nM. For each additional 384-well plate, an additional 19.1 μL of [$^3$H] EC was added to 4.0 mL of additional 2×SPA buffer. The final concentration of [$^3$H] EC in the well was 50 nM. LXRα lysate (prepared as above) was diluted with protein lysate dilution buffer. 1400 μL of diluted LXRα lysate was prepared per 384-well plate, (or 200 wells) and 1120 μL of diluted LXRα lysate was prepared for each additional 384-well plate. LXRβ lysate (prepared as above) was diluted with protein lysate dilution buffer. 1400 μL of diluted LXRβ lysate was prepared per 384-well plate, (or 200 wells) and 1120 μL of diluted LXRβ lysate was prepared for each additional 384-well plate. SPA bead solution: For a 384-well plate (or 400 wells), 3.75 mL of 2×SPA buffer w/o EDTA, 2.25 mL of $H_2O$, and 1.5 mL of Ysi His-tag SPA beads (vortex well before taking) were mixed together. For each additional 384-well plate, an additional 3.5 mL of 2×SPA buffer w/o EDTA, 2.1 mL of $H_2O$, and 1.4 mL of Ysi His-tag SPA beads were mixed together.

Procedure:

Appropriate dilutions of each compound were prepared and pipetted into the appropriate wells of a multiwell plate. 9.1 L of [$^3$H] EC was added to each well of column 2-23 of the multiwell plate. 5 μl of diluted LXRα lysate was added to each well of column 2-23 on odd rows of the multiwell plate. 5 μL of diluted LXRβ lysate was added to each well of column 2-23 on even rows of the multiwell plate. 17.5 μL of SPA bead solution was added to each well of column 2-23 of the multiwell plate.

The plates were covered with clear sealer and placed in an incubator at ambient temperature for 1 hour. After incubation plates were analyzed using a luminescent plate reader (MicroBeta, Wallac) using the program n ABASE 3H_384DPM. The setting for n ABASE 3H_384DPM was: Counting Mode: DPM; Sample Type: SPA; ParaLux Mode: low background; Count time: 30 sec.

Assays for LXRα and LXRβ 3 were performed in the identical manner. The determined Ki represents the average of at least two independent dose response experiments. The binding affinity for each compound may be determined by non-linear regression analysis using the one site competition formula to determine the IC; where:

$$Y = \text{Bottom} + \frac{(\text{Top} - \text{Bottom})}{(1 + 10^{X - \log IC_{50}})}$$

The Ki is than calculated using the Cheng and Prusoff equation where:

$K_i = IC_{50}/(1+[\text{Concentration of Ligand}]/Kd \text{ of Ligand})$

For this assay, typically the Concentration of Ligand=50 nM and the Kd of EC for the receptor is 200 nM as determined by saturation binding.

The compounds of the invention demonstrated the ability to bind to LXRα and/or LXR$^3$ when tested in this assay.

EXAMPLE 33

Co-Transfection Assay

To measure the ability of compounds to activate or inhibit the transcriptional activity of LXR in a cell based assay, the co-transfection assay was used. It has been shown that LXR functions as a heterodimer with RXR . For the co-transfection assay, expression plasmids for LXR and RXR are introduced via transient transfection into mammalian cells along with a luciferase reporter plasmid that contains one copy of a DNA sequence that is bound by LXR-RXR heterodimers (LXRE; Willy, P. et. al. 1995). Treatment of transfected cells with an LXR agonist increases the transcriptional activity of LXR, which is measured by an increase in luciferase activity. Similarly, LXR antagonist activity can be measured by determining the ability of a compound to competitively inhibit the activity of a LXR agonist.

Required Materials

CV-1 African Green Monkey Kidney Cells Co-transfection expression plasmids, comprising full-length LXRα (pCMX-h LXRα, LXRβ (pCMX-hLXRβ), or RXRα (pCMX-RXR), reporter plasmid (LXREx1-Tk-Luciferase), and control (pCMX-Galactosidase expression vector) (Willey et al. Genes & Development 9 1033-1045 (1995)). Transfection reagent such as FuGENE6 (Roche). 1× Cell lysis buffer (1% Triton X 100 (JT Baker X200-07), 10% Glycerol (JT Baker M778-07), 5 mM Ditriotreitol (Quantum Bioprobe DTT03; add fresh before lysing), 1 mM EGTA (Ethylene Glycol-bis (B-Amino ethyl ether)-N,N,N',N'-Tetracetic Acid) (Sigma E-4378), 25 mM Tricine (ICN 807420) pH 7.8) 1× Luciferase assay buffer (pH at 7.8) (0.73 mM ATP, 22.3 mM Tricine, 0.11 mM EDTA, 33.3 mM DTT) 1× Luciferrin/CoA (11 mM Luciferin, 3.05 mM Coenzyme A, 10 mM HEPES)

Preparation of Screening Reagents

CV-1 cells were prepared 24 hours prior to the experiment by plating them into T-175 flasks or 500 cm$^2$ dishes in order to achieve 70-80% confluency on the day of the transfection. The number of cells to be transfected was determined by the number of plates to be screened. Each 384 well plate requires $1.92 \times 10^6$ cells or 5000 cells per well. DNA Transfection Reagent was prepared by mixing the required plasmid DNAs with a cationic lipid transfection reagent FuGENE6 (Roche) by following the instructions provided with the reagents. Optimal DNA amounts were determined empirically per cell line and size of vessel to be transfected. 10-12 mL of media was added to the DNA Transfection Reagent and this mixture was added to the cells after aspirating media from the T175 cm$^2$ flask. Cells were then incubated at least 5 hours at 37° C. to prepare screening cells.

Luciferase assay reagent was prepared by combining before use (per 10 mL): 10 mL 1× Luciferase assay buffer; 0.54 mL of 1× Luciferrin/CoA; 0.54 mL of 0.2 M Magnesium sulfate Procedure Assay plates were prepared by dispensing 5 µL of compound per well of a 384 well plate to achieve final compound concentration of 10 µM and no more than 1% DMSO. Media was removed from the screening cells, the cells trypsinized, harvested cells by centrifugation, counted, and plated at a density of approximately 5000 cells per well in the 384 well assay plate prepared above in a volume of about 45 µL. Assay plates containing both compounds and screening cells (50 µL in total volume) were incubated for 20 hours at 37° C.

After incubation with compounds, media was removed from the cells and lysis buffer (30 µL/well) added. After 30 minutes at ambient temperature, luciferase assay buffer (30 µL/well) was added and the assay plates read on a luminometer (PE Biosystems Northstar reader with on-board injectors, or equivalent). Plates were read immediately after addition of luciferase assay buffer.

The LXR/LXRE co-transfection assay can be used to establish the $EC_{50}$ so/$IC_{50}$ values for potency and percent activity or inhibition for efficacy. Efficacy defines the activity of a compound relative to a high control ((N-(3-((4-fluorophenyl)-(naphthalene-2-sulfonyl)amino)propyl)-2,2-dimethylpropionamide)) or a low control (DMSO/vehicle). The dose response curves are generated from an 8 point curve with concentrations differing by ½ LOG units. Each point represents the average of 4 wells of data from a 384 well plate.

The data from this assay is fitted to the following equation, from the $EC_{50}$ value may be solved:

$$Y = \text{Bottom} + (\text{Top} - \text{Bottom})/(1 + 10^{(logEC50-X)*HillSlope})$$

The $EC_{50}/IC_{50}$ is therefore defined as the concentration at which an agonist or antagonist elicits a response that is half way between the Top (maximum) and Bottom (baseline) values. The $EC_{50}/IC_{50}$ values represented are the averages of at least 3 independent experiments. The determination of the relative efficacy or % control for an agonist is by comparison to the maximum response achieved by ((N-(3-((4-fluorophenyl)-(naphthalene-2-sulfonyl)-amino)propyl)-2,2-dimethylpropionamide) that is measured individually in each dose response experiment.

For the antagonist assay, a LXR agonist can be added to each well of a 384 well plate to elicit a response. The % inhibition for each antagonist is therefore a measurement of the inhibition of the activity of the agonist. In this example, 100% inhibition would indicate that the activity of a specific concentration of LXR agonist has been reduced to baseline levels, defined as the activity of the assay in the presence of DMSO only.

Compounds of the invention, when tested in this assay, demonstrated the ability to modulate the activity of LXRα and/or LXRβ. Preferably, the active compounds modulate the activity of LXR with a EC50 or IC50 of about 10 µM or less. More preferably, the EC50 or $IC_{50}$ of the preferred active compounds is about 1 µM or less.

EXAMPLE 34

In Vivo Studies

In order to evaluate direct regulation of key target genes by the compounds of the invention, animals are administered a single oral dose of the test compound and tissues collected at various time points. Male C57BL/6 mice (n=8) are dosed by oral gavage with vehicle or compound. At various time points after the dose, animals are bled via the retro orbital sinus for plasma collection. Animals are then euthanized and tissues, such as liver and intestinal mucosa are collected and snap frozen for further analysis. Plasma is analyzed for a lipid parameters, such as total cholesterol, HDL cholesterol and triglyceride levels. RNA is extracted for frozen tissues and can be analyzed by quantitative real time PCR for regulation of key target genes. To identify specificity of target gene regulation by LXR subtypes, LXR deficient mice (LXR−/− or LXP−/−) and C57BL/6 wild-type controls are used in this same protocol.

Plasma Lipid Evaluation:

To compare the effects of compounds on plasma cholesterol and triglycerides, animals are dosed with compound for one week and plasma lipid levels are monitored throughout the study. Male C57BL/6 mice (n=8) are dosed daily by oral gavage with vehicle or compound. Plasma samples are taken on day −1 (in order to group animals), day 1, 3, and 7. Samples are collected three hours after the daily dose. On day 7 of the study, following plasma collection, animals are euthanized and tissues, such as liver and intestinal mucosa are collected and snap frozen for further analysis. Plasma is analyzed for lipid parameters, such as total cholesterol, HDL cholesterol and triglyceride levels. RNA is extracted for frozen tissues and can be analyzed by quantitative real time PCR for regulation of key target genes. To identify specificity of target gene regulation by LXR subtypes, LXR deficient mice (LXRα−/− or LXRβ−/−) and C57BL/6 wild-type controls are used in this same protocol.

EXAMPLE 35

Measured $EC_{50}$ or $IC_{50}$ for LXR for Compounds of the Invention

Compounds of the invention, when tested as described in Example 33, demonstrated the ability to modulate the activity of $LXR_\alpha$ and/or $LXR_\beta$. LXR activities for various compounds of the invention are presented in the following table; those compounds with $EC_{50}$ or $IC_{50}$ values <10 μM for at least one of $LXR_\alpha$ and $LXR_\beta$ are considered to be active. In the following Table, $IC_{50}$ or $EC_{50}$ data is represented as follows: A=<1 μM, B=1–10 μm, and C=>10 μM

| Cpd # | activity |
| --- | --- |
| 1 | A |
| 2 | A |
| 3 | A |
| 4 | A |
| 5 | A |
| 6 | A |
| 7 | A |
| 8 | A |
| 9 | A |
| 10 | A |
| 11 | A |
| 12 | A |
| 13 | A |
| 14 | A |
| 15 | A |
| 16 | A |
| 17 | A |
| 18 | A |
| 19 | A |
| 20 | A |
| 21 | A |
| 22 | A |
| 23 | A |
| 24 | A |
| 25 | A |
| 26 | A |
| 27 | A |
| 28 | A |
| 29 | A |
| 30 | A |
| 31 | A |
| 32 | A |
| 33 | A |
| 34 | A |
| 35 | B |
| 36 | B |
| 37 | C |
| 38 | C |
| 41 | B |
| 42 | A |
| 44 | B |
| 45 | B |
| 58 | A |
| 59 | A |
| 60 | A |
| 61 | A |
| 62 | A |
| 63 | A |
| 64 | A |
| 65 | A |
| 66 | A |
| 67 | A |
| 68 | A |
| 69 | A |
| 70 | A |
| 71 | A |
| 72 | A |
| 73 | A |
| 74 | A |
| 75 | A |
| 76 | A |
| 77 | A |
| 78 | A |
| 80 | B |
| 82 | A |
| 83 | B |
| 84 | A |
| 85 | A |
| 86 | A |
| 87 | A |
| 88 | A |
| 89 | A |
| 90 | A |
| 91 | B |
| 92 | B |
| 93 | A |
| 94 | A |
| 95 | A |
| 96 | A |
| 97 | B |
| 98 | A |
| 99 | A |
| 100 | B |
| 101 | A |
| 102 | A |
| 103 | B |
| 104 | A |
| 105 | A |
| 106 | B |
| 107 | A |
| 108 | A |
| 109 | A |
| 110 | A |
| 111 | A |
| 112 | A |
| 113 | A |
| 114 | A |
| 115 | A |
| 116 | A |
| 117 | A |
| 118 | A |
| 119 | A |
| 120 | A |
| 121 | A |
| 122 | A |
| 123 | A |
| 124 | A |
| 125 | A |
| 126 | A |
| 127 | B |
| 128 | A |
| 129 | A |
| 130 | B |
| 131 | B |
| 132 | B |
| 133 | A |
| 134 | A |
| 135 | A |
| 136 | A |
| 137 | A |
| 138 | A |
| 139 | A |
| 140 | A |
| 141 | A |
| 142 | A |
| 143 | A |
| 144 | A |
| 145 | A |
| 146 | A |
| 147 | A |
| 148 | A |
| 149 | A |
| 150 | A |

403
-continued

| Cpd # | activity |
|---|---|
| 151 | A |
| 152 | A |
| 153 | A |
| 154 | A |
| 155 | A |
| 156 | A |
| 157 | A |
| 158 | A |
| 159 | A |
| 160 | A |
| 161 | A |
| 162 | A |
| 163 | A |
| 164 | B |
| 165 | B |
| 168 | B |
| 169 | A |
| 170 | A |
| 171 | A |
| 172 | A |
| 173 | A |
| 174 | A |
| 175 | A |
| 176 | A |
| 177 | A |
| 178 | A |
| 179 | A |
| 180 | A |
| 181 | A |
| 182 | A |
| 183 | A |
| 184 | A |
| 185 | A |
| 186 | A |
| 187 | A |
| 188 | A |
| 189 | A |
| 190 | A |
| 191 | A |
| 192 | A |
| 193 | A |
| 194 | A |
| 195 | A |
| 196 | A |
| 197 | A |
| 198 | A |
| 199 | B |
| 200 | A |
| 201 | A |
| 220 | A |
| 274 | B |
| 281 | A |
| 344 | A |
| 357 | A |
| 358 | A |
| 359 | A |
| 360 | A |
| 361 | B |
| 362 | A |
| 363 | B |
| 364 | A |
| 365 | A |
| 366 | B |
| 367 | A |
| 368 | B |
| 369 | A |
| 370 | A |
| 371 | A |
| 372 | A |
| 373 | A |
| 374 | B |
| 375 | A |
| 376 | A |
| 377 | B |
| 378 | B |
| 379 | A |
| 380 | B |
| 381 | B |

404
-continued

| Cpd # | activity |
|---|---|
| 382 | A |
| 383 | A |
| 384 | B |
| 385 | B |
| 386 | A |
| 387 | B |
| 388 | B |
| 389 | B |
| 390 | B |
| 391 | B |
| 392 | A |
| 393 | A |
| 394 | A |
| 395 | B |
| 396 | B |
| 397 | A |
| 398 | A |
| 399 | B |
| 400 | A |
| 401 | B |
| 402 | A |
| 403 | A |
| 404 | B |
| 405 | B |
| 406 | A |
| 407 | A |
| 408 | A |
| 409 | B |
| 410 | B |
| 411 | A |
| 412 | A |
| 413 | A |
| 415 | B |
| 416 | B |
| 417 | A |
| 418 | A |
| 419 | B |
| 420 | B |
| 421 | B |
| 443 | A |
| 444 | A |
| 445 | A |
| 448 | C |
| 449 | A |
| 450 | A |
| 451 | A |
| 452 | A |
| 453 | B |
| 454 | B |
| 455 | A |
| 456 | A |
| 457 | A |
| 458 | B |
| 459 | A |
| 460 | A |
| 461 | C |
| 462 | A |
| 463 | A |
| 464 | A |
| 465 | A |
| 466 | C |
| 467 | A |
| 468 | A |
| 469 | B |
| 470 | A |
| 471 | A |
| 472 | A |
| 473 | A |
| 474 | A |
| 475 | B |
| 476 | B |
| 477 | B |
| 479 | A |
| 480 | A |
| 481 | A |
| 482 | A |

It is understood that the examples and embodiments described herein are for illustrative purposes only and that various modifications or changes in light thereof will be suggested to persons skilled in the art and are to be incorporated within the spirit and purview of this application and scope of the appended claims. All publications, patents, and patent applications cited herein are hereby incorporated herein by reference for all purposes.

All of the U.S. patents, U.S. patent application publications, U.S. patent applications, foreign patents, foreign patent applications and non-patent publications referred to in this specification and/or listed in the Application Data Sheet, are incorporated herein by reference, in their entirety.

From the foregoing it will be appreciated that, although specific embodiments of the invention have been described herein for purposes of illustration, various modifications may be made without deviating from the spirit and scope of the invention. Accordingly, the invention is not limited except as by the appended claims. This invention also encompasses all combinations of alternative aspects of the invention noted herein. It is understood that any and all embodiments of the present invention may be taken in conjunction with any other embodiment to describe additional embodiments of the present invention. Furthermore, any elements of an embodiment may be combined with any and all other elements from any of the embodiments to describe additional embodiments.

We claim:
1. A compound according to the formula,

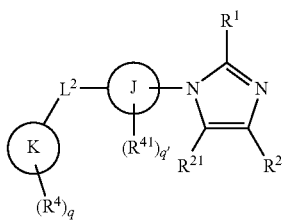

or a pharmaceutically acceptable salt thereof, wherein
$R^1$ is -$L^1$-$R^5$, wherein
  $L^1$ is a bond; and
  $R^5$ is aryl optionally substituted with one or more $R^{5a}$; wherein
    each $R^{5a}$ is independently halogen, nitro, heteroaryl, heterocyclyl, $C_2$-$C_6$ alkenyl, $C_2$-$C_6$ alkynyl, $C_3$-$C_8$ cycloalkyl, ($C_3$-$C_8$ cycloalkyl)-$C_1$-$C_6$ alkyl-, ($C_3$-$C_8$ cycloalkenyl)-$C_1$-$C_6$ alkyl-, ($C_3$-$C_8$ cycloalkyl)-$C_2$-$C_6$ alkenyl-, aryl, arylalkyl, aryloxy, aryloxyaryl, aryl$C_{1-6}$ alkoxy, $C_1$-$C_6$ alkyl, $C_1$-$C_6$ haloalkyl, $SO_2R^{11}$, $OR^{11}$, $SR^{11}$, $N_3$, $SO_2R^{11}$, $COR^{11}$, $SO_2N(R^{11})_2$, $SO_2NR^{11}COR^{11}$, C≡N, C(O)O$R^{11}$, CON($R^{11}$)$_2$, CON($R^{11}$)O$R^{11}$, OCON($R^{11}$)$_2$, $NR^{11}COR^{11}$, $NR^{11}CON(R^{11})_2$, $NR^{11}COOR^{11}$, or $N(R^{11})_2$, wherein
      each $R^{5a}$ is optionally substituted with one or more groups which independently are -halogen, —$C_1$-$C_6$ alkyl, aryloxy $C_{0-6}$ alkylSO$_2R^{11}$, $C_{0-6}$ alkyl-COO$R^{11}$, $C_{0-6}$ alkoxyaryl, $C_1$-$C_6$ haloalkyl, —SO$_2R^{11}$, —O$R^{11}$, —S$R^{11}$, —$N_3$, —SO$_2R^{11}$, —CO$R^{11}$, —SO$_2N(R^{11})_2$, —SO$_2NR^{11}COR^{11}$, —C≡N, —C(O)O$R^{11}$, —CON($R^{11}$)$_2$, —CON($R^{11}$)O$R^{11}$, —OCON($R^{11}$)$_2$, —NR$^{11}$COR$^{11}$, —NR$^{11}$CON(R$^{11}$)$_2$, —NR$^{11}$COO$R^{11}$, or —N($R^{11}$)$_2$;

$R^{21}$ is hydrogen, halogen, nitro, cyano, $C_1$-$C_6$alkyl, or $C_1$-$C_6$haloalkyl;
$R^2$ is —H, —[C($R^{15}$)$_2$]$_m$—OH, —$C_1$-$C_6$alkyl, —$C_1$-$C_6$ haloalkyl, halogen, —C(O)N($R^{11}$)$_2$, or —COO$R^{11}$;
provided that $R^2$ and $R^{21}$ are not simultaneously hydrogen;
J is aryl or heteroaryl;
K is aryl or heteroaryl;
each $R^4$ and $R^{41}$ is independently halogen, oxo, nitro, $CR^{11}$=$CR^{11}COOR^{11}$, aryloxy, aralkyloxy, aryloxyalkyl, aryl$C_0$-$C_6$ alkylcarboxy, aryl, heteroaryl, heterocyclyl, heteroaryloxy, heterocyclyloxy, -$G^1$, -E-$G^{1'}$ or -D-E-$G^1$, wherein
  D is —O—;
  E is —[C($R^{15}$)$_2$]$_m$— or —$C_3$-$C_8$cycloalkyl; and
  $G^1$ is —$C_1$-$C_6$alkyl, —$C_1$-$C_6$haloalkyl, —CO$R^{11}$, —COO$R^{11}$, —CON($R^{11}$)$_2$, —C≡N, —O$R^{11}$, —OCON($R^{11}$)$_2$, —OCOO$R^{11}$, —$N_3$, —NR$^{11}$COR$^{11}$, —NR$^{11}$SO$_2R^{11}$, —N($R^{11}$)$_2$, —NR$^{11}$COO$R^{11}$, —SO$_2R^{11}$, —SO$_2NR^{11}COR^{11}$, —SO$_2N(R^{11})_2$, —SO$R^{11}$, or —S$R^{11}$;
wherein each $R^4$ is optionally substituted with one or more $R^{4a}$,
  wherein each $R^{4a}$ is independently halogen, aryloxy, aralkyloxy, aryloxyalkyl, $C_1$-$C_6$ alkoxyaryl, aryl$C_0$-$C_6$ alkylcarboxy, -G', -E'-G', or -D'-E'-G', wherein
    D' is —O—;
    E' is —[C($R^{15}$)$_2$]$_m$— or —$C_3$-$C_8$cycloalkyl-; and
    G' is —H, -halogen, —CO$R^{11}$, —COO$R^{11}$, —COO$R^{11}$, —C≡N, —O$R^{11}$, —NR$^{11}$SO$_2R^{11}$, —SO$_2R^{11}$, —SO$_2N(R^{11})_2$, or —S$R^{11}$;
$L^2$ is a bond;
each m is 0, 1, 2, 3, 4, 5, or 6;
q is 0, 1, 2, 3, 4, or 5, provided that q is 0 if and only if K is not phenyl; and
q' is 0, 1, 2, 3, or 4,
each $R^{10}$ is independently —$R^{11}$, —C(=O)$R^{11}$, —CO$_2R^{11}$, or —SO$_2R^{11}$;
each $R^{11}$ is independently -hydrogen, —$C_1$-$C_6$ alkyl, $C_2$-$C_6$ alkenyl, $C_2$-$C_6$ alkynyl, $C_3$-$C_8$ cycloalkyl, ($C_3$-$C_8$ cycloalkyl)-$C_1$-$C_6$ alkyl-, ($C_3$-$C_8$ cycloalkenyl)-$C_1$-$C_6$ alkyl-, ($C_3$-$C_8$ cycloalkyl)-$C_2$-$C_6$ alkenyl-, —$C_1$-$C_6$ haloalkyl, —N($R^{12}$)$_2$, aryl, —($C_1$-$C_6$)alkyl-aryl, heteroaryl, —($C_1$-$C_6$)alkyl-heteroaryl, heterocyclyl, or —($C_1$-$C_6$)alkyl-heterocyclyl,
wherein any of $R^{11}$ is optionally substituted with one or more radicals of $R^{12}$;
  each $R^{12}$ is independently halogen, $C_1$-$C_6$haloalkyl, $C_1$-$C_6$ alkyl, $C_1$-$C_6$ alkoxy, ($C_0$-$C_6$ alkyl)C=O (O$R^{13}$); $C_0$-$C_6$ alkylO$R^{13}$, $C_0$-$C_6$ alkylCO$R^{13}$, $C_0$-$C_6$ alkylSO$_2R^{13}$, $C_0$-$C_6$ alkylCON($R^{13}$)$_2$, $C_0$-$C_6$ alkylCONR$^{13}$O$R^{13}$, $C_0$-$C_6$ alkylSO$_2$N($R^{13}$)$_2$, $C_0$-$C_6$ alkylS$R^{13}$, $C_0$-$C_6$ haloalkylO$R^{13}$, aryloxy, aralkyloxy, aryloxyalkyl, $C_{0-6}$alkoxyaryl, aryl$C_{0-6}$ alkylcarboxy, —$C_0$-$C_6$ alkylN($R^{13}$)$_2$, —NR$^{13}$SO$_2$ $R^{13}$, or —O$C_{0-6}$ alkylCOO$R^{13}$;
each $R^{13}$ is independently hydrogen, $C_1$-$C_6$ alkyl, $C_2$-$C_6$ alkenyl, $C_2$-$C_6$ alkynyl, $C_3$-$C_8$ cycloalkyl, ($C_3$-$C_8$ cycloalkyl)-$C_1$-$C_6$ alkyl-, ($C_3$-$C_8$ cycloalkenyl)-$C_1$-$C_6$ alkyl-, or ($C_3$-$C_8$ cycloalkyl)-$C_2$-$C_6$ alkenyl-;
and each $R^{15}$ is independently hydrogen, halogen, ($C_1$-$C_6$) alkyl, ($C_3$-$C_6$)cycloalkyl, or ($C_1$-$C_6$)haloalkyl.

2. The compound according to claim 1, wherein at least one of J and K is phenyl.
3. The compound according to claim 2, of the formula,

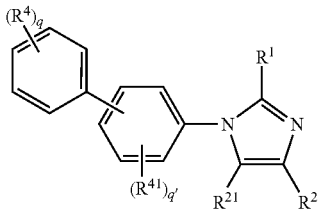

or a pharmaceutically acceptable salt thereof.
4. The compound according to claim 3, of the formula,

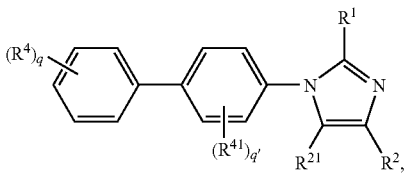

or a pharmaceutically acceptable salt thereof, wherein $R^{21}$ is —H, -halogen, —$C_1$-$C_6$alkyl, or —$C_1$-$C_6$haloalkyl.
5. The compound according to claim 3 wherein
each $R^4$ is independently halogen, aryl, heteroaryl, heterocyclyl, -$G^1$, or -E-$G^1$, wherein
E is —[C($R^{15}$)$_2$]$_m$—, wherein each $R^{15}$ is independently hydrogen or halogen; and
$G^1$ is —$C_1$-$C_6$alkyl, —$C_1$-$C_6$haloalkyl, —$OR^{11}$, or —$SO_2R^{11}$.
6. The compound according to claim 3, wherein
each $R^{41}$ is independently halogen, -$G^2$, or -E-$G^2$, wherein
E is —[C($R^{15}$)$_2$]$_m$—, wherein each $R^{15}$ is independently hydrogen or halogen; and
$G^2$ is —$C_1$-$C_6$alkyl, —$C_1$-$C_6$haloalkyl, or halogen; and
each $R^4$ is independently halogen, aryl, heteroaryl, heterocyclyl, -$G^1$, or -E-$G^1$, wherein
E is —[C($R^{15}$)$_2$]$_m$—, wherein each $R^{15}$ is independently hydrogen or halogen; and
$G^1$ is —$C_1$-$C_6$alkyl, —$C_1$-$C_6$haloalkyl, —$OR^{11}$, or —$SO_2R^{11}$.
7. The compound according to claim 4, wherein each $R^{5a}$ is independently halogen, $C_1$-$C_6$ alkyl, $C_1$-$C_6$ haloalkyl, $C_3$-$C_8$cycloalkyl, $OR^{11}$, $SO_2R^{11}$, $COR^{11}$, $SO_2N(R^{11})_2$, C≡N, C(O)$OR^{11}$, CON($R^{11}$)$_2$, $NR^{11}$ $COR^{11}$, or N($R^{11}$)$_2$.
8. A compound according to the formula,

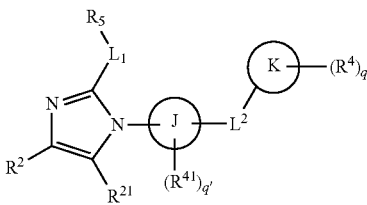

or a pharmaceutically acceptable salt thereof, wherein,
$L^1$ is —[C($R^{15}$)$_2$]$_{m'}$— or —$C_3$-$C_8$ cycloalkyl; wherein m' is any of 1 to 3; and
each $R^{15}$ is independently hydrogen, halogen, ($C_1$-$C_6$) alkyl, or ($C_1$-$C_6$)haloalkyl;

$R^5$ is aryl, heterocyclyl, heteroaryl, —($C_3$-$C_6$)cycloalkyl, —C, or —B—C, wherein
B is —[C($R^{15}$)$_2$]$_m$— or —$C_3$-$C_8$ cycloalkyl-; and
C is halogen, —$C_1$-$C_6$alkyl, —$C_1$-$C_6$haloalkyl, —$SO_2R^{11}$, —$SR^{11}$, —$SO_2N(R^{11})_2$, —$SO_2NR^{11}COR^{11}$, —C≡N, —C(O)$OR^{11}$, —CON($R^{11}$)$_2$, or —N($R^{11}$)$_2$,
wherein $R^5$ is optionally substituted with one or more $R^{5a}$, wherein
each $R^{5a}$ is independently halogen, nitro, heteroaryl, heterocyclyl, $C_2$-$C_6$ alkenyl, $C_2$-$C_6$ alkynyl, $C_3$-$C_8$ cycloalkyl, ($C_3$-$C_8$ cycloalkyl)-$C_1$-$C_6$ alkyl-, ($C_3$-$C_8$ cycloalkenyl)-$C_1$-$C_6$ alkyl-, ($C_3$-$C_8$ cycloalkyl)-$C_2$-$C_6$ alkenyl-, aryl, arylalkyl, aryloxy, aryloxyaryl, aryl$C_{1-6}$ alkoxy, $C_1$-$C_6$ alkyl, $C_1$-$C_6$ haloalkyl, $SO_2R^{11}$, $OR^{11}$, $SR^{11}$, $N_3$, $SO_2R^{11}$, $COR^{11}$, $SO_2N(R^{11})_2$, $SO_2NR^{11}COR^{11}$, C≡N, C(O)$OR^{11}$, CON($R^{11}$)$_2$, CON($R^{11}$)$OR^{11}$, OCON($R^{11}$)$_2$, $NR^{11}COR^{11}$, $NR^{11}CON(R^{11})_2$, $NR^{11}COOR^{11}$, or N($R^{11}$)$_2$, wherein
each $R^{5a}$ is optionally substituted with one or more groups which independently are -halogen, —$C_1$-$C_6$ alkyl, aryloxy $C_{0-6}$ alkyl$SO_2R^{11}$, $C_{0-6}$ alkyl-$COOR^{11}$, $C_{0-6}$ alkoxyaryl, $C_1$-$C_6$ haloalkyl, —$SO_2R^{11}$, —$OR^{11}$, —$SR^{11}$, —$N_3$, —$SO_2R^{11}$, —$COR^{11}$, —$SO_2N(R^{11})_2$, —$SO_2NR^{11}COR^{11}$, —C≡N, —C(O)$OR^{11}$, —CON($R^{11}$)$_2$, —CON ($R^{11}$)$OR^{11}$, —OCON($R^{11}$)$_2$, —$NR^{11}COR^{11}$, —$NR^{11}CON(R^{11})_2$, —$NR^{11}COOR^{11}$, or —N($R^{11}$)$_2$;
$R^{21}$ is hydrogen, halogen, nitro, cyano, $C_1$-$C_6$alkyl, or $C_1$-$C_6$haloalkyl;
$R^2$ is —H, —[C($R^{15}$)$_2$]$_m$—OH, —$C_1$-$C_6$alkyl, —$C_1$-$C_6$ haloalkyl, halogen, —C(O)N($R^{11}$)$_2$, or —$COOR^{11}$;
provided that $R^2$ and $R^{21}$ are not simultaneously hydrogen;
J and K are both phenyl;
each $R^4$ and $R^{41}$ is independently halogen, oxo, nitro, $CR^{11}$=$CR^{11}COOR^{11}$, aryloxy, aralkyloxy, aryloxyalkyl, aryl$C_0$-$C_6$ alkylcarboxy, aryl, heteroaryl, heterocyclyl, heteroaryloxy, heterocyclyloxy, -$G^1$, -E-$G^{1'}$ or -D-E-$G^1$, wherein
D is —O—;
E is —[C($R^{15}$)$_2$]$_m$— or —$C_3$-$C_8$cycloalkyl; and
$G^1$ is —$C_1$-$C_6$alkyl, —$C_1$-$C_6$haloalkyl, —$COR^{11}$, —$COOR^{11}$, —CON($R^{11}$)$_2$, —C≡N, —$OR^{11}$, —OCON($R^{11}$)$_2$, —$OCOOR^{11}$, —$N_3$, —$NR^{11}COR^{11}$, —$NR^{11}SO_2R^{11}$, —N($R^{11}$)$_2$, —$NR^{11}COOR^{11}$, —$SO_2R^{11}$, —$SO_2NR^{11}COR^{11}$, —$SO_2N(R^{11})_2$, —$SOR^{11}$, or —$SR^{11}$;
wherein each $R^4$ is optionally substituted with one or more $R^{4a}$,
wherein each $R^{4a}$ is independently halogen, aryloxy, aralkyloxy, aryloxyalkyl, $C_1$-$C_6$ alkoxyaryl, aryl$C_0$-$C_6$ alkylcarboxy, -G', -E'-G', or -D'-E'-G', wherein
D' is —O—;
E' is —[C($R^{15}$)$_2$]$_m$— or —$C_3$-$C_8$cycloalkyl-; and
G' is —H, -halogen, —$COR^{11}$, —$COOR^{11}$, —C≡N, $OR^{11}$, —$NR^{11}SO_2R^{11}$, —$SO_2R^{11}$, —$SO_2N(R^{11})_2$, or —$SR^{11}$;
$L^2$ is a bond or —[C($R^{15}$)$_2$]$_m$—$V^2$—[C($R^{15}$)$_2$]$_n$—, wherein
$V^2$ is independently —C($R^{11}$)$_2$—, —C($R^{11}$)$_2$C($R^{11}$)$_2$—, —C($R^{11}$)=C($R^{11}$)—, —C($R^{11}$)$_2$O—, —C($R^{11}$)$_2$$NR^{11}$—, —C≡C—, —O—, —S—, —$SO_2$—, —N($R^{10}$)CO—, —N($R^{10}$)$CO_2$—, —CON ($R^{10}$)—, —CON($R^{11}$)—, —CON($R^{11}$)O—, —CO—, —CS—, —CO$_2$—, —OC(=O)—, —OC(=O)N(R$^{10}$)—, —N(R$^{10}$)SO$_2$—, —SO$_2$N(R$^{10}$)—, —NR$^{10}$CONR$^{10}$—, —NR$^{10}$CSNR$^{10}$—, C$_3$-C$_6$cycloalkyl-, or C$_3$-C$_6$cyclohaloalkyl, or V$^2$ is C$_{2-6}$ alidiyl, wherein alidiyl chain is optionally interrupted by —C(R$^{11}$)$_2$—, —C(R$^{11}$)$_2$C(R$^{11}$)$_2$—, —C(R$^{11}$)=C(R$^{11}$)—, —C(R$^{11}$)$_2$O—, —C(R$^{11}$)$_2$NR$^{11}$—, —C(R$^{11}$)$_2$NR$^{11}$—, —C≡C—, —O—, —S—, —N(R$^{10}$)CO—, —N(R$^{10}$)CO$_2$—, —CON(R$^{10}$)—, —CON(R$^{11}$)—, —CON(R$^{11}$)O—, —CO—, —CO$_2$—, —OC(=O)—, —OC(=O)N(R$^{10}$)—, —SO$_2$—, —N(R$^{10}$)SO$_2$— or —SO$_2$N(R$^{10}$)—;

or V$^2$ is aryl, heteroaryl, or heterocyclyl, each of which is optionally substituted with one or more R$^9$, wherein each R$^9$ is independently halogen, C$_1$-C$_6$ haloalkyl, C$_1$-C$_6$ alkyl, C$_1$-C$_6$ alkyloxy, C$_0$-C$_6$ alkyl or C$_1$-C$_6$ alkylCOOR$^{11}$;

each m is 0, 1, 2, 3, 4, 5, or 6;

q is 1, 2, 3, 4, or 5, q' is 0, 1, 2, 3, or 4, each R$^{10}$ is independently —R$^{11}$, —C(=O)R$^{11}$, —CO$_2$R$^{11}$, or —SO$_2$R$^{11}$;

each R$^{11}$ is independently -hydrogen, —C$_1$-C$_6$ alkyl, C$_2$-C$_6$ alkenyl, C$_2$-C$_6$ alkynyl, C$_3$-C$_8$ cycloalkyl, (C$_3$-C$_8$ cycloalkyl)-C$_1$-C$_6$ alkyl-, (C$_3$-C$_8$ cycloalkenyl)-C$_1$-C$_6$ alkyl-, (C$_3$-C$_8$ cycloalkyl)-C$_2$-C$_6$ alkenyl-, —C$_1$-C$_6$ haloalkyl, —N(R$^{12}$)$_2$, aryl, —(C$_1$-C$_6$)alkyl-aryl, heteroaryl, —(C$_1$-C$_6$)alkyl-heteroaryl, heterocyclyl, or —(C$_1$-C$_6$)alkyl-heterocyclyl, wherein any of R$^{11}$ is optionally substituted with one or more radicals of R$^{12}$;

each R$^{12}$ is independently halogen, C$_1$-C$_6$haloalkyl, C$_1$-C$_6$ alkyl, C$_1$-C$_6$ alkoxy, (C$_0$-C$_6$ alkyl)C=O (OR$^{13}$); C$_0$-C$_6$ alkylOR$^{13}$, C$_0$-C$_6$ alkylCOR$^{13}$, C$_0$-C$_6$ alkylSO$_2$R$^{13}$, C$_0$-C$_6$ alkylCON(R$^{13}$)$_2$, C$_0$-C$_6$ alkylCONR$^{13}$OR$^{13}$, C$_0$-C$_6$ alkylSO$_2$N(R$^{13}$)$_2$, C$_0$-C$_6$ alkylSR$^{13}$, C$_0$-C$_6$ haloalkylOR$^{13}$, aryloxy, aralkyloxy, aryloxyalkyl, C$_{0-6}$alkoxyaryl, arylC$_{0-6}$ alkylcarboxy, —C$_0$-C$_6$ alkylN(R$^{13}$)$_2$, —NR$^{13}$SO$_2$R$^{13}$, or —OC$_{0-6}$ alkylCOOR$^{13}$; and each R$^{13}$ is independently hydrogen, C$_1$-C$_6$ alkyl, C$_2$-C$_6$ alkenyl, C$_2$-C$_6$ alkynyl, C$_3$-C$_8$ cycloalkyl, (C$_3$-C$_8$ cycloalkyl)-C$_1$-C$_6$ alkyl-, (C$_3$-C$_8$ cycloalkenyl)-C$_1$-C$_6$ alkyl-, or (C$_3$-C$_8$ cycloalkyl)-C$_2$-C$_6$ alkenyl.

9. The compound according to claim 8, wherein L$^2$ is a bond.

10. The compound according to claim 9, of the formula,

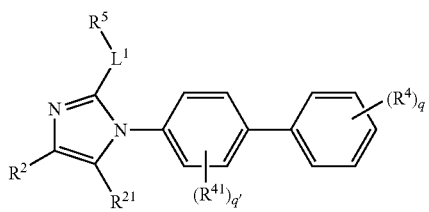

or a pharmaceutically acceptable salt thereof.

11. The compound according to claim 10, wherein each R$^{15}$ is independently —H or —(C$_1$-C$_2$)alkyl;

m' is 1 or 2; and

R$^5$ is phenyl optionally substituted with one or more R$^{5a}$.

12. The compound according to claim 11, wherein each R$^4$ is independently halogen, aryl, heteroaryl, heterocyclyl, -G$^1$, or -E-G$^1$, wherein E is —[C(R$^{15}$)$_2$]$_m$—, wherein each R$^{15}$ is independently hydrogen or halogen; and G$^1$ is —C$_1$-C$_6$alkyl, —C$_1$-C$_6$haloalkyl, —OR$^{11}$, or —SO$_2$R$^{11}$.

13. The compound according to claim 11, wherein each R$^{41}$ is independently halogen, -G$^1$, or -E-G$^1$, wherein E is —[C(R$^{15}$)$_2$]$_m$—, wherein each R$^{15}$ is independently hydrogen or halogen; and G$^1$ is —C$_1$-C$_6$alkyl or —C$_1$-C$_6$haloalkyl.

14. The compound according to claim 10, wherein R$^{15}$ is —H;

m is 1, 2, or 3; and

R$^5$ is heterocyclyl optionally substituted with one or more R$^{5a}$.

15. The compound according to claim 14, wherein each R$^4$ is independently halogen, aryl, heteroaryl, heterocyclyl, -G$^1$, or -E-G$^1$, wherein E is —[C(R$^{15}$)$_2$]$_m$—, wherein each R$^{15}$ is independently hydrogen or halogen; and G$^1$ is —C$_1$-C$_6$alkyl, —C$_1$-C$_6$haloalkyl, —OR$^{11}$, or —SO$_2$R$^{11}$.

16. The compound according to claim 14, wherein each R$^{41}$ is independently halogen, -G$^1$, or -E-G$^1$, wherein E is —[C(R$^{15}$)$_2$]$_m$—, wherein each R$^{15}$ is independently hydrogen or halogen; and G$^1$ is —C$_1$-C$_6$alkyl or —C$_1$-C$_6$haloalkyl.

17. A compound according to one of the following formulas,

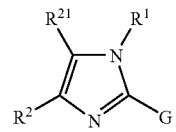

IIa

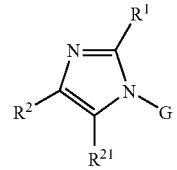

IIb

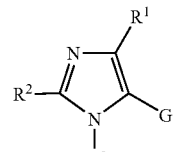

IIc

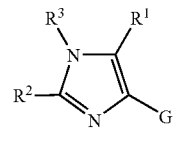

IId or a pharmaceutically acceptable salt thereof, wherein,

R$^1$ is -L$^1$-R$^5$, wherein

L$^1$ is a bond, —[C(R$^{15}$)$_2$]$_m$—, or —C$_3$-C$_8$ cycloalkyl-; and

R$^5$ is phenyl or pyridyl, each optionally substituted with one or two R$^{5a}$, wherein each R$^{5a}$ is independently -halogen, —C$_1$-C$_6$ alkoxy, —C$_1$-C$_6$ alkyl, or —C$_1$-C$_6$haloalkyl;

$R^2$, $R^{21}$, and $R^3$ are each independently —H, —[C(R$^{15}$)$_2$]$_m$—OH, —C$_1$-C$_6$ alkyl, —C$_1$-C$_6$ haloalkyl, halogen, —C(O)N(R$^{11}$)$_2$, or —COOR$^{11}$;

provided that $R^2$ and $R^{21}$ are not simultaneously hydrogen;

G is a group of the formula,

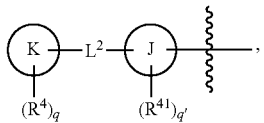

wherein $L^2$ is a bond;

J is phenyl, pyridyl, or thienyl;

K is phenyl or pyridyl;

q is 0, 1, 2, 3, 4, or 5, provided that q is 0 if and only if K is not phenyl;

q' is 0, 1, 2, 3, or 4, each $R^{41}$ is -halogen, —C$_1$-C$_6$ alkyl, or C$_1$-C$_6$ -haloalkyl; and each $R^4$ is -halogen, —[C(R$^{15}$)$_2$]$_m$—OH, —SO$_2$R$^{11}$, —SO$_2$N(R$^{11}$)$_2$, —C(O)N(R$^{11}$)$_2$, —COOR$^{11}$, —C$_1$-C$_6$ alkyl, or —C$_1$-C$_6$ haloalkyl;

each m is 0, 1, 2, 3, 4, 5, or 6;

each $R^{15}$ is independently hydrogen, halogen, (C$_1$-C$_6$) alkyl, (C$_3$-C$_6$)cycloalkyl, or (C$_1$-C$_6$)haloalkyl; and each $R^{11}$ is independently -hydrogen, —C$_1$-C$_6$ alkyl, C$_2$-C$_6$ alkenyl, C$_2$-C$_6$ alkynyl, C$_3$-C$_8$ cycloalkyl, (C$_3$-C$_8$ cycloalkyl)-C$_1$-C$_6$ alkyl-, (C$_3$-C$_8$ cycloalkenyl)-C$_1$-C$_6$ alkyl-, (C$_3$-C$_8$ cycloalkyl)-C$_2$-C$_6$ alkenyl-, —C$_1$-C$_6$ haloalkyl, —N(R$^{12}$)$_2$, heterocyclyl, or —(C$_1$-C$_6$)alkyl-heterocyclyl, wherein any of R$^{11}$ is optionally substituted with one or more radicals of R$^{12}$;

each $R^{12}$ is independently halogen, C$_1$-C$_6$haloalkyl, C$_1$-C$_6$ alkyl, C$_1$-C$_6$ alkoxy, (C$_0$-C$_6$ alkyl)C=O(OR$^{13}$); C$_0$-C$_6$ alkylOR$^{13}$, C$_0$-C$_6$ alkylCOR$^{13}$, C$_0$-C$_6$ alkylSO$_2$R$^{13}$, C$_0$-C$_6$ alkylCON(R$^{13}$)$_2$, C$_0$-C$_6$ alkylCONR$^{13}$OR$^{13}$, C$_0$-C$_6$ alkylSO$_2$N(R$^{13}$)$_2$, C$_0$-C$_6$ alkylSR$^{13}$, C$_0$-C$_6$ haloalkylOR$^{13}$, aryloxy, aralkyloxy, aryloxyalkyl, C$_{0-6}$ alkoxyaryl, arylC$_{0-6}$ alkylcarboxy, -C$_0$-C$_6$ alkylN(R$^{13}$)$_2$, —NR$^{13}$SO$_2$ R$^{13}$, or —OC$_{0-6}$ alkylCOOR$^{13}$; and each $R^{13}$ is independently hydrogen, C$_1$-C$_6$ alkyl, C$_2$-C$_6$ alkenyl, C$_2$-C$_6$ alkynyl, C$_3$-C$_8$ cycloalkyl, (C$_3$-C$_8$ cycloalkyl)-C$_1$-C$_6$ alkyl-, (C$_3$-C$_8$ cycloalkenyl)-C$_1$-C$_6$ alkyl-, or (C$_3$-C$_8$ cycloalkyl)-C$_2$-C$_6$ alkenyl-.

18. The compound according to claim 10, wherein each $R^{15}$ is independently —H or —(C$_1$-C$_2$)alkyl;
m' is 1 or 2; and
$R^5$ is heteroaryl optionally substituted with one or more $R^{5a}$.

19. The compound according to claim 18, wherein each $R^4$ is independently halogen, aryl, heteroaryl, heterocyclyl, -G$^1$, or -E-G$^1$, wherein
E is —[C(R$^{15}$)$_2$]$_m$—, wherein
each $R^{15}$ is independently hydrogen or halogen; and
G$^1$ is —C$_1$-C$_6$alkyl, —C$_1$-C$_6$haloalkyl, —OR$^{11}$, or —SO$_2$R$^{11}$.

20. The compound according to claim 18, wherein each $R^{41}$ is independently halogen, -G$^1$, or -E-G$^1$, wherein
E is —[C(R$^{15}$)$_2$]$_m$—,
wherein each $R^{15}$ is independently hydrogen or halogen; and
G$^1$ is —C$_1$-C$_6$alkyl or —C$_1$-C$_6$haloalkyl.

21. A compound according to the formula,

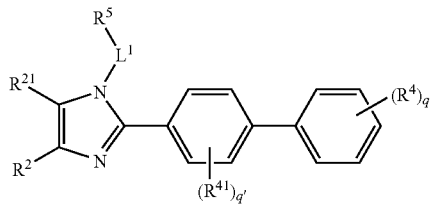

or a pharmaceutically acceptable salt thereof, wherein
$L^1$ is —[C(R$^{15}$)$_2$]$_{m'}$— or —C$_3$-C$_8$ cycloalkyl; wherein m' is 1 or 2; and
$R^5$ is heteroaryl optionally substituted with one or more $R^{5a}$, wherein
each $R^{5a}$ is independently halogen, nitro, heteroaryl, heterocyclyl, C$_2$-C$_6$ alkenyl, C$_2$-C$_6$ alkynyl, C$_3$-C$_8$ cycloalkyl, (C$_3$-C$_8$ cycloalkyl)-C$_1$-C$_6$ alkyl-, (C$_3$-C$_8$ cycloalkenyl)-C$_1$-C$_6$ alkyl-, (C$_3$-C$_8$ cycloalkyl)-C$_2$-C$_6$ alkenyl-, aryl, arylalkyl, aryloxy, aryloxyaryl, arylC$_{1-6}$ alkoxy, C$_1$-C$_6$ alkyl, C$_1$-C$_6$ haloalkyl, SO$_2$R$^{11}$, OR$^{11}$, SR$^{11}$, N$_3$, SO$_2$R$^{11}$, COR$^{11}$, SO$_2$N(R$^{11}$)$_2$, SO$_2$NR$^{11}$COR$^{11}$, C≡N, C(O)OR$^{11}$, CON(R$^{11}$)$_2$, CON(R$^{11}$)OR$^{11}$, OCON(R$^{11}$)$_2$, NR$^{11}$COR$^{11}$, NR$^{11}$CON(R$^{11}$)$_2$, NR$^{11}$COOR$^{11}$, or N(R$^{11}$)$_2$, wherein
each $R^{5a}$ is optionally substituted with one or more groups which independently are -halogen, —C$_1$-C$_6$ alkyl, aryloxy C$_{0-6}$ alkylSO$_2$R$^{11}$, C$_{0-6}$ alkyl-COOR$^{11}$, C$_{0-6}$ alkoxyaryl, C$_1$-C$_6$ haloalkyl, —SO$_2$R$^{11}$, —OR$^{11}$, —SR$^{11}$, —N$_3$, —SO$_2$R$^{11}$, —COR$^{11}$, —SO$_2$N(R$^{11}$)$_2$, —SO$_2$NR$^{11}$COR$^{11}$, —C≡N, —C(O)OR$^{11}$, —CON(R$^{11}$)$_2$, —CON(R$^{11}$)OR$^{11}$, —OCON(R$^{11}$)$_2$, —NR$^{11}$COR$^{11}$, —NR$^{11}$CON(R$^{11}$)$_2$, —NR$^{11}$COOR$^{11}$, or —N(R$^{11}$)$_2$;

$R^{21}$ is hydrogen, halogen, nitro, cyano, C$_1$-C$_6$alkyl, or C$_1$-C$_6$haloalkyl;

$R^2$ is —H, —[C(R$^{15}$)$_2$]$_m$—OH, —C$_1$-C$_6$ alkyl, —C$_1$-C$_6$ haloalkyl, halogen, —C(O)N(R$^{11}$)$_2$, or —COOR$^{11}$;

provided that $R^2$ and $R^{21}$ are not simultaneously hydrogen;

each m is 0, 1, 2, 3, 4, 5, or 6;

q is 1, 2, 3, 4, or 5, q' is 0, 1, 2, 3, or 4, and each $R^4$ and $R^{41}$ is independently halogen, oxo, nitro, CR$^{11}$=CR$^{11}$COOR$^{11}$, aryloxy, aralkyloxy, aryloxyalkyl, arylC$_0$-C$_6$ alkylcarboxy, aryl, heteroaryl, heterocyclyl, heteroaryloxy, heterocyclyloxy, -G$^1$, -E-G$^1$' or -D-E-G$^1$, wherein D is —O—;

E is —[C(R$^{15}$)$_2$]$_m$— or —C$_3$-C$_8$cycloalkyl; and

G$^1$ is —C$_1$-C$_6$alkyl, —C$_1$-C$_6$haloalkyl, —COR$^{11}$, —COOR$^{11}$, —CON(R$^{11}$)$_2$, —C≡N, —OR$^{11}$, —OCON(R$^{11}$)$_2$, —OCOOR$^{11}$, —N$_3$, —NR$^{11}$COR$^{11}$, —NR$^{11}$SO$_2$R$^{11}$, —N(R$^{11}$)$_2$, —NR$^{11}$COOR$^{11}$, —SO$_2$R$^{11}$, —SO$_2$NR$^{11}$COR$^{11}$, —SO$_2$N(R$^{11}$)$_2$, —SOR$^{11}$, or —SR$^{11}$;

wherein each $R^4$ is optionally substituted with one or more $R^{4a}$,
wherein each $R^{4a}$ is independently halogen, aryloxy, aralkyloxy, aryloxyalkyl, C$_1$-C$_6$ alkoxyaryl, arylC$_0$-C$_6$ alkylcarboxy, -G', -E'-G', or-D'-E'-G', wherein D' is —O—;

E' is —[C(R$^{15}$)$_2$]$_m$— or —C$_3$-C$_8$cycloalkyl-; and

G' is —H, -halogen, —COR$^{11}$, —COOR$^{11}$, —C≡N, OR$^{11}$, —NR$^{11}$SO$_2$R$^{11}$, —SO$_2$R$^{11}$, —SO$_2$N(R$^{11}$)$_2$, or —SR$^{11}$;

each R$^{11}$ is independently -hydrogen, —C$_1$-C$_6$ alkyl, C$_2$-C$_6$ alkenyl, C$_2$-C$_6$ alkynyl, C$_3$-C$_8$ cycloalkyl, (C$_3$-C$_8$ cycloalkyl)-C$_1$-C$_6$ alkyl-, (C$_3$-C$_8$ cycloalkenyl)-C$_1$-C$_6$ alkyl-, (C$_3$-C$_8$ cycloalkyl)-C$_2$-C$_6$ alkenyl-, -C$_1$-C$_6$ haloalkyl, —N(R$^{12}$)$_2$, aryl, -(C$_1$-C$_6$)alkyl-aryl, heteroaryl, —(C$_1$-C$_6$)alkyl-heteroaryl, heterocyclyl, or —(C$_1$-C$_6$)alkyl-heterocyclyl, wherein any of R$^{11}$ is optionally substituted with one or more radicals of R$^{12}$;

each R$^{12}$ is independently halogen, C$_1$-C$_6$haloalkyl, C$_1$-C$_6$ alkyl, C$_1$-C$_6$ alkoxy, (C$_0$-C$_6$ alkyl)C=O (OR$^{13}$); C$_0$-C$_6$ alkylOR$^{13}$, C$_0$-C$_6$ alkylCOR$^{13}$, C$_0$-C$_6$ alkylSO$_2$R$^{13}$, C$_0$-C$_6$ alkylCON(R$^{13}$)$_2$, C$_0$-C$_6$alkylCONR$^{13OR13}$, C$_0$-C$_6$alkylSO$_2$N(R$^{13}$)$_2$, C$_0$-C$_6$ alkylSR$^{13}$, C$_0$-C$_6$ haloalkylOR$^{13}$, aryloxy, aralkyloxy, aryloxyalkyl, C$_{0-6}$alkoxyaryl, arylC$_{0-6}$alkylcarboxy, —C$_0$-C$_6$ alkylN(R$^{13}$)$_2$, —NR$^{13}$SO$_2$R$^{13}$, or —OC$_{0-6}$ alkylCOOR$^{13}$;

each R$^{13}$ is independently hydrogen, C$_1$-C$_6$ alkyl, C$_2$-C$_6$ alkenyl, C$_2$-C$_6$ alkynyl, C$_3$-C$_8$ cycloalkyl, (C$_3$-C$_8$ cycloalkyl)-C$_1$-C$_6$ alkyl-, (C$_3$-C$_8$ cycloalkenyl)-C$_1$-C$_6$ alkyl-, or (C$_3$-C$_8$ cycloalkyl)-C$_2$-C$_6$ alkenyl-;

and each R$^{15}$ is independently H, halogen, or (C$_1$-C$_6$)alkyl.

22. The compound according to claim 21, wherein each R$^4$ is independently halogen, aryl, heteroaryl, heterocyclyl, -G$^1$, or -E-G$^1$, wherein E is —[C(R$^{15}$)$_2$]$_m$—, wherein each R$^{15}$ is independently hydrogen or halogen; and G$^1$ is —C$_1$-C$_6$alkyl, —C$_1$-C$_6$haloalkyl, —OR$^{11}$, or —SO$_2$R$^{11}$.

23. A compound according to one of the following formulas,

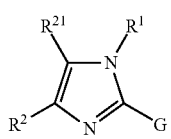

IIa

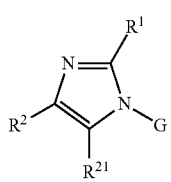

IIb or a pharmaceutically acceptable salt thereof, wherein,

R$^1$ is -L$^1$-R$^5$, wherein

L$^1$ is a bond, —C$_3$-C$_8$ cycloalkyl- or L$^5$, wherein each L$^5$ is independently —[C(R$^{15}$)$_2$]$_m$—, wherein m is 0, 1, 2, or 3; and each R$^{15}$ is independently hydrogen, halogen, (C$_1$-C$_6$) alkyl, or (C$_1$-C$_6$)haloalkyl; and R$^5$ is aryl, heterocyclyl, heteroaryl, —C, or -B-C, wherein B is —[C(R$^{15}$)$_2$]$_m$—, —C$_3$-C$_6$cycloalkyl-; and C is —C$_1$-C$_6$alkyl or —C$_1$-C$_6$haloalkyl;

wherein R$^5$ is optionally substituted with one or more R$^{5a}$, wherein each R$^{5a}$ is independently halogen, nitro, heteroaryl, heterocyclyl, C$_2$-C$_6$ alkenyl, C$_2$-C$_6$ alkynyl, (C$_3$-C$_8$ cycloalkyl)-C$_1$-C$_6$ alkyl-, (C$_3$-C$_8$ cycloalkenyl)-C$_1$-C$_6$ alkyl-, (C$_3$-C$_8$ cycloalkyl)-C$_2$-C$_6$ alkenyl-, aryl, arylalkyl, aryloxy, aryloxyaryl, arylC$_{1-6}$ alkoxy, C$_1$-C$_6$ alkyl, C$_1$-C$_6$ haloalkyl, C$_3$-C$_6$cycloalkyl, SO$_2$R$^{11}$, OR$^{11}$, SR$^{11}$, N$_3$, SO$_2$R$^{11}$, COR$^{11}$, SO$_2$N(R$^{11}$)$_2$, SO$_2$NR$^{11}$COR$^{11}$, C≡N, C(O)OR$^{11}$, CON(R$^{11}$)$_2$, CON(R$^{11}$)OR$^{11}$, OCON(R$^{11}$)$_2$, NR$^{11}$COR$^{11}$, NR$^{11}$CON(R$^{11}$)$_2$, NR$^{11}$COOR$^{11}$, or N(R$^{11}$)$_2$, wherein each R$^{5a}$ is optionally substituted with one or more groups which independently are -halogen, —C$_1$-C$_6$ alkyl, aryloxy, C$_{0-6}$ alkylSO$_2$R$^{11}$, C$_{0-6}$ alkyl-COOR$^{11}$, C$_{0-6}$ alkoxyaryl, —C$_1$-C$_6$ haloalkyl, —SO$_2$R$^{11}$, OR$^{11}$, —SR$^{11}$, —N$_3$, —SO$_2$R$^{11}$, —COR$^{11}$, —SO$_2$N(R$^{11}$)$_2$, —SO$_2$NR$^{11}$COR$^{11}$, —C≡N, —C(O)O R$^{11}$, —CON(R$^{11}$)$_2$, —CON(R$^{11}$)OR$^{11}$, —OCON(R$^{11}$)$_2$, —NR$^{11}$COR$^{11}$, —NR$^{11}$CON(R$^{11}$)$_2$, —NR$^{11}$COOR$^{11}$, or —N(R$^{11}$)$_2$;

R$^2$ is —H, —[C(R$^{15}$)$_2$]$_m$—OH, —C$_1$-C$_6$alkyl, —C$_1$-C$_6$ haloalkyl, halogen, —C(O)N(R$^{11}$)$_2$, or —COOR$^{11}$;

R$^{21}$ is hydrogen, halogen, C$_1$-C$_6$ alkyl, or C$_1$-C$_6$ haloalkyl; and provided that R$^2$ and R$^{21}$ are not simultaneously hydrogen;

G is a group of the formula,

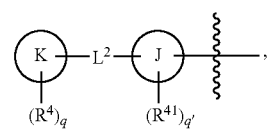

wherein

J is aryl or heteroaryl;

K is aryl or heteroaryl;

each R$^4$ and R$^{41}$ is independently halogen, heteroaryl, heterocyclyl, -G$^1$, -E- G$^1$, or -D-E- G$^1$, wherein D is —O—;

E is —[C(R$^{15}$)$_2$]$_m$— or —C$_3$-C$_6$cycloalkyl; and

G$^1$ is —C$_1$-C$_6$alkyl, —C$_1$-C$_6$haloalkyl, —COR$^{11}$, —COOR$^{11}$, —CON(R$^{11}$)$_2$, —C≡N, —OR$^{11}$, —SOR$^{11}$, —SO$_2$R$^{11}$, —SO$_2$N(R$^{11}$)$_2$, or —SR$^{11}$, L$^2$ is a bond;

q is 1, 2, or 3, and q' is 0, 1, 2 or 3, each R$^{11}$ is independently -hydrogen, —C$_1$-C$_6$ alkyl, C$_2$-C$_6$ alkenyl, C$_2$-C$_6$ alkynyl, (C$_3$-C$_8$ cycloalkyl)-C$_1$-C$_6$ alkyl-, (C$_3$-C$_8$ cycloalkenyl)-C$_1$-C$_6$ alkyl-, (C$_3$-C$_8$ cycloalkyl)-C$_2$-C$_6$ alkenyl-, —C$_3$-C$_8$ cycloalkyl, —(C$_1$-C$_6$)alkyl-(C$_3$-C$_8$)cycloalkyl, —C$_1$-C$_6$ haloalkyl, —N(R$^{12}$)$_2$, aryl, —(C$_1$-C$_6$)alkyl-aryl, heteroaryl, —(C$_1$-C$_6$)alkyl-heteroaryl, heterocyclyl, or —(C$_1$-C$_6$) alkyl-heterocyclyl, wherein any of R$^{11}$ is optionally substituted with one or more radicals of R$^{12}$;

each $R^{12}$ is independently halogen, $OR^{13}$, $N(R^{13})_2$, $C_1$-$C_6$haloalkyl, $C_1$-$C_6$ alkyl, $C_1$-$C_6$ alkoxy, $C_0$-$C_6$ alkyl$OR^{13}$, $C_0$-$C_6$ alkyl$COR^{13}$, $C_0$-$C_6$ alkyl$SO_2R^{13}$, $C_0$-$C_6$ alkyl$CON(R^{13})_2$, $C_0$-$C_6$ alkyl$CONR^{13}OR^{13}$, $C_0$-$C_6$ alkyl$SO_2N(R^{13})_2$, $C_0$-$C_6$ alkyl$SR^{13}$, $C_0$-$C_6$ haloalkyl$OR^{13}$, aryloxy, aralkyloxy, aryloxyalkyl, $C_{0-6}$alkoxyaryl, aryl$C_{0-6}$ alkylcarboxy, $C_0$-$C_6$ alkyl, —$NR^{13}SO_2 R^{13}$, or —$OC_{0-6}$ alkyl$COOR^{13}$;

each $R^{13}$ is independently hydrogen $C_1$-$C_6$ alkyl, $C_2$-$C_6$ alkenyl, $C_2$-$C_6$ alkynyl, ($C_3$-$C_8$ cycloalkyl)$C_1$-$C_6$ alkyl-, ($C_3$-$C_8$ cycloalkenyl)-$C_1$-$C_6$ alkyl-, or ($C_3$-$C_8$ cycloalkyl)-$C_2$-$C_6$ alkenyl-.

24. A compound which is one of the species selected from the group consisting of:

| Cpd # | Structure | Name |
|---|---|---|
| 1 | 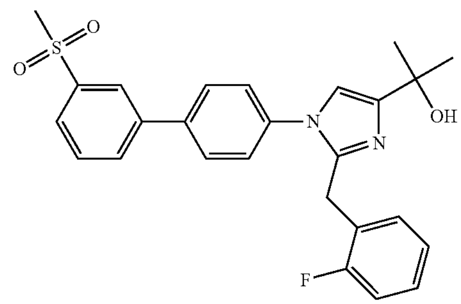 [SMILES: CC(C)(O)c1cn(-c2ccc(-c3cccc(S(C)(=O)=O)c3)cc2)c(Cc2ccccc2F)n1] | 2-(2-(2-fluorobenzyl)-1-(3'-(methylsulfonyl)biphenyl-4-yl)-1H-imidazol-4-yl)propan-2-ol; |
| 2 | 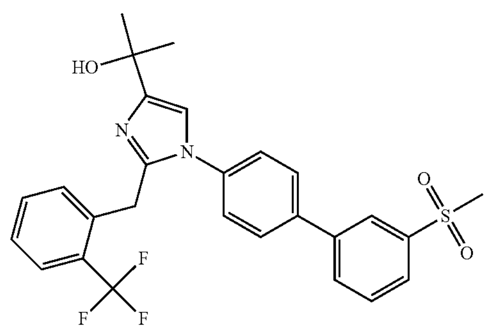 [SMILES: CC(C)(O)c1cn(-c2ccc(-c3cccc(S(C)(=O)=O)c3)cc2)c(Cc2ccccc2C(F)(F)F)n1] | 2-(1-(3'-(methylsulfonyl)biphenyl-4-yl)-2-(2-(trifluoromethyl)benzyl)-1H-imidazol-4-yl)propan-2-ol; |
| 3 | 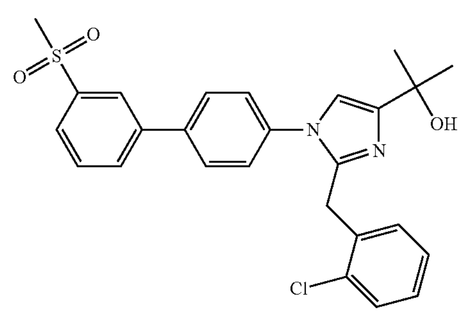 [SMILES: CC(C)(O)c1cn(-c2ccc(-c3cccc(S(C)(=O)=O)c3)cc2)c(Cc2ccccc2Cl)n1] | 2-(2-(2-chlorobenzyl)-1-(3'-(methylsulfonyl)biphenyl-4-yl)-1H-imidazol-4-yl)propan-2-ol; |
| 4 | 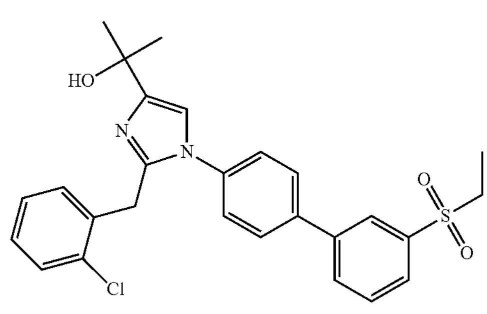 [SMILES: CCS(=O)(=O)c1cccc(-c2ccc(-n3cc(C(C)(C)O)nc3Cc3ccccc3Cl)cc2)c1] | 2-(2-(2-chlorobenzyl)-1-(3'-(ethylsulfonyl)biphenyl-4-yl)-1H-imidazol-4-yl)propan-2-ol; |

-continued

| Cpd # | Structure | Name |
|---|---|---|
| 5 | 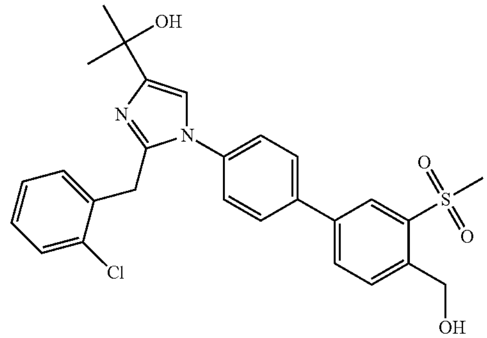 [SMILES: CC(C)(O)c1cn(-c2ccc(-c3ccc(CO)c(S(C)(=O)=O)c3)cc2)c(Cc2ccccc2Cl)n1] | 2-(2-(2-chlorobenzyl)-1-(4'-(hydroxymethyl)-3'-(methylsulfonyl)biphenyl-4-yl)-1H-imidazol-4-yl)propan-2-ol; |
| 6 | 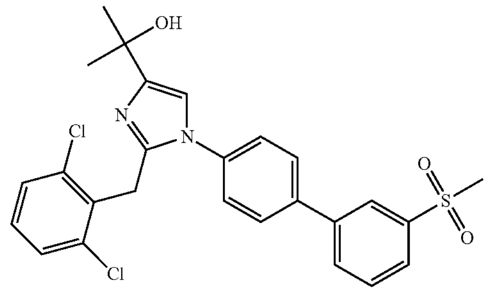 | 2-(2-(2,6-dichlorobenzyl)-1-(3'-(methylsulfonyl)biphenyl-4-yl)-1H-imidazol-4-yl)propan-2-ol; |
| 7 | 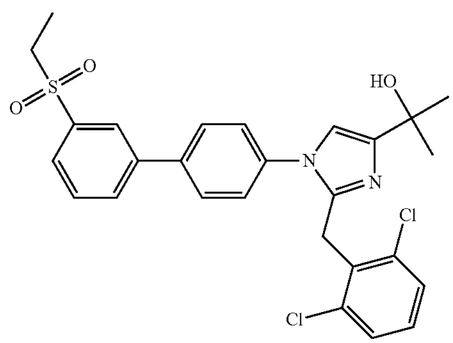 | 2-(2-(2,6-dichlorobenzyl)-1-(3'-(ethylsulfonyl)biphenyl-4-yl)-1H-imidazol-4-yl)propan-2-ol; |
| 8 | 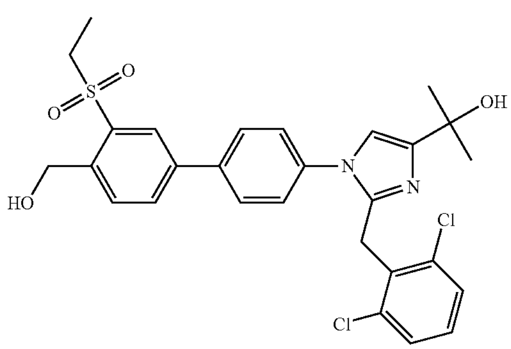 [SMILES: CCS(=O)(=O)c1cc(-c2ccc(-n3cc(C(C)(C)O)nc3Cc3c(Cl)cccc3Cl)cc2)ccc1CO] | 2-(2-(2,6-dichlorobenzyl)-1-(3'-(ethylsulfonyl)-4'-(hydroxymethyl)biphenyl-4-yl)-1H-imidazol-4-yl)propan-2-ol; |
| 9 | 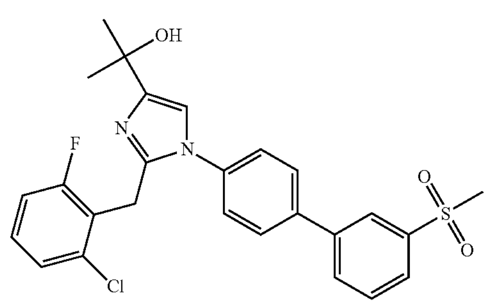 [SMILES: CC(C)(O)c1cn(-c2ccc(-c3cccc(S(C)(=O)=O)c3)cc2)c(Cc2c(F)cccc2Cl)n1] | 2-(2-(2-chloro-6-fluorobenzyl)-1-(3'-(methylsulfonyl)biphenyl-4-yl)-1H-imidazol-4-yl)propan-2-ol; |

-continued

| Cpd # | Structure | Name |
|---|---|---|
| 10 | 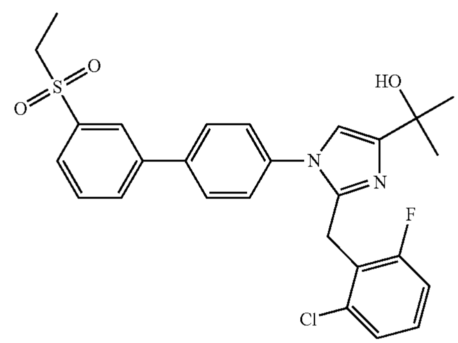 [SMILES: CCS(=O)(=O)c1cccc(-c2ccc(-n3cc(C(C)(C)O)nc3Cc3c(F)cccc3Cl)cc2)c1] | 2-(2-(2-chloro-6-fluorobenzyl)-1-(3'-(ethylsulfonyl)biphenyl-4-yl)-1H-imidazol-4-yl)propan-2-ol; |
| 11 | 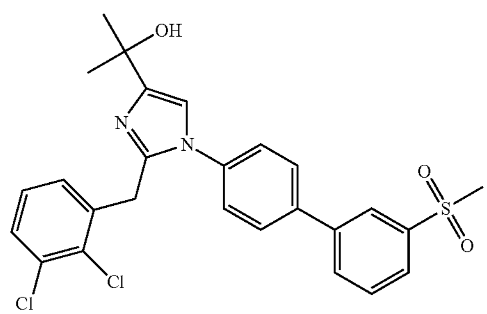 [SMILES: CC(C)(O)c1cn(-c2ccc(-c3cccc(S(C)(=O)=O)c3)cc2)c(Cc2cccc(Cl)c2Cl)n1] | 2-(2-(2,3-dichlorobenzyl)-1-(3'-(methylsulfonyl)biphenyl-4-yl)-1H-imidazol-4-yl)propan-2-ol; |
| 12 | 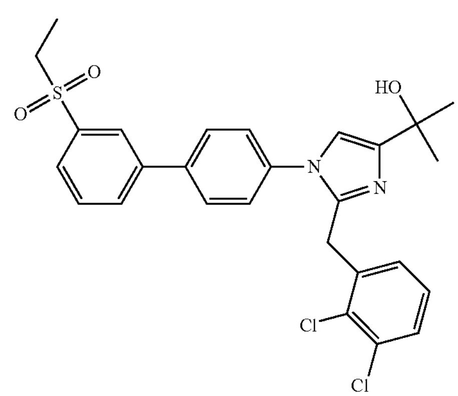 [SMILES: CCS(=O)(=O)c1cccc(-c2ccc(-n3cc(C(C)(C)O)nc3Cc3cccc(Cl)c3Cl)cc2)c1] | 2-(2-(2,3-dichlorobenzyl)-1-(3'-(ethylsulfonyl)biphenyl-4-yl)-1H-imidazol-4-yl)propan-2-ol; |
| 13 | 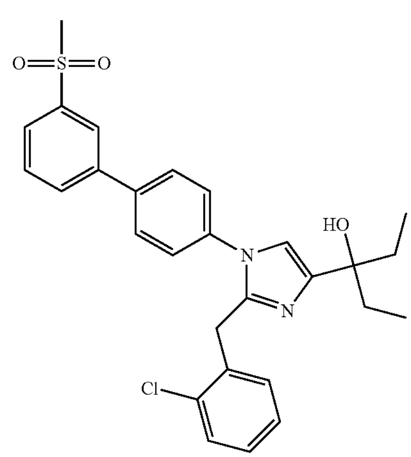 [SMILES: CCC(O)(CC)c1cn(-c2ccc(-c3cccc(S(C)(=O)=O)c3)cc2)c(Cc2ccccc2Cl)n1] | 3-(2-(2-chlorobenzyl)-1-(3'-(methylsulfonyl)biphenyl-4-yl)-1H-imidazol-4-yl)pentan-3-ol; |

| Cpd # | Structure | Name |
| --- | --- | --- |
| 14 | 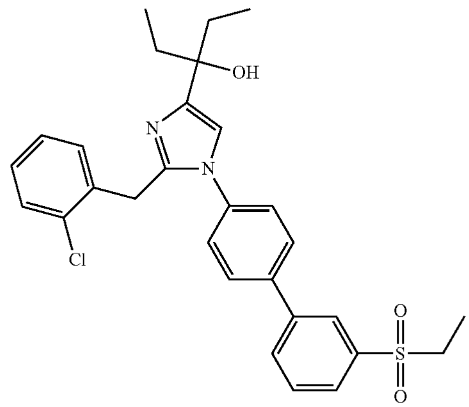 [SMILES: CCC(O)(CC)c1cn(-c2ccc(-c3cccc(S(=O)(=O)CC)c3)cc2)c(Cc2ccccc2Cl)n1] | 3-(2-(2-chlorobenzyl)-1-(3'-(ethylsulfonyl)biphenyl-4-yl)-1H-imidazol-4-yl)pentan-3-ol; |
| 15 | 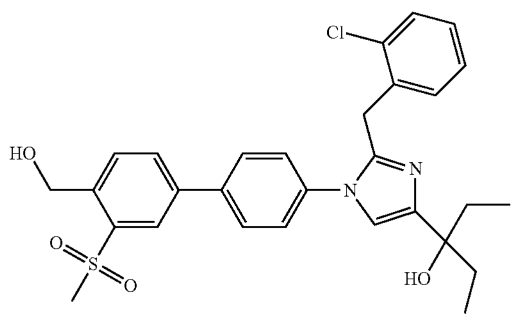 [SMILES: CCC(O)(CC)c1cn(-c2ccc(-c3ccc(CO)c(S(C)(=O)=O)c3)cc2)c(Cc2ccccc2Cl)n1] | 3-(2-(2-chlorobenzyl)-1-(4'-(hydroxymethyl)-3'-(methylsulfonyl)biphenyl-4-yl)-1H-imidazol-4-yl)pentan-3-ol; |
| 16 | 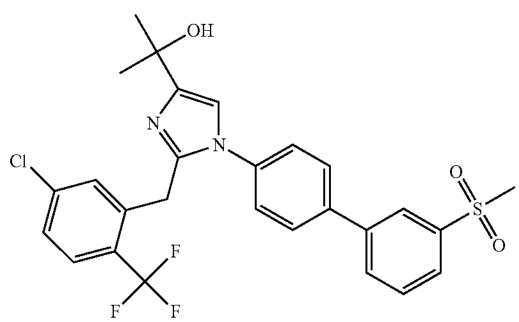 [SMILES: CC(C)(O)c1cn(-c2ccc(-c3cccc(S(C)(=O)=O)c3)cc2)c(Cc2cc(Cl)ccc2C(F)(F)F)n1] | 2-(2-(5-chloro-2-(trifluoromethyl)benzyl)-1-(3'-(methylsulfonyl)biphenyl-4-yl)-1H-imidazol-4-yl)propan-2-ol; |
| 17 | 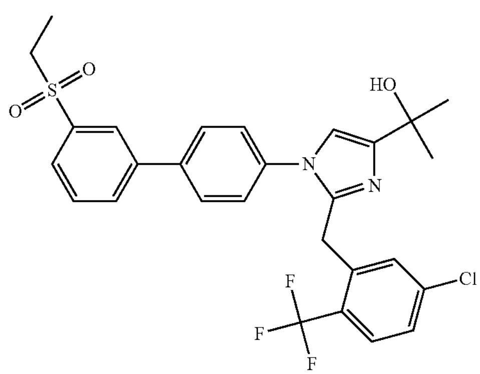 [SMILES: CCS(=O)(=O)c1cccc(-c2ccc(-n3cc(C(C)(C)O)nc3Cc3cc(Cl)ccc3C(F)(F)F)cc2)c1] | 2-(2-(5-chloro-2-(trifluoromethyl)benzyl)-1-(3'-(ethylsulfonyl)biphenyl-4-yl)-1H-imidazol-4-yl)propan-2-ol; |

-continued

| Cpd # | Structure | Name |
|---|---|---|
| 18 | 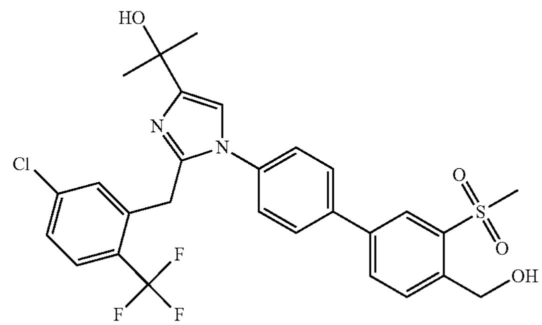 [SMILES: CC(C)(O)c1cn(-c2ccc(-c3ccc(CO)c(S(C)(=O)=O)c3)cc2)c(Cc2cc(Cl)ccc2C(F)(F)F)n1] | 2-(2-(5-chloro-2-(trifluoromethyl)benzyl)-1-(4'-(hydroxymethyl)-3'-(methylsulfonyl)biphenyl-4-yl)-1H-imidazol-4-yl)propan-2-ol; |
| 19 | 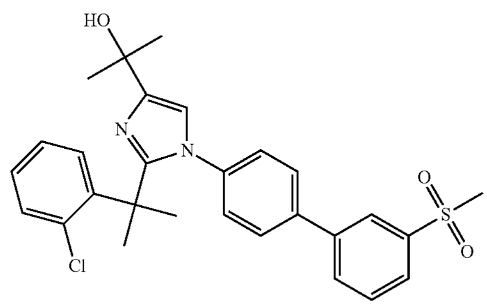 [SMILES: CC(C)(O)c1cn(-c2ccc(-c3cccc(S(C)(=O)=O)c3)cc2)c(C(C)(C)c2ccccc2Cl)n1] | 2-(2-(2-(2-chlorophenyl)propan-2-yl)-1-(3'-(methylsulfonyl)biphenyl-4-yl)-1H-imidazol-4-yl)propan-2-ol; |
| 20 | 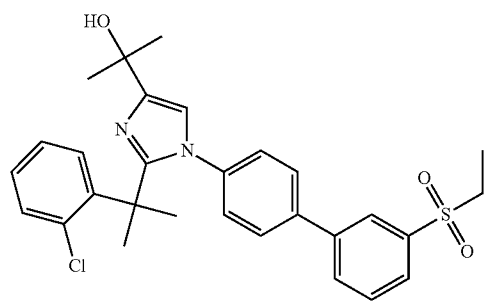 [SMILES: CCS(=O)(=O)c1cccc(-c2ccc(-n3cc(C(C)(C)O)nc3C(C)(C)c3ccccc3Cl)cc2)c1] | 2-(2-(2-(2-chlorophenyl)propan-2-yl)-1-(3'-(ethylsulfonyl)biphenyl-4-yl)-1H-imidazol-4-yl)propan-2-ol; |
| 21 | 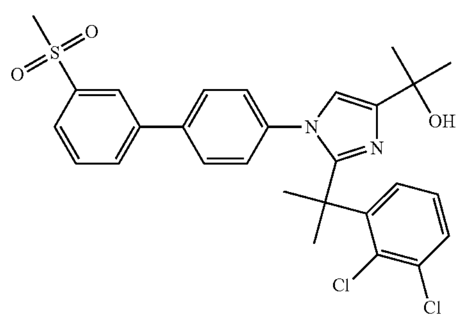 [SMILES: CC(C)(O)c1cn(-c2ccc(-c3cccc(S(C)(=O)=O)c3)cc2)c(C(C)(C)c2cccc(Cl)c2Cl)n1] | 2-(2-(2-(2,3-dichlorophenyl)propan-2-yl)-1-(3'-(methylsulfonyl)biphenyl-4-yl)-1H-imidazol-4-yl)propan-2-ol; |
| 22 | 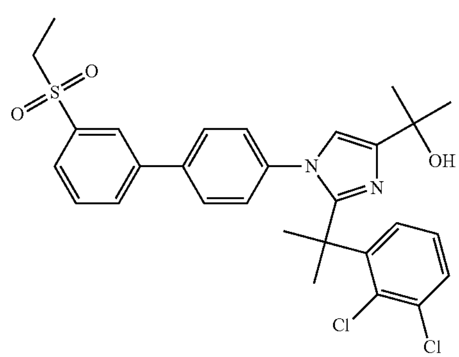 [SMILES: CCS(=O)(=O)c1cccc(-c2ccc(-n3cc(C(C)(C)O)nc3C(C)(C)c3cccc(Cl)c3Cl)cc2)c1] | 2-(2-(2-(2,3-dichlorophenyl)propan-2-yl)-1-(3'-(ethylsulfonyl)biphenyl-4-yl)-1H-imidazol-4-yl)propan-2-ol; |

-continued

| Cpd # | Structure | Name |
|---|---|---|
| 23 | 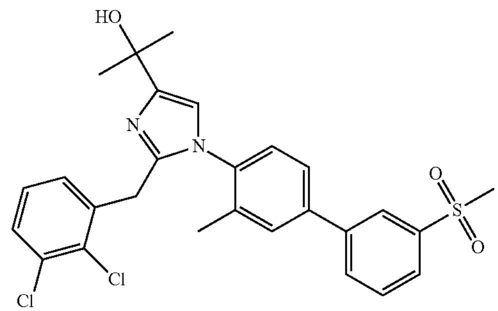 [SMILES: Cc1cc(-c2cccc(S(C)(=O)=O)c2)ccc1-n1cc(C(C)(C)O)nc1Cc1cccc(Cl)c1Cl] | 2-(2-(2,3-dichlorobenzyl)-1-(3-methyl-3'-(methylsulfonyl)biphenyl-4-yl)-1H-imidazol-4-yl)propan-2-ol; |
| 24 | 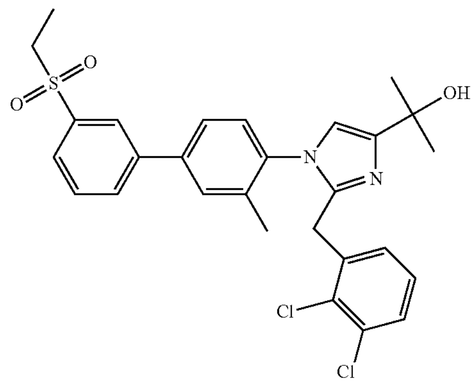 [SMILES: CCS(=O)(=O)c1cccc(-c2ccc(-n3cc(C(C)(C)O)nc3Cc3cccc(Cl)c3Cl)c(C)c2)c1] | 2-(2-(2,3-dichlorobenzyl)-1-(3'-(ethylsulfonyl)-3-methylbiphenyl-4-yl)-1H-imidazol-4-yl)propan-2-ol; |
| 25 | 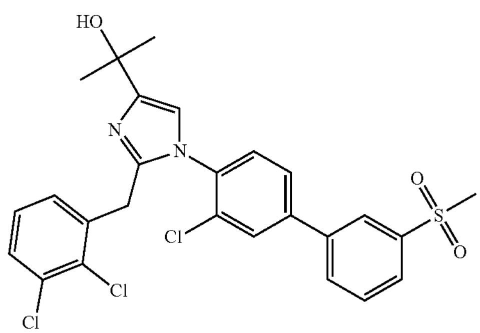 [SMILES: CC(C)(O)c1cn(-c2ccc(-c3cccc(S(C)(=O)=O)c3)cc2Cl)c(Cc2cccc(Cl)c2Cl)n1] | 2-(1-(3-chloro-3'-(methylsulfonyl)biphenyl-4-yl)-2-(2,3-dichlorobenzyl)-1H-imidazol-4-yl)propan-2-ol; |
| 26 | | 2-(1-(3-chloro-3'-(ethylsulfonyl)biphenyl-4-yl)-2-(2,3-dichlorobenzyl)-1H-imidazol-4-yl)propan-2-ol; |
| 27 | | 2-(2-(2-chlorophenethyl)-1-(3'-(methylsulfonyl)biphenyl-4-yl)-1H-imidazol-4-yl)propan-2-ol; |
| 28 | | 2-(2-(2-chlorophenethyl)-1-(3'-(ethylsulfonyl)biphenyl-4-yl)-1H-imidazol-4-yl)propan-2-ol; |
| 29 | | 2-(2-(2-chlorophenethyl)-1-(4'-(hydroxymethyl)-3'-(methylsulfonyl)biphenyl-4-yl)-1H-imidazol-4-yl)propan-2-ol; |

-continued

| Cpd # | Structure | Name |
|---|---|---|
| 30 | | 2-(1-(3-chloro-3'-(methylsulfonyl)biphenyl-4-yl)-2-(naphthalen-1-yl)-1H-imidazol-4-yl)propan-2-ol; |
| 31 | | 2-(1-(3-chloro-3'-(ethylsulfonyl)biphenyl-4-yl)-2-(naphthalen-1-yl)-1H-imidazol-4-yl)propan-2-ol; |
| 32 | 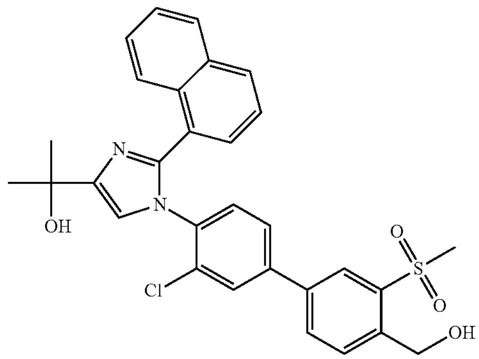 [SMILES: CC(C)(O)c1cn(-c2ccc(-c3ccc(CO)c(S(C)(=O)=O)c3)cc2Cl)c(-c2cccc3ccccc23)n1] | 2-(1-(3-chloro-4'-(hydroxymethyl)-3'-(methylsulfonyl)biphenyl-4-yl)-2-(naphthalen-1-yl)-1H-imidazol-4-yl)propan-2-ol; |
| 33 | 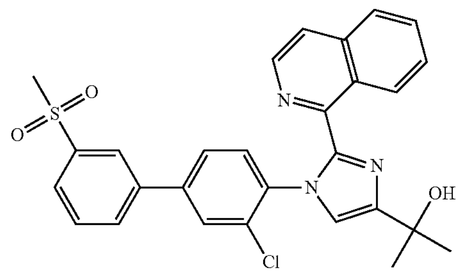 [SMILES: CC(C)(O)c1cn(-c2ccc(-c3cccc(S(C)(=O)=O)c3)cc2Cl)c(-c2nccc3ccccc23)n1] | 2-(1-(3-chloro-3'-(methylsulfonyl)biphenyl-4-yl)-2-(isoquinolin-1-yl)-1H-imidazol-4-yl)propan-2-ol; |
| 34 | 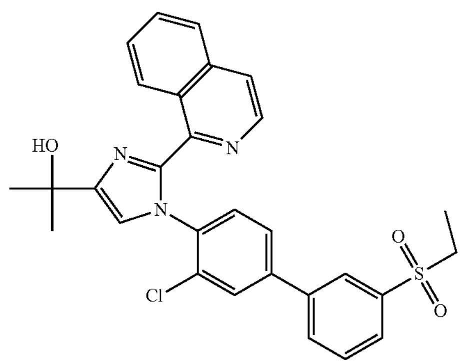 [SMILES: CCS(=O)(=O)c1cccc(-c2ccc(-n3cc(C(C)(C)O)nc3-c3nccc4ccccc34)c(Cl)c2)c1] | 2-(1-(3-chloro-3'-(ethylsulfonyl)biphenyl-4-yl)-2-(isoquinolin-1-yl)-1H-imidazol-4-yl)propan-2-ol; |
| 35 | 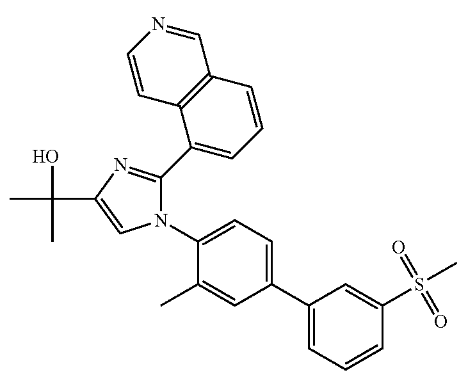 [SMILES: Cc1cc(-c2cccc(S(C)(=O)=O)c2)ccc1-n1cc(C(C)(C)O)nc1-c1cccc2cnccc12] | 2-(2-(isoquinolin-5-yl)-1-(3-methyl-3'-(methylsulfonyl)biphenyl-4-yl)-1H-imidazol-4-yl)propan-2-ol; |

-continued

| Cpd # | Structure | Name |
|---|---|---|
| 36 | 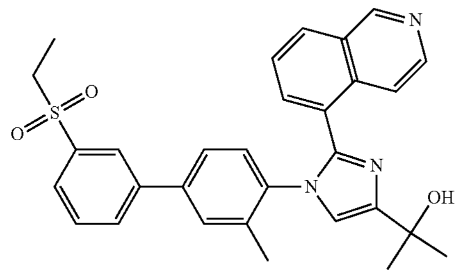 [SMILES: CCS(=O)(=O)c1cccc(-c2ccc(-n3cc(C(C)(C)O)nc3-c3cccc4cnccc34)c(C)c2)c1] | 2-(1-(3'-(ethylsulfonyl)-3-methylbiphenyl-4-yl)-2-(isoquinolin-5-yl)-1H-imidazol-4-yl)propan-2-ol; |
| 37 | 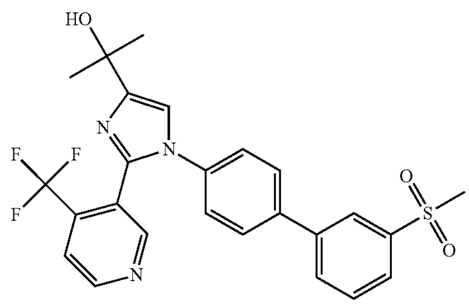 [SMILES: CC(C)(O)c1cn(-c2ccc(-c3cccc(S(C)(=O)=O)c3)cc2)c(-c2cnccc2C(F)(F)F)n1] | 2-(1-(3'-(methylsulfonyl)biphenyl-4-yl)-2-(4-(trifluoromethyl)pyridin-3-yl)-1H-imidazol-4-yl)propan-2-ol; |
| 38 | 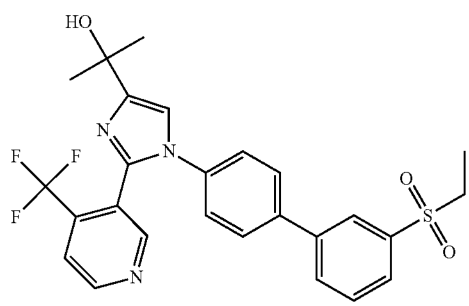 [SMILES: CCS(=O)(=O)c1cccc(-c2ccc(-n3cc(C(C)(C)O)nc3-c3cnccc3C(F)(F)F)cc2)c1] | 2-(1-(3'-(ethylsulfonyl)biphenyl-4-yl)-2-(4-(trifluoromethyl)pyridin-3-yl)-1H-imidazol-4-yl)propan-2-ol; |
| 39 | 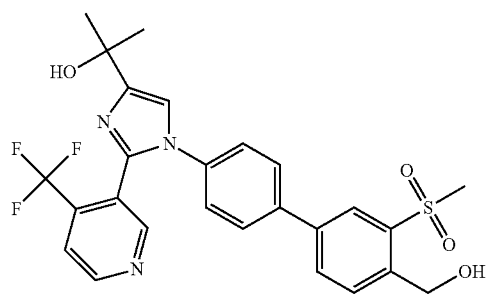 [SMILES: CC(C)(O)c1cn(-c2ccc(-c3ccc(CO)c(S(C)(=O)=O)c3)cc2)c(-c2cnccc2C(F)(F)F)n1] | 2-(1-(4'-(hydroxymethyl)-3'-(methylsulfonyl)biphenyl-4-yl)-2-(4-(trifluoromethyl)pyridin-3-yl)-1H-imidazol-4-yl)propan-2-ol; |
| 40 | 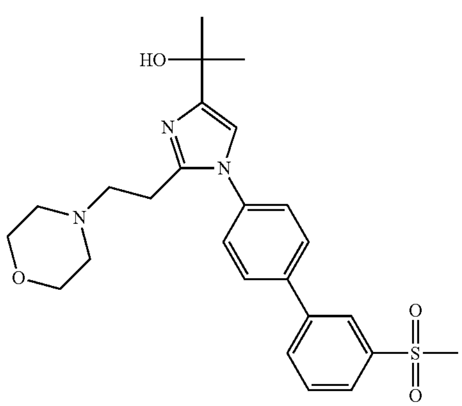 [SMILES: CC(C)(O)c1cn(-c2ccc(-c3cccc(S(C)(=O)=O)c3)cc2)c(CCN2CCOCC2)n1] | 2-(1-(3'-(methylsulfonyl)biphenyl-4-yl)-2-(2-morpholinoethyl)-1H-imidazol-4-yl)propan-2-ol; |

-continued

| Cpd # | Structure | Name |
|---|---|---|
| 41 | 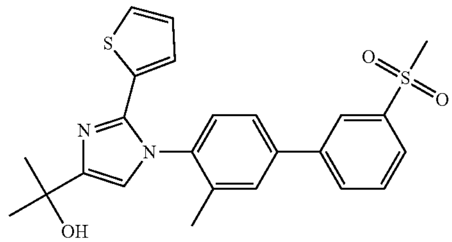 [SMILES: Cc1cc(-c2cccc(S(C)(=O)=O)c2)ccc1-n1cc(C(C)(C)O)nc1-c1cccs1] | 2-(1-(3-methyl-3'-(methylsulfonyl)biphenyl-4-yl)-2-(thiophen-2-yl)-1H-imidazol-4-yl)propan-2-ol; |
| 42 | 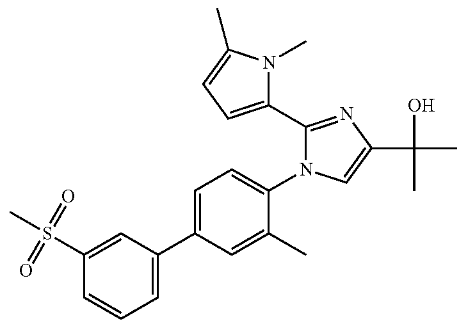 [SMILES: Cc1cc(-c2cccc(S(C)(=O)=O)c2)ccc1-n1cc(C(C)(C)O)nc1-c1ccc(C)n1C] | 2-(2-(1,5-dimethyl-1H-pyrrol-2-yl)-1-(3-methyl-3'-(methylsulfonyl)biphenyl-4-yl)-1H-imidazol-4-yl)propan-2-ol; |
| 43 | 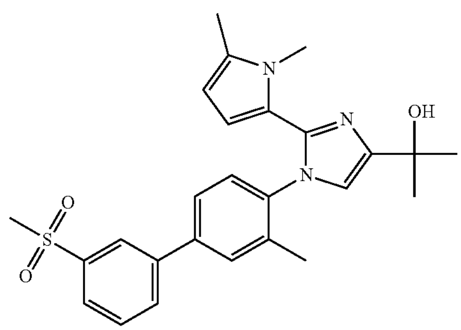 [SMILES: Cc1cc(-c2cccc(S(C)(=O)=O)c2)ccc1-n1cc(C(C)(C)O)nc1-c1ccc(C)n1C] | 2-(2-(1,5-dimethyl-1H-pyrrol-2-yl)-1-(3-methyl-3'-(methylsulfonyl)biphenyl-4-yl)-1H-imidazol-4-yl)propan-2-ol; |
| 44 | 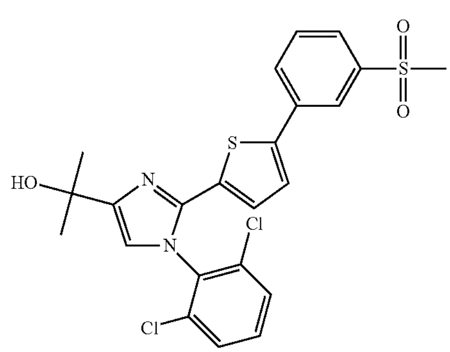 [SMILES: CC(C)(O)c1cn(-c2c(Cl)cccc2Cl)c(-c2ccc(-c3cccc(S(C)(=O)=O)c3)s2)n1] | 2-(1-(2,6-dichlorophenyl)-2-(5-(3-(methylsulfonyl)phenyl)thiophen-2-yl)-1H-imidazol-4-yl)propan-2-ol; |

-continued

| Cpd # | Structure | Name |
|---|---|---|
| 45 | 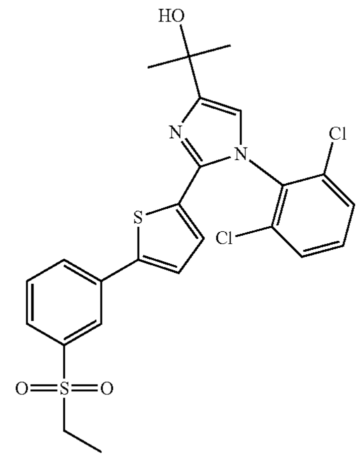 [SMILES: CCS(=O)(=O)c1cccc(-c2ccc(-c3nc(C(C)(C)O)cn3-c3c(Cl)cccc3Cl)s2)c1] | 2-(1-(2,6-dichlorophenyl)-2-(5-(3-(ethylsulfonyl)phenyl)thiophen-2-yl)-1H-imidazol-4-yl)propan-2-ol; |
| 46 | 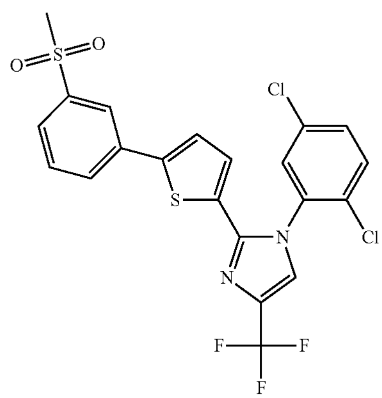 [SMILES: CS(=O)(=O)c1cccc(-c2ccc(-c3nc(C(F)(F)F)cn3-c3cc(Cl)ccc3Cl)s2)c1] | 1-(2,5-dichlorophenyl)-2-{5-[3-(methylsulfonyl)phenyl]-2-thienyl}-4-(trifluoromethyl)-1H-imidazole; |
| 47 | 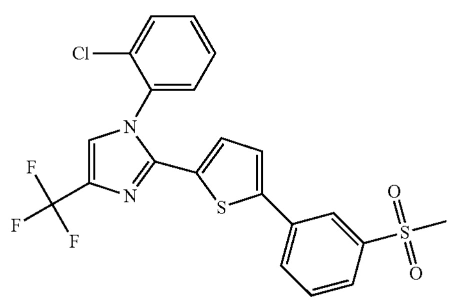 [SMILES: CS(=O)(=O)c1cccc(-c2ccc(-c3nc(C(F)(F)F)cn3-c3ccccc3Cl)s2)c1] | 1-(2-chlorophenyl)-2-{5-[3-(methylsulfonyl)phenyl]-2-thienyl}-4-(trifluoromethyl)-1H-imidazole; |
| 48 | 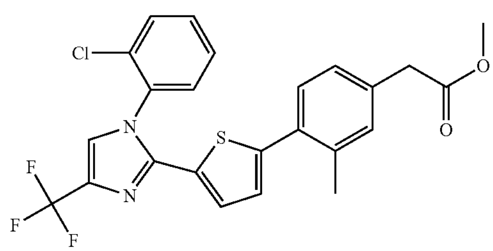 [SMILES: COC(=O)Cc1ccc(-c2ccc(-c3nc(C(F)(F)F)cn3-c3ccccc3Cl)s2)c(C)c1] | methyl (4-{5-[1-(2-chlorophenyl)-4-(trifluoromethyl)-1H-imidazol-2-yl]-2-thienyl}-3-methylphenyl)acetate; |

| Cpd # | Structure | Name |
|---|---|---|
| 49 | 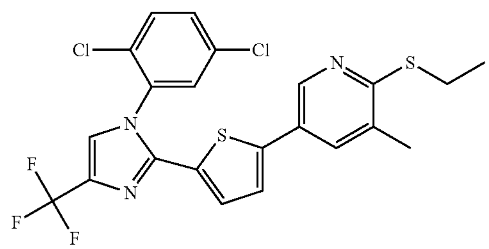 [SMILES: CCSc1ncc(-c2ccc(-c3nc(C(F)(F)F)cn3-c3cc(Cl)ccc3Cl)s2)cc1C] | 5-{5-[1-(2,5-dichlorophenyl)-4-(trifluoromethyl)-1H-imidazol-2-yl]-2-thienyl}-2-(ethylthio)-3-methylpyridine; |
| 50 | 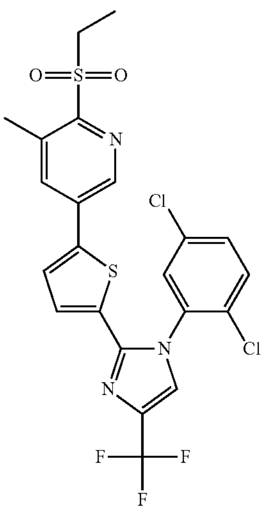 [SMILES: CCS(=O)(=O)c1ncc(-c2ccc(-c3nc(C(F)(F)F)cn3-c3cc(Cl)ccc3Cl)s2)cc1C] | 5-{5-[1-(2,5-dichlorophenyl)-4-(trifluoromethyl)-1H-imidazol-2-yl]-2-thienyl}-2-(ethylsulfonyl)-3-methylpyridine; |
| 51 | 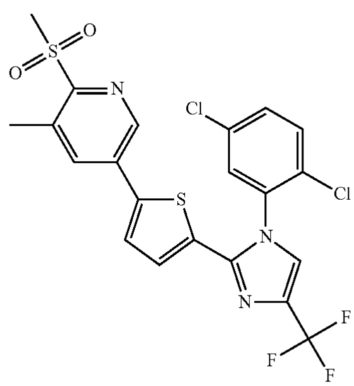 [SMILES: Cc1cc(-c2ccc(-c3nc(C(F)(F)F)cn3-c3cc(Cl)ccc3Cl)s2)cnc1S(C)(=O)=O] | 5-{5-[1-(2,5-dichlorophenyl)-4-(trifluoromethyl)-1H-imidazol-2-yl]-2-thienyl}-3-methyl-2-(methylsulfonyl)pyridine; |
| 52 | 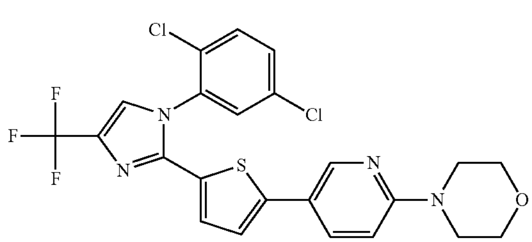 [SMILES: FC(F)(F)c1cn(-c2cc(Cl)ccc2Cl)c(-c2ccc(-c3ccc(N4CCOCC4)nc3)s2)n1] | 4-(5-{5-[1-(2,5-dichlorophenyl)-4-(trifluoromethyl)-1H-imidazol-2-yl]-2-thienyl}pyridin-2-yl)morpholine; |

| Cpd # | Structure | Name |
|---|---|---|
| 53 | 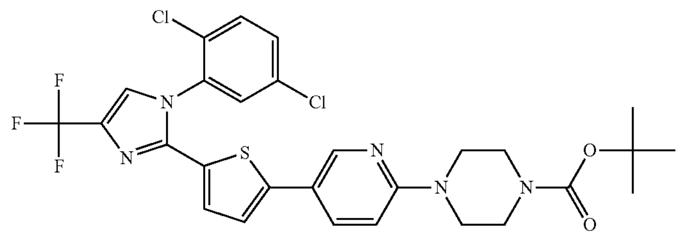 [SMILES: CC(C)(C)OC(=O)N1CCN(c2ccc(-c3ccc(-c4nc(C(F)(F)F)cn4-c4cc(Cl)ccc4Cl)s3)cn2)CC1] | 1,1-dimethylethyl 4-(5-{5-[1-(2,5-dichlorophenyl)-4-(trifluoromethyl)-1H-imidazol-2-yl]-2-thienyl}pyridin-2-yl)piperazine-1-carboxylate; |
| 54 | 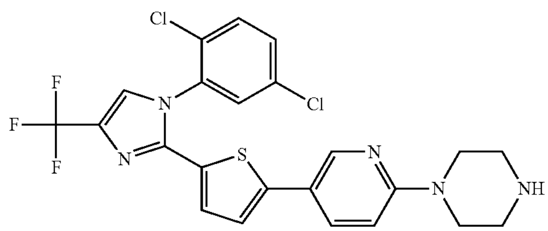 [SMILES: FC(F)(F)c1cn(-c2cc(Cl)ccc2Cl)c(-c2ccc(-c3ccc(N4CCNCC4)nc3)s2)n1] | 1-(5-{5-[1-(2,5-dichlorophenyl)-4-(trifluoromethyl)-1H-imidazol-2-yl]-2-thienyl}pyridin-2-yl)piperazine; |
| 55 | 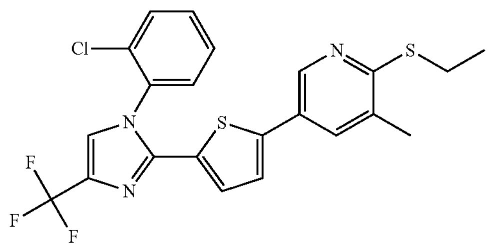 [SMILES: CCSc1ncc(-c2ccc(-c3nc(C(F)(F)F)cn3-c3ccccc3Cl)s2)cc1C] | 5-{5-[1-(2-chlorophenyl)-4-(trifluoromethyl)-1H-imidazol-2-yl]-2-thienyl}-2-(ethylthio)-3-methylpyridine; |
| 56 | 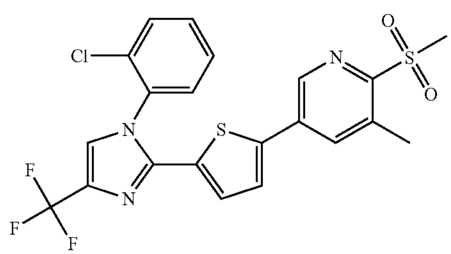 [SMILES: Cc1cc(-c2ccc(-c3nc(C(F)(F)F)cn3-c3ccccc3Cl)s2)cnc1S(C)(=O)=O] | 5-{5-[1-(2-chlorophenyl)-4-(trifluoromethyl)-1H-imidazol-2-yl]-2-thienyl}-3-methyl-2-(methylsulfonyl)pyridine; |
| 57 | 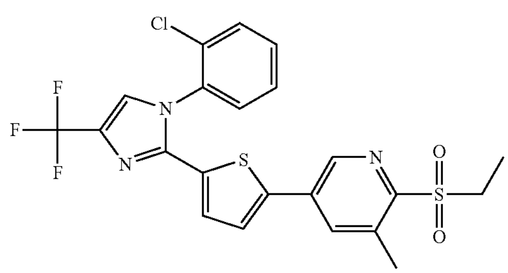 [SMILES: CCS(=O)(=O)c1ncc(-c2ccc(-c3nc(C(F)(F)F)cn3-c3ccccc3Cl)s2)cc1C] | 5-{5-[1-(2-chlorophenyl)-4-(trifluoromethyl)-1H-imidazol-2-yl]-2-thienyl}-2-(ethylsulfonyl)-3-methylpyridine; |
| 58 | 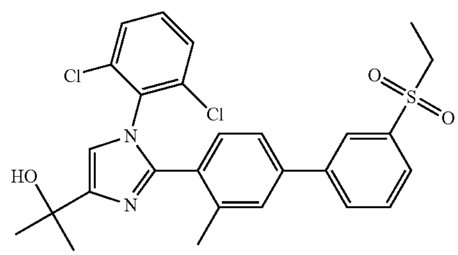 [SMILES: CCS(=O)(=O)c1cccc(-c2ccc(-c3nc(C(C)(C)O)cn3-c3c(Cl)cccc3Cl)c(C)c2)c1] | 2-(1-(2,6-dichlorophenyl)-2-(3'-(ethylsulfonyl)-3-methylbiphenyl-4-yl)-1H-imidazol-4-yl)propan-2-ol; |

-continued

| Cpd # | Structure | Name |
|---|---|---|
| 59 | 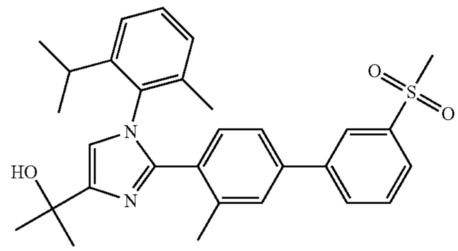 [SMILES: Cc1cc(-c2cccc(S(C)(=O)=O)c2)ccc1-c1nc(C(C)(C)O)cn1-c1c(C)cccc1C(C)C] | 2-(1-(2-isopropyl-6-methylphenyl)-2-(3-methyl-3'-(methylsulfonyl)biphenyl-4-yl)-1H-imidazol-4-yl)propan-2-ol; |
| 60 | 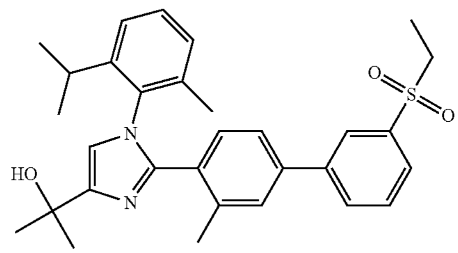 [SMILES: CCS(=O)(=O)c1cccc(-c2ccc(-c3nc(C(C)(C)O)cn3-c3c(C)cccc3C(C)C)c(C)c2)c1] | 2-(2-(3'-(ethylsulfonyl)-3-methylbiphenyl-4-yl)-1-(2-isopropyl-6-methylphenyl)-1H-imidazol-4-yl)propan-2-ol; |
| 61 | 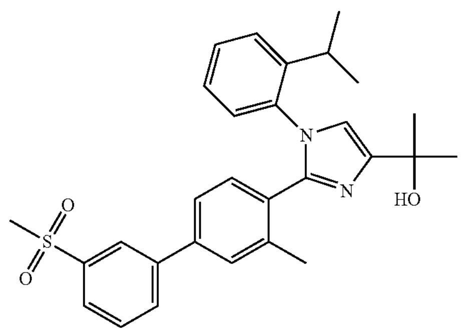 [SMILES: Cc1cc(-c2cccc(S(C)(=O)=O)c2)ccc1-c1nc(C(C)(C)O)cn1-c1ccccc1C(C)C] | 2-(1-(2-isopropylphenyl)-2-(3-methyl-3'-(methylsulfonyl)biphenyl-4-yl)-1H-imidazol-4-yl)propan-2-ol; |
| 62 | 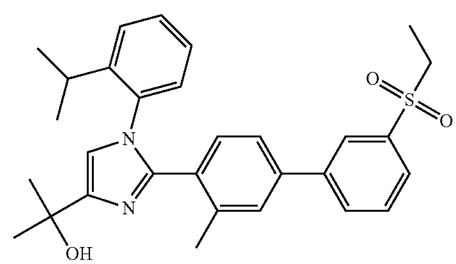 [SMILES: CCS(=O)(=O)c1cccc(-c2ccc(-c3nc(C(C)(C)O)cn3-c3ccccc3C(C)C)c(C)c2)c1] | 2-(2-(3'-(ethylsulfonyl)-3-methylbiphenyl-4-yl)-1-(2-isopropylphenyl)-1H-imidazol-4-yl)propan-2-ol; |
| 63 | 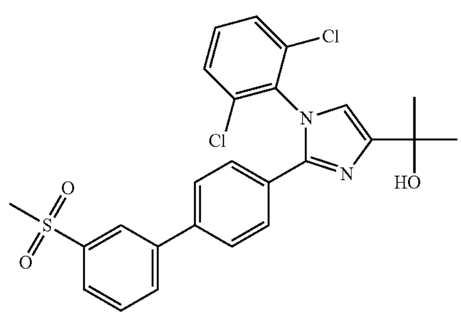 [SMILES: CC(C)(O)c1cn(-c2c(Cl)cccc2Cl)c(-c2ccc(-c3cccc(S(C)(=O)=O)c3)cc2)n1] | 2-(1-(2,6-dichlorophenyl)-2-(3'-(methylsulfonyl)biphenyl-4-yl)-1H-imidazol-4-yl)propan-2-ol; |

| Cpd # | Structure | Name |
|---|---|---|
| 64 | 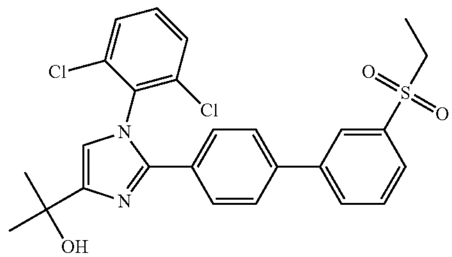 [SMILES: CCS(=O)(=O)c1cccc(-c2ccc(-c3nc(C(C)(C)O)cn3-c3c(Cl)cccc3Cl)cc2)c1] | 2-(1-(2,6-dichlorophenyl)-2-(3'-(ethylsulfonyl)biphenyl-4-yl)-1H-imidazol-4-yl)propan-2-ol; |
| 65 | 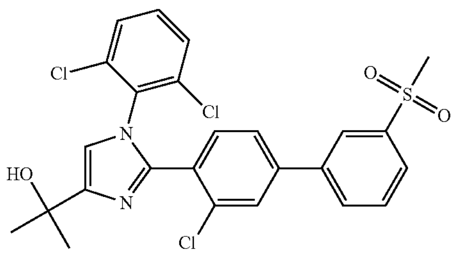 | 2-(2-(3-chloro-3'-(methylsulfonyl)biphenyl-4-yl)-1-(2,6-dichlorophenyl)-1H-imidazol-4-yl)propan-2-ol; |
| 66 | 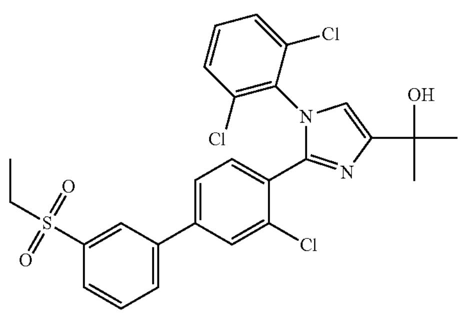 [SMILES: CCS(=O)(=O)c1cccc(-c2ccc(-c3nc(C(C)(C)O)cn3-c3c(Cl)cccc3Cl)c(Cl)c2)c1] | 2-(2-(3-chloro-3'-(ethylsulfonyl)biphenyl-4-yl)-1-(2,6-dichlorophenyl)-1H-imidazol-4-yl)propan-2-ol; |
| 67 | 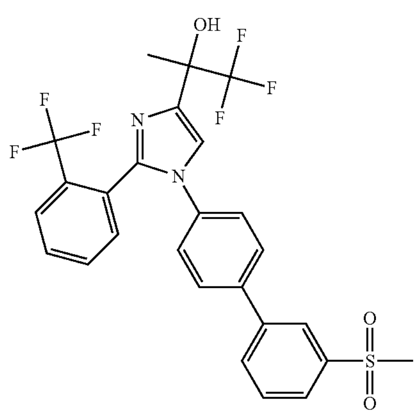 [SMILES: CC(O)(c1cn(-c2ccc(-c3cccc(S(C)(=O)=O)c3)cc2)c(-c2ccccc2C(F)(F)F)n1)C(F)(F)F] | 1,1,1-trifluoro-2-(1-(3'-(methylsulfonyl)biphenyl-4-yl)-2-(2-(trifluoromethyl)phenyl)-1H-imidazol-4-yl)propan-2-ol; |
| 68 | 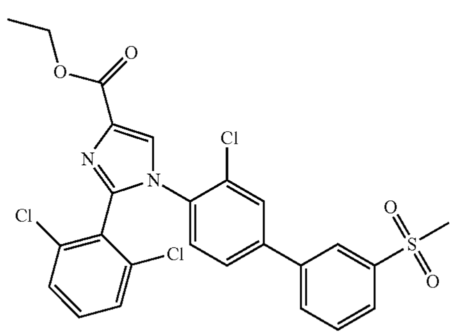 [SMILES: CCOC(=O)c1cn(-c2ccc(-c3cccc(S(C)(=O)=O)c3)cc2Cl)c(-c2c(Cl)cccc2Cl)n1] | ethyl 1-(3-chloro-3'-(methylsulfonyl)biphenyl-4-yl)-2-(2,6-dichlorophenyl)-1H-imidazole-4-carboxylate; |

-continued

| Cpd # | Structure | Name |
|---|---|---|
| 72 | 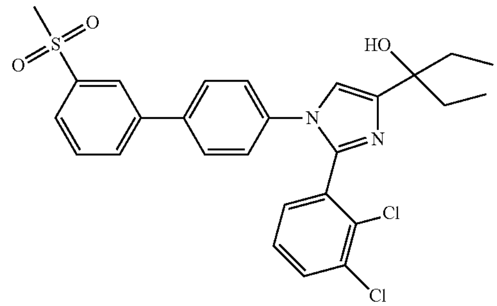 [SMILES: CCC(O)(CC)c1cn(-c2ccc(-c3cccc(S(C)(=O)=O)c3)cc2)c(-c2cccc(Cl)c2Cl)n1] | 3-(2-(2,3-dichlorophenyl)-1-(3'-(methylsulfonyl)biphenyl-4-yl)-1H-imidazol-4-yl)pentan-3-ol; |
| 73 | 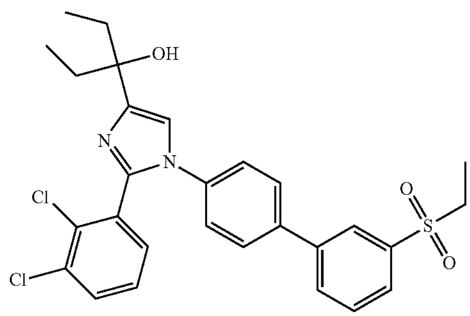 [SMILES: CCC(O)(CC)c1cn(-c2ccc(-c3cccc(S(=O)(=O)CC)c3)cc2)c(-c2cccc(Cl)c2Cl)n1] | 3-(2-(2,3-dichlorophenyl)-1-(3'-(ethylsulfonyl)biphenyl-4-yl)-1H-imidazol-4-yl)pentan-3-ol; |
| 74 | 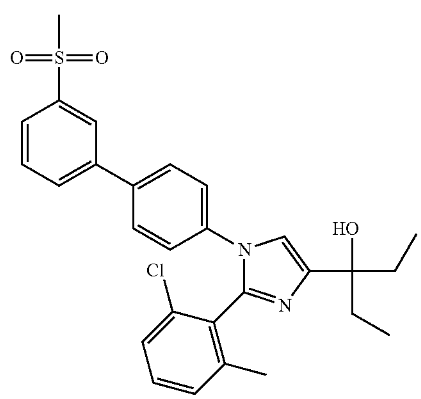 [SMILES: CCC(O)(CC)c1cn(-c2ccc(-c3cccc(S(C)(=O)=O)c3)cc2)c(-c2c(C)cccc2Cl)n1] | 3-(2-(2,6-dichlorophenyl)-1-(3'-(methylsulfonyl)biphenyl-4-yl)-1H-imidazol-4-yl)pentan-3-ol; |
| 80 | 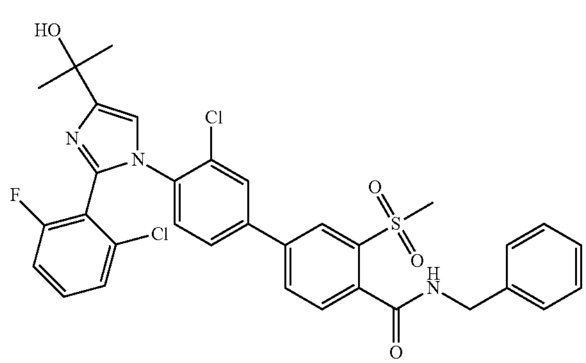 [SMILES: CC(C)(O)c1cn(-c2ccc(-c3ccc(C(=O)NCc4ccccc4)c(S(C)(=O)=O)c3)cc2Cl)c(-c2c(F)cccc2Cl)n1] | N-benzyl-3'-chloro-4'-(2-(2-chloro-6-fluorophenyl)-4-(2-hydroxypropan-2-yl)-1H-imidazol-1-yl)-3-(methylsulfonyl)biphenyl-4-carboxamide; |

-continued

| Cpd # | Structure | Name |
|---|---|---|
| 81 | 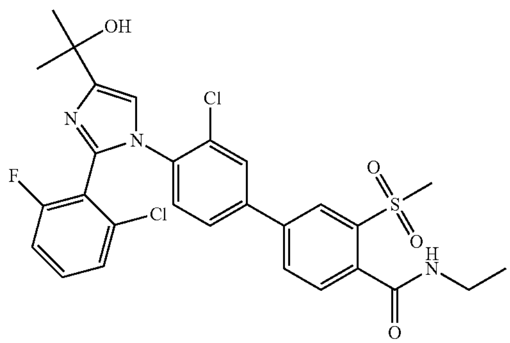 [SMILES: CCNC(=O)c1ccc(-c2ccc(-n3cc(C(C)(C)O)nc3-c3c(F)cccc3Cl)c(Cl)c2)cc1S(C)(=O)=O] | 3'-chloro-4'-(2-(2-chloro-6-fluorophenyl)-4-(2-hydroxypropan-2-yl)-1H-imidazol-1-yl)-N-ethyl-3-(methylsulfonyl)biphenyl-4-carboxamide; |
| 82 | 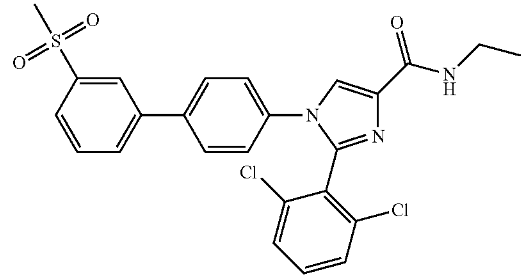 [SMILES: CCNC(=O)c1cn(-c2ccc(-c3cccc(S(C)(=O)=O)c3)cc2)c(-c2c(Cl)cccc2Cl)n1] | 2-(2,6-dichlorophenyl)-N-ethyl-1-(3'-(methylsulfonyl)biphenyl-4-yl)-1H-imidazole-4-carboxamide; |
| 83 | 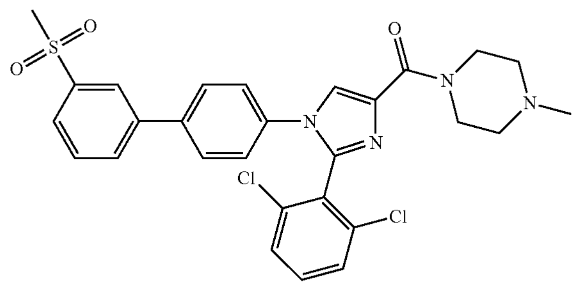 [SMILES: CN1CCN(C(=O)c2cn(-c3ccc(-c4cccc(S(C)(=O)=O)c4)cc3)c(-c3c(Cl)cccc3Cl)n2)CC1] | (2-(2,6-dichlorophenyl)-1-(3'-(methylsulfonyl)biphenyl-4-yl)-1H-imidazol-4-yl)(4-methylpiperazin-1-yl)methanone; |
| 84 | 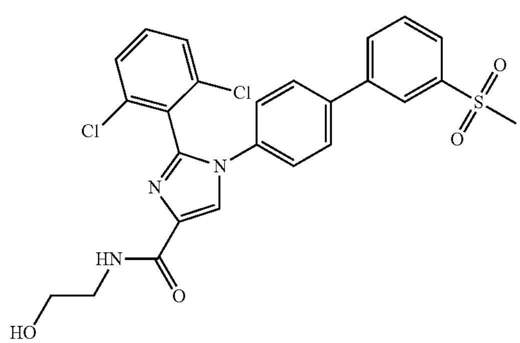 [SMILES: CS(=O)(=O)c1cccc(-c2ccc(-n3cc(C(=O)NCCO)nc3-c3c(Cl)cccc3Cl)cc2)c1] | 2-(2,6-dichlorophenyl)-N-(2-hydroxyethyl)-1-(3'-(methylsulfonyl)biphenyl-4-yl)-1H-imidazole-4-carboxamide; |
| 85 | 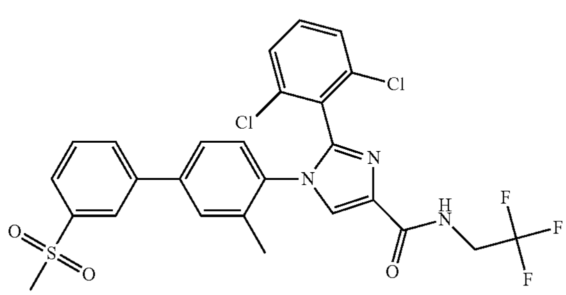 [SMILES: Cc1cc(-c2cccc(S(C)(=O)=O)c2)ccc1-n1cc(C(=O)NCC(F)(F)F)nc1-c1c(Cl)cccc1Cl] | 2-(2,6-dichlorophenyl)-1-(3-methyl-3'-(methylsulfonyl)biphenyl-4-yl)-N-(2,2,2-trifluoroethyl)-1H-imidazole-4-carboxamide; |

| Cpd # | Structure | Name |
|---|---|---|
| 86 | 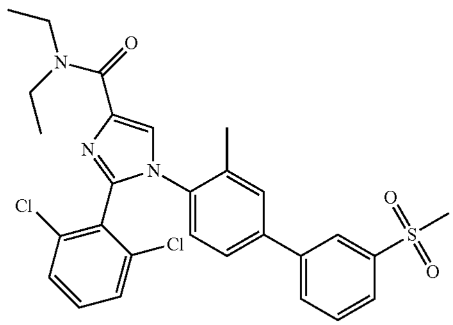 [SMILES: CCN(CC)C(=O)c1cn(-c2ccc(-c3cccc(S(C)(=O)=O)c3)cc2C)c(-c2c(Cl)cccc2Cl)n1] | 2-(2,6-dichlorophenyl)-N,N-diethyl-1-(3-methyl-3'-(methylsulfonyl)biphenyl-4-yl)-1H-imidazole-4-carboxamide |
| 87 | 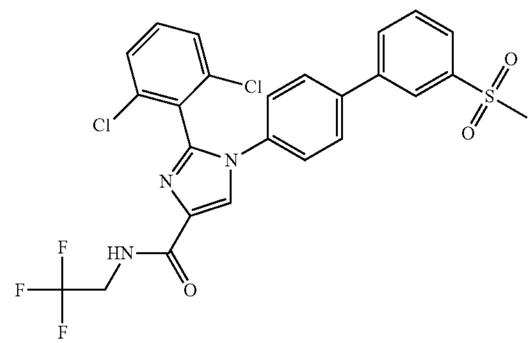 [SMILES: CS(=O)(=O)c1cccc(-c2ccc(-n3cc(C(=O)NCC(F)(F)F)nc3-c3c(Cl)cccc3Cl)cc2)c1] | 2-(2,6-dichlorophenyl)-1-(3'-(methylsulfonyl)biphenyl-4-yl)-N-(2,2,2-trifluoroethyl)-1H-imidazole-4-carboxamide; |
| 88 | 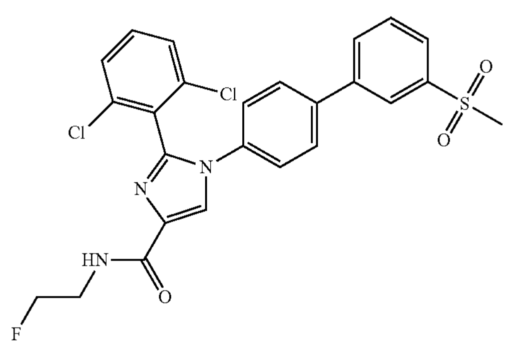 [SMILES: CS(=O)(=O)c1cccc(-c2ccc(-n3cc(C(=O)NCCF)nc3-c3c(Cl)cccc3Cl)cc2)c1] | 2-(2,6-dichlorophenyl)-N-(2-fluoroethyl)-1-(3'-(methylsulfonyl)biphenyl-4-yl)-1H-imidazole-4-carboxamide; |
| 89 | 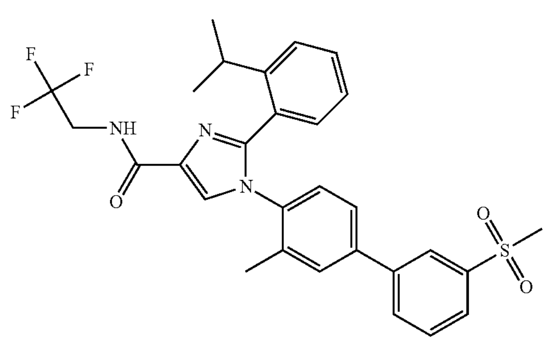 [SMILES: Cc1cc(-c2cccc(S(C)(=O)=O)c2)ccc1-n1cc(C(=O)NCC(F)(F)F)nc1-c1ccccc1C(C)C] | 2-(2-isopropylphenyl)-1-(3-methyl-3'-(methylsulfonyl)biphenyl-4-yl)-N-(2,2,2-trifluoroethyl)-1H-imidazole-4-carboxamide; |

-continued

| Cpd # | Structure | Name |
|---|---|---|
| 90 | 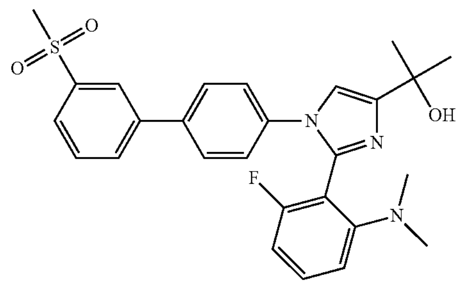 [SMILES: CN(C)c1cccc(F)c1-c1nc(C(C)(C)O)cn1-c1ccc(-c2cccc(S(C)(=O)=O)c2)cc1] | 2-(2-(2-(dimethylamino)-6-fluorophenyl)-1-(3'-(methylsulfonyl)biphenyl-4-yl)-1H-imidazol-4-yl)propan-2-ol; |
| 91 | 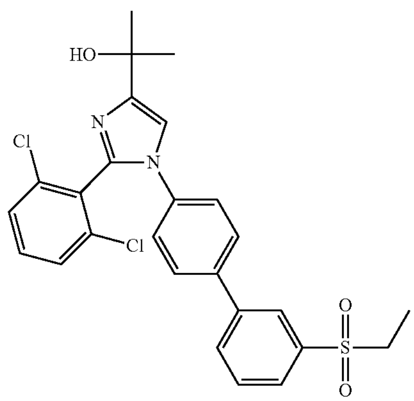 [SMILES: CCS(=O)(=O)c1cccc(-c2ccc(-n3cc(C(C)(C)O)nc3-c3c(Cl)cccc3Cl)cc2)c1] | 2-(2-(2,6-dichlorophenyl)-1-(3'-(ethylsulfonyl)biphenyl-4-yl)-1H-imidazol-4-yl)propan-2-ol; |
| 92 | 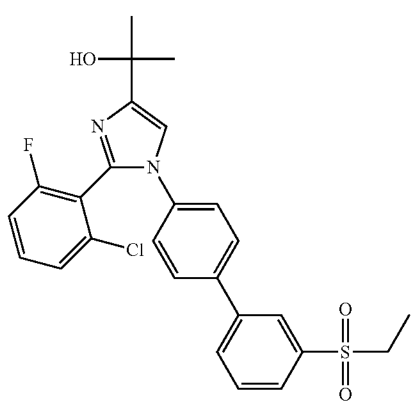 [SMILES: CCS(=O)(=O)c1cccc(-c2ccc(-n3cc(C(C)(C)O)nc3-c3c(F)cccc3Cl)cc2)c1] | 2-(2-(2-chloro-6-fluorophenyl)-1-(3'-(ethylsulfonyl)biphenyl-4-yl)-1H-imidazol-4-yl)propan-2-ol; |
| 93 | 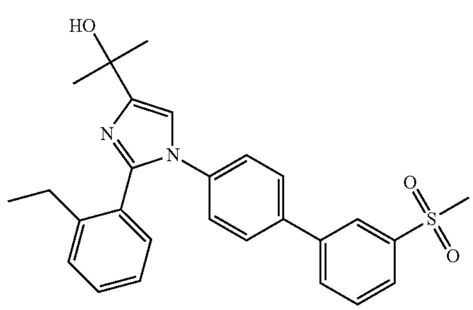 [SMILES: CCc1ccccc1-c1nc(C(C)(C)O)cn1-c1ccc(-c2cccc(S(C)(=O)=O)c2)cc1] | 2-(2-(2-ethylphenyl)-1-(3'-(methylsulfonyl)biphenyl-4-yl)-1H-imidazol-4-yl)propan-2-ol; |

-continued

| Cpd # | Structure | Name |
| --- | --- | --- |
| 94 | 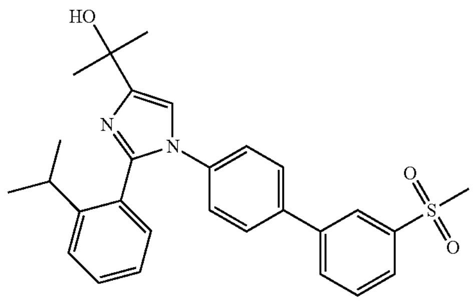 [SMILES: CC(C)c1ccccc1-c1nc(C(C)(C)O)cn1-c1ccc(-c2cccc(S(C)(=O)=O)c2)cc1] | 2-(2-(2-isopropylphenyl)-1-(3'-(methylsulfonyl)biphenyl-4-yl)-1H-imidazol-4-yl)propan-2-ol; |
| 95 | 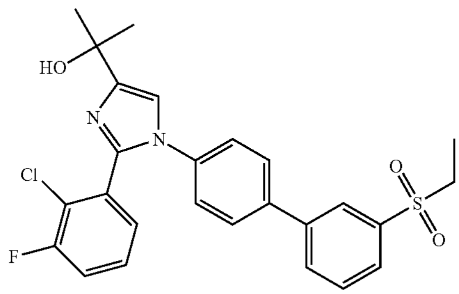 [SMILES: CCS(=O)(=O)c1cccc(-c2ccc(-n3cc(C(C)(C)O)nc3-c3cccc(F)c3Cl)cc2)c1] | 2-(2-(2-chloro-3-fluorophenyl)-1-(3'-(ethylsulfonyl)biphenyl-4-yl)-1H-imidazol-4-yl)propan-2-ol; |
| 96 | 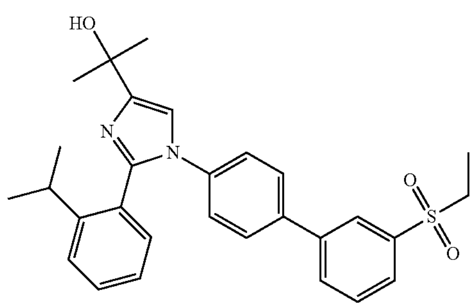 [SMILES: CCS(=O)(=O)c1cccc(-c2ccc(-n3cc(C(C)(C)O)nc3-c3ccccc3C(C)C)cc2)c1] | 2-(1-(3'-(ethylsulfonyl)biphenyl-4-yl)-2-(2-isopropylphenyl)-1H-imidazol-4-yl)propan-2-ol; |
| 97 | 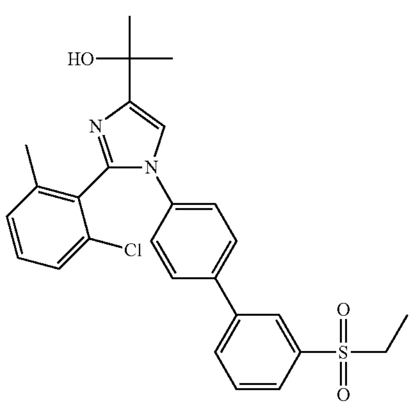 [SMILES: CCS(=O)(=O)c1cccc(-c2ccc(-n3cc(C(C)(C)O)nc3-c3c(C)cccc3Cl)cc2)c1] | 2-(2-(2-chloro-6-methylphenyl)-1-(3'-(ethylsulfonyl)biphenyl-4-yl)-1H-imidazol-4-yl)propan-2-ol; |

-continued

| Cpd # | Structure | Name |
|---|---|---|
| 98 | 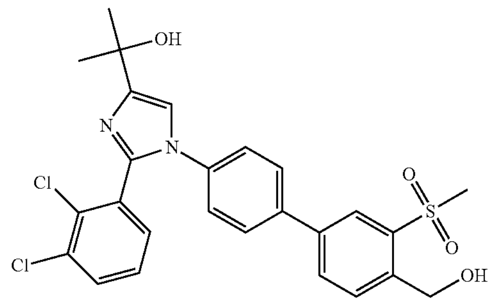 [SMILES: CC(C)(O)c1cn(-c2ccc(-c3ccc(CO)c(S(C)(=O)=O)c3)cc2)c(-c2cccc(Cl)c2Cl)n1] | 2-(2-(2,3-dichlorophenyl)-1-(4'-(hydroxymethyl)-3'-(methylsulfonyl)biphenyl-4-yl)-1H-imidazol-4-yl)propan-2-ol; |
| 99 | 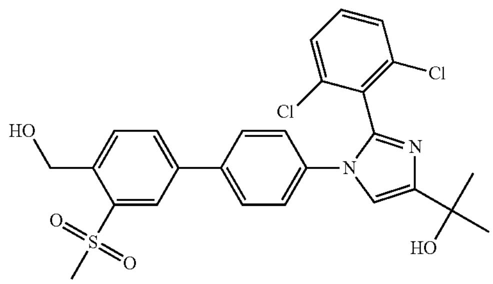 [SMILES: CC(C)(O)c1cn(-c2ccc(-c3ccc(CO)c(S(C)(=O)=O)c3)cc2)c(-c2c(Cl)cccc2Cl)n1] | 2-(2-(2,6-dichlorophenyl)-1-(4'-(hydroxymethyl)-3'-(methylsulfonyl)biphenyl-4-yl)-1H-imidazol-4-yl)propan-2-ol; |
| 100 | 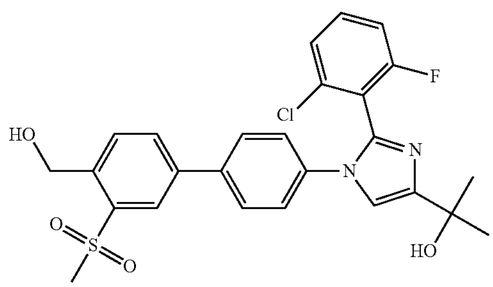 | 2-(2-(2-chloro-6-fluorophenyl)-1-(4'-(hydroxymethyl)-3'-(methylsulfonyl)biphenyl-4-yl)-1H-imidazol-4-yl)propan-2-ol; |
| 101 | 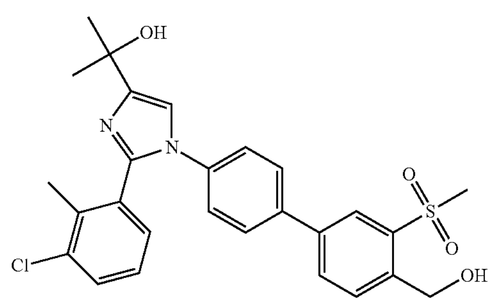 [SMILES: Cc1c(Cl)cccc1-c1nc(C(C)(C)O)cn1-c1ccc(-c2ccc(CO)c(S(C)(=O)=O)c2)cc1] | 2-(2-(3-chloro-2-methylphenyl)-1-(4'-(hydroxymethyl)-3'-(methylsulfonyl)biphenyl-4-yl)-1H-imidazol-4-yl)propan-2-ol; |
| 102 | 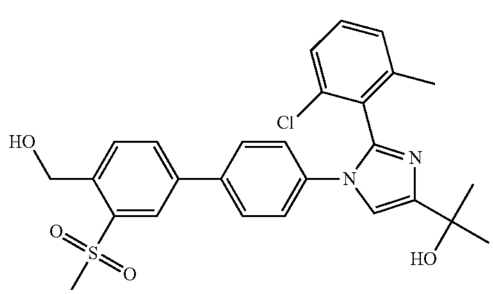 [SMILES: Cc1cccc(Cl)c1-c1nc(C(C)(C)O)cn1-c1ccc(-c2ccc(CO)c(S(C)(=O)=O)c2)cc1] | 2-(2-(2-chloro-6-methylphenyl)-1-(4'-(hydroxymethyl)-3'-(methylsulfonyl)biphenyl-4-yl)-1H-imidazol-4-yl)propan-2-ol; |

| Cpd # | Structure | Name |
|---|---|---|
| 103 | 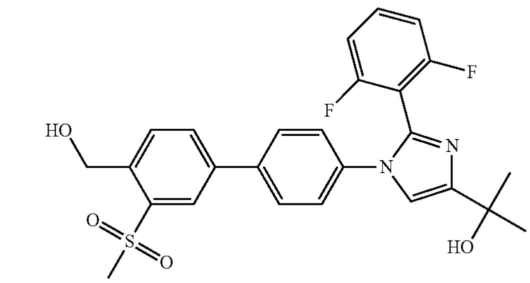 [SMILES: CC(C)(O)c1cn(-c2ccc(-c3ccc(CO)c(S(C)(=O)=O)c3)cc2)c(-c2c(F)cccc2F)n1] | 2-(2-(2,6-difluorophenyl)-1-(4'-(hydroxymethyl)-3'-(methylsulfonyl)biphenyl-4-yl)-1H-imidazol-4-yl)propan-2-ol; |
| 104 | 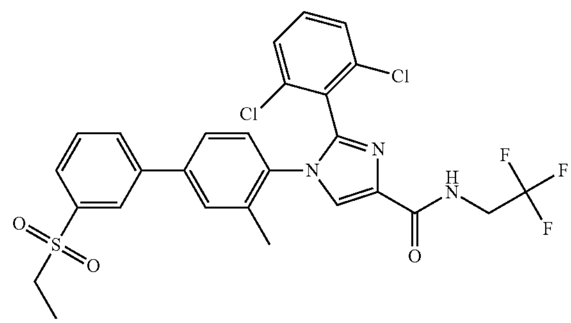 [SMILES: CCS(=O)(=O)c1cccc(-c2ccc(-n3cc(C(=O)NCC(F)(F)F)nc3-c3c(Cl)cccc3Cl)c(C)c2)c1] | 2-(2,6-dichlorophenyl)-1-(3'-(ethylsulfonyl)-3-methylbiphenyl-4-yl)-N-(2,2,2-trifluoroethyl)-1H-imidazole-4-carboxamide; |
| 105 | 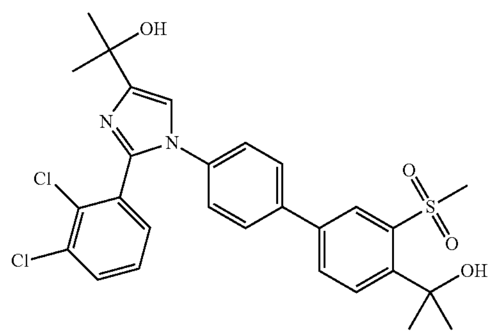 [SMILES: CC(C)(O)c1cn(-c2ccc(-c3ccc(C(C)(C)O)c(S(C)(=O)=O)c3)cc2)c(-c2cccc(Cl)c2Cl)n1] | 2-(2-(2,3-dichlorophenyl)-1-(4'-(2-hydroxypropan-2-yl)-3'-(methylsulfonyl)biphenyl-4-yl)-1H-imidazol-4-yl)propan-2-ol; |
| 106 | 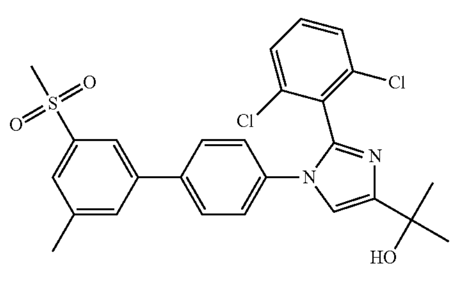 [SMILES: Cc1cc(-c2ccc(-n3cc(C(C)(C)O)nc3-c3c(Cl)cccc3Cl)cc2)cc(S(C)(=O)=O)c1] | 2-(2-(2,6-dichlorophenyl)-1-(3'-methyl-5'-(methylsulfonyl)biphenyl-4-yl)-1H-imidazol-4-yl)propan-2-ol; |
| 107 | 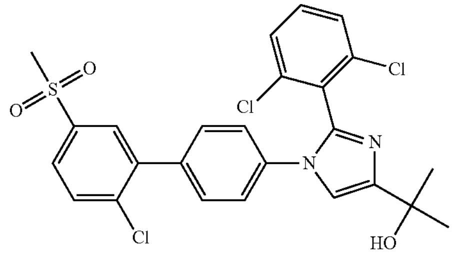 [SMILES: CC(C)(O)c1cn(-c2ccc(-c3cc(S(C)(=O)=O)ccc3Cl)cc2)c(-c2c(Cl)cccc2Cl)n1] | 2-(1-(2'-chloro-5'-(methylsulfonyl)biphenyl-4-yl)-2-(2,6-dichlorophenyl)-1H-imidazol-4-yl)propan-2-ol; |

-continued

| Cpd # | Structure | Name |
|---|---|---|
| 108 | 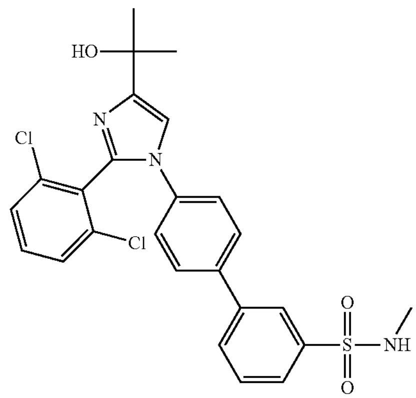 [SMILES: CNS(=O)(=O)c1cccc(-c2ccc(-n3cc(C(C)(C)O)nc3-c3c(Cl)cccc3Cl)cc2)c1] | 4'-(2-(2,6-dichlorophenyl)-4-(2-hydroxypropan-2-yl)-1H-imidazol-1-yl)-N-methylbiphenyl-3-sulfonamide; |
| 109 | 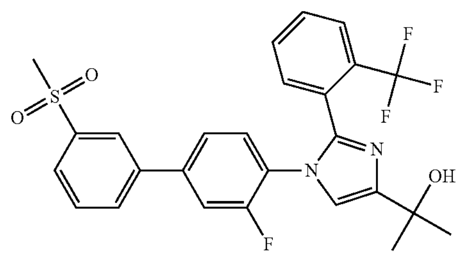 | 2-(1-(3-fluoro-3'-(methylsulfonyl)biphenyl-4-yl)-2-(2-(trifluoromethyl)phenyl)-1H-imidazol-4-yl)propan-2-ol; |
| 110 | 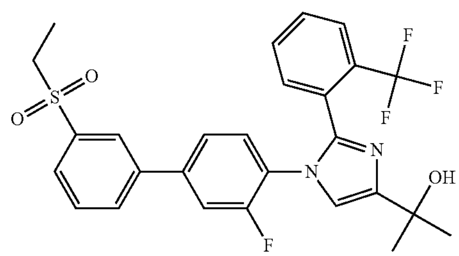 [SMILES: CCS(=O)(=O)c1cccc(-c2ccc(-n3cc(C(C)(C)O)nc3-c3ccccc3C(F)(F)F)c(F)c2)c1] | 2-(1-(3'-(ethylsulfonyl)-3-fluorobiphenyl-4-yl)-2-(2-(trifluoromethyl)phenyl)-1H-imidazol-4-yl)propan-2-ol; |
| 111 | 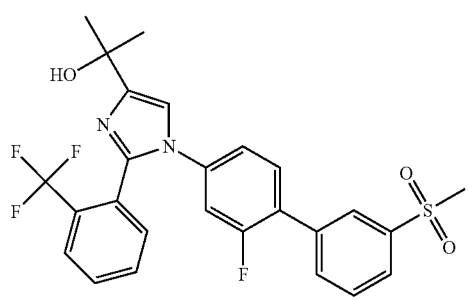 [SMILES: CC(C)(O)c1cn(-c2ccc(-c3cccc(S(C)(=O)=O)c3)c(F)c2)c(-c2ccccc2C(F)(F)F)n1] | 2-(1-(2-fluoro-3'-(methylsulfonyl)biphenyl-4-yl)-2-(2-(trifluoromethyl)phenyl)-1H-imidazol-4-yl)propan-2-ol; |
| 112 | 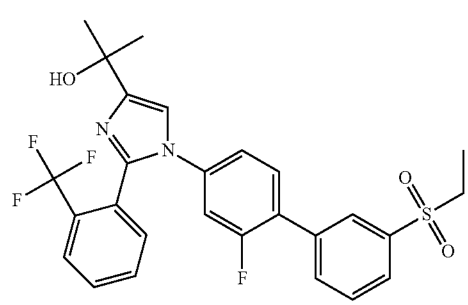 [SMILES: CCS(=O)(=O)c1cccc(-c2ccc(-n3cc(C(C)(C)O)nc3-c3ccccc3C(F)(F)F)cc2F)c1] | 2-(1-(3'-(ethylsulfonyl)-2-fluorobiphenyl-4-yl)-2-(2-(trifluoromethyl)phenyl)-1H-imidazol-4-yl)propan-2-ol; |

-continued

| Cpd # | Structure | Name |
|---|---|---|
| 113 | 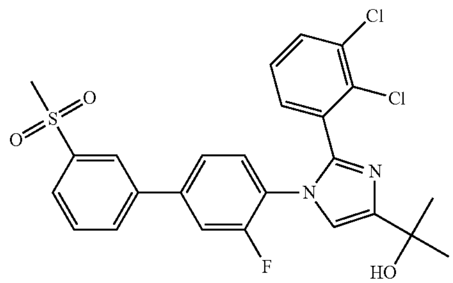 | 2-(2-(2,3-dichlorophenyl)-1-(3-fluoro-3'-(methylsulfonyl)biphenyl-4-yl)-1H-imidazol-4-yl)propan-2-ol; |
| 114 | 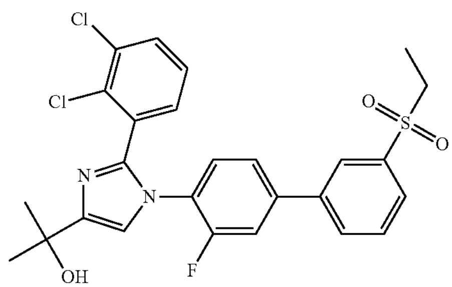 [SMILES: CCS(=O)(=O)c1cccc(-c2ccc(-n3cc(C(C)(C)O)nc3-c3cccc(Cl)c3Cl)c(F)c2)c1] | 2-(2-(2,3-dichlorophenyl)-1-(3'-(ethylsulfonyl)-3-fluorobiphenyl-4-yl)-1H-imidazol-4-yl)propan-2-ol; |
| 115 | 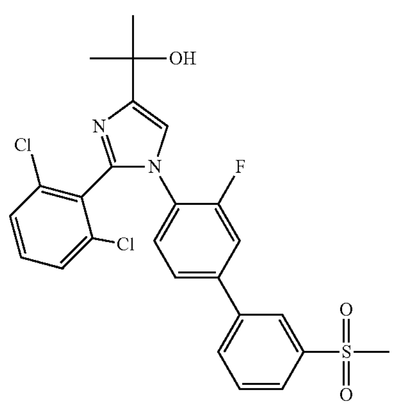 | 2-(2-(2,6-dichlorophenyl)-1-(3-fluoro-3'-(methylsulfonyl)biphenyl-4-yl)-1H-imidazol-4-yl)propan-2-ol; |
| 116 | 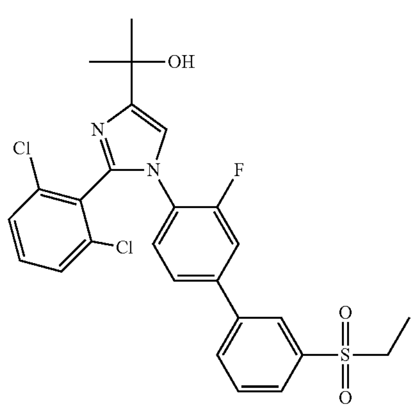 [SMILES: CCS(=O)(=O)c1cccc(-c2ccc(-n3cc(C(C)(C)O)nc3-c3c(Cl)cccc3Cl)c(F)c2)c1] | 2-(2-(2,6-dichlorophenyl)-1-(3'-(ethylsulfonyl)-3-fluorobiphenyl-4-yl)-1H-imidazol-4-yl)propan-2-ol; |

-continued

| Cpd # | Structure | Name |
|---|---|---|
| 117 | 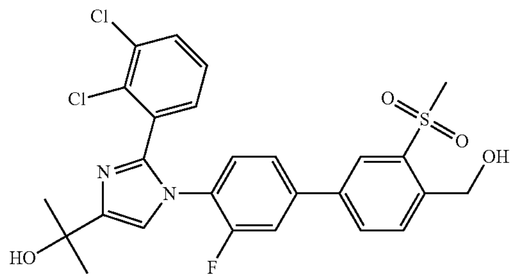 | 2-(2-(2,3-dichlorophenyl)-1-(3-fluoro-4'-(hydroxymethyl)-3'-(methylsulfonyl)biphenyl-4-yl)-1H-imidazol-4-yl)propan-2-ol; |
| 118 | 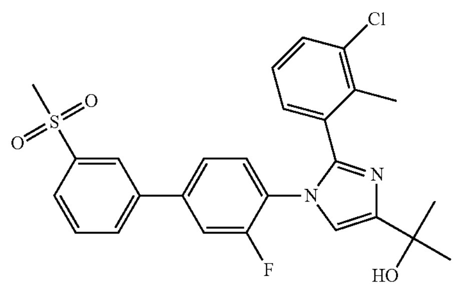 | 2-(2-(3-chloro-2-methylphenyl)-1-(3-fluoro-3'-(methylsulfonyl)biphenyl-4-yl)-1H-imidazol-4-yl)propan-2-ol; |
| 119 | 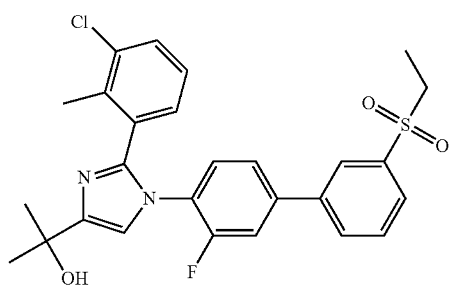 | 2-(2-(3-chloro-2-methylphenyl)-1-(3'-(ethylsulfonyl)-3-fluorobiphenyl-4-yl)-1H-imidazol-4-yl)propan-2-ol; |
| 120 | 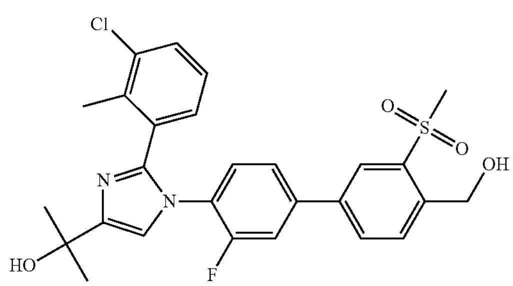 | 2-(2-(3-chloro-2-methylphenyl)-1-(3-fluoro-4'-(hydroxymethyl)-3'-(methylsulfonyl)biphenyl-4-yl)-1H-imidazol-4-yl)propan-2-ol; |
| 121 | 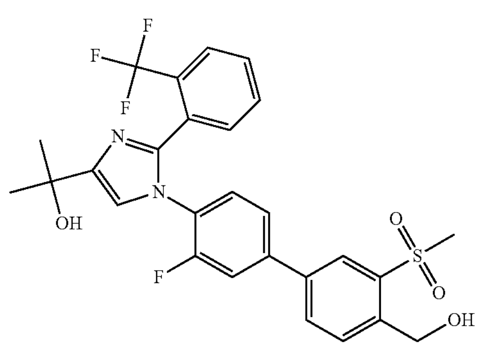 [SMILES: CC(C)(O)c1cn(-c2ccc(-c3ccc(CO)c(S(C)(=O)=O)c3)cc2F)c(-c2ccccc2C(F)(F)F)n1] | 2-(1-(3-fluoro-4'-(hydroxymethyl)-3'-(methylsulfonyl)biphenyl-4-yl)-2-(2-(trifluoromethyl)phenyl)-1H-imidazol-4-yl)propan-2-ol; |

-continued

| Cpd # | Structure | Name |
|---|---|---|
| 122 | 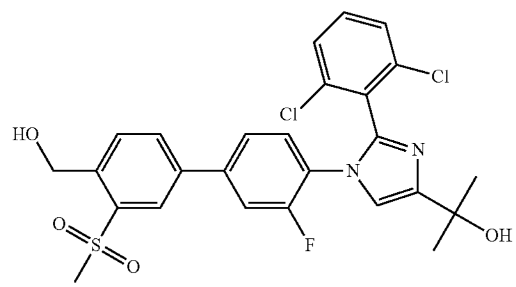 [SMILES: CC(C)(O)c1cn(-c2ccc(-c3ccc(CO)c(S(C)(=O)=O)c3)cc2F)c(-c2c(Cl)cccc2Cl)n1] | 2-(2-(2,6-dichlorophenyl)-1-(3-fluoro-4'-(hydroxymethyl)-3'-(methylsulfonyl)biphenyl-4-yl)-1H-imidazol-4-yl)propan-2-ol; |
| 123 | 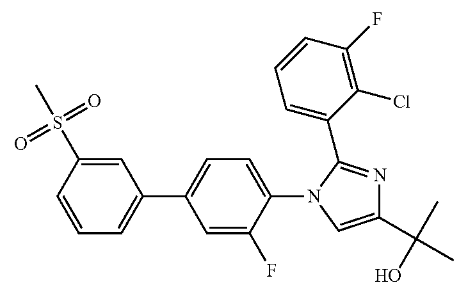 | 2-(2-(2-chloro-3-fluorophenyl)-1-(3-fluoro-3'-(methylsulfonyl)biphenyl-4-yl)-1H-imidazol-4-yl)propan-2-ol; |
| 124 | 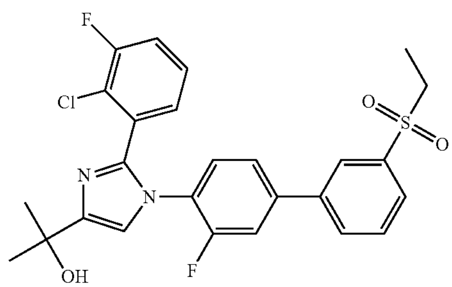 [SMILES: CCS(=O)(=O)c1cccc(-c2ccc(-n3cc(C(C)(C)O)nc3-c3cccc(F)c3Cl)c(F)c2)c1] | 2-(2-(2-chloro-3-fluorophenyl)-1-(3'-(ethylsulfonyl)-3-fluorobiphenyl-4-yl)-1H-imidazol-4-yl)propan-2-ol; |
| 125 | 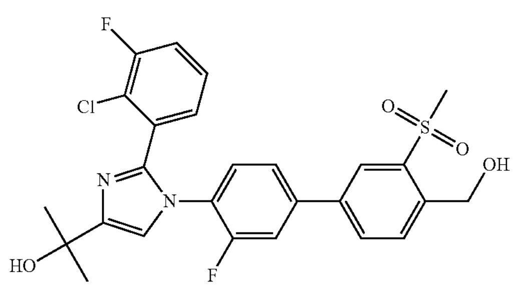 [SMILES: CC(C)(O)c1cn(-c2ccc(-c3ccc(CO)c(S(C)(=O)=O)c3)cc2F)c(-c2cccc(F)c2Cl)n1] | 2-(2-(2-chloro-3-fluorophenyl)-1-(3-fluoro-4'-(hydroxymethyl)-3'-(methylsulfonyl)biphenyl-4-yl)-1H-imidazol-4-yl)propan-2-ol; |
| 126 | 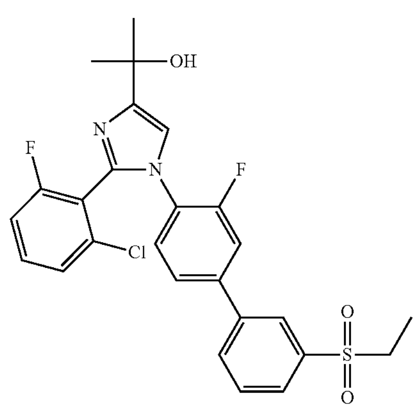 [SMILES: CCS(=O)(=O)c1cccc(-c2ccc(-n3cc(C(C)(C)O)nc3-c3c(F)cccc3Cl)c(F)c2)c1] | 2-(2-(2-chloro-6-fluorophenyl)-1-(3'-(ethylsulfonyl)-3-fluorobiphenyl-4-yl)-1H-imidazol-4-yl)propan-2-ol; |

-continued

| Cpd # | Structure | Name |
|---|---|---|
| 127 | 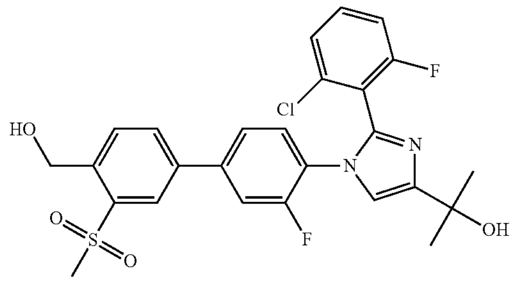 [SMILES: CC(C)(O)c1cn(-c2ccc(-c3ccc(CO)c(S(C)(=O)=O)c3)cc2F)c(-c2c(F)cccc2Cl)n1] | 2-(2-(2-chloro-6-fluorophenyl)-1-(3-fluoro-4'-(hydroxymethyl)-3'-(methylsulfonyl)biphenyl-4-yl)-1H-imidazol-4-yl)propan-2-ol; |
| 128 | 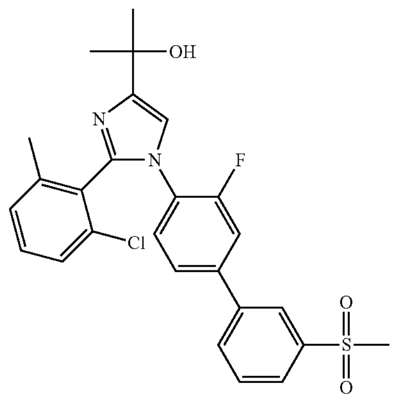 [SMILES: Cc1cccc(Cl)c1-c1nc(C(C)(C)O)cn1-c1ccc(-c2cccc(S(C)(=O)=O)c2)cc1F] | 2-(2-(2-chloro-6-methylphenyl)-1-(3-fluoro-3'-(methylsulfonyl)biphenyl-4-yl)-1H-imidazol-4-yl)propan-2-ol; |
| 129 | 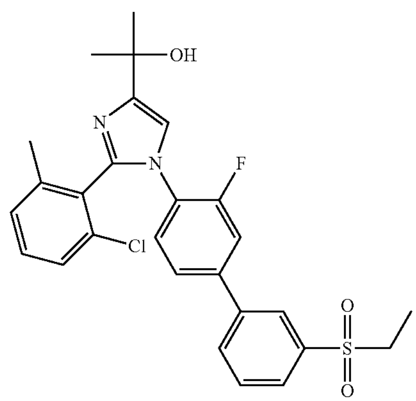 [SMILES: CCS(=O)(=O)c1cccc(-c2ccc(-n3cc(C(C)(C)O)nc3-c3c(C)cccc3Cl)c(F)c2)c1] | 2-(2-(2-chloro-6-methylphenyl)-1-(3'-(ethylsulfonyl)-3-fluorobiphenyl-4-yl)-1H-imidazol-4-yl)propan-2-ol; |
| 130 | 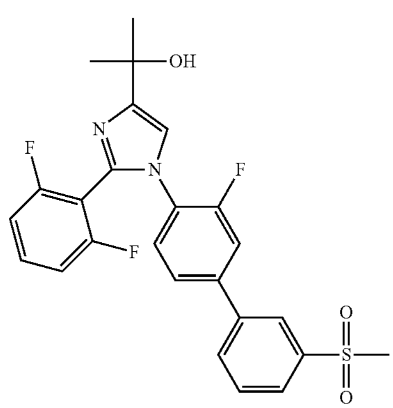 [SMILES: CC(C)(O)c1cn(-c2ccc(-c3cccc(S(C)(=O)=O)c3)cc2F)c(-c2c(F)cccc2F)n1] | 2-(2-(2,6-difluorophenyl)-1-(3-fluoro-3'-(methylsulfonyl)biphenyl-4-yl)-1H-imidazol-4-yl)propan-2-ol; |

-continued

| Cpd # | Structure | Name |
|---|---|---|
| 131 | 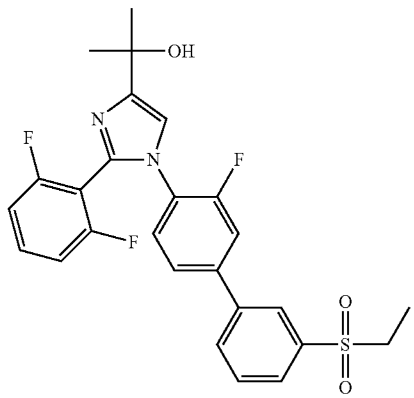 | 2-(2-(2,6-difluorophenyl)-1-(3'-(ethylsulfonyl)-3-fluorobiphenyl-4-yl)-1H-imidazol-4-yl)propan-2-ol; |
| 132 | 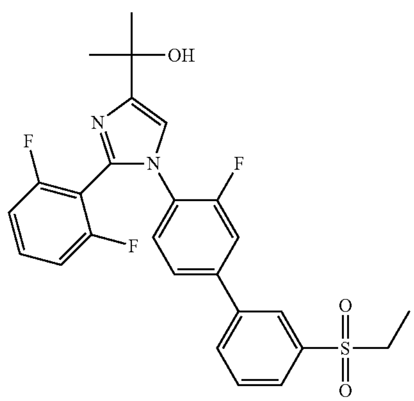 | 2-(2-(2,6-difluorophenyl)-1-(3'-(ethylsulfonyl)-3-fluorobiphenyl-4-yl)-1H-imidazol-4-yl)propan-2-ol; |
| 133 | 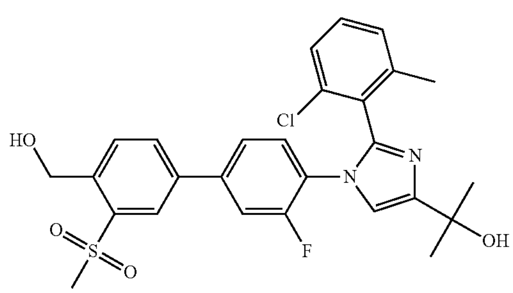 [SMILES: Cc1cccc(Cl)c1-c1nc(C(C)(C)O)cn1-c1ccc(-c2ccc(CO)c(S(C)(=O)=O)c2)cc1F] | 2-(2-(2-chloro-6-methylphenyl)-1-(3-fluoro-4'-(hydroxymethyl)-3'-(methylsulfonyl)biphenyl-4-yl)-1H-imidazol-4-yl)propan-2-ol; |
| 134 | 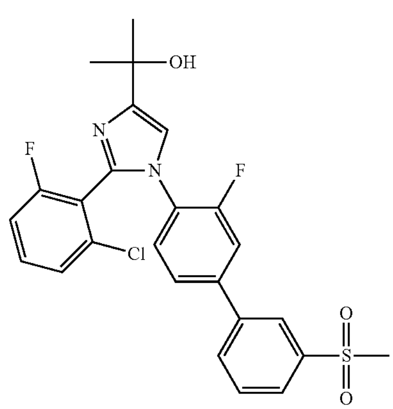 | 2-(2-(2-chloro-6-fluorophenyl)-1-(3-fluoro-3'-(methylsulfonyl)biphenyl-4-yl)-1H-imidazol-4-yl)propan-2-ol; |

-continued

| Cpd # | Structure | Name |
|---|---|---|
| 135 | 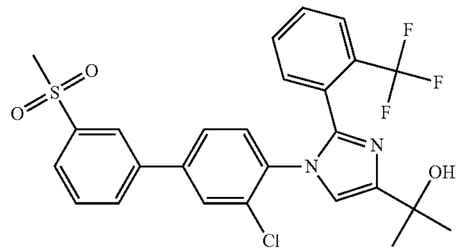 [SMILES: CC(C)(O)c1cn(-c2ccc(-c3cccc(S(C)(=O)=O)c3)cc2Cl)c(-c2ccccc2C(F)(F)F)n1] | 2-(1-(3-chloro-3'-(methylsulfonyl)biphenyl-4-yl)-2-(2-(trifluoromethyl)phenyl)-1H-imidazol-4-yl)propan-2-ol; |
| 136 | 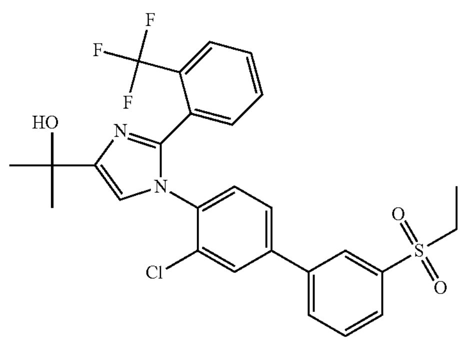 [SMILES: CCS(=O)(=O)c1cccc(-c2ccc(-n3cc(C(C)(C)O)nc3-c3ccccc3C(F)(F)F)c(Cl)c2)c1] | 2-(1-(3-chloro-3'-(ethylsulfonyl)biphenyl-4-yl)-2-(2-(trifluoromethyl)phenyl)-1H-imidazol-4-yl)propan-2-ol; |
| 137 | 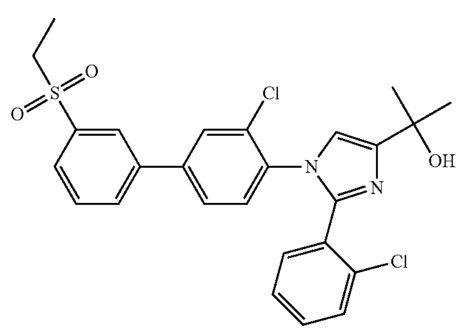 [SMILES: CCS(=O)(=O)c1cccc(-c2ccc(-n3cc(C(C)(C)O)nc3-c3ccccc3Cl)c(Cl)c2)c1] | 2-(1-(3-chloro-3'-(ethylsulfonyl)biphenyl-4-yl)-2-(2-chlorophenyl)-1H-imidazol-4-yl)propan-2-ol; |
| 138 | 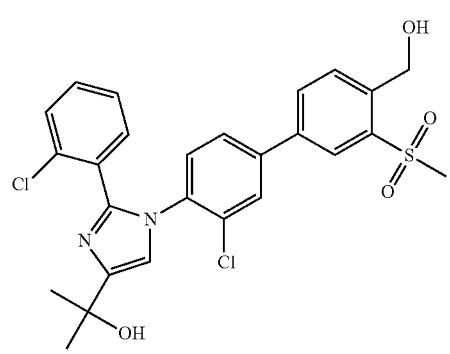 [SMILES: CC(C)(O)c1cn(-c2ccc(-c3ccc(CO)c(S(C)(=O)=O)c3)cc2Cl)c(-c2ccccc2Cl)n1] | 2-(1-(3-chloro-4'-(hydroxymethyl)-3'-(methylsulfonyl)biphenyl-4-yl)-2-(2-chlorophenyl)-1H-imidazol-4-yl)propan-2-ol; |

| Cpd # | Structure | Name |
|---|---|---|
| 139 | 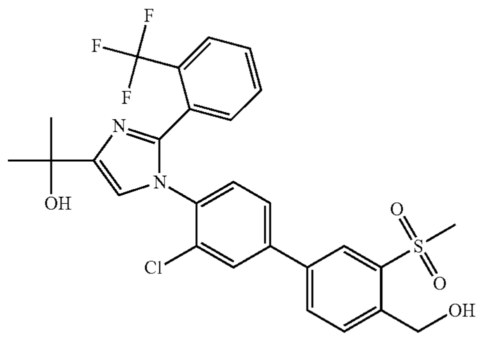 [SMILES: CC(C)(O)c1cn(-c2ccc(-c3ccc(CO)c(S(C)(=O)=O)c3)cc2Cl)c(-c2ccccc2C(F)(F)F)n1] | 2-(1-(3-chloro-4'-(hydroxymethyl)-3'-(methylsulfonyl)biphenyl-4-yl)-2-(2-(trifluoromethyl)phenyl)-1H-imidazol-4-yl)propan-2-ol; |
| 140 | 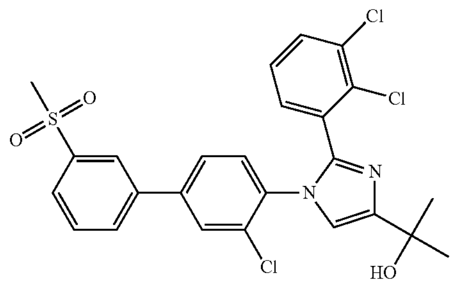 | 2-(1-(3-chloro-3'-(methylsulfonyl)biphenyl-4-yl)-2-(2,3-dichlorophenyl)-1H-imidazol-4-yl)propan-2-ol; |
| 141 | 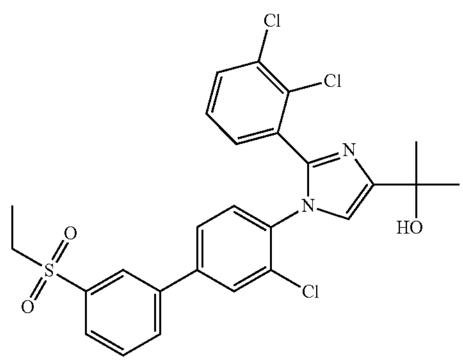 [SMILES: CCS(=O)(=O)c1cccc(-c2ccc(-n3cc(C(C)(C)O)nc3-c3cccc(Cl)c3Cl)c(Cl)c2)c1] | 2-(1-(3-chloro-3'-(ethylsulfonyl)biphenyl-4-yl)-2-(2,3-dichlorophenyl)-1H-imidazol-4-yl)propan-2-ol; |
| 142 | 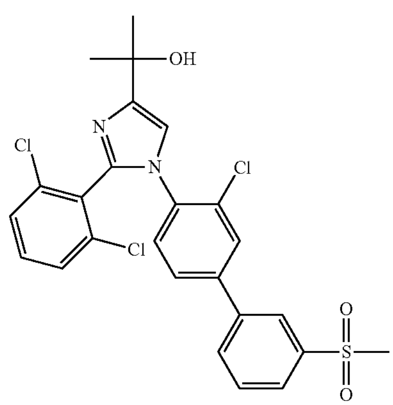 [SMILES: CC(C)(O)c1cn(-c2ccc(-c3cccc(S(C)(=O)=O)c3)cc2Cl)c(-c2c(Cl)cccc2Cl)n1] | 2-(1-(3-chloro-3'-(methylsulfonyl)biphenyl-4-yl)-2-(2,6-dichlorophenyl)-1H-imidazol-4-yl)propan-2-ol; |

-continued

| Cpd # | Structure | Name |
|---|---|---|
| 143 | 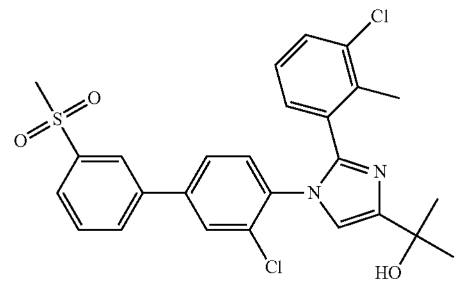 [SMILES: Cc1c(Cl)cccc1-c1nc(C(C)(C)O)cn1-c1ccc(-c2cccc(S(C)(=O)=O)c2)cc1Cl] | 2-(2-(3-chloro-2-methylphenyl)-1-(3-chloro-3'-(methylsulfonyl)biphenyl-4-yl)-1H-imidazol-4-yl)propan-2-ol; |
| 144 | 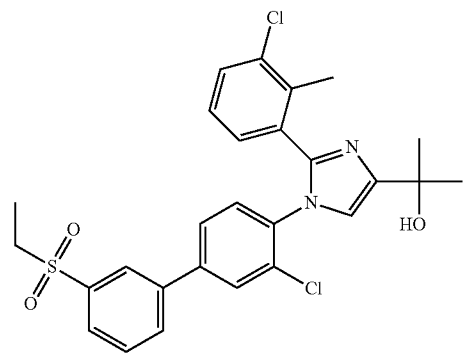 [SMILES: CCS(=O)(=O)c1cccc(-c2ccc(-n3cc(C(C)(C)O)nc3-c3cccc(Cl)c3C)c(Cl)c2)c1] | 2-(2-(3-chloro-2-methylphenyl)-1-(3-chloro-3'-(ethylsulfonyl)biphenyl-4-yl)-1H-imidazol-4-yl)propan-2-ol; |
| 145 | 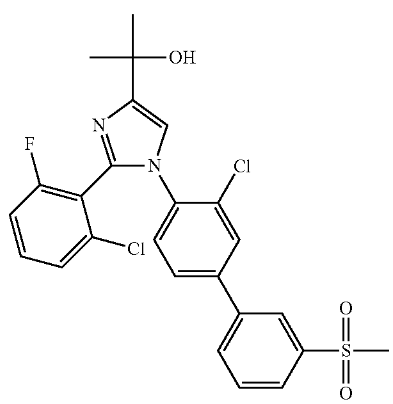 | 2-(1-(3-chloro-3'-(methylsulfonyl)biphenyl-4-yl)-2-(2-chloro-6-fluorophenyl)-1H-imidazol-4-yl)propan-2-ol; |
| 146 | 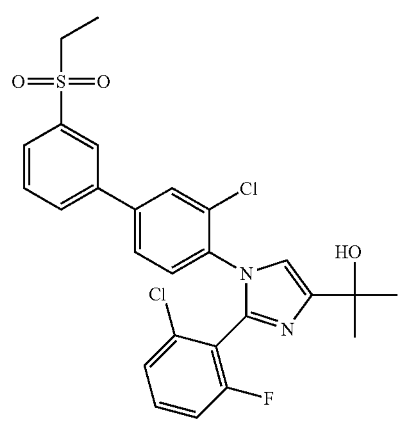 | 2-(1-(3-chloro-3'-(ethylsulfonyl)biphenyl-4-yl)-2-(2-chloro-6-fluorophenyl)-1H-imidazol-4-yl)propan-2-ol; |

-continued

| Cpd # | Structure | Name |
|---|---|---|
| 147 | 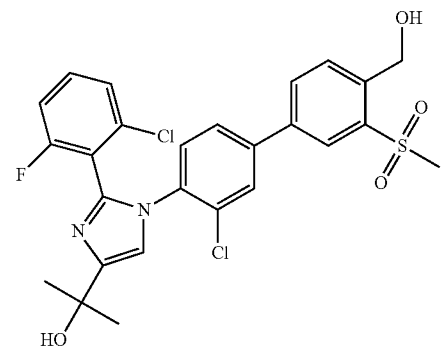 [SMILES: CC(C)(O)c1cn(-c2ccc(-c3ccc(CO)c(S(C)(=O)=O)c3)cc2Cl)c(-c2c(F)cccc2Cl)n1] | 2-(1-(3-chloro-4'-(hydroxymethyl)-3'-(methylsulfonyl)biphenyl-4-yl)-2-(2-chloro-6-fluorophenyl)-1H-imidazol-4-yl)propan-2-ol; |
| 148 | 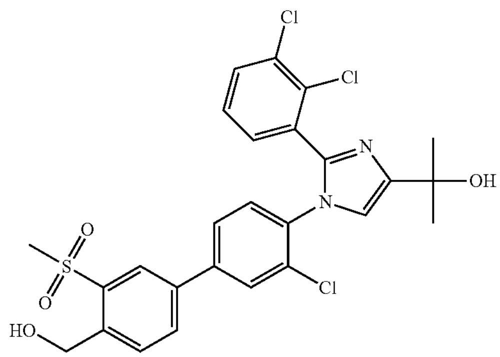 [SMILES: CC(C)(O)c1cn(-c2ccc(-c3ccc(CO)c(S(C)(=O)=O)c3)cc2Cl)c(-c2cccc(Cl)c2Cl)n1] | 2-(1-(3-chloro-4'-(hydroxymethyl)-3'-(methylsulfonyl)biphenyl-4-yl)-2-(2,3-dichlorophenyl)-1H-imidazol-4-yl)propan-2-ol; |
| 149 | 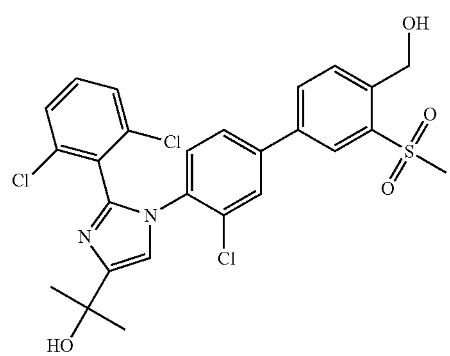 [SMILES: CC(C)(O)c1cn(-c2ccc(-c3ccc(CO)c(S(C)(=O)=O)c3)cc2Cl)c(-c2c(Cl)cccc2Cl)n1] | 2-(1-(3-chloro-4'-(hydroxymethyl)-3'-(methylsulfonyl)biphenyl-4-yl)-2-(2,6-dichlorophenyl)-1H-imidazol-4-yl)propan-2-ol; |
| 150 | 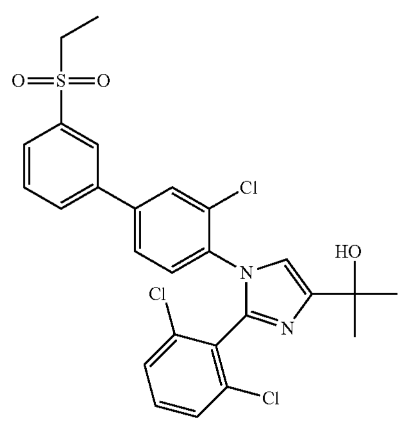 [SMILES: CCS(=O)(=O)c1cccc(-c2ccc(-n3cc(C(C)(C)O)nc3-c3c(Cl)cccc3Cl)c(Cl)c2)c1] | 2-(1-(3-chloro-3'-(ethylsulfonyl)biphenyl-4-yl)-2-(2,6-dichlorophenyl)-1H-imidazol-4-yl)propan-2-ol; |

-continued

| Cpd # | Structure | Name |
|---|---|---|
| 151 | 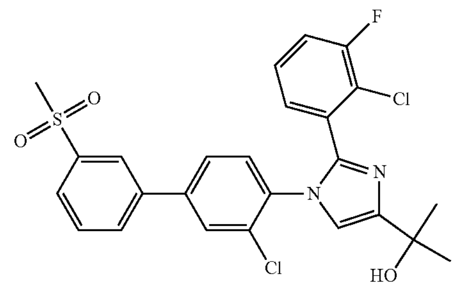 [SMILES: CC(C)(O)c1cn(-c2ccc(-c3cccc(S(C)(=O)=O)c3)cc2Cl)c(-c2cccc(F)c2Cl)n1] | 2-(1-(3-chloro-3'-(methylsulfonyl)biphenyl-4-yl)-2-(2-chloro-3-fluorophenyl)-1H-imidazol-4-yl)propan-2-ol; |
| 152 | 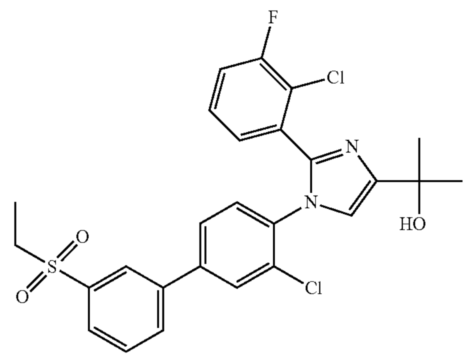 [SMILES: CCS(=O)(=O)c1cccc(-c2ccc(-n3cc(C(C)(C)O)nc3-c3cccc(F)c3Cl)c(Cl)c2)c1] | 2-(1-(3-chloro-3'-(ethylsulfonyl)biphenyl-4-yl)-2-(2-chloro-3-fluorophenyl)-1H-imidazol-4-yl)propan-2-ol; |
| 153 | 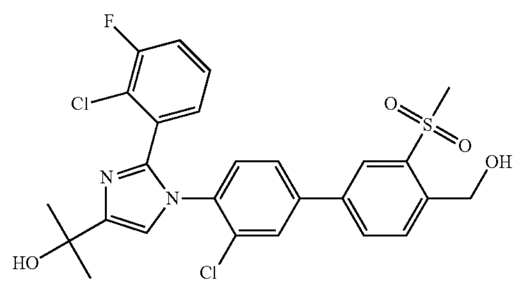 | 2-(2-(2-chloro-3-fluorophenyl)-1-(3-chloro-4'-(hydroxymethyl)-3'-(methylsulfonyl)biphenyl-4-yl)-1H-imidazol-4-yl)propan-2-ol; |
| 154 | 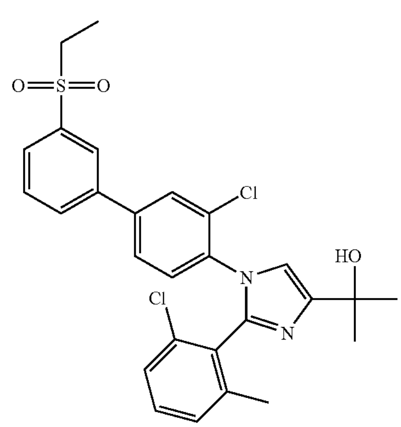 [SMILES: CCS(=O)(=O)c1cccc(-c2ccc(-n3cc(C(C)(C)O)nc3-c3c(C)cccc3Cl)c(Cl)c2)c1] | 2-(1-(3-chloro-3'-(ethylsulfonyl)biphenyl-4-yl)-2-(2-chloro-6-methylphenyl)-1H-imidazol-4-yl)propan-2-ol; |

| Cpd # | Structure | Name |
|---|---|---|
| 155 | 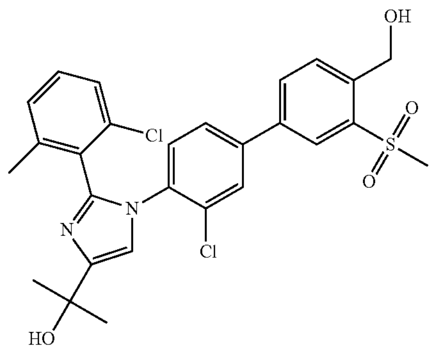 | 2-(1-(3-chloro-4'-(hydroxymethyl)-3'-(methylsulfonyl)biphenyl-4-yl)-2-(2-chloro-6-methylphenyl)-1H-imidazol-4-yl)propan-2-ol; |
| 156 | 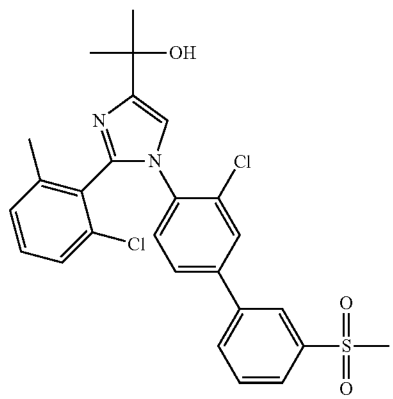 [SMILES: Cc1cccc(Cl)c1-c1nc(C(C)(C)O)cn1-c1ccc(-c2cccc(S(C)(=O)=O)c2)cc1Cl] | 2-(1-(3-chloro-3'-(methylsulfonyl)biphenyl-4-yl)-2-(2-chloro-6-methylphenyl)-1H-imidazol-4-yl)propan-2-ol; |
| 157 | 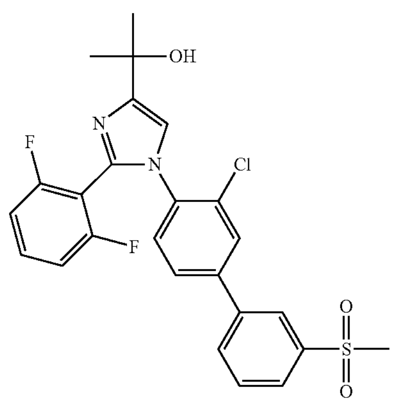 [SMILES: CC(C)(O)c1cn(-c2ccc(-c3cccc(S(C)(=O)=O)c3)cc2Cl)c(-c2c(F)cccc2F)n1] | 2-(1-(3-chloro-3'-(methylsulfonyl)biphenyl-4-yl)-2-(2,6-difluorophenyl)-1H-imidazol-4-yl)propan-2-ol; |
| 158 | 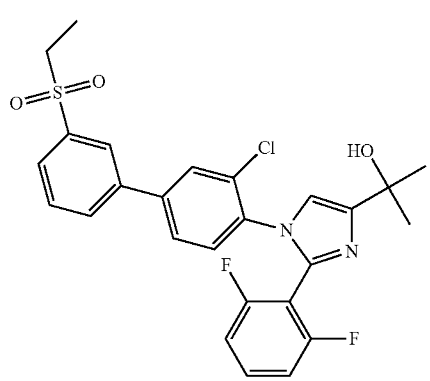 [SMILES: CCS(=O)(=O)c1cccc(-c2ccc(-n3cc(C(C)(C)O)nc3-c3c(F)cccc3F)c(Cl)c2)c1] | 2-(1-(3-chloro-3'-(ethylsulfonyl)biphenyl-4-yl)-2-(2,6-difluorophenyl)-1H-imidazol-4-yl)propan-2-ol; |

-continued

| Cpd # | Structure | Name |
|---|---|---|
| 159 | 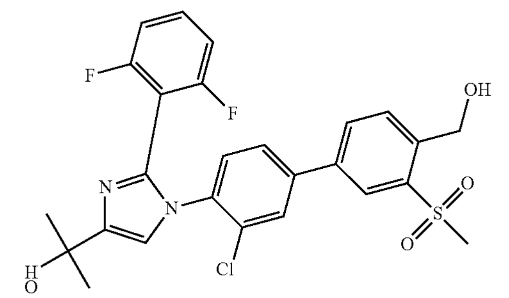 [SMILES: CC(C)(O)c1cn(-c2ccc(-c3ccc(CO)c(S(C)(=O)=O)c3)cc2Cl)c(-c2c(F)cccc2F)n1] | 2-(1-(3-chloro-4'-(hydroxymethyl)-3'-(methylsulfonyl)biphenyl-4-yl)-2-(2,6-difluorophenyl)-1H-imidazol-4-yl)propan-2-ol; |
| 160 | 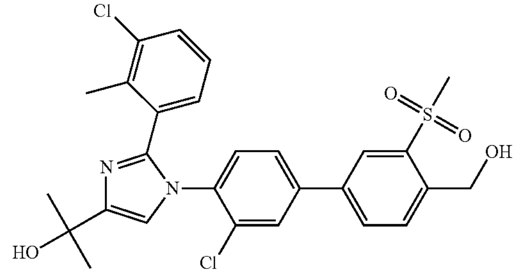 [SMILES: Cc1c(Cl)cccc1-c1nc(C(C)(C)O)cn1-c1ccc(-c2ccc(CO)c(S(C)(=O)=O)c2)cc1Cl] | 2-(2-(3-chloro-2-methylphenyl)-1-(3-chloro-4'-(hydroxymethyl)-3'-(methylsulfonyl)biphenyl-4-yl)-1H-imidazol-4-yl)propan-2-ol; |
| 161 | 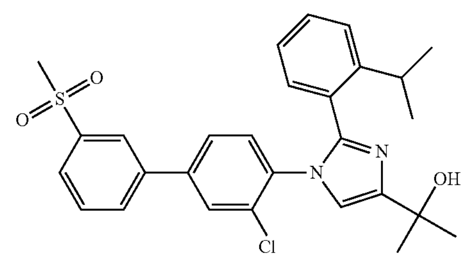 [SMILES: CC(C)c1ccccc1-c1nc(C(C)(C)O)cn1-c1ccc(-c2cccc(S(C)(=O)=O)c2)cc1Cl] | 2-(1-(3-chloro-3'-(methylsulfonyl)biphenyl-4-yl)-2-(2-isopropylphenyl)-1H-imidazol-4-yl)propan-2-ol; |
| 162 | 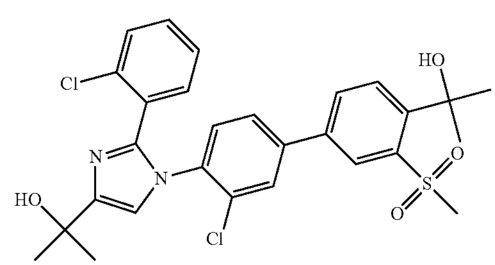 [SMILES: CC(C)(O)c1cn(-c2ccc(-c3ccc(C(C)(C)O)c(S(C)(=O)=O)c3)cc2Cl)c(-c2ccccc2Cl)n1] | 2-(3'-chloro-4'-(2-(2-chlorophenyl)-4-(2-hydroxypropan-2-yl)-1H-imidazol-1-yl)-3-(methylsulfonyl)biphenyl-4-yl)propan-2-ol; |
| 163 | 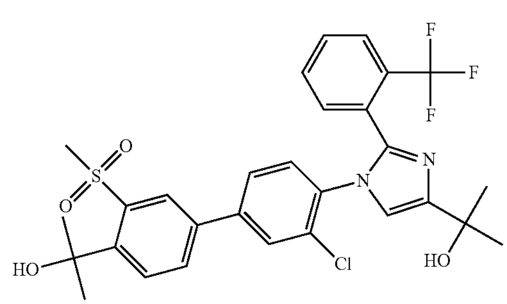 [SMILES: CC(C)(O)c1cn(-c2ccc(-c3ccc(C(C)(C)O)c(S(C)(=O)=O)c3)cc2Cl)c(-c2ccccc2C(F)(F)F)n1] | 2-(1-(3-chloro-4'-(2-hydroxypropan-2-yl)-3'-(methylsulfonyl)biphenyl-4-yl)-2-(2-(trifluoromethyl)phenyl)-1H-imidazol-4-yl)propan-2-ol; |

-continued

| Cpd # | Structure | Name |
|---|---|---|
| 164 | 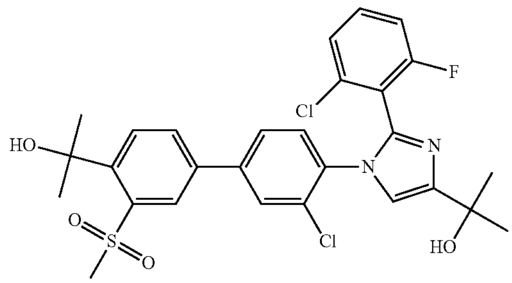 [SMILES: CC(C)(O)c1cn(-c2ccc(-c3ccc(C(C)(C)O)c(S(C)(=O)=O)c3)cc2Cl)c(-c2c(F)cccc2Cl)n1] | 2-(3'-chloro-4'-(2-(2-chloro-6-fluorophenyl)-4-(2-hydroxypropan-2-yl)-1H-imidazol-1-yl)-3-(methylsulfonyl)biphenyl-4-yl)propan-2-ol; |
| 165 | 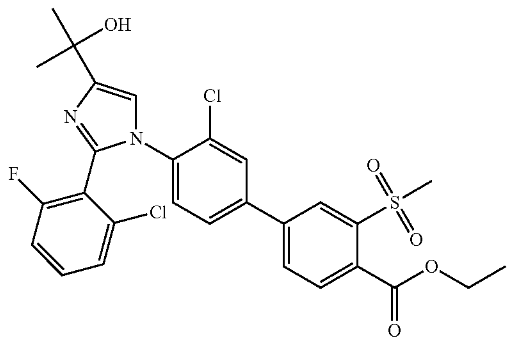 [SMILES: CCOC(=O)c1ccc(-c2ccc(-n3cc(C(C)(C)O)nc3-c3c(F)cccc3Cl)c(Cl)c2)cc1S(C)(=O)=O] | ethyl 3'-chloro-4'-(2-(2-chloro-6-fluorophenyl)-4-(2-hydroxypropan-2-yl)-1H-imidazol-1-yl)-3-(methylsulfonyl)biphenyl-4-carboxylate; |
| 166 | 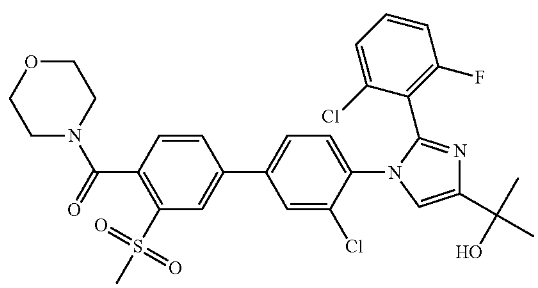 [SMILES: CC(C)(O)c1cn(-c2ccc(-c3ccc(C(=O)N4CCOCC4)c(S(C)(=O)=O)c3)cc2Cl)c(-c2c(F)cccc2Cl)n1] | (3'-chloro-4'-(2-(2-chloro-6-fluorophenyl)-4-(2-hydroxypropan-2-yl)-1H-imidazol-1-yl)-3-(methylsulfonyl)biphenyl-4-yl)(morpholino)methanone; |
| 167 | 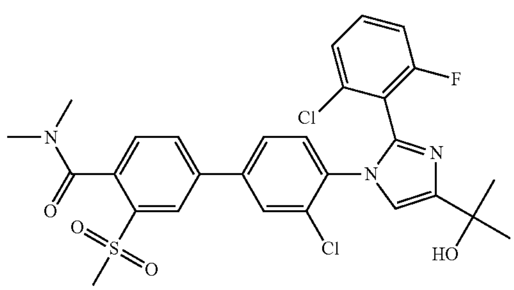 [SMILES: CN(C)C(=O)c1ccc(-c2ccc(-n3cc(C(C)(C)O)nc3-c3c(F)cccc3Cl)c(Cl)c2)cc1S(C)(=O)=O] | 3'-chloro-4'-(2-(2-chloro-6-fluorophenyl)-4-(2-hydroxypropan-2-yl)-1H-imidazol-1-yl)-N,N-dimethyl-3-(methylsulfonyl)biphenyl-4-carboxamide; |
| 168 | 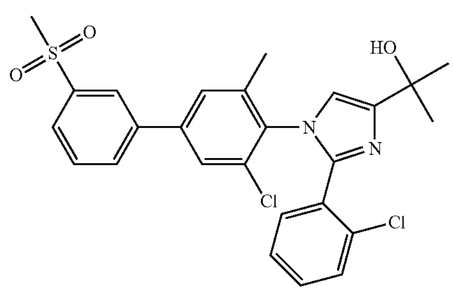 [SMILES: Cc1cc(-c2cccc(S(C)(=O)=O)c2)cc(Cl)c1-n1cc(C(C)(C)O)nc1-c1ccccc1Cl] | 2-(1-(3-chloro-5-methyl-3'-(methylsulfonyl)biphenyl-4-yl)-2-(2-chlorophenyl)-1H-imidazol-4-yl)propan-2-ol; |

-continued

| Cpd # | Structure | Name |
|---|---|---|
| 169 | 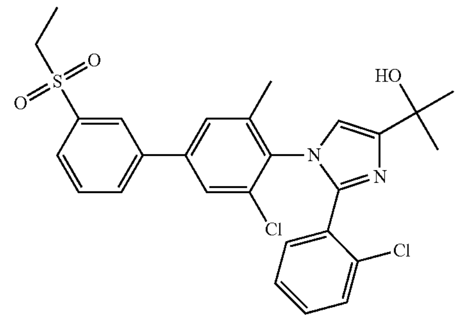 [SMILES: CCS(=O)(=O)c1cccc(-c2cc(C)c(-n3cc(C(C)(C)O)nc3-c3ccccc3Cl)c(Cl)c2)c1] | 2-(1-(3-chloro-3'-(ethylsulfonyl)-5-methylbiphenyl-4-yl)-2-(2-chlorophenyl)-1H-imidazol-4-yl)propan-2-ol; |
| 170 | 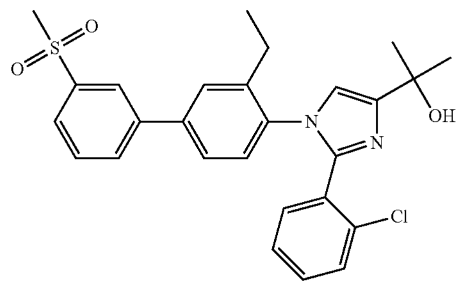 [SMILES: CCc1cc(-c2cccc(S(C)(=O)=O)c2)ccc1-n1cc(C(C)(C)O)nc1-c1ccccc1Cl] | 2-(2-(2-chlorophenyl)-1-(3-ethyl-3'-(methylsulfonyl)biphenyl-4-yl)-1H-imidazol-4-yl)propan-2-ol; |
| 171 | 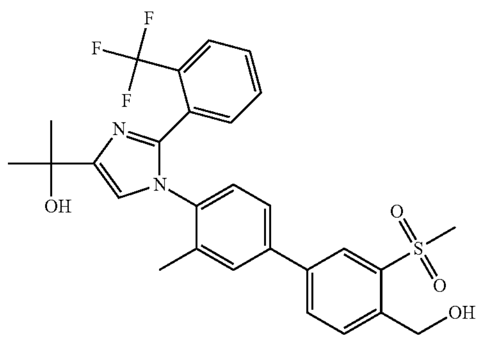 [SMILES: Cc1cc(-c2ccc(CO)c(S(C)(=O)=O)c2)ccc1-n1cc(C(C)(C)O)nc1-c1ccccc1C(F)(F)F] | 2-(1-(4'-(hydroxymethyl)-3-methyl-3'-(methylsulfonyl)biphenyl-4-yl)-2-(2-(trifluoromethyl)phenyl)-1H-imidazol-4-yl)propan-2-ol; |
| 172 | 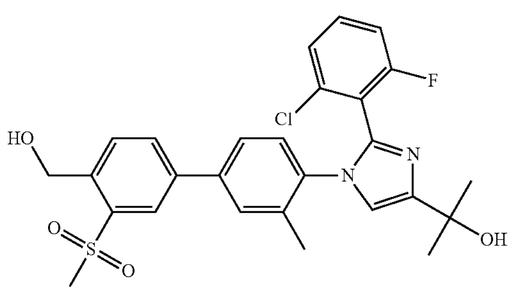 [SMILES: Cc1cc(-c2ccc(CO)c(S(C)(=O)=O)c2)ccc1-n1cc(C(C)(C)O)nc1-c1c(F)cccc1Cl] | 2-(2-(2-chloro-6-fluorophenyl)-1-(4'-(hydroxymethyl)-3-methyl-3'-methylsulfonyl)biphenyl-4-yl)-1H-imidazol-4-yl)propan-2-ol; |
| 173 | 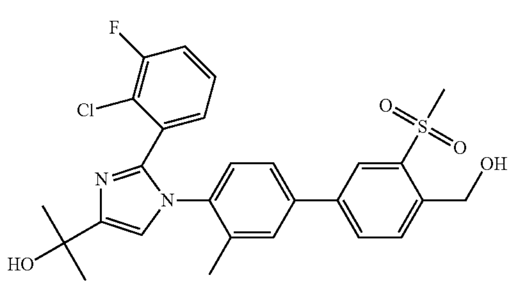 [SMILES: Cc1cc(-c2ccc(CO)c(S(C)(=O)=O)c2)ccc1-n1cc(C(C)(C)O)nc1-c1cccc(F)c1Cl] | 2-(2-(2-chloro-3-fluorophenyl)-1-(4'-(hydroxymethyl)-3-methyl-3'-(methylsulfonyl)biphenyl-4-yl)-1H-imidazol-4-yl)propan-2-ol; |

-continued

| Cpd # | Structure | Name |
|---|---|---|
| 174 | 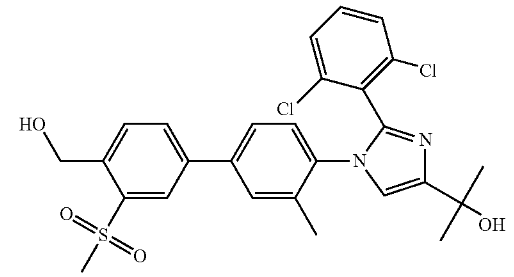 [SMILES: Cc1cc(-c2ccc(CO)c(S(C)(=O)=O)c2)ccc1-n1cc(C(C)(C)O)nc1-c1c(Cl)cccc1Cl] | 2-(2-(2,6-dichlorophenyl)-1-(4'-(hydroxymethyl)-3-methyl-3'-(methylsulfonyl)biphenyl-4-yl)-1H-imidazol-4-yl)propan-2-ol; |
| 175 | 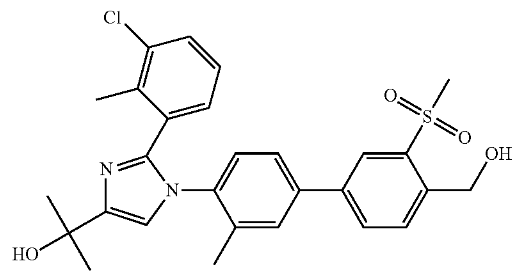 [SMILES: Cc1cc(-c2ccc(CO)c(S(C)(=O)=O)c2)ccc1-n1cc(C(C)(C)O)nc1-c1cccc(Cl)c1C] | 2-(2-(3-chloro-2-methylphenyl)-1-(4'-(hydroxymethyl)-3-methyl-3'-(methylsulfonyl)biphenyl-4-yl)-1H-imidazol-4-yl)propan-2-ol; |
| 176 | 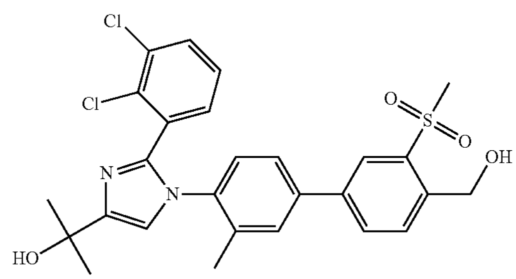 [SMILES: Cc1cc(-c2ccc(CO)c(S(C)(=O)=O)c2)ccc1-n1cc(C(C)(C)O)nc1-c1cccc(Cl)c1Cl] | 2-(2-(2,3-dichlorophenyl)-1-(4'-(hydroxymethyl)-3-methyl-3'-(methylsulfonyl)biphenyl-4-yl)-1H-imidazol-4-yl)propan-2-ol; |
| 177 | 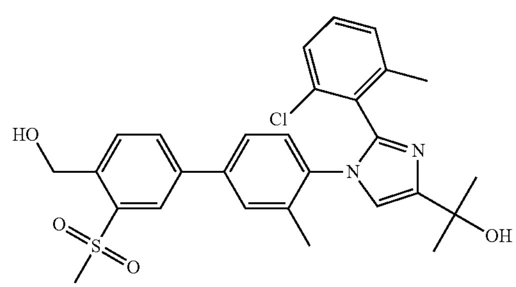 [SMILES: Cc1cc(-c2ccc(CO)c(S(C)(=O)=O)c2)ccc1-n1cc(C(C)(C)O)nc1-c1c(C)cccc1Cl] | 2-(2-(2-chloro-6-methylphenyl)-1-(4'-(hydroxymethyl)-3-methyl-3'-(methylsulfonyl)biphenyl-4-yl)-1H-imidazol-4-yl)propan-2-ol; |
| 178 | 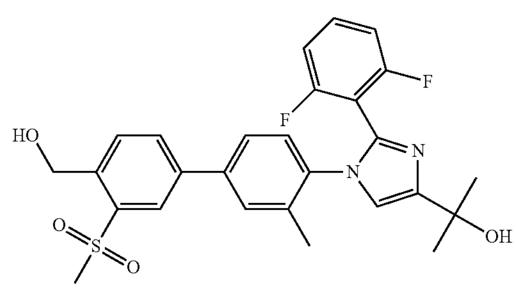 [SMILES: Cc1cc(-c2ccc(CO)c(S(C)(=O)=O)c2)ccc1-n1cc(C(C)(C)O)nc1-c1c(F)cccc1F] | 2-(2-(2,6-difluorophenyl)-1-(4'-(hydroxymethyl)-3-methyl-3'-(methylsulfonyl)biphenyl-4-yl)-1H-imidazol-4-yl)propan-2-ol; |

| Cpd # | Structure | Name |
| --- | --- | --- |
| 179 | 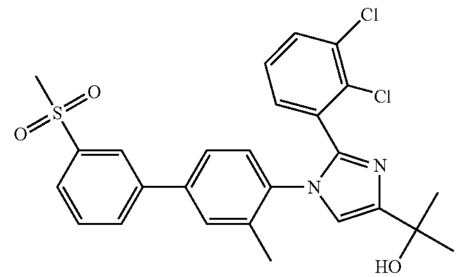 | 2-(2-(2,3-dichlorophenyl)-1-(3-methyl-3'-(methylsulfonyl)biphenyl-4-yl)-1H-imidazol-4-yl)propan-2-ol; |
| 180 | 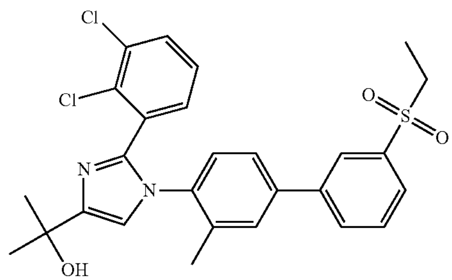 | 2-(2-(2,3-dichlorophenyl)-1-(3'-(ethylsulfonyl)-3-methylbiphenyl-4-yl)-1H-imidazol-4-yl)propan-2-ol; |
| 181 | 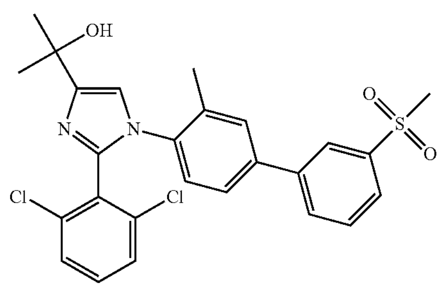 [SMILES: Cc1cc(-c2cccc(S(C)(=O)=O)c2)ccc1-n1cc(C(C)(C)O)nc1-c1c(Cl)cccc1Cl] | 2-(2-(2,6-dichlorophenyl)-1-(3-methyl-3'-(methylsulfonyl)biphenyl-4-yl)-1H-imidazol-4-yl)propan-2-ol; |
| 182 | 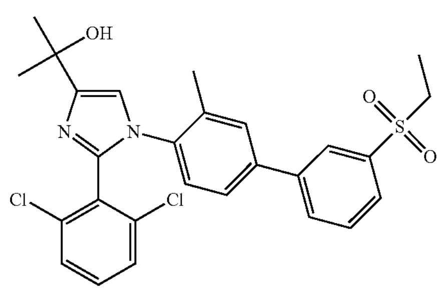 [SMILES: CCS(=O)(=O)c1cccc(-c2ccc(-n3cc(C(C)(C)O)nc3-c3c(Cl)cccc3Cl)c(C)c2)c1] | 2-(2-(2,6-dichlorophenyl)-1-(3'-(ethylsulfonyl)-3-methylbiphenyl-4-yl)-1H-imidazol-4-yl)propan-2-ol; |
| 183 | 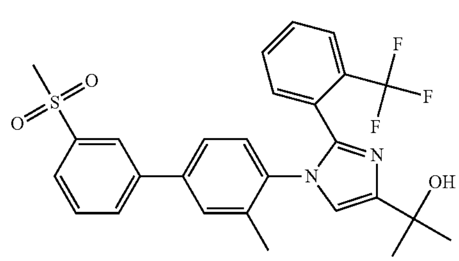 [SMILES: Cc1cc(-c2cccc(S(C)(=O)=O)c2)ccc1-n1cc(C(C)(C)O)nc1-c1ccccc1C(F)(F)F] | 2-(1-(3-methyl-3'-(methylsulfonyl)biphenyl-4-yl)-2-(2-(trifluoromethyl)phenyl)-1H-imidazol-4-yl)propan-2-ol; |

| Cpd # | Structure | Name |
|---|---|---|
| 184 | 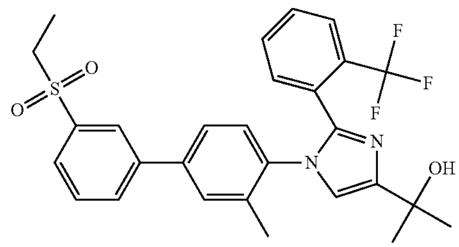 | 2-(1-(3'-(ethylsulfonyl)-3-methylbiphenyl-4-yl)-2-(2-(trifluoromethyl)phenyl)-1H-imidazol-4-yl)propan-2-ol; |
| 185 | 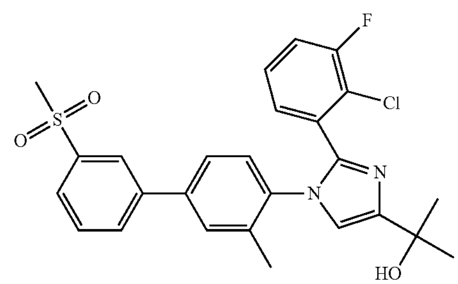 [SMILES: Cc1cc(-c2cccc(S(C)(=O)=O)c2)ccc1-n1cc(C(C)(C)O)nc1-c1cccc(F)c1Cl] | 2-(2-(2-chloro-3-fluorophenyl)-1-(3-methyl-3'-(methylsulfonyl)biphenyl-4-yl)-1H-imidazol-4-yl)propan-2-ol; |
| 186 | 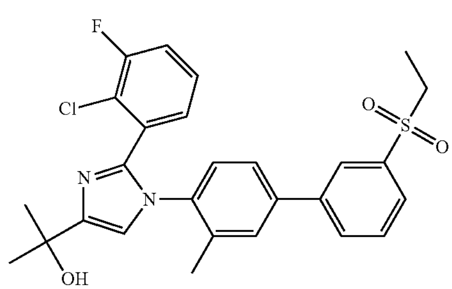 [SMILES: CCS(=O)(=O)c1cccc(-c2ccc(-n3cc(C(C)(C)O)nc3-c3cccc(F)c3Cl)c(C)c2)c1] | 2-(2-(2-chloro-3-fluorophenyl)-1-(3'-(ethylsulfonyl)-3-methylbiphenyl-4-yl)-1H-imidazol-4-yl)propan-2-ol; |
| 187 | 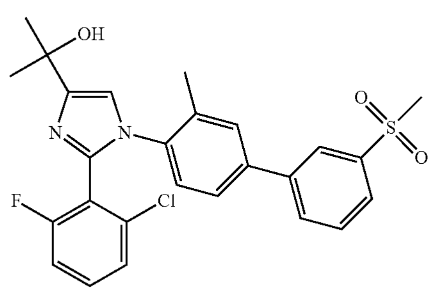 [SMILES: Cc1cc(-c2cccc(S(C)(=O)=O)c2)ccc1-n1cc(C(C)(C)O)nc1-c1c(F)cccc1Cl] | 2-(2-(2-chloro-6-fluorophenyl)-1-(3-methyl-3'-(methylsulfonyl)biphenyl-4-yl)-1H-imidazol-4-yl)propan-2-ol; |
| 188 | 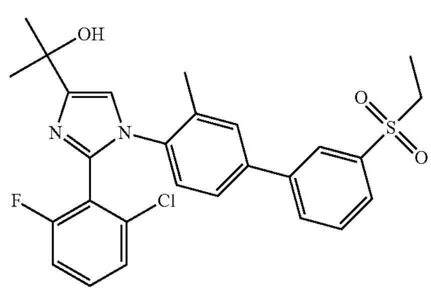 [SMILES: CCS(=O)(=O)c1cccc(-c2ccc(-n3cc(C(C)(C)O)nc3-c3c(F)cccc3Cl)c(C)c2)c1] | 2-(2-(2-chloro-6-fluorophenyl)-1-(3'-(ethylsulfonyl)-3-methylbiphenyl-4-yl)-1H-imidazol-4-yl)propan-2-ol; |

-continued

| Cpd # | Structure | Name |
|---|---|---|
| 189 | 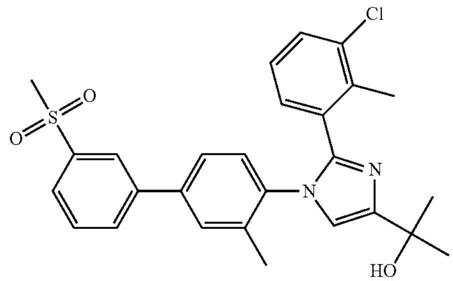 [SMILES: Cc1cc(-c2cccc(S(C)(=O)=O)c2)ccc1-n1cc(C(C)(C)O)nc1-c1cccc(Cl)c1C] | 2-(2-(3-chloro-2-methylphenyl)-1-(3-methyl-3'-(methylsulfonyl)biphenyl-4-yl)-1H-imidazol-4-yl)propan-2-ol; |
| 190 | 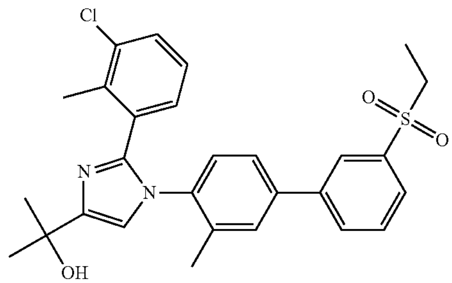 [SMILES: CCS(=O)(=O)c1cccc(-c2ccc(-n3cc(C(C)(C)O)nc3-c3cccc(Cl)c3C)c(C)c2)c1] | 2-(2-(3-chloro-2-methylphenyl)-1-(3'-(ethylsulfonyl)-3-methylbiphenyl-4-yl)-1H-imidazol-4-yl)propan-2-ol; |
| 191 | 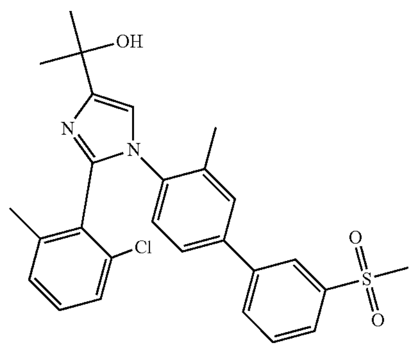 | 2-(2-(2-chloro-6-methylphenyl)-1-(3-methyl-3'-(methylsulfonyl)biphenyl-4-yl)-1H-imidazol-4-yl)propan-2-ol; |
| 192 | 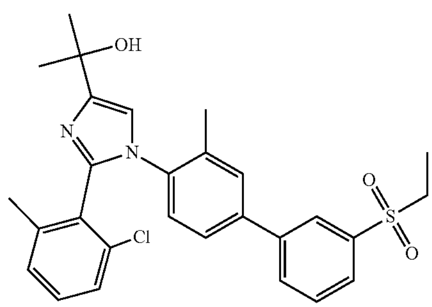 [SMILES: CCS(=O)(=O)c1cccc(-c2ccc(-n3cc(C(C)(C)O)nc3-c3c(C)cccc3Cl)c(C)c2)c1] | 2-(2-(2-chloro-6-methylphenyl)-1-(3'-(ethylsulfonyl)-3-methylbiphenyl-4-yl)-1H-imidazol-4-yl)propan-2-ol; |
| 193 | 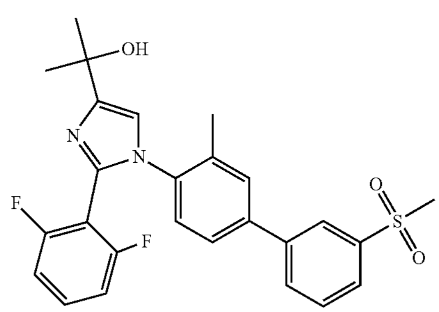 [SMILES: CCS(=O)(=O)c1cccc(-c2ccc(-n3cc(C(C)(C)O)nc3-c3c(F)cccc3F)c(C)c2)c1] | 2-(2-(2,6-difluorophenyl)-1-(3-methyl-3'-(methylsulfonyl)biphenyl-4-yl)-1H-imidazol-4-yl)propan-2-ol; |

-continued

| Cpd # | Structure | Name |
|---|---|---|
| 194 | 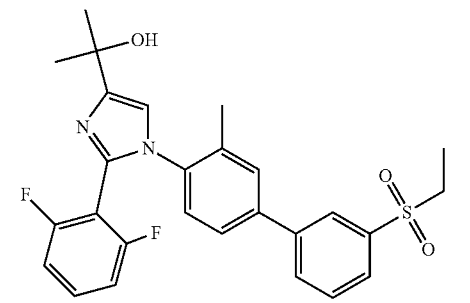 | 2-(2-(2,6-difluorophenyl)-1-(3'-(ethylsulfonyl)-3-methylbiphenyl-4-yl)-1H-imidazol-4-yl)propan-2-ol; |
| 195 | 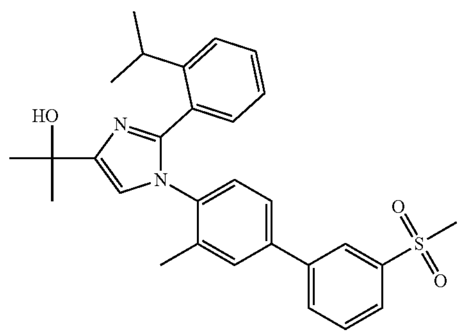 [SMILES: Cc1cc(-c2cccc(S(C)(=O)=O)c2)ccc1-n1cc(C(C)(C)O)nc1-c1ccccc1C(C)C] | 2-(2-(2-isopropylphenyl)-1-(3-methyl-3'-(methylsulfonyl)biphenyl-4-yl)-1H-imidazol-4-yl)propan-2-ol; |
| 196 | 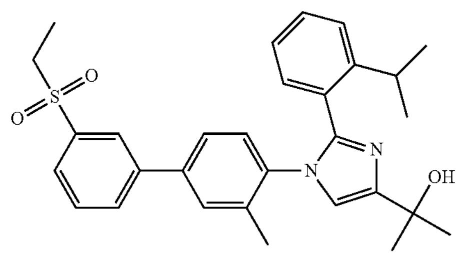 [SMILES: CCS(=O)(=O)c1cccc(-c2ccc(-n3cc(C(C)(C)O)nc3-c3ccccc3C(C)C)c(C)c2)c1] | 2-(1-(3'-(ethylsulfonyl)-3-methylbiphenyl-4-yl)-2-(2-isopropylphenyl)-1H-imidazol-4-yl)propan-2-ol; |
| 197 | 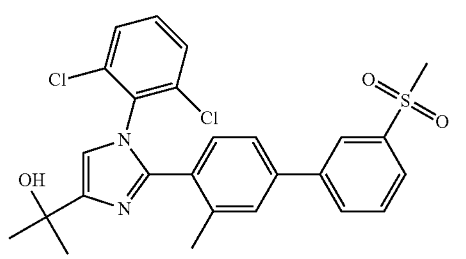 [SMILES: Cc1cc(-c2cccc(S(C)(=O)=O)c2)ccc1-c1nc(C(C)(C)O)cn1-c1c(Cl)cccc1Cl] | 2-(1-(2,6-dichlorophenyl)-2-(3-methyl-3'-(methylsulfonyl)biphenyl-4-yl)-1H-imidazol-4-yl)propan-2-ol; |
| 198 | 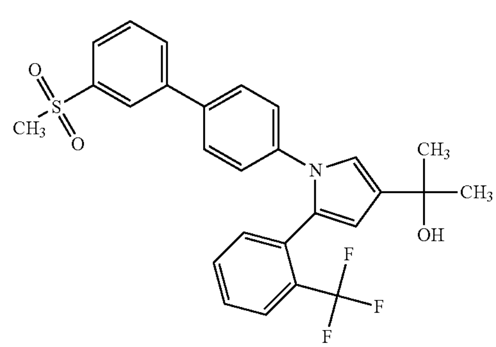 [SMILES: CC(C)(O)c1cc(-c2ccccc2C(F)(F)F)n(-c2ccc(-c3cccc(S(C)(=O)=O)c3)cc2)c1] | 2-{1-[3'-(methylsulfonyl)biphenyl-4-yl]-2-[2-(trifluoromethyl)phenyl]-1H-imidazol-4-yl}propan-2-ol; |

-continued

| Cpd # | Structure | Name |
|---|---|---|
| 199 | 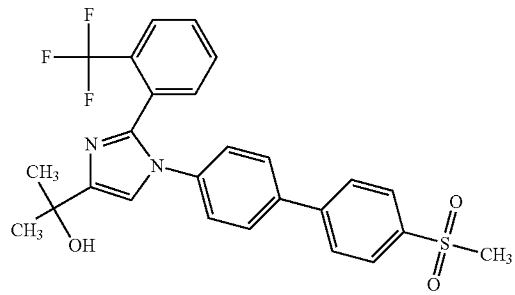 [SMILES: CC(C)(O)c1cn(-c2ccc(-c3ccc(S(C)(=O)=O)cc3)cc2)c(-c2ccccc2C(F)(F)F)n1] | 2-{1-[4'-(methylsulfonyl)biphenyl-4-yl]-2-[2-(trifluoromethyl)phenyl]-1H-imidazol-4-yl}propan-2-ol; |
| 200 | 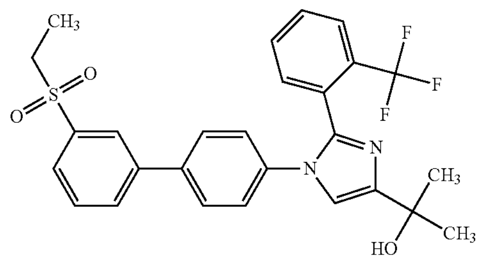 [SMILES: CCS(=O)(=O)c1cccc(-c2ccc(-n3cc(C(C)(C)O)nc3-c3ccccc3C(F)(F)F)cc2)c1] | 2-{1-[3'-(ethylsulfonyl)biphenyl-4-yl]-2-[2-(trifluoromethyl)phenyl]-1H-imidazol-4-yl}propan-2-ol; |
| 201 | 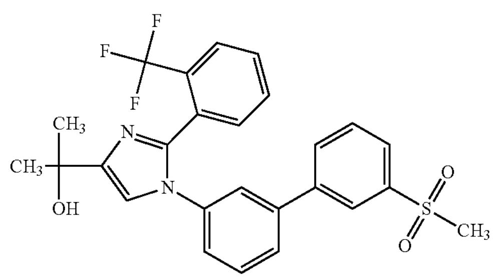 [SMILES: CC(C)(O)c1cn(-c2cccc(-c3cccc(S(C)(=O)=O)c3)c2)c(-c2ccccc2C(F)(F)F)n1] | 2-{1-[3'-(methylsulfonyl)biphenyl-3-yl]-2-[2-(trifluoromethyl)phenyl]-1H-imidazol-4-yl}propan-2-ol; |
| 202 | 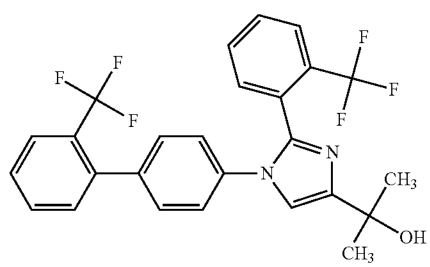 [SMILES: CC(C)(O)c1cn(-c2ccc(-c3ccccc3C(F)(F)F)cc2)c(-c2ccccc2C(F)(F)F)n1] | 2-{1-[2'-(trifluoromethyl)biphenyl-4-yl]-2-[2-(trifluoromethyl)phenyl]-1H-imidazol-4-yl}propan-2-ol; |
| 203 | 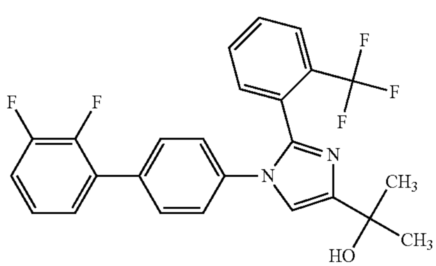 [SMILES: CC(C)(O)c1cn(-c2ccc(-c3cccc(F)c3F)cc2)c(-c2ccccc2C(F)(F)F)n1] | 2-{1-(2',3'-difluorobiphenyl-4-yl)-2-[2-(trifluoromethyl)phenyl]-1H-imidazol-4-yl}propan-2-ol; |

| Cpd # | Structure | Name |
| --- | --- | --- |
| 204 | 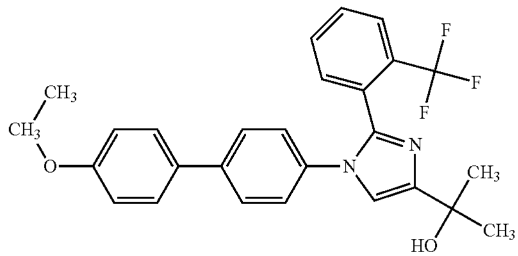 [SMILES: CCOc1ccc(-c2ccc(-n3cc(C(C)(C)O)nc3-c3ccccc3C(F)(F)F)cc2)cc1] | 2-(1-{4'-[(1-methylethyl)oxy]biphenyl-4-yl}-2-[2-(trifluoromethyl)phenyl]-1H-imidazol-4-yl)propan-2-ol; |
| 205 | 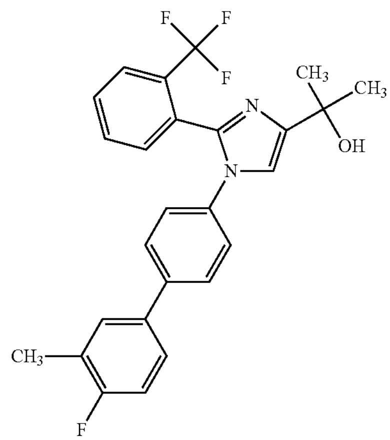 [SMILES: Cc1cc(-c2ccc(-n3cc(C(C)(C)O)nc3-c3ccccc3C(F)(F)F)cc2)ccc1F] | 2-{1-(4'-fluoro-3'-methylbiphenyl-4-yl)-2-[2-(trifluoromethyl)phenyl]-1H-imidazol-4-yl}propan-2-ol; |
| 206 | 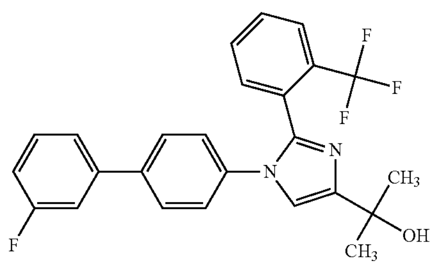 [SMILES: CC(C)(O)c1cn(-c2ccc(-c3cccc(F)c3)cc2)c(-c2ccccc2C(F)(F)F)n1] | 2-{1-(3'-fluorobiphenyl-4-yl)-2-[2-(trifluoromethyl)phenyl]-1H-imidazol-4-yl}propan-2-ol; |
| 207 | 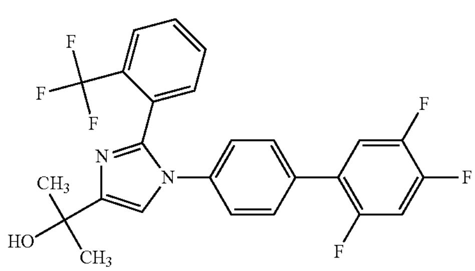 [SMILES: CC(C)(O)c1cn(-c2ccc(-c3cc(F)c(F)cc3F)cc2)c(-c2ccccc2C(F)(F)F)n1] | 2-{1-(2',4',5'-trifluorobiphenyl-4-yl)-2-[2-(trifluoromethyl)phenyl]-1H-imidazol-4-yl}propan-2-ol; |

-continued

| Cpd # | Structure | Name |
|---|---|---|
| 208 | 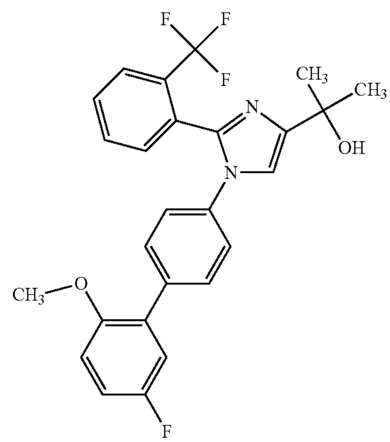 [SMILES: COc1ccc(F)cc1-c1ccc(-n2cc(C(C)(C)O)nc2-c2ccccc2C(F)(F)F)cc1] | 2-{1-[5'-fluoro-2'-(methyloxy)biphenyl-4-yl]-2-[2-(trifluoromethyl)phenyl]-1H-imidazol-4-yl}propan-2-ol; |
| 209 | 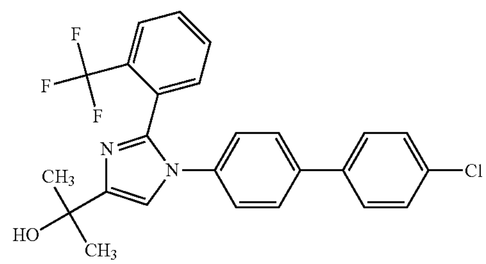 [SMILES: CC(C)(O)c1cn(-c2ccc(-c3ccc(Cl)cc3)cc2)c(-c2ccccc2C(F)(F)F)n1] | 2-{1-(4'-chlorobiphenyl-4-yl)-2-[2-(trifluoromethyl)phenyl]-1H-imidazol-4-yl}propan-2-ol; |
| 210 | 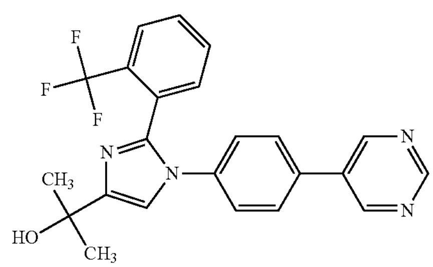 [SMILES: CC(C)(O)c1cn(-c2ccc(-c3cncnc3)cc2)c(-c2ccccc2C(F)(F)F)n1] | 2-{1-(4-pyrimidin-5-ylphenyl)-2-[2-(trifluoromethyl)phenyl]-1H-imidazol-4-yl}propan-2-ol; |
| 211 | 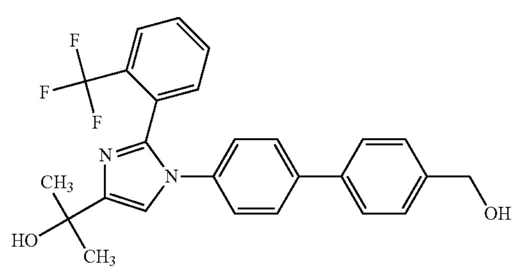 [SMILES: CC(C)(O)c1cn(-c2ccc(-c3ccc(CO)cc3)cc2)c(-c2ccccc2C(F)(F)F)n1] | 2-{1-[4'-(hydroxymethyl)biphenyl-4-yl]-2-[2-(trifluoromethyl)phenyl]-1H-imidazol-4-yl}propan-2-ol; |
| 212 | 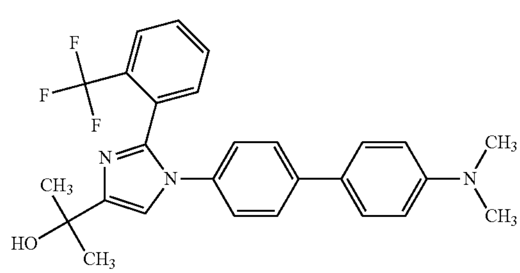 [SMILES: CN(C)c1ccc(-c2ccc(-n3cc(C(C)(C)O)nc3-c3ccccc3C(F)(F)F)cc2)cc1] | 2-{1-[4'-(dimethylamino)biphenyl-4-yl]-2-[2-(trifluoromethyl)phenyl]-1H-imidazol-4-yl}propan-2-ol; |

-continued

| Cpd # | Structure | Name |
|---|---|---|
| 213 | 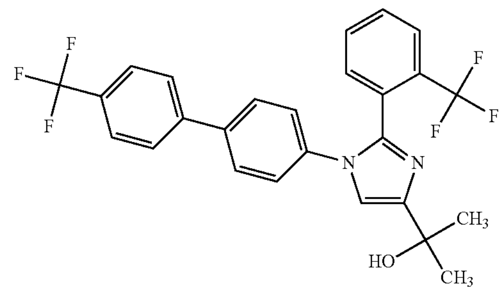 [SMILES: CC(C)(O)c1cn(-c2ccc(-c3ccc(C(F)(F)F)cc3)cc2)c(-c2ccccc2C(F)(F)F)n1] | 2-{1-[4'-(trifluoromethyl)biphenyl-4-yl]-2-[2-(trifluoromethyl)phenyl]-1H-imidazol-4-yl}propan-2-ol; |
| 214 | 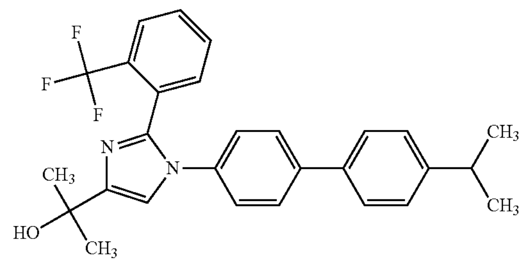 [SMILES: CC(C)c1ccc(-c2ccc(-n3cc(C(C)(C)O)nc3-c3ccccc3C(F)(F)F)cc2)cc1] | 2-{1-[4'-(1-methylethyl)biphenyl-4-yl]-2-[2-(trifluoromethyl)phenyl]-1H-imidazol-4-yl}propan-2-ol; |
| 215 | 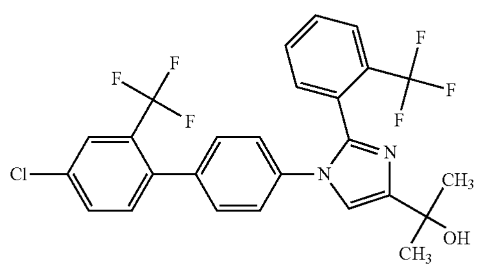 [SMILES: CC(C)(O)c1cn(-c2ccc(-c3ccc(Cl)cc3C(F)(F)F)cc2)c(-c2ccccc2C(F)(F)F)n1] | 2-{1-[4'-chloro-2'-(trifluoromethyl)biphenyl-4-yl]-2-[2-(trifluoromethyl)phenyl]-1H-imidazol-4-yl}propan-2-ol; |
| 216 | 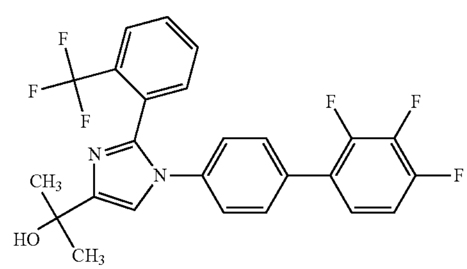 [SMILES: CC(C)(O)c1cn(-c2ccc(-c3ccc(F)c(F)c3F)cc2)c(-c2ccccc2C(F)(F)F)n1] | 2-{1-(2',3',4'-trifluorobiphenyl-4-yl)-2-[2-(trifluoromethyl)phenyl]-1H-imidazol-4-yl}propan-2-ol; |
| 217 | 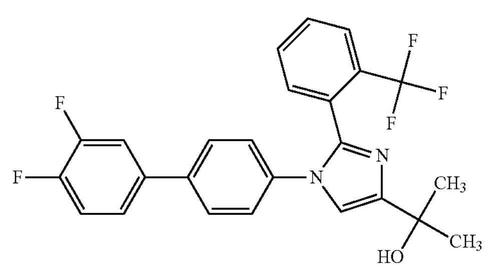 [SMILES: CC(C)(O)c1cn(-c2ccc(-c3ccc(F)c(F)c3)cc2)c(-c2ccccc2C(F)(F)F)n1] | 2-{1-(3',4'-difluorobiphenyl-4-yl)-2-[2-(trifluoromethyl)phenyl]-1H-imidazol-4-yl}propan-2-ol; |

| Cpd # | Structure | Name |
|---|---|---|
| 218 | 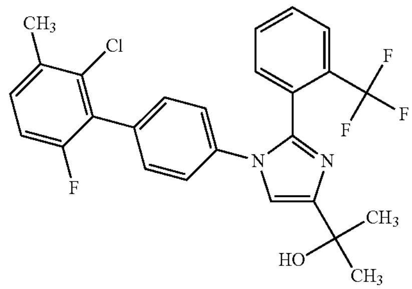 [SMILES: Cc1ccc(F)c(-c2ccc(-n3cc(C(C)(C)O)nc3-c3ccccc3C(F)(F)F)cc2)c1Cl] | 2-{1-(2'-chloro-6'-fluoro-3'-methylbiphenyl-4-yl)-2-[2-(trifluoromethyl)phenyl]-1H-imidazol-4-yl}propan-2-ol; |
| 219 | 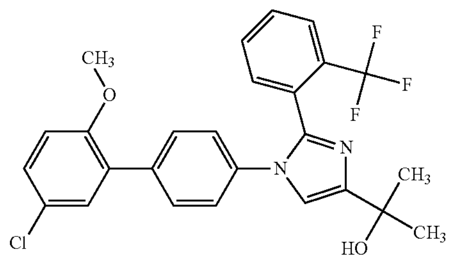 [SMILES: COc1ccc(Cl)cc1-c1ccc(-n2cc(C(C)(C)O)nc2-c2ccccc2C(F)(F)F)cc1] | 2-{1-[5'-chloro-2'-(methyloxy)biphenyl-4-yl]-2-[2-(trifluoromethyl)phenyl]-1H-imidazol-4-yl}propan-2-ol; |
| 220 | 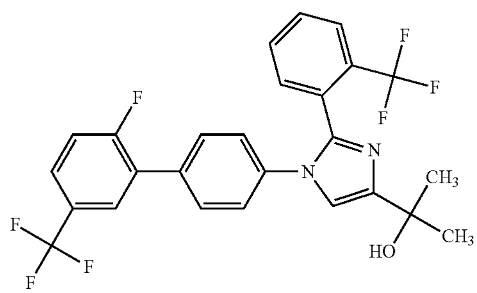 [SMILES: CC(C)(O)c1cn(-c2ccc(-c3cc(C(F)(F)F)ccc3F)cc2)c(-c2ccccc2C(F)(F)F)n1] | 2-{1-[2'-fluoro-5'-(trifluoromethyl)biphenyl-4-yl]-2-[2-(trifluoromethyl)phenyl]-1H-imidazol-4-yl}propan-2-ol; |
| 221 | 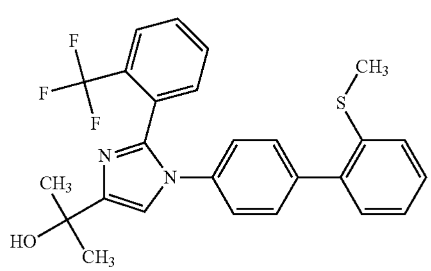 [SMILES: CSc1ccccc1-c1ccc(-n2cc(C(C)(C)O)nc2-c2ccccc2C(F)(F)F)cc1] | 2-{1-[2'-(methylthio)biphenyl-4-yl]-2-[2-(trifluoromethyl)phenyl]-1H-imidazol-4-yl}propan-2-ol; |
| 222 | 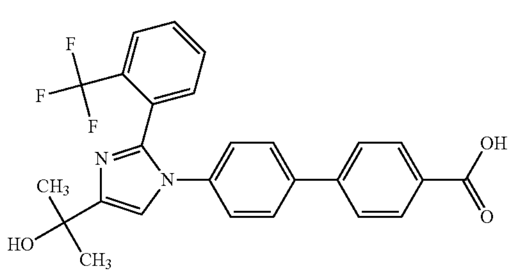 [SMILES: CC(C)(O)c1cn(-c2ccc(-c3ccc(C(=O)O)cc3)cc2)c(-c2ccccc2C(F)(F)F)n1] | 4'-{4-(1-hydroxy-1-methylethyl)-2-[2-(trifluoromethyl)phenyl]-1H-imidazol-1-yl}biphenyl-4-carboxylic acid; |

-continued

| Cpd # | Structure | Name |
|---|---|---|
| 223 | 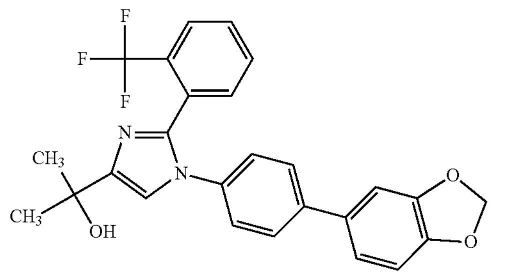 [SMILES: CC(C)(O)c1cn(-c2ccc(-c3ccc4c(c3)OCO4)cc2)c(-c2ccccc2C(F)(F)F)n1] | 2-{1-[4-(1,3-benzodioxol-5-yl)phenyl]-2-[2-(trifluoromethyl)phenyl]-1H-imidazol-4-yl}propan-2-ol; |
| 224 | 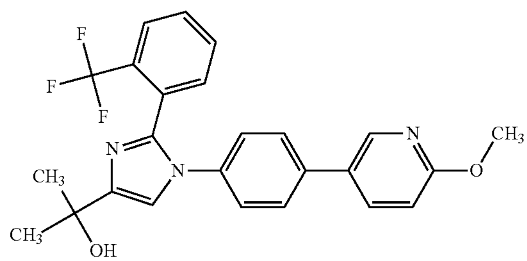 [SMILES: COc1ccc(-c2ccc(-n3cc(C(C)(C)O)nc3-c3ccccc3C(F)(F)F)cc2)cn1] | 2-(1-{4-[6-(methyloxy)pyridin-3-yl]phenyl}-2-[2-(trifluoromethyl)phenyl]-1H-imidazol-4-yl)propan-2-ol; |
| 226 | 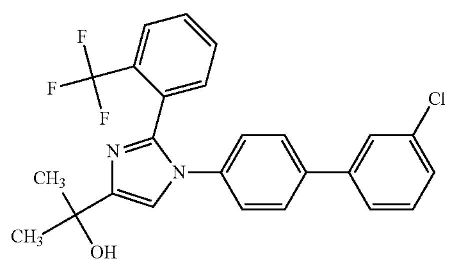 [SMILES: CC(C)(O)c1cn(-c2ccc(-c3cccc(Cl)c3)cc2)c(-c2ccccc2C(F)(F)F)n1] | 2-{1-(3'-chlorobiphenyl-4-yl)-2-[2-(trifluoromethyl)phenyl]-1H-imidazol-4-yl}propan-2-ol; |
| 227 | 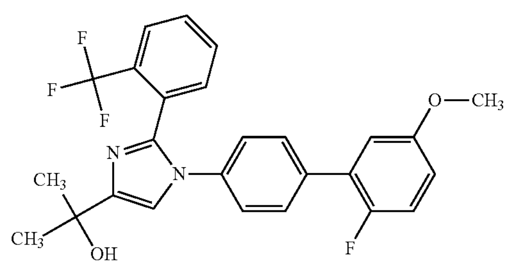 [SMILES: COc1ccc(F)c(-c2ccc(-n3cc(C(C)(C)O)nc3-c3ccccc3C(F)(F)F)cc2)c1] | 2-{1-[2'-fluoro-5'-(methyloxy)biphenyl-4-yl]-2-[2-(trifluoromethyl)phenyl]-1H-imidazol-4-yl}propan-2-ol; |
| 228 | 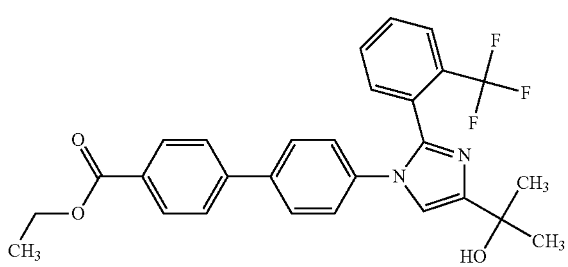 [SMILES: CCOC(=O)c1ccc(-c2ccc(-n3cc(C(C)(C)O)nc3-c3ccccc3C(F)(F)F)cc2)cc1] | ethyl 4'-{4-(1-hydroxy-1-methylethyl)-2-[2-(trifluoromethyl)phenyl]-1H-imidazol-1-yl}biphenyl-4-carboxylate; |

-continued

| Cpd # | Structure | Name |
|---|---|---|
| 229 | 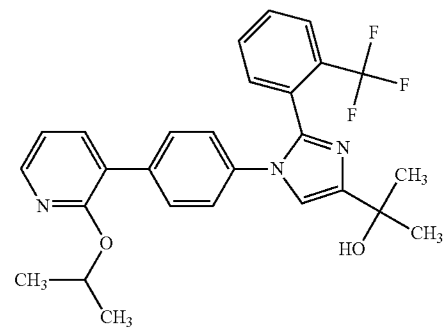 [SMILES: CC(C)Oc1ncccc1-c1ccc(-n2cc(C(C)(C)O)nc2-c2ccccc2C(F)(F)F)cc1] | 2-{1-(4-{2-[(1-methylethyl)oxy]pyridin-3-yl}phenyl)-2-[2-(trifluoromethyl)phenyl]-1H-imidazol-4-yl}propan-2-ol; |
| 230 | 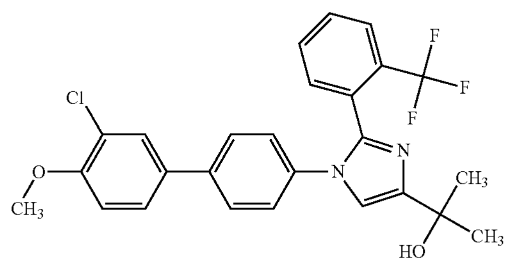 [SMILES: COc1ccc(-c2ccc(-n3cc(C(C)(C)O)nc3-c3ccccc3C(F)(F)F)cc2)cc1Cl] | 2-{1-[3'-chloro-4'-(methyloxy)biphenyl-4-yl]-2-[2-(trifluoromethyl)phenyl]-1H-imidazol-4-yl}propan-2-ol; |
| 232 | 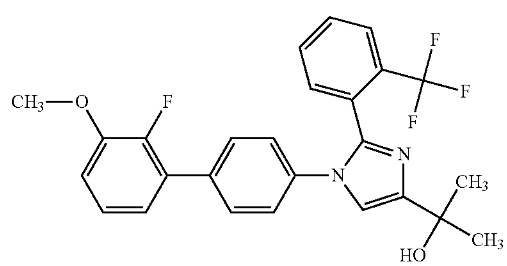 [SMILES: COc1cccc(-c2ccc(-n3cc(C(C)(C)O)nc3-c3ccccc3C(F)(F)F)cc2)c1F] | 2-{1-[2'-fluoro-3'-(methyloxy)biphenyl-4-yl]-2-[2-(trifluoromethyl)phenyl]-1H-imidazol-4-yl}propan-2-ol; |
| 233 | 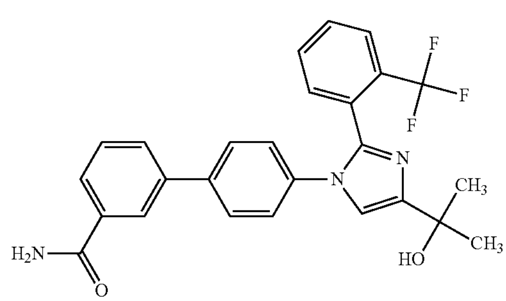 [SMILES: CC(C)(O)c1cn(-c2ccc(-c3cccc(C(N)=O)c3)cc2)c(-c2ccccc2C(F)(F)F)n1] | 4'-{4-(1-hydroxy-1-methylethyl)-2-[2-(trifluoromethyl)phenyl]-1H-imidazol-1-yl}biphenyl-3-carboxamide; |
| 234 | 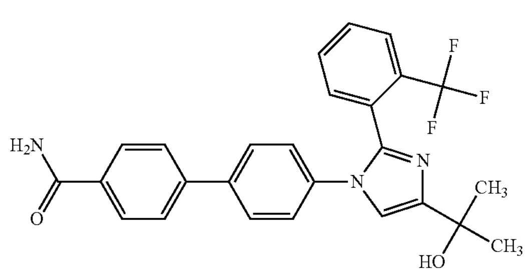 [SMILES: CC(C)(O)c1cn(-c2ccc(-c3ccc(C(N)=O)cc3)cc2)c(-c2ccccc2C(F)(F)F)n1] | 4'-{4-(1-hydroxy-1-methylethyl)-2-[2-(trifluoromethyl)phenyl]-1H-imidazol-1-yl}biphenyl-4-carboxamide; |

| Cpd # | Structure | Name |
|---|---|---|
| 235 | 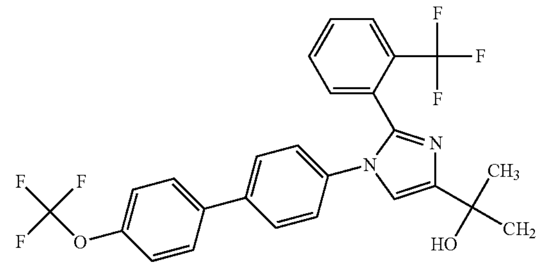 [SMILES: CC(C)(O)c1cn(-c2ccc(-c3ccc(OC(F)(F)F)cc3)cc2)c(-c2ccccc2C(F)(F)F)n1] | 2-(1-{4'-[(trifluoromethyl)oxy]biphenyl-4-yl}-2-[2-(trifluoromethyl)phenyl]-1H-imidazol-4-yl)propan-2-ol; |
| 236 | 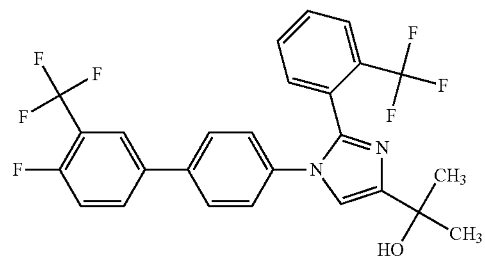 [SMILES: CC(C)(O)c1cn(-c2ccc(-c3ccc(F)c(C(F)(F)F)c3)cc2)c(-c2ccccc2C(F)(F)F)n1] | 2-{1-[4'-fluoro-3'-(trifluoromethyl)biphenyl-4-yl]-2-[2-(trifluoromethyl)phenyl]-1H-imidazol-4-yl}propan-2-ol; |
| 237 | 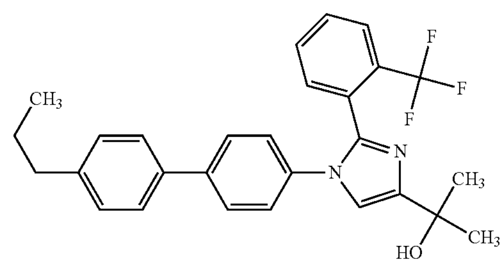 [SMILES: CCCc1ccc(-c2ccc(-n3cc(C(C)(C)O)nc3-c3ccccc3C(F)(F)F)cc2)cc1] | 2-{1-(4'-propylbiphenyl-4-yl)-2-[2-(trifluoromethyl)phenyl]-1H-imidazol-4-yl}propan-2-ol; |
| 238 | 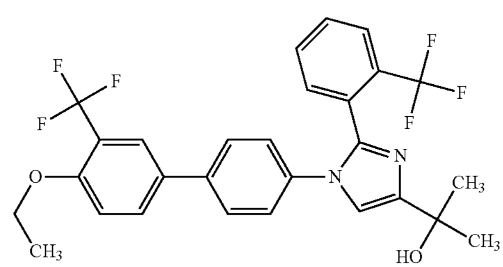 [SMILES: CCOc1ccc(-c2ccc(-n3cc(C(C)(C)O)nc3-c3ccccc3C(F)(F)F)cc2)cc1C(F)(F)F] | 2-{1-[4'-(ethyloxy)-3'-(trifluoromethyl)biphenyl-4-yl]-2-[2-(trifluoromethyl)phenyl]-1H-imidazol-4-yl}propan-2-ol; |
| 239 | 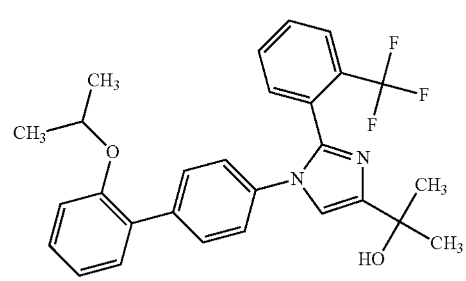 [SMILES: CC(C)Oc1ccccc1-c1ccc(-n2cc(C(C)(C)O)nc2-c2ccccc2C(F)(F)F)cc1] | 2-(1-{2'-[(1-methylethyl)oxy]biphenyl-4-yl}-2-[2-(trifluoromethyl)phenyl]-1H-imidazol-4-yl)propan-2-ol; |
| 240 | 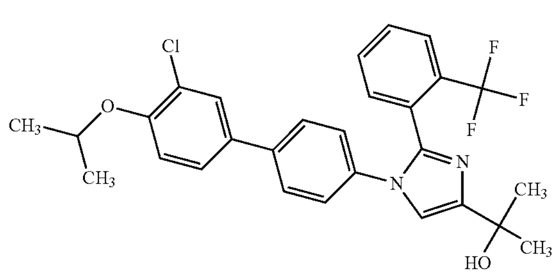 [SMILES: CC(C)Oc1ccc(-c2ccc(-n3cc(C(C)(C)O)nc3-c3ccccc3C(F)(F)F)cc2)cc1Cl] | 2-(1-{3'-chloro-4'-[(1-methylethyl)oxy]biphenyl-4-yl}-2-[2-(trifluoromethyl)phenyl]-1H-imidazol-4-yl)propan-2-ol; |

-continued

| Cpd # | Structure | Name |
|---|---|---|
| 241 | 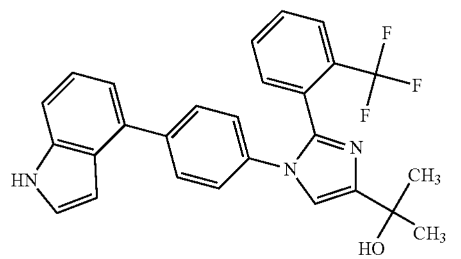 [SMILES: CC(C)(O)c1cn(-c2ccc(-c3cccc4[nH]ccc34)cc2)c(-c2ccccc2C(F)(F)F)n1] | 2-{1-[4-(1H-indol-4-yl)phenyl]-2-[2-(trifluoromethyl)phenyl]-1H-imidazol-4-yl}propan-2-ol; |
| 242 | 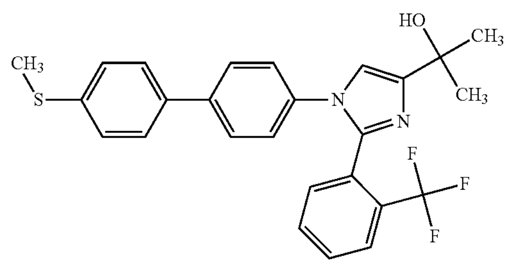 [SMILES: CSc1ccc(-c2ccc(-n3cc(C(C)(C)O)nc3-c3ccccc3C(F)(F)F)cc2)cc1] | 2-{1-[4'-(methylthio)biphenyl-4-yl]-2-[2-(trifluoromethyl)phenyl]-1H-imidazol-4-yl}propan-2-ol; |
| 243 | 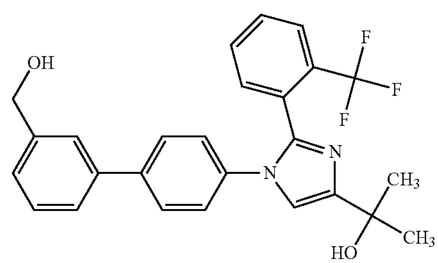 [SMILES: CC(C)(O)c1cn(-c2ccc(-c3cccc(CO)c3)cc2)c(-c2ccccc2C(F)(F)F)n1] | 2-{1-[3'-(hydroxymethyl)biphenyl-4-yl]-2-[2-(trifluoromethyl)phenyl]-1H-imidazol-4-yl}propan-2-ol; |
| 244 | 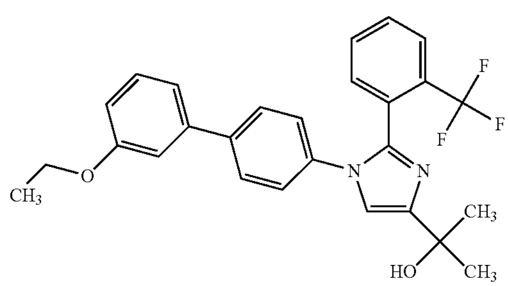 [SMILES: CCOc1cccc(-c2ccc(-n3cc(C(C)(C)O)nc3-c3ccccc3C(F)(F)F)cc2)c1] | 2-{1-[3'-(ethyloxy)biphenyl-4-yl]-2-[2-(trifluoromethyl)phenyl]-1H-imidazol-4-yl}propan-2-ol; |
| 245 | 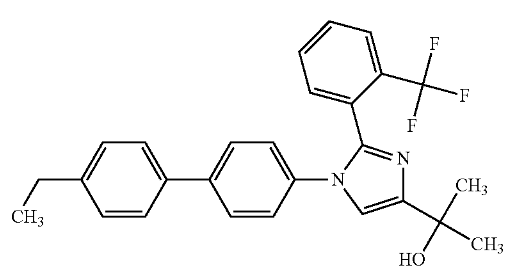 [SMILES: CCc1ccc(-c2ccc(-n3cc(C(C)(C)O)nc3-c3ccccc3C(F)(F)F)cc2)cc1] | 2-{1-(4'-ethylbiphenyl-4-yl)-2-[2-(trifluoromethyl)phenyl]-1H-imidazol-4-yl}propan-2-ol; |

-continued

| Cpd # | Structure | Name |
|---|---|---|
| 246 | 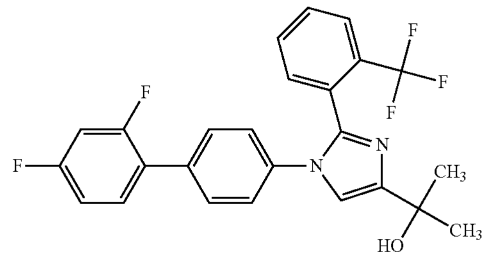 [SMILES: CC(C)(O)c1cn(-c2ccc(-c3ccc(F)cc3F)cc2)c(-c2ccccc2C(F)(F)F)n1] | 2-{1-(2',4'-difluorobiphenyl-4-yl)-2-[2-(trifluoromethyl)phenyl]-1H-imidazol-4-yl}propan-2-ol; |
| 247 | 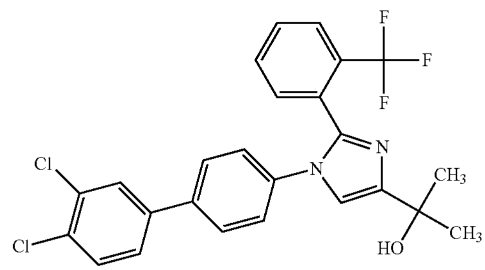 [SMILES: CC(C)(O)c1cn(-c2ccc(-c3ccc(Cl)c(Cl)c3)cc2)c(-c2ccccc2C(F)(F)F)n1] | 2-{1-(3',4'-dichlorobiphenyl-4-yl)-2-[2-(trifluoromethyl)phenyl]-1H-imidazol-4-yl}propan-2-ol; |
| 248 | 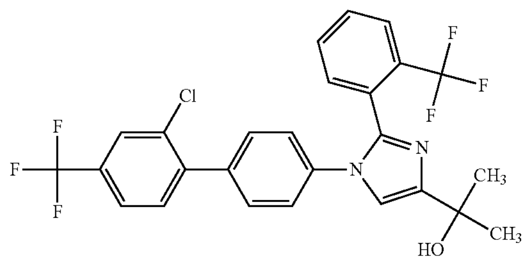 [SMILES: CC(C)(O)c1cn(-c2ccc(-c3ccc(C(F)(F)F)cc3Cl)cc2)c(-c2ccccc2C(F)(F)F)n1] | 2-{1-[2'-chloro-4'-(trifluoromethyl)biphenyl-4-yl]-2-[2-(trifluoromethyl)phenyl]-1H-imidazol-4-yl}propan-2-ol; |
| 249 | 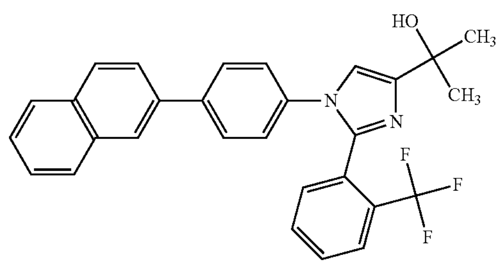 [SMILES: CC(C)(O)c1cn(-c2ccc(-c3ccc4ccccc4c3)cc2)c(-c2ccccc2C(F)(F)F)n1] | 2-{1-(4-naphthalen-2-ylphenyl)-2-[2-(trifluoromethyl)phenyl]-1H-imidazol-4-yl}propan-2-ol; |
| 250 | 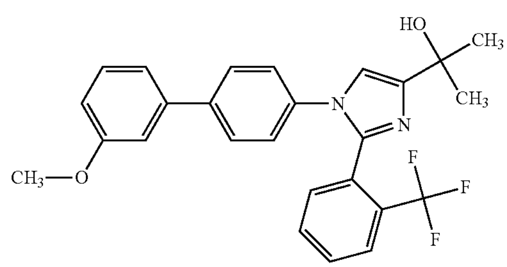 [SMILES: COc1cccc(-c2ccc(-n3cc(C(C)(C)O)nc3-c3ccccc3C(F)(F)F)cc2)c1] | 2-{1-[3'-(methyloxy)biphenyl-4-yl]-2-[2-(trifluoromethyl)phenyl]-1H-imidazol-4-yl}propan-2-ol |
| 251 | 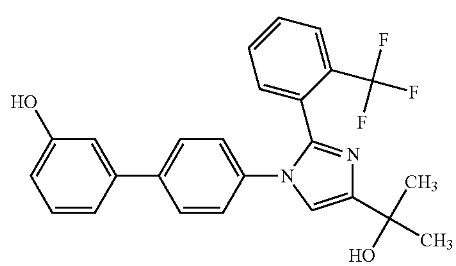 [SMILES: CC(C)(O)c1cn(-c2ccc(-c3cccc(O)c3)cc2)c(-c2ccccc2C(F)(F)F)n1] | 4'-{4-(1-hydroxy-1-methylethyl)-2-[2-(trifluoromethyl)phenyl]-1H-imidazol-1-yl}biphenyl-3-ol; |

-continued

| Cpd # | Structure | Name |
|---|---|---|
| 252 | 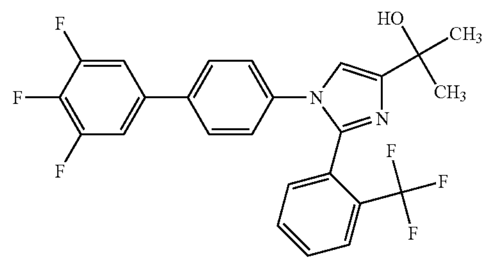 [SMILES: CC(C)(O)c1cn(-c2ccc(-c3cc(F)c(F)c(F)c3)cc2)c(-c2ccccc2C(F)(F)F)n1] | 2-{1-(3',4',5'-trifluorobiphenyl-4-yl)-2-[2-(trifluoromethyl)phenyl]-1H-imidazol-4-yl}propan-2-ol; |
| 253 | 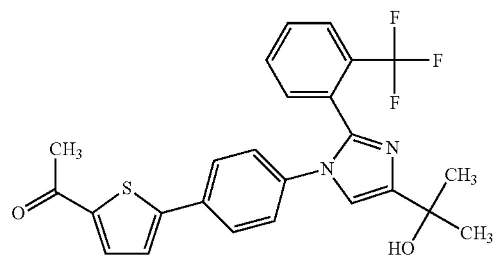 [SMILES: CC(=O)c1ccc(-c2ccc(-n3cc(C(C)(C)O)nc3-c3ccccc3C(F)(F)F)cc2)s1] | 1-[5-(4-{4-(1-hydroxy-1-methylethyl)-2-[2-(trifluoromethyl)phenyl]-1H-imidazol-1-yl}phenyl)-2-thienyl]ethanone; |
| 254 | 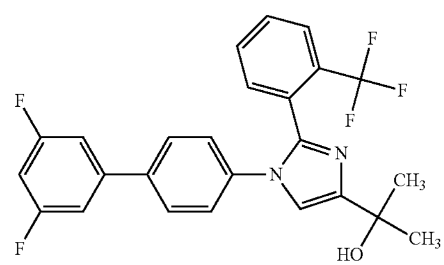 [SMILES: CC(C)(O)c1cn(-c2ccc(-c3cc(F)cc(F)c3)cc2)c(-c2ccccc2C(F)(F)F)n1] | 2-{1-(3',5'-difluorobiphenyl-4-yl)-2-[2-(trifluoromethyl)phenyl]-1H-imidazol-4-yl}propan-2-ol; |
| 255 | 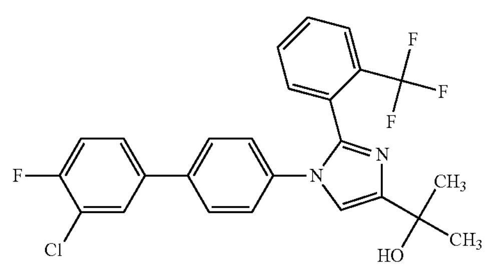 [SMILES: CC(C)(O)c1cn(-c2ccc(-c3ccc(F)c(Cl)c3)cc2)c(-c2ccccc2C(F)(F)F)n1] | 2-{1-(3'-chloro-4'-fluorobiphenyl-4-yl)-2-[2-(trifluoromethyl)phenyl]-1H-imidazol-4-yl}propan-2-ol; |
| 256 | 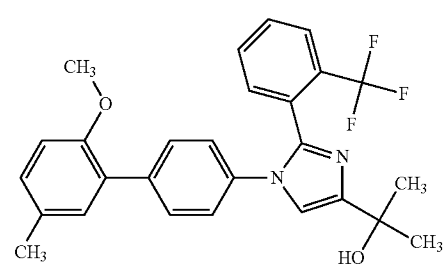 [SMILES: COc1ccc(C)cc1-c1ccc(-n2cc(C(C)(C)O)nc2-c2ccccc2C(F)(F)F)cc1] | 2-{1-[5'-methyl-2'-(methyloxy)biphenyl-4-yl]-2-[2-(trifluoromethyl)phenyl]-1H-imidazol-4-yl}propan-2-ol; |
| 257 | 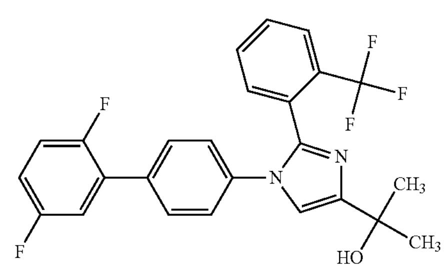 [SMILES: CC(C)(O)c1cn(-c2ccc(-c3cc(F)ccc3F)cc2)c(-c2ccccc2C(F)(F)F)n1] | 2-{1-(2',5'-difluorobiphenyl-4-yl)-2-[2-(trifluoromethyl)phenyl]-1H-imidazol-4-yl}propan-2-ol; |

-continued

| Cpd # | Structure | Name |
|---|---|---|
| 258 | 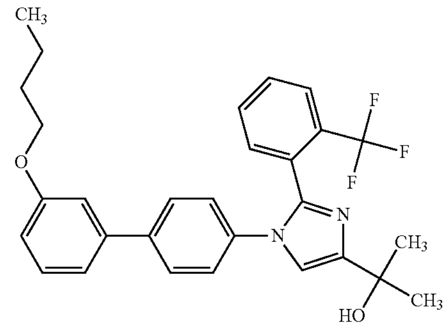 [SMILES: CCCCOc1cccc(-c2ccc(-n3cc(C(C)(C)O)nc3-c3ccccc3C(F)(F)F)cc2)c1] | 2-{1-[3'-(butyloxy)biphenyl-4-yl]-2-[2-(trifluoromethyl)phenyl]-1H-imidazol-4-yl}propan-2-ol; |
| 259 | 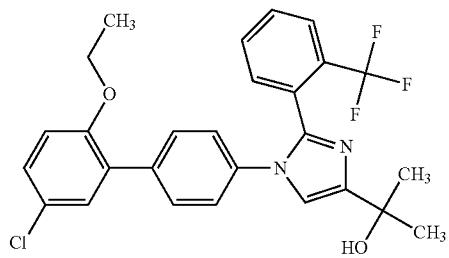 [SMILES: CCOc1ccc(Cl)cc1-c1ccc(-n2cc(C(C)(C)O)nc2-c2ccccc2C(F)(F)F)cc1] | 2-{1-[5'-chloro-2'-(ethyloxy)biphenyl-4-yl]-2-[2-(trifluoromethyl)phenyl]-1H-imidazol-4-yl}propan-2-ol; |
| 260 | 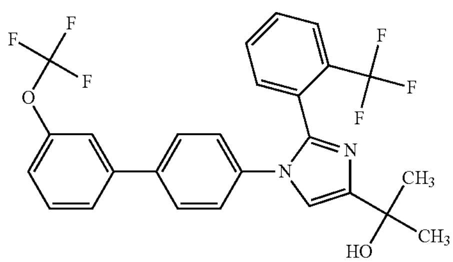 [SMILES: CC(C)(O)c1cn(-c2ccc(-c3cccc(OC(F)(F)F)c3)cc2)c(-c2ccccc2C(F)(F)F)n1] | 2-(1-{3'-[(trifluoromethyl)oxy]biphenyl-4-yl}-2-[2-(trifluoromethyl)phenyl]-1H-imidazol-4-yl)propan-2-ol; |
| 261 | 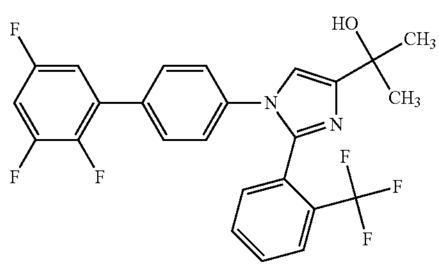 [SMILES: CC(C)(O)c1cn(-c2ccc(-c3cc(F)cc(F)c3F)cc2)c(-c2ccccc2C(F)(F)F)n1] | 2-{1-(2',3',5'-trifluorobiphenyl-4-yl)-2-[2-(trifluoromethyl)phenyl]-1H-imidazol-4-yl}propan-2-ol; |
| 262 | 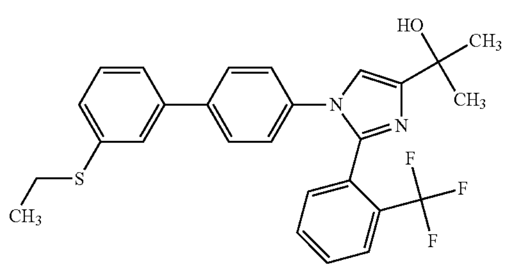 [SMILES: CCSc1cccc(-c2ccc(-n3cc(C(C)(C)O)nc3-c3ccccc3C(F)(F)F)cc2)c1] | 2-{1-[3'-(ethylthio)biphenyl-4-yl]-2-[2-(trifluoromethyl)phenyl]-1H-imidazol-4-yl}propan-2-ol; |

-continued

| Cpd # | Structure | Name |
|---|---|---|
| 263 | 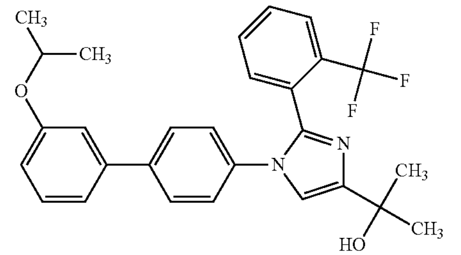 [SMILES: CC(C)Oc1cccc(-c2ccc(-n3cc(C(C)(C)O)nc3-c3ccccc3C(F)(F)F)cc2)c1] | 2-(1-{3'-[(1-methylethyl)oxy]biphenyl-4-yl}-2-[2-(trifluoromethyl)phenyl]-1H-imidazol-4-yl)propan-2-ol; |
| 264 | 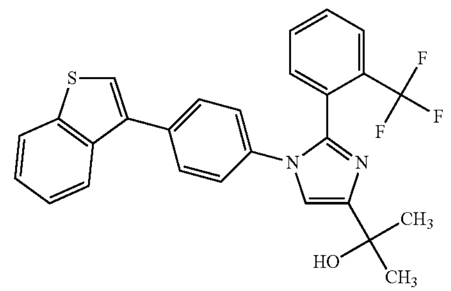 [SMILES: CC(C)(O)c1cn(-c2ccc(-c3csc4ccccc34)cc2)c(-c2ccccc2C(F)(F)F)n1] | 2-{1-[4-(1-benzothien-3-yl)phenyl]-2-[2-(trifluoromethyl)phenyl]-1H-imidazol-4-yl}propan-2-ol; |
| 265 | 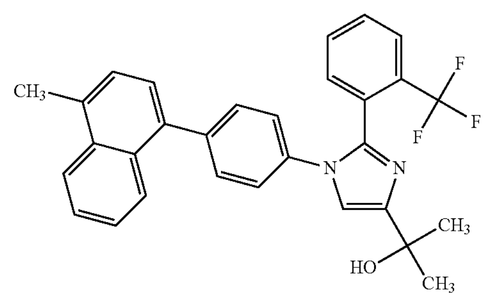 [SMILES: Cc1ccc(-c2ccc(-n3cc(C(C)(C)O)nc3-c3ccccc3C(F)(F)F)cc2)c2ccccc12] | 2-{1-[4-(4-methylnaphthalen-1-yl)phenyl]-2-[2-(trifluoromethyl)phenyl]-1H-imidazol-4-yl}propan-2-ol; |
| 266 | 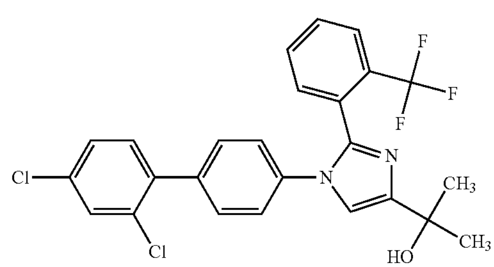 [SMILES: CC(C)(O)c1cn(-c2ccc(-c3ccc(Cl)cc3Cl)cc2)c(-c2ccccc2C(F)(F)F)n1] | 2-{1-(2',4'-dichlorobiphenyl-4-yl)-2-[2-(trifluoromethyl)phenyl]-1H-imidazol-4-yl}propan-2-ol; |
| 267 | 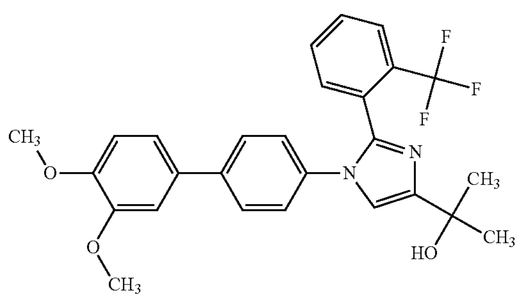 [SMILES: COc1ccc(-c2ccc(-n3cc(C(C)(C)O)nc3-c3ccccc3C(F)(F)F)cc2)cc1OC] | 2-{1-[3',4'-bis(methyloxy)biphenyl-4-yl]-2-[2-(trifluoromethyl)phenyl]-1H-imidazol-4-yl}propan-2-ol; |

-continued

| Cpd # | Structure | Name |
|---|---|---|
| 268 | 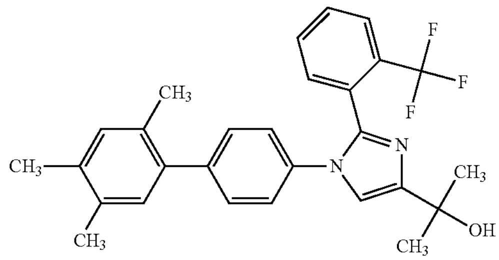 [SMILES: Cc1cc(C)c(-c2ccc(-n3cc(C(C)(C)O)nc3-c3ccccc3C(F)(F)F)cc2)cc1C] | 2-{2-[2-(trifluoromethyl)phenyl]-1-(2',4',5'-trimethylbiphenyl-4-yl)-1H-imidazol-4-yl}propan-2-ol; |
| 269 | 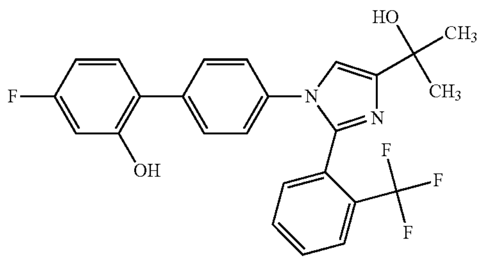 [SMILES: CC(C)(O)c1cn(-c2ccc(-c3ccc(F)cc3O)cc2)c(-c2ccccc2C(F)(F)F)n1] | 4-fluoro-4'-{4-(1-hydroxy-1-methylethyl)-2-[2-(trifluoromethyl)phenyl]-1H-imidazol-1-yl}biphenyl-2-ol; |
| 270 | 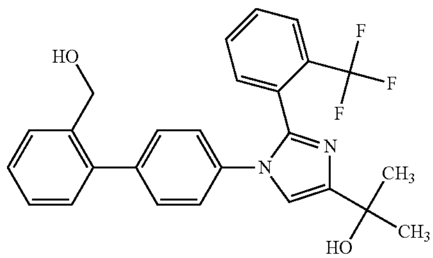 [SMILES: CC(C)(O)c1cn(-c2ccc(-c3ccccc3CO)cc2)c(-c2ccccc2C(F)(F)F)n1] | 2-{1-[2'-(hydroxymethyl)biphenyl-4-yl]-2-[2-(trifluoromethyl)phenyl]-1H-imidazol-4-yl}propan-2-ol; |
| 271 | 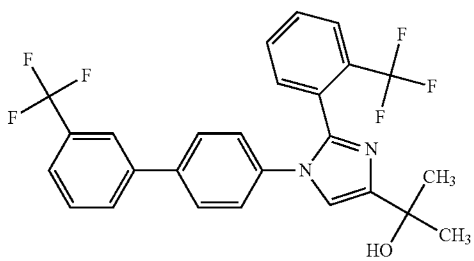 [SMILES: CC(C)(O)c1cn(-c2ccc(-c3cccc(C(F)(F)F)c3)cc2)c(-c2ccccc2C(F)(F)F)n1] | 2-{1-[3'-(trifluoromethyl)biphenyl-4-yl]-2-[2-(trifluoromethyl)phenyl]-1H-imidazol-4-yl}propan-2-ol; |
| 272 | 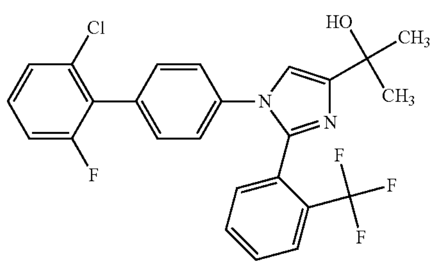 [SMILES: CC(C)(O)c1cn(-c2ccc(-c3c(F)cccc3Cl)cc2)c(-c2ccccc2C(F)(F)F)n1] | 2-{1-(2'-chloro-6'-fluorobiphenyl-4-yl)-2-[2-(trifluoromethyl)phenyl]-1H-imidazol-4-yl}propan-2-ol; |
| 273 | 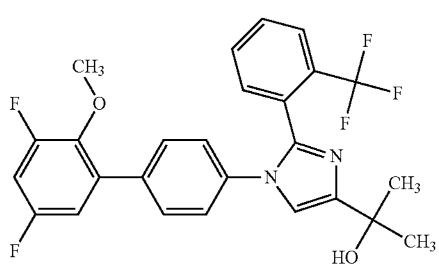 [SMILES: COc1c(F)cc(F)cc1-c1ccc(-n2cc(C(C)(C)O)nc2-c2ccccc2C(F)(F)F)cc1] | 2-{1-[3',5'-difluoro-2'-(methyloxy)biphenyl-4-yl]-2-[2-(trifluoromethyl)phenyl]-1H-imidazol-4-yl}propan-2-ol; |

| Cpd # | Structure | Name |
|---|---|---|
| 274 | 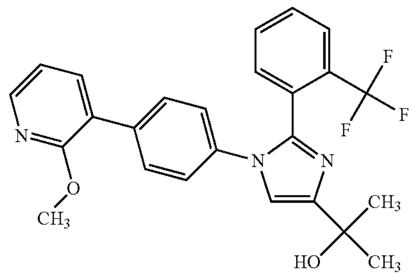 [SMILES: COc1ncccc1-c1ccc(-n2cc(C(C)(C)O)nc2-c2ccccc2C(F)(F)F)cc1] | 2-(1-{4-[2-(methyloxy)pyridin-3-yl]phenyl}-2-[2-(trifluoromethyl)phenyl]-1H-imidazol-4-yl)propan-2-ol; |
| 275 | 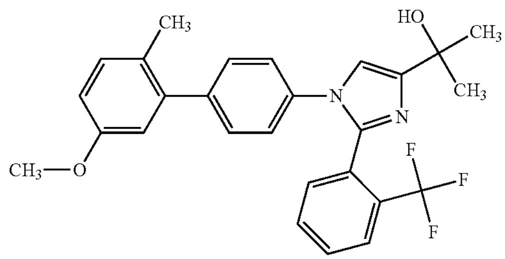 [SMILES: COc1ccc(C)c(-c2ccc(-n3cc(C(C)(C)O)nc3-c3ccccc3C(F)(F)F)cc2)c1] | 2-{1-[2'-methyl-5'-(methyloxy)biphenyl-4-yl]-2-[2-(trifluoromethyl)phenyl]-1H-imidazol-4-yl}propan-2-ol; |
| 276 | 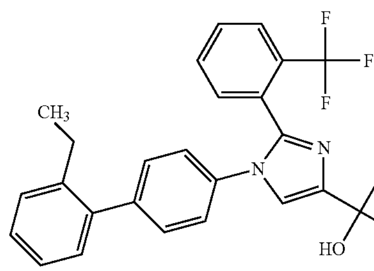 | 2-{1-(2'-ethylbiphenyl-4-yl)-2-[2-(trifluoromethyl)phenyl]-1H-imidazol-4-yl}propan-2-ol; |
| 277 | 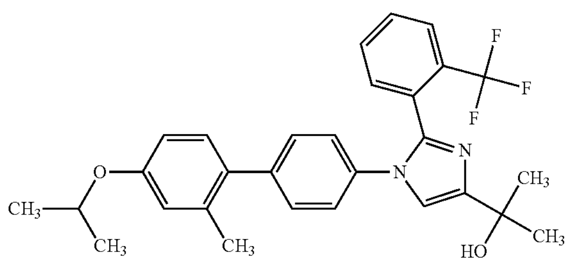 [SMILES: Cc1cc(OC(C)C)ccc1-c1ccc(-n2cc(C(C)(C)O)nc2-c2ccccc2C(F)(F)F)cc1] | 2-(1-{2'-methyl-4'-[(1-methylethyl)oxy]biphenyl-4-yl}-2-[2-(trifluoromethyl)phenyl]-1H-imidazol-4-yl)propan-2-ol; |
| 278 | 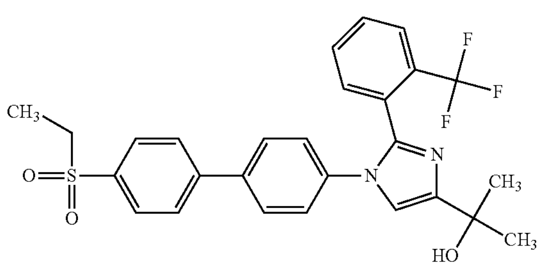 [SMILES: CCS(=O)(=O)c1ccc(-c2ccc(-n3cc(C(C)(C)O)nc3-c3ccccc3C(F)(F)F)cc2)cc1] | 2-{1-[4'-(ethylsulfonyl)biphenyl-4-yl]-2-[2-(trifluoromethyl)phenyl]-1H-imidazol-4-yl}propan-2-ol; |
| 279 | 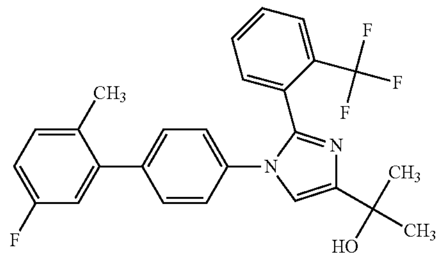 [SMILES: Cc1ccc(F)cc1-c1ccc(-n2cc(C(C)(C)O)nc2-c2ccccc2C(F)(F)F)cc1] | 2-{1-(5'-fluoro-2'-methylbiphenyl-4-yl)-2-[2-(trifluoromethyl)phenyl]-1H-imidazol-4-yl}propan-2-ol; |

-continued

| Cpd # | Structure | Name |
|---|---|---|
| 280 | 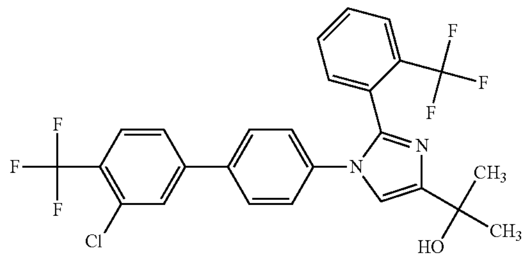 [SMILES: CC(C)(O)c1cn(-c2ccc(-c3ccc(C(F)(F)F)c(Cl)c3)cc2)c(-c2ccccc2C(F)(F)F)n1] | 2-{1-[3'-chloro-4'-(trifluoromethyl)biphenyl-4-yl]-2-[2-(trifluoromethyl)phenyl]-1H-imidazol-4-yl}propan-2-ol; |
| 281 | 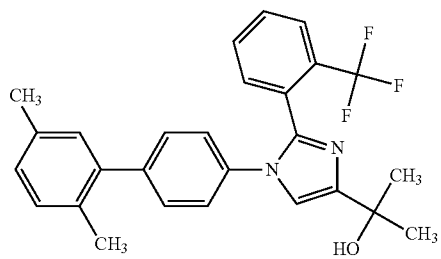 [SMILES: Cc1ccc(C)c(-c2ccc(-n3cc(C(C)(C)O)nc3-c3ccccc3C(F)(F)F)cc2)c1] | 2-{1-(5'-chloro-2'-methylbiphenyl-4-yl)-2-[2-(trifluoromethyl)phenyl]-1H-imidazol-4-yl}propan-2-ol; |
| 282 | 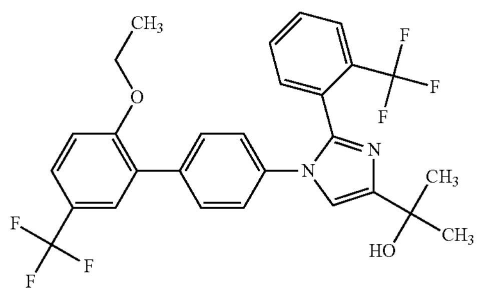 [SMILES: CCOc1ccc(C(F)(F)F)cc1-c1ccc(-n2cc(C(C)(C)O)nc2-c2ccccc2C(F)(F)F)cc1] | 2-{1-[2'-(ethyloxy)-5'-(trifluoromethyl)biphenyl-4-yl]-2-[2-(trifluoromethyl)phenyl]-1H-imidazol-4-yl}propan-2-ol; |
| 283 | 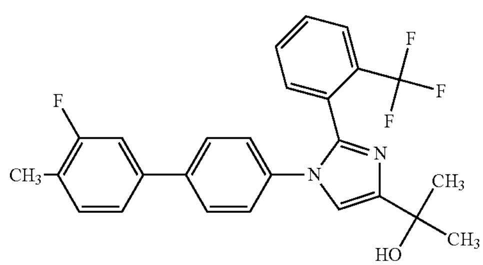 [SMILES: Cc1ccc(-c2ccc(-n3cc(C(C)(C)O)nc3-c3ccccc3C(F)(F)F)cc2)cc1F] | 2-{1-(3'-fluoro-4'-methylbiphenyl-4-yl)-2-[2-(trifluoromethyl)phenyl]-1H-imidazol-4-yl}propan-2-ol; |
| 284 | 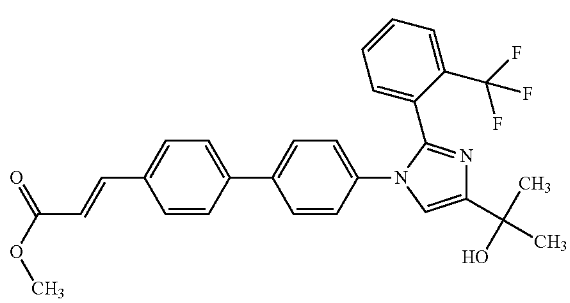 [SMILES: COC(=O)/C=C/c1ccc(-c2ccc(-n3cc(C(C)(C)O)nc3-c3ccccc3C(F)(F)F)cc2)cc1] | methyl (2E)-3-(4'-{4-(1-hydroxy-1-methylethyl)-2-[2-(trifluoromethyl)phenyl]-1H-imidazol-1-yl}biphenyl-4-yl)prop-2-enoate; |

-continued

| Cpd # | Structure | Name |
|---|---|---|
| 285 | 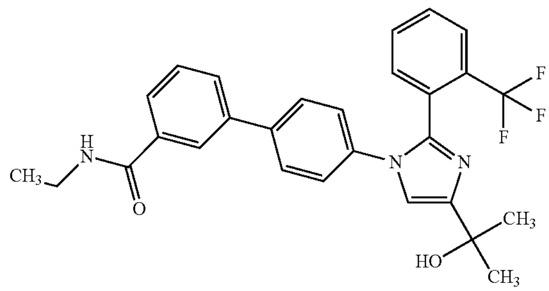 [SMILES: CCNC(=O)c1cccc(-c2ccc(-n3cc(C(C)(C)O)nc3-c3ccccc3C(F)(F)F)cc2)c1] | N-ethyl-4'-{4-(1-hydroxy-1-methylethyl)-2-[2-(trifluoromethyl)phenyl]-1H-imidazol-1-yl}biphenyl-3-carboxamide; |
| 286 | 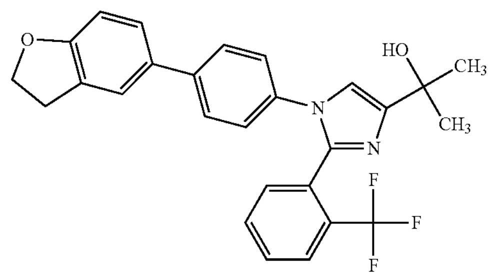 [SMILES: CC(C)(O)c1cn(-c2ccc(-c3ccc4c(c3)CCO4)cc2)c(-c2ccccc2C(F)(F)F)n1] | 2-{1-[4-(2,3-dihydro-1-benzofuran-5-yl)phenyl]-2-[2-(trifluoromethyl)phenyl]-1H-imidazol-4-yl}propan-2-ol; |
| 287 | 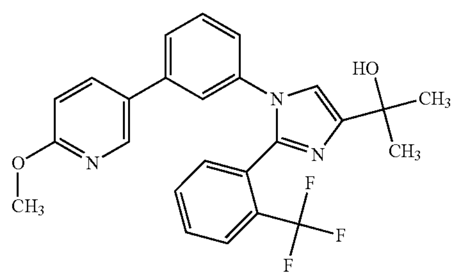 [SMILES: COc1ccc(-c2cccc(-n3cc(C(C)(C)O)nc3-c3ccccc3C(F)(F)F)c2)cn1] | 2-(1-{3-[6-(methyloxy)pyridin-3-yl]phenyl}-2-[2-(trifluoromethyl)phenyl]-1H-imidazol-4-yl)propan-2-ol; |
| 288 | 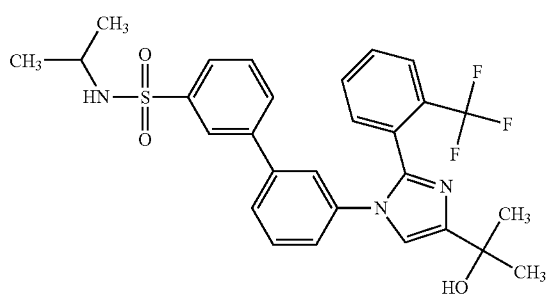 [SMILES: CC(C)NS(=O)(=O)c1cccc(-c2cccc(-n3cc(C(C)(C)O)nc3-c3ccccc3C(F)(F)F)c2)c1] | 3'-{4-(1-hydroxy-1-methylethyl)-2-[2-(trifluoromethyl)phenyl]-1H-imidazol-1-yl}-N-(1-methylethyl)biphenyl-3-sulfonamide; |
| 289 | 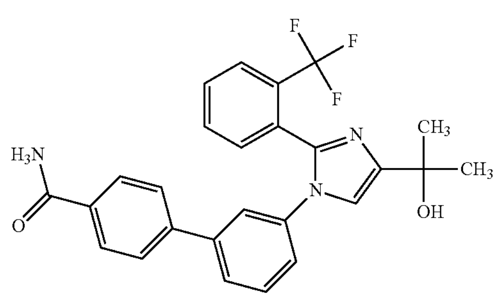 [SMILES: CC(C)(O)c1cn(-c2cccc(-c3ccc(C(N)=O)cc3)c2)c(-c2ccccc2C(F)(F)F)n1] | 3'-{4-(1-hydroxy-1-methylethyl)-2-[2-(trifluoromethyl)phenyl]-1H-imidazol-1-yl}biphenyl-4-carboxamide; |

-continued

| Cpd # | Structure | Name |
|---|---|---|
| 290 | 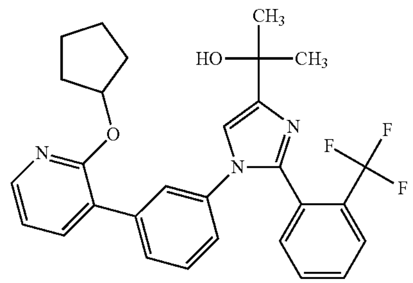 [SMILES: CC(C)(O)c1cn(-c2cccc(-c3cccnc3OC3CCCC3)c2)c(-c2ccccc2C(F)(F)F)n1] | 2-(1-{3-[2-(cyclopentyloxy)pyridin-3-yl]phenyl}-2-[2-(trifluoromethyl)phenyl]-1H-imidazol-4-yl)propan-2-ol; |
| 291 | 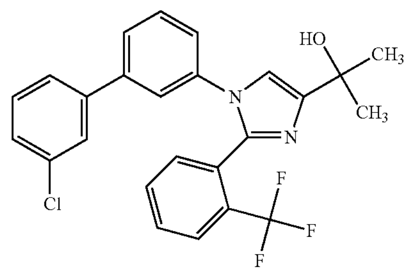 [SMILES: CC(C)(O)c1cn(-c2cccc(-c3cccc(Cl)c3)c2)c(-c2ccccc2C(F)(F)F)n1] | 2-{1-(3'-chlorobiphenyl-3-yl)-2-[2-(trifluoromethyl)phenyl]-1H-imidazol-4-yl}propan-2-ol; |
| 292 | 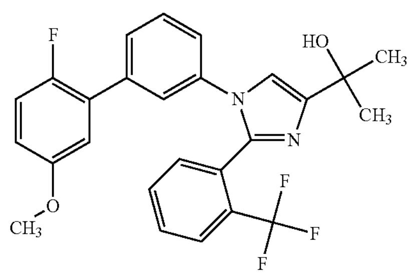 [SMILES: COc1ccc(F)c(-c2cccc(-n3cc(C(C)(C)O)nc3-c3ccccc3C(F)(F)F)c2)c1] | 2-{1-[2'-fluoro-5'-(methyloxy)biphenyl-3-yl]-2-[2-(trifluoromethyl)phenyl]-1H-imidazol-4-yl}propan-2-ol; |
| 293 | 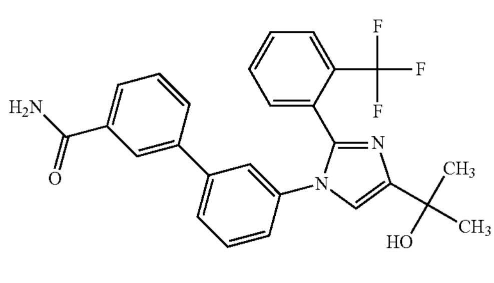 [SMILES: CC(C)(O)c1cn(-c2cccc(-c3cccc(C(N)=O)c3)c2)c(-c2ccccc2C(F)(F)F)n1] | 3'-{4-(1-hydroxy-1-methylethyl)-2-[2-(trifluoromethyl)phenyl]-1H-imidazol-1-yl}biphenyl-3-carboxamide; |
| 294 | 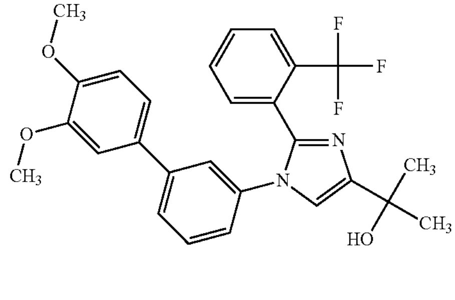 [SMILES: COc1ccc(-c2cccc(-n3cc(C(C)(C)O)nc3-c3ccccc3C(F)(F)F)c2)cc1OC] | 2-{1-[3',4'-bis(methyloxy)biphenyl-3-yl]-2-[2-(trifluoromethyl)phenyl]-1H-imidazol-4-yl}propan-2-ol; |

-continued

| Cpd # | Structure | Name |
|---|---|---|
| 295 | 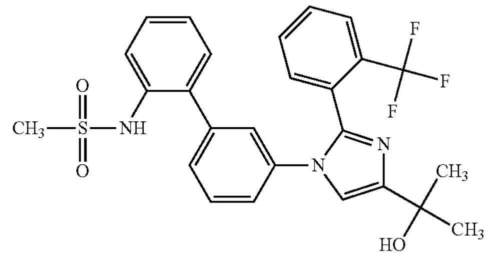 [SMILES: CC(C)(O)c1cn(-c2cccc(-c3ccccc3NS(C)(=O)=O)c2)c(-c2ccccc2C(F)(F)F)n1] | N-(3'-{4-(1-hydroxy-1-methylethyl)-2-[2-(trifluoromethyl)phenyl]-1H-imidazol-1-yl}biphenyl-2-yl)methanesulfonamide; |
| 296 | 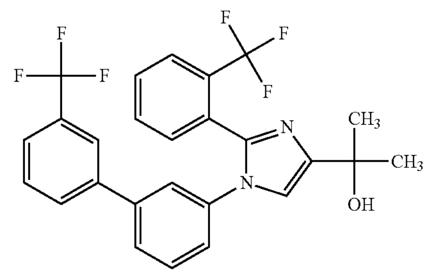 [SMILES: CC(C)(O)c1cn(-c2cccc(-c3cccc(C(F)(F)F)c3)c2)c(-c2ccccc2C(F)(F)F)n1] | 2-{1-[3'-(trifluoromethyl)biphenyl-3-yl]-2-[2-(trifluoromethyl)phenyl]-1H-imidazol-4-yl}propan-2-ol; |
| 297 | 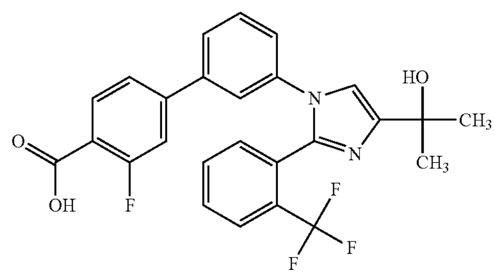 [SMILES: CC(C)(O)c1cn(-c2cccc(-c3ccc(C(=O)O)c(F)c3)c2)c(-c2ccccc2C(F)(F)F)n1] | 3-fluoro-3'-{4-(1-hydroxy-1-methylethyl)-2-[2-(trifluoromethyl)phenyl]-1H-imidazol-1-yl}biphenyl-4-carboxylic acid; |
| 298 | 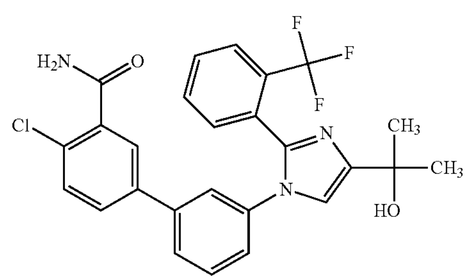 [SMILES: CC(C)(O)c1cn(-c2cccc(-c3ccc(Cl)c(C(N)=O)c3)c2)c(-c2ccccc2C(F)(F)F)n1] | 4-chloro-3'-{4-(1-hydroxy-1-methylethyl)-2-[2-(trifluoromethyl)phenyl]-1H-imidazol-1-yl}biphenyl-3-carboxamide; |
| 299 | 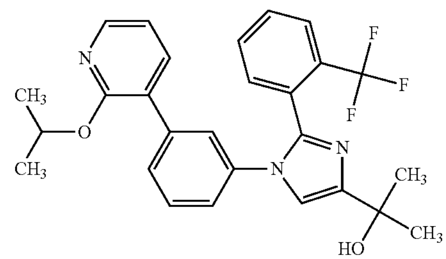 [SMILES: CC(C)Oc1ncccc1-c1cccc(-n2cc(C(C)(C)O)nc2-c2ccccc2C(F)(F)F)c1] | 2-{1-(3-{2-[(1-methylethyl)oxy]pyridin-3-yl}phenyl)-2-[2-(trifluoromethyl)phenyl]-1H-imidazol-4-yl}propan-2-ol; |

-continued

| Cpd # | Structure | Name |
|---|---|---|
| 300 | 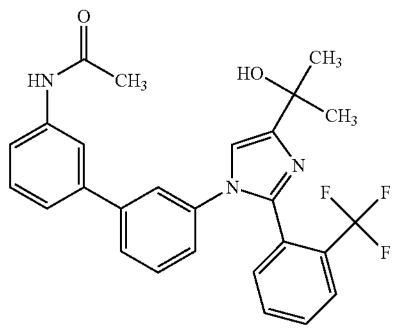 [SMILES: CC(=O)Nc1cccc(-c2cccc(-n3cc(C(C)(C)O)nc3-c3ccccc3C(F)(F)F)c2)c1] | N-(3'-{4-(1-hydroxy-1-methylethyl)-2-[2-(trifluoromethyl)phenyl]-1H-imidazol-1-yl}biphenyl-3-yl)acetamide; |
| 301 | 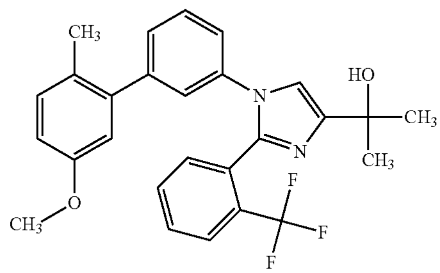 [SMILES: COc1ccc(C)c(-c2cccc(-n3cc(C(C)(C)O)nc3-c3ccccc3C(F)(F)F)c2)c1] | 2-{1-[2'-methyl-5'-(methyloxy)biphenyl-3-yl]-2-[2-(trifluoromethyl)phenyl]-1H-imidazol-4-yl}propan-2-ol; |
| 302 | 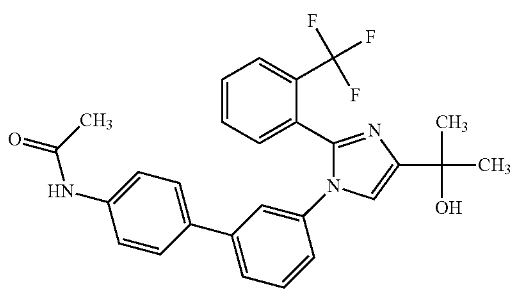 [SMILES: CC(=O)Nc1ccc(-c2cccc(-n3cc(C(C)(C)O)nc3-c3ccccc3C(F)(F)F)c2)cc1] | N-(3'-{4-(1-hydroxy-1-methylethyl)-2-[2-(trifluoromethyl)phenyl]-1H-imidazol-1-yl}biphenyl-4-yl)acetamide; |
| 303 | 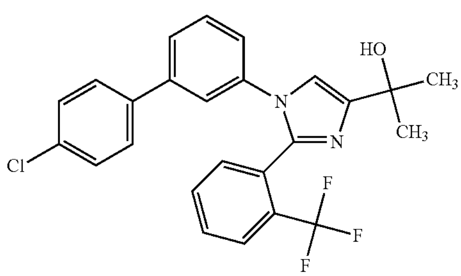 [SMILES: CC(C)(O)c1cn(-c2cccc(-c3ccc(Cl)cc3)c2)c(-c2ccccc2C(F)(F)F)n1] | 2-{1-(4'-chlorobiphenyl-3-yl)-2-[2-(trifluoromethyl)phenyl]-1H-imidazol-4-yl}propan-2-ol; |
| 304 | 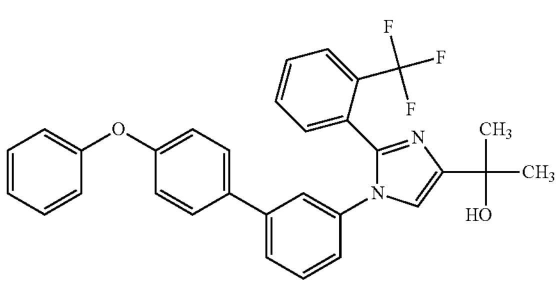 [SMILES: CC(C)(O)c1cn(-c2cccc(-c3ccc(Oc4ccccc4)cc3)c2)c(-c2ccccc2C(F)(F)F)n1] | 2-{1-[4'-(phenyloxy)biphenyl-3-yl]-2-[2-(trifluoromethyl)phenyl]-1H-imidazol-4-yl}propan-2-ol; |

-continued

| Cpd # | Structure | Name |
|---|---|---|
| 305 | 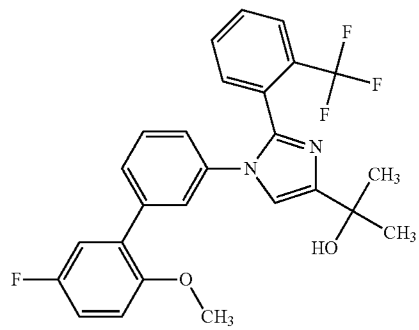 | 2-{1-[5'-fluoro-2'-(methyloxy)biphenyl-3-yl]-2-[2-(trifluoromethyl)phenyl]-1H-imidazol-4-yl}propan-2-ol; |
| 306 | 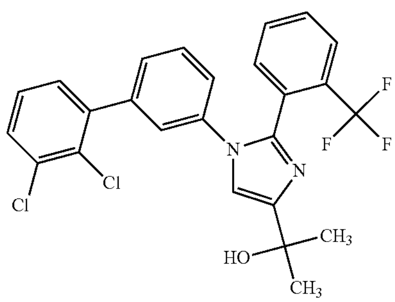 [SMILES: CC(C)(O)c1cn(-c2cccc(-c3cccc(Cl)c3Cl)c2)c(-c2ccccc2C(F)(F)F)n1] | 2-{1-(2',3'-dichlorobiphenyl-3-yl)-2-[2-(trifluoromethyl)phenyl]-1H-imidazol-4-yl}propan-2-ol; |
| 307 | 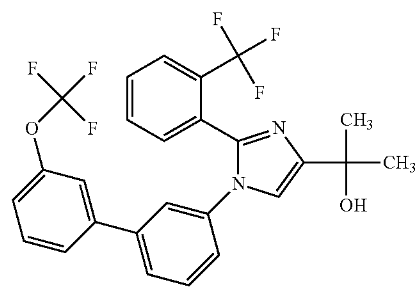 [SMILES: CC(C)(O)c1cn(-c2cccc(-c3cccc(OC(F)(F)F)c3)c2)c(-c2ccccc2C(F)(F)F)n1] | 2-(1-{3'-[(trifluoromethyl)oxy]biphenyl-3-yl}-2-[2-(trifluoromethyl)phenyl]-1H-imidazol-4-yl)propan-2-ol; |
| 308 | 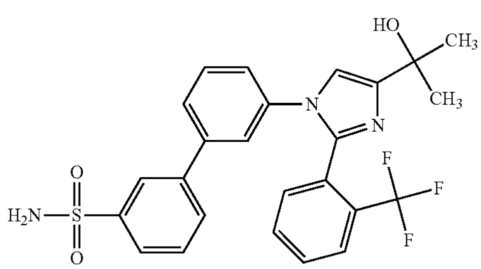 [SMILES: CC(C)(O)c1cn(-c2cccc(-c3cccc(S(N)(=O)=O)c3)c2)c(-c2ccccc2C(F)(F)F)n1] | 3'-{4-(1-hydroxy-1-methylethyl)-2-[2-(trifluoromethyl)phenyl]-1H-imidazol-1-yl}biphenyl-3-sulfonamide; |
| 309 | 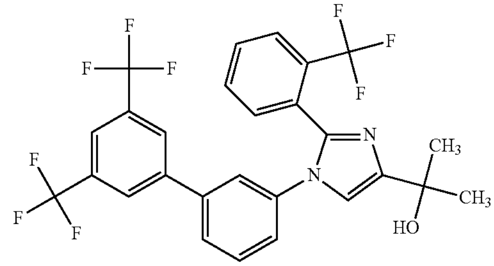 [SMILES: CC(C)(O)c1cn(-c2cccc(-c3cc(C(F)(F)F)cc(C(F)(F)F)c3)c2)c(-c2ccccc2C(F)(F)F)n1] | 2-{1-[3',5'-bis(trifluoromethyl)biphenyl-3-yl]-2-[2-(trifluoromethyl)phenyl]-1H-imidazol-4-yl}propan-2-ol; |

| Cpd # | Structure | Name |
|---|---|---|
| 310 | 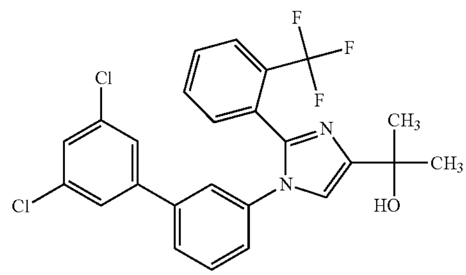 [SMILES: CC(C)(O)c1cn(-c2cccc(-c3cc(Cl)cc(Cl)c3)c2)c(-c2ccccc2C(F)(F)F)n1] | 2-{1-(3',5'-dichlorobiphenyl-3-yl)-2-[2-(trifluoromethyl)phenyl]-1H-imidazol-4-yl}propan-2-ol; |
| 311 | 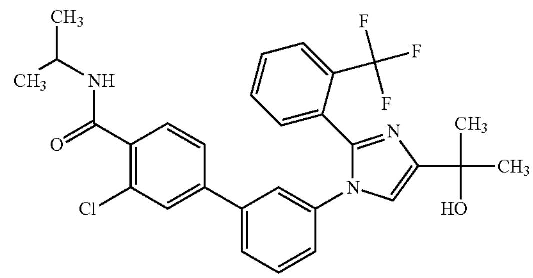 [SMILES: CC(C)NC(=O)c1ccc(-c2cccc(-n3cc(C(C)(C)O)nc3-c3ccccc3C(F)(F)F)c2)cc1Cl] | 3-chloro-3'-{4-(1-hydroxy-1-methylethyl)-2-[2-(trifluoromethyl)phenyl]-1H-imidazol-1-yl}-N-(1-methylethyl)biphenyl-4-carboxamide; |
| 312 | 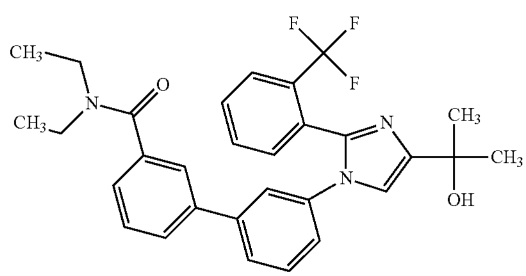 [SMILES: CCN(CC)C(=O)c1cccc(-c2cccc(-n3cc(C(C)(C)O)nc3-c3ccccc3C(F)(F)F)c2)c1] | N,N-diethyl-3'-{4-(1-hydroxy-1-methylethyl)-2-[2-(trifluoromethyl)phenyl]-1H-imidazol-1-yl}biphenyl-3-carboxamide; |
| 313 | 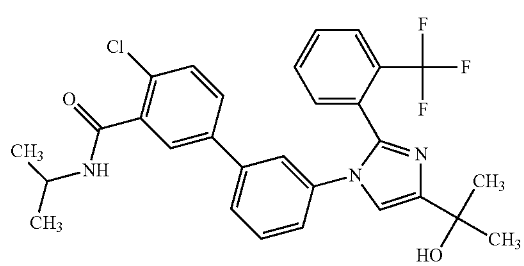 [SMILES: CC(C)NC(=O)c1cc(-c2cccc(-n3cc(C(C)(C)O)nc3-c3ccccc3C(F)(F)F)c2)ccc1Cl] | 4-chloro-3'-{4-(1-hydroxy-1-methylethyl)-2-[2-(trifluoromethyl)phenyl]-1H-imidazol-1-yl}-N-(1-methylethyl)biphenyl-3-carboxamide; |
| 314 | 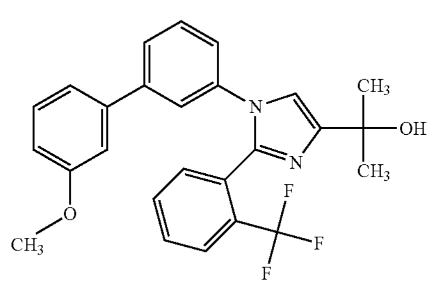 [SMILES: COc1cccc(-c2cccc(-n3cc(C(C)(C)O)nc3-c3ccccc3C(F)(F)F)c2)c1] | 2-{1-[3'-(methyloxy)biphenyl-3-yl]-2-[2-(trifluoromethyl)phenyl]-1H-imidazol-4-yl}propan-2-ol; |

| Cpd # | Structure | Name |
|---|---|---|
| 315 | 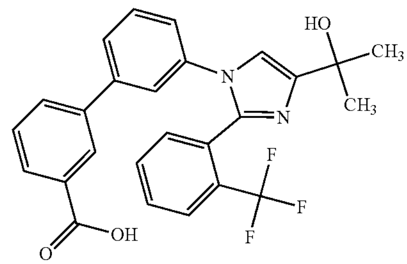 [SMILES: CC(C)(O)c1cn(-c2cccc(-c3cccc(C(=O)O)c3)c2)c(-c2ccccc2C(F)(F)F)n1] | 3'-{4-(1-hydroxy-1-methylethyl)-2-[2-(trifluoromethyl)phenyl]-1H-imidazol-1-yl}biphenyl-3-carboxylic acid; |
| 316 | 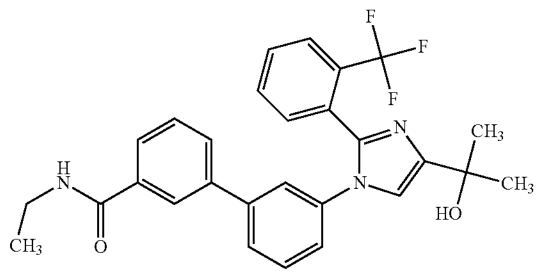 [SMILES: CCNC(=O)c1cccc(-c2cccc(-n3cc(C(C)(C)O)nc3-c3ccccc3C(F)(F)F)c2)c1] | N-ethyl-3'-{4-(1-hydroxy-1-methylethyl)-2-[2-(trifluoromethyl)phenyl]-1H-imidazol-1-yl}biphenyl-3-carboxamide; |
| 317 | 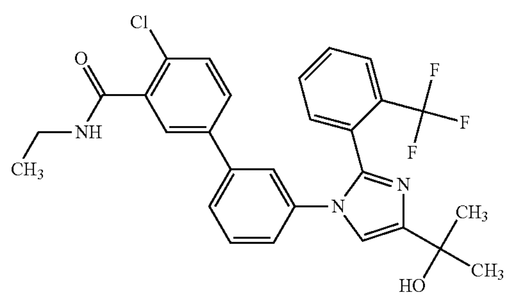 [SMILES: CCNC(=O)c1cc(-c2cccc(-n3cc(C(C)(C)O)nc3-c3ccccc3C(F)(F)F)c2)ccc1Cl] | 4-chloro-N-ethyl-3'-{4-(1-hydroxy-1-methylethyl)-2-[2-(trifluoromethyl)phenyl]-1H-imidazol-1-yl}biphenyl-3-carboxamide; |
| 318 | 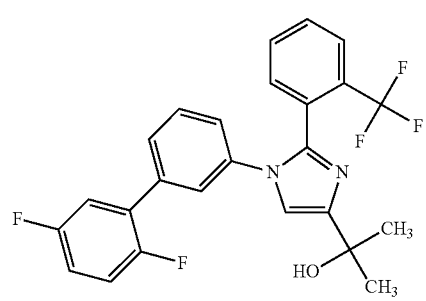 [SMILES: CC(C)(O)c1cn(-c2cccc(-c3cc(F)ccc3F)c2)c(-c2ccccc2C(F)(F)F)n1] | 2-{1-(2',5'-difluorobiphenyl-3-yl)-2-[2-(trifluoromethyl)phenyl]-1H-imidazol-4-yl}propan-2-ol; |
| 319 | 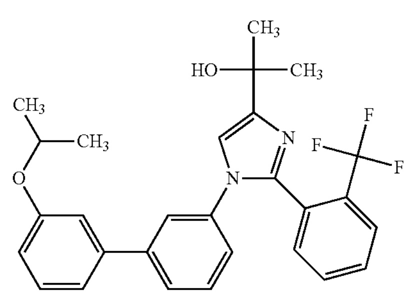 [SMILES: CC(C)Oc1cccc(-c2cccc(-n3cc(C(C)(C)O)nc3-c3ccccc3C(F)(F)F)c2)c1] | 2-(1-{3'-[(1-methylethyl)oxy]biphenyl-3-yl}-2-[2-(trifluoromethyl)phenyl]-1H-imidazol-4-yl)propan-2-ol; |

| Cpd # | Structure | Name |
|---|---|---|
| 320 | 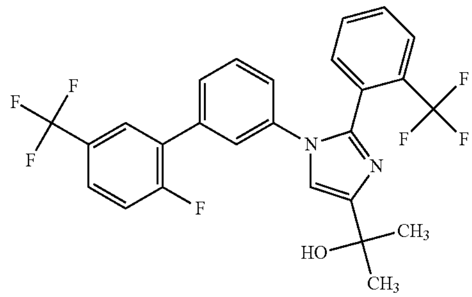 [SMILES: CC(C)(O)c1cn(-c2cccc(-c3cc(C(F)(F)F)ccc3F)c2)c(-c2ccccc2C(F)(F)F)n1] | 2-{1-[2'-fluoro-5'-(trifluoromethyl)biphenyl-3-yl]-2-[2-(trifluoromethyl)phenyl]-1H-imidazol-4-yl}propan-2-ol; |
| 321 | 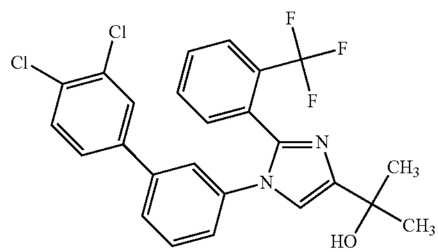 [SMILES: CC(C)(O)c1cn(-c2cccc(-c3ccc(Cl)c(Cl)c3)c2)c(-c2ccccc2C(F)(F)F)n1] | 2-{1-(3',4'-dichlorobiphenyl-3-yl)-2-[2-(trifluoromethyl)phenyl]-1H-imidazol-4-yl}propan-2-ol; |
| 322 | 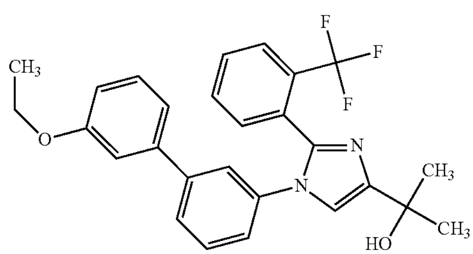 [SMILES: CCOc1cccc(-c2cccc(-n3cc(C(C)(C)O)nc3-c3ccccc3C(F)(F)F)c2)c1] | 2-{1-[3'-(ethyloxy)biphenyl-3-yl]-2-[2-(trifluoromethyl)phenyl]-1H-imidazol-4-yl}propan-2-ol; |
| 323 | 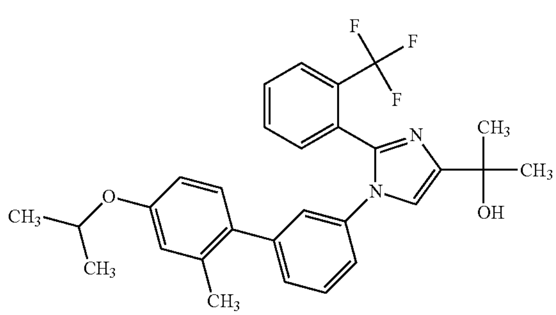 [SMILES: Cc1cc(OC(C)C)ccc1-c1cccc(-n2cc(C(C)(C)O)nc2-c2ccccc2C(F)(F)F)c1] | 2-(1-{2'-methyl-4'-[(1-methylethyl)oxy]biphenyl-3-yl}-2-[2-(trifluoromethyl)phenyl]-1H-imidazol-4-yl)propan-2-ol; |
| 324 | 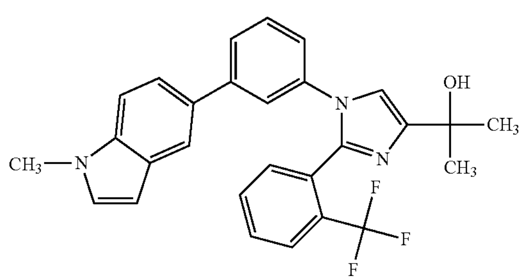 [SMILES: Cn1ccc2cc(-c3cccc(-n4cc(C(C)(C)O)nc4-c4ccccc4C(F)(F)F)c3)ccc21] | 2-{1-[3-(1-methyl-1H-indol-5-yl)phenyl]-2-[2-(trifluoromethyl)phenyl]-1H-imidazol-4-yl}propan-2-ol; |

| Cpd # | Structure | Name |
|---|---|---|
| 325 | 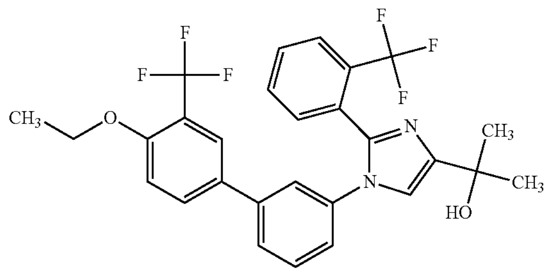 [SMILES: CCOc1ccc(-c2cccc(-n3cc(C(C)(C)O)nc3-c3ccccc3C(F)(F)F)c2)cc1C(F)(F)F] | 2-{1-[4'-(ethyloxy)-3'-(trifluoromethyl)biphenyl-3-yl]-2-[2-(trifluoromethyl)phenyl]-1H-imidazol-4-yl}propan-2-ol; |
| 326 | 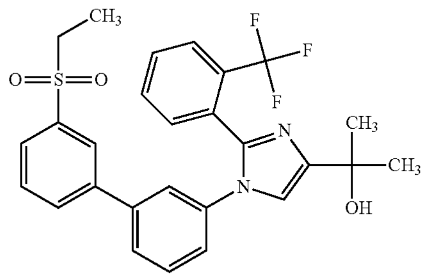 [SMILES: CCS(=O)(=O)c1cccc(-c2cccc(-n3cc(C(C)(C)O)nc3-c3ccccc3C(F)(F)F)c2)c1] | 2-{1-[3'-(ethylsulfonyl)biphenyl-3-yl]-2-[2-(trifluoromethyl)phenyl]-1H-imidazol-4-yl}propan-2-ol; |
| 327 | 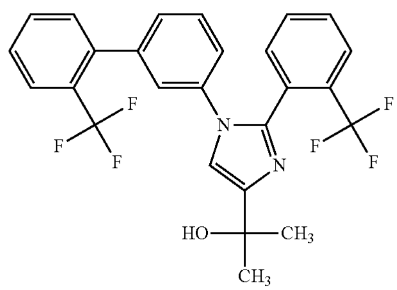 [SMILES: CC(C)(O)c1cn(-c2cccc(-c3ccccc3C(F)(F)F)c2)c(-c2ccccc2C(F)(F)F)n1] | 2-{1-[2'-(trifluoromethyl)biphenyl-3-yl]-2-[2-(trifluoromethyl)phenyl]-1H-imidazol-4-yl}propan-2-ol; |
| 328 | 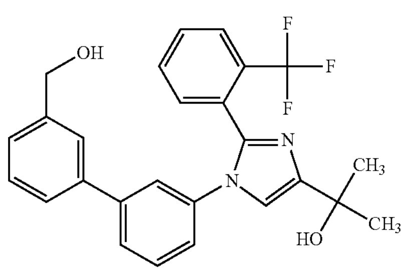 [SMILES: CC(C)(O)c1cn(-c2cccc(-c3cccc(CO)c3)c2)c(-c2ccccc2C(F)(F)F)n1] | 2-{1-[3'-(hydroxymethyl)biphenyl-3-yl]-2-[2-(trifluoromethyl)phenyl]-1H-imidazol-4-yl}propan-2-ol; |
| 329 | 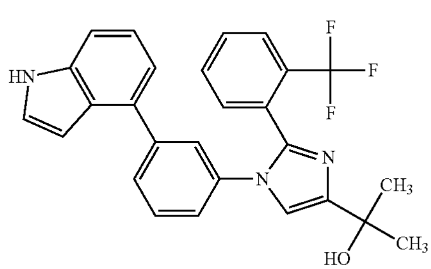 [SMILES: CC(C)(O)c1cn(-c2cccc(-c3cccc4[nH]ccc34)c2)c(-c2ccccc2C(F)(F)F)n1] | 2-{1-[3-(1H-indol-4-yl)phenyl]-2-[2-(trifluoromethyl)phenyl]-1H-imidazol-4-yl}propan-2-ol; |

| Cpd # | Structure | Name |
|---|---|---|
| 330 | 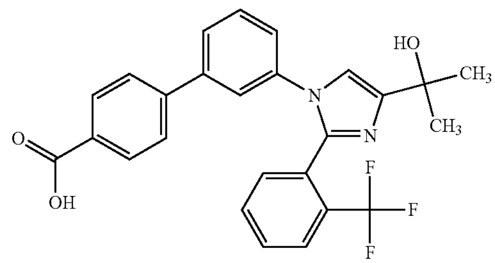 [SMILES: CC(C)(O)c1cn(-c2cccc(-c3ccc(C(=O)O)cc3)c2)c(-c2ccccc2C(F)(F)F)n1] | 3'-{4-(1-hydroxy-1-methylethyl)-2-[2-(trifluoromethyl)phenyl]-1H-imidazol-1-yl}biphenyl-4-carboxylic acid; |
| 331 | 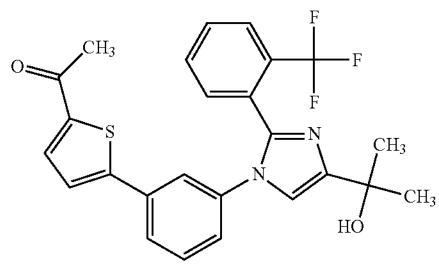 [SMILES: CC(=O)c1ccc(-c2cccc(-n3cc(C(C)(C)O)nc3-c3ccccc3C(F)(F)F)c2)s1] | 1-[5-(3-{4-(1-hydroxy-1-methylethyl)-2-[2-(trifluoromethyl)phenyl]-1H-imidazol-1-yl}phenyl)-2-thienyl]ethanone; |
| 332 | 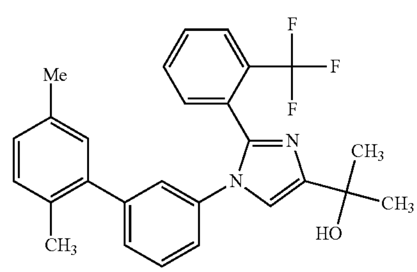 [SMILES: Cc1ccc(C)c(-c2cccc(-n3cc(C(C)(C)O)nc3-c3ccccc3C(F)(F)F)c2)c1] | 2-{1-(5'-chloro-2'-methylbiphenyl-3-yl)-2-[2-(trifluoromethyl)phenyl]-1H-imidazol-4-yl}propan-2-ol; |
| 333 | 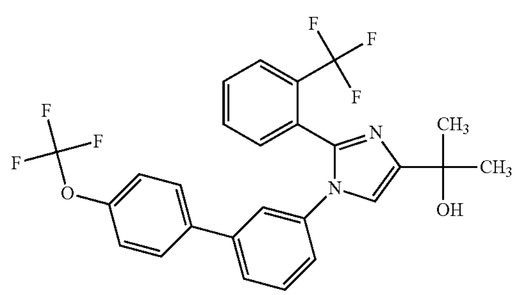 [SMILES: CC(C)(O)c1cn(-c2cccc(-c3ccc(OC(F)(F)F)cc3)c2)c(-c2ccccc2C(F)(F)F)n1] | 2-(1-{4'-[(trifluoromethy)oxy]biphenyl-3-yl}-2-[2-(trifluoromethyl)phenyl]-1H-imidazol-4-yl)propan-2-ol; |
| 334 | 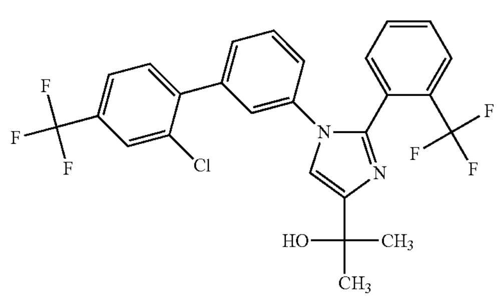 [SMILES: CC(C)(O)c1cn(-c2cccc(-c3ccc(C(F)(F)F)cc3Cl)c2)c(-c2ccccc2C(F)(F)F)n1] | 2-{1-[2'-chloro-4'-(trifluoromethyl)biphenyl-3-yl]-2-[2-(trifluoromethyl)phenyl]-1H-imidazol-4-yl}propan-2-ol; |

| Cpd # | Structure | Name |
|---|---|---|
| 335 | 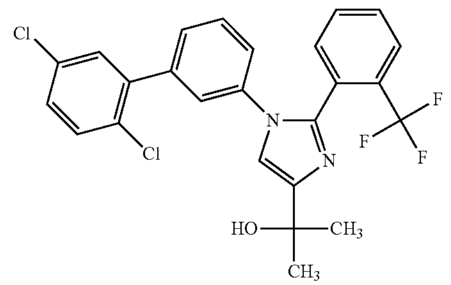 [SMILES: CC(C)(O)c1cn(-c2cccc(-c3cc(Cl)ccc3Cl)c2)c(-c2ccccc2C(F)(F)F)n1] | 2-{1-(2',5'-dichlorobiphenyl-3-yl)-2-[2-(trifluoromethyl)phenyl]-1H-imidazol-4-yl}propan-2-ol; |
| 336 | 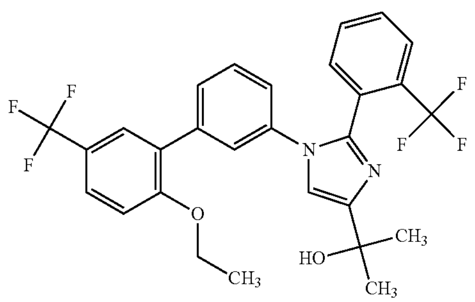 [SMILES: CCOc1ccc(C(F)(F)F)cc1-c1cccc(-n2cc(C(C)(C)O)nc2-c2ccccc2C(F)(F)F)c1] | 2-{1-[2'-(ethyloxy)-5'-(trifluoromethyl)biphenyl-3-yl]-2-[2-(trifluoromethyl)phenyl]-1H-imidazol-4-yl}propan-2-ol; |
| 337 | 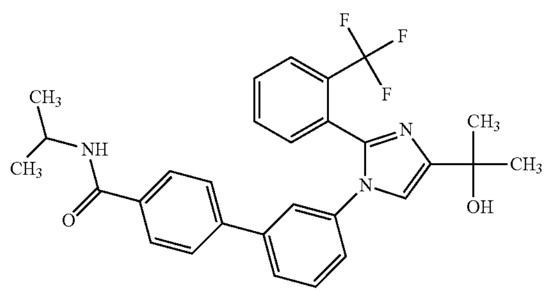 [SMILES: CC(C)NC(=O)c1ccc(-c2cccc(-n3cc(C(C)(C)O)nc3-c3ccccc3C(F)(F)F)c2)cc1] | 3'-{4-(1-hydroxy-1-methylethyl)-2-[2-(trifluoromethyl)phenyl]-1H-imidazol-1-yl}-N-(1-methylethyl)biphenyl-4-carboxamide; |
| 338 | 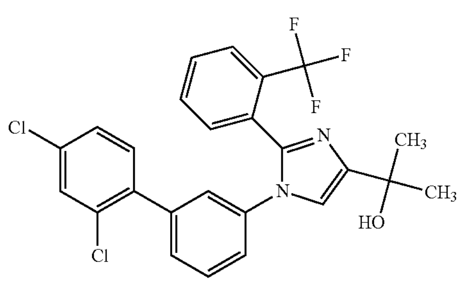 [SMILES: CC(C)(O)c1cn(-c2cccc(-c3ccc(Cl)cc3Cl)c2)c(-c2ccccc2C(F)(F)F)n1] | 2-{1-(2',4'-dichlorobiphenyl-3-yl)-2-[2-(trifluoromethyl)phenyl]-1H-imidazol-4-yl}propan-2-ol; |
| 339 | 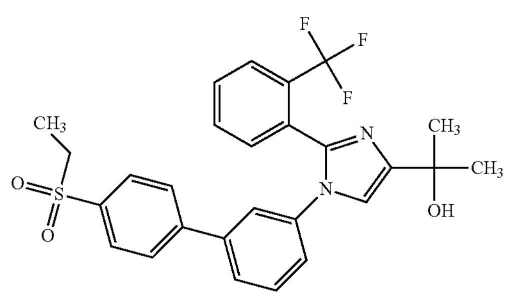 [SMILES: CCS(=O)(=O)c1ccc(-c2cccc(-n3cc(C(C)(C)O)nc3-c3ccccc3C(F)(F)F)c2)cc1] | 2-{1-[4-(ethylsulfonyl)biphenyl-3-yl]-2-[2-(trifluoromethyl)phenyl]-1H-imidazol-4-yl}propan-2-ol; |

-continued

| Cpd # | Structure | Name |
|---|---|---|
| 340 | 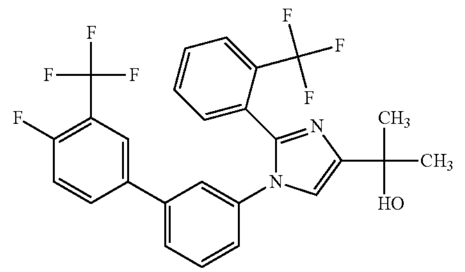 [SMILES: CC(C)(O)c1cn(-c2cccc(-c3ccc(F)c(C(F)(F)F)c3)c2)c(-c2ccccc2C(F)(F)F)n1] | 2-{1-[4'-fluoro-3'-(trifluoromethyl)biphenyl-3-yl]-2-[2-(trifluoromethyl)phenyl]-1H-imidazol-4-yl}propan-2-ol; |
| 341 | 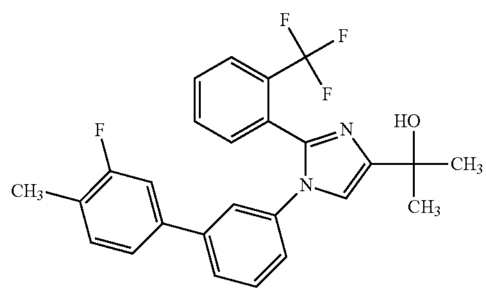 [SMILES: Cc1ccc(-c2cccc(-n3cc(C(C)(C)O)nc3-c3ccccc3C(F)(F)F)c2)cc1F] | 2-{1-(3'-fluoro-4'-methylbiphenyl-3-yl)-2-[2-(trifluoromethyl)phenyl]-1H-imidazol-4-yl}propan-2-ol; |
| 342 | 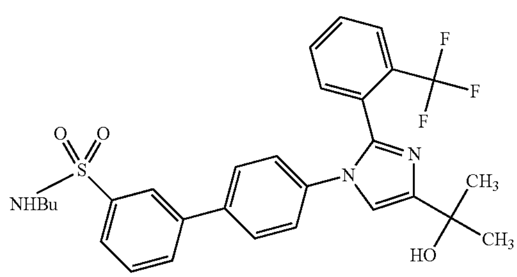 | N-butyl-4'-{4-(1-hydroxy-1-methylethyl)-2-[2-(trifluoromethyl)phenyl]-1H-imidazol-1-yl}biphenyl-3-sulfonamide; |
| 343 | 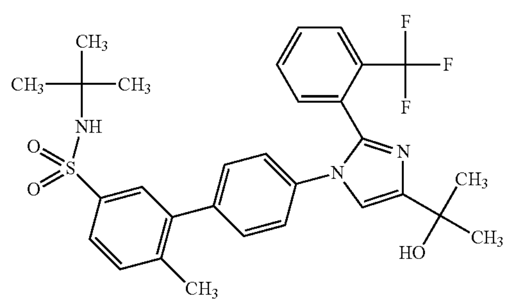 [SMILES: Cc1ccc(S(=O)(=O)NC(C)(C)C)cc1-c1ccc(-n2cc(C(C)(C)O)nc2-c2ccccc2C(F)(F)F)cc1] | N-(1,1-dimethylethyl)-4'-{4-(1-hydroxy-1-methylethyl)-2-[2-(trifluoromethyl)phenyl]-1H-imidazol-1-yl}-6-methylbiphenyl-3-sulfonamide; |
| 344 | 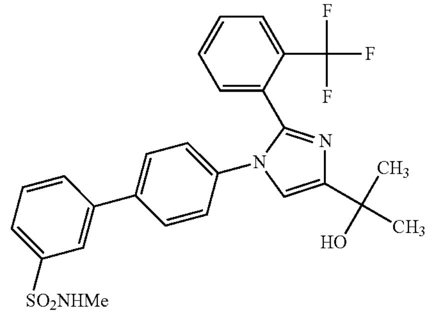 | 4'-{4-(1-hydroxy-1-methylethyl)-2-[2-(trifluoromethyl)phenyl]-1H-imidazol-1-yl}-N-methylbiphenyl-3-sulfonamide; |

-continued

| Cpd # | Structure | Name |
|---|---|---|
| 345 | 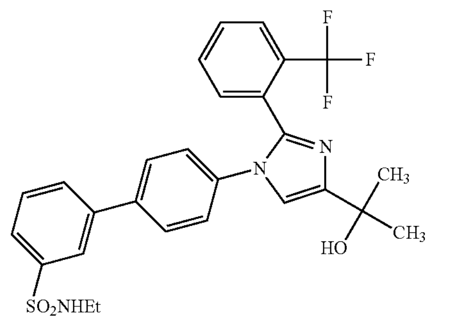 | N-ethyl-4'-{4-(1-hydroxy-1-methylethyl)-2-[2-(trifluoromethyl)phenyl]-1H-imidazol-1-yl}biphenyl-3-sulfonamide; |
| 346 | 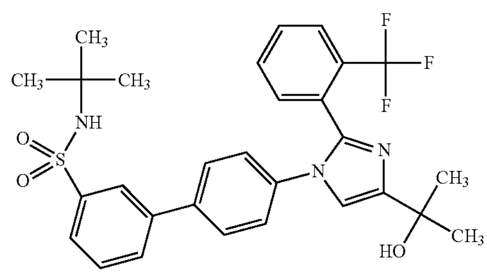 [SMILES: CC(C)(C)NS(=O)(=O)c1cccc(-c2ccc(-n3cc(C(C)(C)O)nc3-c3ccccc3C(F)(F)F)cc2)c1] | N-(1,1-dimethylethyl)-4'-{4-(1-hydroxy-1-methylethyl)-2-[2-(trifluoromethyl)phenyl]-1H-imidazol-1-yl}biphenyl-3-sulfonamide; |
| 347 | 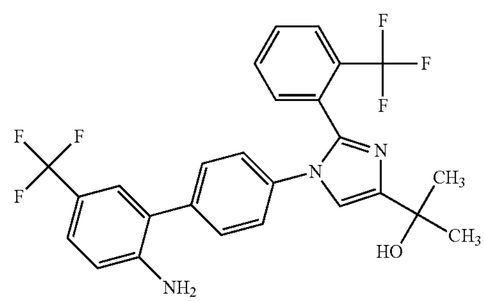 [SMILES: CC(C)(O)c1cn(-c2ccc(-c3cc(C(F)(F)F)ccc3N)cc2)c(-c2ccccc2C(F)(F)F)n1] | 2-{1-[2'-amino-5'-(trifluoromethyl)biphenyl-4-yl]-2-[2-(trifluoromethyl)phenyl]-1H-imidazol-4-yl}propan-2-ol; |
| 348 | 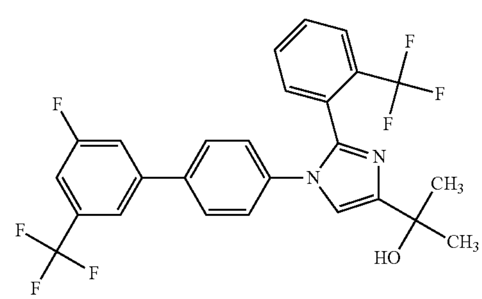 [SMILES: CC(C)(O)c1cn(-c2ccc(-c3cc(F)cc(C(F)(F)F)c3)cc2)c(-c2ccccc2C(F)(F)F)n1] | 2-{1-[3'-fluoro-5'-(trifluoromethyl)biphenyl-4-yl]-2-[2-(trifluoromethyl)phenyl]-1H-imidazol-4-yl}propan-2-ol; |
| 349 | 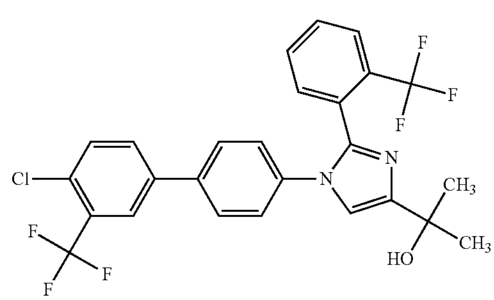 [SMILES: CC(C)(O)c1cn(-c2ccc(-c3ccc(Cl)c(C(F)(F)F)c3)cc2)c(-c2ccccc2C(F)(F)F)n1] | 2-{1-[4'-chloro-3'-(trifluoromethyl)biphenyl-4-yl]-2-[2-(trifluoromethyl)phenyl]-1H-imidazol-4-yl}propan-2-ol; |

-continued

| Cpd # | Structure | Name |
|---|---|---|
| 350 | 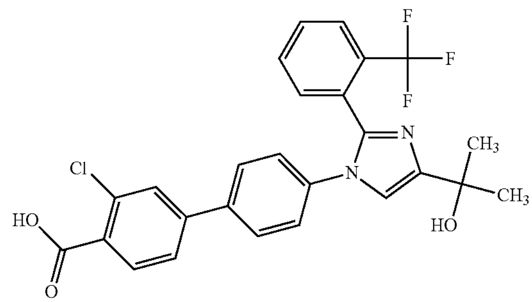 [SMILES: CC(C)(O)c1cn(-c2ccc(-c3ccc(C(=O)O)c(Cl)c3)cc2)c(-c2ccccc2C(F)(F)F)n1] | 3-chloro-4'-{4-(1-hydroxy-1-methylethyl)-2-[2-(trifluoromethyl)phenyl]-1H-imidazol-1-yl}biphenyl-4-carboxylic acid; |
| 351 | 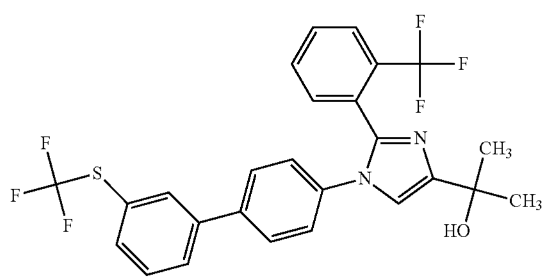 [SMILES: CC(C)(O)c1cn(-c2ccc(-c3cccc(SC(F)(F)F)c3)cc2)c(-c2ccccc2C(F)(F)F)n1] | 2-(2-[2-(trifluoromethyl)phenyl]-1-{3'-[(trifluoromethyl)thio]biphenyl-4-yl}-1H-imidazol-4-yl)propan-2-ol; |
| 352 | 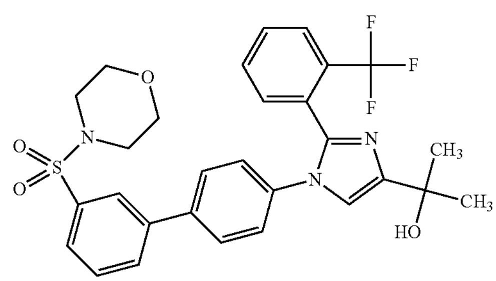 [SMILES: CC(C)(O)c1cn(-c2ccc(-c3cccc(S(=O)(=O)N4CCOCC4)c3)cc2)c(-c2ccccc2C(F)(F)F)n1] | 2-{1-[3'-(morpholin-4-ylsulfonyl)biphenyl-4-yl]-2-[2-(trifluoromethyl)phenyl]-1H-imidazol-4-yl}propan-2-ol; |
| 353 | 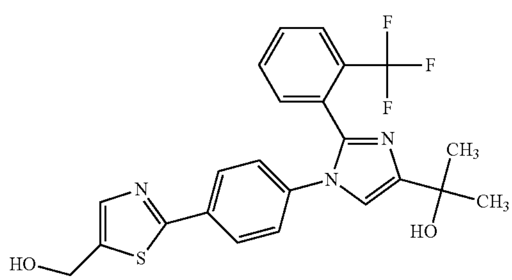 [SMILES: CC(C)(O)c1cn(-c2ccc(-c3ncc(CO)s3)cc2)c(-c2ccccc2C(F)(F)F)n1] | 2-(1-{4-[5-(hydroxymethyl)-1,3-thiazol-2-yl]phenyl}-2-[2-(trifluoromethyl)phenyl]-1H-imidazol-4-yl)propan-2-ol; |
| 354 | 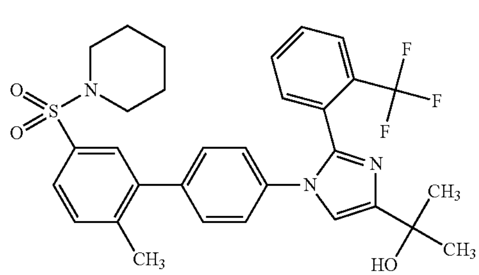 [SMILES: Cc1ccc(S(=O)(=O)N2CCCCC2)cc1-c1ccc(-n2cc(C(C)(C)O)nc2-c2ccccc2C(F)(F)F)cc1] | 2-{1-[2'-methyl-5'-(piperidin-1-ylsulfonyl)biphenyl-4-yl]-2-[2-(trifluoromethyl)phenyl]-1H-imidazol-4-yl}propan-2-ol; |

-continued

| Cpd # | Structure | Name |
|---|---|---|
| 355 | 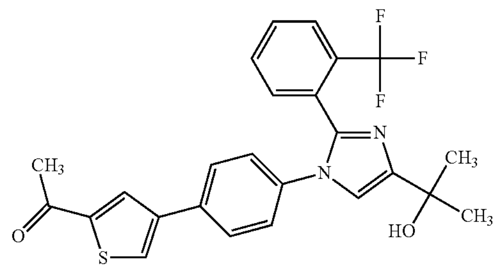 [SMILES: CC(=O)c1cc(-c2ccc(-n3cc(C(C)(C)O)nc3-c3ccccc3C(F)(F)F)cc2)cs1] | 1-[4-(4-{4-(1-hydroxy-1-methylethyl)-2-[2-(trifluoromethyl)phenyl]-1H-imidazol-1 yl}phenyl)-2-thienyl]ethanone; |
| 356 | 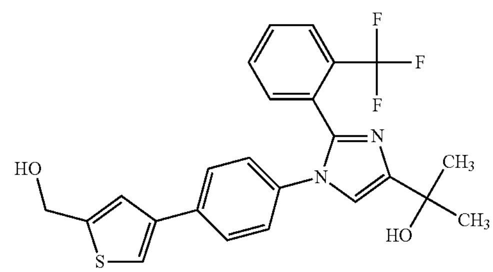 [SMILES: CC(C)(O)c1cn(-c2ccc(-c3csc(CO)c3)cc2)c(-c2ccccc2C(F)(F)F)n1] | 2-(1-{4-[5-(hydroxymethyl)-3-thienyl]phenyl}-2-[2-(trifluoromethyl)phenyl]-1H-imidazol-4-yl)propan-2-ol; |
| 357 | 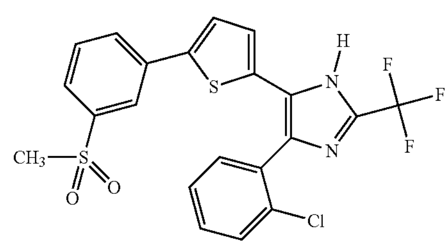 [SMILES: CS(=O)(=O)c1cccc(-c2ccc(-c3[nH]c(C(F)(F)F)nc3-c3ccccc3Cl)s2)c1] | 4-(2-chlorophenyl)-5-{5-[3-(methylsulfonyl)phenyl]-2-thienyl}-2-(trifluoromethyl)-1H-imidazole; |
| 358 | 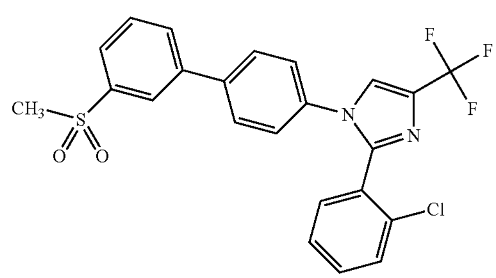 [SMILES: CS(=O)(=O)c1cccc(-c2ccc(-n3cc(C(F)(F)F)nc3-c3ccccc3Cl)cc2)c1] | 2-(2-chlorophenyl)-1-[3'-(methylsulfonyl)biphenyl-4-yl]-4-(trifluoromethyl)-1H-imidazole; |
| 359 | 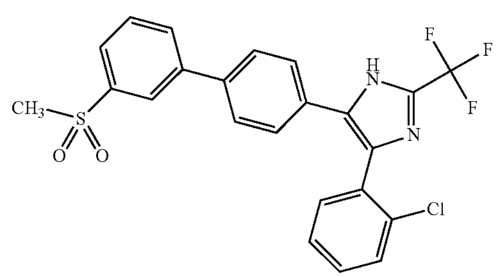 [SMILES: CS(=O)(=O)c1cccc(-c2ccc(-c3[nH]c(C(F)(F)F)nc3-c3ccccc3Cl)cc2)c1] | 4-(2-chlorophenyl)-5-[3'-(methylsulfonyl)biphenyl-4-yl]-2-(trifluoromethyl)-1H-imidazole; |

-continued

| Cpd # | Structure | Name |
|---|---|---|
| 360 | 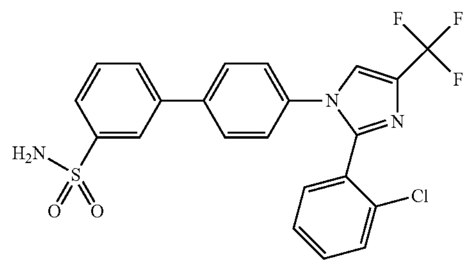 [SMILES: NS(=O)(=O)c1cccc(-c2ccc(-n3cc(C(F)(F)F)nc3-c3ccccc3Cl)cc2)c1] | 4'-[2-(2-chlorophenyl)-4-(trifluoromethyl)-1H-imidazol-1-yl]biphenyl-3-sulfonamide; |
| 361 | 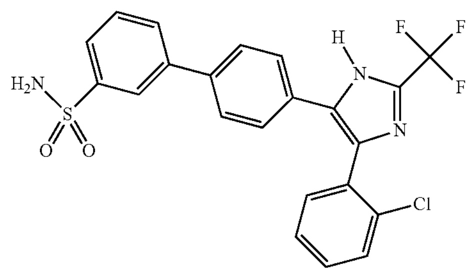 [SMILES: NS(=O)(=O)c1cccc(-c2ccc(-c3[nH]c(C(F)(F)F)nc3-c3ccccc3Cl)cc2)c1] | 4'-[4-(2-chlorophenyl)-2-(trifluoromethyl)-1H-imidazol-5-yl]biphenyl-3-sulfonamide; |
| 362 | 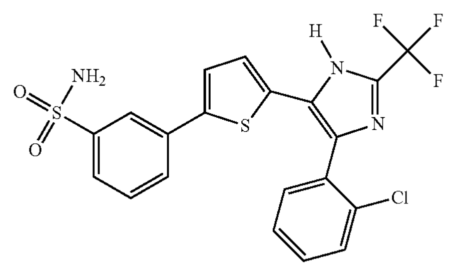 [SMILES: NS(=O)(=O)c1cccc(-c2ccc(-c3[nH]c(C(F)(F)F)nc3-c3ccccc3Cl)s2)c1] | 3-{5-[4-(2-chlorophenyl)-2-(trifluoromethyl)-1H-imidazol-5-yl]-2-thienyl}benzenesulfonamide; |
| 364 | 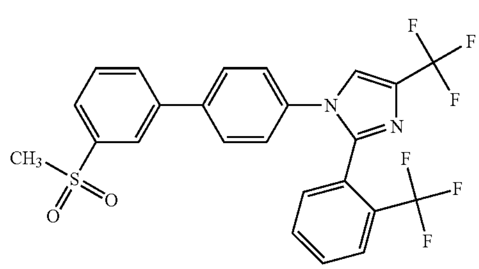 [SMILES: CS(=O)(=O)c1cccc(-c2ccc(-n3cc(C(F)(F)F)nc3-c3ccccc3C(F)(F)F)cc2)c1] | 1-[3'-(methylsulfonyl)biphenyl-4-yl]-4-(trifluoromethyl)-2-[2-(trifluoromethyl)phenyl]-1H-imidazole; |
| 365 | 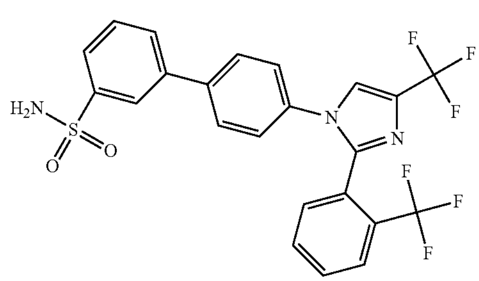 [SMILES: NS(=O)(=O)c1cccc(-c2ccc(-n3cc(C(F)(F)F)nc3-c3ccccc3C(F)(F)F)cc2)c1] | 4'-{4-(trifluoromethyl)-2-[2-(trifluoromethyl)phenyl]-1H-imidazol-1-yl}biphenyl-3-sulfonamide; |

-continued

| Cpd # | Structure | Name |
|---|---|---|
| 367 | 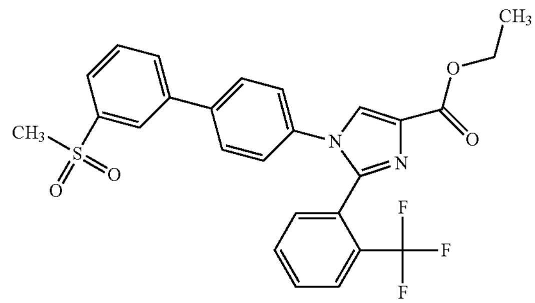 [SMILES: CCOC(=O)c1cn(-c2ccc(-c3cccc(S(C)(=O)=O)c3)cc2)c(-c2ccccc2C(F)(F)F)n1] | ethyl 1-[3'-(methylsulfonyl)biphenyl-4-yl]-2-[2-(trifluoromethyl)phenyl]-1H-imidazole-4-carboxylate; |
| 369 | 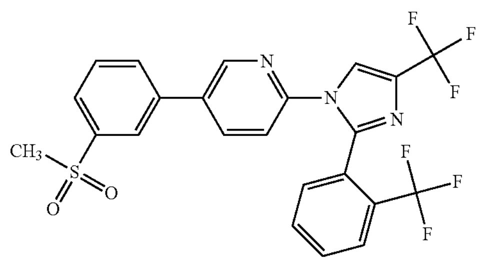 | 5-[3-(methylsulfonyl)phenyl]-2-{4-(trifluoromethyl)-2-[2-(trifluoromethyl)phenyl]-1H-imidazol-1-yl}pyridine; |
| 370 | 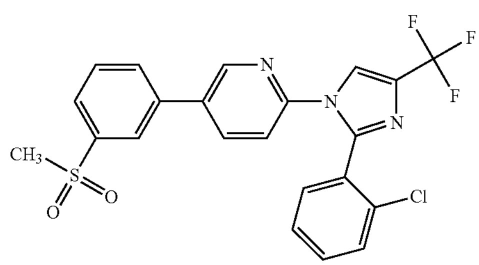 [SMILES: CS(=O)(=O)c1cccc(-c2ccc(-n3cc(C(F)(F)F)nc3-c3ccccc3Cl)nc2)c1] | 2-[2-(2-chlorophenyl)-4-(trifluoromethyl)-1H-imidazol-1-yl]-5-[3-(methylsulfonyl)phenyl]pyridine; |
| 371 | 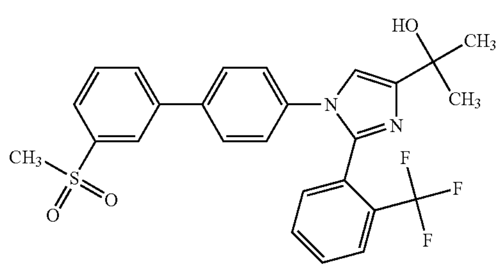 [SMILES: CC(C)(O)c1cn(-c2ccc(-c3cccc(S(C)(=O)=O)c3)cc2)c(-c2ccccc2C(F)(F)F)n1] | 2-{1-[3'-(methylsulfonyl)biphenyl-4-yl]-2-[2-(trifluoromethyl)phenyl]-1H-imidazol-4-yl}propan-2-ol; |
| 372 | 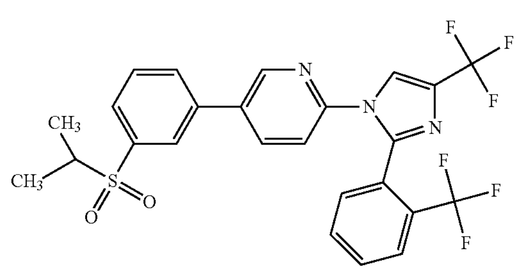 [SMILES: CC(C)S(=O)(=O)c1cccc(-c2ccc(-n3cc(C(F)(F)F)nc3-c3ccccc3C(F)(F)F)nc2)c1] | 5-{3-[(1-methylethyl)sulfonyl]phenyl}-2-{4-(trifluoromethyl)-2-[2-(trifluoromethyl)phenyl]-1H-imidazol-1-yl}pyridine; |

-continued

| Cpd # | Structure | Name |
|---|---|---|
| 373 | 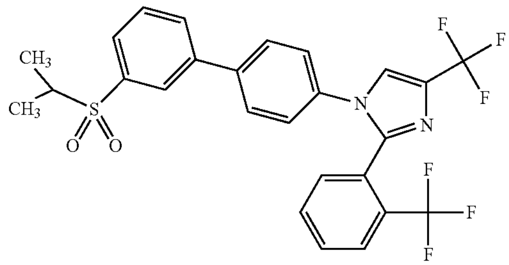 [SMILES: CC(C)S(=O)(=O)c1cccc(-c2ccc(-n3cc(C(F)(F)F)nc3-c3ccccc3C(F)(F)F)cc2)c1] | 1-{3'-[(1-methylethyl)sulfonyl]biphenyl-4-yl}-4-(trifluoromethyl)-2-[2-(trifluoromethyl)phenyl]-1H-imidazole; |
| 375 | 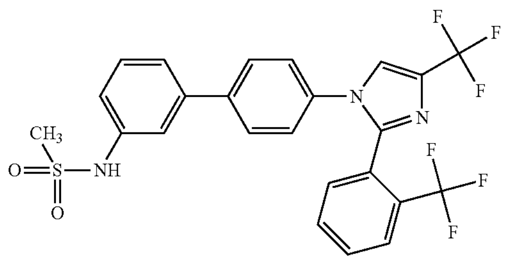 [SMILES: CS(=O)(=O)Nc1cccc(-c2ccc(-n3cc(C(F)(F)F)nc3-c3ccccc3C(F)(F)F)cc2)c1] | N-(4'-{4-(trifluoromethyl)-2-[2-(trifluoromethyl)phenyl]-1H-imidazol-1-yl}biphenyl-3-yl)methanesulfonamide; |
| 376 | 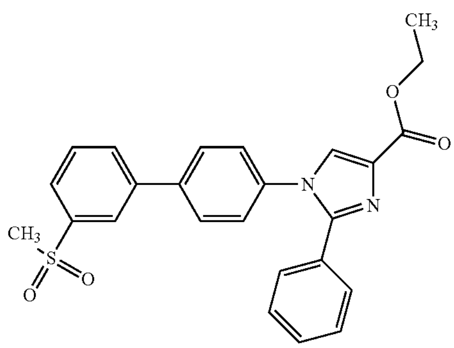 [SMILES: CCOC(=O)c1cn(-c2ccc(-c3cccc(S(C)(=O)=O)c3)cc2)c(-c2ccccc2)n1] | ethyl 1-[3'-(methylsulfonyl)biphenyl-4-yl]-2-phenyl-1H-imidazole-4-carboxylate; |
| 378 | 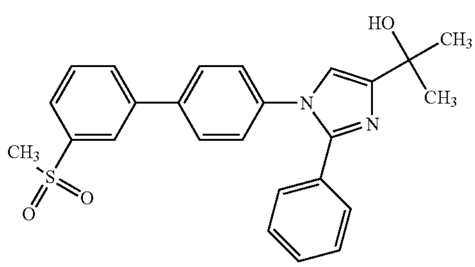 [SMILES: CC(C)(O)c1cn(-c2ccc(-c3cccc(S(C)(=O)=O)c3)cc2)c(-c2ccccc2)n1] | 2-{1-[3'-(methylsulfonyl)biphenyl-4-yl]-2-phenyl-1H-imidazol-4-yl}propan-2-ol; |
| 379 | 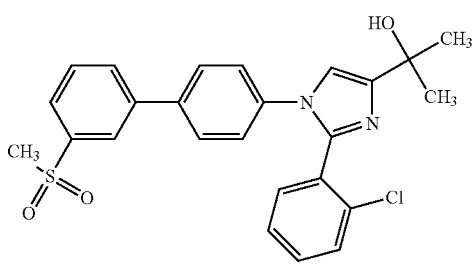 [SMILES: CC(C)(O)c1cn(-c2ccc(-c3cccc(S(C)(=O)=O)c3)cc2)c(-c2ccccc2Cl)n1] | 2-{2-(2-chlorophenyl)-1-[3'-(methylsulfonyl)biphenyl-4-yl]-1H-imidazol-4-yl}propan-2-ol; |

-continued

| Cpd # | Structure | Name |
|---|---|---|
| 380 | 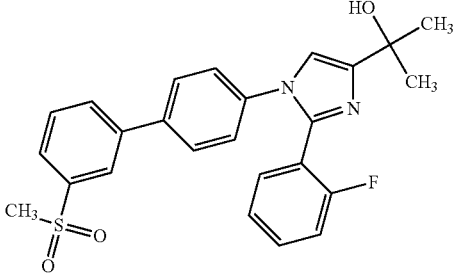 [SMILES: CC(C)(O)c1cn(-c2ccc(-c3cccc(S(C)(=O)=O)c3)cc2)c(-c2ccccc2F)n1] | 2-{2-(2-fluorophenyl)-1-[3'-(methylsulfonyl)biphenyl-4-yl]-1H-imidazol-4-yl}propan-2-ol; |
| 382 | 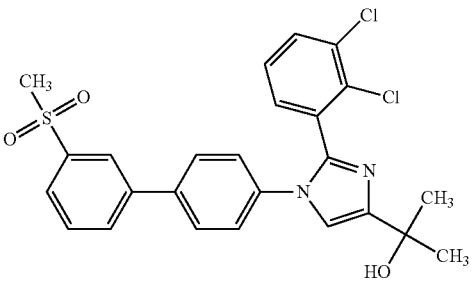 [SMILES: CC(C)(O)c1cn(-c2ccc(-c3cccc(S(C)(=O)=O)c3)cc2)c(-c2cccc(Cl)c2Cl)n1] | 2-{2-(2,3-dichlorophenyl)-1-[3'-(methylsulfonyl)biphenyl-4-yl]-1H-imidazol-4-yl}propan-2-ol; |
| 383 | 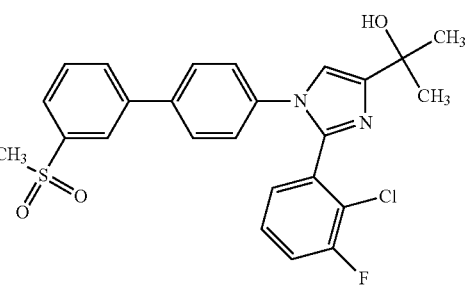 | 2-{2-(2-chloro-3-fluorophenyl)-1-[3'-(methylsulfonyl)biphenyl-4-yl]-1H-imidazol-4-yl}propan-2-ol; |
| 384 | 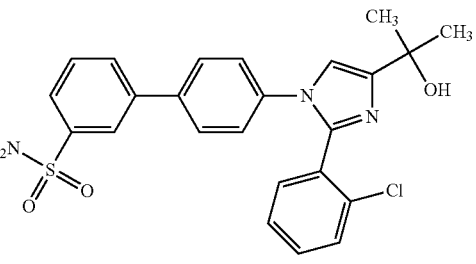 | 4'-[2-(2-chlorophenyl)-4-(1-hydroxy-1-methylethyl)-1H-imidazol-1-yl]biphenyl-3-sulfonamide; |
| 385 | 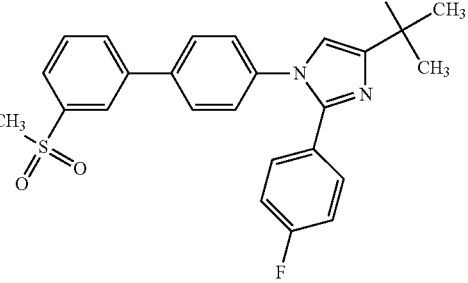 | 2-{2-(4-fluorophenyl)-1-[3'-(methylsulfony)biphenyl-4-yl]-1H-imidazol-4-yl}propan-2-ol; |

-continued

| Cpd # | Structure | Name |
|---|---|---|
| 386 | 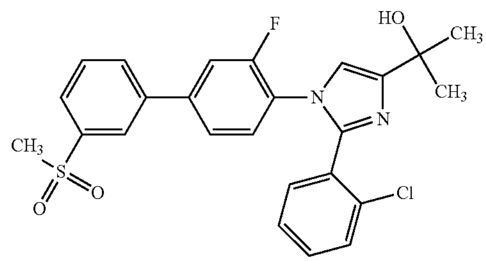 [SMILES: CC(C)(O)c1cn(-c2ccc(-c3cccc(S(C)(=O)=O)c3)cc2F)c(-c2ccccc2Cl)n1] | 2-{2-(2-chlorophenyl)-1-[3-fluoro-3'-(methylsulfonyl)biphenyl-4-yl]-1H-imidazol-4-yl}propan-2-ol; |
| 387 | 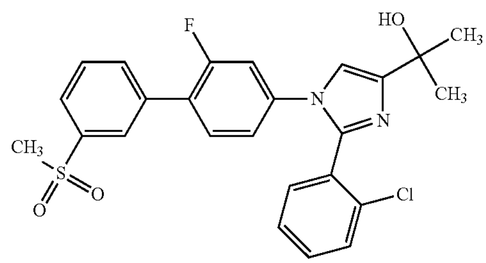 [SMILES: CC(C)(O)c1cn(-c2ccc(-c3cccc(S(C)(=O)=O)c3)c(F)c2)c(-c2ccccc2Cl)n1] | 2-{2-(2-chlorophenyl)-1-[2-fluoro-3'-(methylsulfonyl)biphenyl-4-yl]-1H-imidazol-4-yl}propan-2-ol; |
| 388 | 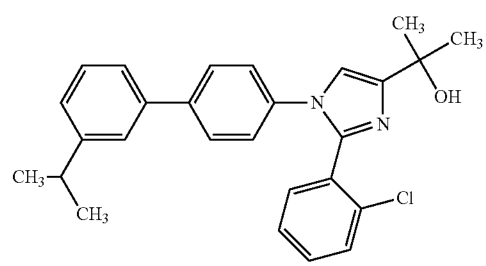 [SMILES: CC(C)c1cccc(-c2ccc(-n3cc(C(C)(C)O)nc3-c3ccccc3Cl)cc2)c1] | 2-{2-(2-chlorophenyl)-1-[3'-(1-methylethyl)biphenyl-4-yl]-1H-imidazol-4-yl}propan-2-ol; |
| 389 | 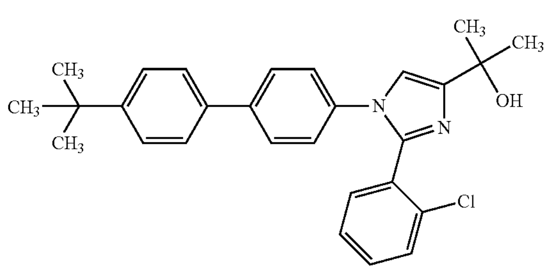 [SMILES: CC(C)(C)c1ccc(-c2ccc(-n3cc(C(C)(C)O)nc3-c3ccccc3Cl)cc2)cc1] | 2-{2-(2-chlorophenyl)-1-[4'-(1,1-dimethylethyl)biphenyl-4-yl]-1H-imidazol-4-yl}propan-2-ol; |
| 390 | 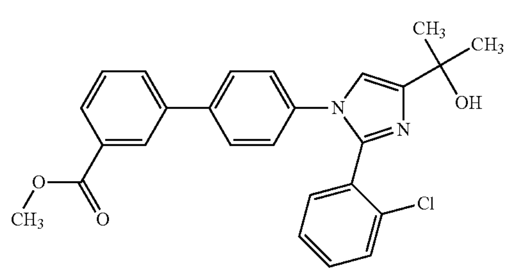 [SMILES: COC(=O)c1cccc(-c2ccc(-n3cc(C(C)(C)O)nc3-c3ccccc3Cl)cc2)c1] | methyl 4'-[2-(2-chlorophenyl)-4-(1-hydroxy-1-methylethyl)-1H-imidazol-1-yl]biphenyl-3-carboxylate; |

-continued

| Cpd # | Structure | Name |
|---|---|---|
| 391 | 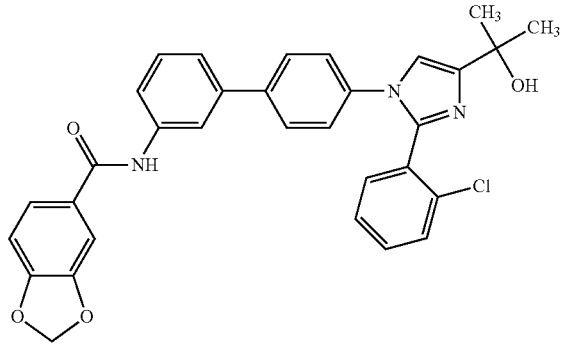 [SMILES: CC(C)(O)c1cn(-c2ccc(-c3cccc(NC(=O)c4ccc5c(c4)OCO5)c3)cc2)c(-c2ccccc2Cl)n1] | N-{4'-[2-(2-chlorophenyl)-4-(1-hydroxy-1-methylethyl)-1H-imidazol-1-yl]biphenyl-3-yl}-1,3-benzodioxole-5-carboxamide; |
| 392 | 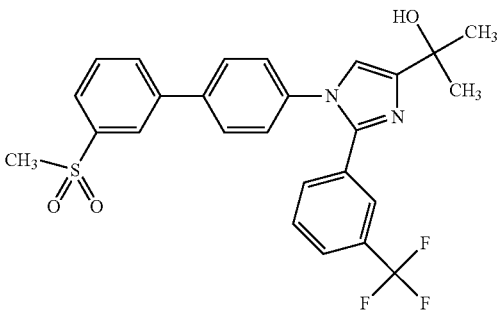 [SMILES: CC(C)(O)c1cn(-c2ccc(-c3cccc(S(C)(=O)=O)c3)cc2)c(-c2cccc(C(F)(F)F)c2)n1] | 2-{1-[3'-(methylsulfonyl)biphenyl-4-yl]-2-[3-(trifluoromethyl)phenyl]-1H-imidazol-4-yl}propan-2-ol; |
| 393 | 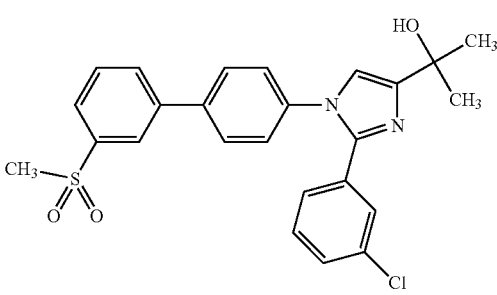 [SMILES: CC(C)(O)c1cn(-c2ccc(-c3cccc(S(C)(=O)=O)c3)cc2)c(-c2cccc(Cl)c2)n1] | 2-{2-(3-chlorophenyl)-1-[3'-(methylsulfonyl)biphenyl-4-yl]-1H-imidazol-4-yl}propan-2-ol; |
| 394 | 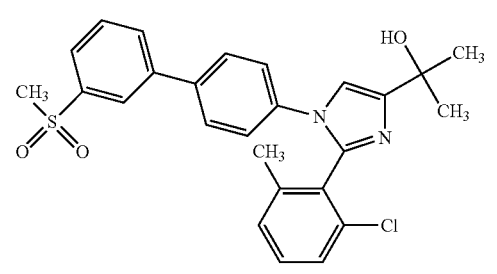 [SMILES: Cc1cccc(Cl)c1-c1nc(C(C)(C)O)cn1-c1ccc(-c2cccc(S(C)(=O)=O)c2)cc1] | 2-{2-(2-chloro-6-methylphenyl)-1-[3'-(methylsulfonyl)biphenyl-4-yl]-1H-imidazol-4-yl}propan-2-ol; |
| 395 | 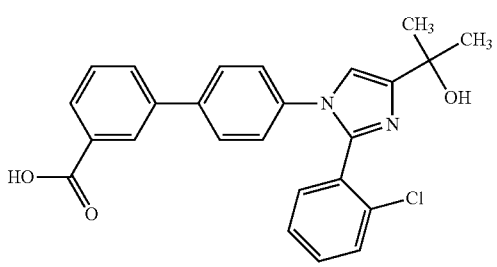 [SMILES: CC(C)(O)c1cn(-c2ccc(-c3cccc(C(=O)O)c3)cc2)c(-c2ccccc2Cl)n1] | 4'-[2-(2-chlorophenyl)-4-(1-hydroxy-1-methylethyl)-1H-imidazol-1-yl]biphenyl-3-carboxylic acid; |

| Cpd # | Structure | Name |
|---|---|---|
| 397 | 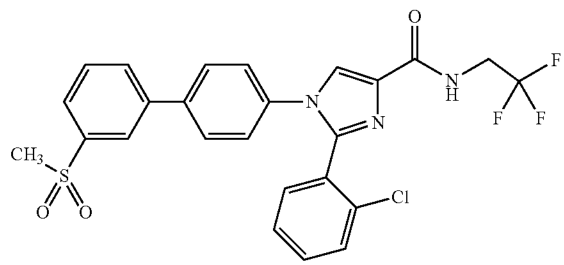 [SMILES: CS(=O)(=O)c1cccc(-c2ccc(-n3cc(C(=O)NCC(F)(F)F)nc3-c3ccccc3Cl)cc2)c1] | 2-(2-chlorophenyl)-1-[3'-(methylsulfonyl)biphenyl-4-yl]-N-(2,2,2-trifluoroethyl)-1H-imidazole-4-carboxamide; |
| 399 | 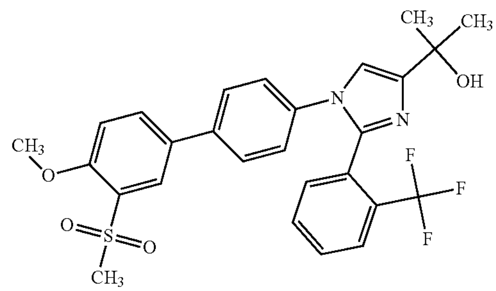 [SMILES: COc1ccc(-c2ccc(-n3cc(C(C)(C)O)nc3-c3ccccc3C(F)(F)F)cc2)cc1S(C)(=O)=O] | 2-{1-[4'-(methyloxy)-3'-(methylsulfonyl)biphenyl-4-yl]-2-[2-(trifluoromethyl)phenyl]-1H-imidazol-4-yl}propan-2-ol; |
| 400 | 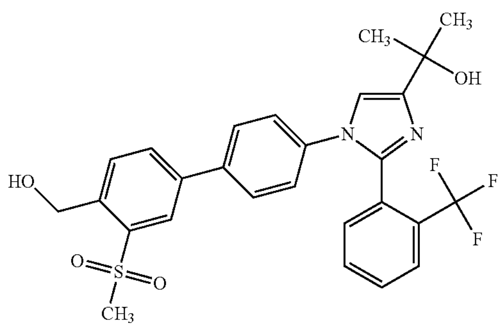 [SMILES: CC(C)(O)c1cn(-c2ccc(-c3ccc(CO)c(S(C)(=O)=O)c3)cc2)c(-c2ccccc2C(F)(F)F)n1] | 2-{1-[4'-(hydroxymethyl)-3'-(methylsulfonyl)biphenyl-4-yl]-2-[2-(trifluoromethyl)phenyl]-1H-imidazol-4-yl}propan-2-ol; |
| 401 | 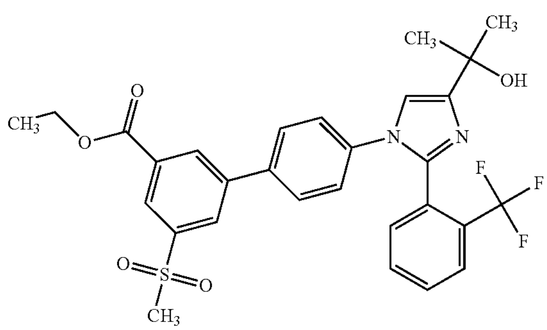 [SMILES: CCOC(=O)c1cc(-c2ccc(-n3cc(C(C)(C)O)nc3-c3ccccc3C(F)(F)F)cc2)cc(S(C)(=O)=O)c1] | ethyl 4'-{4-(1-hydroxy-1-methylethyl)-2-[2-(trifluoromethyl)phenyl]-1H-imidazol-1-yl}-5-(methylsulfonyl)biphenyl-3-carboxylate; |
| 402 | 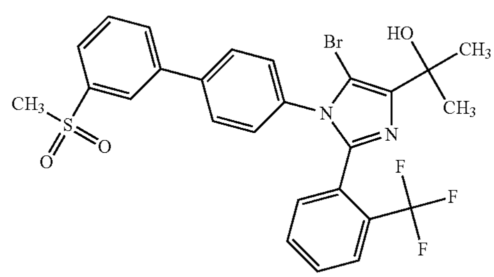 [SMILES: CC(C)(O)c1nc(-c2ccccc2C(F)(F)F)n(-c2ccc(-c3cccc(S(C)(=O)=O)c3)cc2)c1Br] | 2-{5-bromo-1-[3'-(methylsulfonyl)biphenyl-4-yl]-2-[2-(trifluoromethyl)phenyl]-1H-imidazol-4-yl}propan-2-ol; |

-continued

| Cpd # | Structure | Name |
|---|---|---|
| 403 | 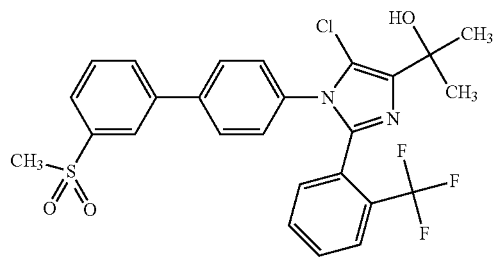 [SMILES: CC(C)(O)c1nc(-c2ccccc2C(F)(F)F)n(-c2ccc(-c3cccc(S(C)(=O)=O)c3)cc2)c1Cl] | 2-{5-chloro-1-[3'-(methylsulfonyl)biphenyl-4-yl]-2-[2-(trifluoromethyl)phenyl]-1H-imidazol-4-yl}propan-2-ol; |
| 404 | 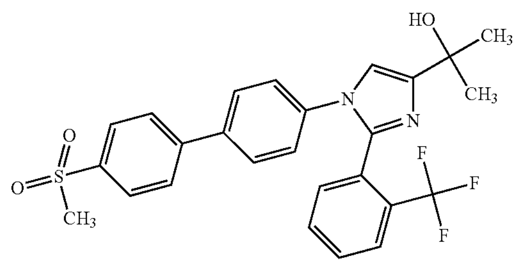 [SMILES: CC(C)(O)c1cn(-c2ccc(-c3ccc(S(C)(=O)=O)cc3)cc2)c(-c2ccccc2C(F)(F)F)n1] | 2-{1-[4'-(methylsulfonyl)biphenyl-4-yl]-2-[2-(trifluoromethyl)phenyl]-1H-imidazol-4-yl}propan-2-ol; |
| 405 | 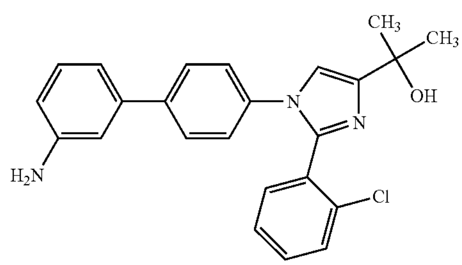 [SMILES: CC(C)(O)c1cn(-c2ccc(-c3cccc(N)c3)cc2)c(-c2ccccc2Cl)n1] | 2-[1-(3'-aminobiphenyl-4-yl)-2-(2-chlorophenyl)-1H-imidazol-4-yl]propan-2-ol; |
| 406 | 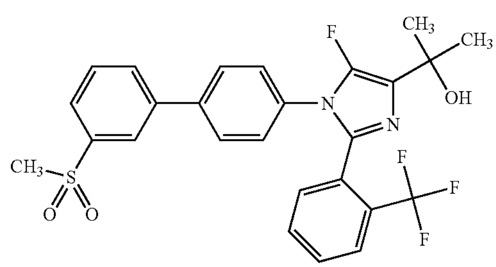 [SMILES: CC(C)(O)c1nc(-c2ccccc2C(F)(F)F)n(-c2ccc(-c3cccc(S(C)(=O)=O)c3)cc2)c1F] | 2-{5-fluoro-1-[3'-(methylsulfonyl)biphenyl-4-yl]-2-[2-(trifluoromethyl)phenyl]-1H-imidazol-4-yl}propan-2-ol; |
| 407 | 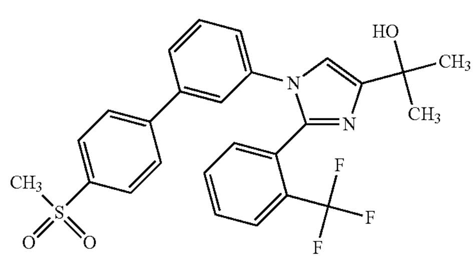 [SMILES: CC(C)(O)c1cn(-c2cccc(-c3ccc(S(C)(=O)=O)cc3)c2)c(-c2ccccc2C(F)(F)F)n1] | 2-{1-[4'-(methylsulfonyl)biphenyl-3-yl]-2-[2-(trifluoromethyl)phenyl]-1H-imidazol-4-yl}propan-2-ol; |
| 409 | 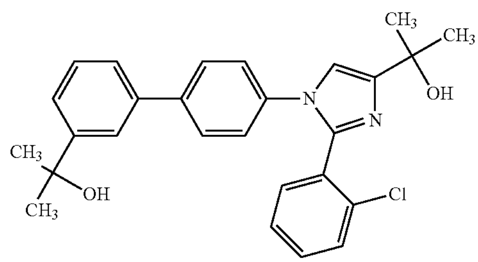 [SMILES: CC(C)(O)c1cccc(-c2ccc(-n3cc(C(C)(C)O)nc3-c3ccccc3Cl)cc2)c1] | 2-{2-(2-chlorophenyl)-1-[3'-(1-hydroxy-1-methylethyl)biphenyl-4-yl]-1H-imidazol-4-yl}propan-2-ol; |

-continued

| Cpd # | Structure | Name |
|---|---|---|
| 410 | 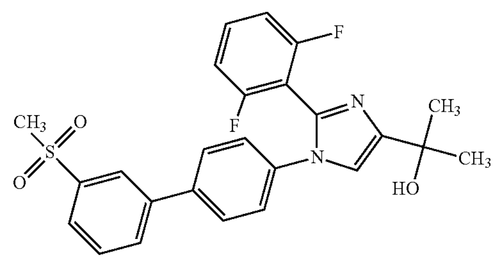 [SMILES: CC(C)(O)c1cn(-c2ccc(-c3cccc(S(C)(=O)=O)c3)cc2)c(-c2c(F)cccc2F)n1] | 2-{2-(2,6-difluorophenyl)-1-[3'-(methylsulfonyl)biphenyl-4-yl]-1H-imidazol-4-yl}propan-2-ol; |
| 413 | 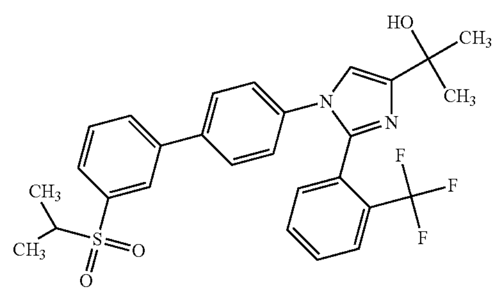 [SMILES: CC(C)S(=O)(=O)c1cccc(-c2ccc(-n3cc(C(C)(C)O)nc3-c3ccccc3C(F)(F)F)cc2)c1] | 2-(1-{3-[(1-methylethyl)sulfonyl]biphenyl-4-yl}-2-[2-(trifluoromethyl)phenyl]-1H-imidazol-4-yl)propan-2-ol; |
| 414 | 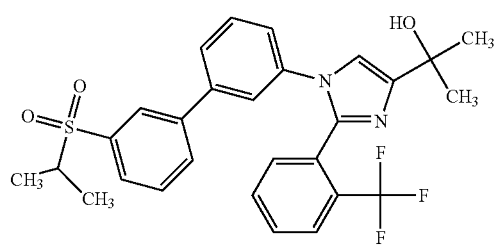 [SMILES: CC(C)S(=O)(=O)c1cccc(-c2cccc(-n3cc(C(C)(C)O)nc3-c3ccccc3C(F)(F)F)c2)c1] | 2-(1-{3'-[(1-methylethyl)sulfonyl]biphenyl-3-yl}-2-[2-(trifluoromethyl)phenyl]-1H-imidazol-4-yl)propan-2-ol; |
| 415 | 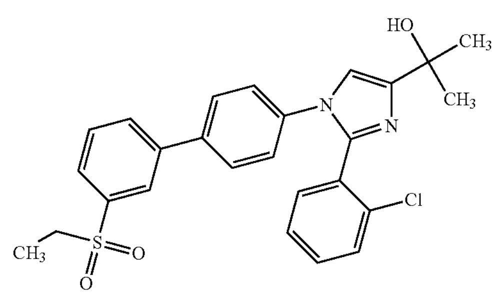 [SMILES: CCS(=O)(=O)c1cccc(-c2ccc(-n3cc(C(C)(C)O)nc3-c3ccccc3Cl)cc2)c1] | 2-{2-(2-chlorophenyl)-1-[3'-(ethylsulfonyl)biphenyl-4-yl]-1H-imidazol-4-yl}propan-2-ol; |
| 416 | 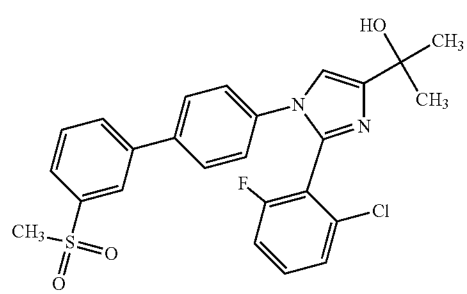 [SMILES: CC(C)(O)c1cn(-c2ccc(-c3cccc(S(C)(=O)=O)c3)cc2)c(-c2c(F)cccc2Cl)n1] | 2-{2-(2-chloro-6-fluorophenyl)-1-[3'-(methylsulfonyl)biphenyl-4-yl]-1H-imidazol-4-yl}propan-2-ol; |

-continued

| Cpd # | Structure | Name |
|---|---|---|
| 417 | 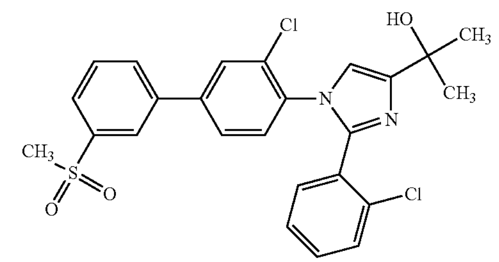 [SMILES: CC(C)(O)c1cn(-c2ccc(-c3cccc(S(C)(=O)=O)c3)cc2Cl)c(-c2ccccc2Cl)n1] | 2-{1-[3-chloro-3'-(methylsulfonyl)biphenyl-4-yl]-2-(2-chlorophenyl)-1H-imidazol-4-yl}propan-2-ol; |
| 418 | 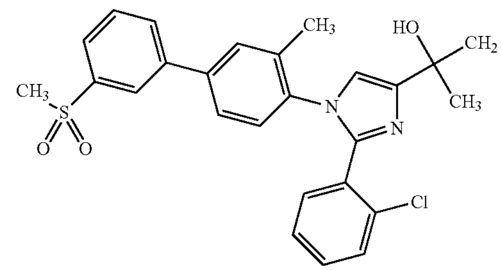 [SMILES: Cc1cc(-c2cccc(S(C)(=O)=O)c2)ccc1-n1cc(C(C)(C)O)nc1-c1ccccc1Cl] | 2-{2-(2-chlorophenyl)-1-[3-methyl-3'-(methylsulfonyl)biphenyl-4-yl]-1H-imidazol-4-yl}propan-2-ol; |
| 419 | 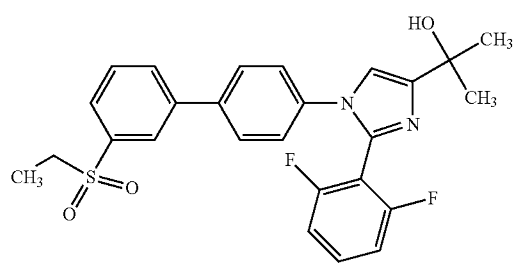 [SMILES: CCS(=O)(=O)c1cccc(-c2ccc(-n3cc(C(C)(C)O)nc3-c3c(F)cccc3F)cc2)c1] | 2-{2-[2,6-difluorophenyl)-1-[3'-(ethylsulfonyl)biphenyl-4-yl]-1H-imidazol-4-yl}propan-2-ol; |
| 420 | 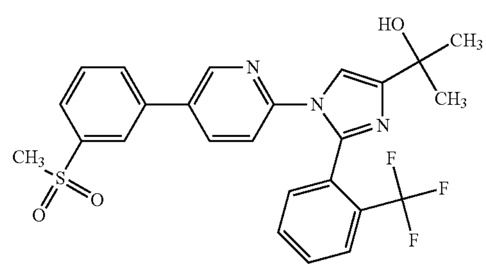 [SMILES: CC(C)(O)c1cn(-c2ccc(-c3cccc(S(C)(=O)=O)c3)cn2)c(-c2ccccc2C(F)(F)F)n1] | 2-(1-{5-[3-(methylsulfonyl)phenyl]pyridin-2-yl}-2-[2-(trifluoromethyl)phenyl]-1H-imidazol-4-yl)propan-2-ol; |
| 421 | 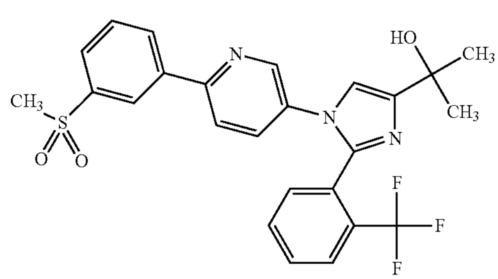 [SMILES: CC(C)(O)c1cn(-c2ccc(-c3cccc(S(C)(=O)=O)c3)nc2)c(-c2ccccc2C(F)(F)F)n1] | 2-(1-{6-[3-(methylsulfonyl)phenyl]pyridin-3-yl}-2-[2-(trifluoromethyl)phenyl]-1H-imidazol-4-yl)propan-2-ol; |

-continued

| Cpd # | Structure | Name |
|---|---|---|
| 422 | 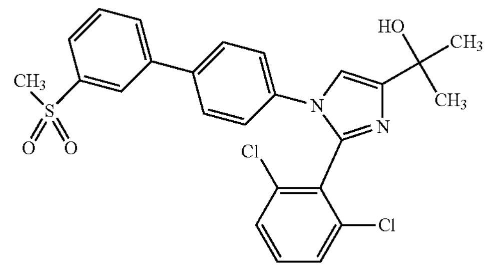 [SMILES: CC(C)(O)c1cn(-c2ccc(-c3cccc(S(C)(=O)=O)c3)cc2)c(-c2c(Cl)cccc2Cl)n1] | 2-{2-(2,6-dichlorophenyl)-1-[3'-(methylsulfonyl)biphenyl-4-yl]-1H-imidazol-4-yl}propan-2-ol; |
| 427 | 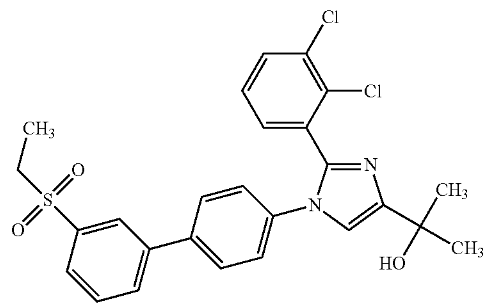 [SMILES: CCS(=O)(=O)c1cccc(-c2ccc(-n3cc(C(C)(C)O)nc3-c3cccc(Cl)c3Cl)cc2)c1] | 2-{2-(2,3-dichlorophenyl)-1-[3'-(ethylsulfonyl)biphenyl-4-yl]-1H-imidazol-4-yl}propan-2-ol; |
| 428 | 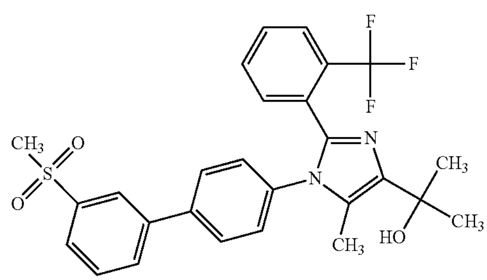 [SMILES: Cc1c(C(C)(C)O)nc(-c2ccccc2C(F)(F)F)n1-c1ccc(-c2cccc(S(C)(=O)=O)c2)cc1] | 2-{5-methyl-1-[3'-(methylsulfonyl)biphenyl-4-yl]-2-[2-(trifluoromethyl)phenyl]-1H-imidazol-4-yl}propan-2-ol; |
| 429 | 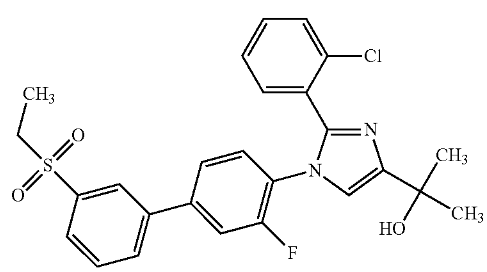 [SMILES: CCS(=O)(=O)c1cccc(-c2ccc(-n3cc(C(C)(C)O)nc3-c3ccccc3Cl)c(F)c2)c1] | 2-{2-(2-chlorophenyl)-1-[3'-(ethylsulfonyl)-3-fluorobiphenyl-4-yl]-1H-imidazol-4-yl}propan-2-ol; |
| 430 | 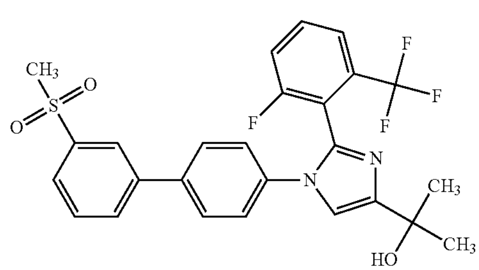 [SMILES: CC(C)(O)c1cn(-c2ccc(-c3cccc(S(C)(=O)=O)c3)cc2)c(-c2c(F)cccc2C(F)(F)F)n1] | 2-{2-[2-fluoro-6-(trifluoromethyl)phenyl]-1-[3'-(methylsulfonyl)biphenyl-4-yl]-1H-imidazol-4-yl}propan-2-ol; |

| Cpd # | Structure | Name |
|---|---|---|
| 431 | 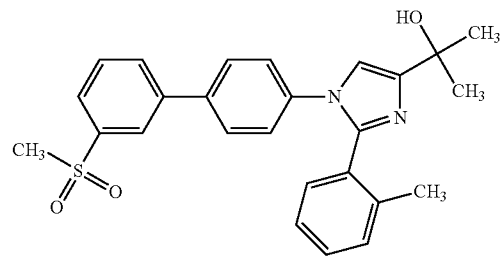 [SMILES: Cc1ccccc1-c1nc(C(C)(C)O)cn1-c1ccc(-c2cccc(S(C)(=O)=O)c2)cc1] | 2-{2-(2-methylphenyl)-1-[3'-(methylsulfonyl)biphenyl-4-yl]-1H-imidazol-4-yl}propan-2-ol; |
| 432 | 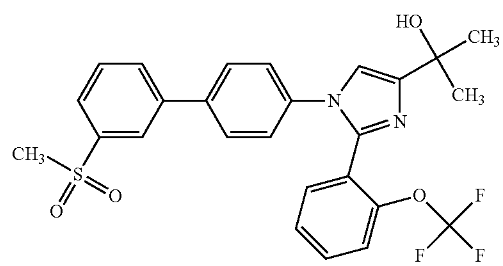 [SMILES: CC(C)(O)c1cn(-c2ccc(-c3cccc(S(C)(=O)=O)c3)cc2)c(-c2ccccc2OC(F)(F)F)n1] | 2-(1-[3'-(methylsulfonyl)biphenyl-4-yl]-2-{2-[(trifluoromethyl)oxy]phenyl}-1H-imidazol-4-yl)propan-2-ol; |
| 436 | 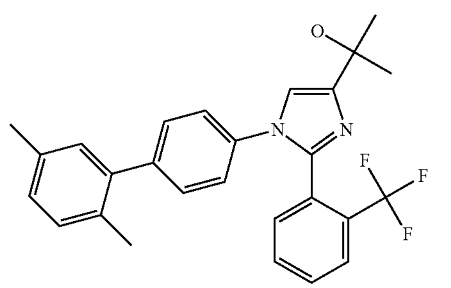 [SMILES: Cc1ccc(C)c(-c2ccc(-n3cc(C(C)(C)O)nc3-c3ccccc3C(F)(F)F)cc2)c1] | 2-(1-(2',5'-dimethylbiphenyl-4-yl-2-(2-trifluoromethyl)phenyl)1H-imidazol-4-yl)propan-2-ol; |
| 437 | 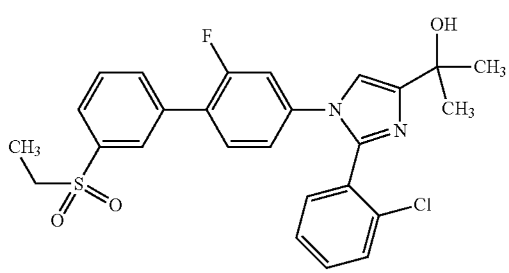 [SMILES: CCS(=O)(=O)c1cccc(-c2ccc(-n3cc(C(C)(C)O)nc3-c3ccccc3Cl)cc2F)c1] | 2-{2-(2-chlorophenyl)-1-[3'-(ethylsulfonyl)-2-fluorobiphenyl-4-yl]-1H-imidazol-4-yl}propan-2-ol; |
| 438 | 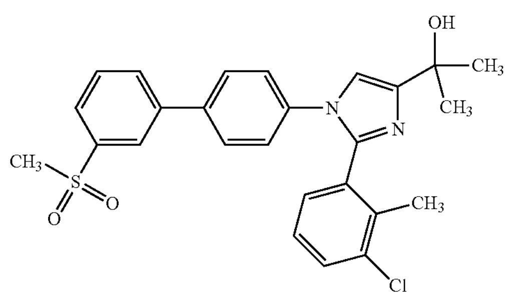 [SMILES: Cc1c(Cl)cccc1-c1nc(C(C)(C)O)cn1-c1ccc(-c2cccc(S(C)(=O)=O)c2)cc1] | 2-{2-(3-chloro-2-methylphenyl)-1-[3'-(methylsulfonyl)biphenyl-4-yl]-1H-imidazol-4-yl}propan-2-ol; |

-continued

| Cpd # | Structure | Name |
|---|---|---|
| 439 | 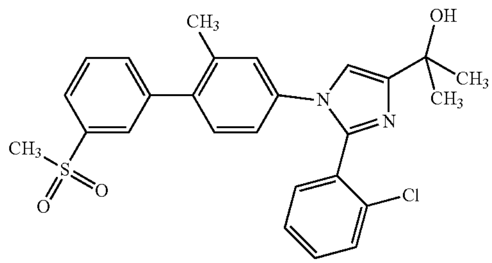 [SMILES: Cc1cc(-n2cc(C(C)(C)O)nc2-c2ccccc2Cl)ccc1-c1cccc(S(C)(=O)=O)c1] | 2-{2-(2-chlorophenyl)-1-[2-methyl-3'-(methylsulfonyl)biphenyl-4-yl]-1H-imidazol-4-yl}propan-2-ol; |
| 440 | | 2-{2-(3-chloro-2-methylphenyl)-1-[3'-(ethylsulfonyl)biphenyl-4-yl]-1H-imidazol-4-yl}propan-2-ol; |
| 443 | | 2-(1-(2-chlorobenzyl)-2-(3'-(methylsulfonyl)biphenyl-4-yl)-1H-imidazol-4-yl)propan-2-ol |
| 444 | | 2-(1-(2,3-dichlorobenzyl)-2-(3'-(methylsulfonyl)biphenyl-4-yl)-1H-imidazol-4-yl)propan-2-ol |
| 445 | | 2-(5-chloro-2-(3-chloro-3'-(methylsulfonyl)biphenyl-4-yl)-1-(2,6-dichlorophenyl)-1H-imidazol-4-yl)propan-2-ol |
| 446 | | 2-(5-chloro-1-(2,6-dichlorophenyl)-2-(3'-(methylsulfonyl)biphenyl-4-yl)-1H-imidazol-4-yl)propan-2-ol |
| 447 | | 3'-chloro-4'-(2-(2-chloro-6-fluorophenyl)-4-(2-hydroxypropan-2-yl)-1H-imidazol-1-yl)-3-(methylsulfonyl)biphenyl-4-carboxylic acid |
| 448 | | 3'-chloro-4'-(2-(2-chloro-6-fluorophenyl)-4-(2-hydroxypropan-2-yl)-1H-imidazol-1-yl)-N-methoxy-N-methyl-3-(methylsulfonyl)biphenyl-4-carboxamide |
| 449 | 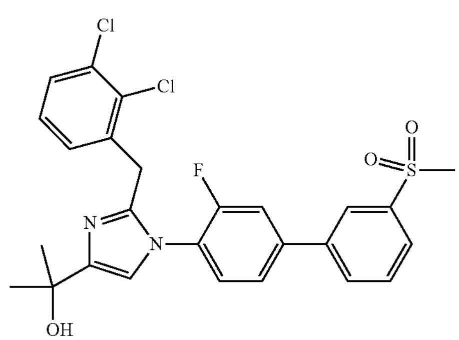 [SMILES: CC(C)(O)c1cn(-c2ccc(-c3cccc(S(C)(=O)=O)c3)cc2F)c(Cc2cccc(Cl)c2Cl)n1] | 2-(2-(2,3-dichlorobenzyl)-1-(3-fluoro-3'-(methylsulfonyl)biphenyl-4-yl)-1H-imidazol-4-yl)propan-2-ol |

| Cpd # | Structure | Name |
|---|---|---|
| 450 | 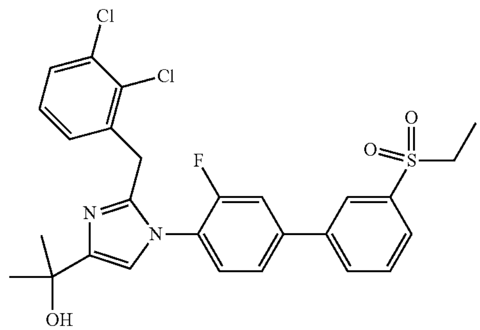 [SMILES: CCS(=O)(=O)c1cccc(-c2ccc(-n3cc(C(C)(C)O)nc3Cc3cccc(Cl)c3Cl)c(F)c2)c1] | 2-(2-(2,3-dichlorobenzyl)-1-(3'-(ethylsulfonyl)-3-fluorobiphenyl-4-yl)-1H-imidazol-4-yl)propan-2-ol |
| 451 | 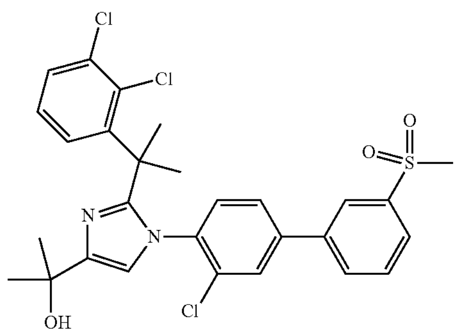 [SMILES: CC(C)(O)c1cn(-c2ccc(-c3cccc(S(C)(=O)=O)c3)cc2Cl)c(C(C)(C)c2cccc(Cl)c2Cl)n1] | 2-(1-(3-chloro-3'-(methylsulfonyl)biphenyl-4-yl)-2-(2-(2,3-dichlorophenyl)propan-2-yl)-1H-imidazol-4-yl)propan-2-ol |
| 452 | 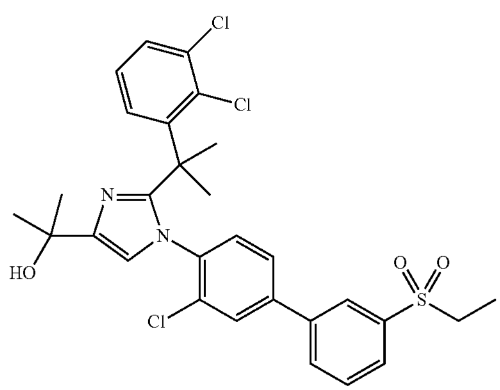 [SMILES: CCS(=O)(=O)c1cccc(-c2ccc(-n3cc(C(C)(C)O)nc3C(C)(C)c3cccc(Cl)c3Cl)c(Cl)c2)c1] | 2-(1-(3-chloro-3'-(ethylsulfonyl)biphenyl-4-yl)-2-(2-(2,3-dichlorophenyl)propan-2-yl)-1H-imidazol-4-yl)propan-2-ol |
| 453 | 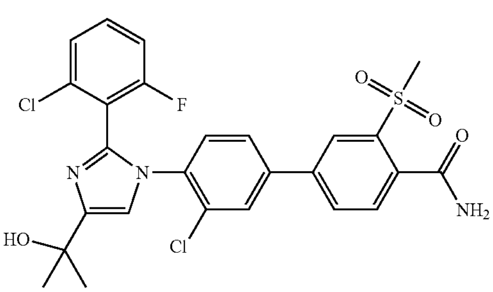 [SMILES: CC(C)(O)c1cn(-c2ccc(-c3ccc(C(N)=O)c(S(C)(=O)=O)c3)cc2Cl)c(-c2c(F)cccc2Cl)n1] | 3'-chloro-4'-(2-(2-chloro-6-fluorophenyl)-4-(2-hydroxypropan-2-yl)-1H-imidazol-1-yl)-3-(methylsulfonyl)biphenyl-4-carboxamide |

| Cpd # | Structure | Name |
| --- | --- | --- |
| 454 | 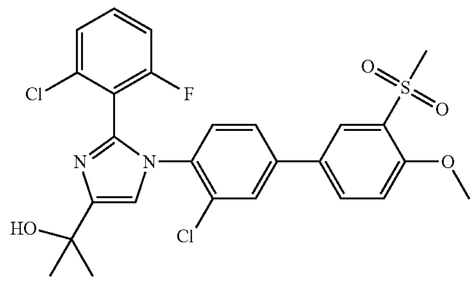 [SMILES: COc1ccc(-c2ccc(-n3cc(C(C)(C)O)nc3-c3c(F)cccc3Cl)c(Cl)c2)cc1S(C)(=O)=O] | 2-(1-(3-chloro-4'-methoxy-3'-(methylsulfonyl)biphenyl-4-yl)-2-(2-chloro-6-fluorophenyl)-1H-imidazol-4-yl)propan-2-ol |
| 455 | 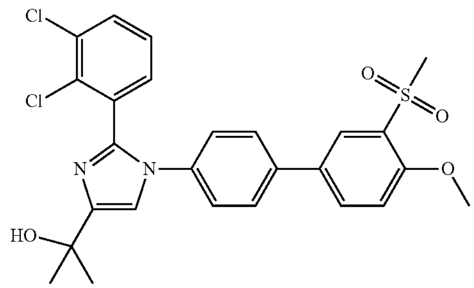 [SMILES: COc1ccc(-c2ccc(-n3cc(C(C)(C)O)nc3-c3cccc(Cl)c3Cl)cc2)cc1S(C)(=O)=O] | 2-(2-(2,3-dichlorophenyl)-1-(4'-methoxy-3'-(methylsulfonyl)biphenyl-4-yl)-1H-imidazol-4-yl)propan-2-ol |
| 456 | 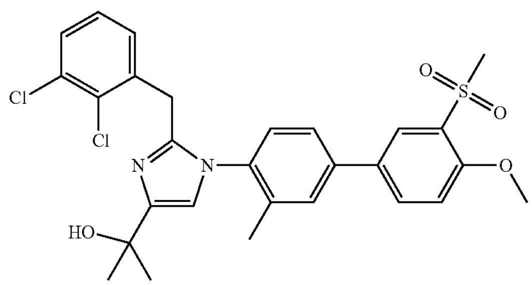 [SMILES: COc1ccc(-c2ccc(-n3cc(C(C)(C)O)nc3Cc3cccc(Cl)c3Cl)c(C)c2)cc1S(C)(=O)=O] | 2-(2-(2,3-dichlorobenzyl)-1-(4'-methoxy-3-methyl-3'-(methylsulfonyl)biphenyl-4-yl)-1H-imidazol-4-yl)propan-2-ol |
| 457 | 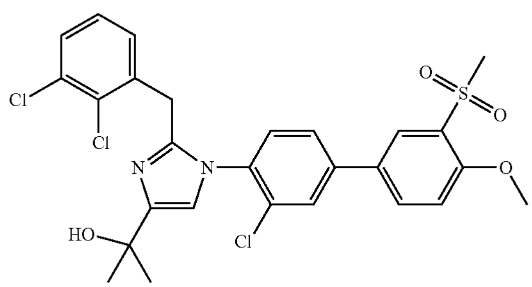 [SMILES: COc1ccc(-c2ccc(-n3cc(C(C)(C)O)nc3Cc3cccc(Cl)c3Cl)c(Cl)c2)cc1S(C)(=O)=O] | 2-(1-(3-chloro-4'-methoxy-3'-(methylsulfonyl)biphenyl-4-yl)-2-(2,3-dichlorobenzyl)-1H-imidazol-4-yl)propan-2-ol |
| 458 | 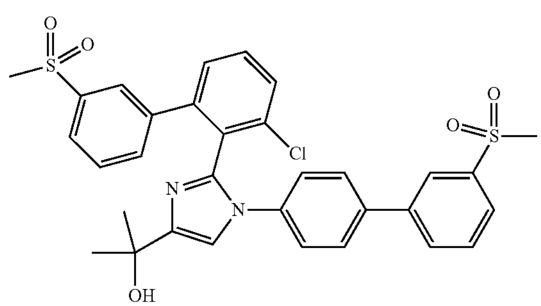 | 2-(2-(3-chloro-3'-(methylsulfonyl)biphenyl-2-yl)-1-(3'-(methylsulfonyl)biphenyl-4-yl)-1H-imidazol-4-yl)propan-2-ol |

| Cpd # | Structure | Name |
|---|---|---|
| 459 | 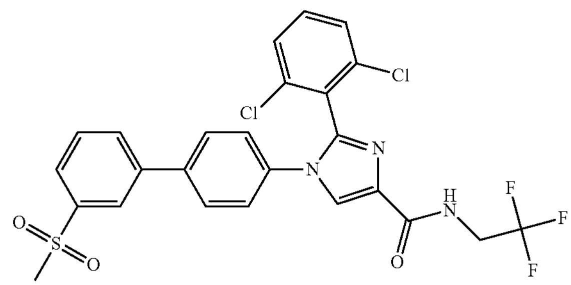 | 1-(3-chloro-3'-(methylsulfonyl)biphenyl-4-yl)-2-(2,6-dichlorophenyl)-N-(2,2,2-trifluoroethyl)-1H-imidazole-4-carboxamide |
| 460 | 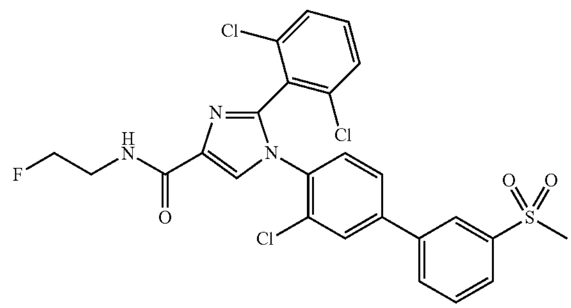 [SMILES: CS(=O)(=O)c1cccc(-c2ccc(-n3cc(C(=O)NCCF)nc3-c3c(Cl)cccc3Cl)c(Cl)c2)c1] | 1-(3-chloro-3'-(methylsulfonyl)biphenyl-4-yl)-2-(2,6-dichlorophenyl)-N-(2-fluoroethyl)-1H-imidazole-4-carboxamide |
| 461 | 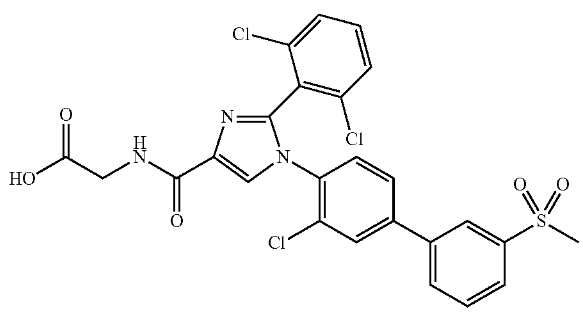 [SMILES: CS(=O)(=O)c1cccc(-c2ccc(-n3cc(C(=O)NCC(=O)O)nc3-c3c(Cl)cccc3Cl)c(Cl)c2)c1] | 2-(1-(3-chloro-3'-(methylsulfonyl)biphenyl-4-yl)-2-(2,6-dichlorophenyl)-1H-imidazole-4-carboxamido)acetic acid |
| 462 | 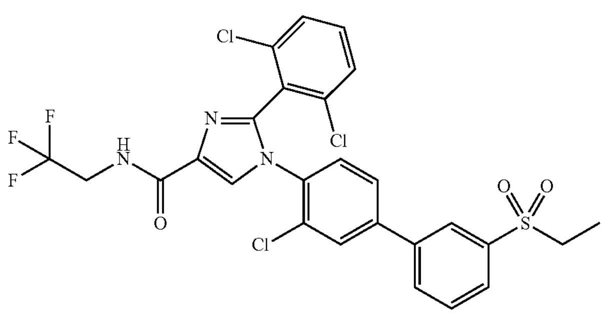 [SMILES: CCS(=O)(=O)c1cccc(-c2ccc(-n3cc(C(=O)NCC(F)(F)F)nc3-c3c(Cl)cccc3Cl)c(Cl)c2)c1] | 1-(3-chloro-3'-(ethylsulfonyl)biphenyl-4-yl)-2-(2,6-dichlorophenyl)-N-(2,2,2-trifluoroethyl)-1H-imidazole-4-carboxamide |
| 463 | 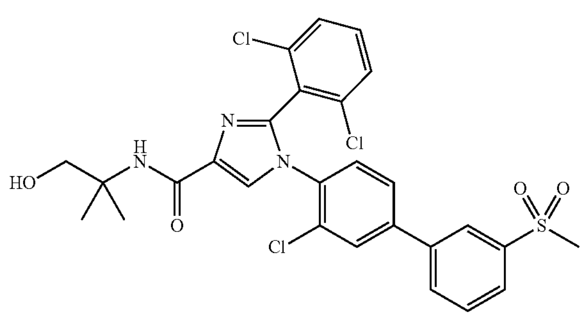 [SMILES: CC(C)(CO)NC(=O)c1cn(-c2ccc(-c3cccc(S(C)(=O)=O)c3)cc2Cl)c(-c2c(Cl)cccc2Cl)n1] | 1-(3-chloro-3'-(methylsulfonyl)biphenyl-4-yl)-2-(2,6-dichlorophenyl)-N-(1-hydroxy-2-methylpropan-2-yl)-1H-imidazole-4-carboxamide |

-continued

| Cpd # | Structure | Name |
|---|---|---|
| 464 | 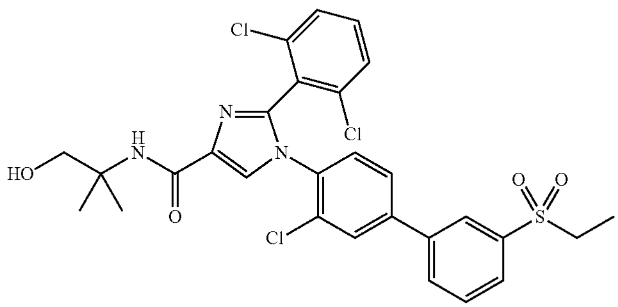 [SMILES: CCS(=O)(=O)c1cccc(-c2ccc(-n3cc(C(=O)NC(C)(C)CO)nc3-c3c(Cl)cccc3Cl)c(Cl)c2)c1] | 1-(3-chloro-3'-(ethylsulfonyl)biphenyl-4-yl)-2-(2,6-dichlorophenyl)-N-(1-hydroxy-2-methylpropan-2-yl)-1H-imidazole-4-carboxamide |
| 465 | 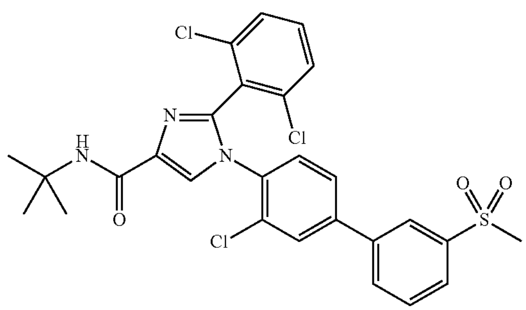 [SMILES: CC(C)(C)NC(=O)c1cn(-c2ccc(-c3cccc(S(C)(=O)=O)c3)cc2Cl)c(-c2c(Cl)cccc2Cl)n1] | N-tert-butyl-1-(3-chloro-3'-(methylsulfonyl)biphenyl-4-yl)-2-(2,6-dichlorophenyl)-1H-imidazole-4-carboxamide |
| 466 | 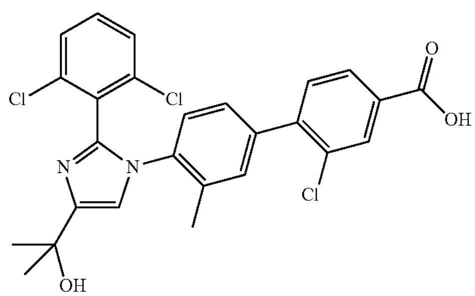 [SMILES: Cc1cc(-c2ccc(C(=O)O)cc2Cl)ccc1-n1cc(C(C)(C)O)nc1-c1c(Cl)cccc1Cl] | 2-chloro-4'-(2-(2,6-dichlorophenyl)-4-(2-hydroxypropan-2-yl)-1H-imidazol-1-yl)-3'-methylbiphenyl-4-carboxylic acid |
| 467 | 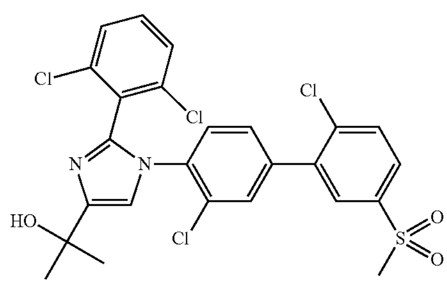 [SMILES: CC(C)(O)c1cn(-c2ccc(-c3cc(S(C)(=O)=O)ccc3Cl)cc2Cl)c(-c2c(Cl)cccc2Cl)n1] | 2-(1-(2',3-dichloro-5'-(methylsulfonyl)biphenyl-4-yl)-2-(2,6-dichlorophenyl)-1H-imidazol-4-yl)propan-2-ol |
| 468 | 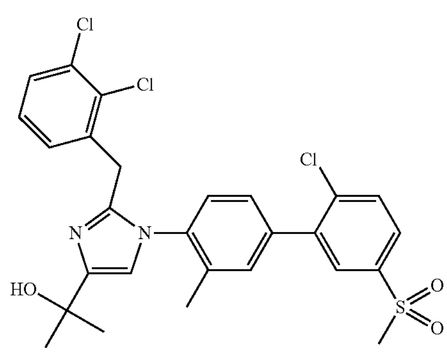 [SMILES: Cc1cc(-c2cc(S(C)(=O)=O)ccc2Cl)ccc1-n1cc(C(C)(C)O)nc1Cc1cccc(Cl)c1Cl] | 2-(1-(2'-chloro-3-methyl-5'-(methylsulfonyl)biphenyl-4-yl)-2-(2,3-dichlorobenzyl)-1H-imidazol-4-yl)propan-2-ol |

| Cpd # | Structure | Name |
|---|---|---|
| 469 | 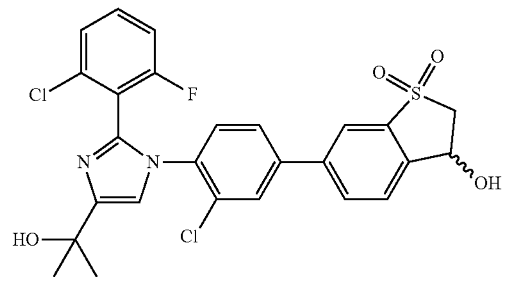 [SMILES: CC(C)(O)c1cn(-c2ccc(-c3ccc4c(c3)S(=O)(=O)CC4O)cc2Cl)c(-c2c(F)cccc2Cl)n1] | 6-{3-chloro-4-[2-(2-chloro-6-fluorophenyl)-4-(1-hydroxy-1-methylethyl)-1H-imidazol-1-yl]phenyl}-2,3-dihydro-1-benzothiophene-3-ol 1,1-dioxide |
| 470 | 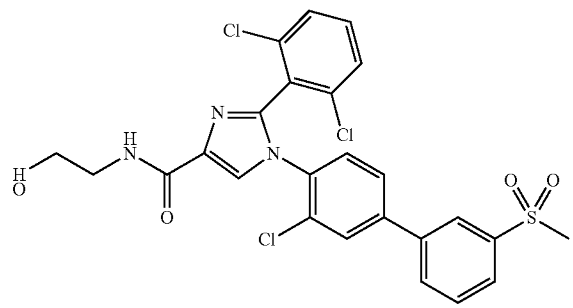 [SMILES: CS(=O)(=O)c1cccc(-c2ccc(-n3cc(C(=O)NCCO)nc3-c3c(Cl)cccc3Cl)c(Cl)c2)c1] | 1-(3-chloro-3'-(methylsulfonyl)biphenyl-4-yl)-2-(2,6-dichlorophenyl)-N-(2-hydroxyethyl)-1H-imidazole-4-carboxamide |
| 471 | 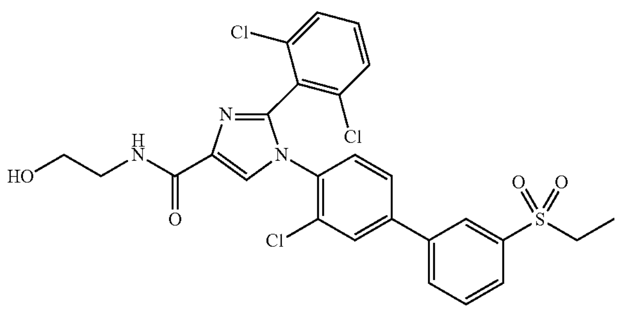 [SMILES: CCS(=O)(=O)c1cccc(-c2ccc(-n3cc(C(=O)NCCO)nc3-c3c(Cl)cccc3Cl)c(Cl)c2)c1] | 1-(3-chloro-3'-(ethylsulfonyl)biphenyl-4-yl)-2-(2,6-dichlorophenyl)-N-(2-hydroxyethyl)-1H-imidazole-4-carboxamide |
| 472 | 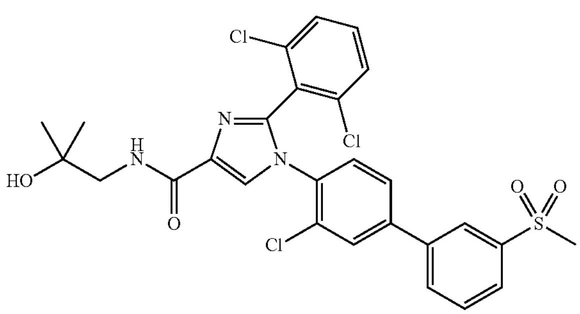 [SMILES: CC(C)(O)CNC(=O)c1cn(-c2ccc(-c3cccc(S(C)(=O)=O)c3)cc2Cl)c(-c2c(Cl)cccc2Cl)n1] | 1-(3-chloro-3'-(methylsulfonyl)biphenyl-4-yl)-2-(2,6-dichlorophenyl)-N-(2-hydroxy-2-methylpropyl)-1H-imidazole-4-carboxamide |
| 473 | 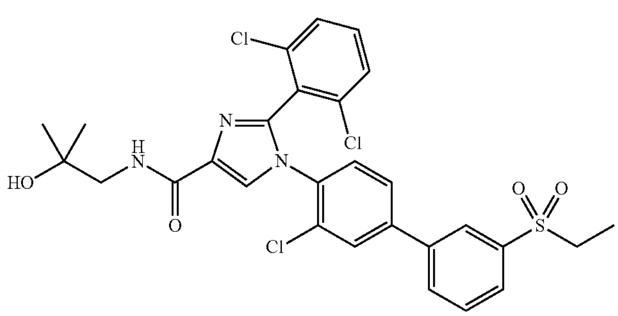 [SMILES: CCS(=O)(=O)c1cccc(-c2ccc(-n3cc(C(=O)NCC(C)(C)O)nc3-c3c(Cl)cccc3Cl)c(Cl)c2)c1] | 1-(3-chloro-3'-(ethylsulfonyl)biphenyl-4-yl)-2-(2,6-dichlorophenyl)-N-(2-hydroxy-2-methylpropyl)-1H-imidazole-4-carboxamide |

-continued

| Cpd # | Structure | Name |
|---|---|---|
| 474 | 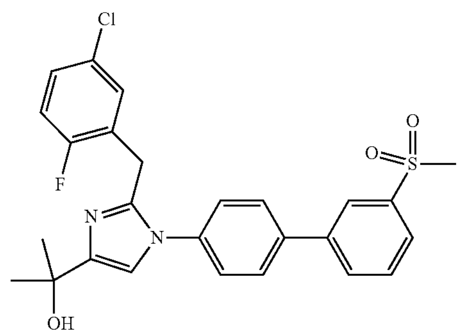 [SMILES: CC(C)(O)c1cn(-c2ccc(-c3cccc(S(C)(=O)=O)c3)cc2)c(Cc2cc(Cl)ccc2F)n1] | 2-(2-(5-chloro-2-fluorobenzyl)-1-(3'-(methylsulfonyl)biphenyl-4-yl)-1H-imidazol-4-yl)propan-2-ol |
| 475 | 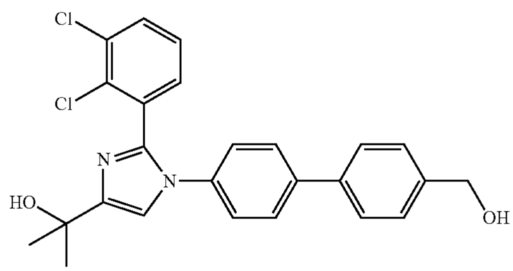 [SMILES: CC(C)(O)c1cn(-c2ccc(-c3ccc(CO)cc3)cc2)c(-c2cccc(Cl)c2Cl)n1] | 2-(2-(2,3-dichlorophenyl)-1-(4'-(hydroxymethyl)biphenyl-4-yl)-1H-imidazol-4-yl)propan-2-ol |
| 476 | 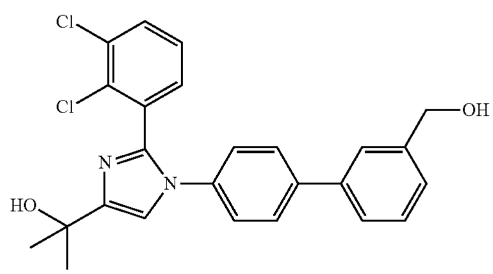 [SMILES: CC(C)(O)c1cn(-c2ccc(-c3cccc(CO)c3)cc2)c(-c2cccc(Cl)c2Cl)n1] | 2-(2-(2,3-dichlorophenyl)-1-(3'-(hydroxymethyl)biphenyl-4-yl)-1H-imidazol-4-yl)propan-2-ol |
| 477 | 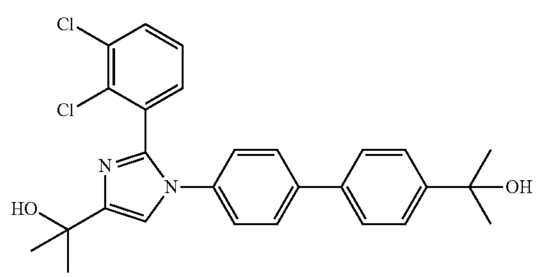 [SMILES: CC(C)(O)c1ccc(-c2ccc(-n3cc(C(C)(C)O)nc3-c3cccc(Cl)c3Cl)cc2)cc1] | 2-(2-(2,3-dichlorophenyl)-1-(4'-(2-hydroxypropan-2-yl)biphenyl-4-yl)-1H-imidazol-4-yl)propan-2-ol |
| 478 | 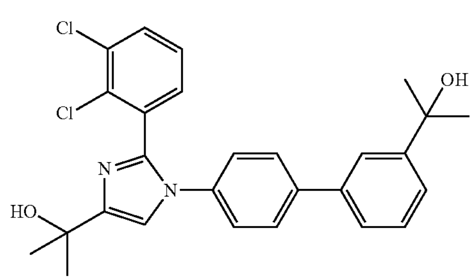 [SMILES: CC(C)(O)c1cccc(-c2ccc(-n3cc(C(C)(C)O)nc3-c3cccc(Cl)c3Cl)cc2)c1] | 2-(2-(2,3-dichlorophenyl)-1-(3'-(2-hydroxypropan-2-yl)biphenyl-4-yl)-1H-imidazol-4-yl)propan-2-ol |

-continued

| Cpd # | Structure | Name |
|---|---|---|
| 479 | 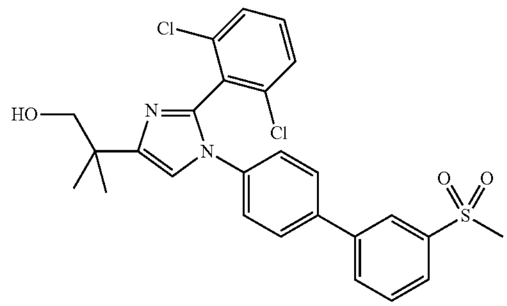 [SMILES: CC(C)(CO)c1cn(-c2ccc(-c3cccc(S(C)(=O)=O)c3)cc2)c(-c2c(Cl)cccc2Cl)n1] | 2-(2-(2,6-dichlorophenyl)-1-(3'-(methylsulfonyl)biphenyl-4-yl)-1H-imidazol-4-yl)-2-methylpropan-1-ol |
| 480 | 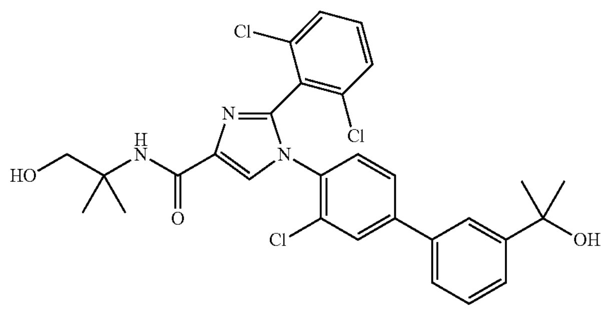 [SMILES: CC(C)(CO)NC(=O)c1cn(-c2ccc(-c3cccc(C(C)(C)O)c3)cc2Cl)c(-c2c(Cl)cccc2Cl)n1] | 1-(3-chloro-3'-(2-hydroxypropan-2-yl)biphenyl-4-yl)-2-(2,6-dichlorophenyl)-N-(1-hydroxy-2-methylpropan-2-yl)-1H-imidazole-4-carboxamide |
| 481 | 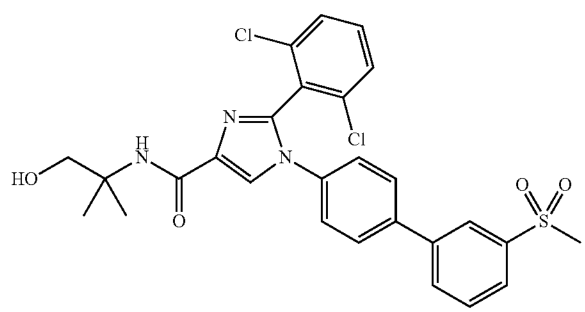 [SMILES: CC(C)(CO)NC(=O)c1cn(-c2ccc(-c3cccc(S(C)(=O)=O)c3)cc2)c(-c2c(Cl)cccc2Cl)n1] | 2-(2,6-dichlorophenyl)-N-(1-hydroxy-2-methylpropan-2-yl)-1-(3'-(methylsulfonyl)biphenyl-4-yl)-1H-imidazole-4-carboxamide |
| 482 | 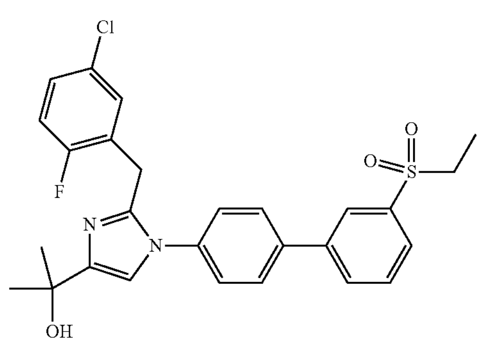 [SMILES: CCS(=O)(=O)c1cccc(-c2ccc(-n3cc(C(C)(C)O)nc3Cc3cc(Cl)ccc3F)cc2)c1] | 2-(2-(5-chloro-2-fluorobenzyl)-1-(3'-(ethylsulfonyl)biphenyl-4-yl)-1H-imidazol-4-yl)propan-2-ol |
| 483 | 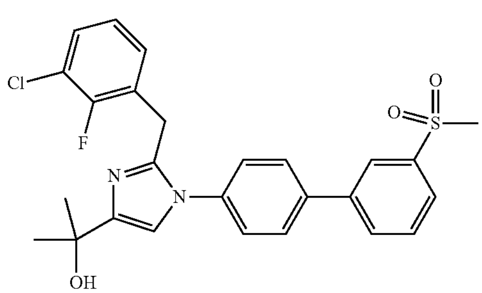 [SMILES: CC(C)(O)c1cn(-c2ccc(-c3cccc(S(C)(=O)=O)c3)cc2)c(Cc2cccc(Cl)c2F)n1] | 2-(2-(3-chloro-2-fluorobenzyl)-1-(3'-(methylsulfonyl)biphenyl-4-yl)-1H-imidazol-4-yl)propan-2-ol |

| Cpd # | Structure | Name |
| --- | --- | --- |
| 484 | 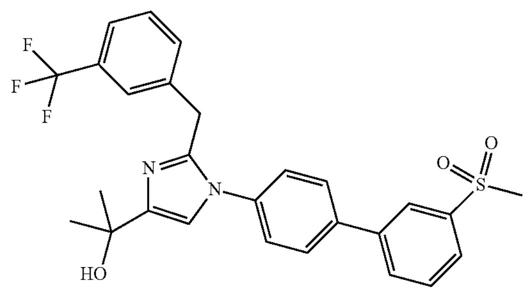 [SMILES: CC(C)(O)c1cn(-c2ccc(-c3cccc(S(C)(=O)=O)c3)cc2)c(Cc2cccc(C(F)(F)F)c2)n1] | 2-(1-(3'-(methylsulfonyl)biphenyl-4-yl)-2-(3-(trifluoromethyl)benzyl)-1H-imidazol-4-yl)propan-2-ol |
| 485 | 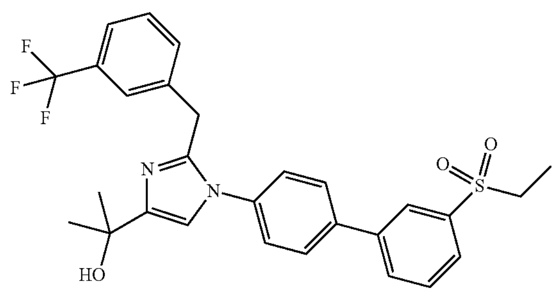 [SMILES: CCS(=O)(=O)c1cccc(-c2ccc(-n3cc(C(C)(C)O)nc3Cc3cccc(C(F)(F)F)c3)cc2)c1] | 2-(1-(3'-(ethylsulfonyl)biphenyl-4-yl)-2-(3-(trifluoromethyl)benzyl)-1H-imidazol-4-yl)propan-2-ol |
| 486 | 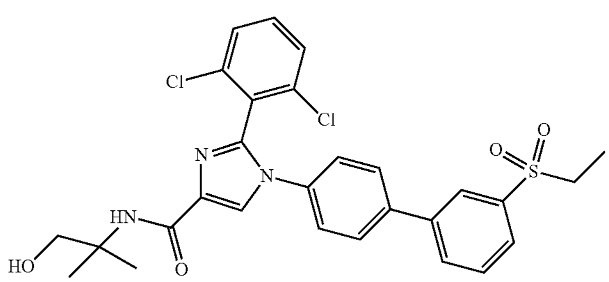 [SMILES: CCS(=O)(=O)c1cccc(-c2ccc(-n3cc(C(=O)NC(C)(C)CO)nc3-c3c(Cl)cccc3Cl)cc2)c1] | 2-(2,6-dichlorophenyl)-1-(3'-(ethylsulfonyl)biphenyl-4-yl)-N-(1-hydroxy-2-methylpropan-2-yl)-1H-imidazole-4-carboxamide, and |
| 487 | 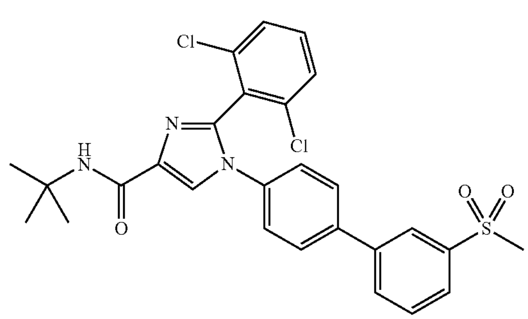 [SMILES: CC(C)(C)NC(=O)c1cn(-c2ccc(-c3cccc(S(C)(=O)=O)c3)cc2)c(-c2c(Cl)cccc2Cl)n1] | N-tert-butyl-2-(2,6-dichlorophenyl)-1-(3'-(methylsulfonyl)biphenyl-4-yl)-1H-imidazole-4-carboxamide. |

25. A pharmaceutical composition comprising a compound of claim 8, or a pharmaceutically acceptable salt thereof in a pharmaceutically acceptable carrier.

26. The compound according to claim 17, of the formula,

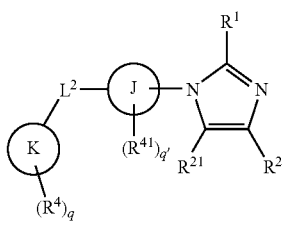

or a pharmaceutically acceptable salt thereof.

27. The compound according to claim 4, wherein $R^2$ is -halogen, —$CF_3$, —$CH_2OH$, or —$C(CH_3)_2OH$.

28. A compound which is

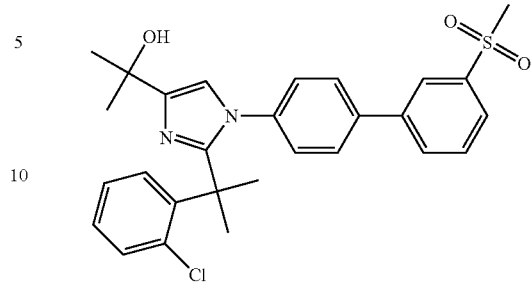

or a pharmaceutically acceptable salt thereof.

29. The compound of claim 23, wherein the compound is according to formula IIa.

30. The compound of claim 23, wherein the compound is according to formula IIb.

31. A pharmaceutical composition comprising a compound of claim 28, or a pharmaceutically acceptable salt thereof in a pharmaceutically acceptable carrier.

* * * * *

UNITED STATES PATENT AND TRADEMARK OFFICE
CERTIFICATE OF CORRECTION

PATENT NO. : 8,569,352 B2  
APPLICATION NO. : 11/993529  
DATED : October 29, 2013  
INVENTOR(S) : Busch et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1638 days.

Signed and Sealed this

Twenty-third Day of May, 2017

Michelle K. Lee
*Director of the United States Patent and Trademark Office*